(12) United States Patent
Jang et al.

(10) Patent No.: US 12,384,781 B2
(45) Date of Patent: *Aug. 12, 2025

(54) COMPOUND, PHOTOSENSITIVE FLUORESCENT RESIN COMPOSITION COMPRISING SAME, COLOR CONVERSION FILM MANUFACTURED THEREFROM, BACKLIGHT UNIT, AND DISPLAY DEVICE

(71) Applicant: LG CHEM, LTD., Seoul (KR)

(72) Inventors: Hanbit Jang, Daejeon (KR); Duy Hieu Le, Daejeon (KR); Jaemyeng Jeong, Daejeon (KR); Hoyong Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 881 days.

This patent is subject to a terminal disclaimer.

(21) Appl. No.: 17/621,640

(22) PCT Filed: Jul. 13, 2020

(86) PCT No.: PCT/KR2020/009177
§ 371 (c)(1),
(2) Date: Dec. 21, 2021

(87) PCT Pub. No.: WO2021/010701
PCT Pub. Date: Jan. 21, 2021

(65) Prior Publication Data
US 2022/0389014 A1    Dec. 8, 2022

(30) Foreign Application Priority Data
Jul. 18, 2019  (KR) .................. 10-2019-0087014

(51) Int. Cl.
| | | |
|---|---|---|
| C07D 471/06 | (2006.01) | |
| C07F 7/18 | (2006.01) | |
| C08K 5/3437 | (2006.01) | |
| G03F 7/033 | (2006.01) | |
| H10K 85/40 | (2023.01) | |
| H10K 85/60 | (2023.01) | |

(52) U.S. Cl.
CPC .......... *C07D 471/06* (2013.01); *C07F 7/1804* (2013.01); *C08K 5/3437* (2013.01); *G03F 7/033* (2013.01); *H10K 85/40* (2023.02); *H10K 85/631* (2023.02); *H10K 85/636* (2023.02); *H10K 85/653* (2023.02); *H10K 85/654* (2023.02); *H10K 85/655* (2023.02); *H10K 85/6572* (2023.02); *H10K 85/6574* (2023.02)

(58) Field of Classification Search
CPC .. C07D 471/06; H10K 85/654; H10K 85/636; H10K 85/631; H10K 85/655; H10K 85/6574; H10K 85/653; H10K 85/6572; H10K 85/40; C08K 5/3437; G03F 7/033
See application file for complete search history.

(56) References Cited

FOREIGN PATENT DOCUMENTS

| | | |
|---|---|---|
| KR | 10-2016-0097147 A | 8/2016 |
| KR | 10-2018-0090541 A | 8/2018 |
| KR | 10-1992084 B1 | 6/2019 |
| WO | 2018-134263 A1 | 7/2018 |

OTHER PUBLICATIONS

Lu et al., 115(37) J. Physical Chem. B., 10871-10876 (2011) (CAS Abstract) (Year: 2011).*
International Search Report issued for International Application No. PCT/KR2020/009177 on Oct. 14, 2020, 5 pages.
Xue et al., Synthesis and characterization of the first soluble nonracemic chiral main-chain perylene tetracarboxylic diimide polymers, Polymer, 2008, 49(24), pp. 5314-5321.
Lu et al., Helical Assembly Induced by Hydrogen Bonding from Chiral Carboxylic Acids Based on Perylene Bisimides, The Journal of Physical Chemistry B, 2011, 115(37), pp. 10871-10876.

* cited by examiner

*Primary Examiner* — Timothy R Rozof
(74) *Attorney, Agent, or Firm* — ROTHWELL, FIGG, ERNST & MANBECK, P.C.

(57) ABSTRACT

The present specification relates to a compound represented by Chemical Formula 1, a photoresist fluorescent resin composition including the same, and a color conversion film manufactured using the same, a backlight unit and a display apparatus.

10 Claims, 1 Drawing Sheet

[FIG. 1]
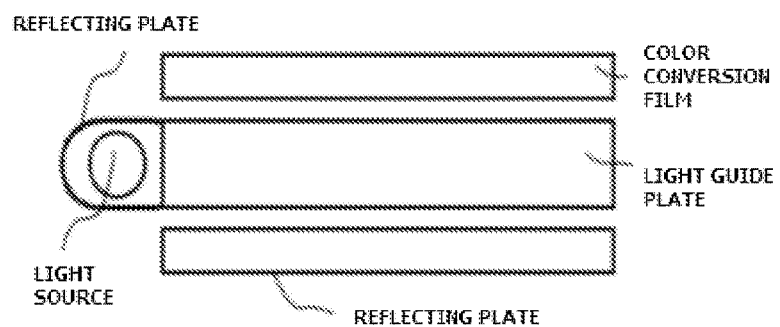
[FIG. 2]
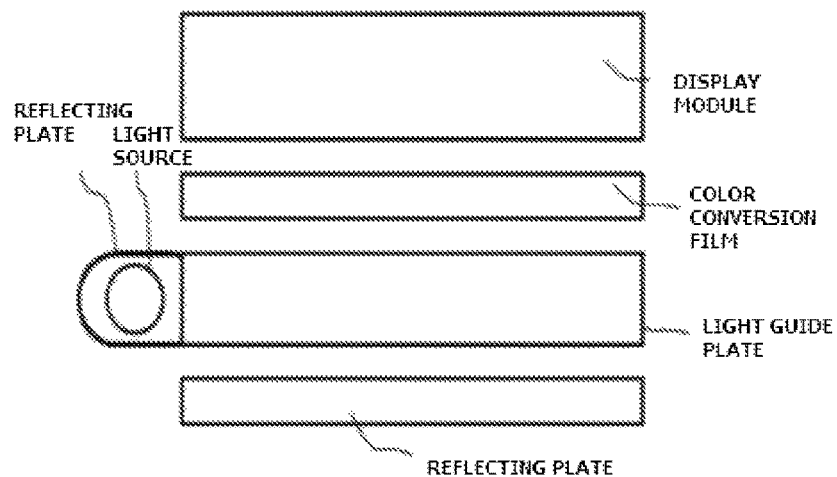

COMPOUND, PHOTOSENSITIVE FLUORESCENT RESIN COMPOSITION COMPRISING SAME, COLOR CONVERSION FILM MANUFACTURED THEREFROM, BACKLIGHT UNIT, AND DISPLAY DEVICE

This application is a 35 U.S.C. 371 National Phase Entry Application from PCT/KR2020/009177, filed on Jul. 13, 2020, which claims priority to and the benefits of Korean Patent Application No. 10-2019-0087014, filed with the Korean Intellectual Property Office on Jul. 18, 2019, the entire contents of which are incorporated herein by reference.

TECHNICAL FIELD

The present specification relates to a compound, a photoresist fluorescent resin composition including the same, and a color conversion film manufactured using the same, a backlight unit and a display apparatus.

BACKGROUND OF THE INVENTION

Existing light emitting diodes (LED) are obtained by mixing a green phosphorescent substance and a red phosphorescent substance to a blue light emitting diode, or mixing a yellow phosphorescent substance and a blue-green phosphorescent substance to a UV light emitting diode. However, with such a method, it is difficult to control colors, and therefore, color rendering is not favorable. Accordingly, color gamut declines.

In order to overcome such color gamut decline and to reduce production costs, methods of obtaining green and red in a manner of filming quantum dots and binding the dots to a blue LED have been recently tried. However, cadmium series quantum dots have safety problems, and other quantum dots have significantly decreased efficiency compared to cadmium series quantum dots. In addition, quantum dots have reduced stability for oxygen and water, and have a disadvantage in that the performance is significantly degraded when aggregated. Furthermore, unit costs of production are high since, when producing quantum dots, maintaining the sizes to be constant is difficult.

Existing compounds having a $BF_2$ or $B(CN)_2$-based bodipy structure provides, as a fluorescent dye having high light efficiency and a narrow full width at half maximum, excellent light properties when used in a color conversion film, but has insufficient light resistance and heat resistance to be commercialized, and development of compounds having high durability has been required.

BRIEF SUMMARY OF THE INVENTION

The present specification is directed to providing a compound, a photoresist fluorescent resin composition including the same, and a color conversion film manufactured using the same, a backlight unit and a display apparatus.

One embodiment of the present specification provides a compound represented by the following Chemical Formula 1.

[Chemical Formula 1]

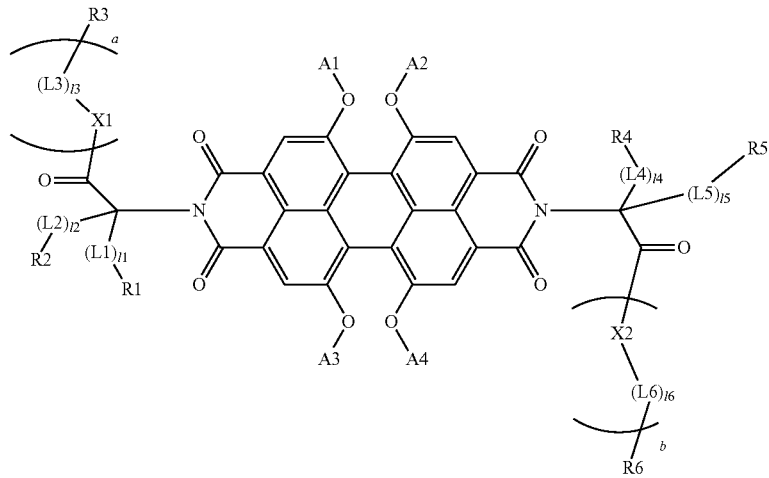

In Chemical Formula 1,
A1 to A4 are each independently a substituted or unsubstituted aryl group, or a substituted or unsubstituted heterocyclic group,
X1 and X2 are each independently O, NH or NR',
R' is $-(G1)_{g1}$-E or -G2-O-G3-E, or forms a ring with adjacent groups,
R1, R2, R4 and R5 are each independently hydrogen, a halogen group, a substituted or unsubstituted alkyl group, a substituted or unsubstituted cycloalkyl group, a substituted or unsubstituted alkoxy group, a substituted or unsubstituted aryl group, or a substituted or unsubstituted heterocyclic group,
R3 and R6 are each independently a polymerizable group,
E is a halogen group, a substituted or unsubstituted alkyl group, a substituted or unsubstituted cycloalkyl group, a substituted or unsubstituted alkoxy group, a substituted or unsubstituted aryl group, a substituted or unsubstituted heterocyclic group, or a polymerizable group,
L1, L2, L4 and L5 are each independently a direct bond, or a substituted or unsubstituted alkylene group,
G1 to G3, L3 and L6 are each independently a direct bond, a substituted or unsubstituted alkylene group, a substituted or unsubstituted cycloalkylene group, a substituted or unsubstituted arylene group, or a substituted or unsubstituted divalent heterocyclic group, a and b are each an integer of 0 to 3, g1 and I1 to I6 are each an integer of 1 to 3, and when a, b, g1 and I1 to I6 are each 2 or greater, structures in the parentheses are the same as or different from each other.

Another embodiment of the present specification provides a photoresist fluorescent resin composition including a binder resin; a multifunctional monomer; and the compound described above.

Another embodiment of the present specification provides a color conversion film including the compound bonding to a binder resin.

Another embodiment of the present specification provides a backlight unit including the color conversion film described above.

Another embodiment of the present specification provides a display apparatus including the backlight unit described above.

Advantageous Effects

A compound according to one embodiment of the present specification is capable of high color reproduction.

A compound according to one embodiment of the present specification has high solubility.

A compound according to one embodiment of the present specification has high light resistance.

A compound according to one embodiment of the present specification has an advantage of being not dyed.

BRIEF DESCRIPTION OF DRAWINGS

FIG. 1 is a mimetic diagram of using a color conversion film according to one embodiment of the present specification in a backlight unit.

FIG. 2 is a mimetic diagram illustrating a structure of a display apparatus according to one embodiment of the present specification.

DETAILED DESCRIPTION OF THE INVENTION

Hereinafter, the present specification will be described in detail.

One embodiment of the present specification provides a compound represented by Chemical Formula 1.

Existing perylene derivatives have a limitation in high color reproduction since absorption and emission wavelengths thereof are short wavelengths. In addition, existing perylene derivatives have disadvantages of being dyed and having weak light resistance.

Meanwhile, the compound according to one embodiment of the present specification is capable of high color reproduction by absorption and emission wavelengths moving to long wavelengths compared to existing perylene derivatives. Specifically, the compound according to one embodiment of the present specification is capable of high color reproduction by absorption and emission wavelengths moving to long wavelengths and thereby accomplishing a wider range of color coordinates compared to existing perylene derivatives.

The compound according to one embodiment of the present specification has superior light resistance compared to existing perylene derivatives. Specifically, the compound according to one embodiment of the present specification has superior light resistance by having an electron withdrawing group at the imide position compared to existing perylene derivatives.

The compound according to one embodiment of the present specification has a reaction group polymerizable with a binder in the molecule and thereby has an advantage of being not dyed due to the bond with a binder.

In the present specification, a certain part "including" certain constituents means capable of further including other constituents, and does not exclude other constituents unless particularly stated on the contrary.

In the present specification, one member being placed "on" another member includes not only a case of the one member being in contact with the another member but a case of still another member being present between the two members.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

Examples of substituents in the present specification are described below, however, the substituents are not limited thereto.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a cyano group; a nitro group; a hydroxyl group; an imide group; an amide group; an ester group; a substituted or unsubstituted amine group; a substituted or unsubstituted silyl group; a substituted or unsubstituted alkyl group; a substituted or unsubstituted cycloalkyl group; a substituted or unsubstituted haloalkyl group; a substituted or unsubstituted alkoxy group; a substituted or unsubstituted aryloxy group; a substituted or unsubstituted alkenyl group; a substituted or unsubstituted alkynyl group; a substituted or unsubstituted aryl group and a substituted or unsubstituted heterocyclic group, or being substituted with a substituent linking two or more substituents among the substituents illustrated above, or having no substituents.

In the present specification, examples of the halogen group may include fluorine, chlorine, bromine or iodine.

In the present specification, the number of carbon atoms of the imide group is not particularly limited, but is preferably from 1 to 30. Specifically, compounds having structures as below may be included, however, the imide group is not limited thereto.

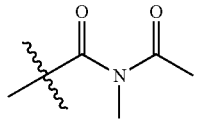

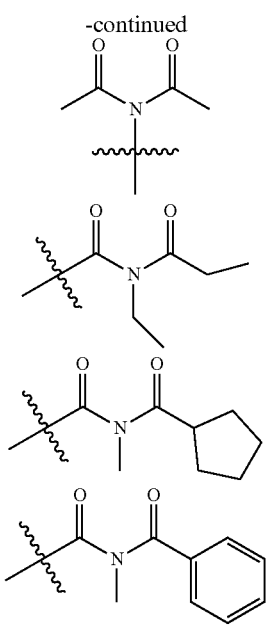

In the present specification, in the amide group, nitrogen of the amide group may be substituted with hydrogen, a linear, branched or cyclic alkyl group having 1 to 30 carbon atoms, or an aryl group having 6 to 30 carbon atoms. Specifically, compounds having the following structural formulae may be included, however, the amide group is not limited thereto.

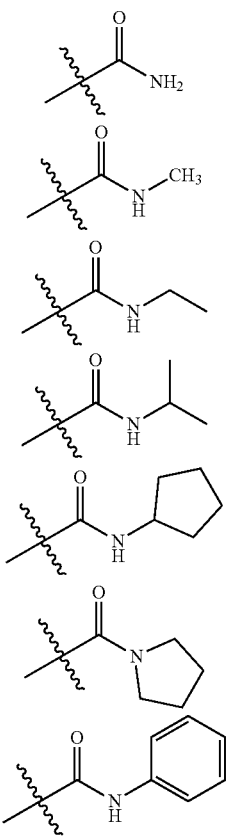

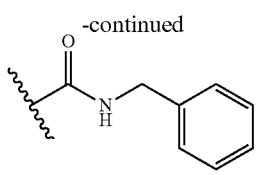

In the present specification, in the ester group, the oxygen of the ester group may be substituted with a linear, branched or cyclic alkyl group having 1 to 25 carbon atoms or an aryl group having 6 to 30 carbon atoms. Specifically, compounds having the following structural formulae may be included, however, the ester group is not limited thereto.

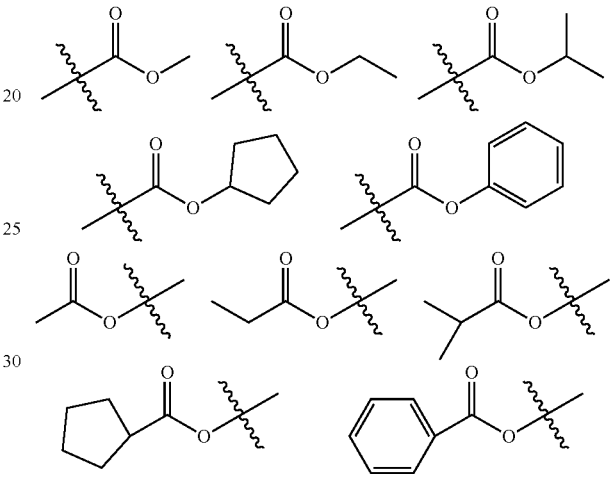

In the present specification, the amine group may be selected from the group consisting of —NH$_2$; a monoalkylamine group; a dialkylamine group; an N-alkylarylamine group; a monoarylamine group; a diarylamine group; an N-arylheteroarylamine group; an N-alkylheteroarylamine group, a monoheteroarylamine group and a diheteroarylamine group, and, although not particularly limited thereto, the number of carbon atoms is preferably from 1 to 30.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, an alkyl group in the alkylamine group, the N-alkylarylamine group and the N-alkylheteroarylamine group is the same as examples of an alkyl group to describe later.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the alkyl group may be linear or branched, and although not particularly limited thereto, the number of carbon atoms is preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methyl pentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl and the like, but are not limited thereto.

In the present specification, the cycloalkyl group is not particularly limited, but preferably has 3 to 30 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the haloalkyl group represents an alkyl group in which one or more hydrogen atoms of the alkyl group are replaced by the same or a different halogen group. The haloalkyl group may be linear or branched, and although not particularly limited thereto, the number of carbon atoms is preferably from 1 to 10. Specific examples thereof may include —$CH_2Cl$, —$CF_3$, —$CH_2CF_3$, —$CF_2CF_3$ and the like, but are not limited thereto.

In the present specification, the alkoxy group may be linear, branched or cyclic. The number of carbon atoms of the alkoxy group is not particularly limited, but is preferably from 1 to 30.

In the present specification, the aryloxy group is a monovalent substituent represented by RO—, and R is an aryl group. Examples thereof may include phenyloxy, naphthyloxy, biphenyloxy and the like, but are not limited thereto.

In the present specification, the alkenyl group may be linear or branched, and although not particularly limited thereto, the number of carbon atoms is preferably from 2 to 30.

In the present specification, the alkynyl group may be linear or branched, and although not particularly limited thereto, the number of carbon atoms is preferably from 2 to 30. Specific examples thereof may include alkynyl groups such as ethynyl, propynyl, 2-methyl-2-propynyl, 2-butynyl, 2-pentynyl and the like, but are not limited thereto.

In the present specification, the aryl group is not particularly limited, but preferably has 6 to 30 carbon atoms, and the aryl group may be monocyclic or polycyclic.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group may include a naphthyl group, an anthracenyl group, a phenanthryl group, a triphenyl group, a pyrenyl group, a perylenyl group, a chrysenyl group, a fluorenyl group and the like, but are not limited thereto.

In the present specification, the fluorenyl group may be substituted, and adjacent groups may bond to each other to form a ring.

When the fluorenyl group is substituted,

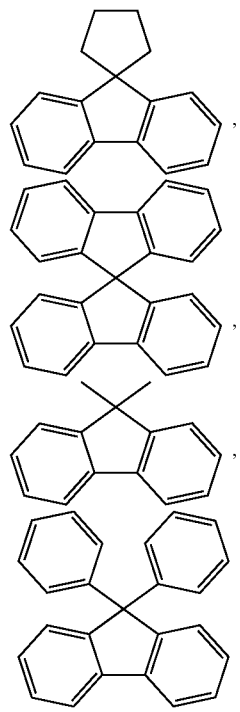

and the like may be included. However, the structure is not limited thereto.

In the present specification, the heterocyclic group is a group including one or more atoms that are not carbon, that is, heteroatoms, and specifically, the heteroatom may include one or more atoms selected from the group consisting of O, N, Se, S and the like. The number of carbon atoms is not particularly limited, but is preferably from 2 to 30, and the heterocyclic group may be monocyclic or polycyclic. Examples of the heterocyclic group may include a thiophenyl group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophenyl group, a dibenzothiophenyl group, a benzofuranyl group, a phenanthrolinyl group, an isoxazolyl group, a thiadiazolyl group, a phenothiazinyl group, a dibenzofuranyl group and the like, but are not limited thereto.

In the present specification, descriptions on the heterocyclic group may be applied to the heteroaryl group except that it is an aromatic heterocyclic group.

In one embodiment of the present specification, the polymerizable group may have at least one selected from the group consisting of a substituted or unsubstituted ethylenically unsaturated group, a substituted or unsubstituted siloxane group and a substituted or unsubstituted epoxy group.

The polymerizable group may be any one of the following structures.

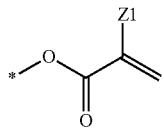

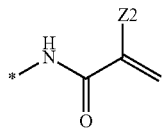

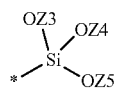

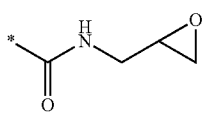

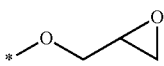

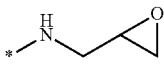

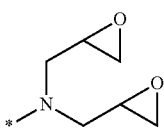

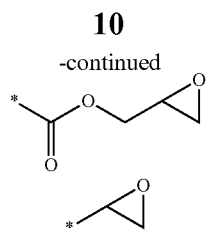

In the structures,
Z1 and Z2 are each independently hydrogen, a halogen group, or a substituted or unsubstituted alkyl group,
Z3 to Z5 are each independently a substituted or unsubstituted alkyl group, and
* represents a bonding position.

In one embodiment of the present specification, Chemical Formula 1 may be represented by the following Chemical Formula 2.

[Chemical Formula 2]

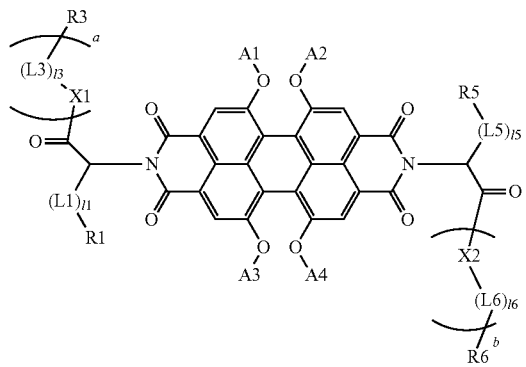

In Chemical Formula 2,
A1 to A4, X1, X2, R1, R3, R5, R6, L1, L3, L5, L6, l1, l3, l5, l6, a and b have the same definitions as in Chemical Formula 1.

In one embodiment of the present specification, Chemical Formula 1 may be represented by any one of the following Chemical Formulae 3 to 7.

[Chemical Formula 3]

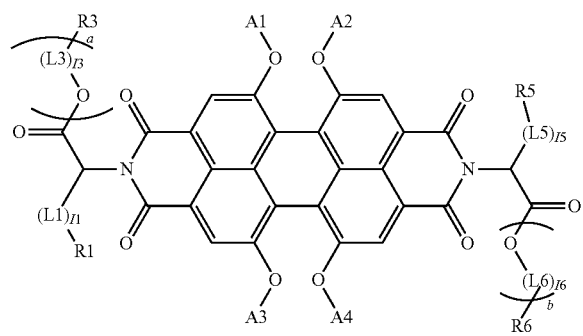

[Chemical Formula 4]

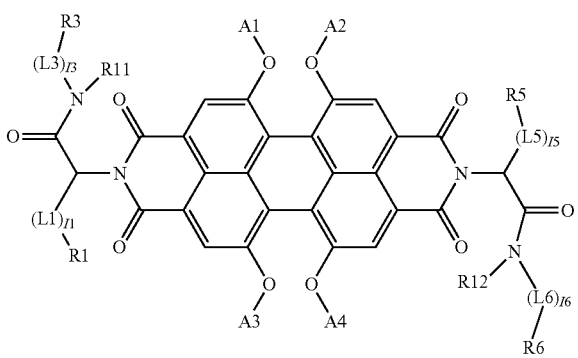

[Chemical Formula 5]

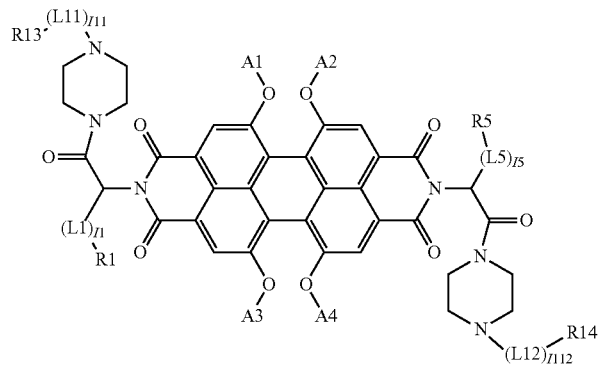

[Chemical Formula 6]

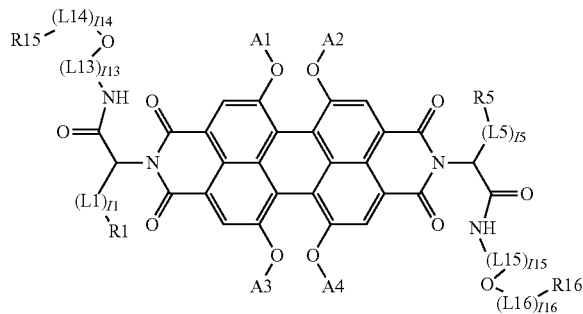

[Chemical Formula 7]

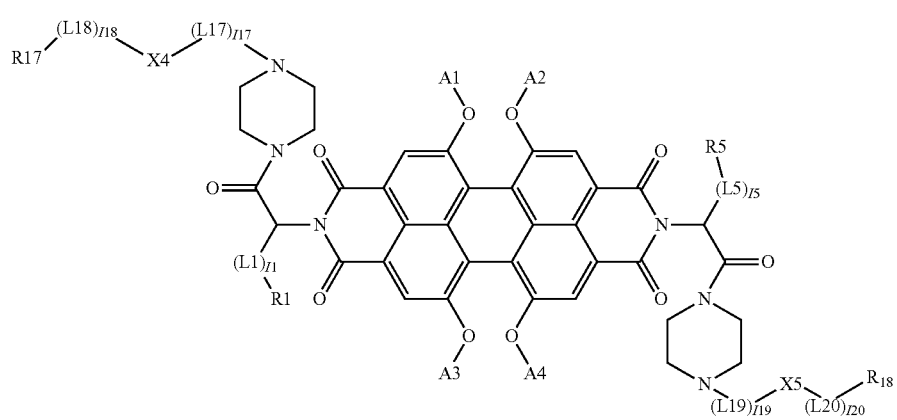

In Chemical Formulae 3 to 7,

R11 and R12 are each independently -(G1)$_{g1}$-E or -G2-O-G3-E,

A1 to A4, R1, R3, R5, R6, L1, L3, L5, L6, G1 to G3, E, g1, I1, I3, I5, I6, a and b have the same definitions as in Chemical Formula 1, R13 to R18 are each independently a polymerizable group, L11 to L20 are each independently a direct bond, or a substituted or unsubstituted alkylene group, I11 to I20 are each an integer of 1 to 3, when I11 to I20 are each 2 or greater, structures in the parentheses are the same as or different from each other, and X4 and X5 are each independently O or NH.

In one embodiment of the present specification, R1, R2, R4 and R5 are each independently hydrogen, a halogen group, a substituted or unsubstituted alkyl group, a substituted or unsubstituted cycloalkyl group, a substituted or unsubstituted alkoxy group, a substituted or unsubstituted aryl group, or a substituted or unsubstituted heterocyclic group.

In one embodiment of the present specification, R1, R2, R4 and R5 are each independently hydrogen, a halogen group, an alkyl group, a haloalkyl group, a cycloalkyl group, an alkoxy group, an aryl group or a heterocyclic group.

In one embodiment of the present specification, R1, R2, R4 and R5 are each independently hydrogen, a halogen group, an alkyl group, a haloalkyl group, a substituted or unsubstituted cyclopentyl group, a substituted or unsubstituted cyclohexyl group, a substituted or unsubstituted cycloheptyl group, a substituted or unsubstituted alkoxy group, a substituted or unsubstituted phenyl group, a substituted or unsubstituted naphthyl group, a substituted or unsubstituted furanyl group, a substituted or unsubstituted thiophenyl group, a substituted or unsubstituted dibenzofuranyl group, a substituted or unsubstituted pyridyl group, or a substituted or unsubstituted quinolinyl group.

In one embodiment of the present specification, R1, R2, R4 and R5 are each independently hydrogen, a halogen group, an alkyl group, a haloalkyl group, a cyclopentyl group unsubstituted or substituted with an alkyl group, a cyclohexyl group unsubstituted or substituted with an alkyl group, a cycloheptyl group unsubstituted or substituted with an alkyl group, an alkoxy group unsubstituted or substituted with an alkyl group, a phenyl group unsubstituted or substituted with an alkyl group, a naphthyl group unsubstituted or substituted with an alkyl group, a furanyl group unsubstituted or substituted with an alkyl group, a thiophenyl group unsubstituted or substituted with an alkyl group, a dibenzofuranyl group unsubstituted or substituted with an alkyl group, a pyridyl group unsubstituted or substituted with an alkyl group, or a quinolinyl group unsubstituted or substituted with an alkyl group.

In one embodiment of the present specification, L1, L2, L4 and L5 are each independently a direct bond, or a substituted or unsubstituted alkylene group.

In one embodiment of the present specification, L1, L2, L4 and L5 are each independently a direct bond, or a linear or branched alkylene group.

In one embodiment of the present specification, G1 to G3, L3 and L6 are each independently a direct bond, a substituted or unsubstituted alkylene group, a substituted or unsubstituted cycloalkylene group, a substituted or unsubstituted arylene group, or a substituted or unsubstituted divalent heterocyclic group.

In one embodiment of the present specification, G1 to G3, L3 and L6 are each independently a direct bond, an alkylene group, a cyclohexylene group unsubstituted or substituted with an alkyl group, a cyclopentylene group unsubstituted or substituted with an alkyl group, a phenylene group unsubstituted or substituted with an alkyl group, a divalent pyridine group unsubstituted or substituted with an alkyl group, a divalent thiophene group unsubstituted or substituted with an alkyl group, or a divalent furan group unsubstituted or substituted with an alkyl group.

In one embodiment of the present specification, E is a halogen group, a substituted or unsubstituted alkyl group, a substituted or unsubstituted cycloalkyl group, a substituted or unsubstituted alkoxy group, a substituted or unsubstituted aryl group, a substituted or unsubstituted heterocyclic group, or a polymerizable group.

In one embodiment of the present specification, E is a halogen group, an alkyl group, a haloalkyl group, a cyclopentyl group unsubstituted or substituted with an alkyl group, a cyclohexyl group unsubstituted or substituted with an alkyl group, a cycloheptyl group unsubstituted or substituted with an alkyl group, an alkoxy group unsubstituted or substituted with an alkyl group, a phenyl group unsubstituted or substituted with an alkyl group, a naphthyl group unsubstituted or substituted with an alkyl group, a furanyl group unsubstituted or substituted with an alkyl group, a thiophenyl group unsubstituted or substituted with an alkyl group, a dibenzofuranyl group unsubstituted or substituted with an alkyl group, a pyridyl group unsubstituted or substituted with an alkyl group, a quinolinyl group unsubstituted or substituted with an alkyl group, or a polymerizable group.

In one embodiment of the present specification, A1 to A4 are each independently a substituted or unsubstituted aryl group, or a substituted or unsubstituted heteroaryl group.

In one embodiment of the present specification, A1 to A4 are each independently a substituted or unsubstituted aryl group.

In one embodiment of the present specification, A1 to A4 are each independently a substituted or unsubstituted phenyl group; or a substituted or unsubstituted biphenyl group.

In one embodiment of the present specification, A1 to A4 are each independently a phenyl group unsubstituted or substituted with a group selected from the group consisting of a halogen group, a cyano group, an alkyl group, a haloalkyl group, an ester group, an alkoxy group, an aryloxy group and an aryl group; or a biphenyl group unsubstituted or substituted with a group selected from the group consisting of a halogen group, a cyano group, an alkyl group, a haloalkyl group, an ester group, an alkoxy group, an aryloxy group and an aryl group.

In one embodiment of the present specification, A1 to A4 are the same as each other.

In one embodiment of the present specification, the compound represented by Chemical Formula 1 is point symmetric, line symmetric or surface symmetric.

The compound represented by Chemical Formula 1 is represented by any one of the following compounds.

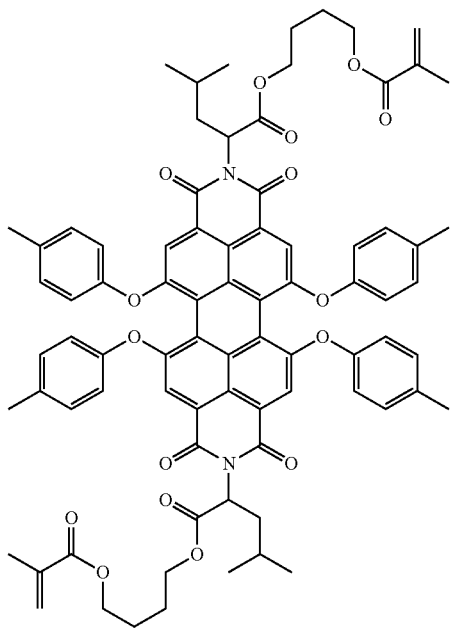

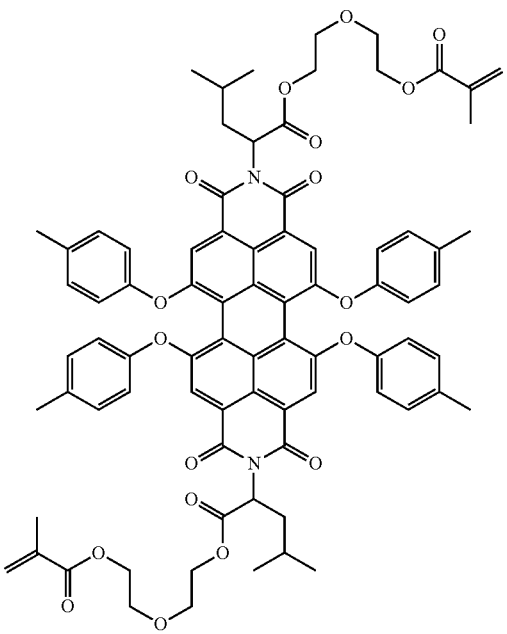

15
-continued
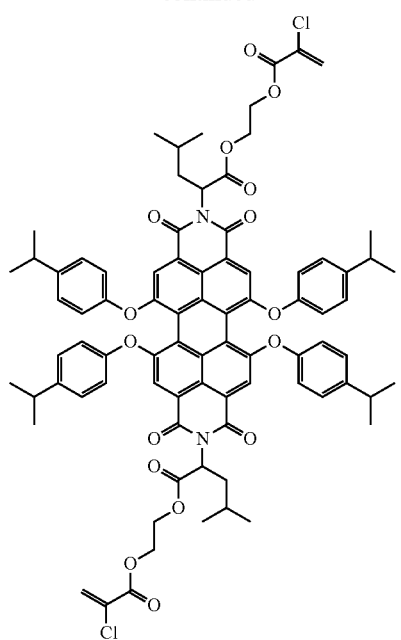
16
-continued
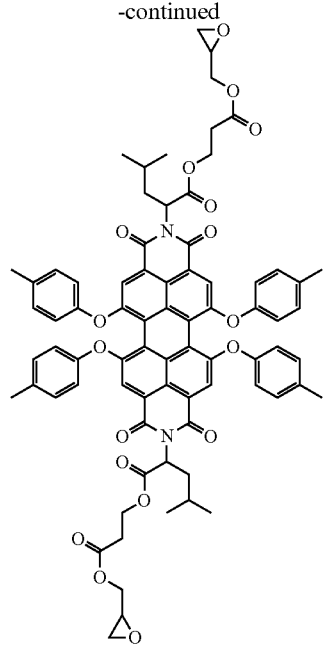
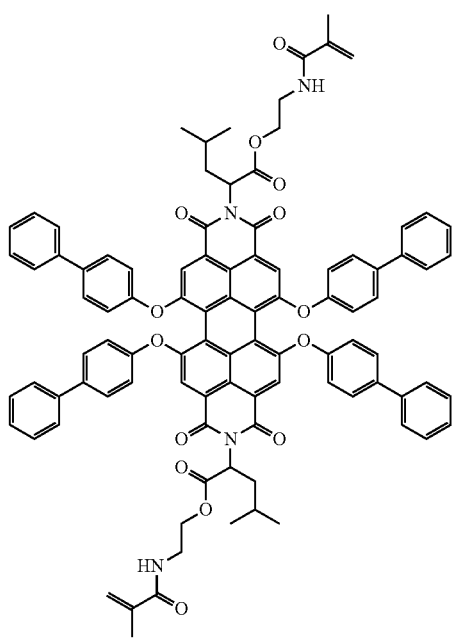
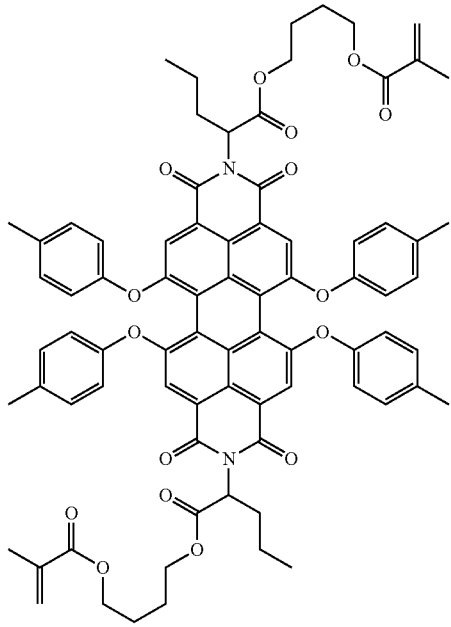

17
-continued
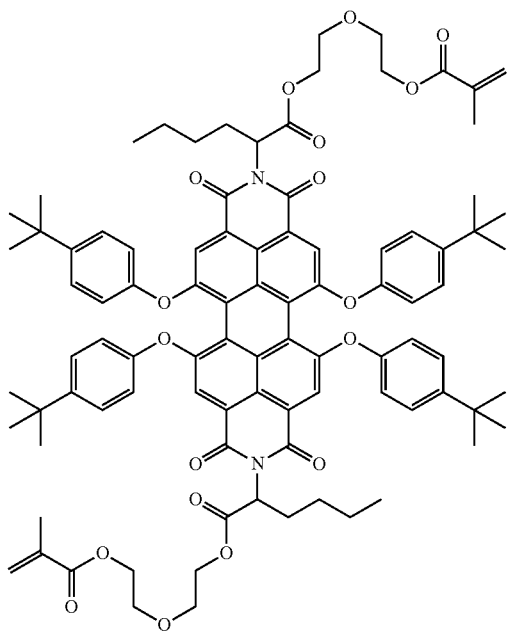
18
-continued
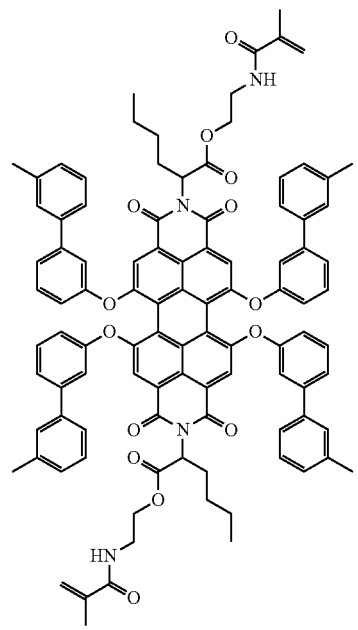
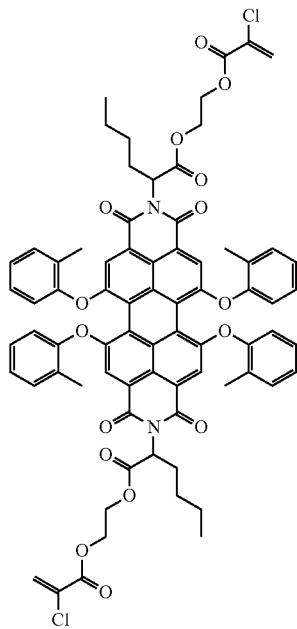
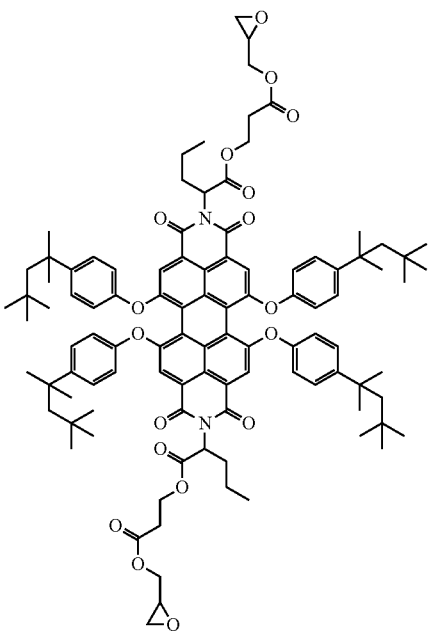

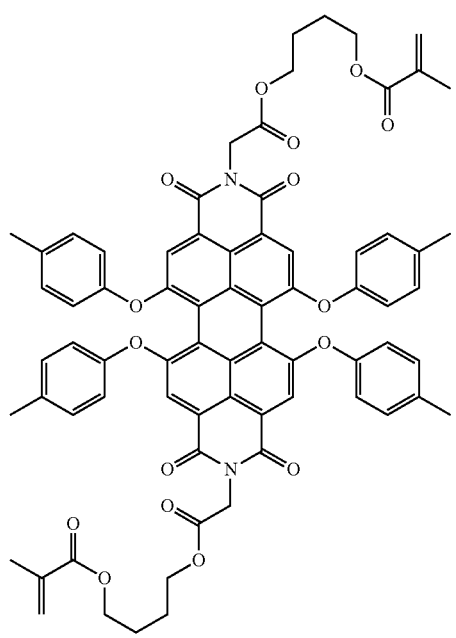
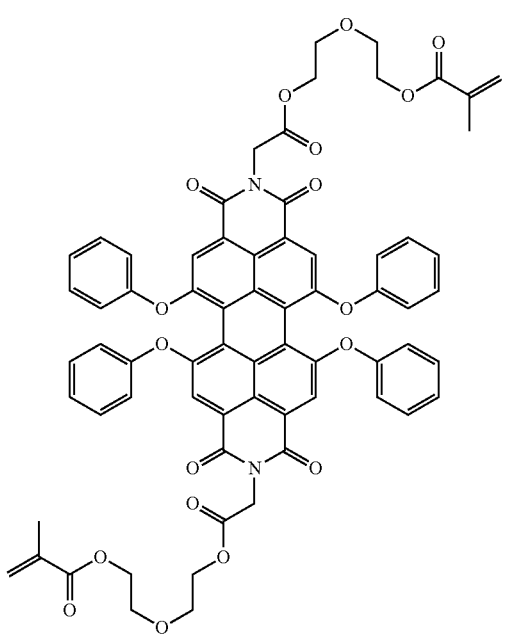
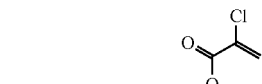
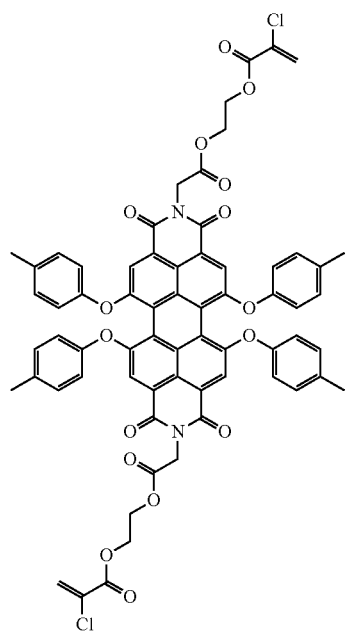
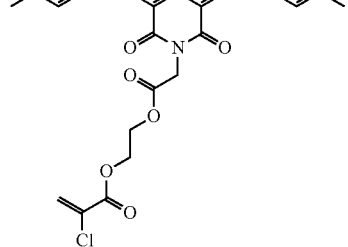
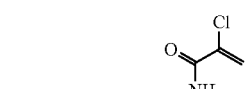
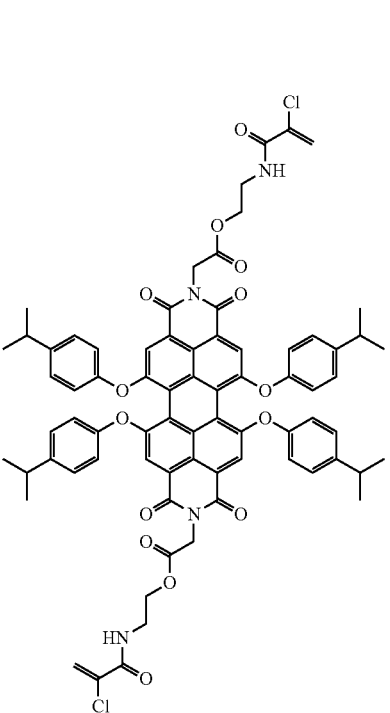

21
-continued
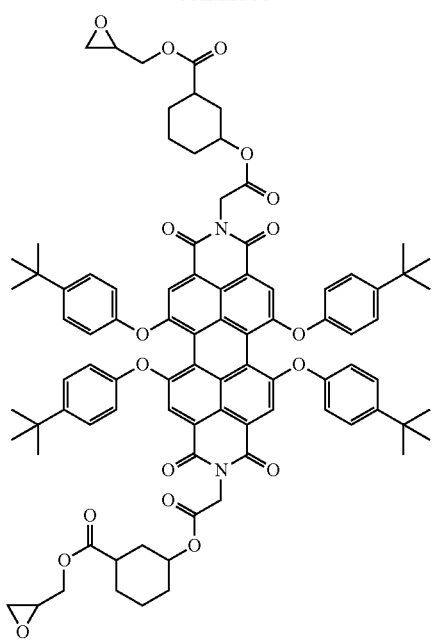
22
-continued
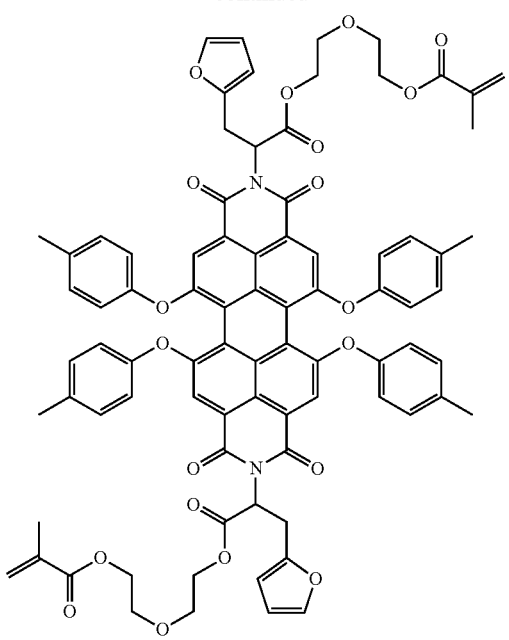
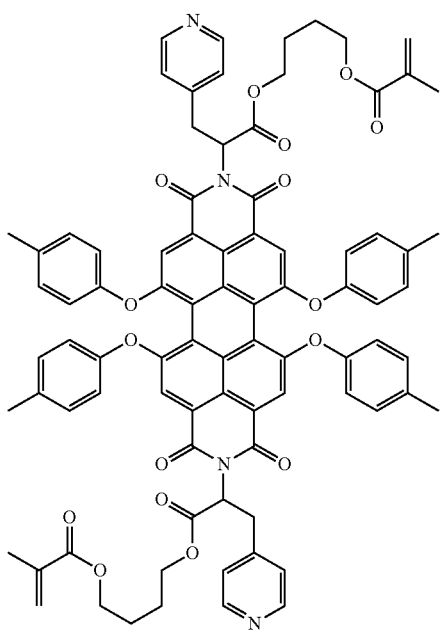
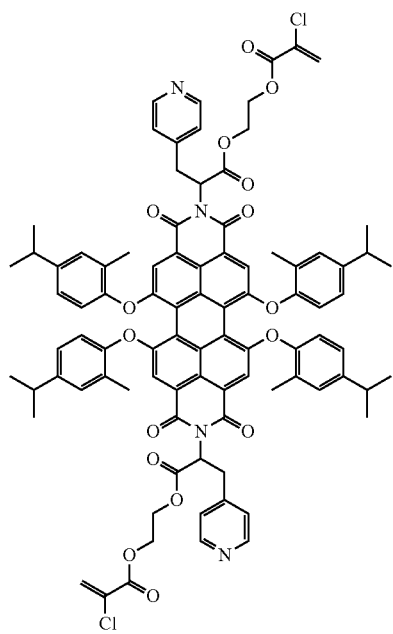

23
-continued
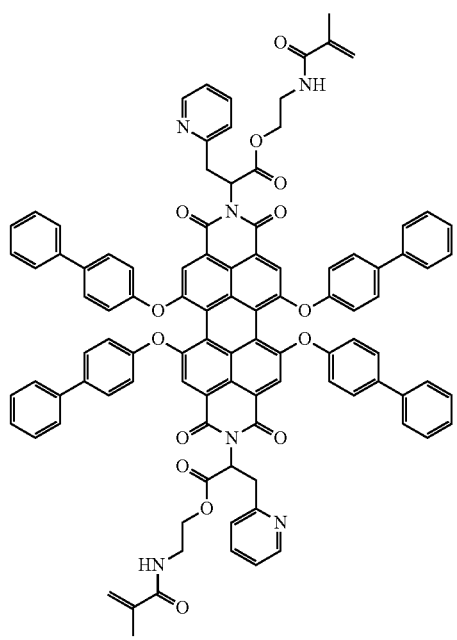
24
-continued
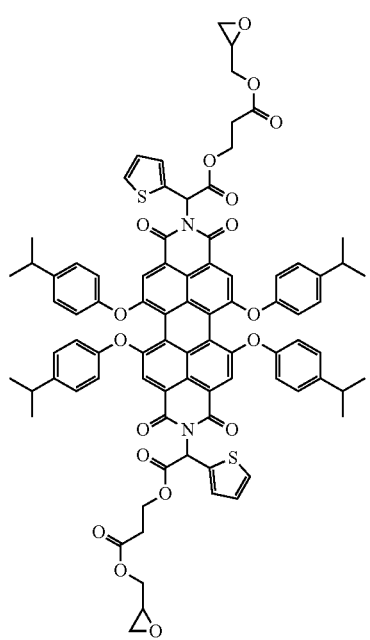
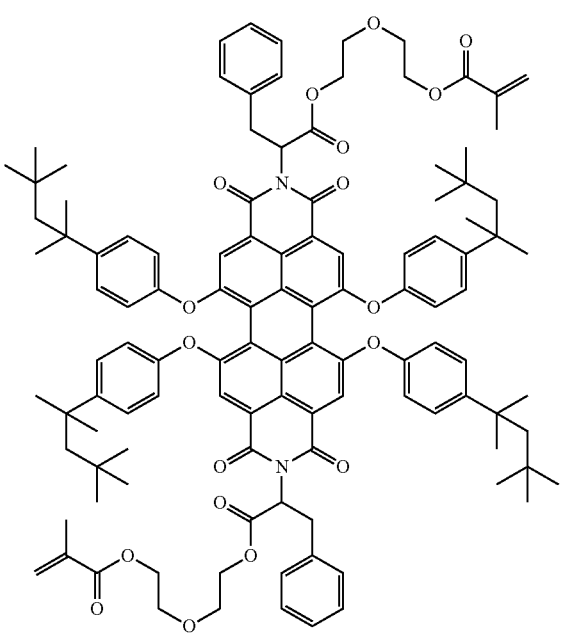

25
-continued
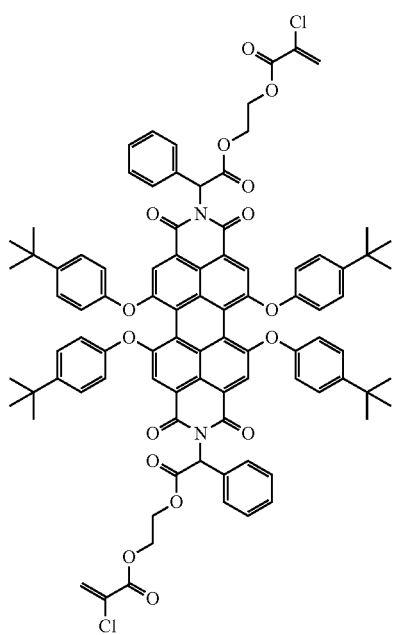
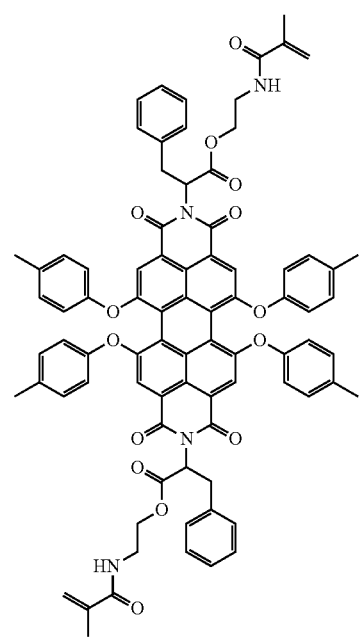
26
-continued
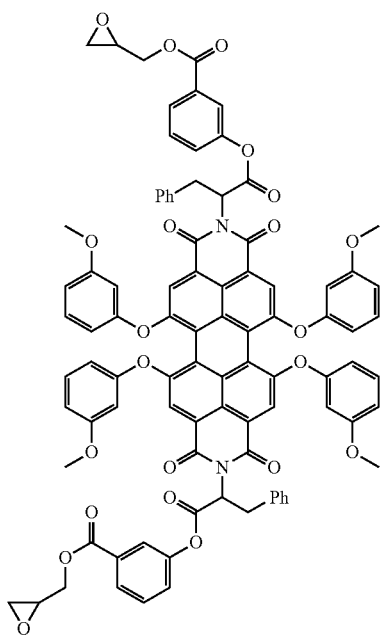 [SMILES: COc1cccc(Oc2cc3c4c(cc(Oc5cccc(OC)c5)c5c6c(Oc7cccc(OC)c7)cc7c8c(cc(Oc9cccc(OC)c9)c(c2c45)c86)C(=O)N(C(Cc2ccccc2)C(=O)Oc2cccc(C(=O)OCC4CO4)c2)C7=O)C(=O)N(C(Cc2ccccc2)C(=O)Oc2cccc(C(=O)OCC4CO4)c2)C3=O)c1]
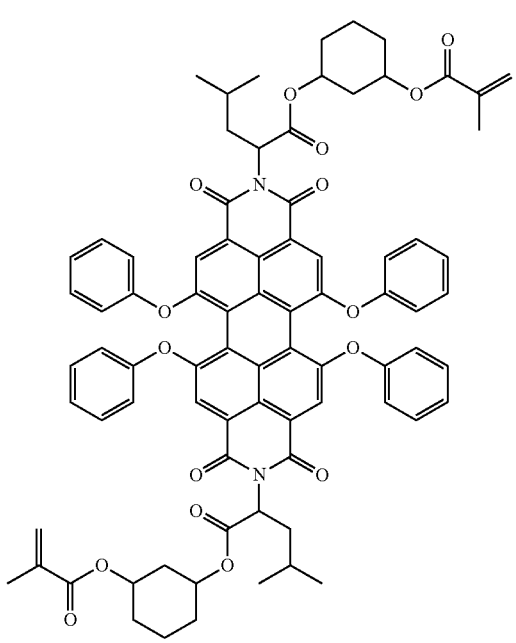

27
-continued
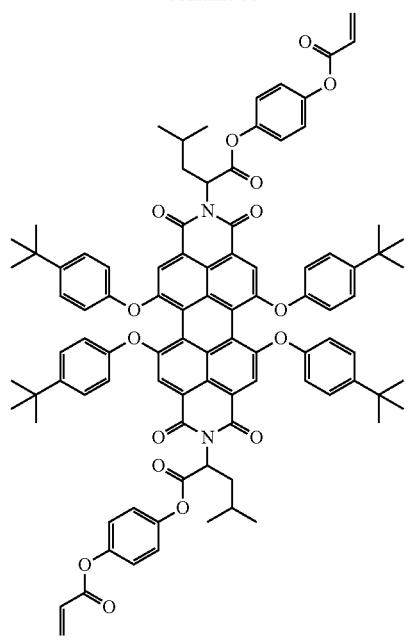
28
-continued
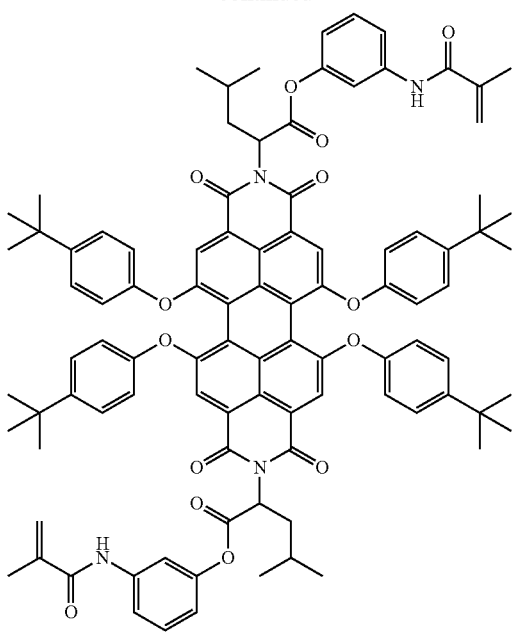
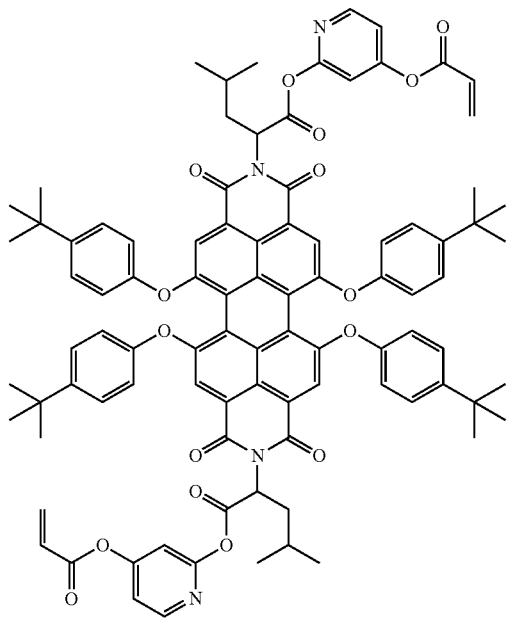
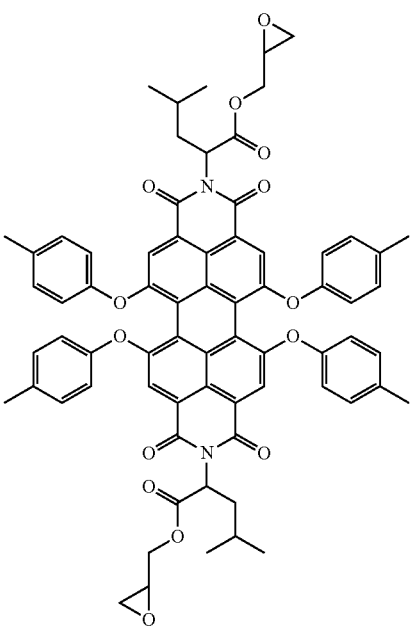

29
-continued
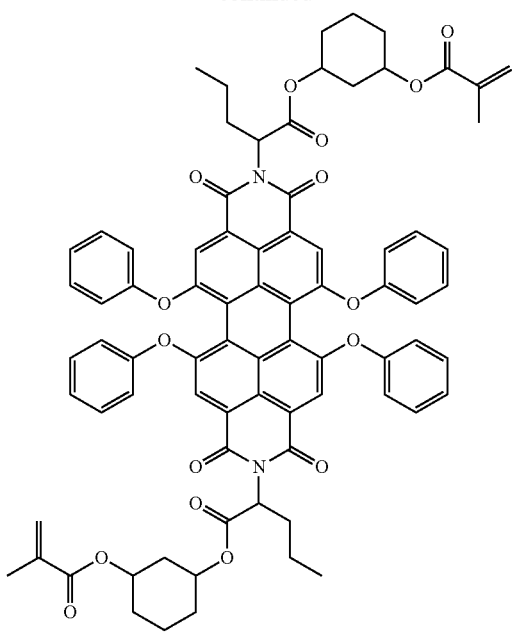
30
-continued
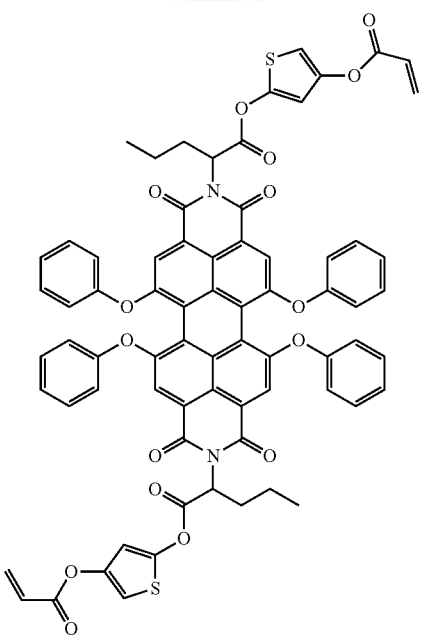
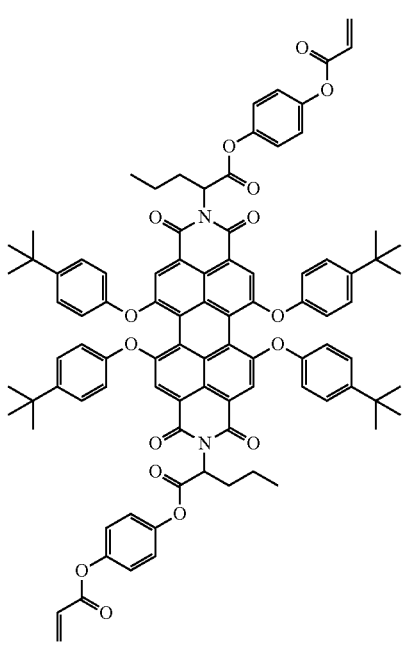
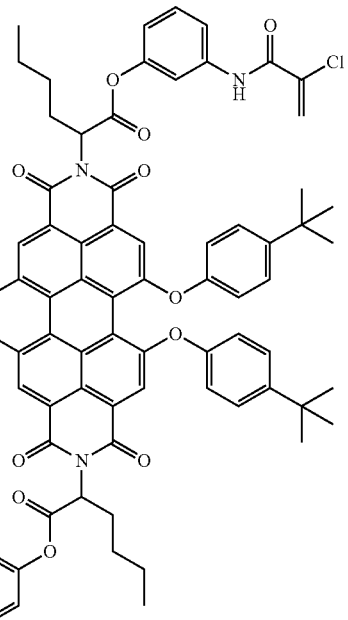

31
-continued
32
-continued
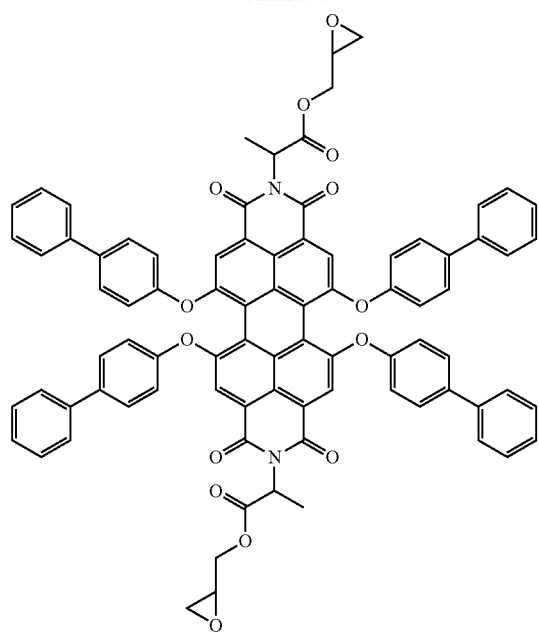
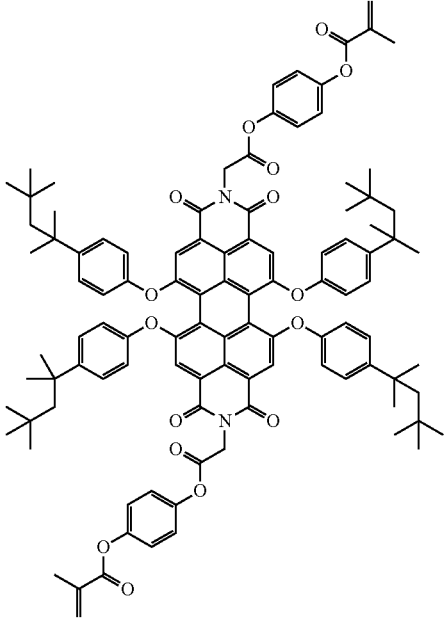
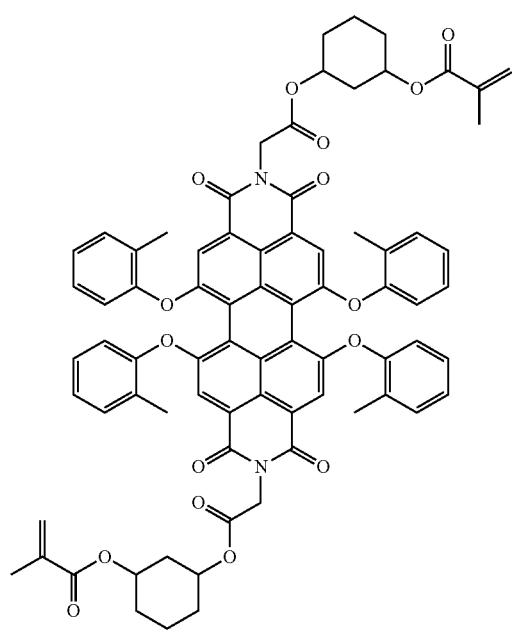

33
-continued
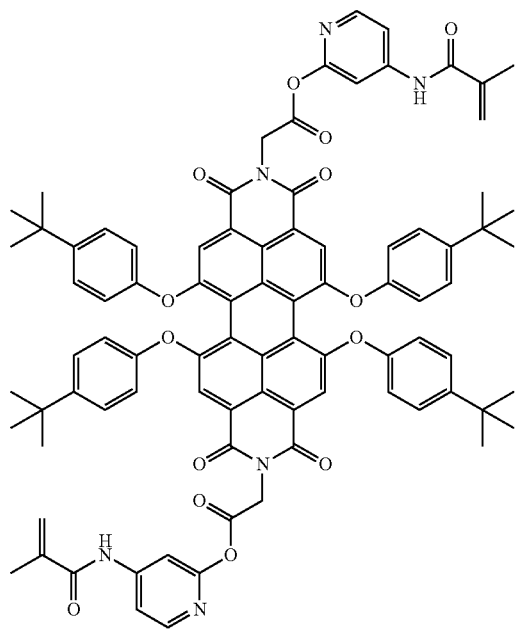
34
-continued
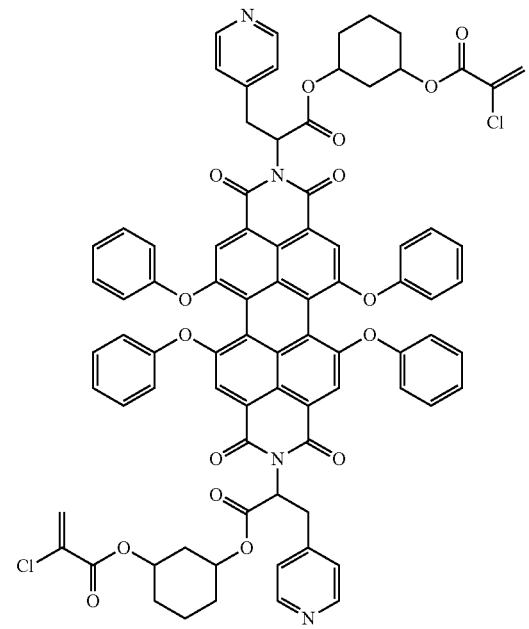
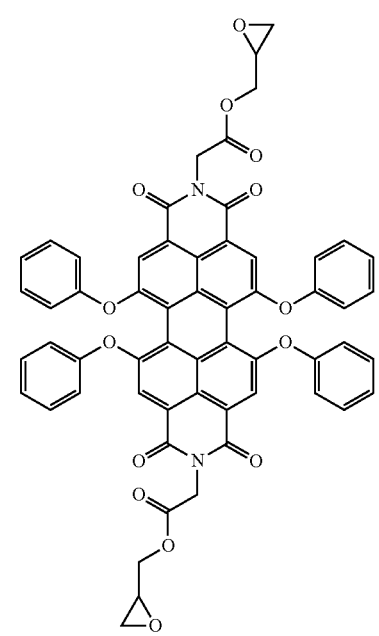
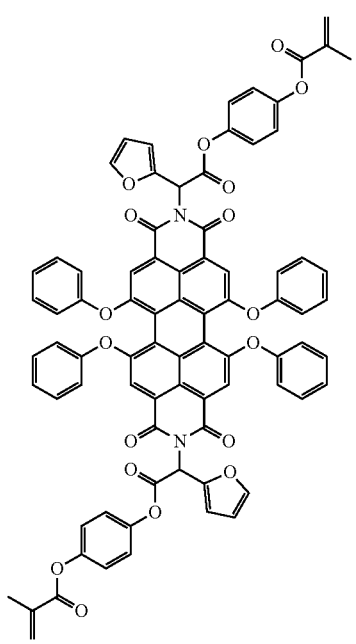

35
-continued
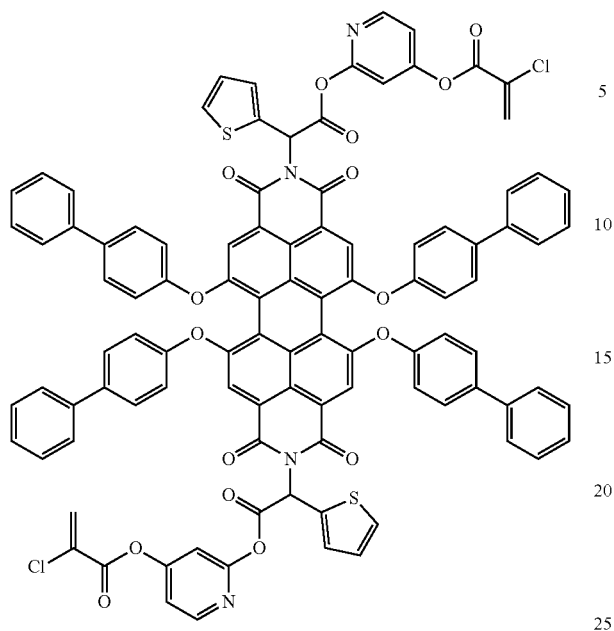
36
-continued
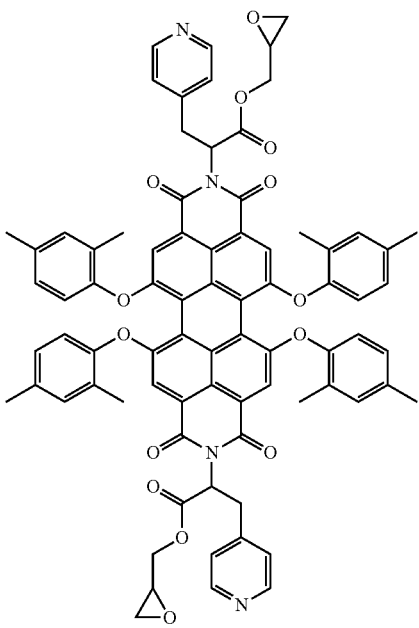
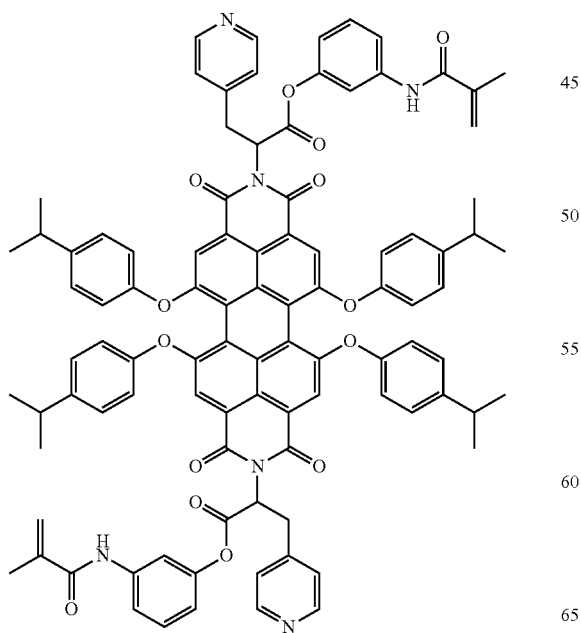
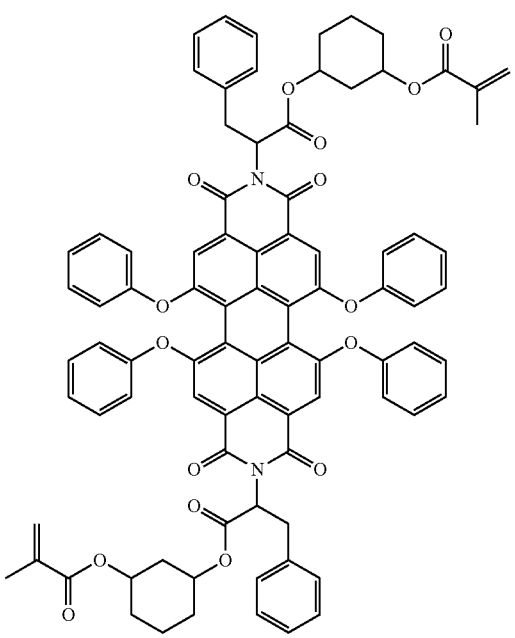

37
-continued
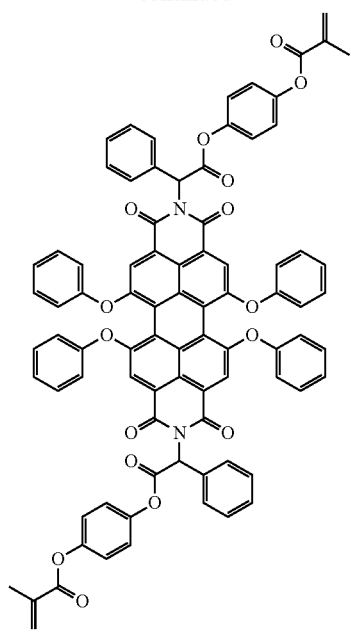
38
-continued
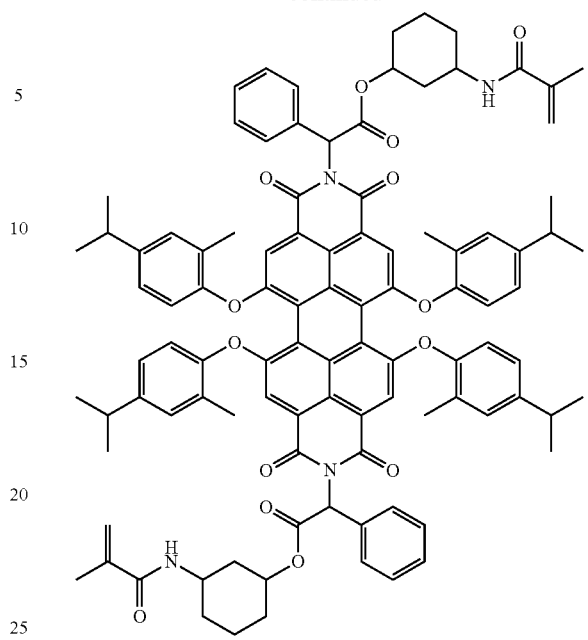
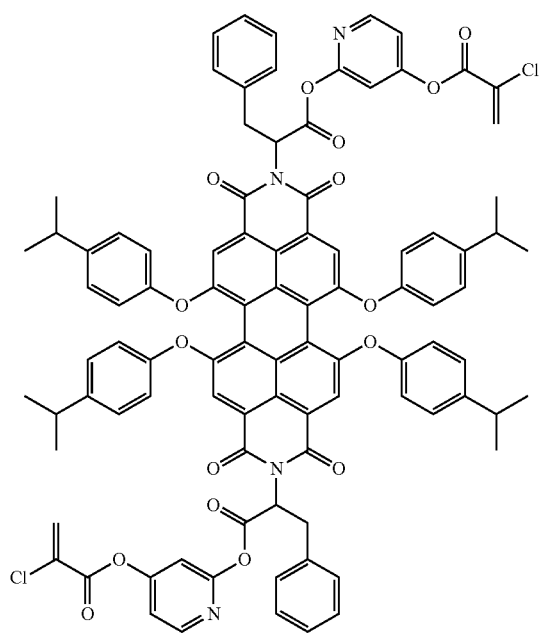
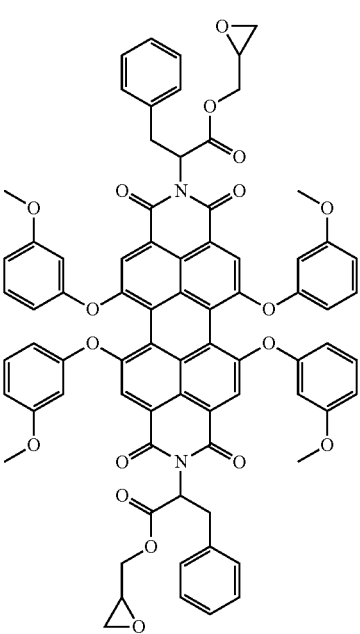

39
-continued
40
-continued
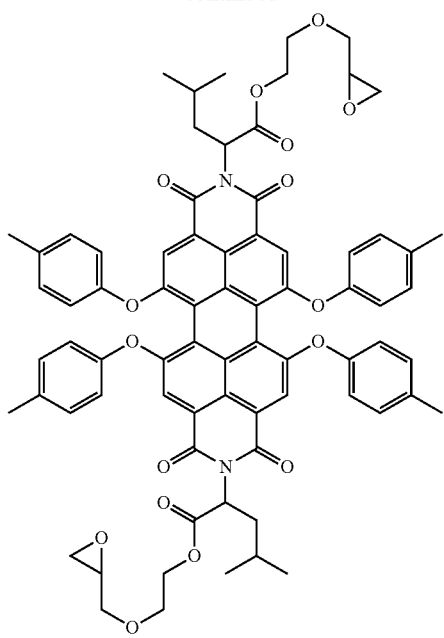
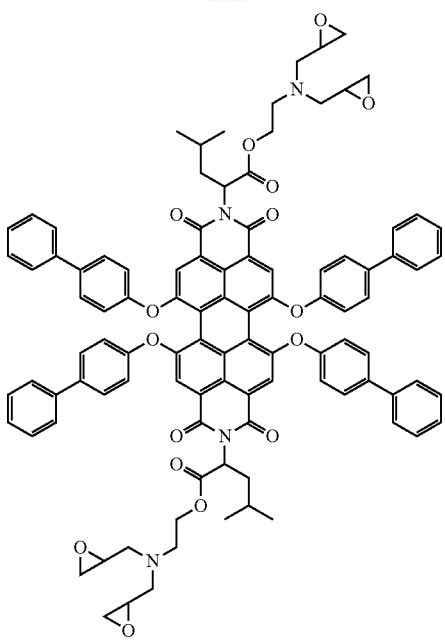

41
-continued
42
-continued
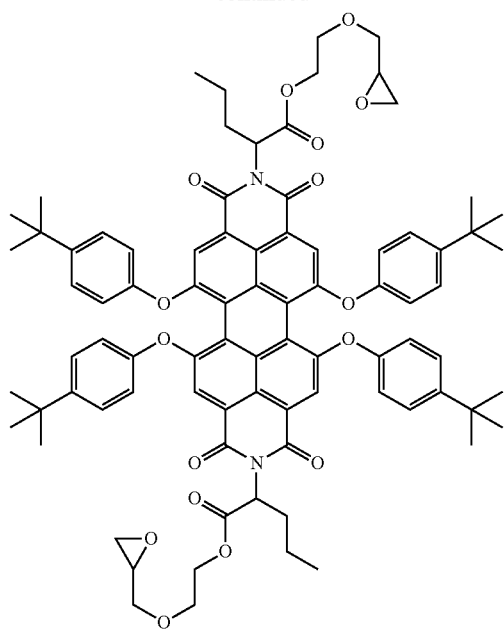
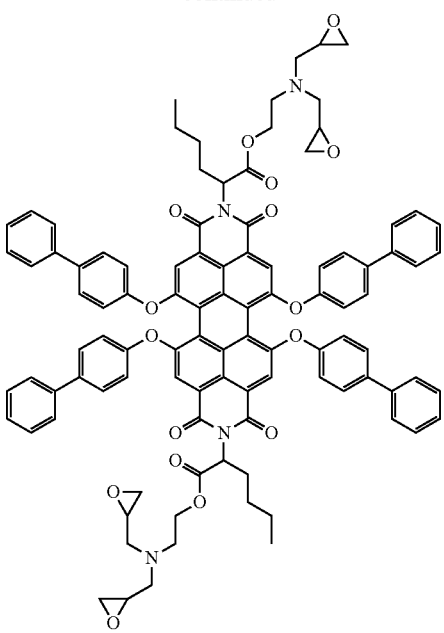
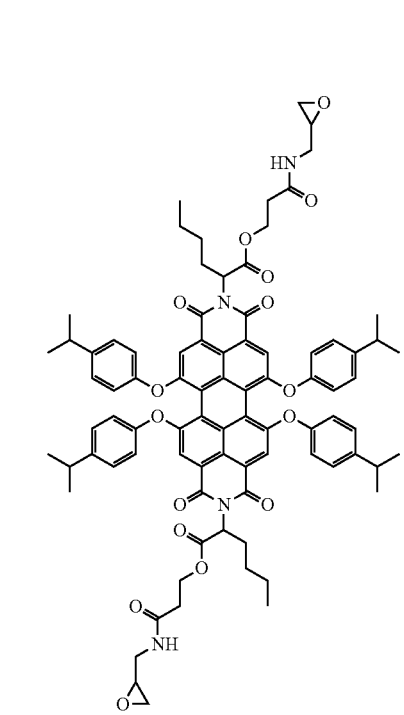

43
-continued
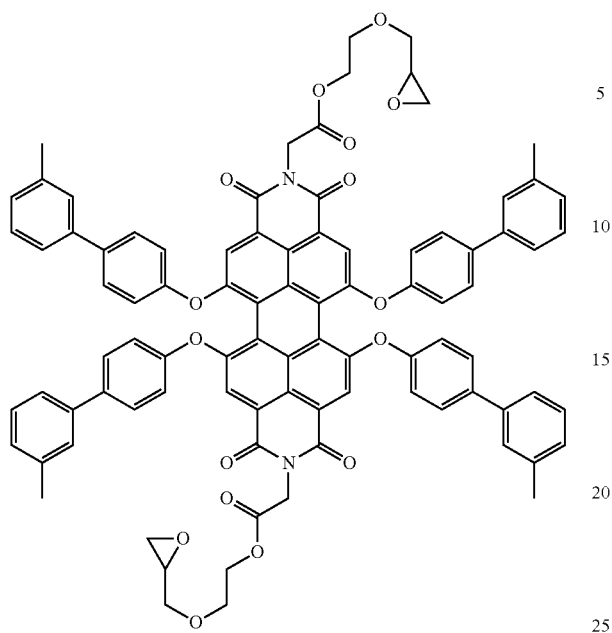
44
-continued
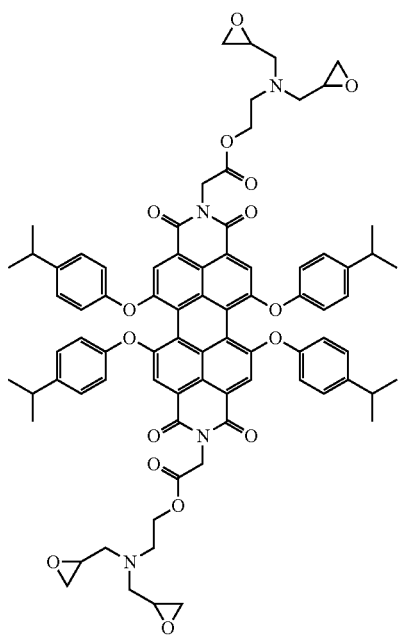
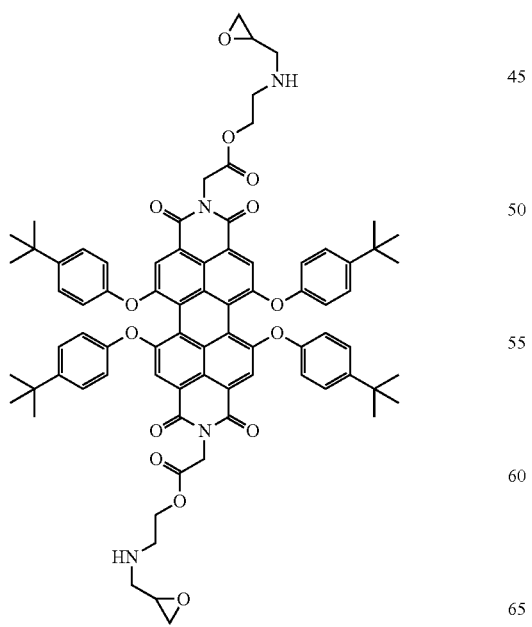
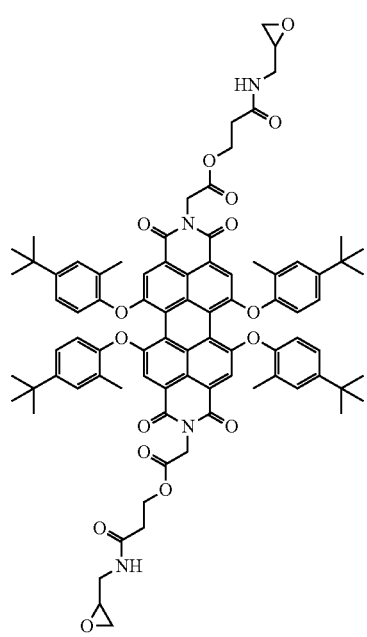

45
-continued
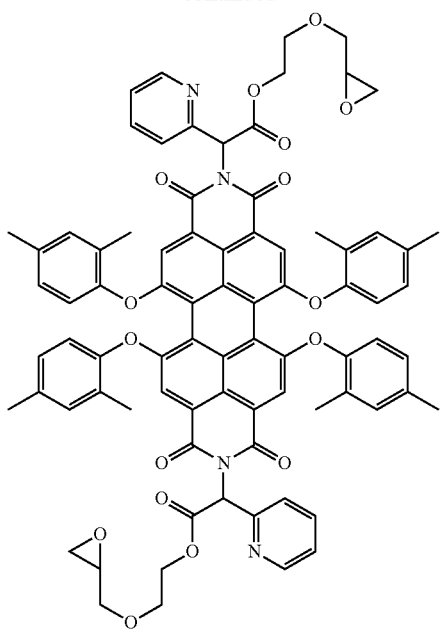
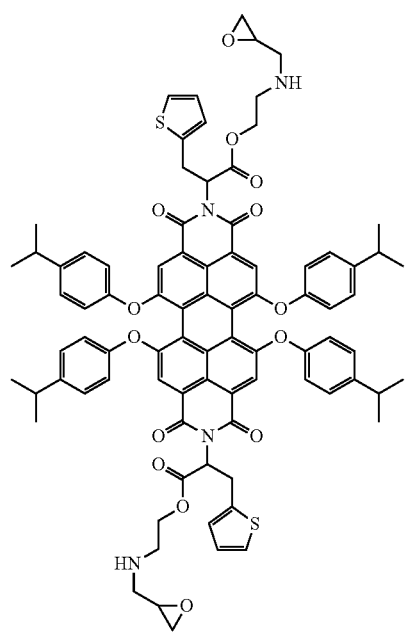
46
-continued
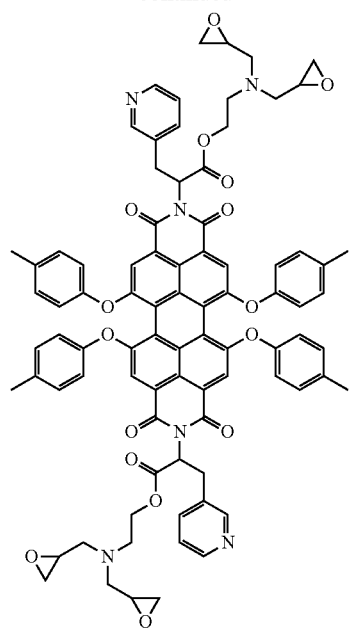
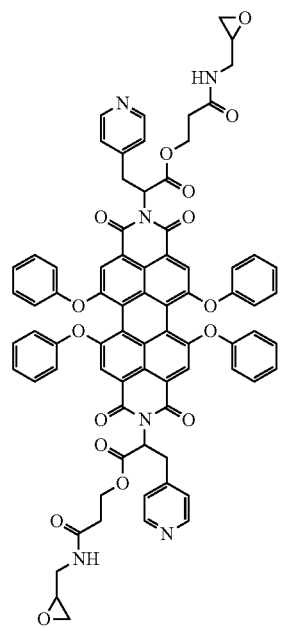

47
-continued
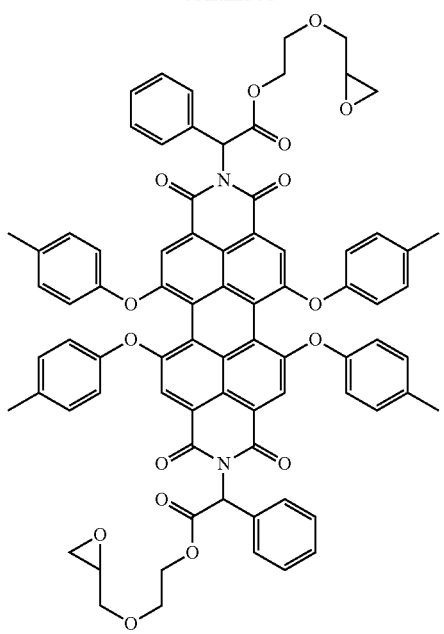
48
-continued
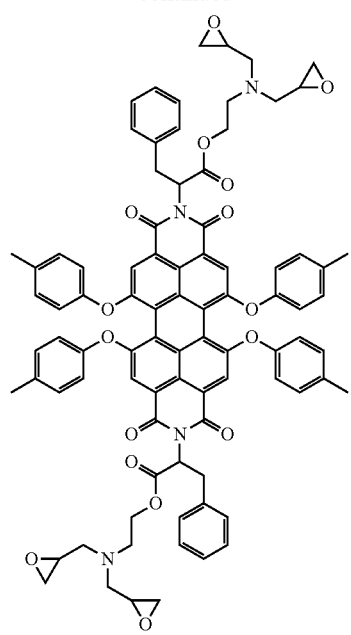
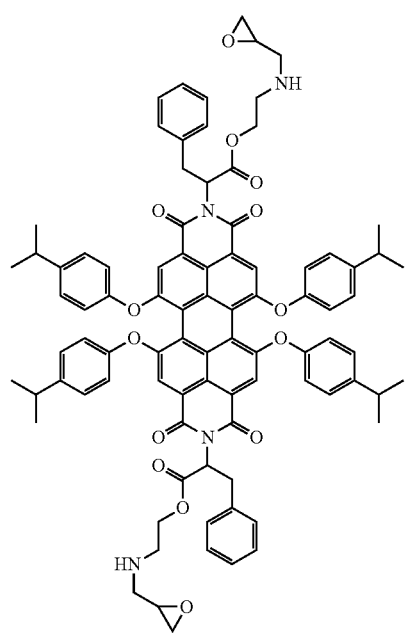
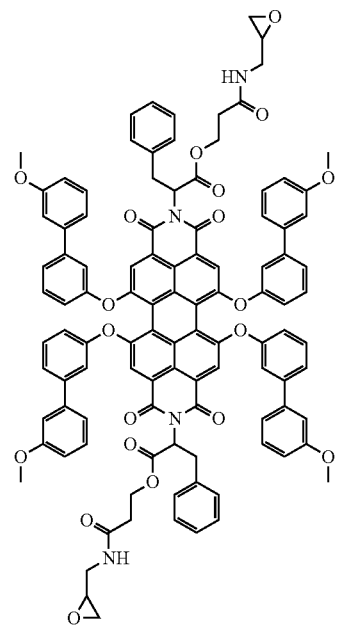

49
-continued
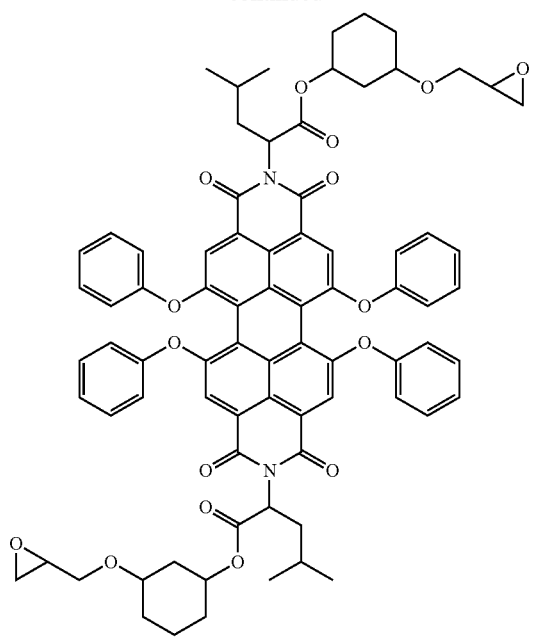
50
-continued
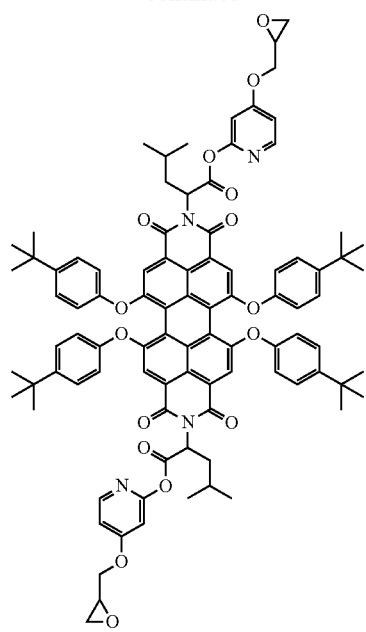
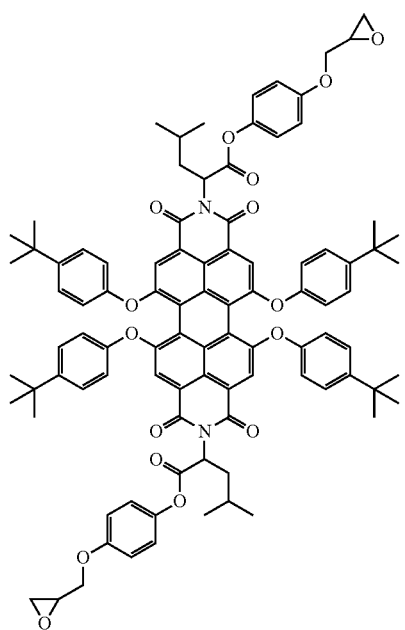
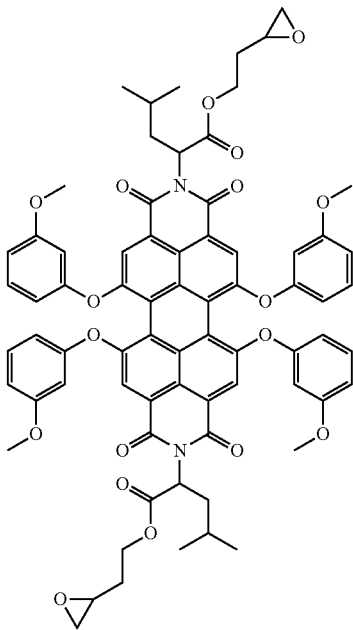

51
-continued
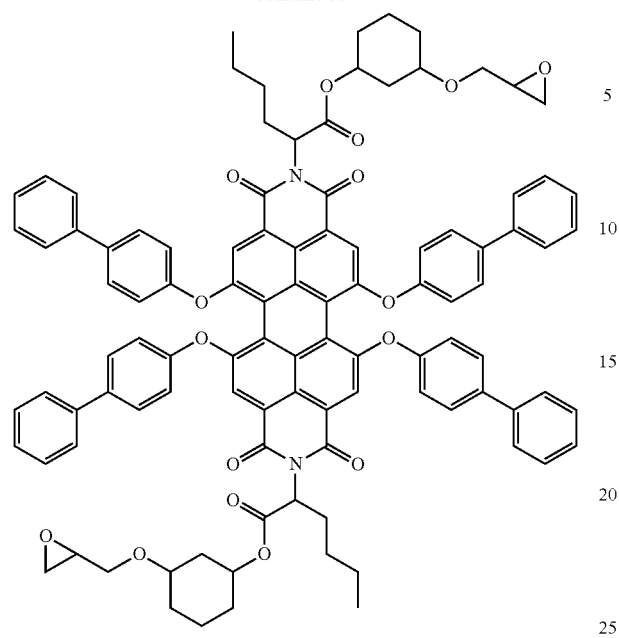
52
-continued
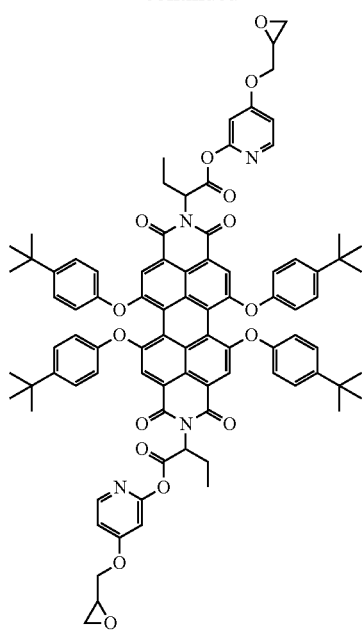
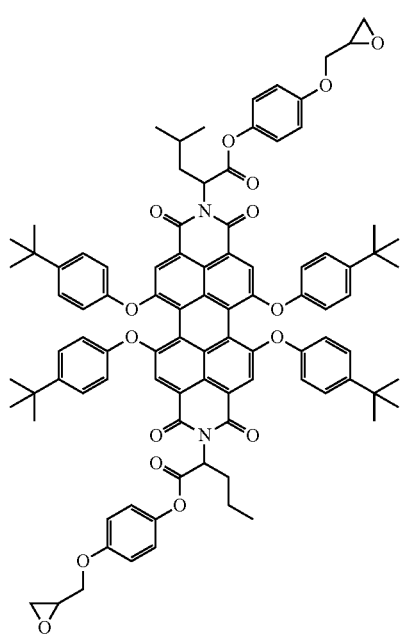
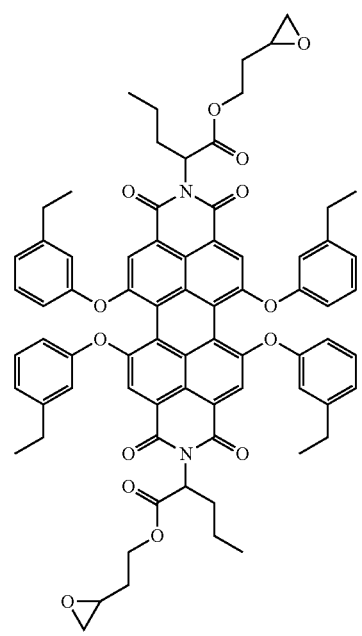

53
-continued
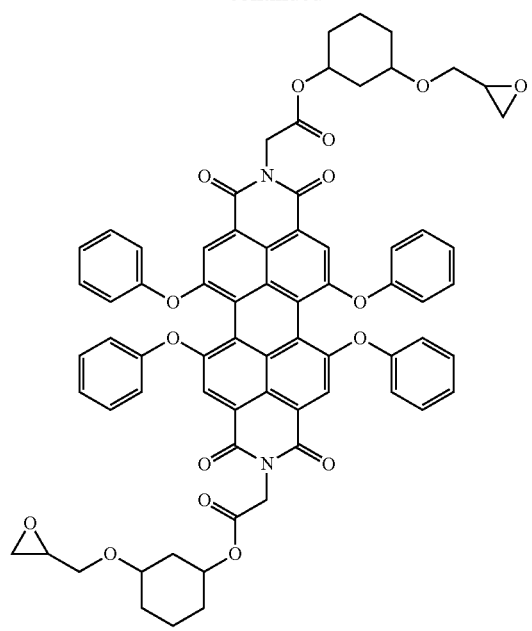
54
-continued
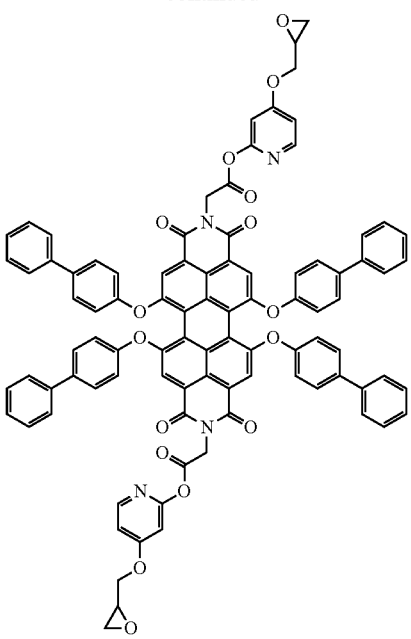
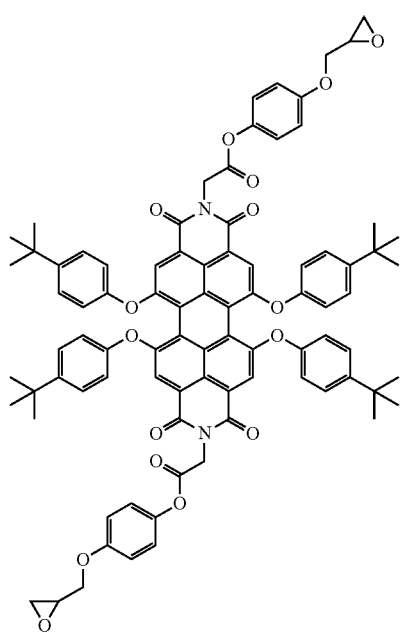
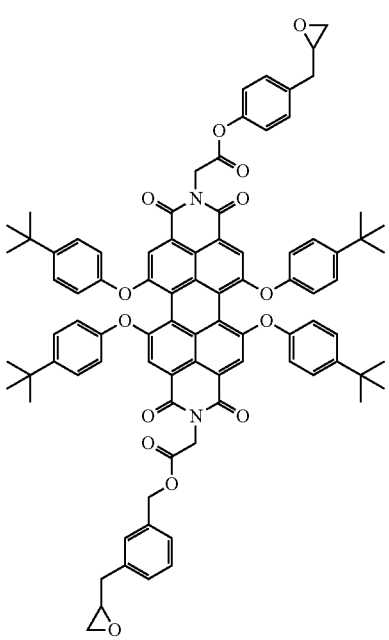

55
-continued
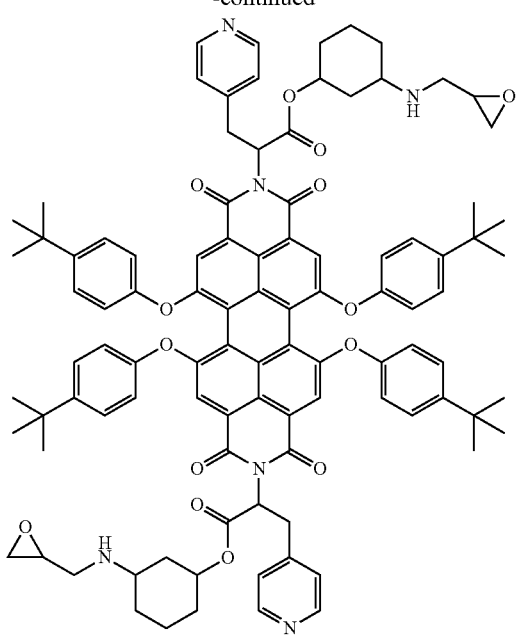
56
-continued
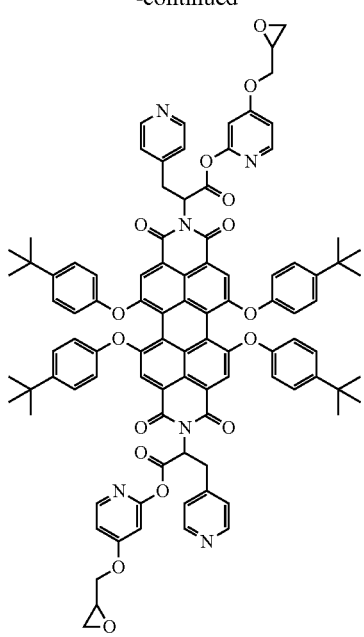
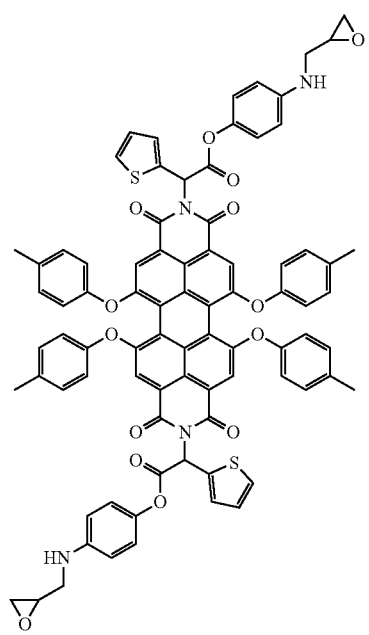
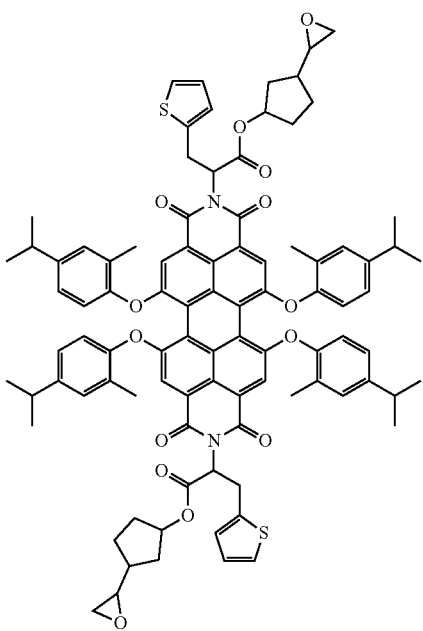

57
-continued
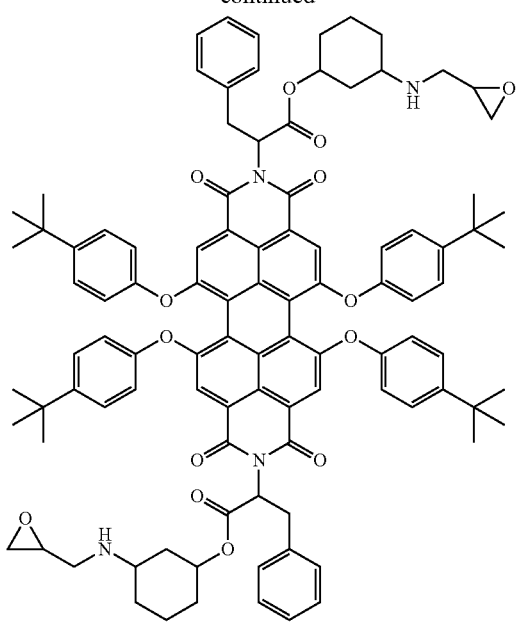
58
-continued
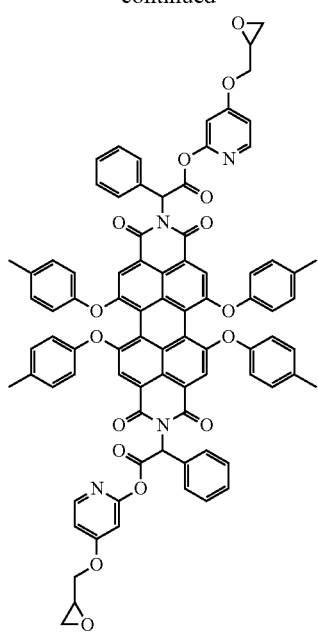
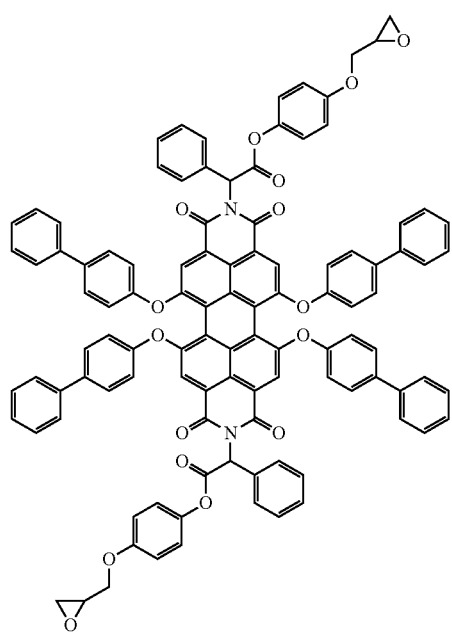
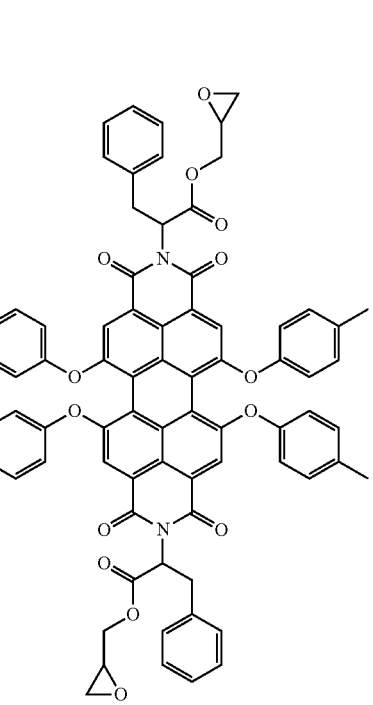

59
-continued
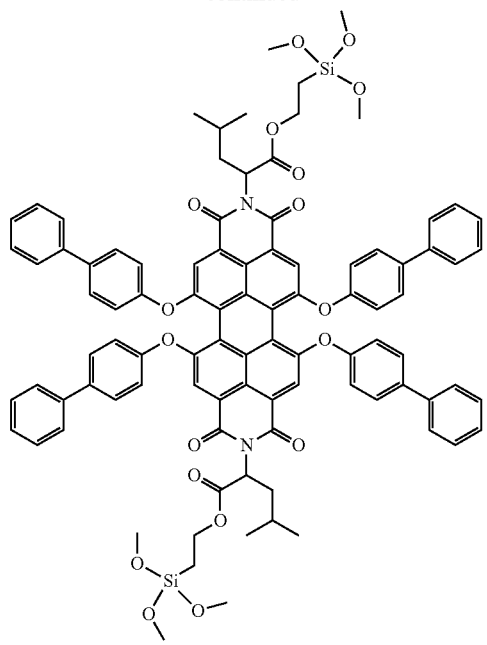
60
-continued
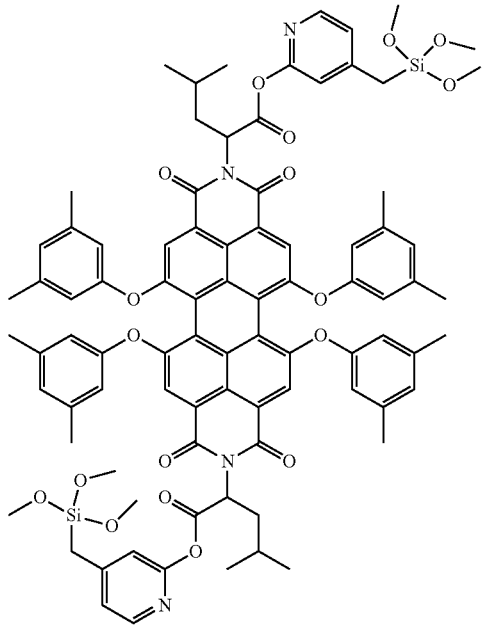
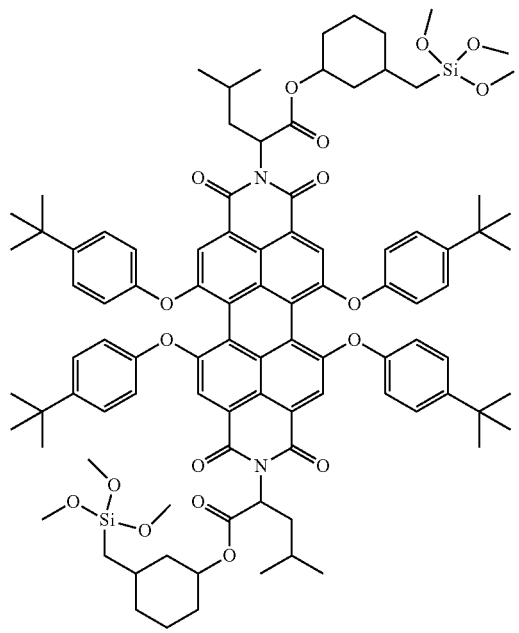
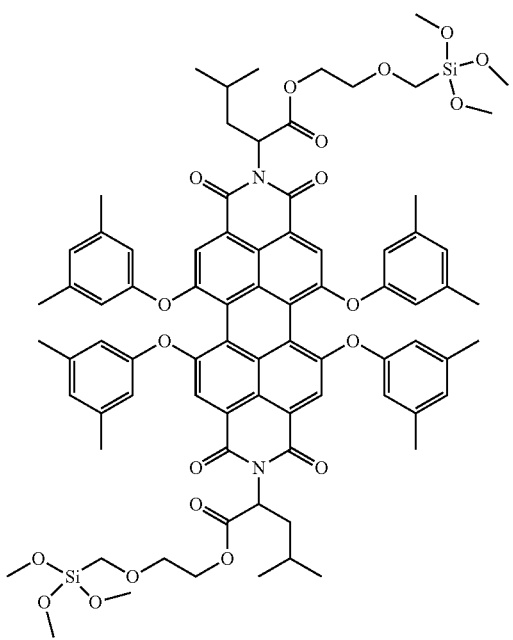

-continued
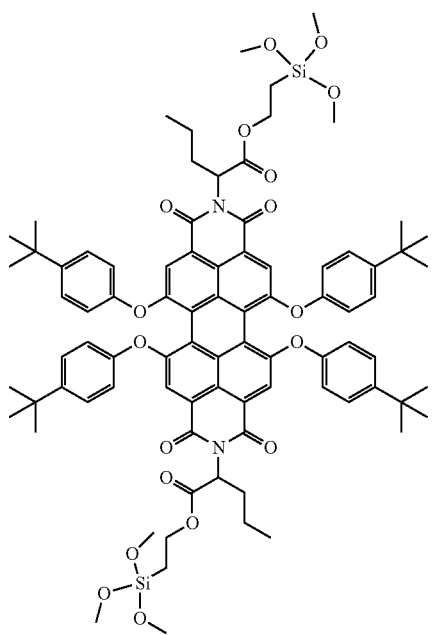
61
-continued
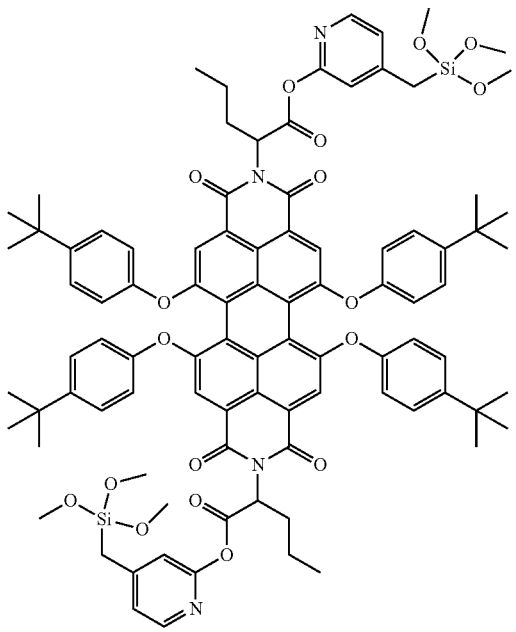
62
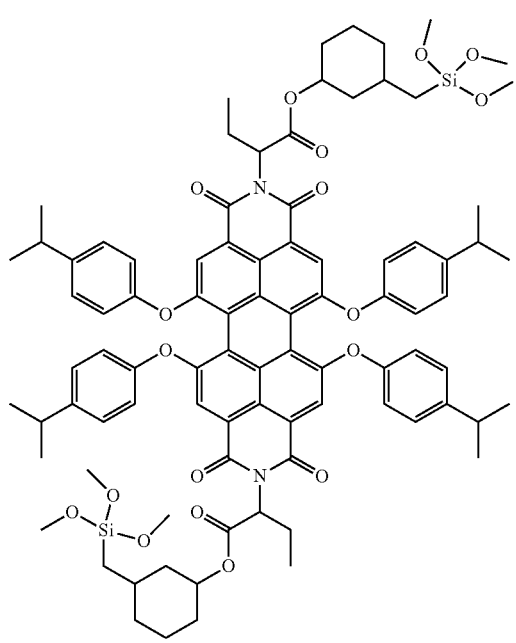
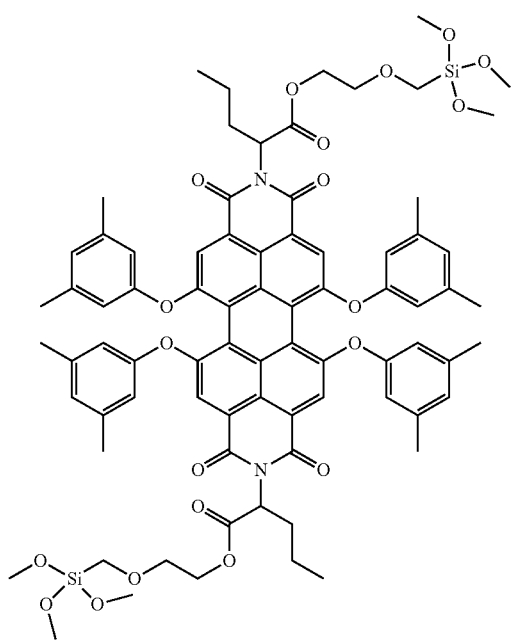

63
-continued
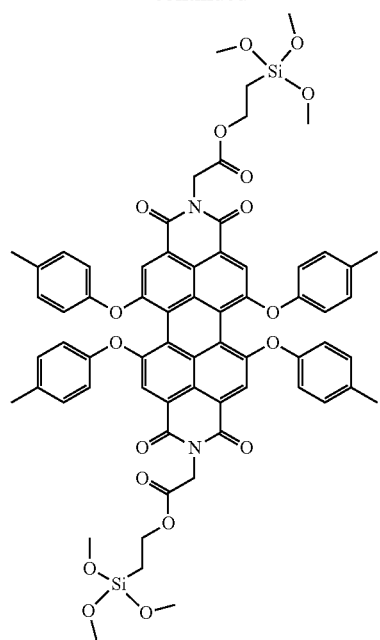
64
-continued
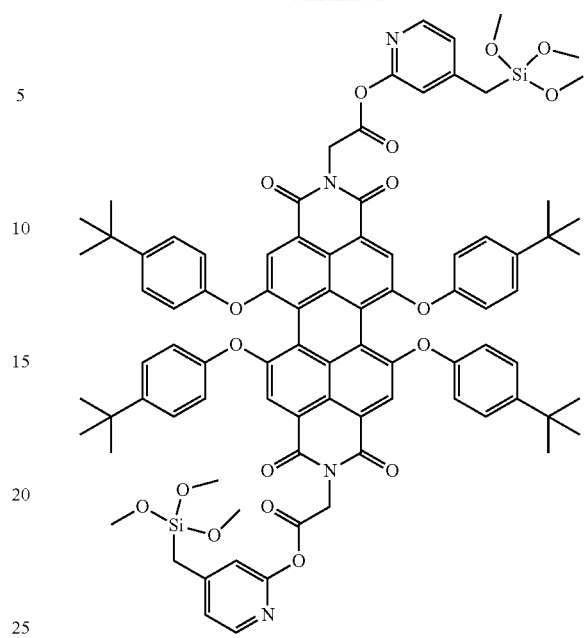
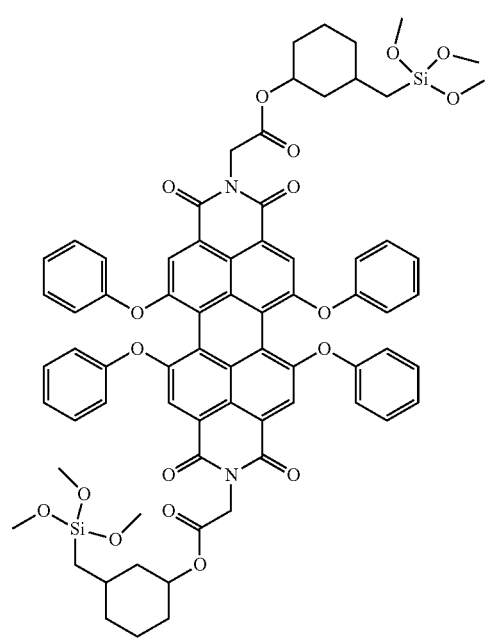
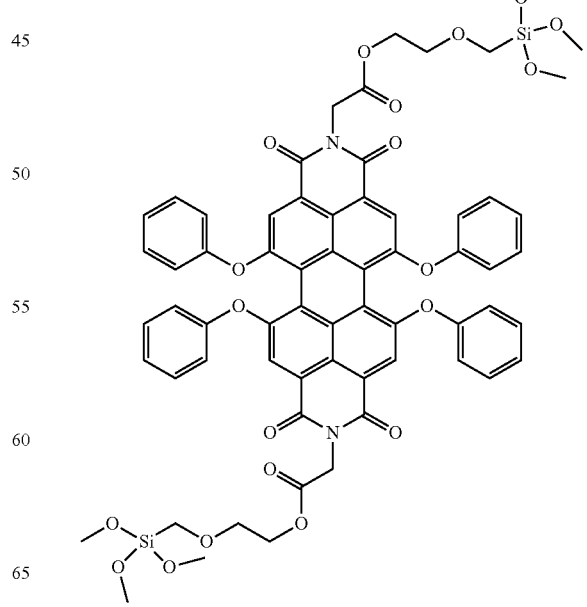

65
-continued
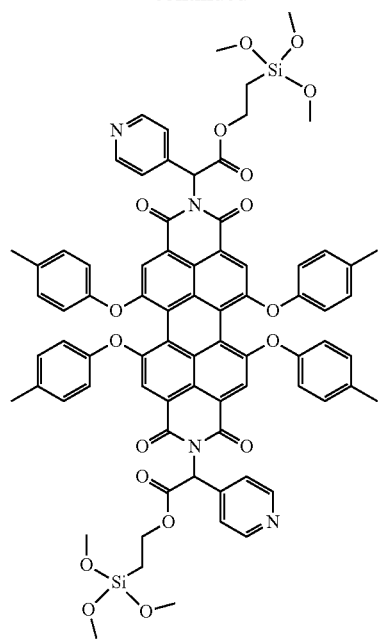
66
-continued
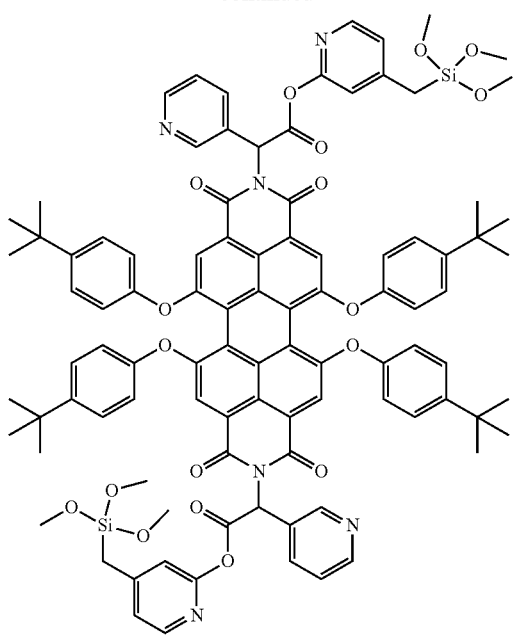
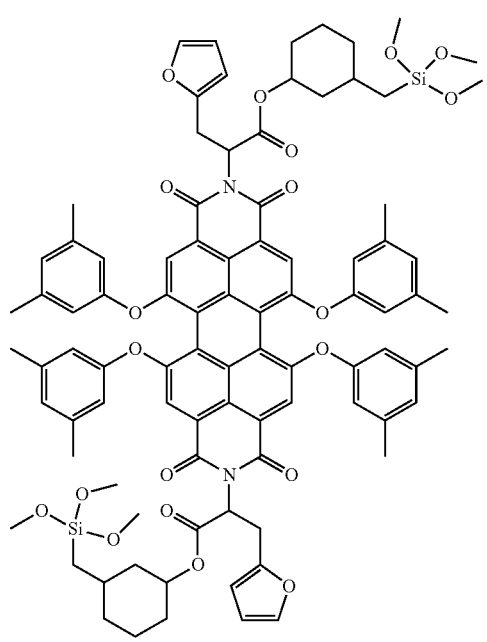
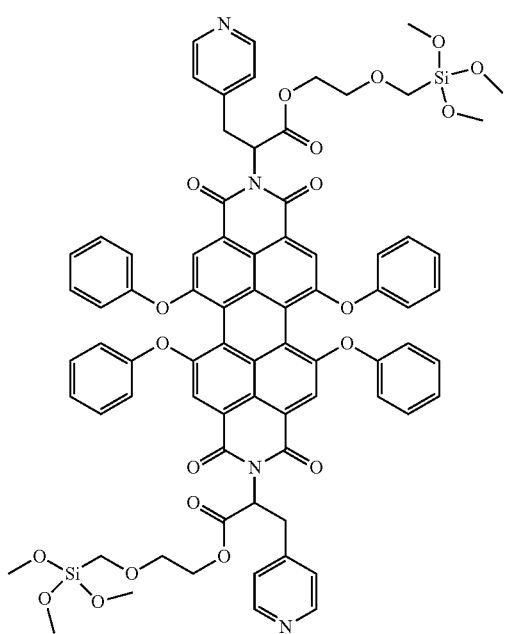

67
-continued
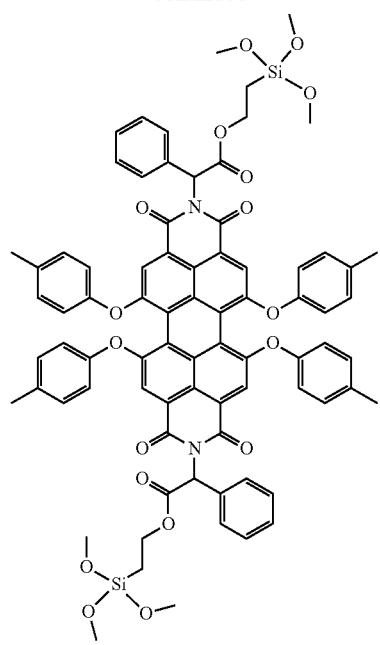
68
-continued
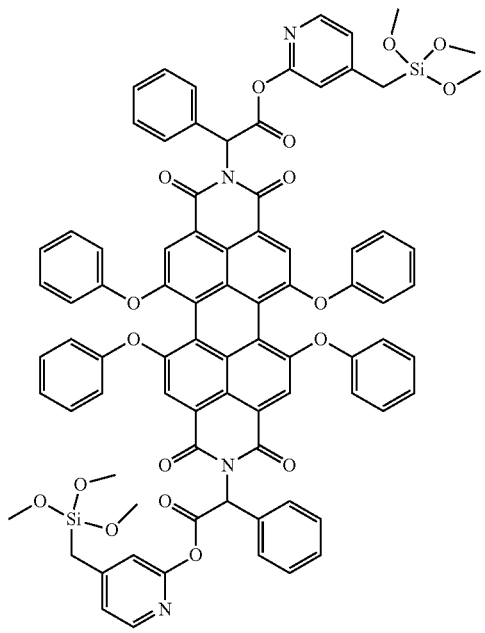
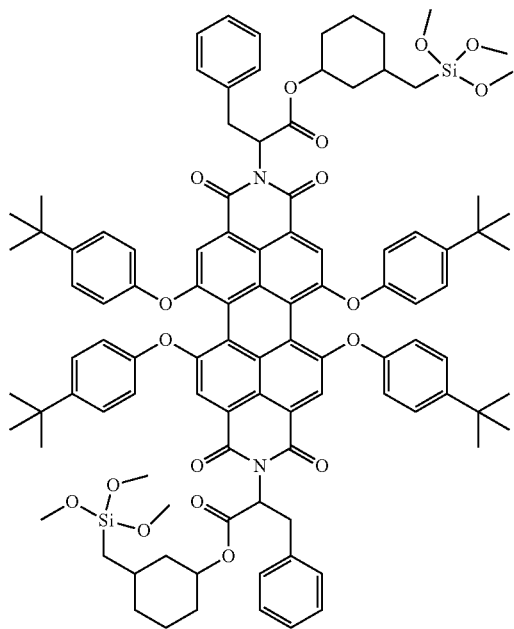
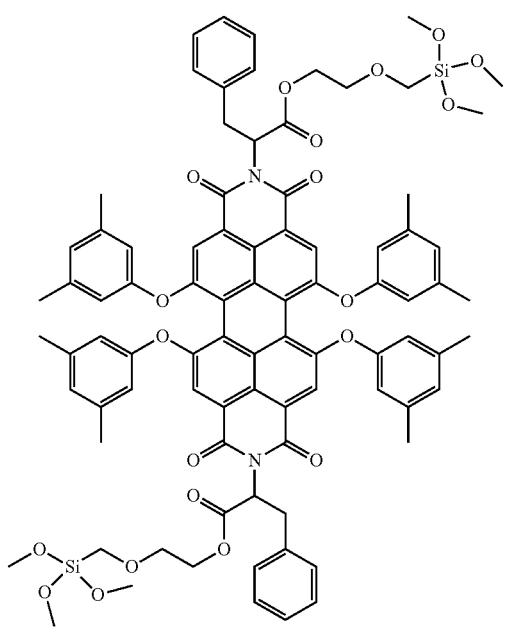

69
-continued
70
-continued
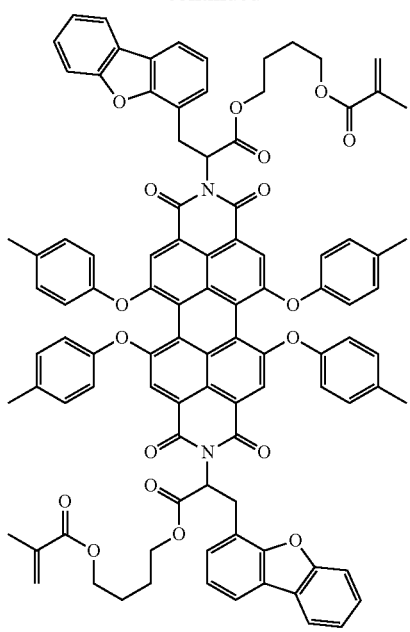
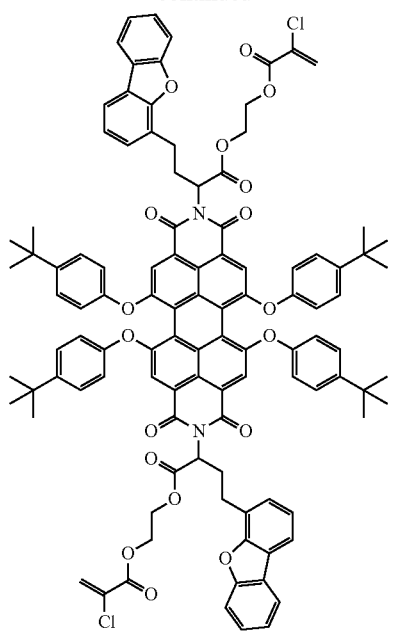

71
-continued
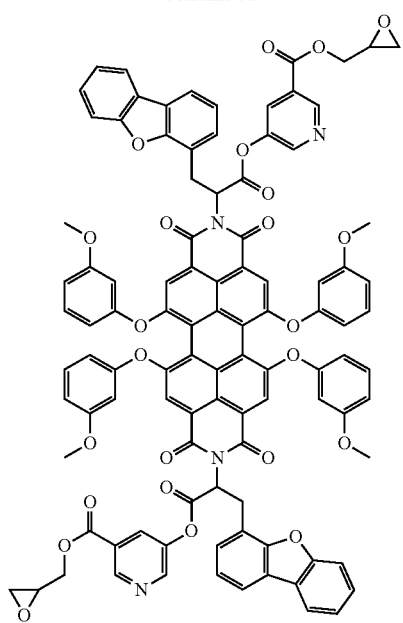
72
-continued
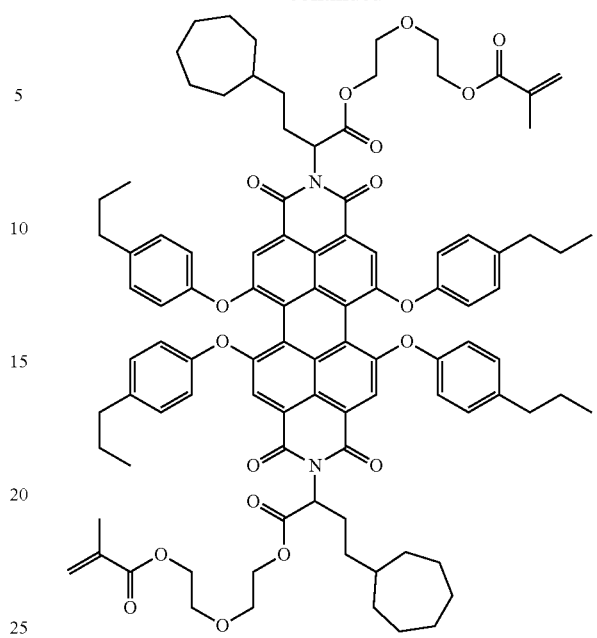
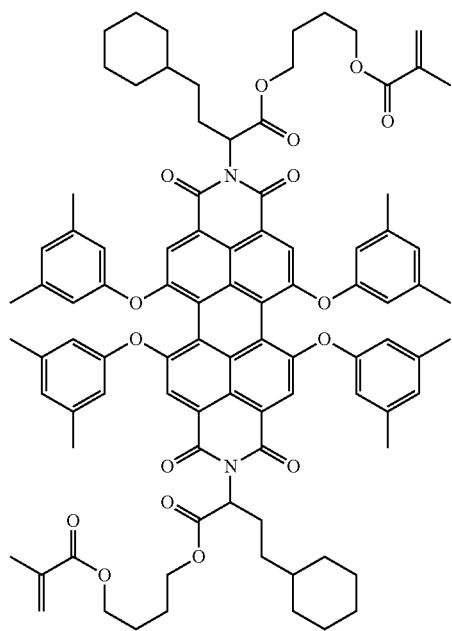
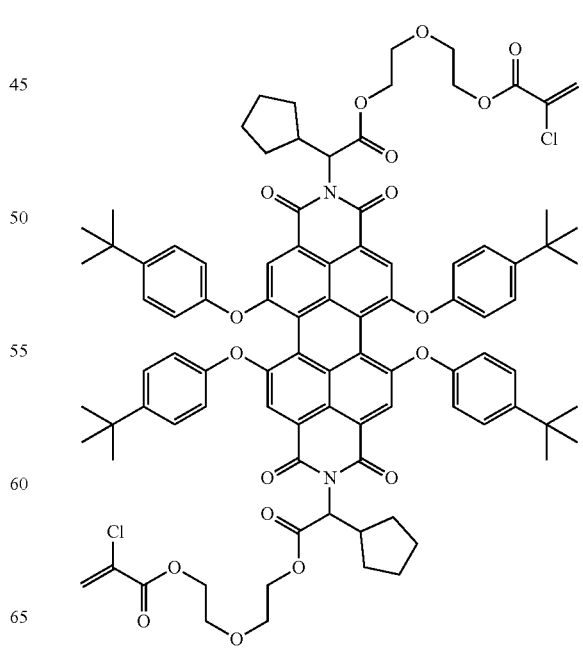

73
-continued
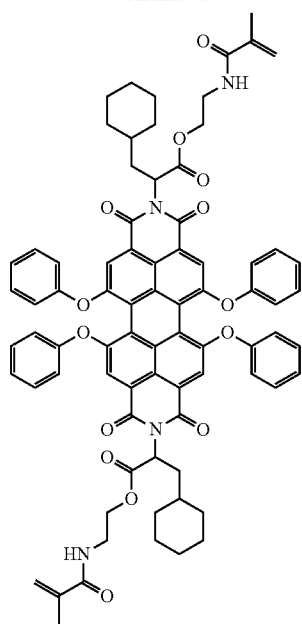
74
-continued
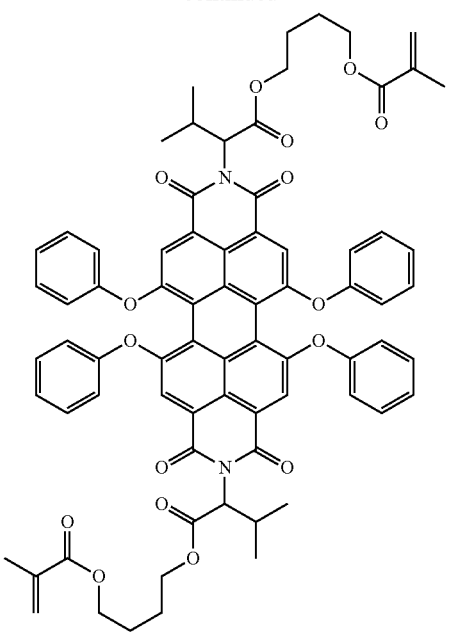
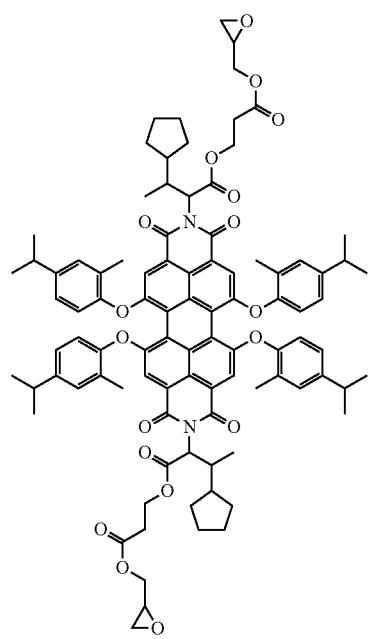
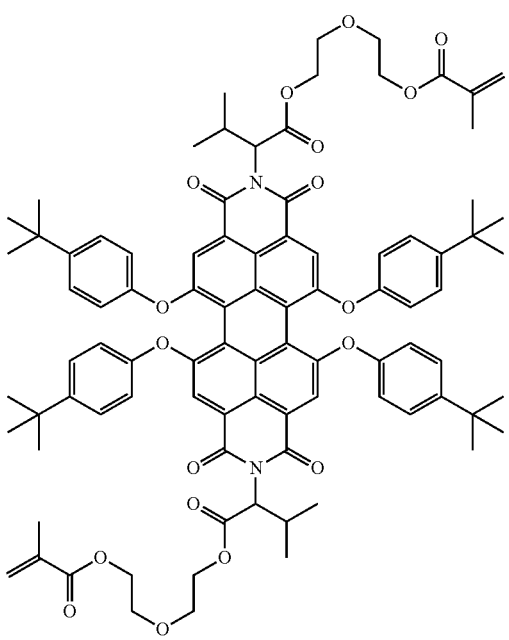

75
-continued
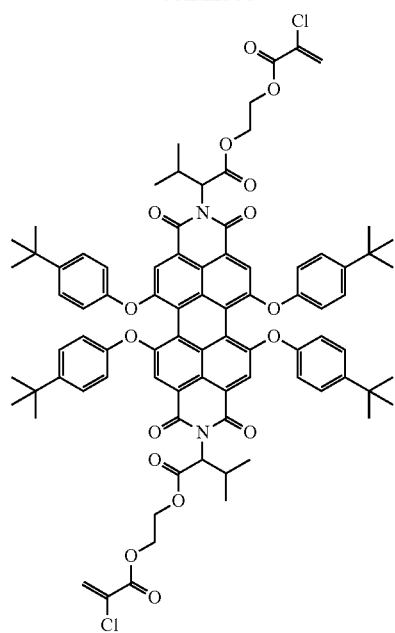
76
-continued
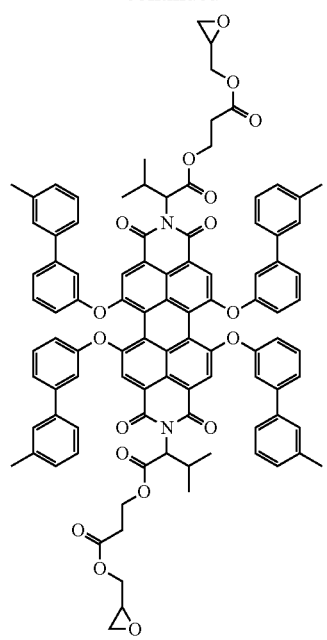
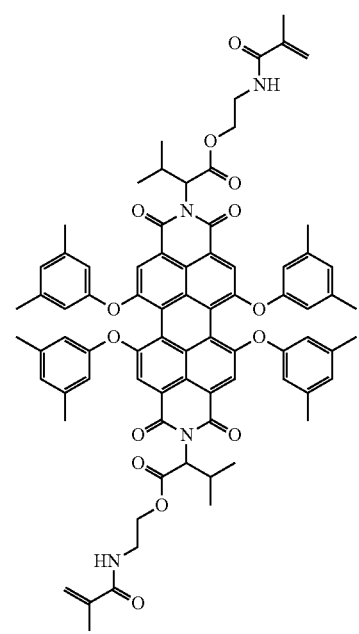
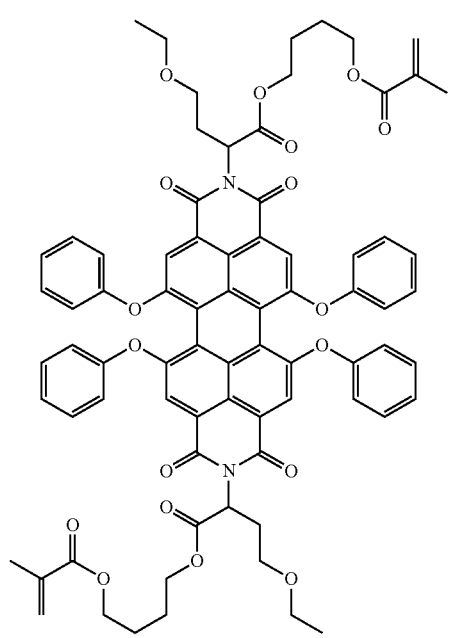

77
-continued
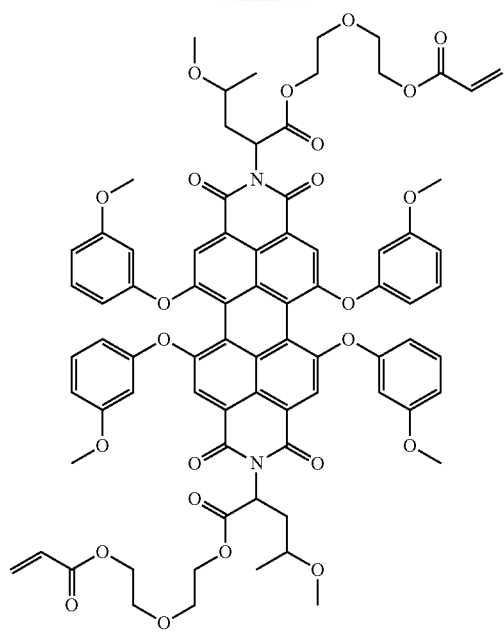
78
-continued
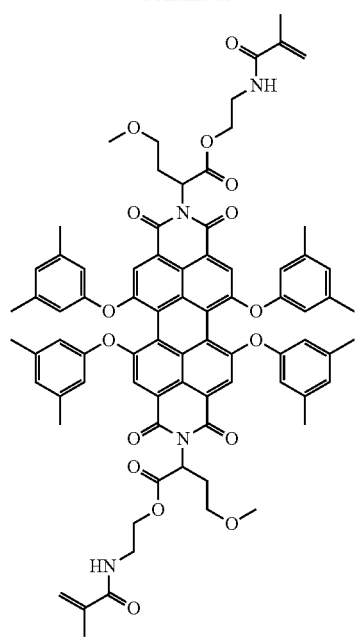
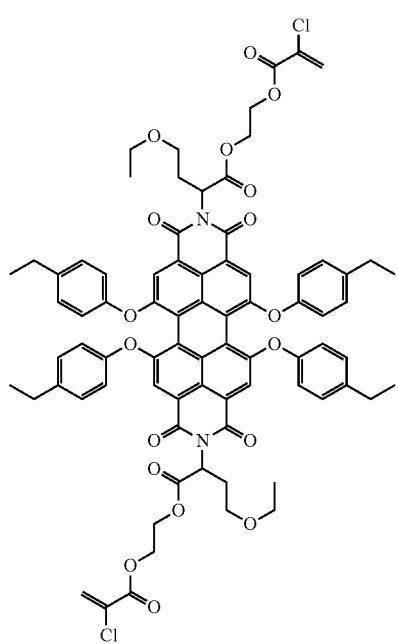
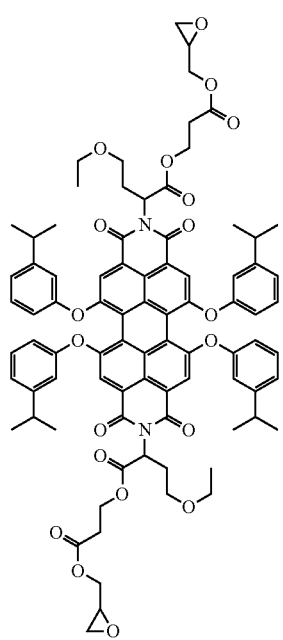

79
-continued
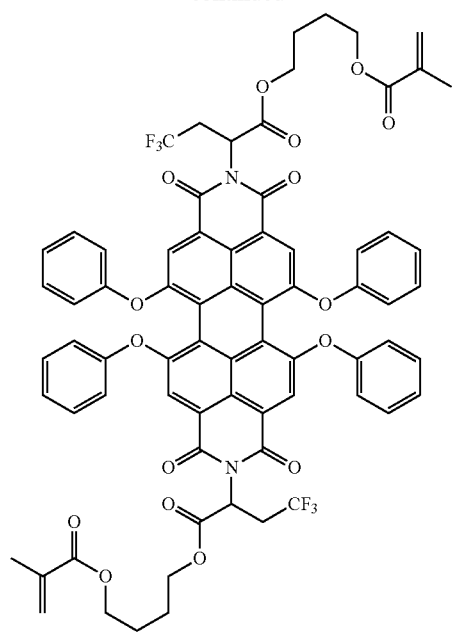
80
-continued
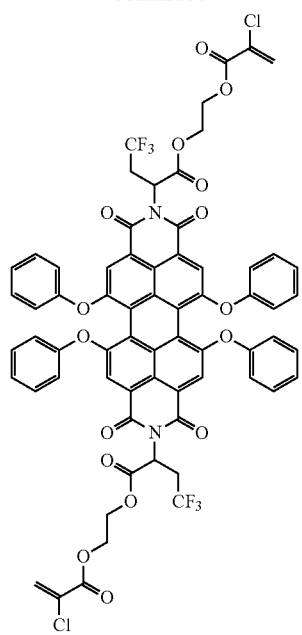
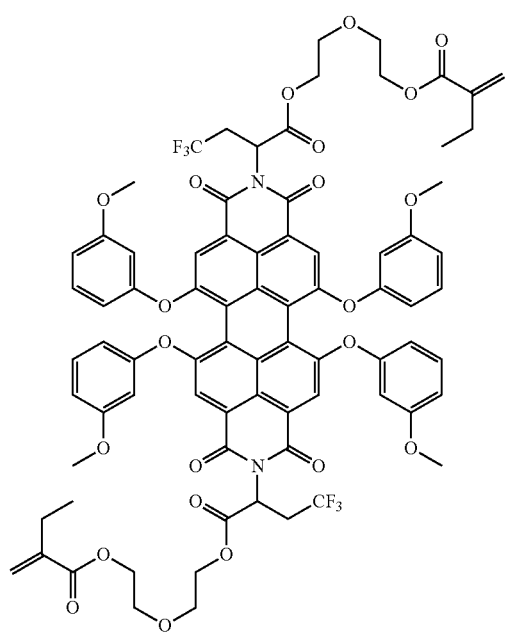
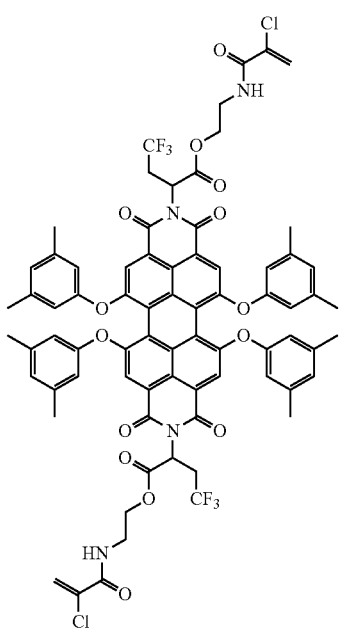

81
-continued
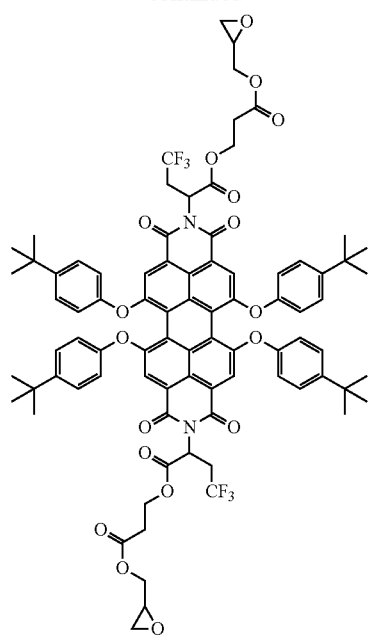
82
-continued
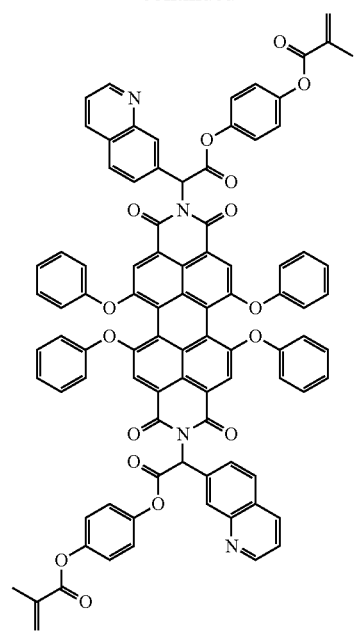
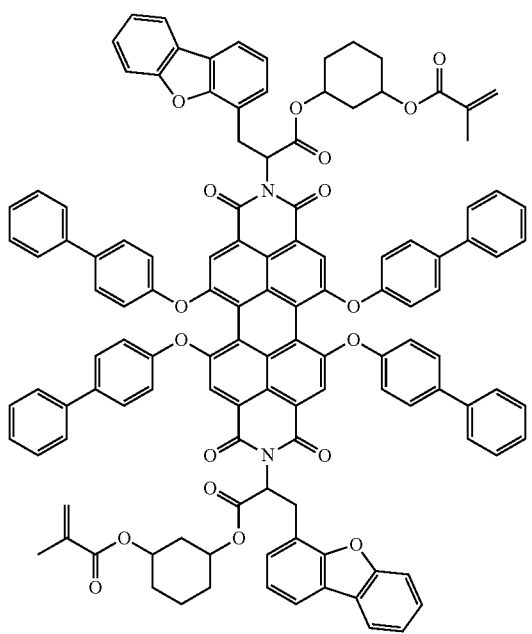
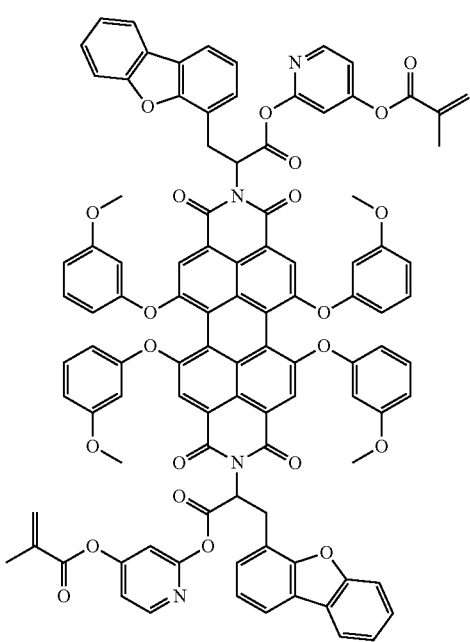

83
-continued
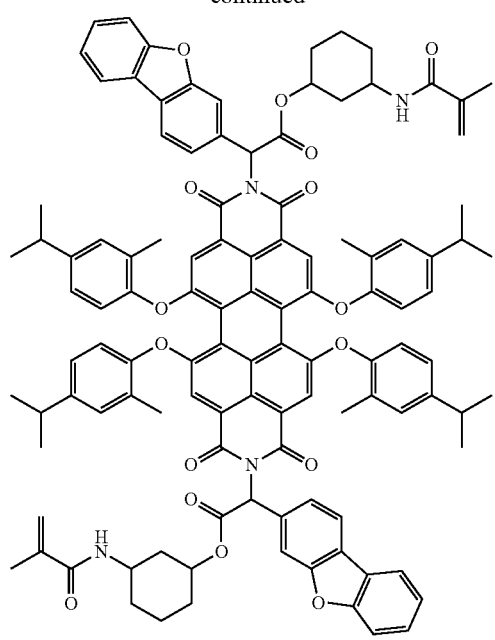
84
-continued
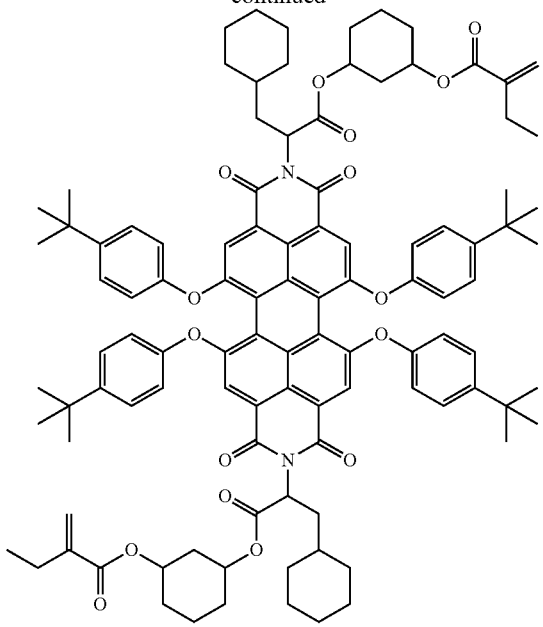
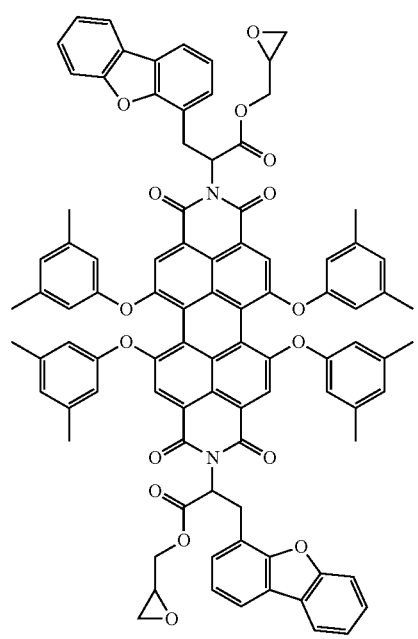
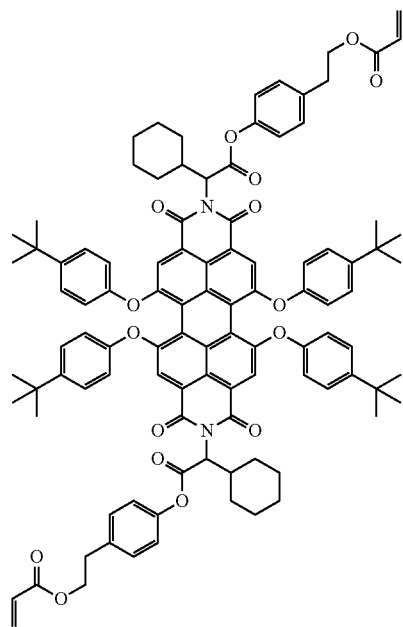

85
-continued
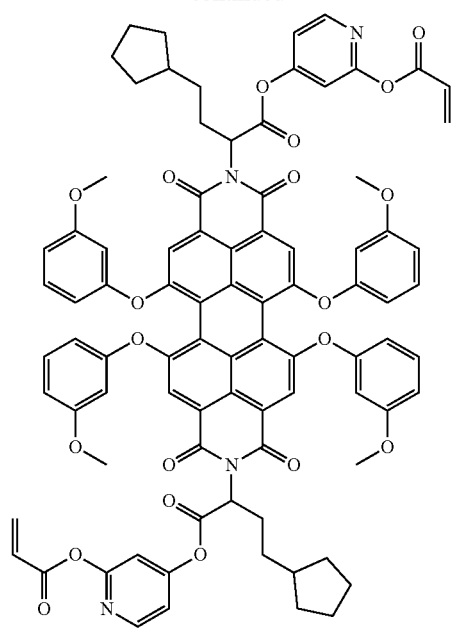
86
-continued
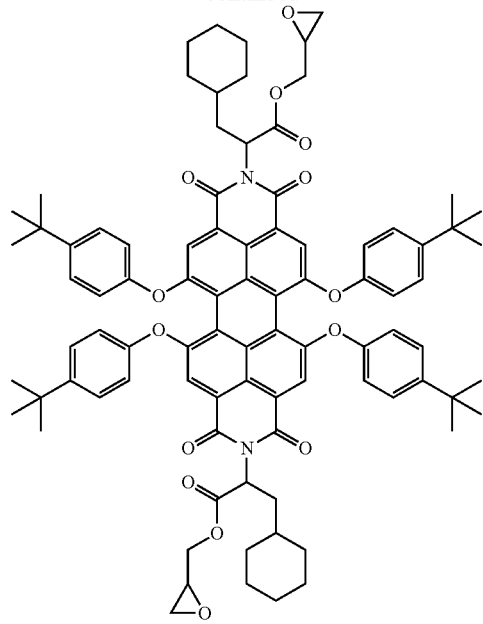
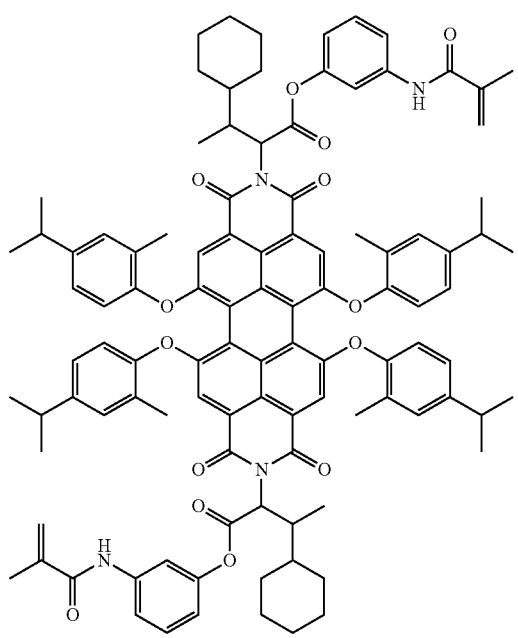
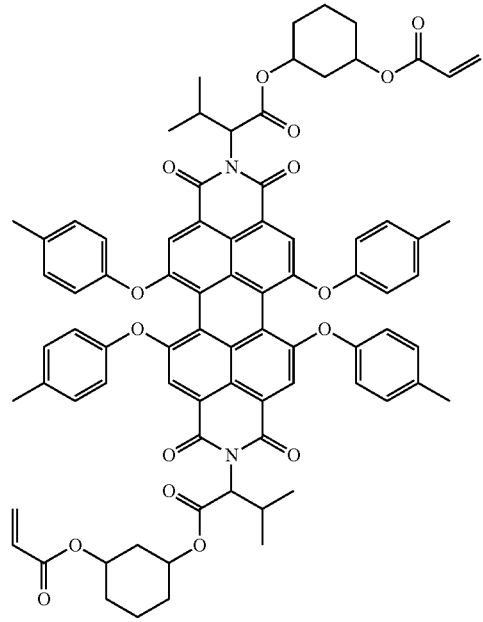

87
-continued
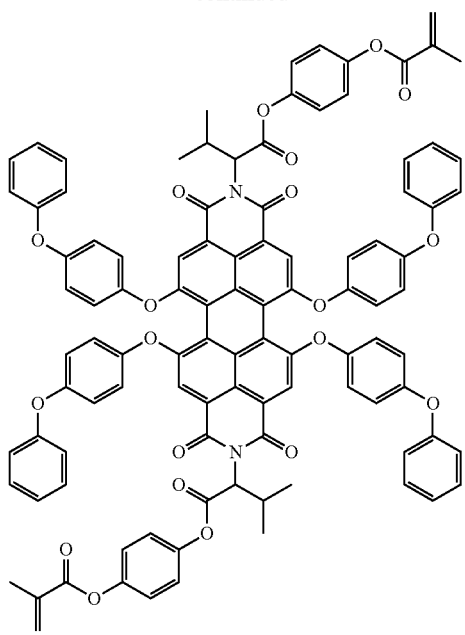
88
-continued
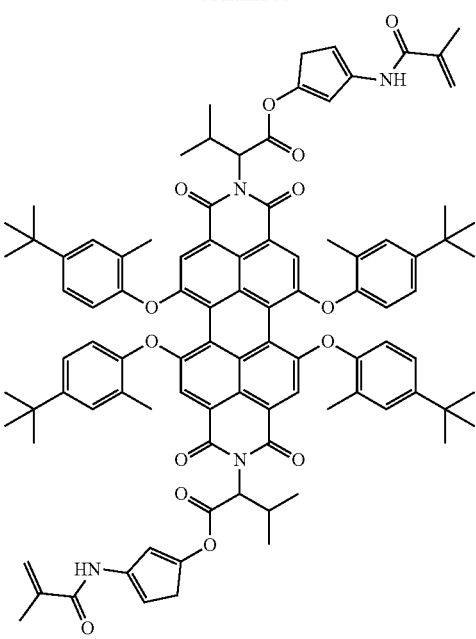
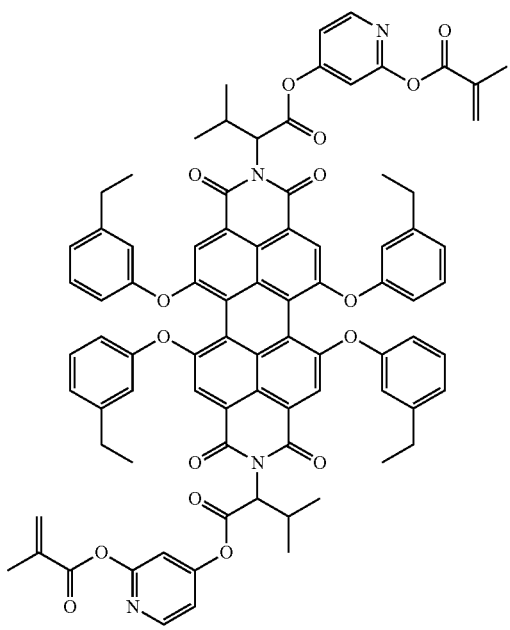
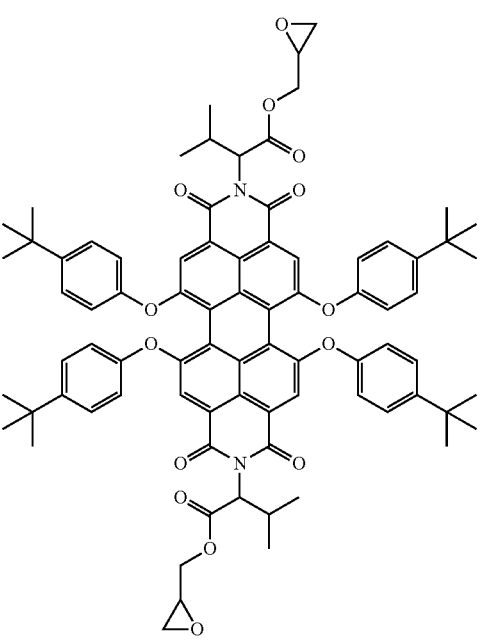

89
-continued
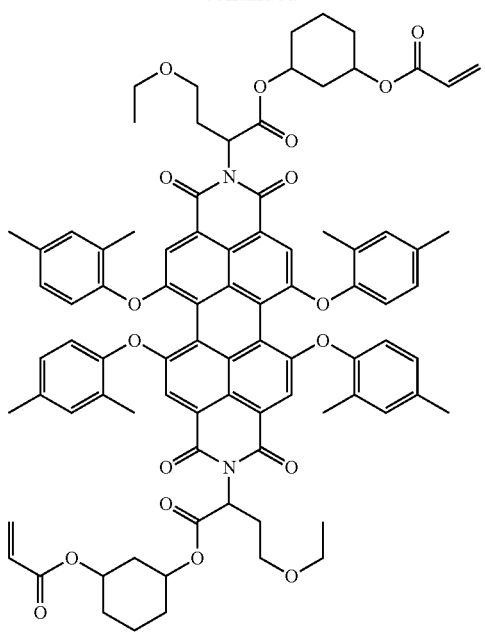
90
-continued
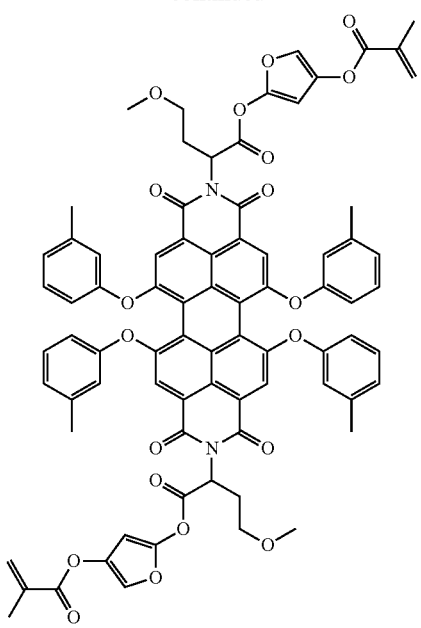
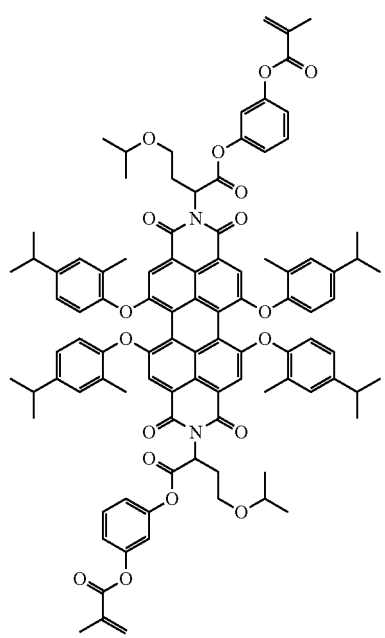
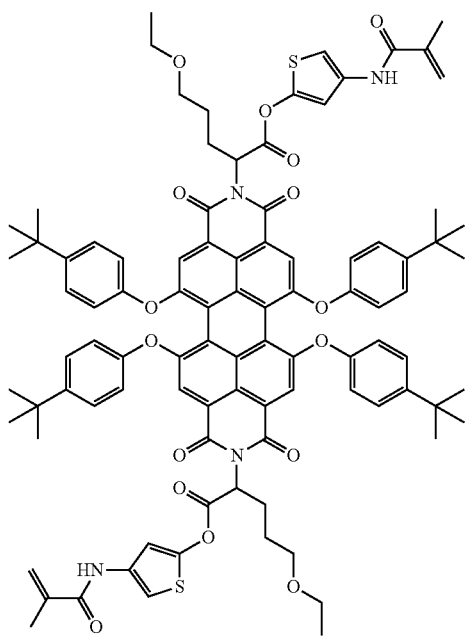

91
-continued
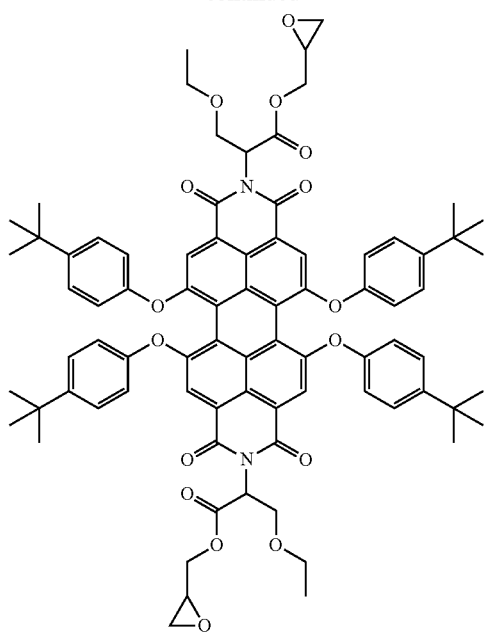
92
-continued
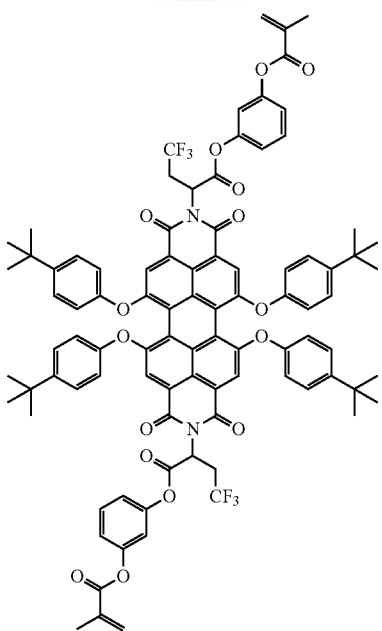
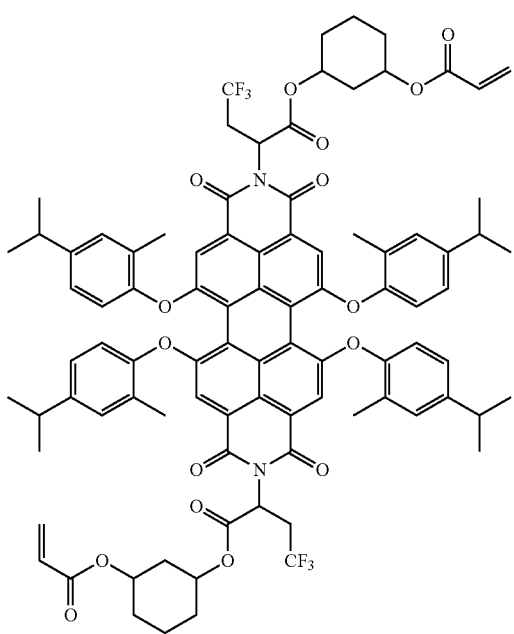
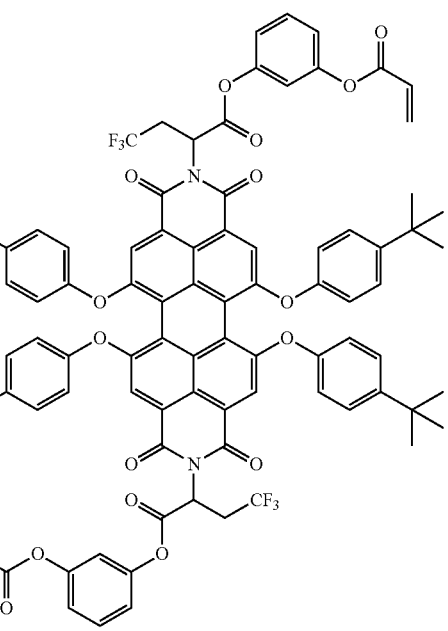

93
-continued
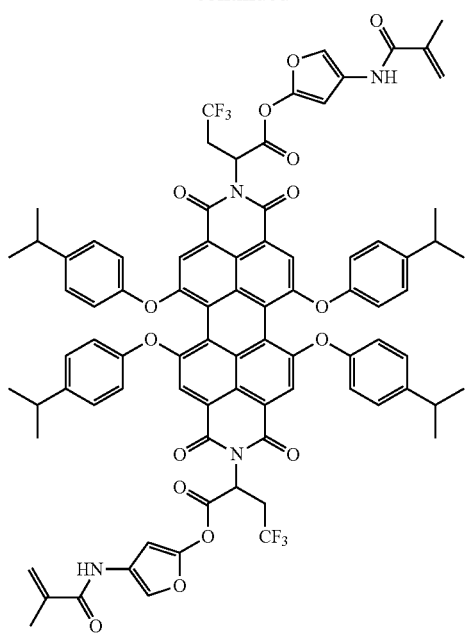
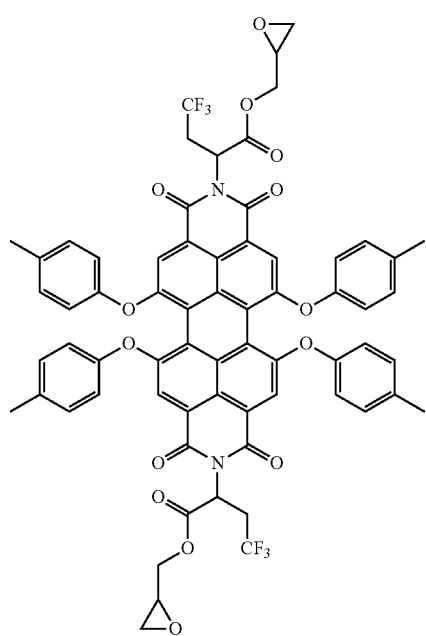
94
-continued
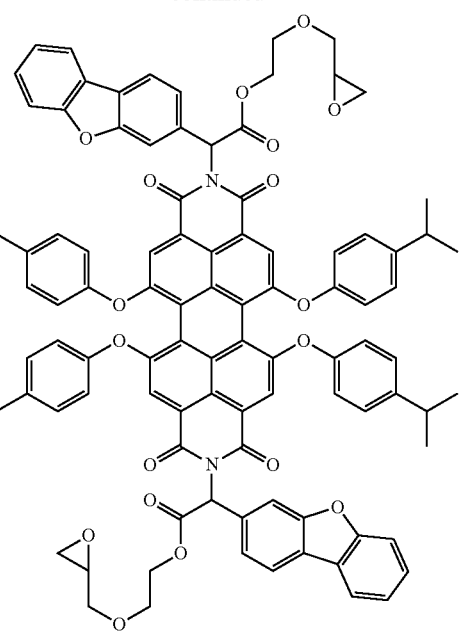
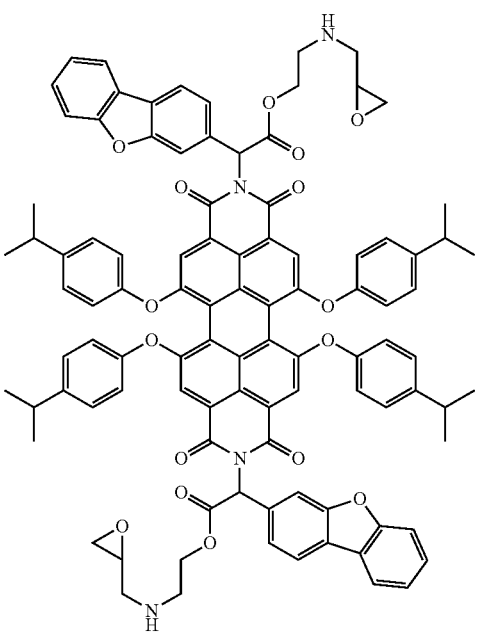

95
-continued
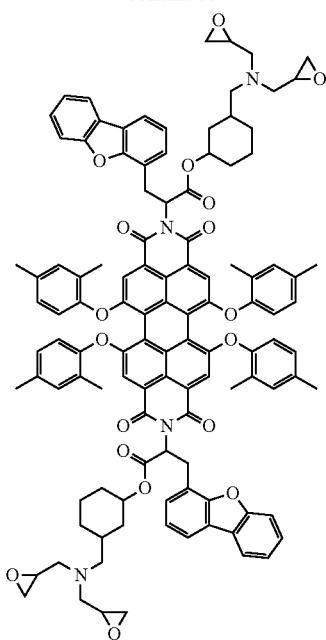
96
-continued
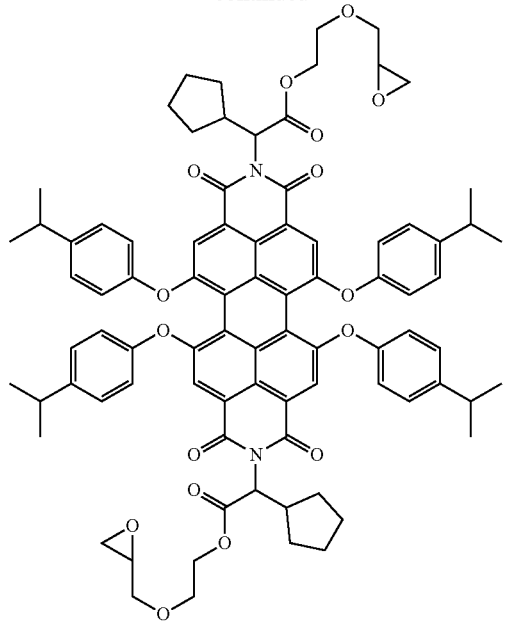
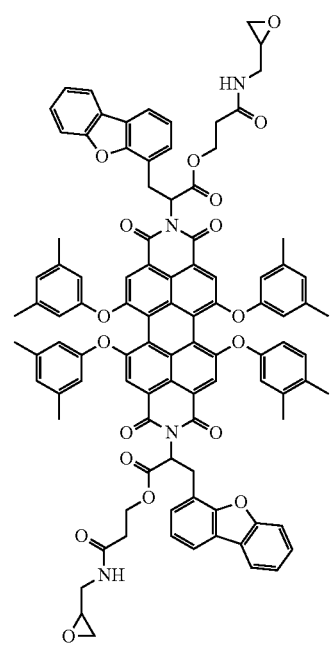

97
-continued
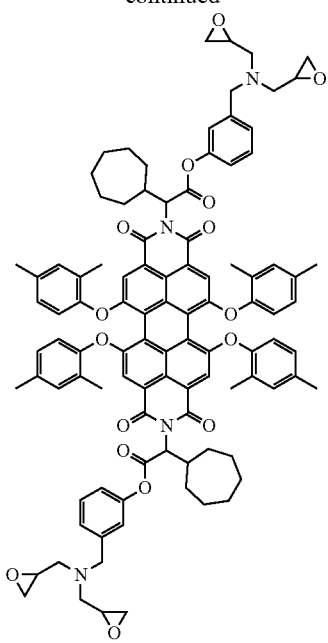
98
-continued
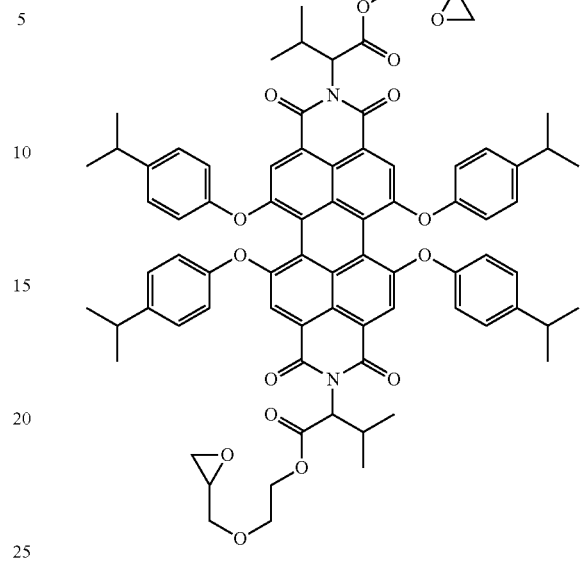
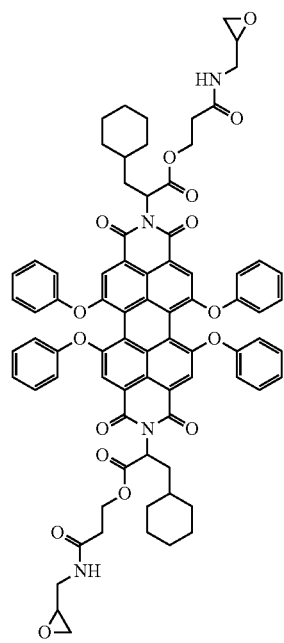
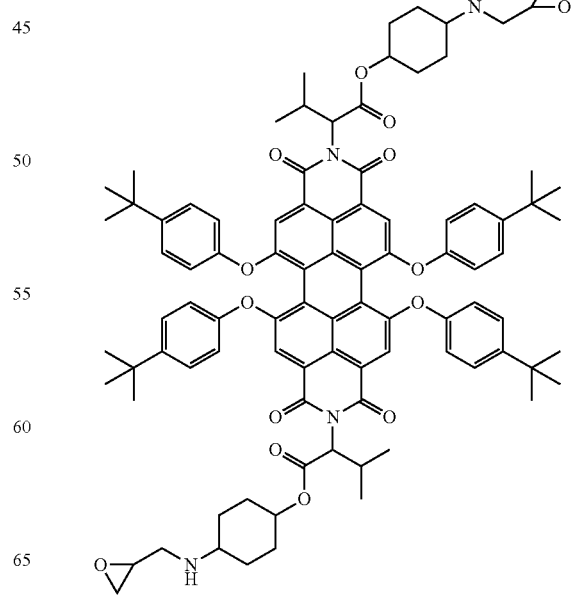

99
-continued
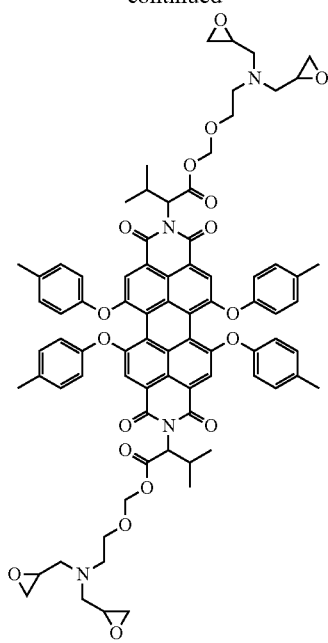
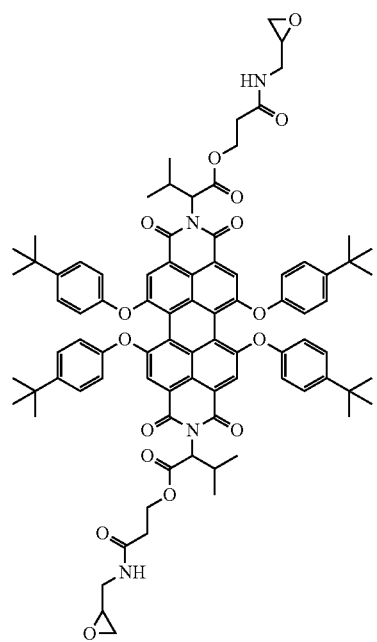
100
-continued
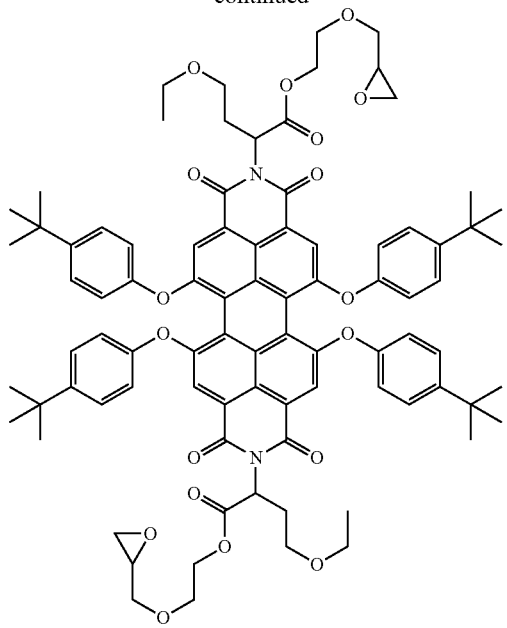
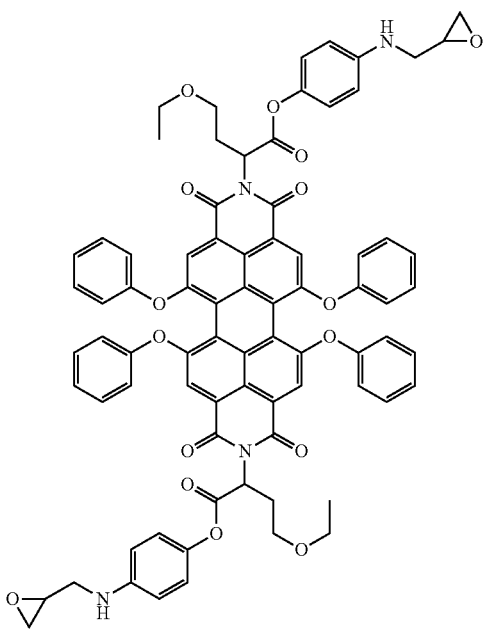

101
-continued
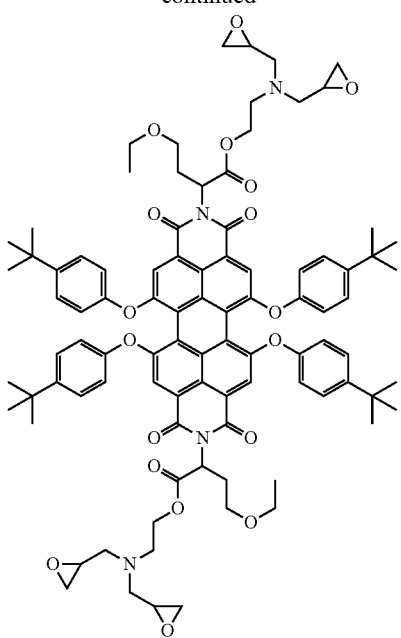
102
-continued
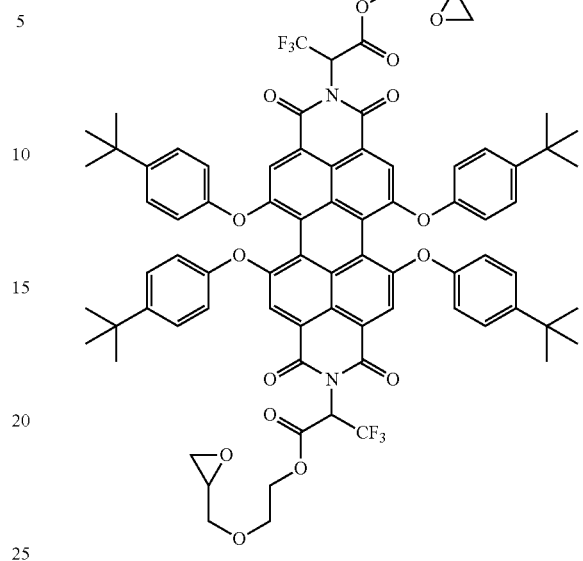
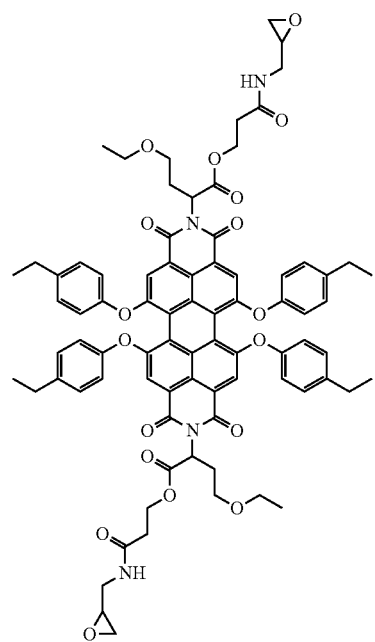
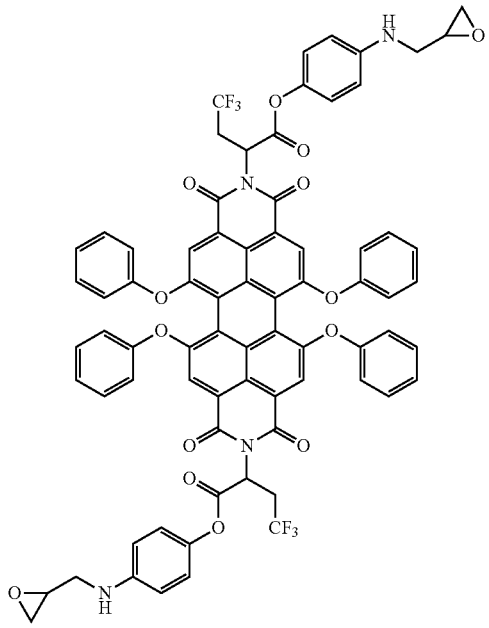

103
-continued
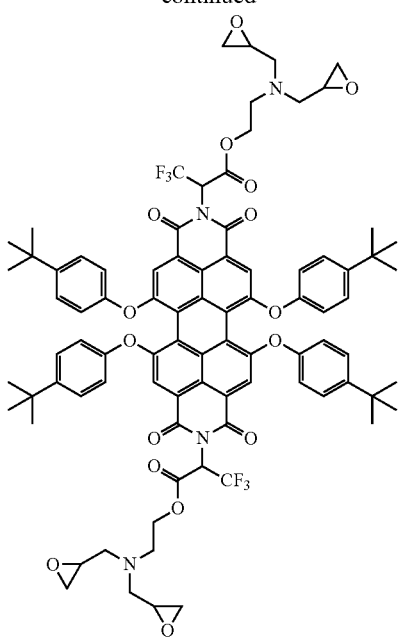
104
-continued
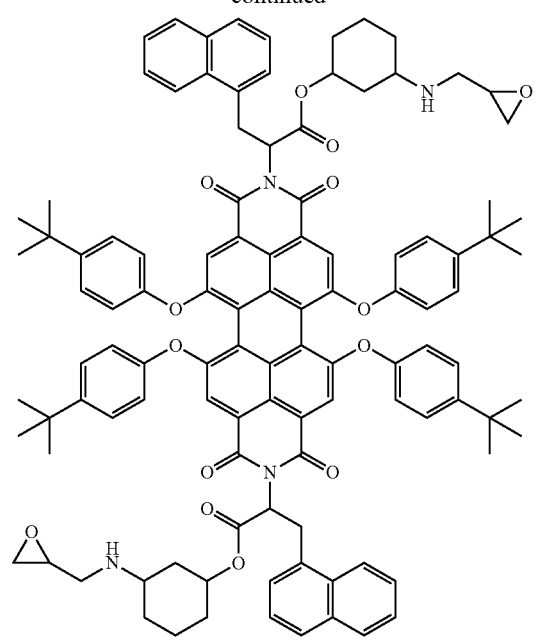
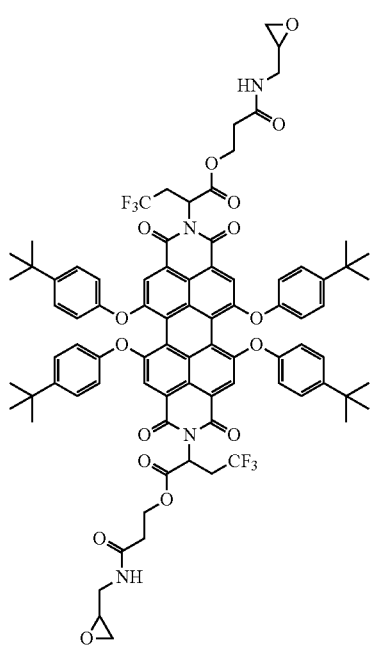
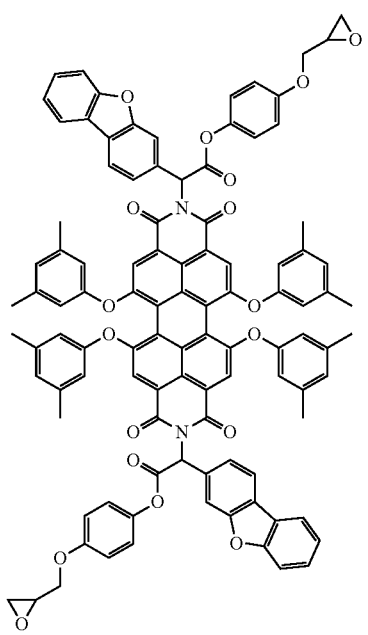

105
-continued
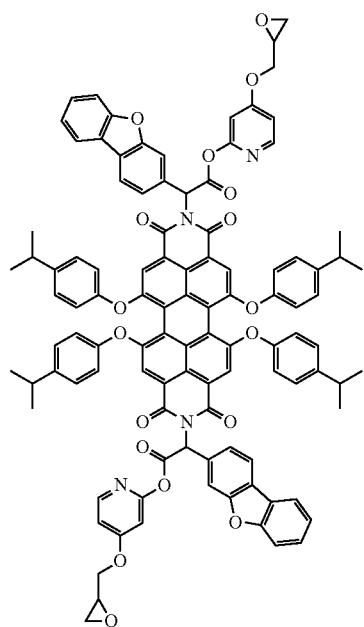
106
-continued
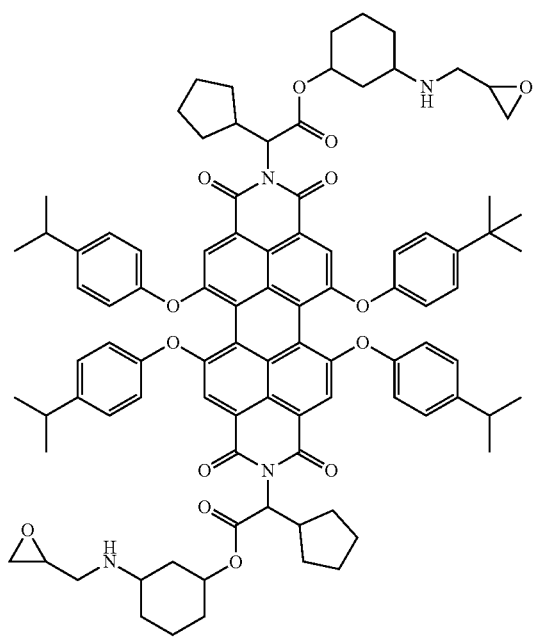
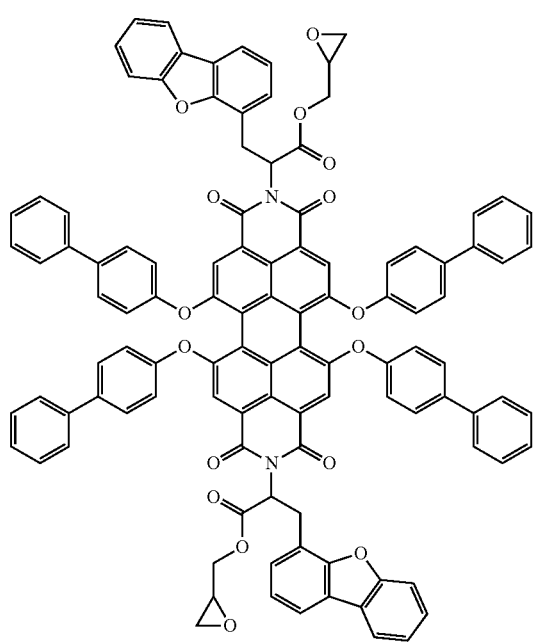

107
-continued
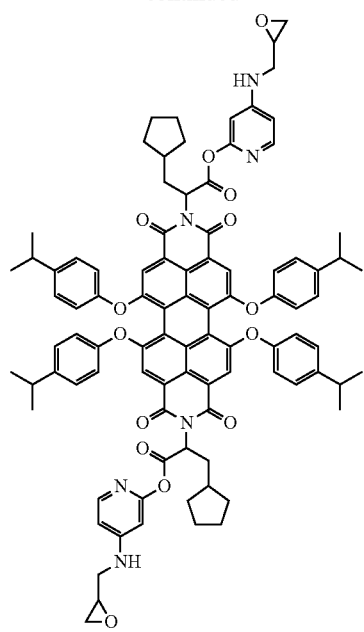
108
-continued
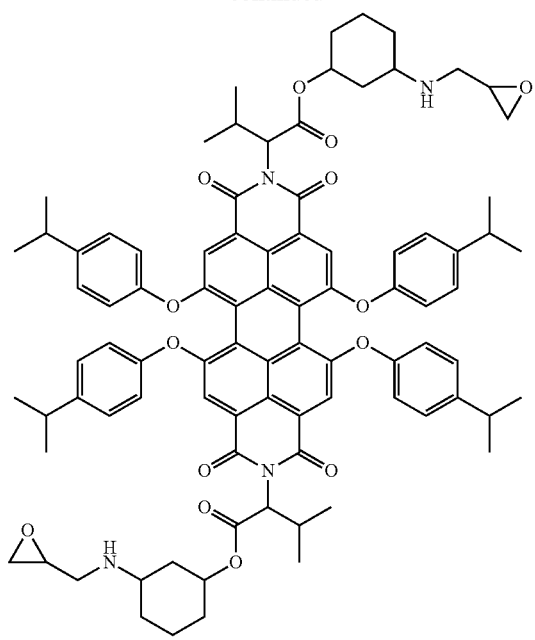
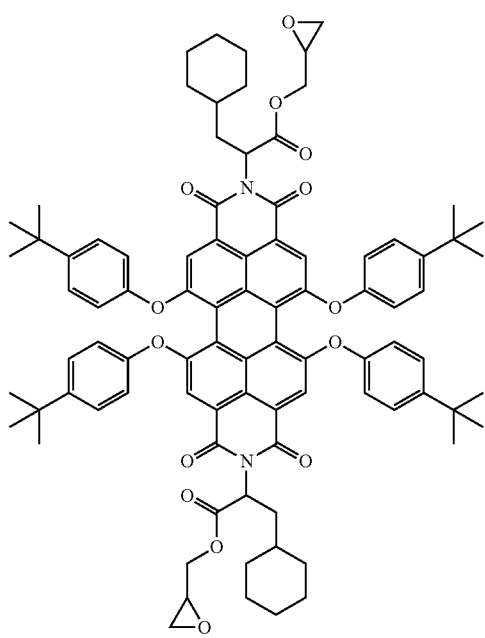
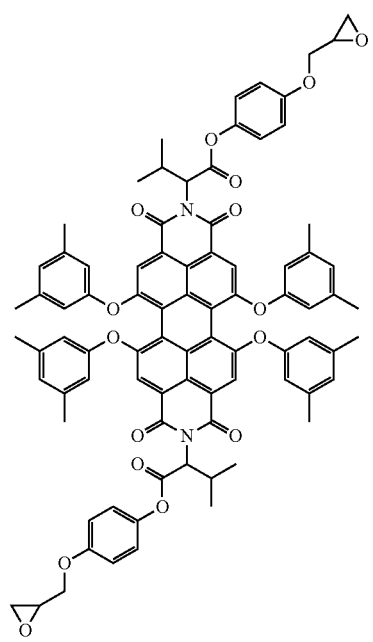

109
-continued
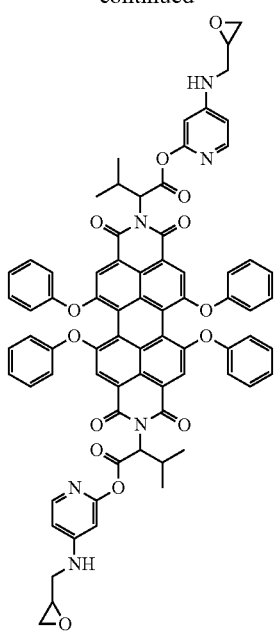
110
-continued
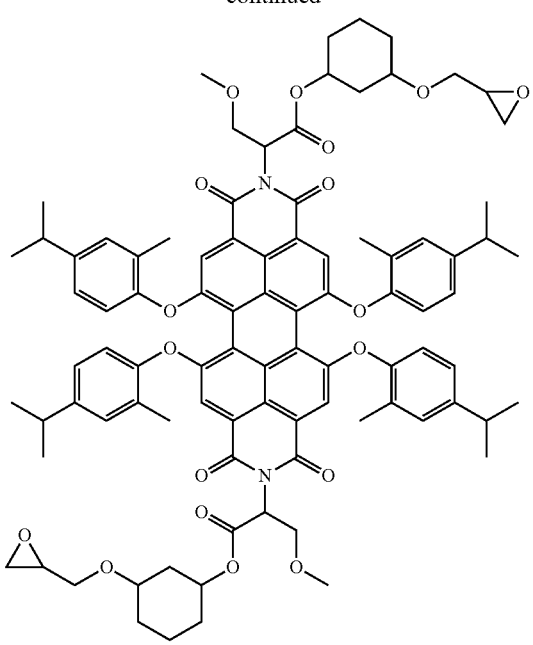
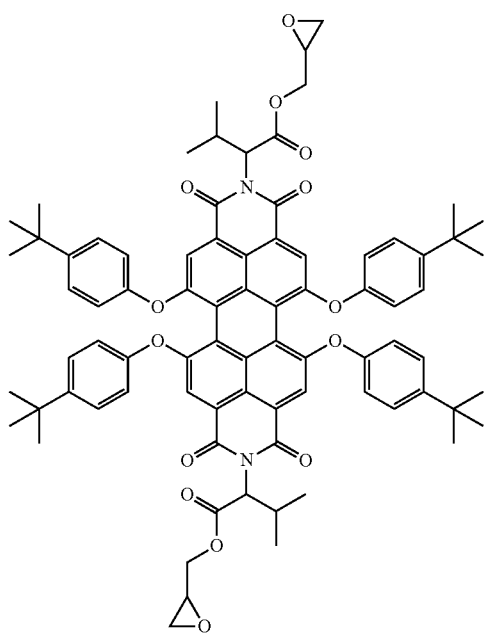
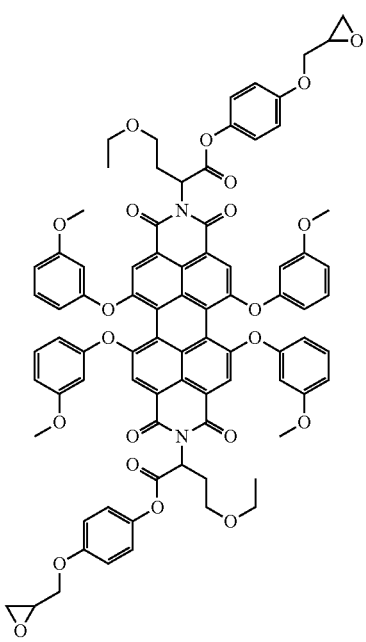

111
-continued
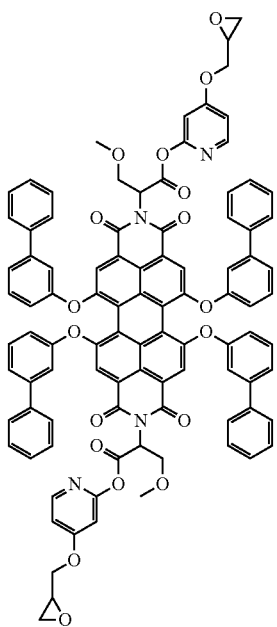
112
-continued
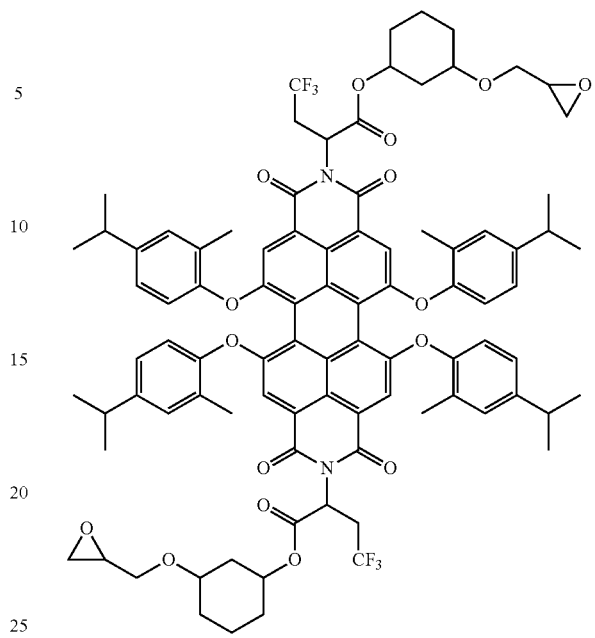
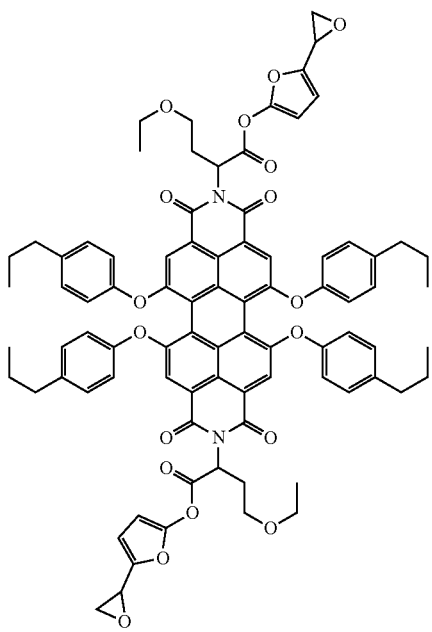
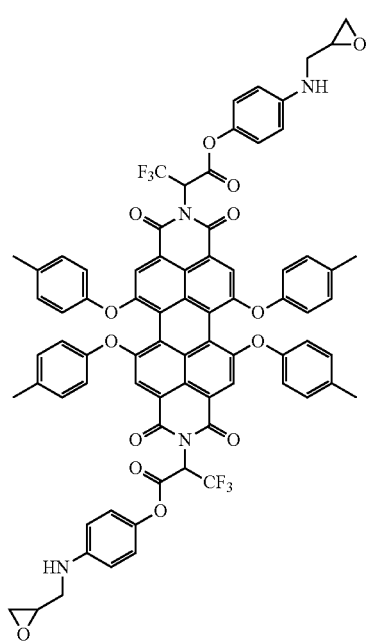

| 113 | 114 |
|---|---|
| -continued | -continued |
| 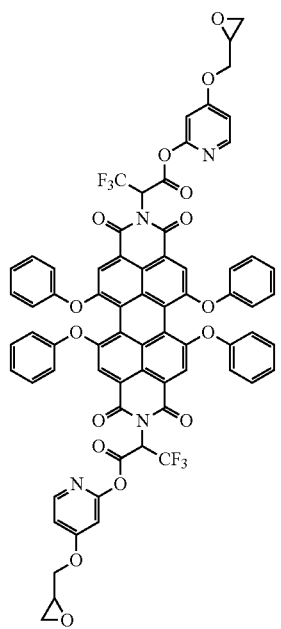 | 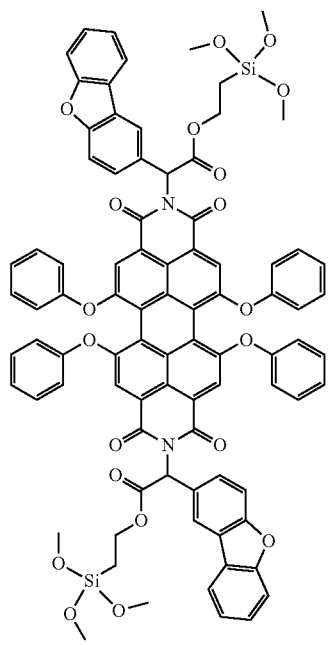 |
| 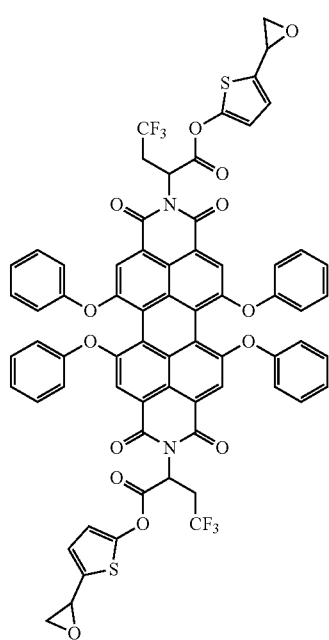 | 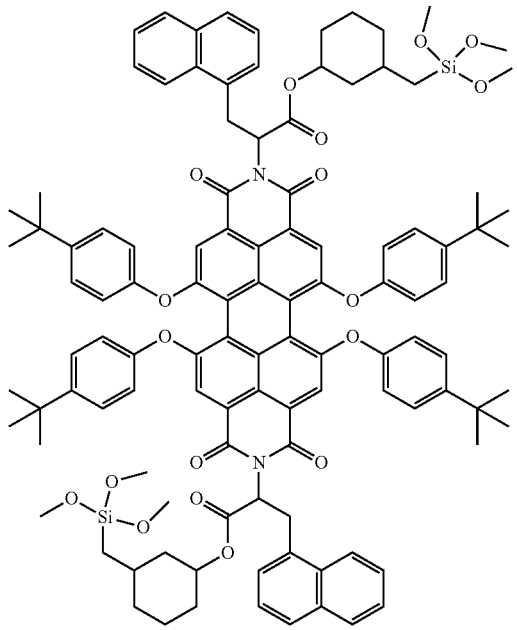 |

115
-continued
116
-continued
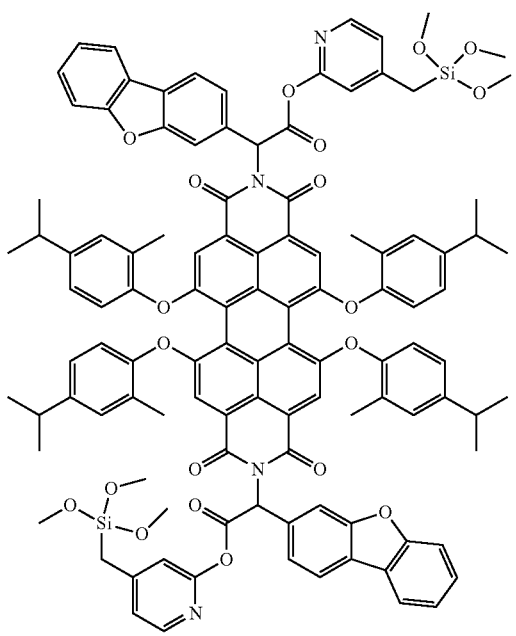
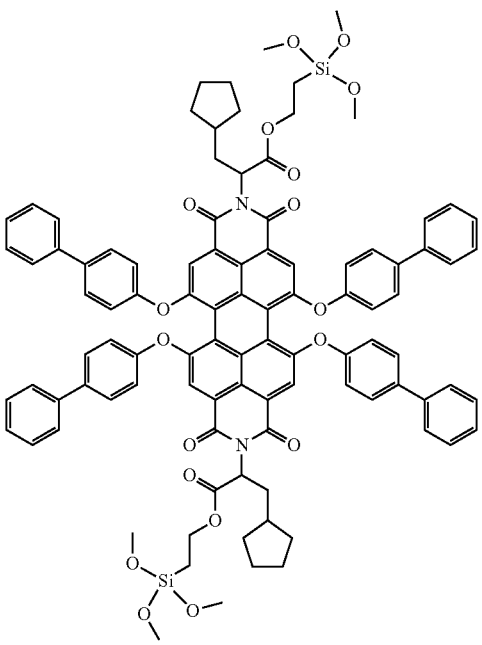

117
-continued
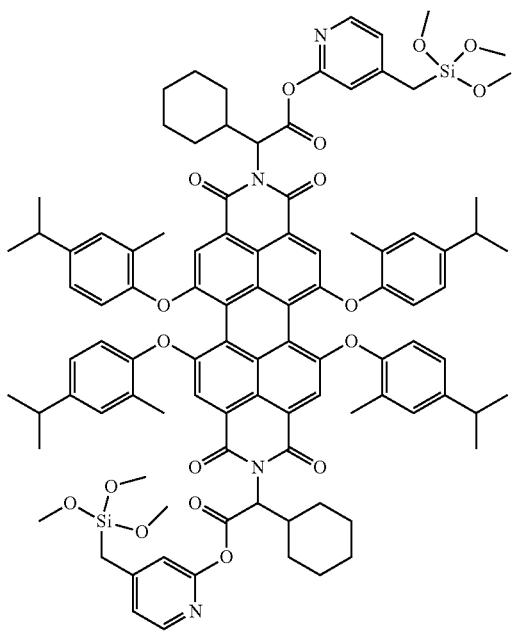
118
-continued
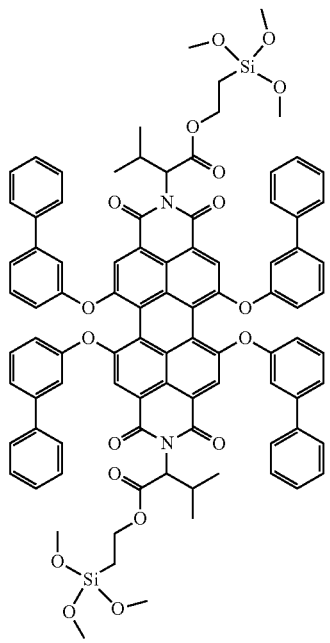
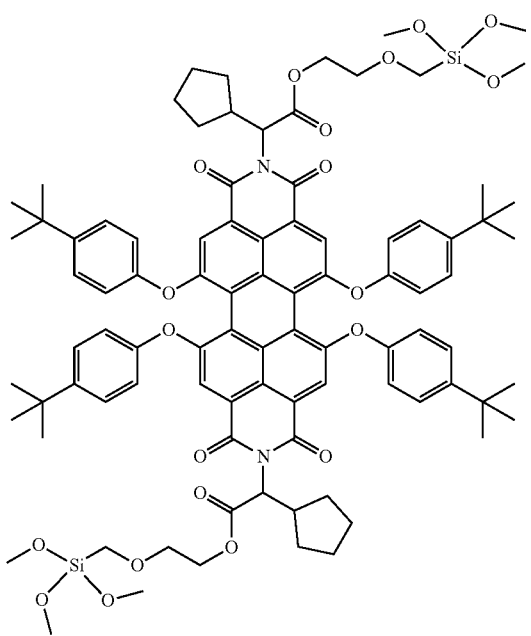
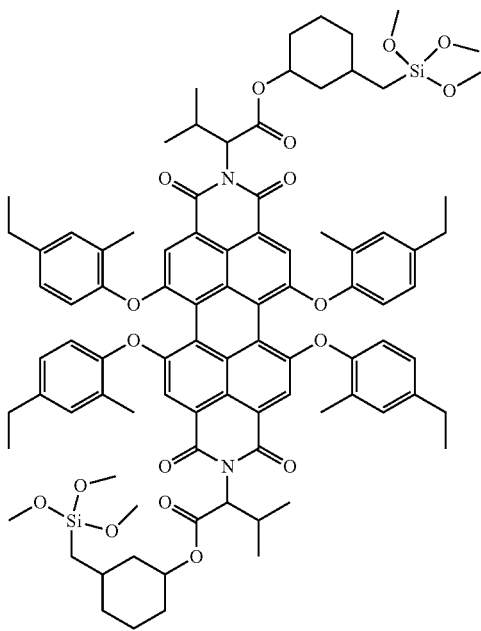

119
-continued
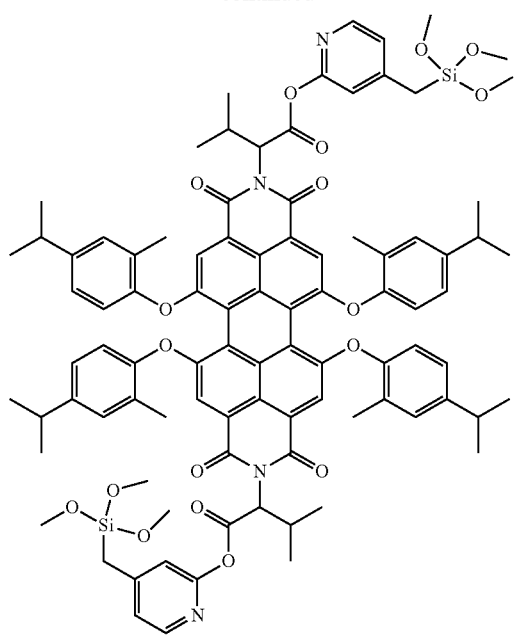
120
-continued
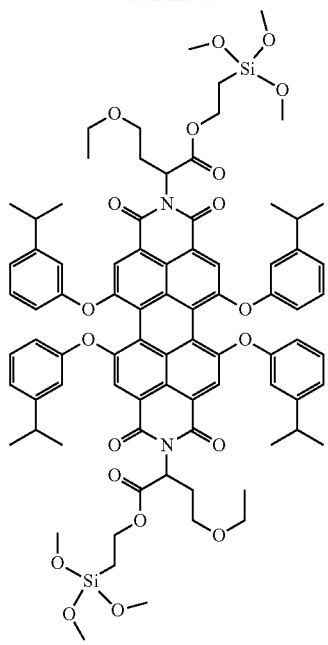
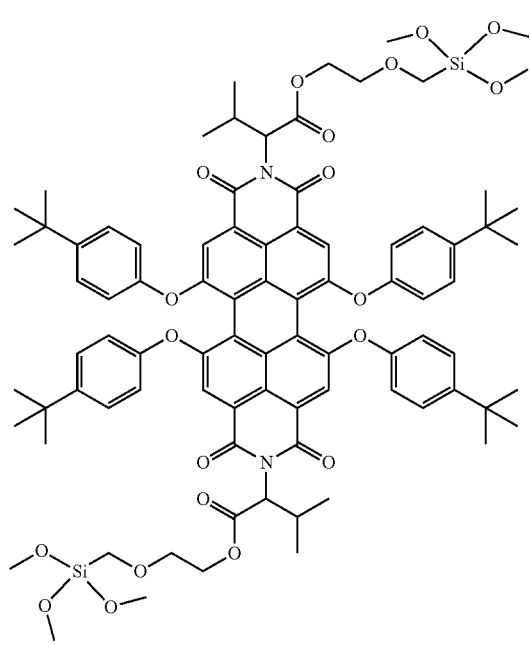
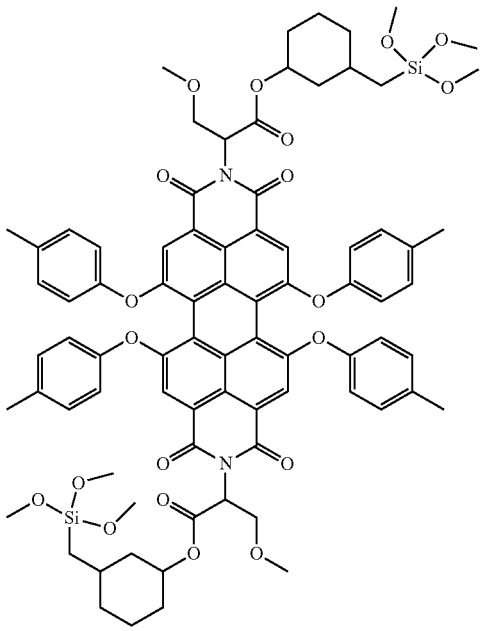

| 121 -continued | 122 -continued |
|---|---|
| 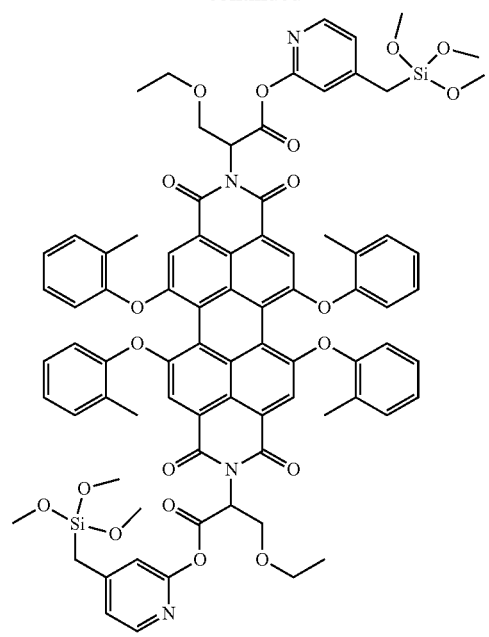 | 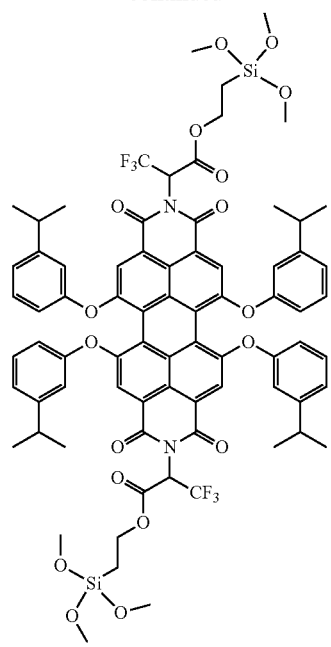 |
| 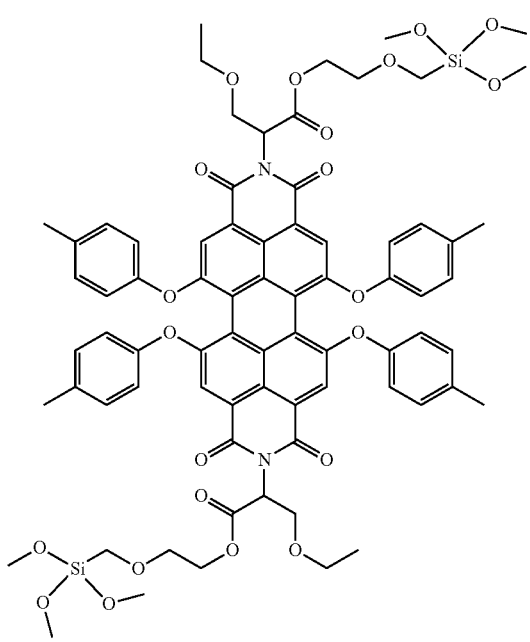 | 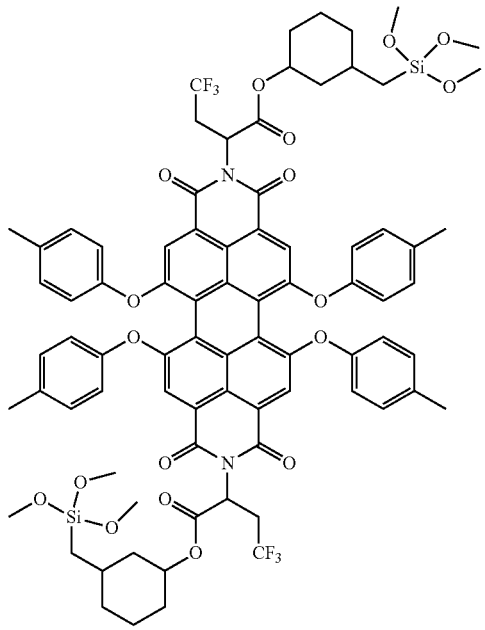 |

123
-continued
124
-continued
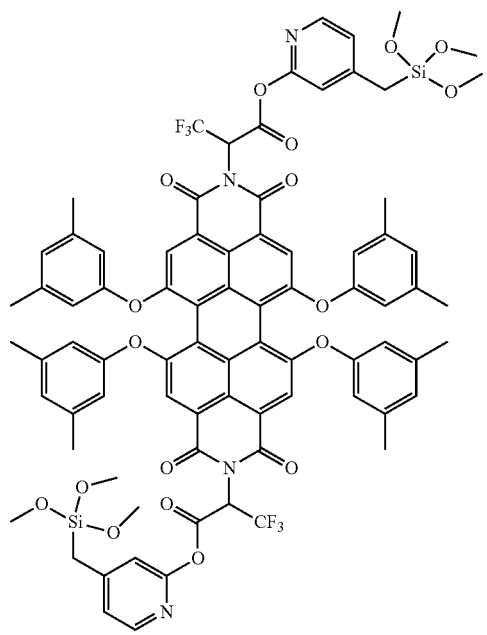

125
-continued
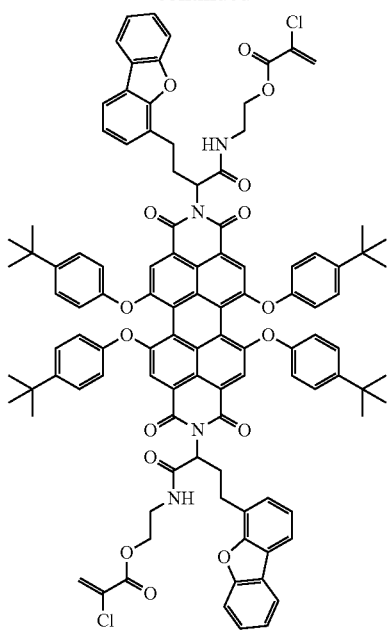
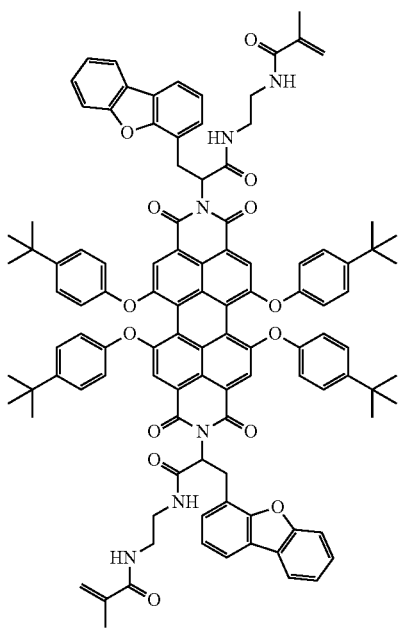
126
-continued
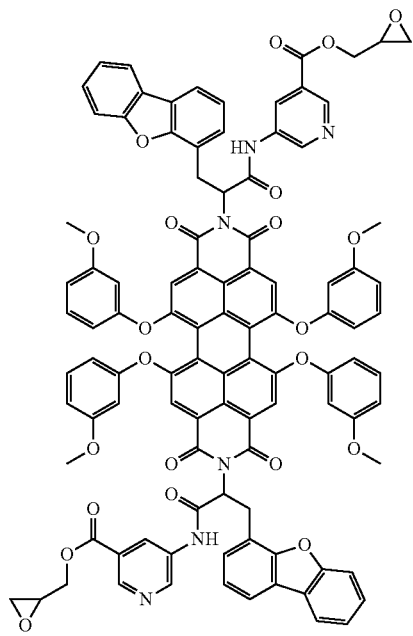
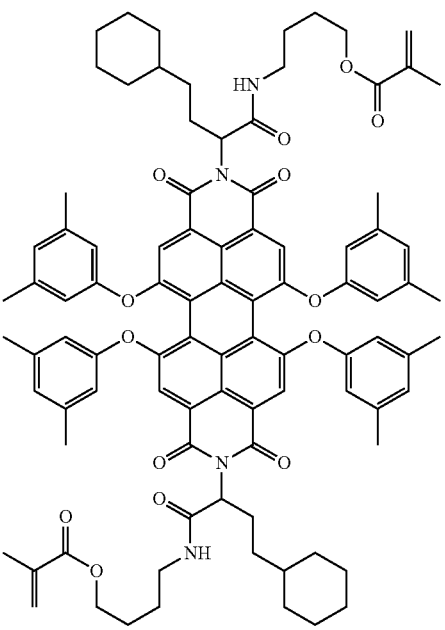

127
-continued
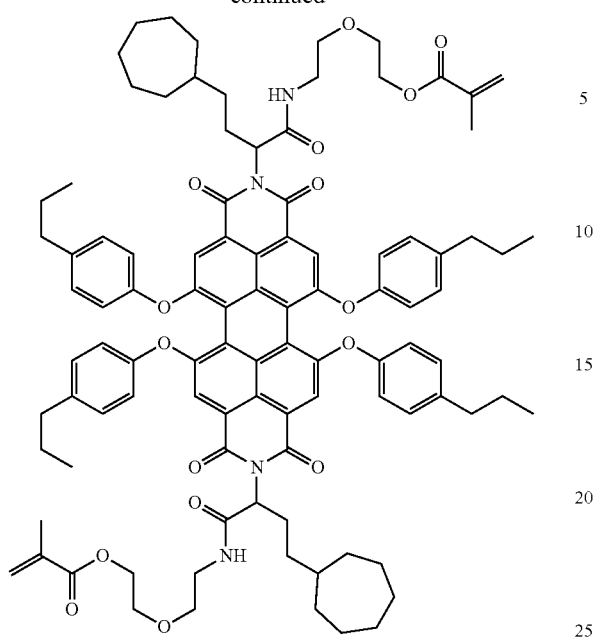
128
-continued
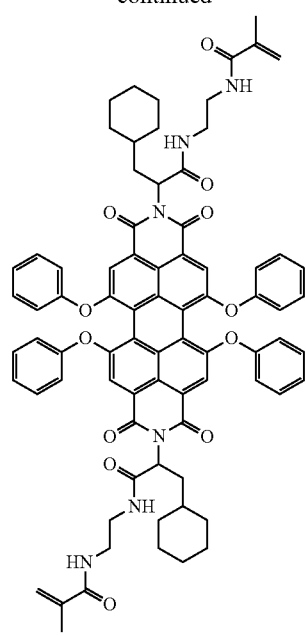
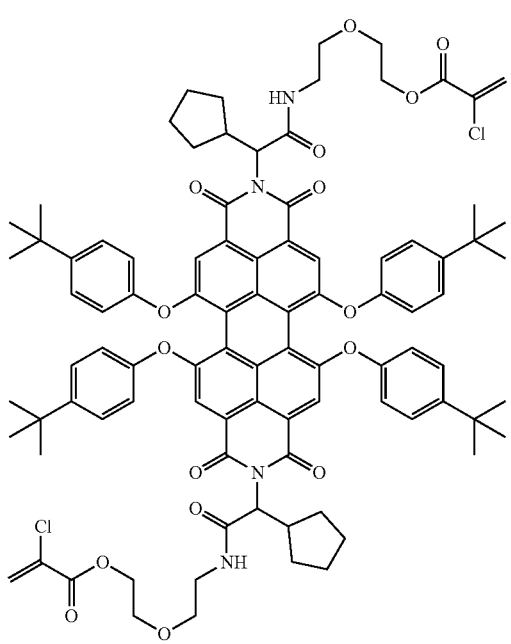
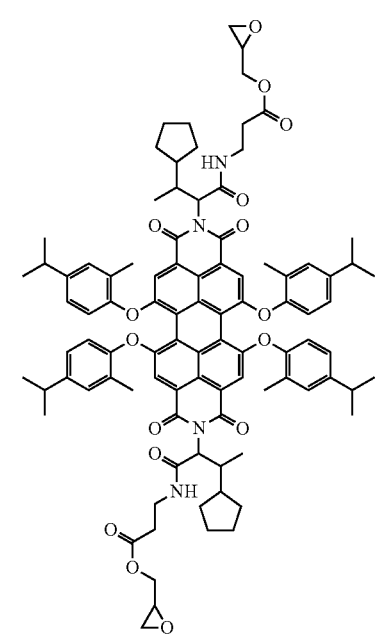

129
-continued
130
-continued
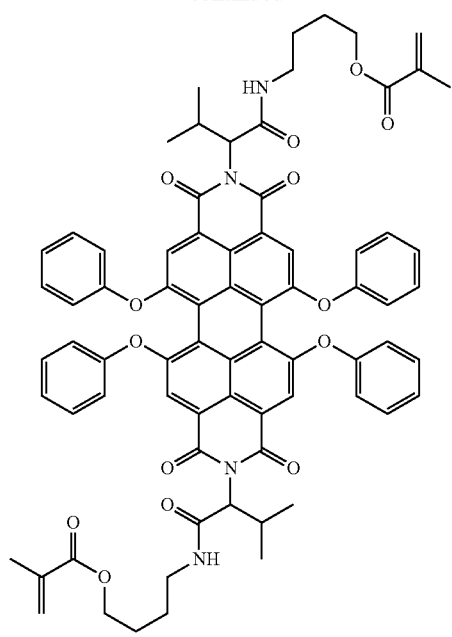
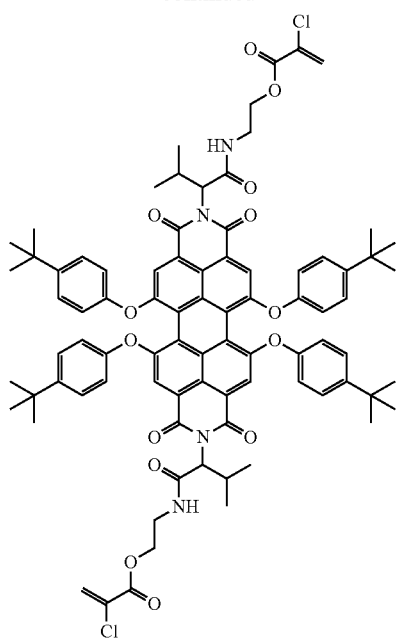

131
-continued
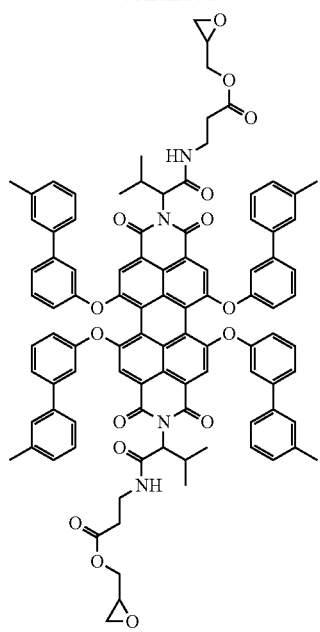
132
-continued
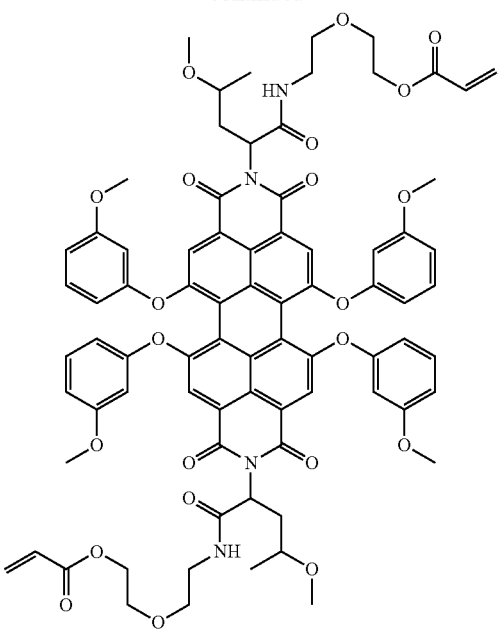
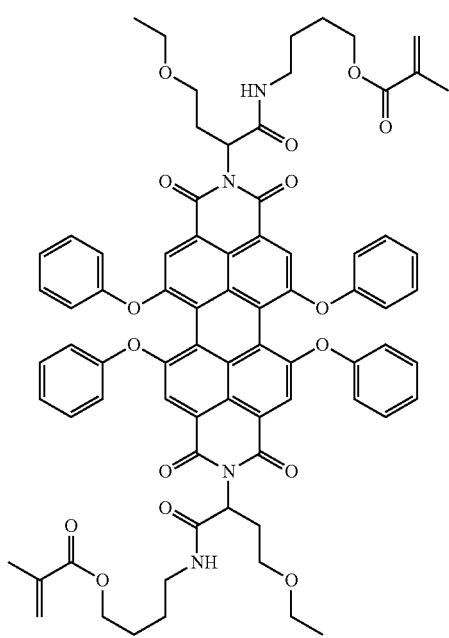
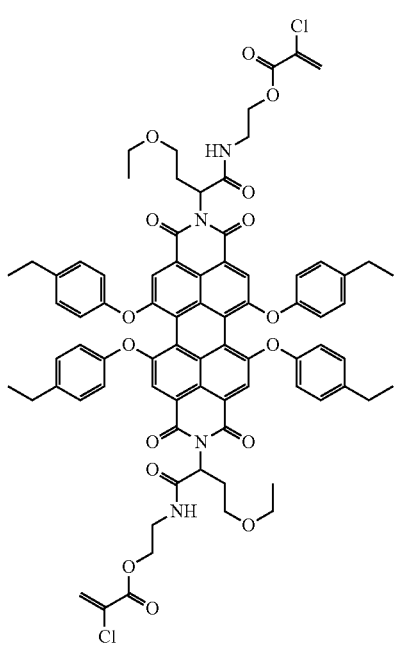

133
-continued
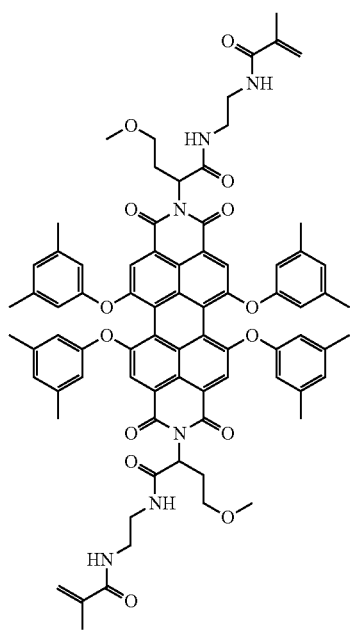
134
-continued
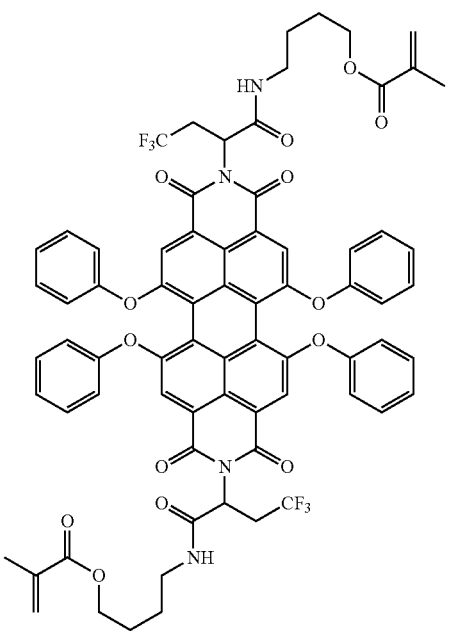
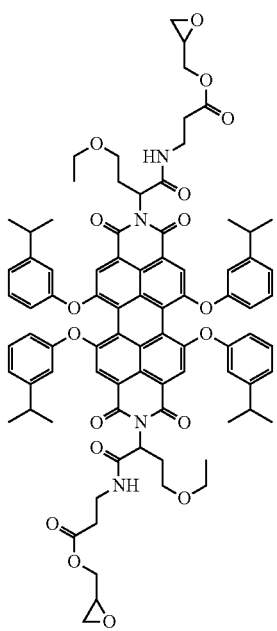
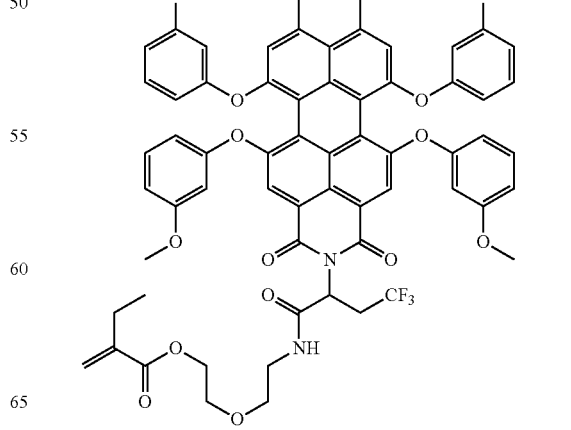

135
-continued
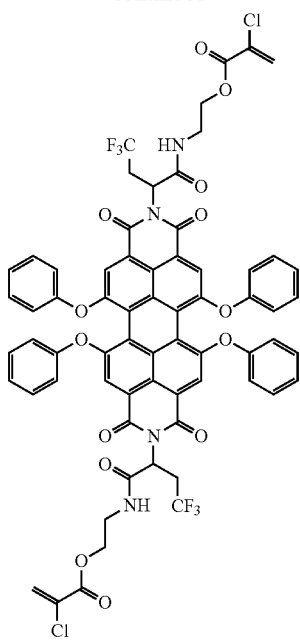
136
-continued
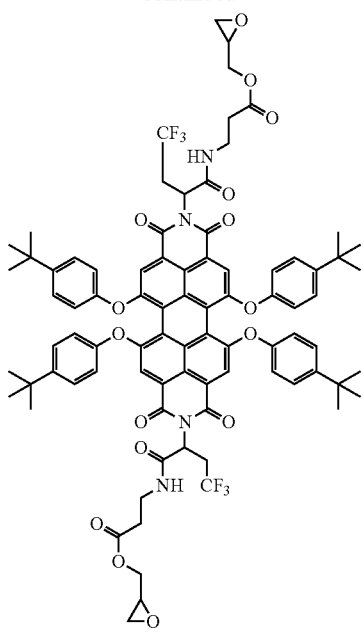
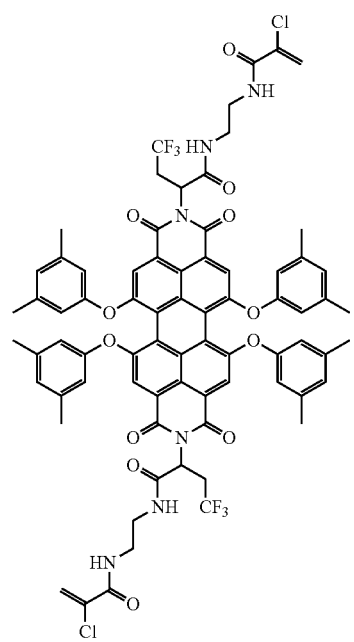
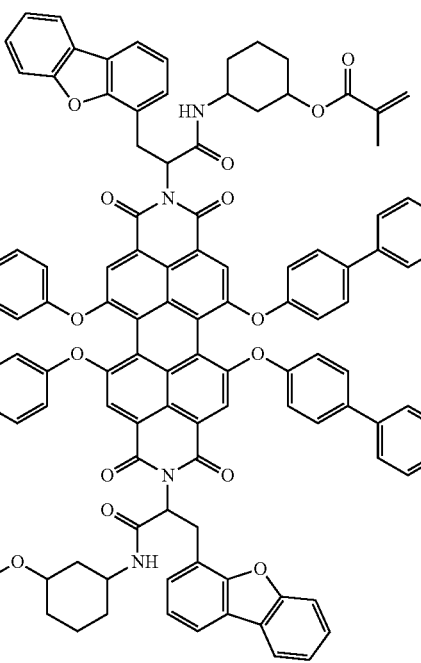

137
-continued
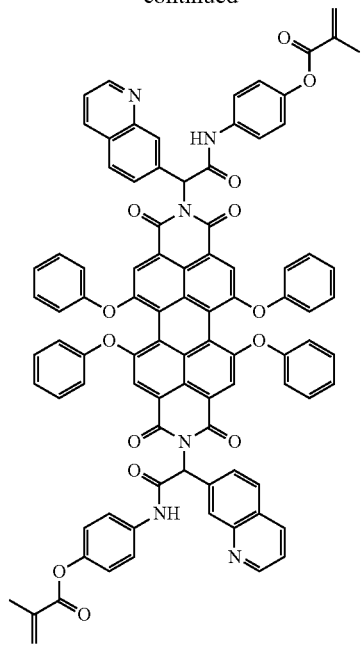
138
-continued
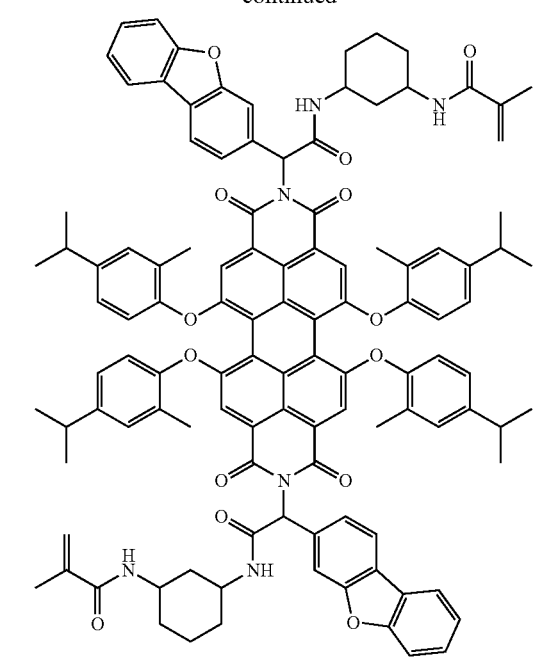
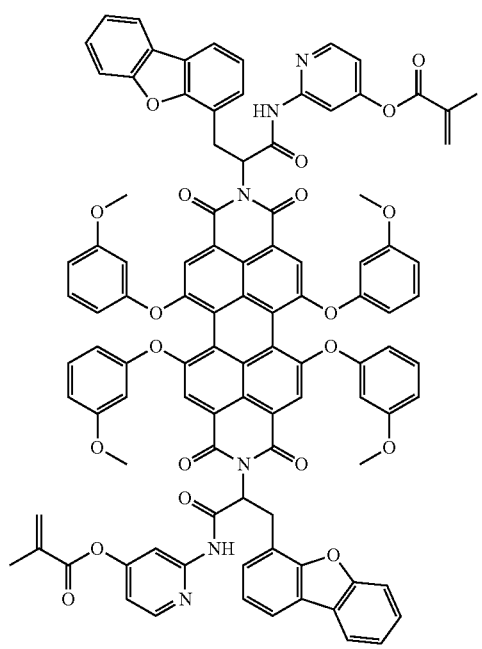
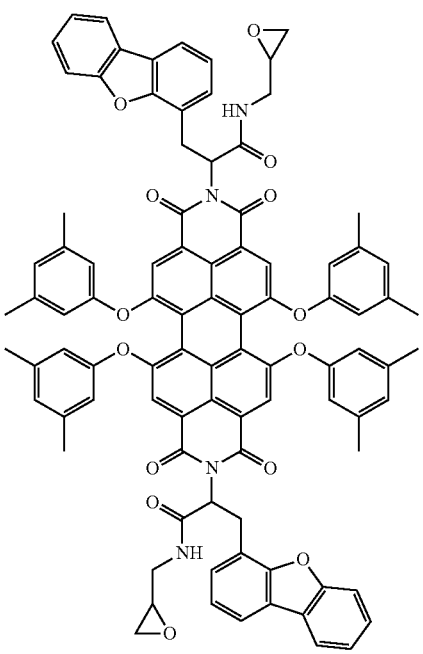

139
-continued
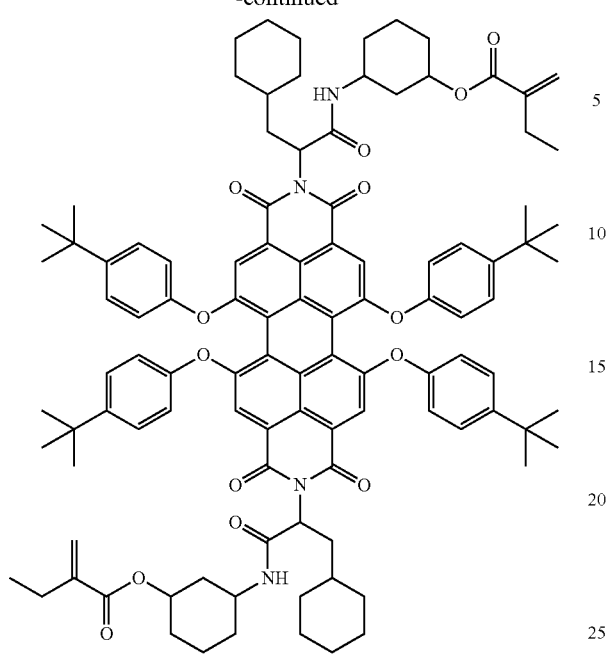
140
-continued
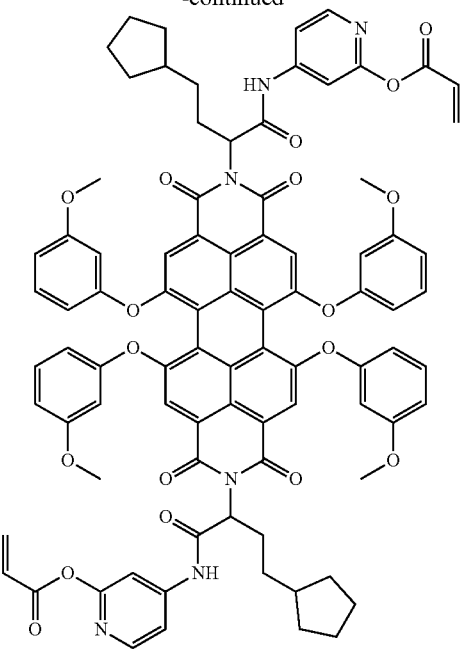
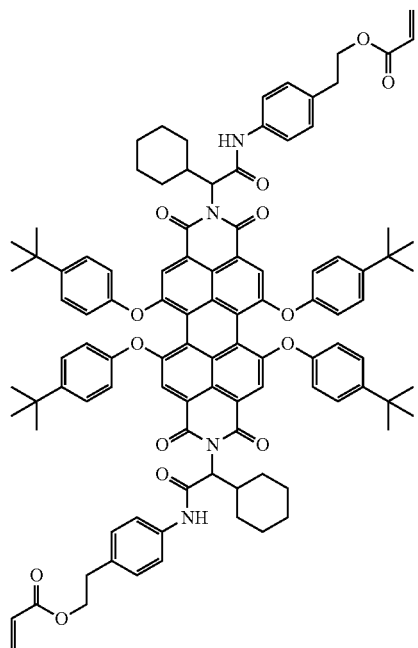
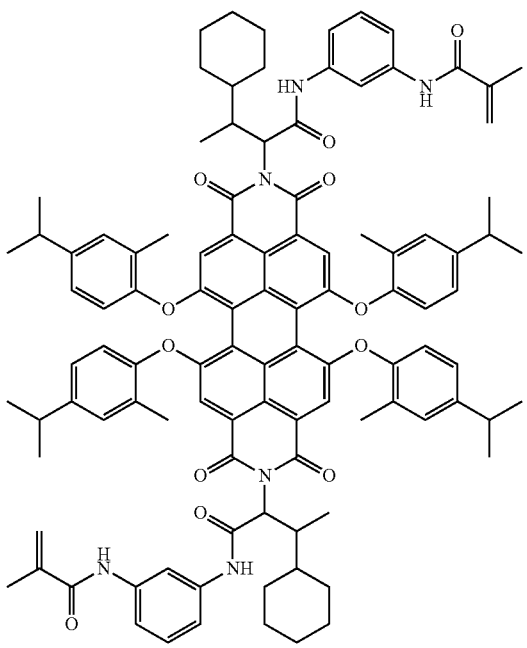

141
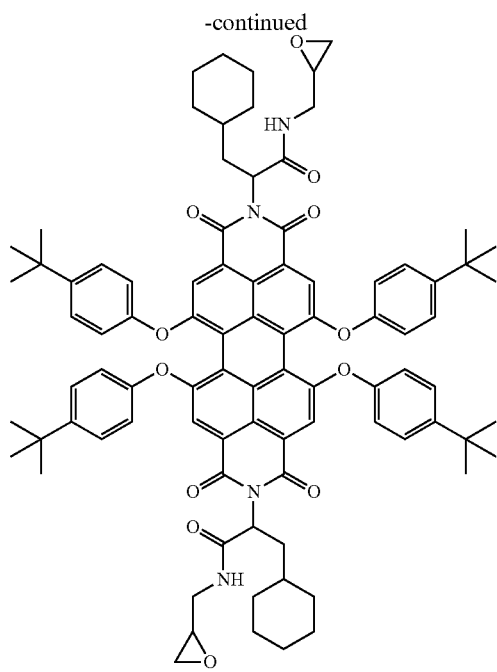
142
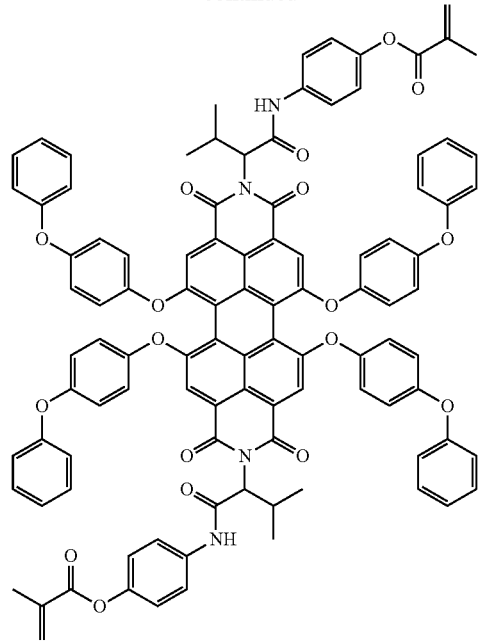
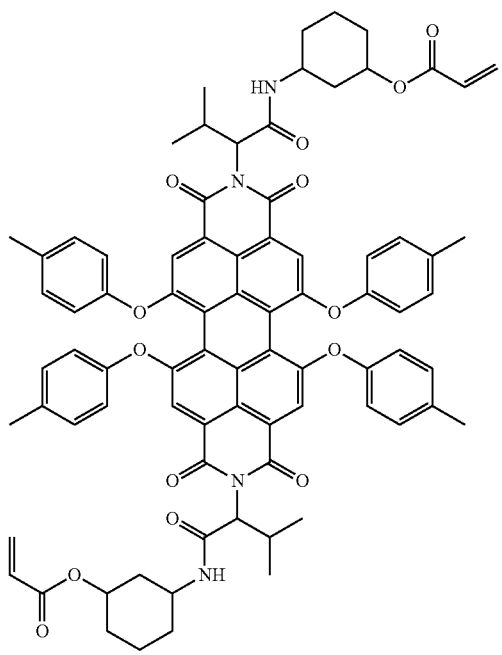
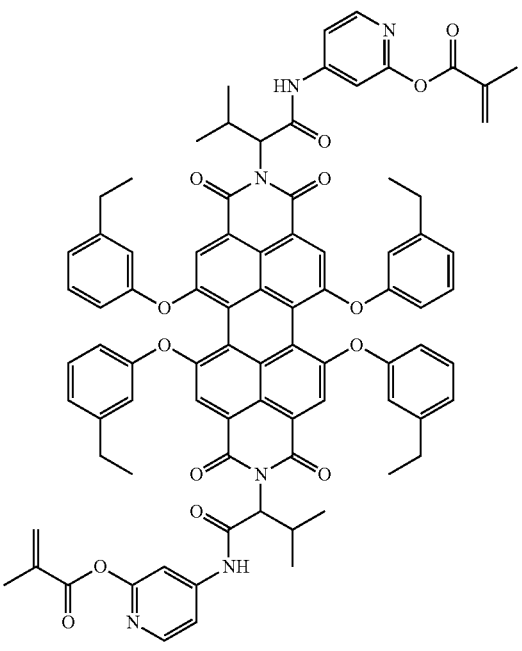

143
-continued
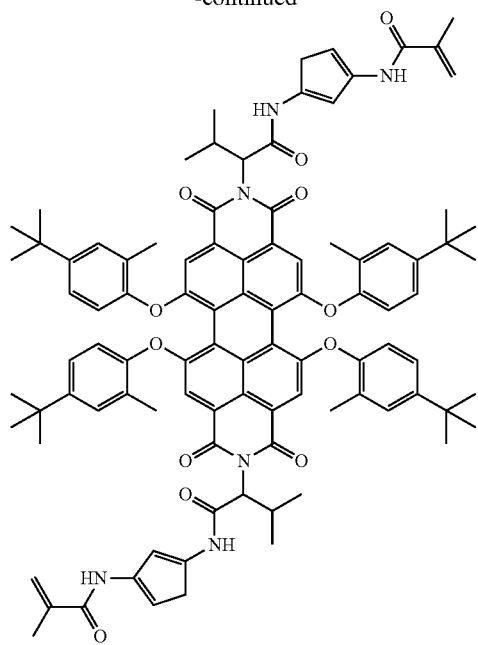
144
-continued
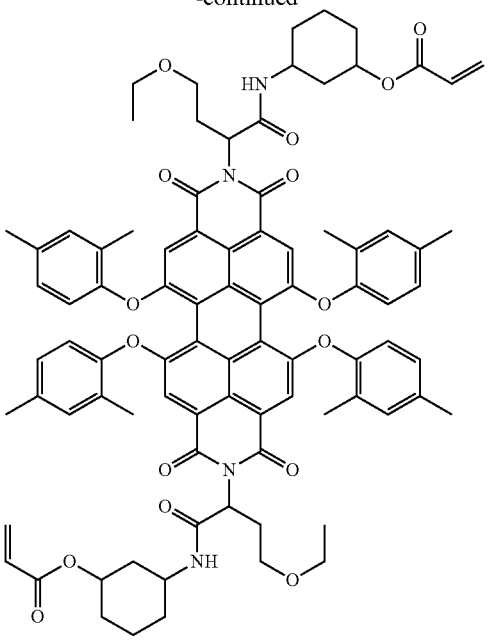
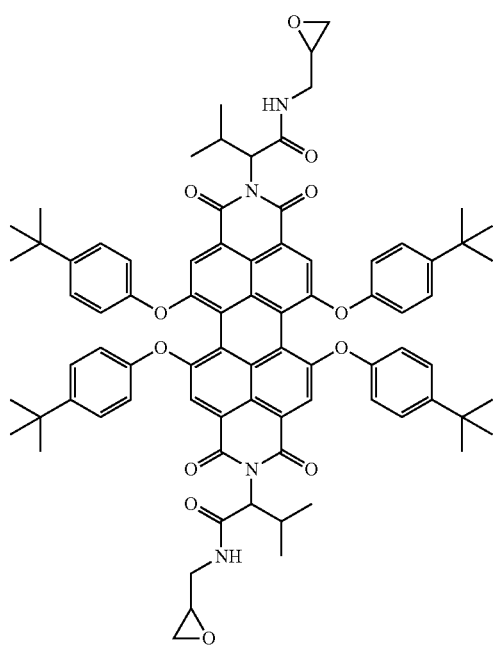

145
-continued
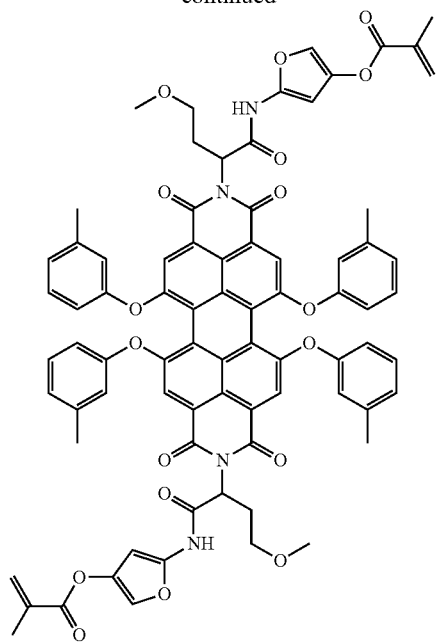
146
-continued
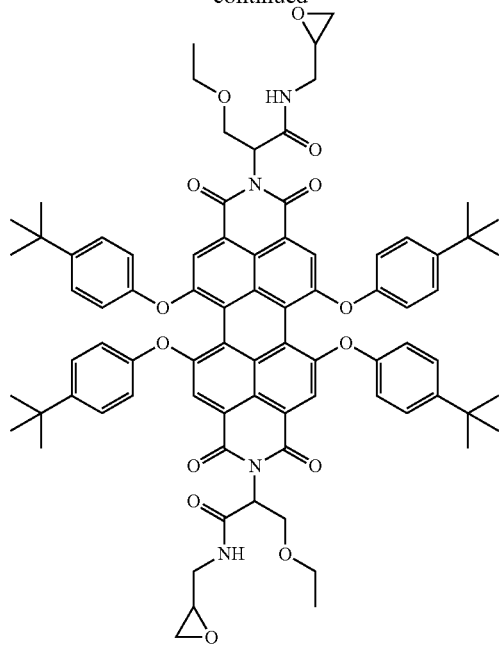
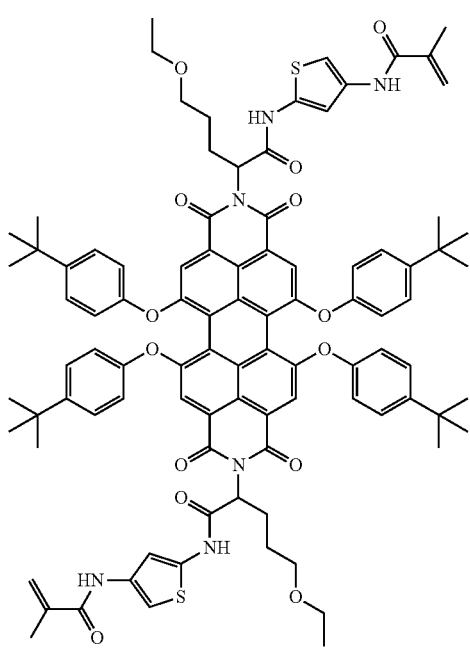
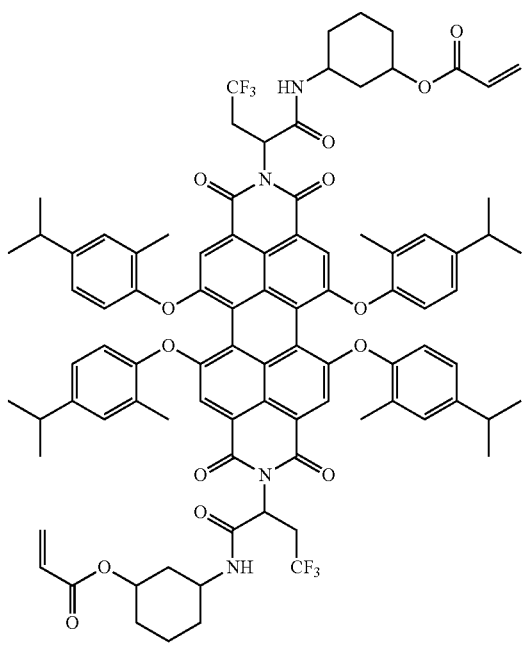

147
-continued
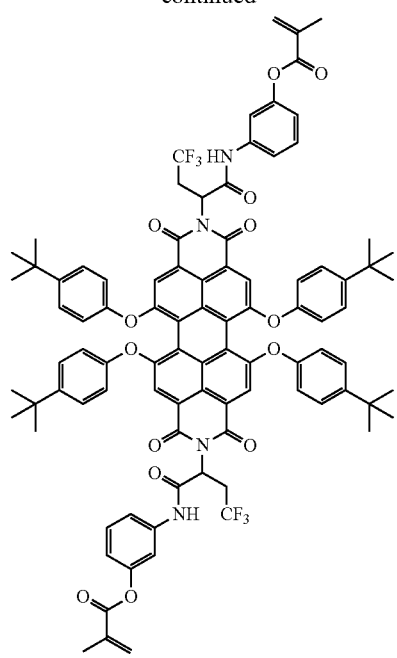
148
-continued
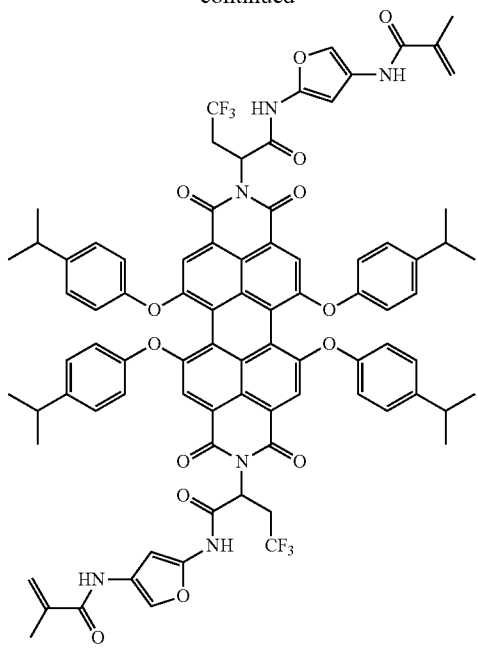
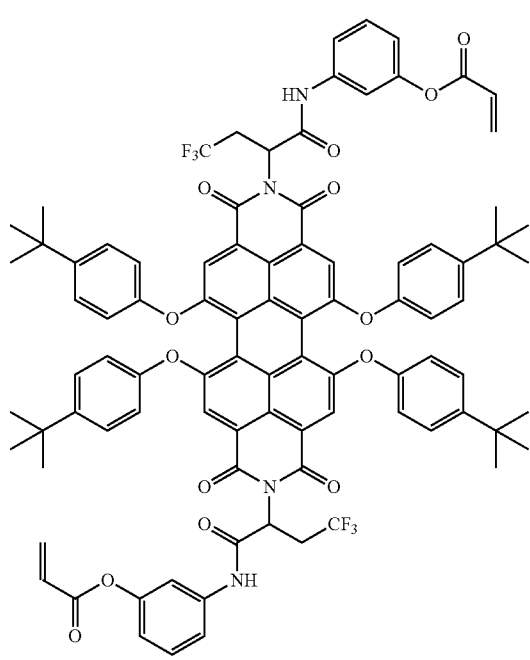
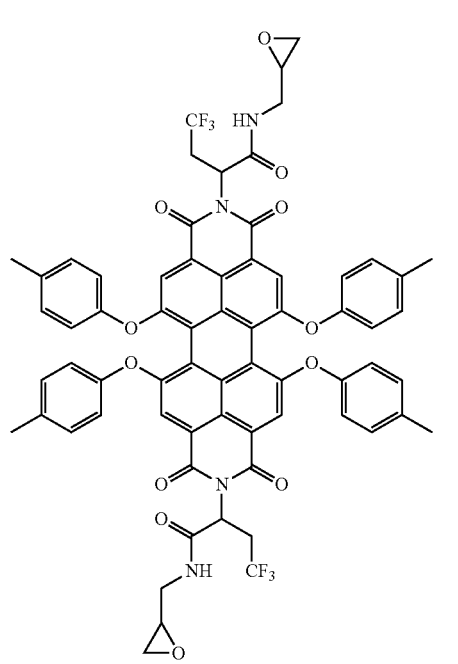

149
-continued
150
-continued
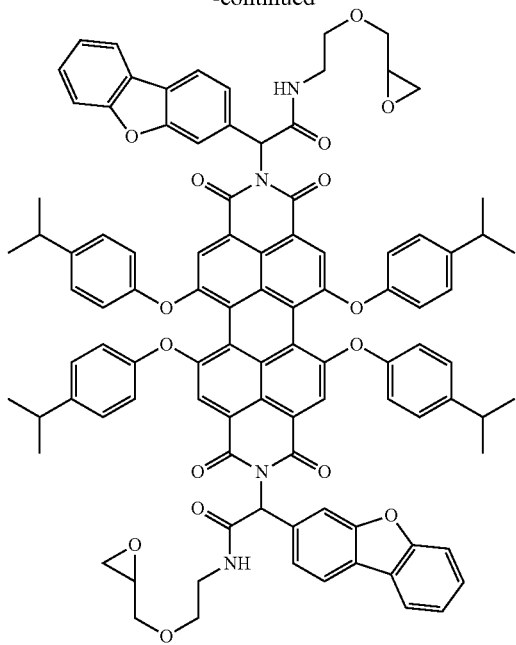
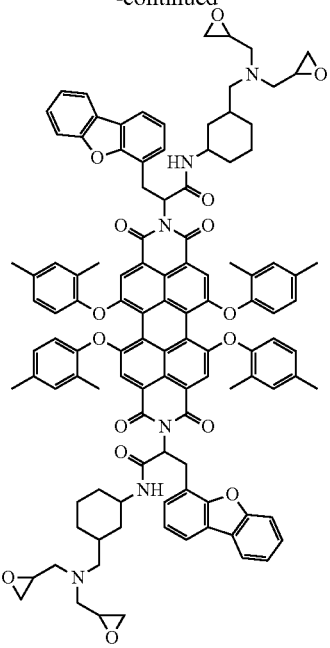
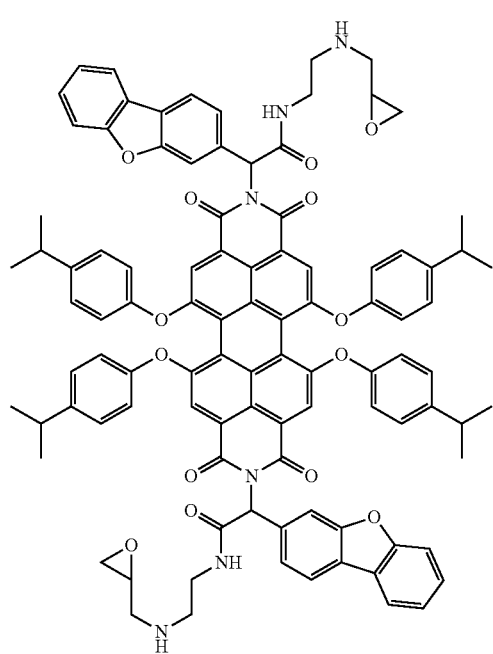

151
-continued
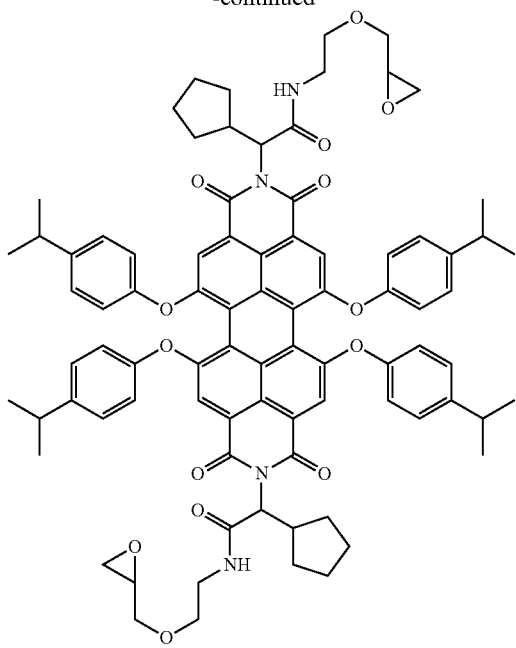
152
-continued
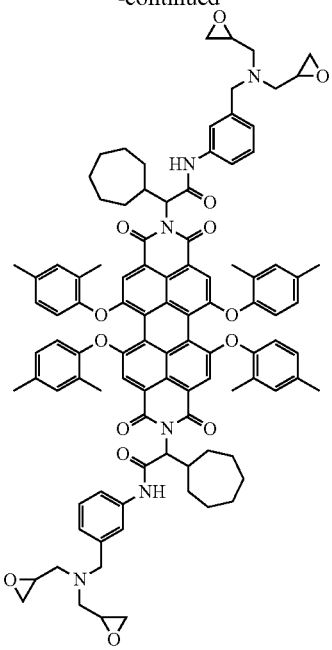
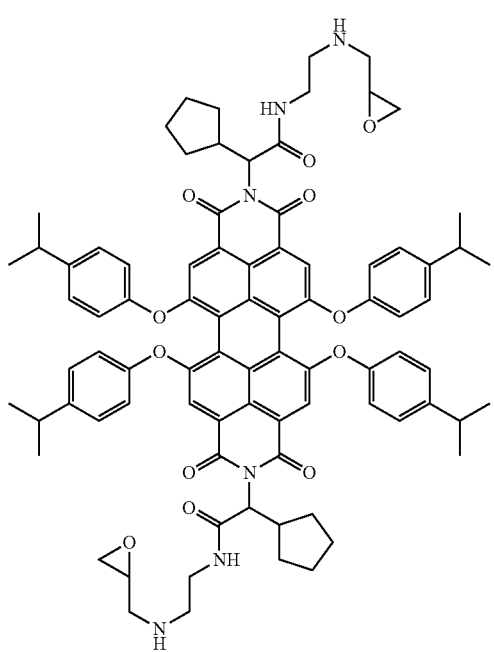
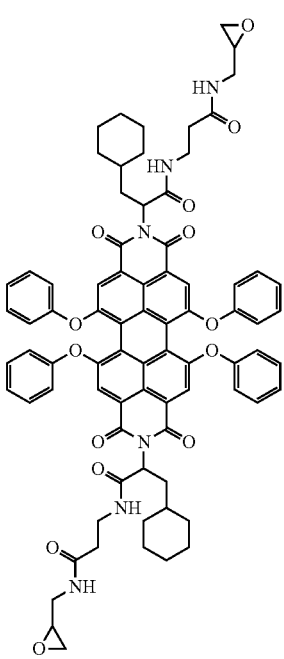

153
-continued
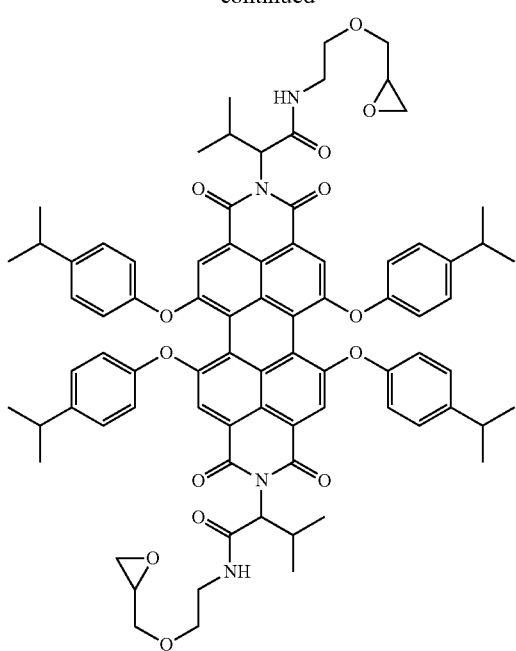
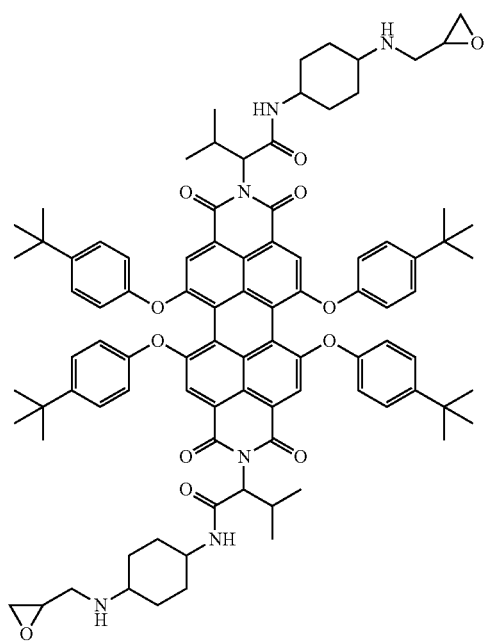
154
-continued

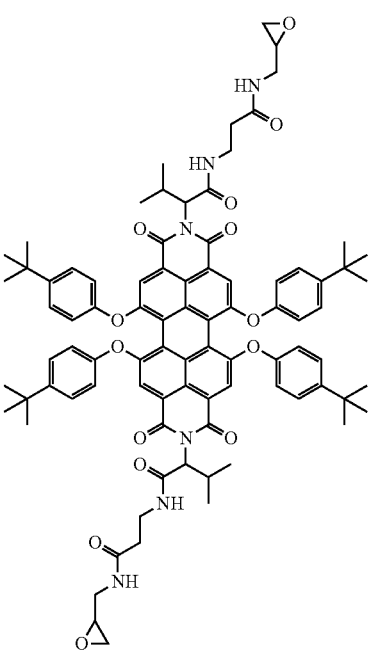

155
-continued
156
-continued
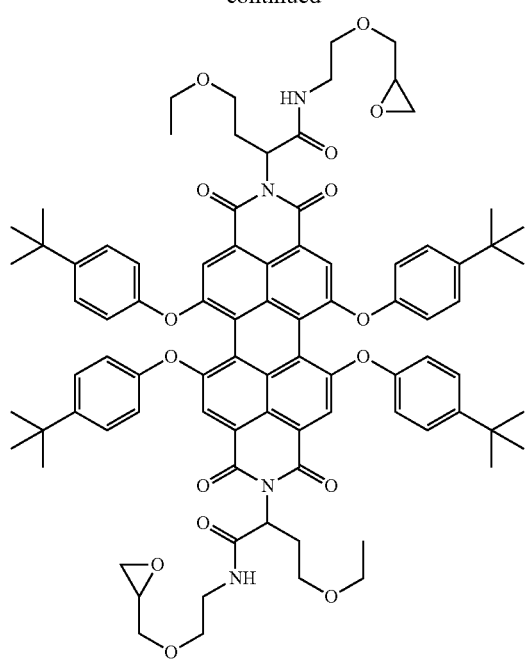
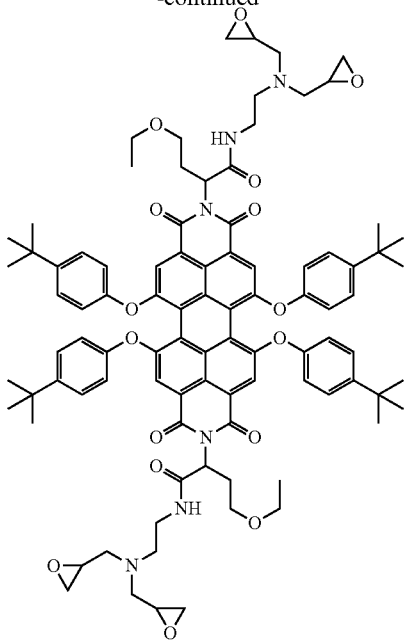
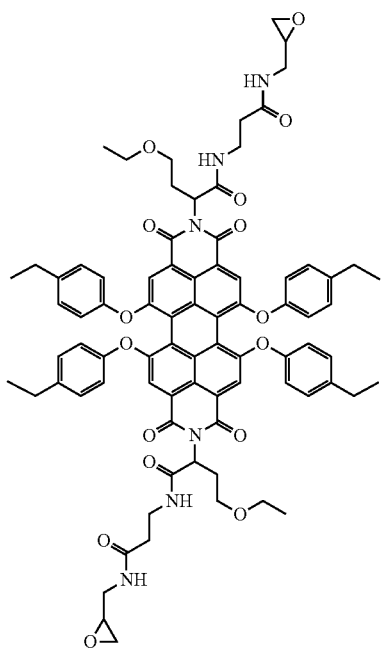

157
-continued
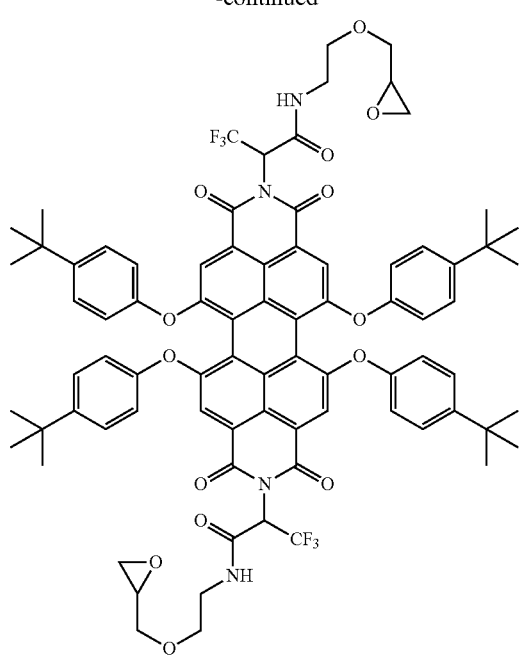
158
-continued
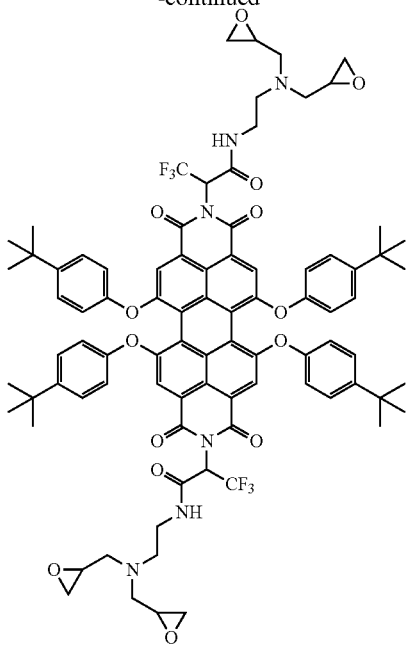

159
-continued
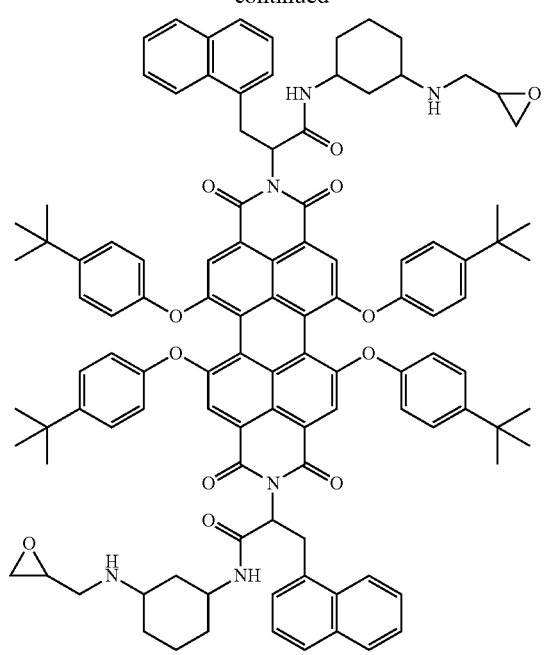
160
-continued
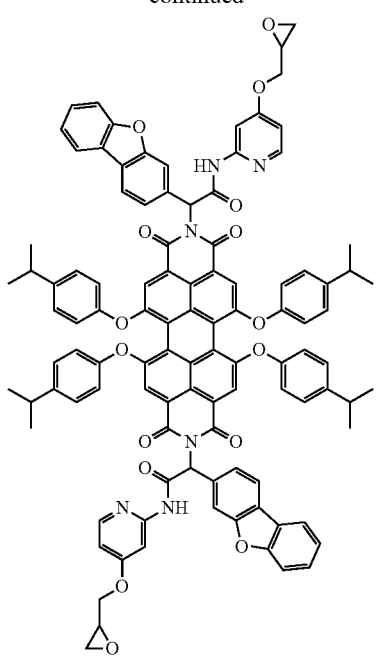
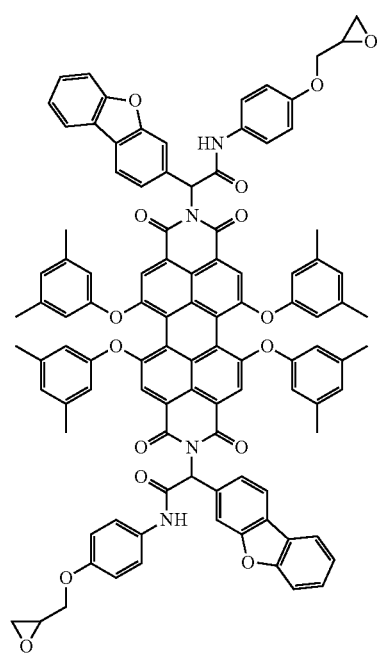
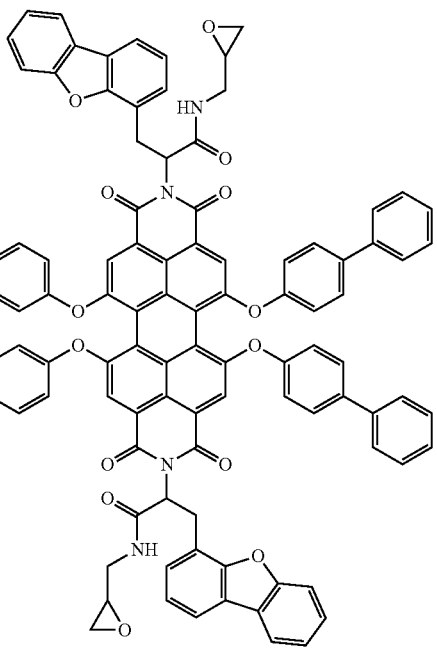

161
-continued
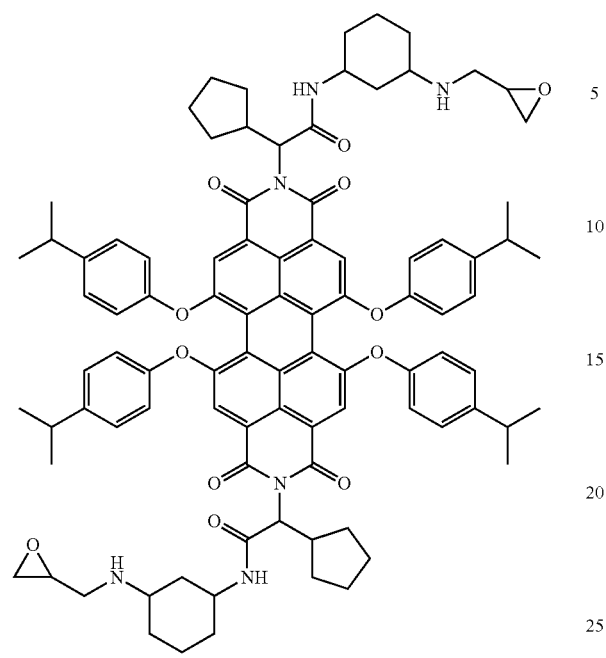
162
-continued
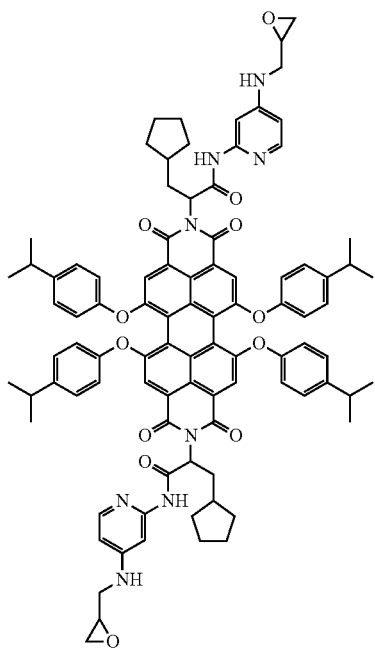
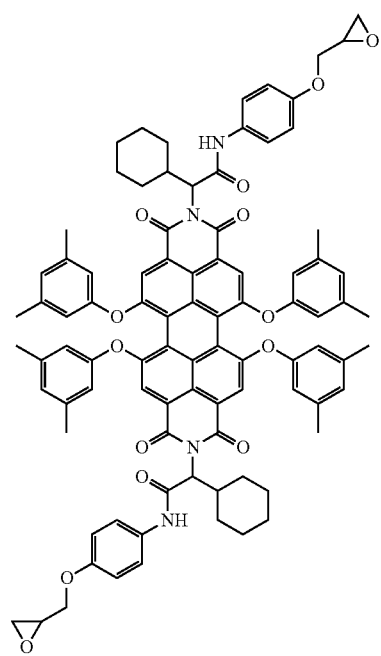
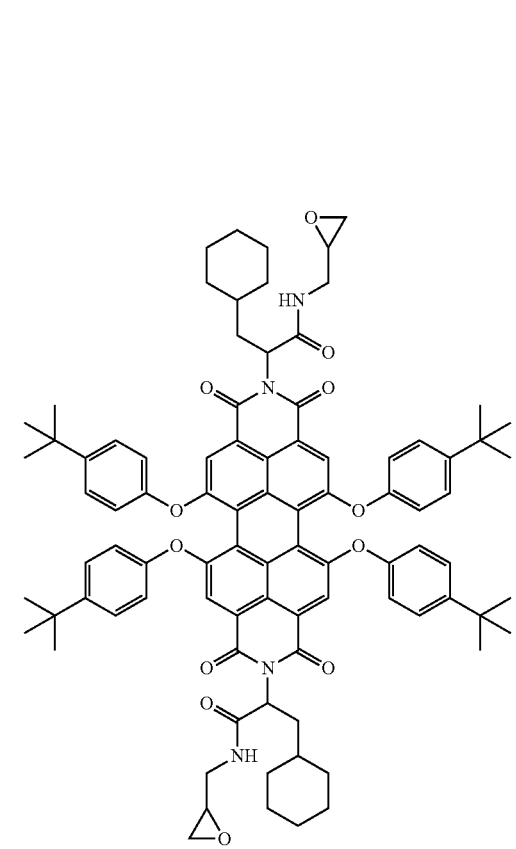

163
-continued
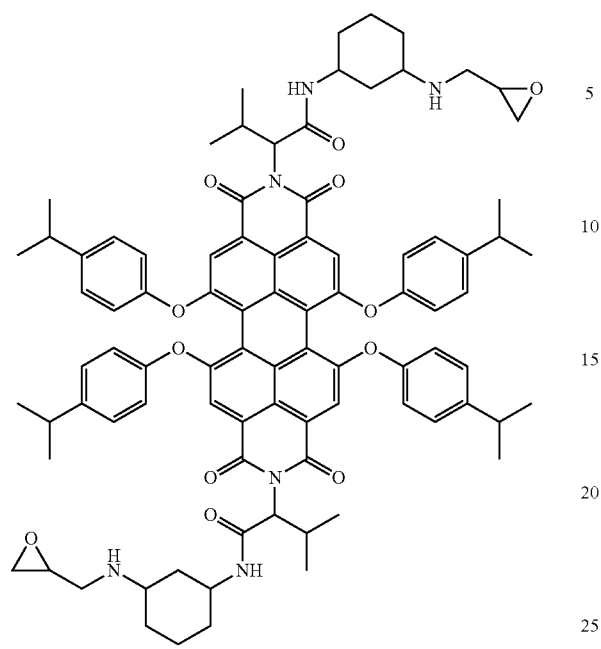
164
-continued
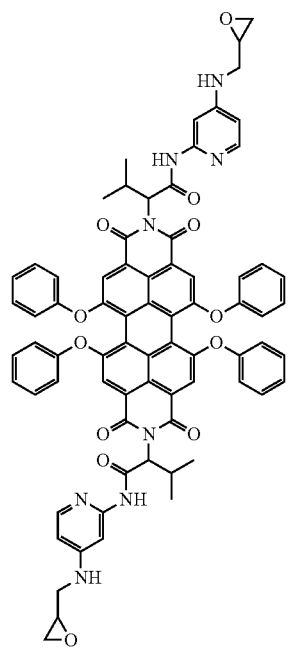
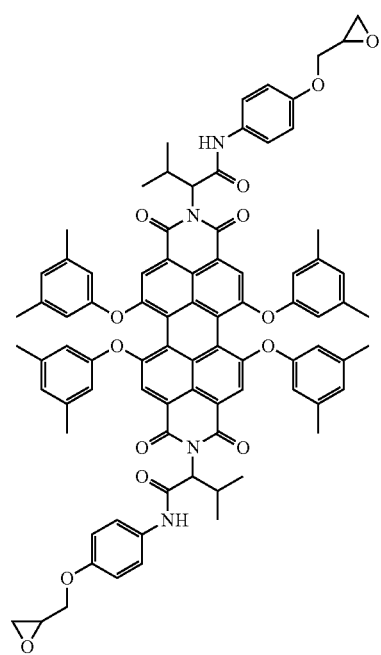
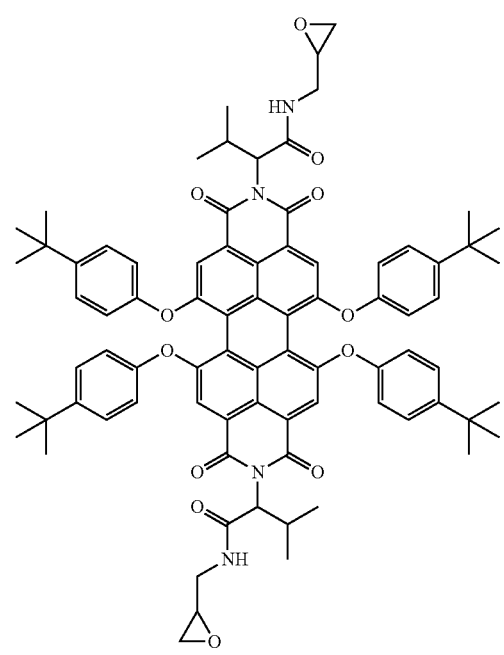

165
-continued
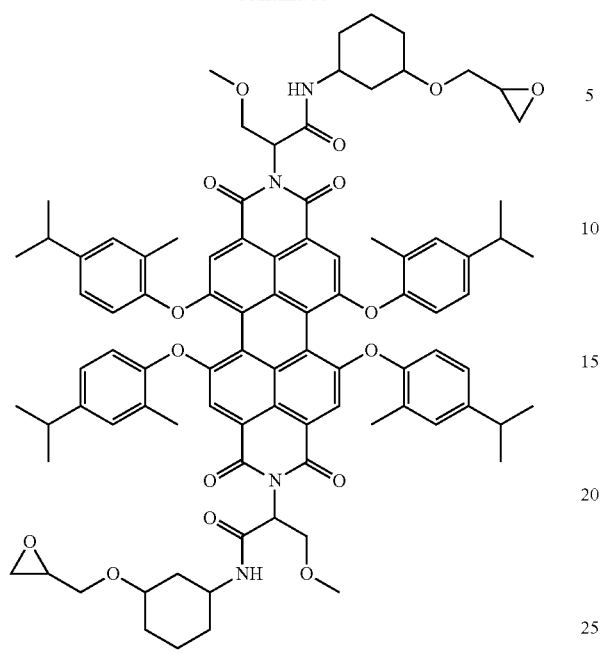
166
-continued
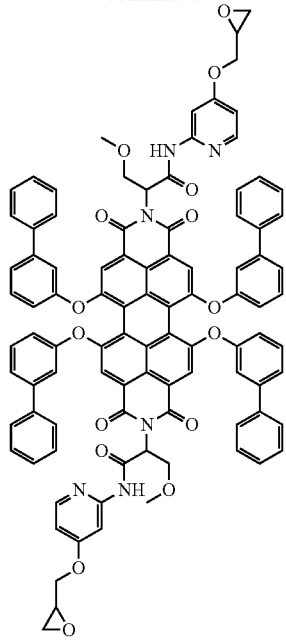
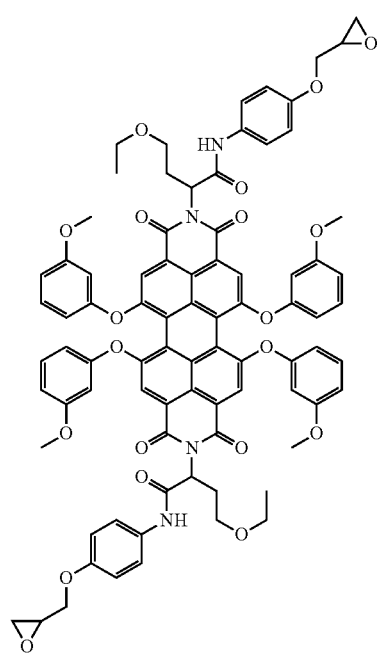
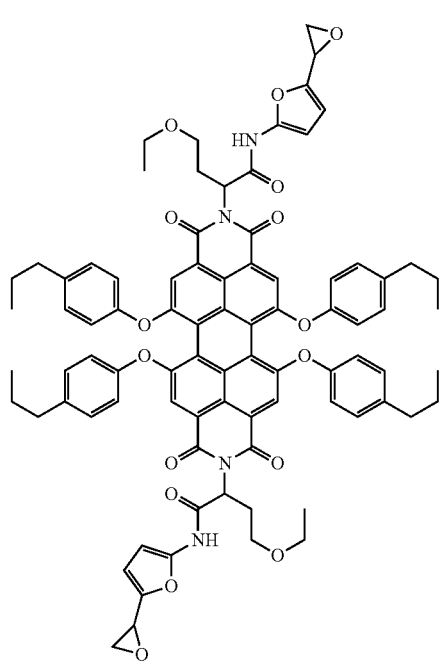

167
-continued
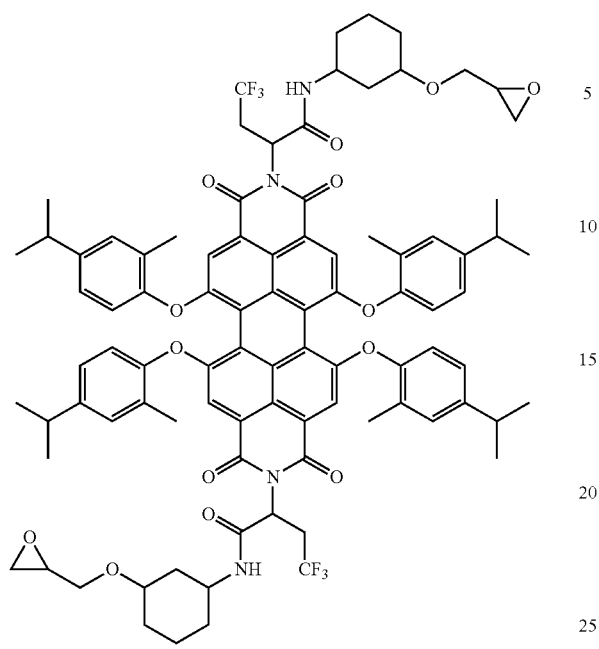
168
-continued
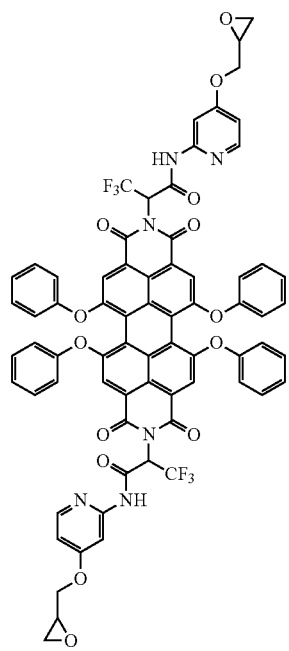
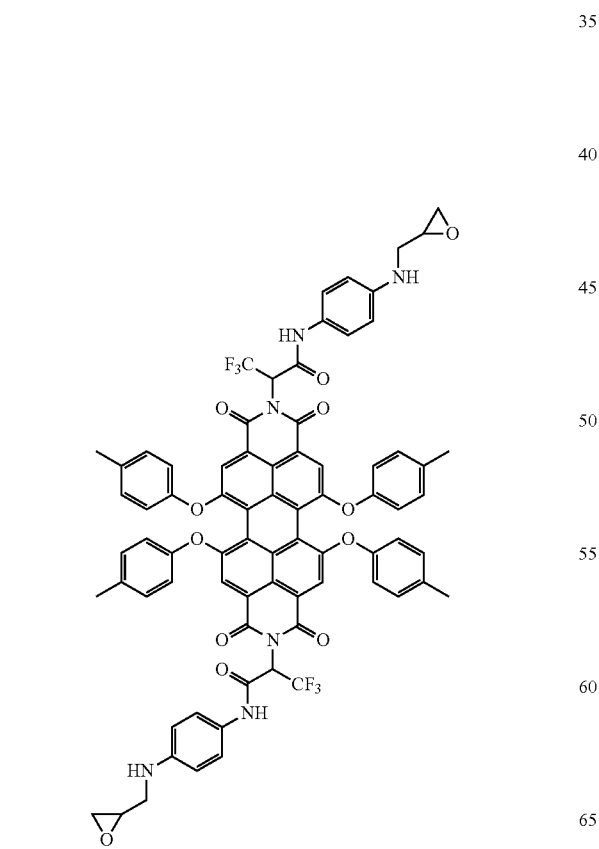
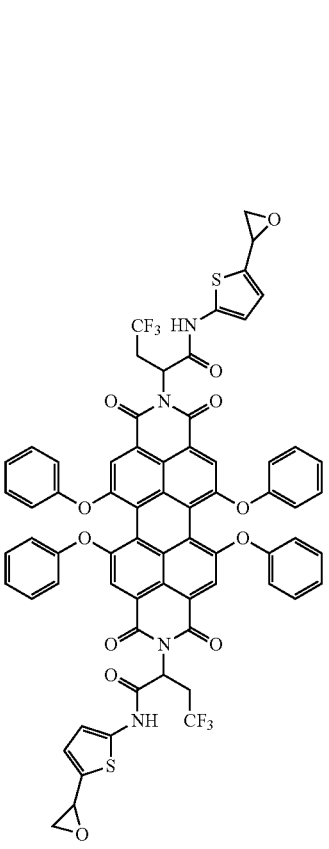

169
-continued
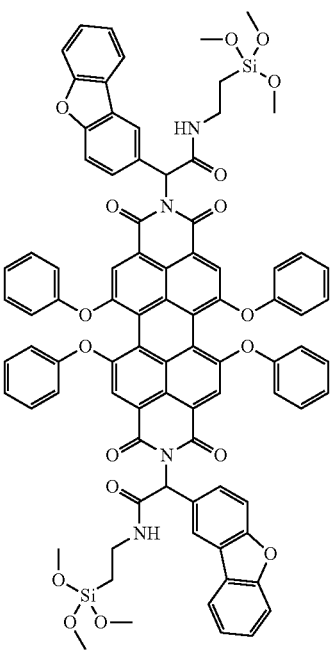
170
-continued
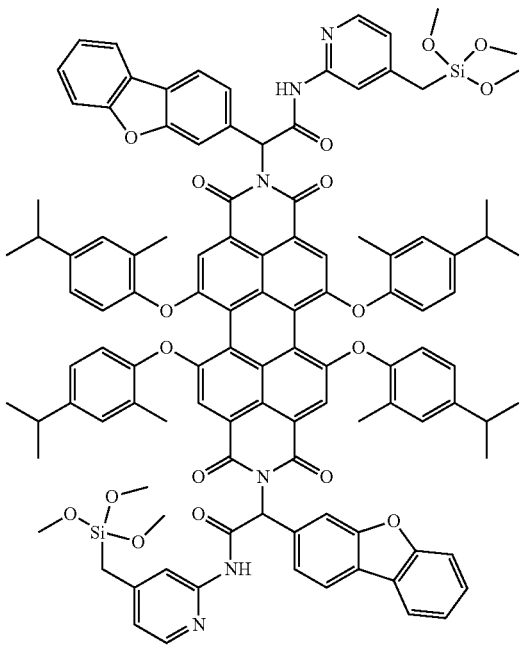
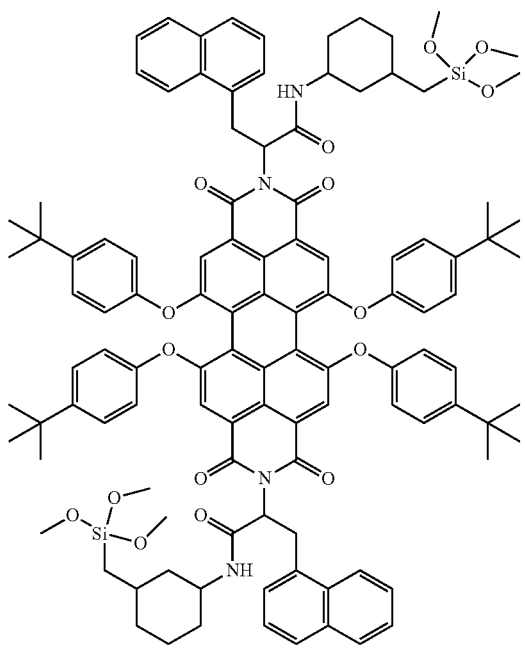
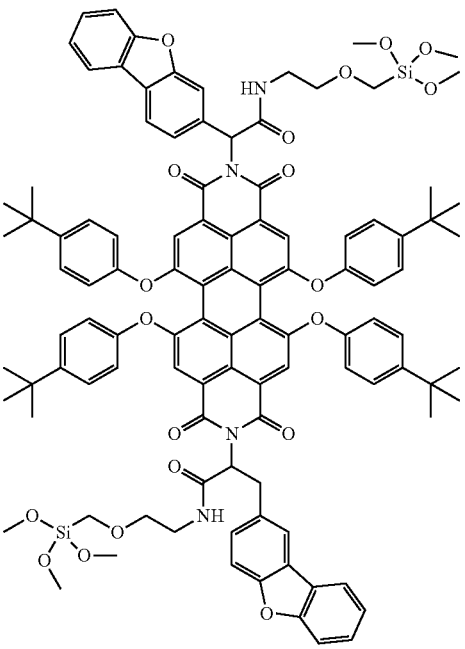

171
-continued
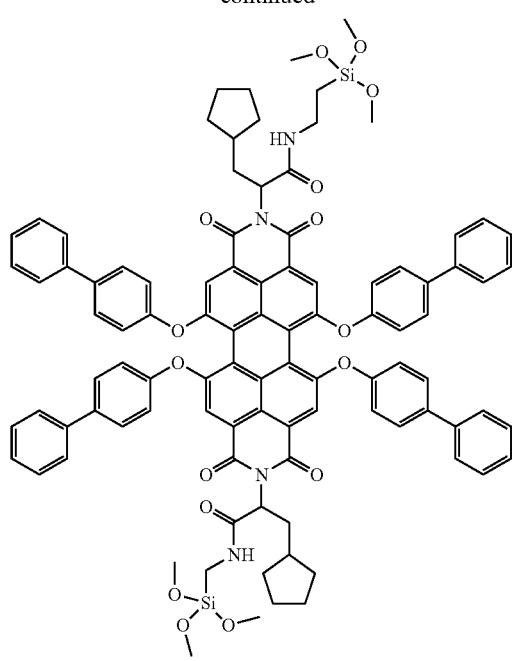
172
-continued
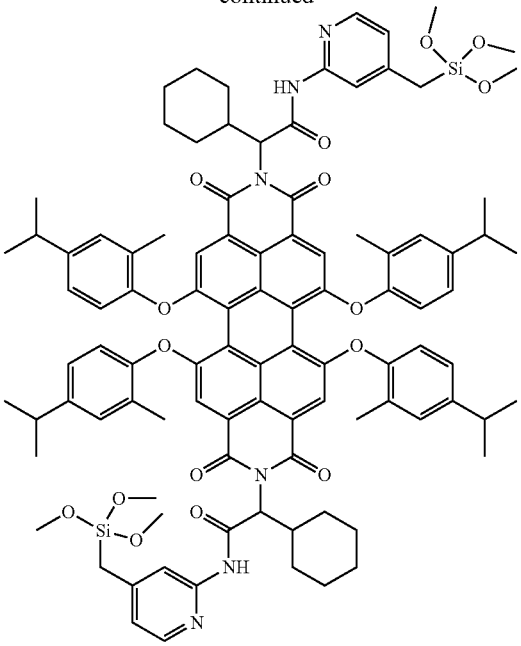
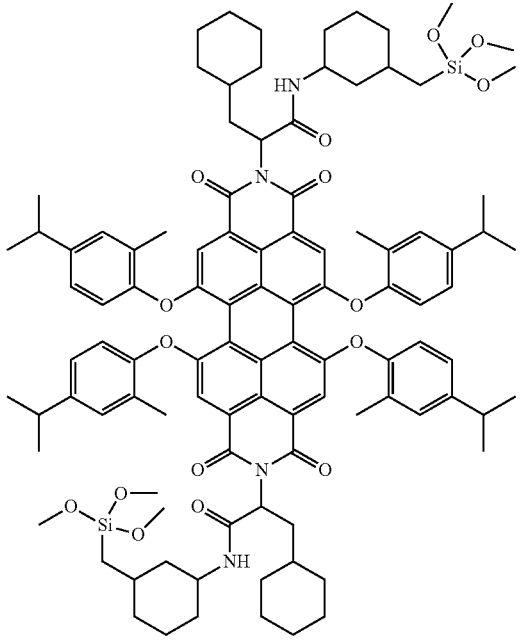
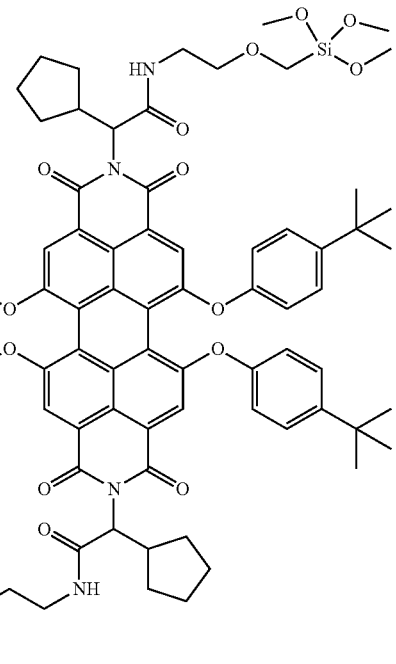

173
-continued
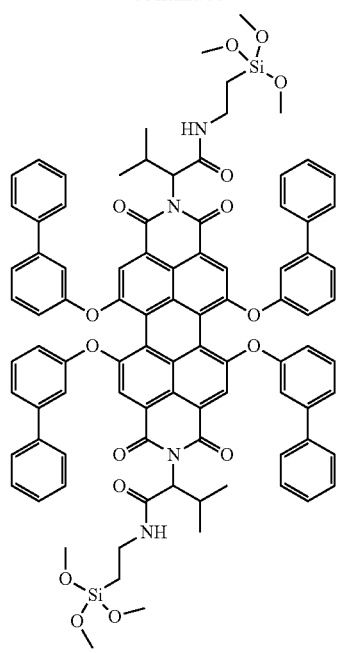
174
-continued
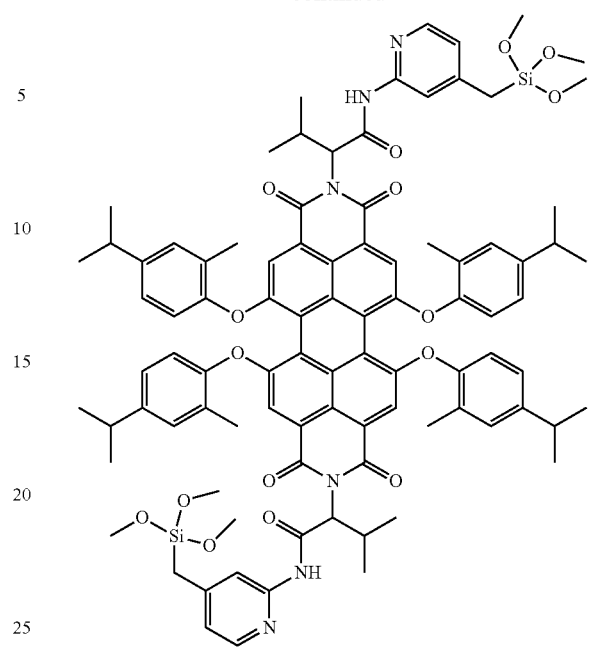
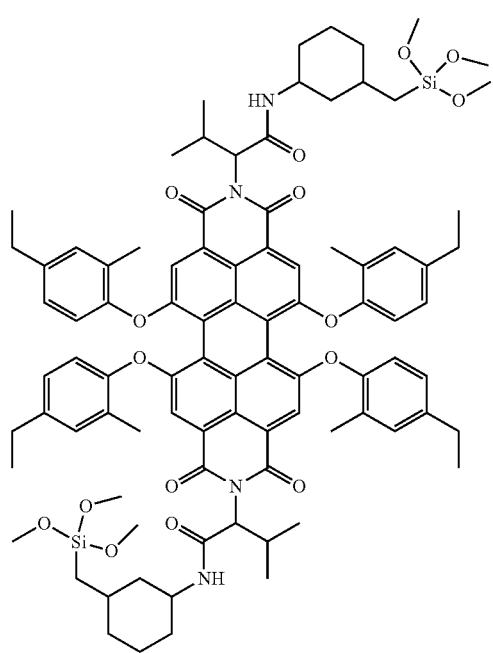
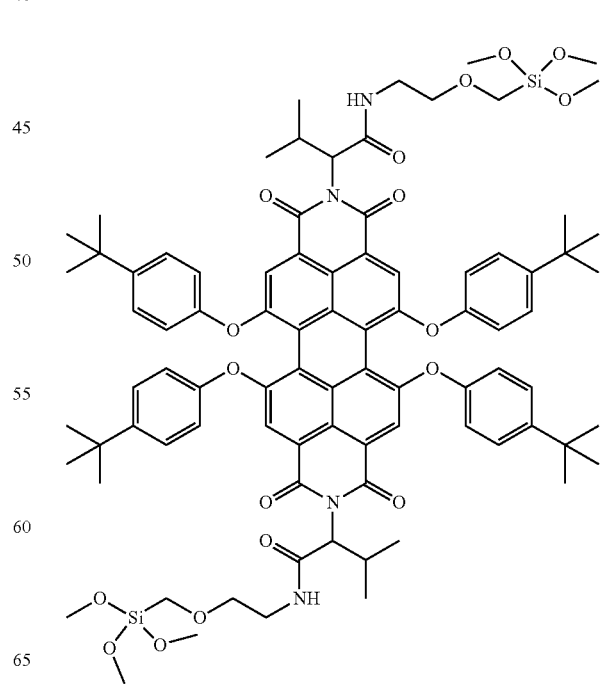

175
-continued
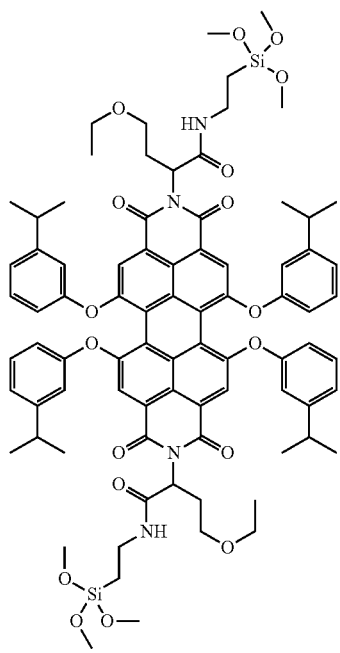
176
-continued
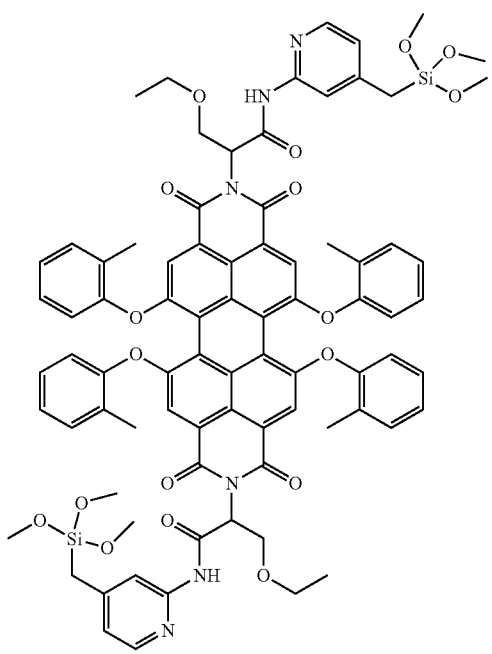
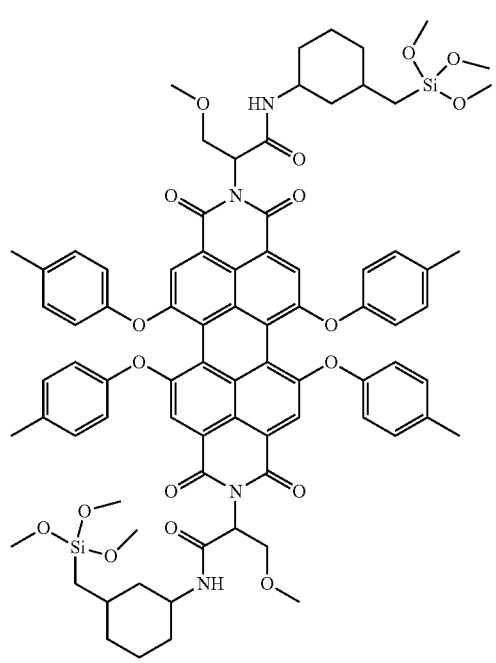
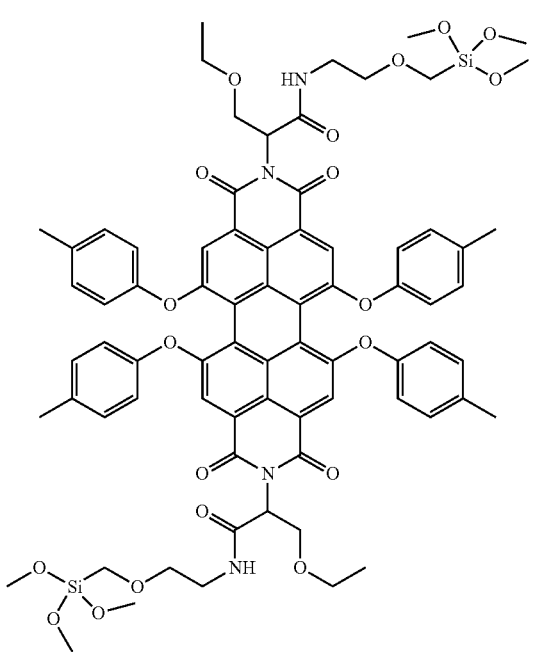

177
-continued
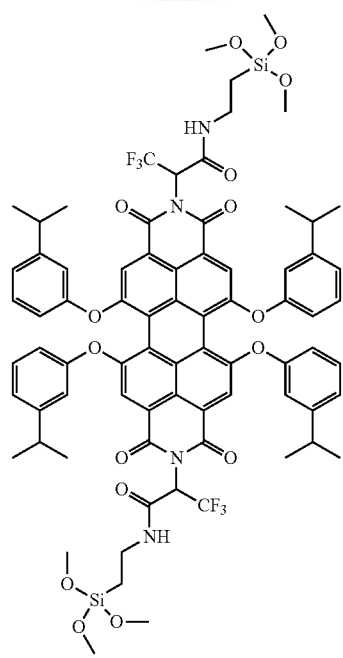
178
-continued
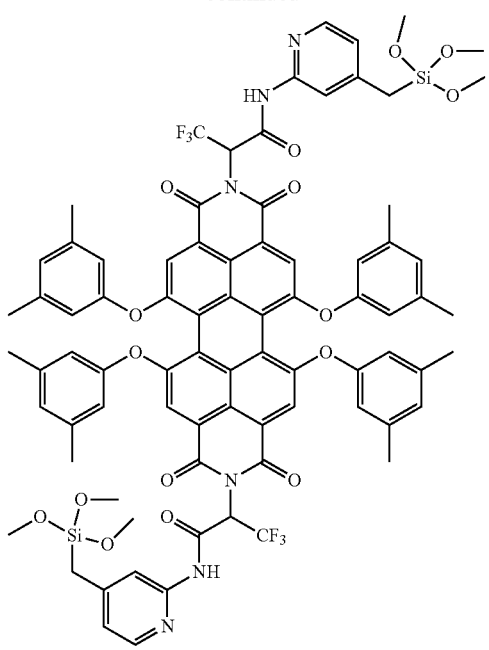
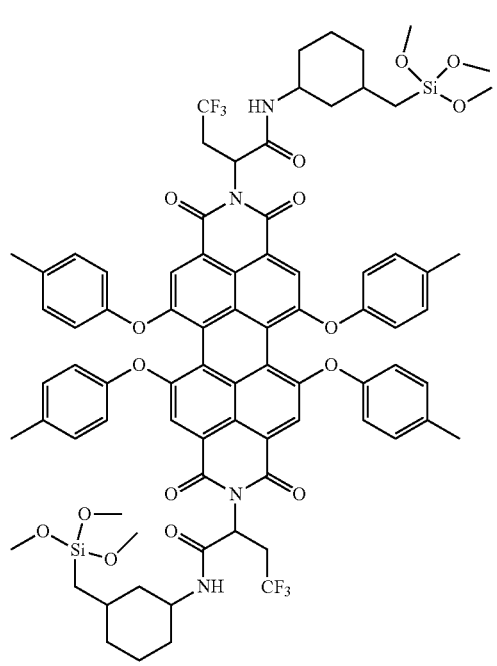

179
-continued
180
-continued
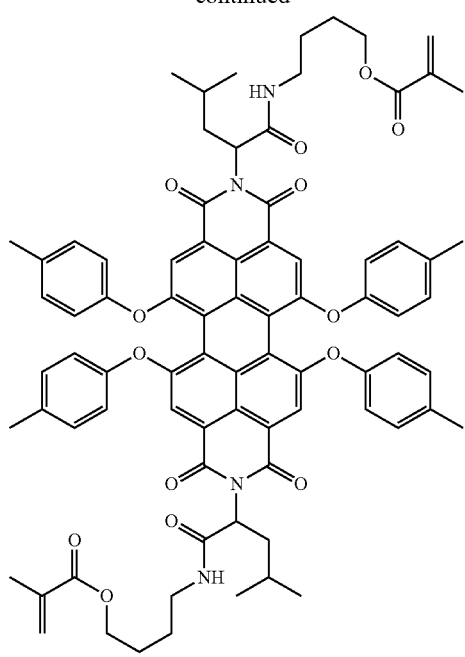
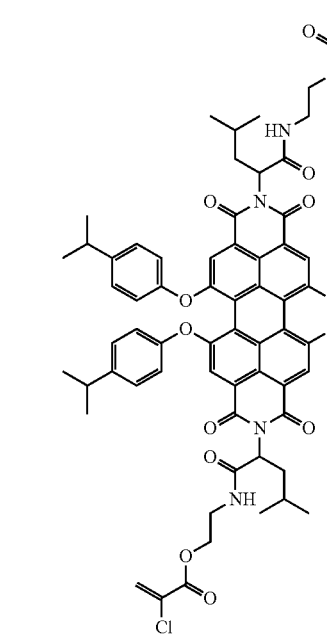
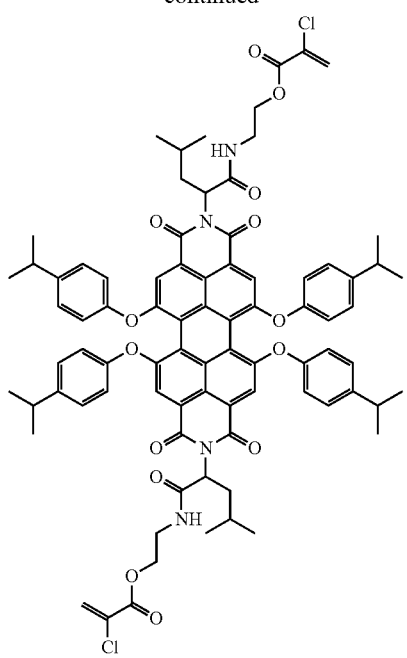
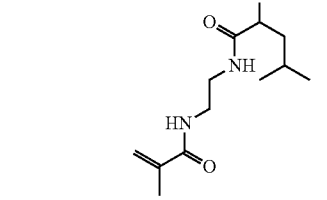

181
-continued
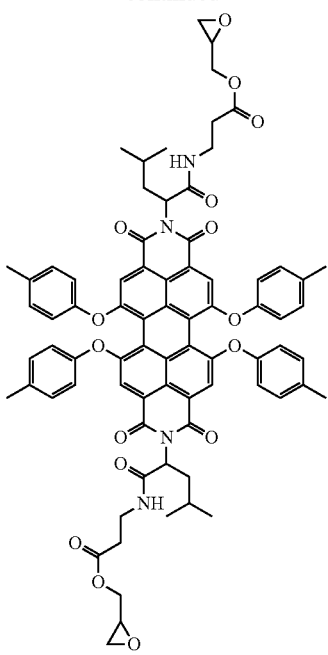
182
-continued
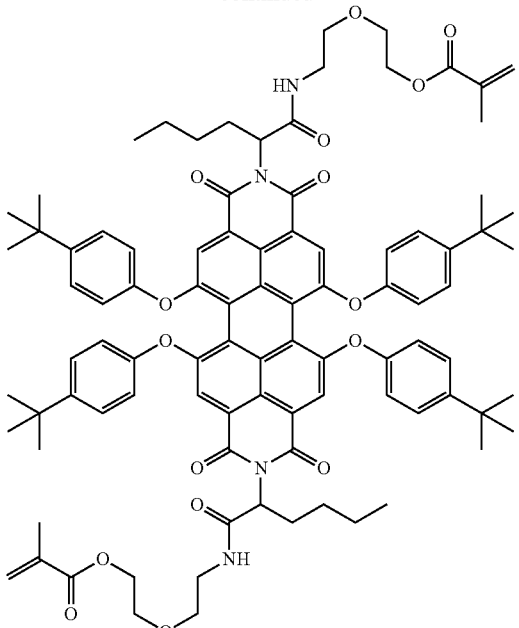
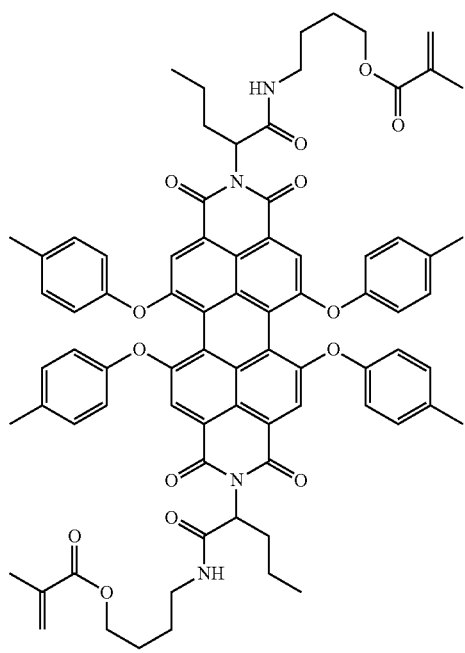
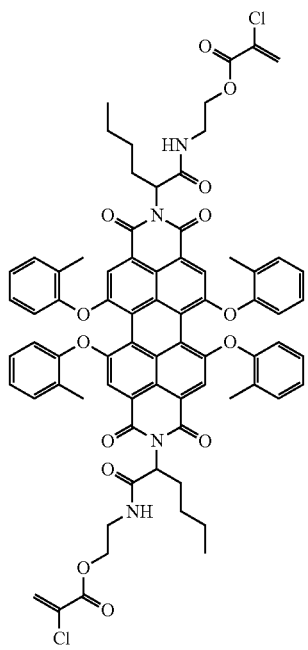

183
-continued
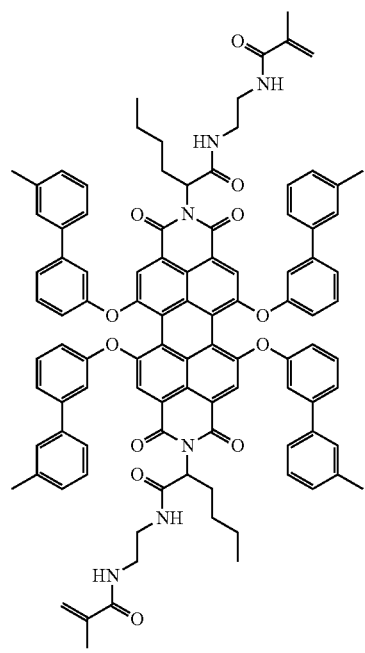
184
-continued
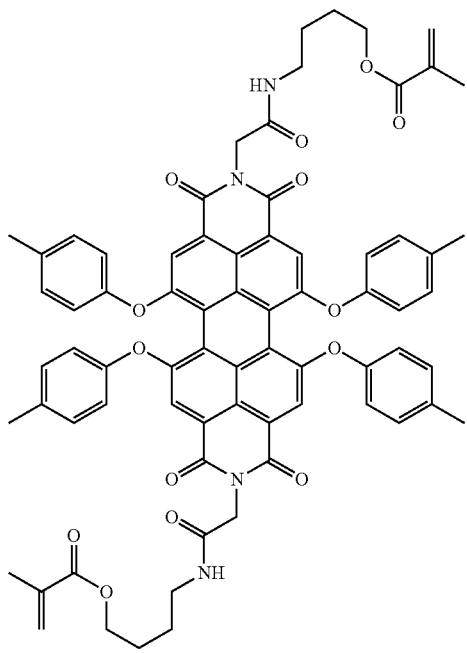
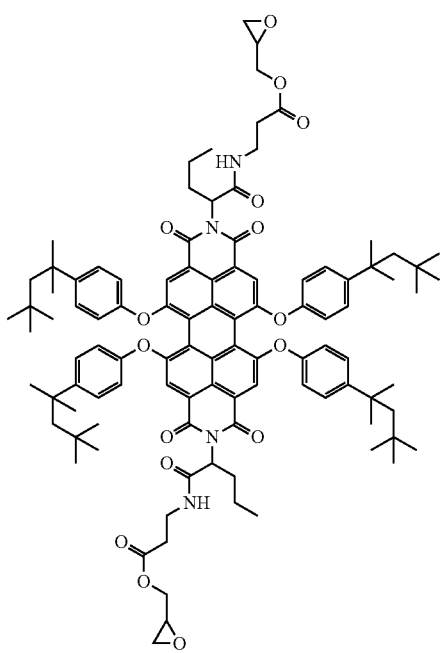
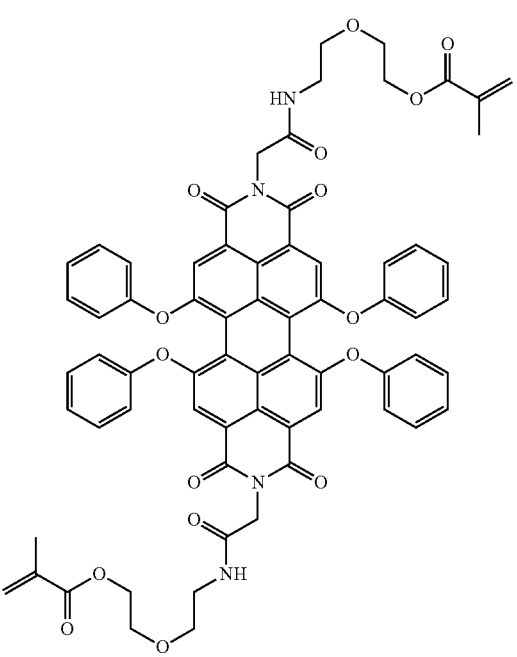

185
-continued
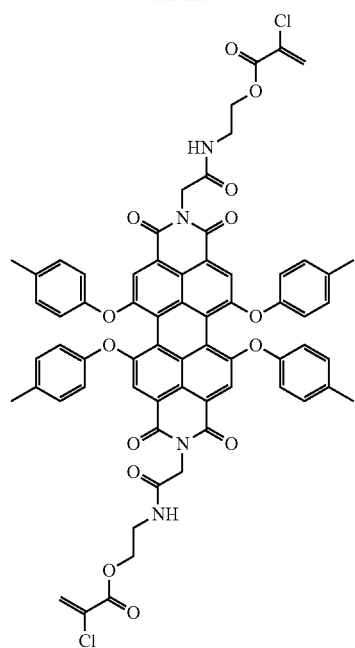
186
-continued
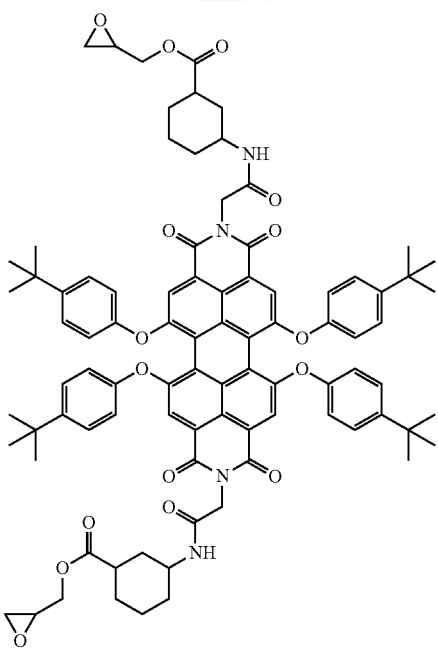
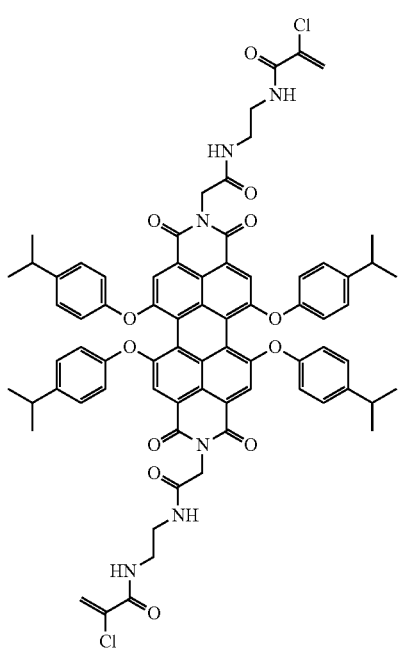
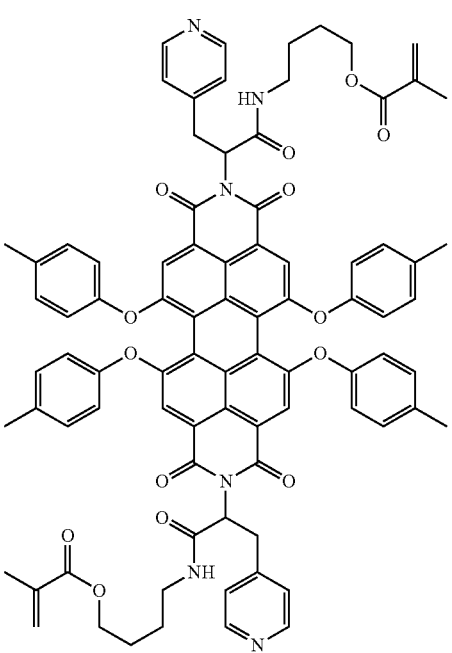

187
-continued
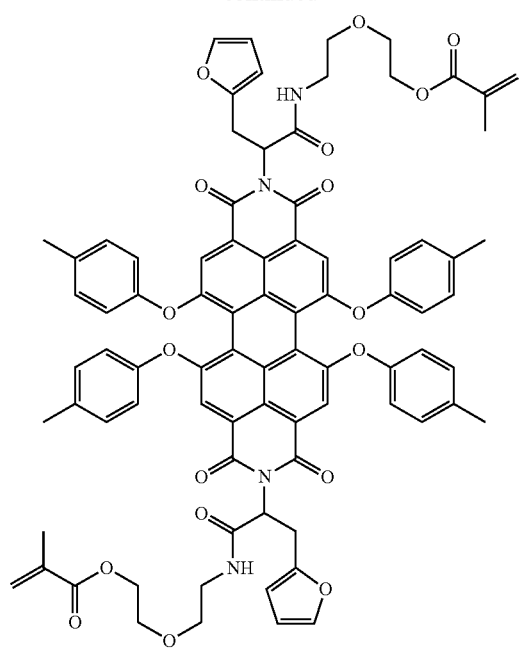
188
-continued
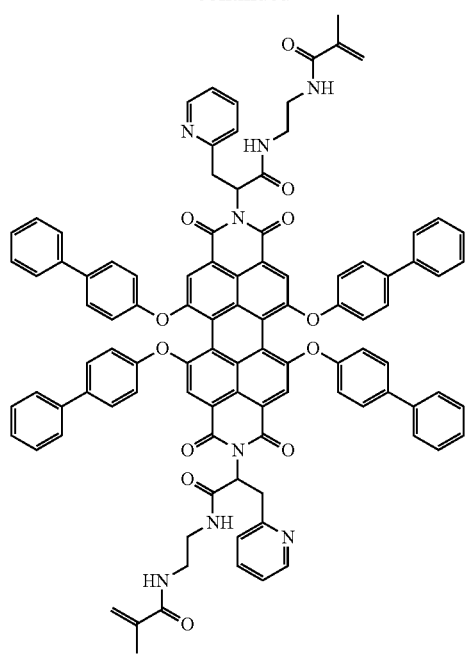
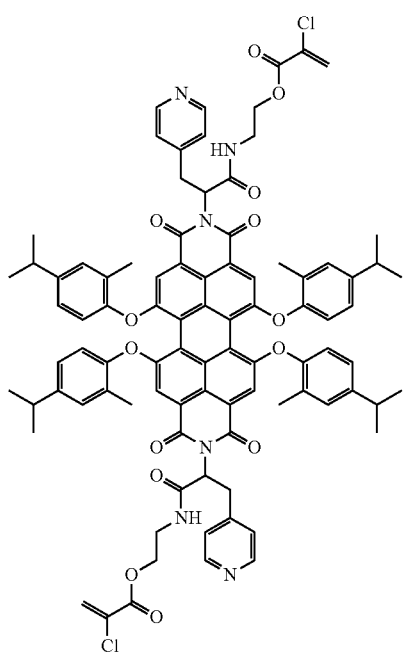
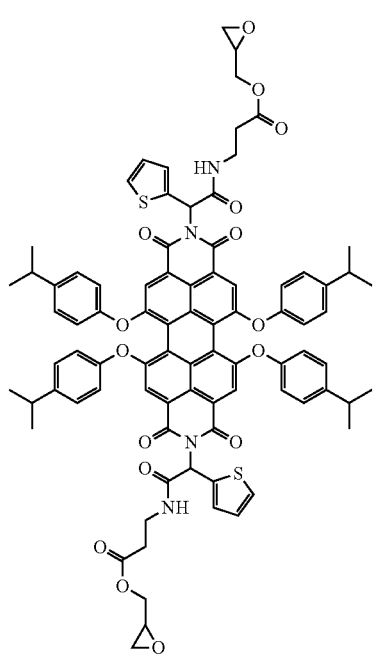

189
-continued
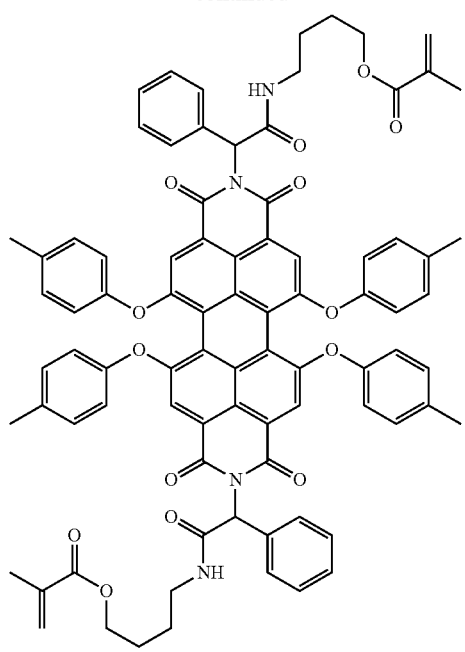
190
-continued
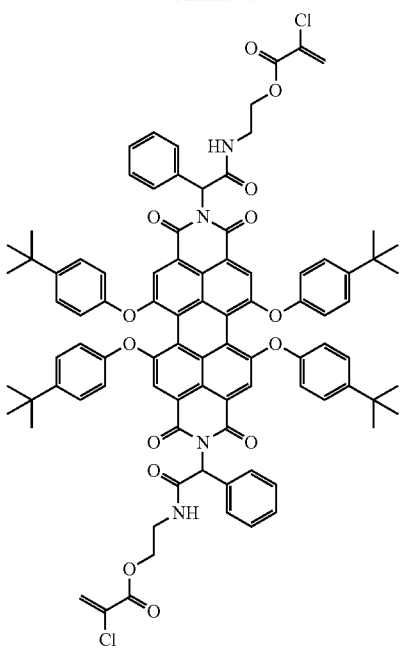
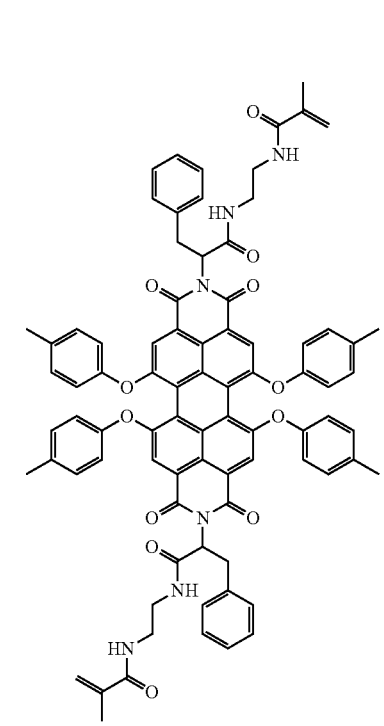

191
-continued
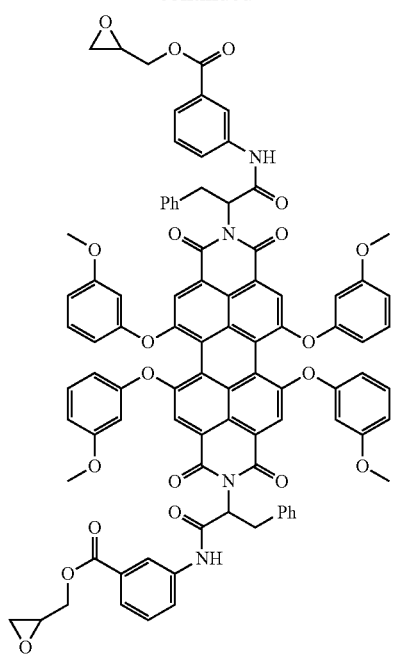
192
-continued
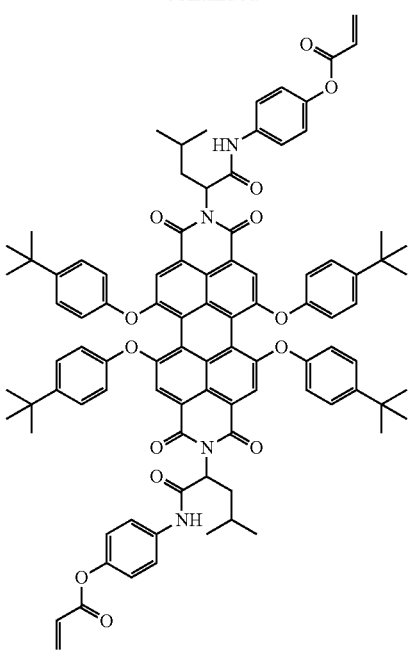
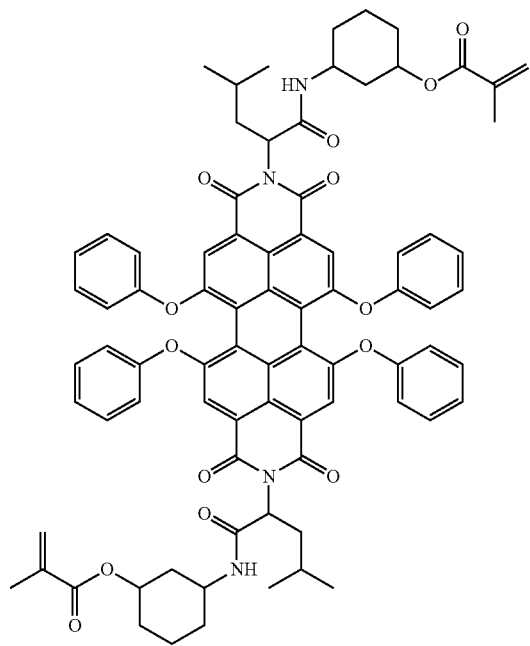
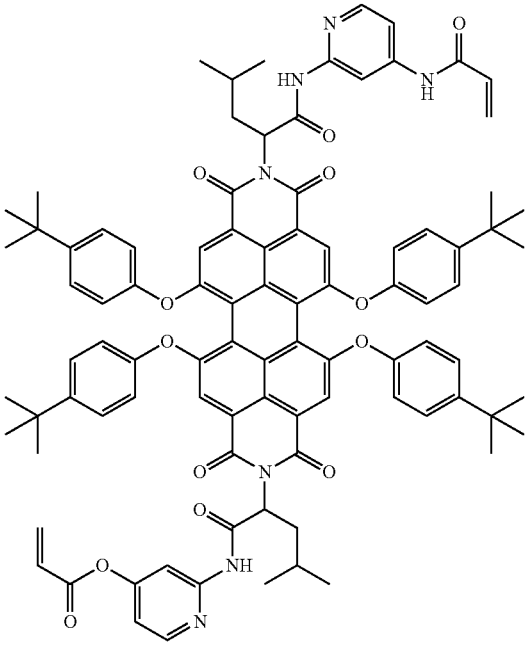

193
-continued
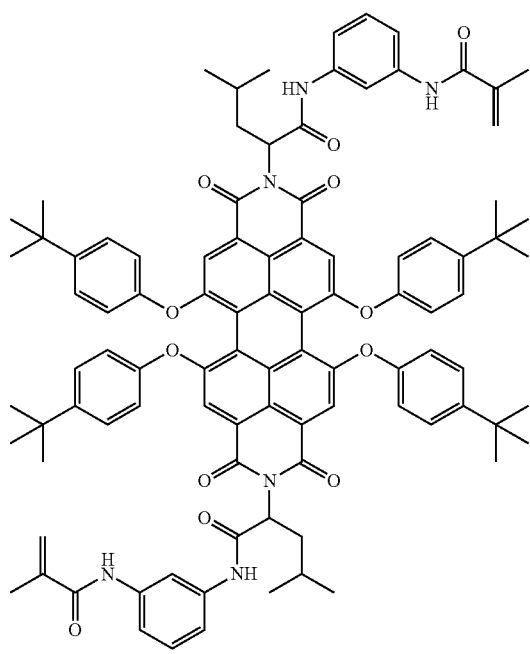
194
-continued
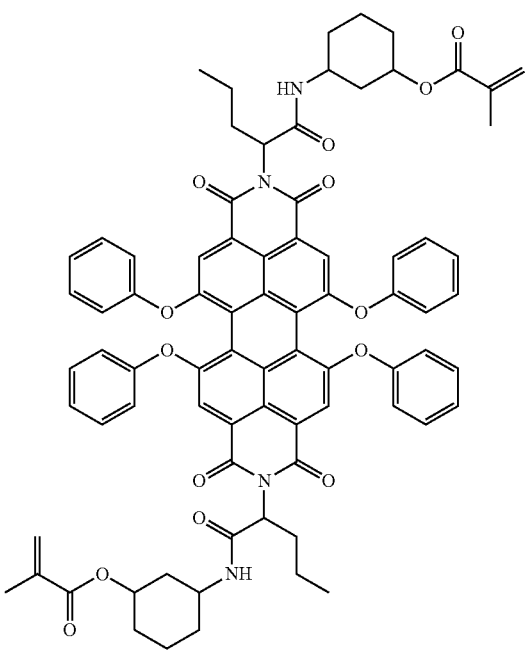
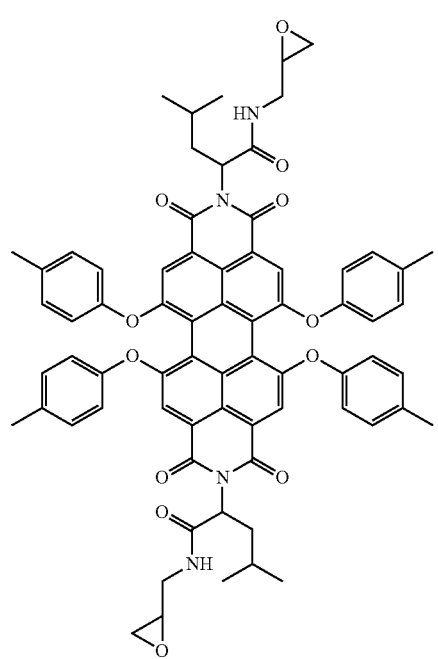
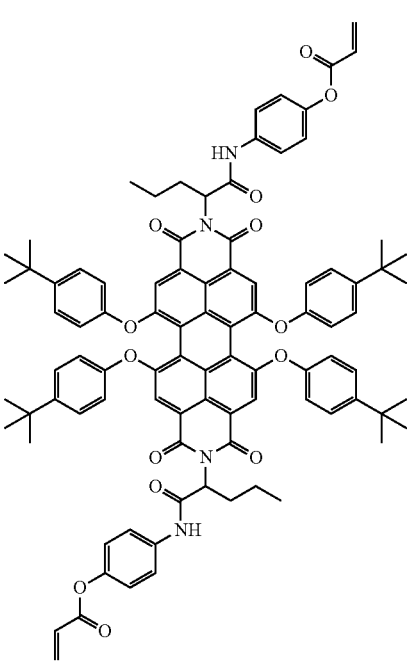

195
-continued
196
-continued
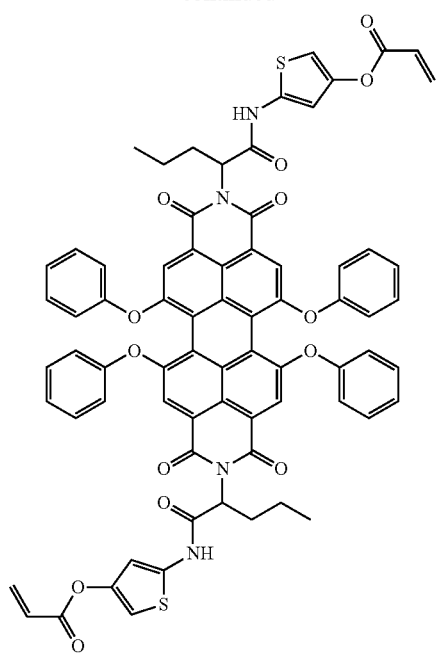
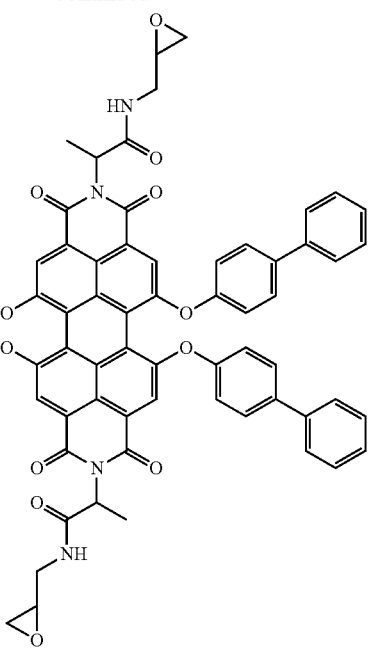

197
-continued
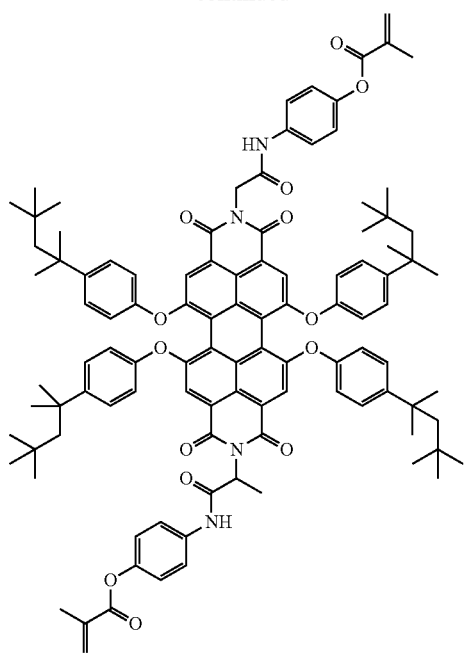
198
-continued
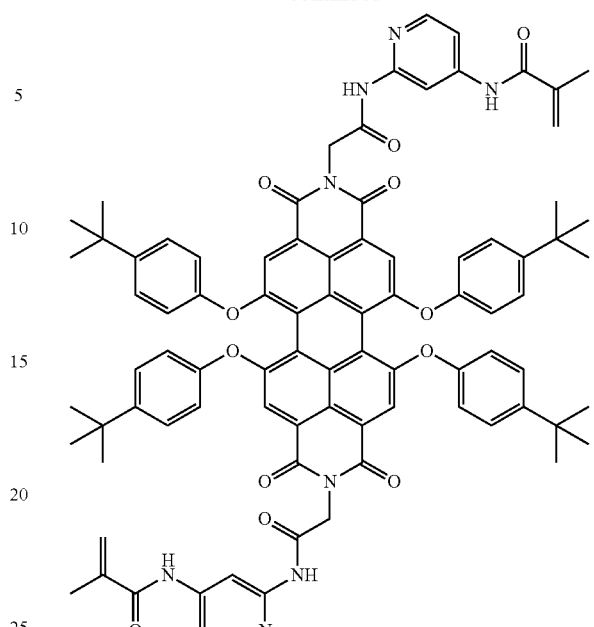
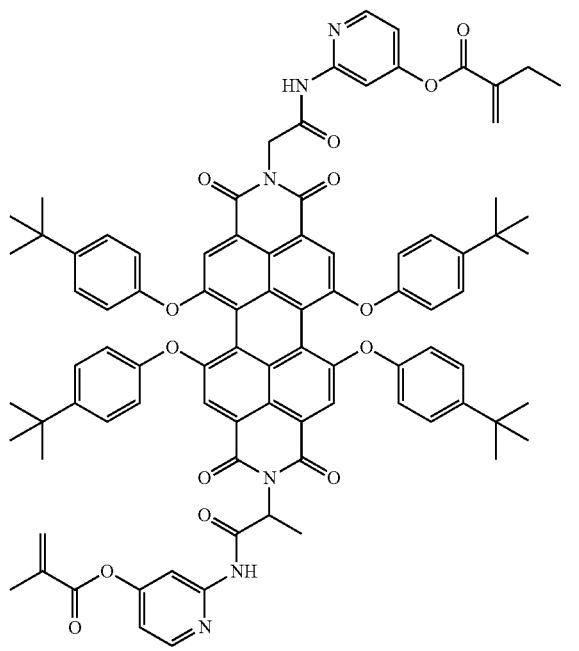
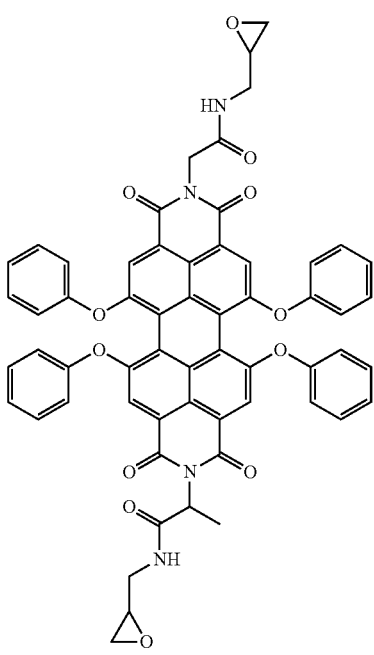

199
-continued
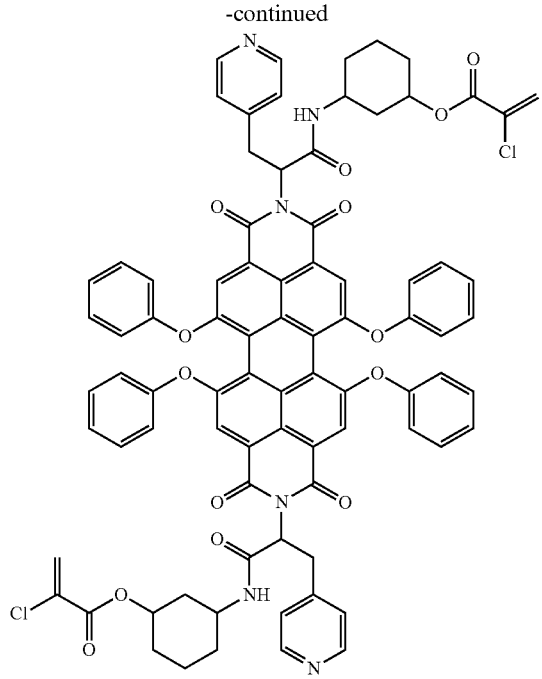
200
-continued
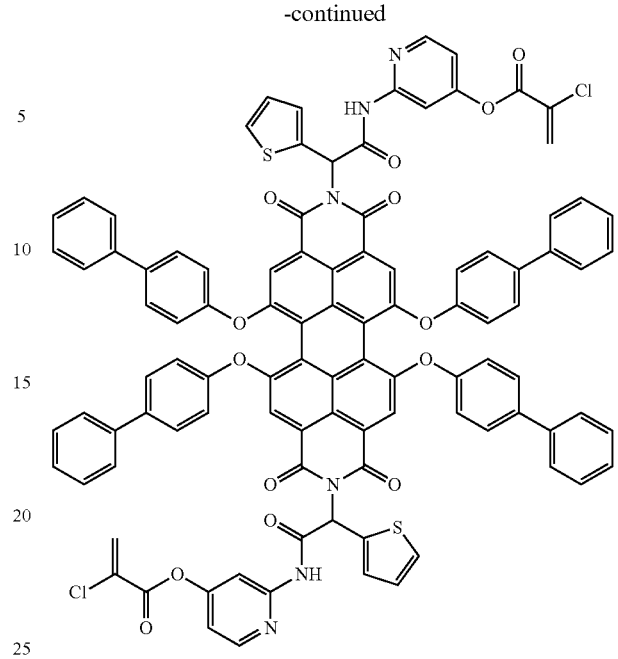
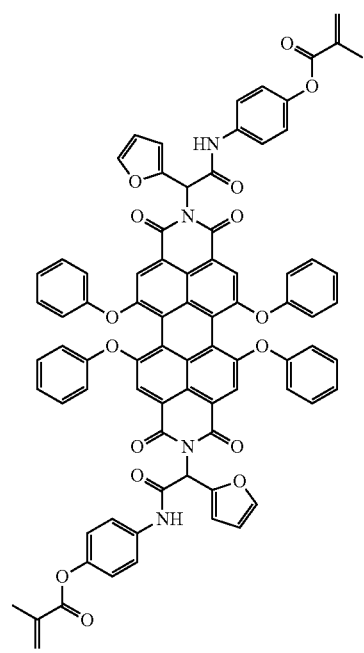
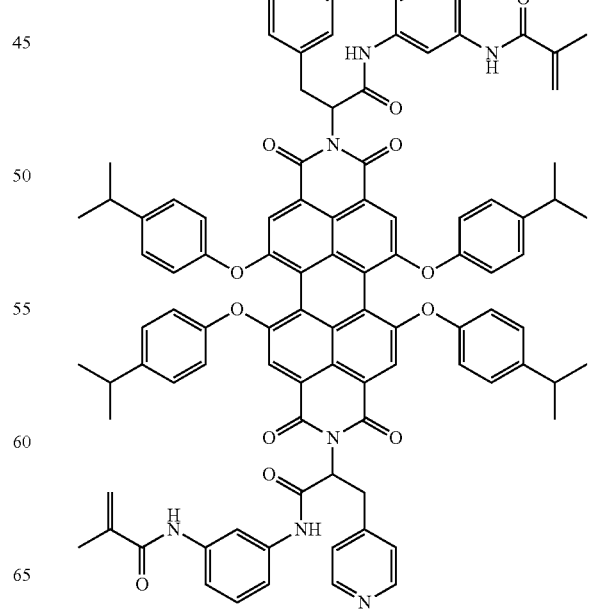

201
-continued
202
-continued
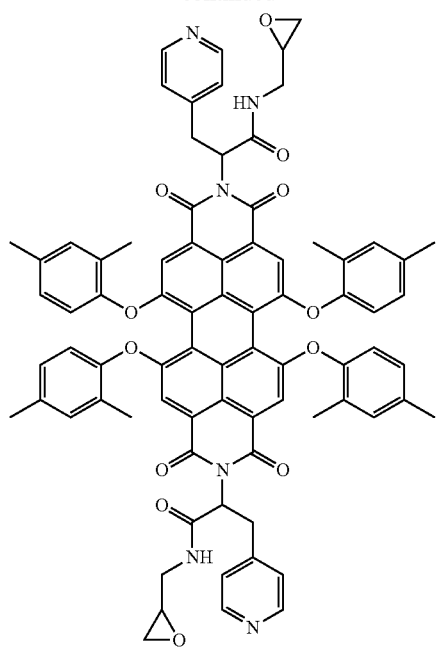
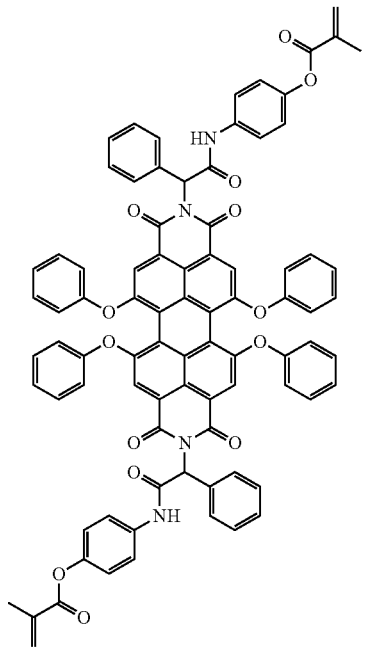

203
-continued
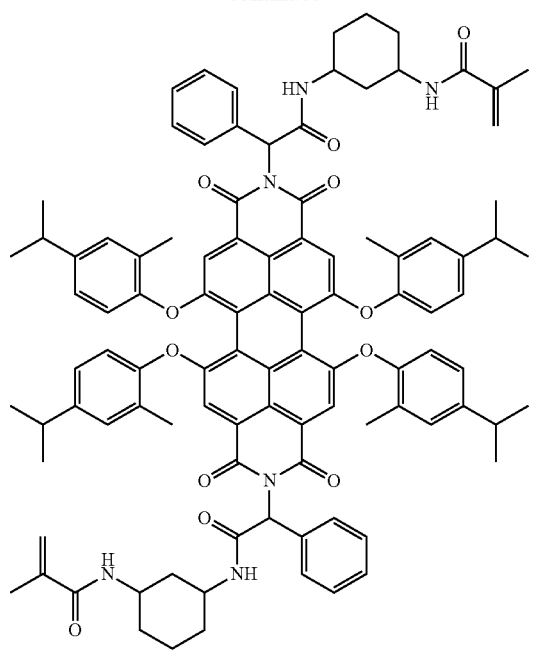
204
-continued
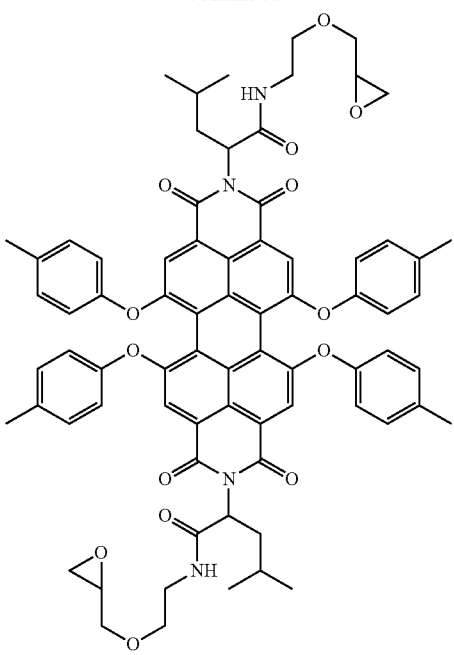
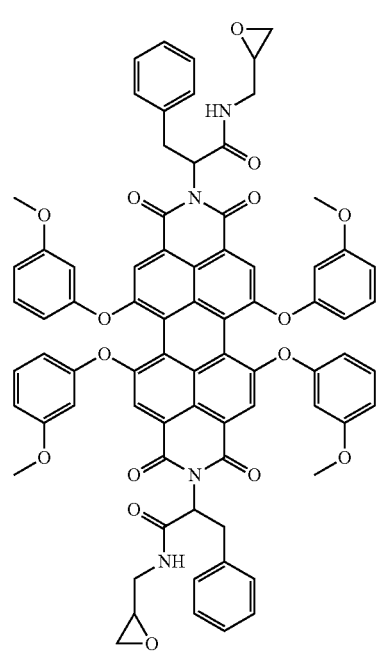
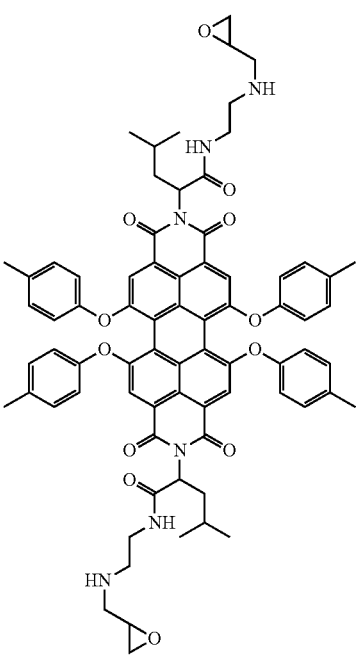

205
-continued
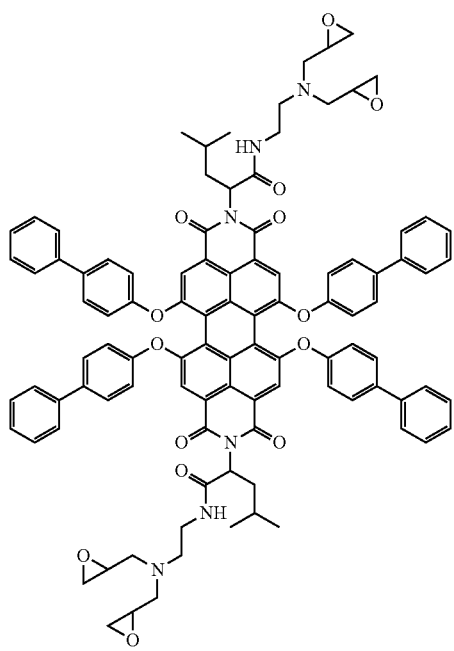
206
-continued
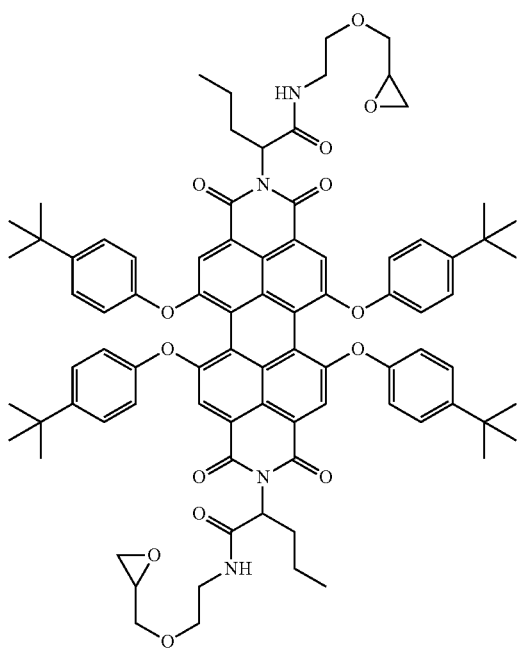
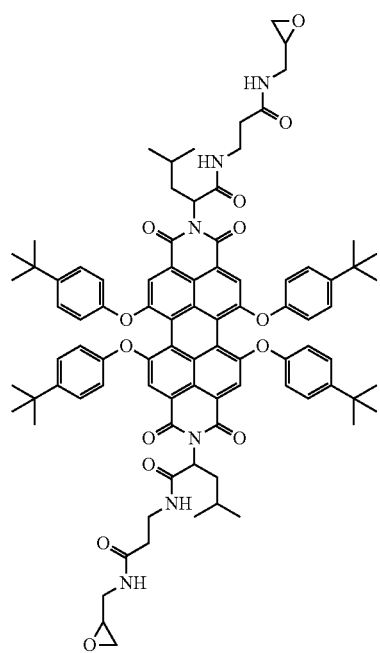
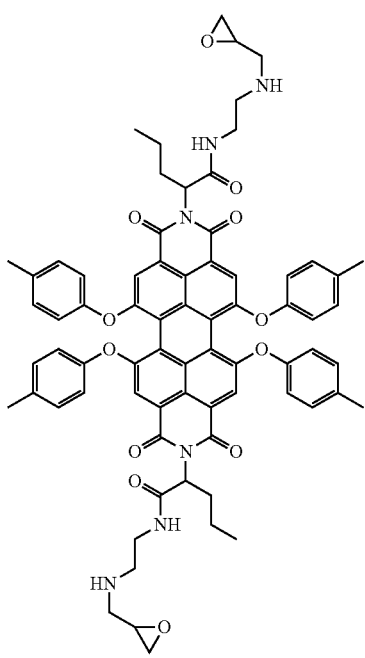

207
-continued
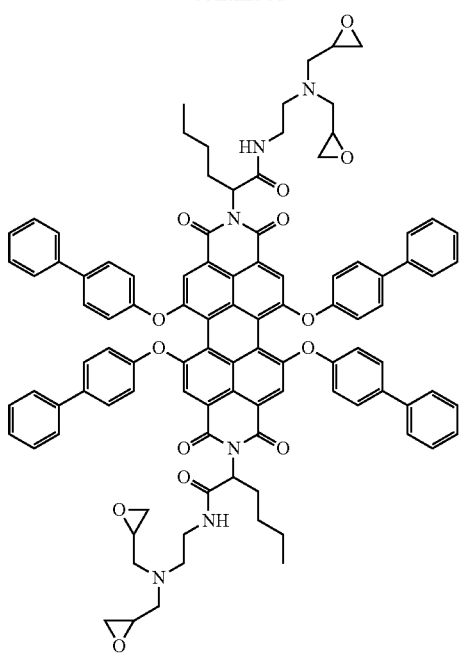
208
-continued
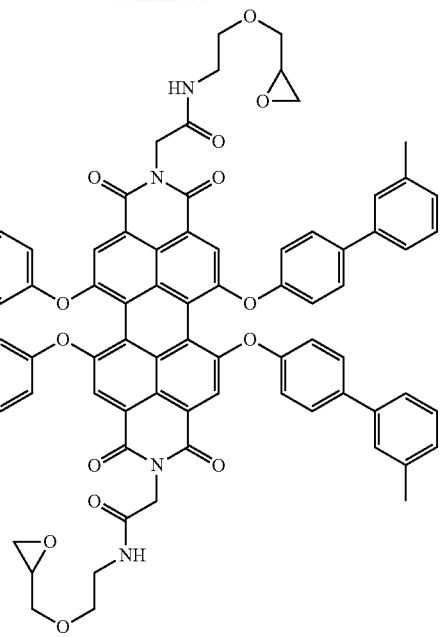
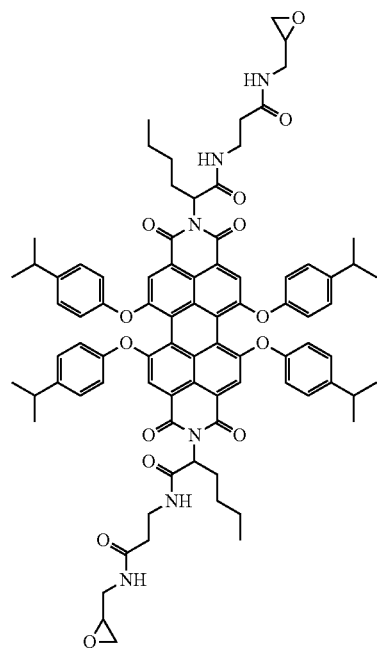
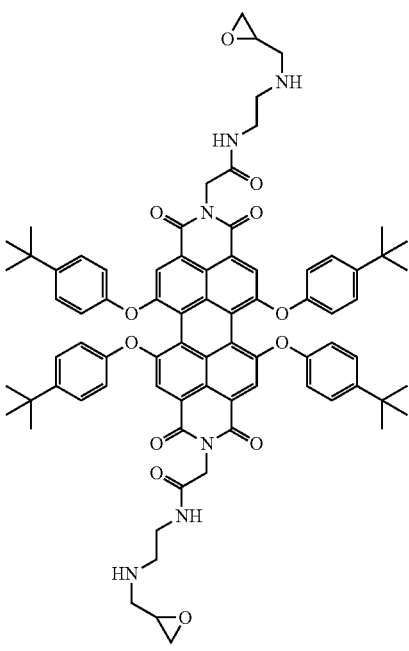

209
-continued
210
-continued
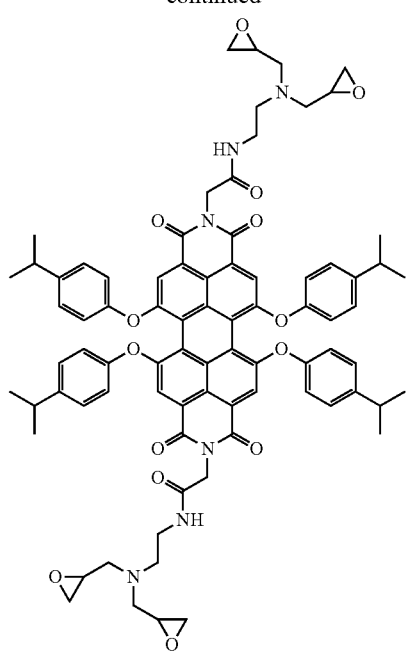
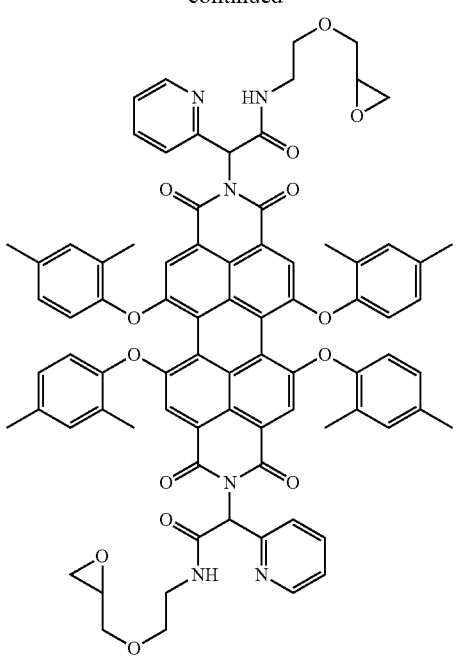

211
-continued
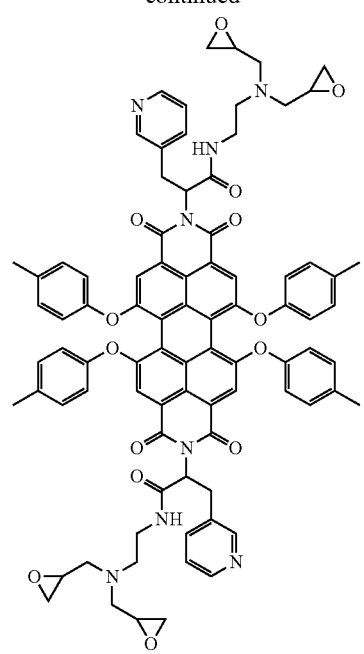
212
-continued
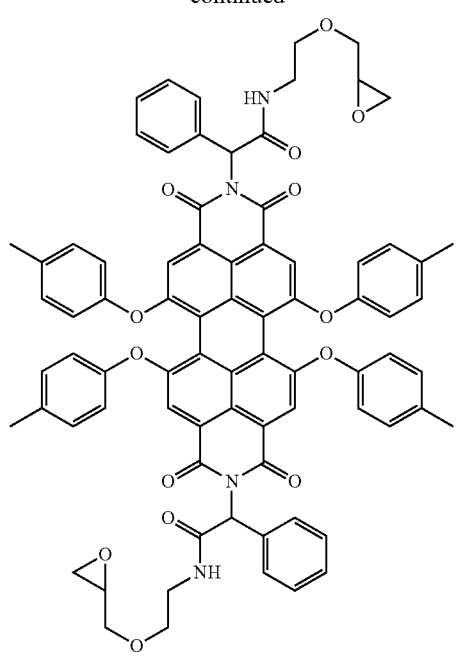
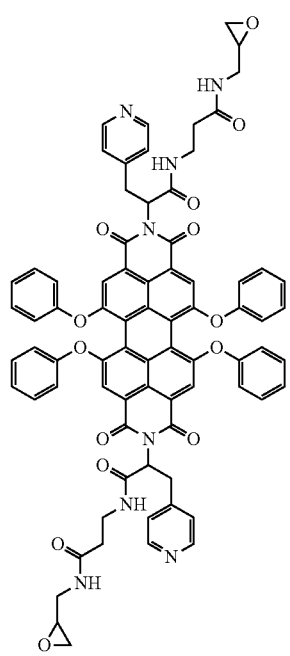
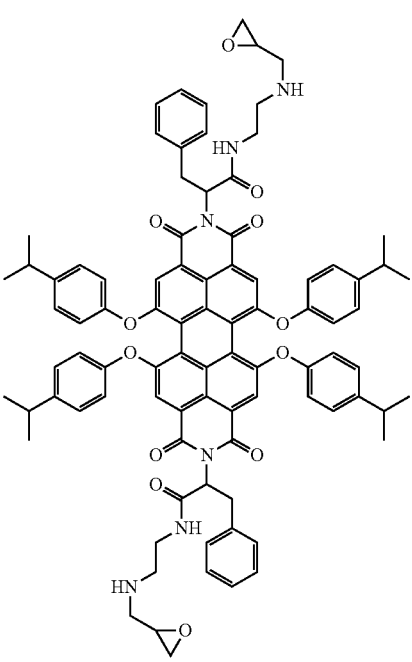

213
-continued
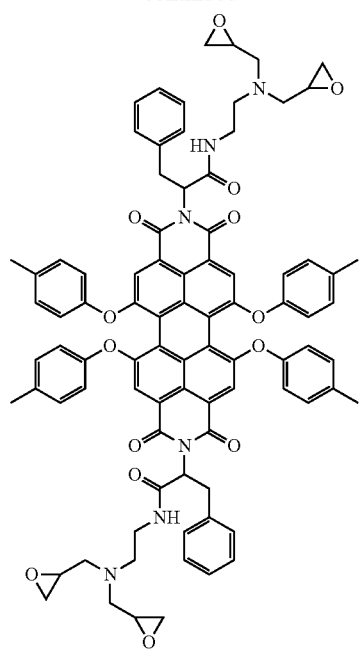
214
-continued
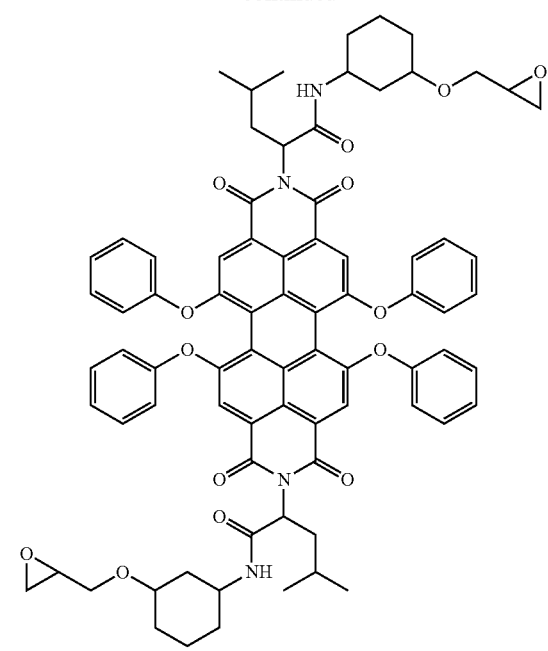
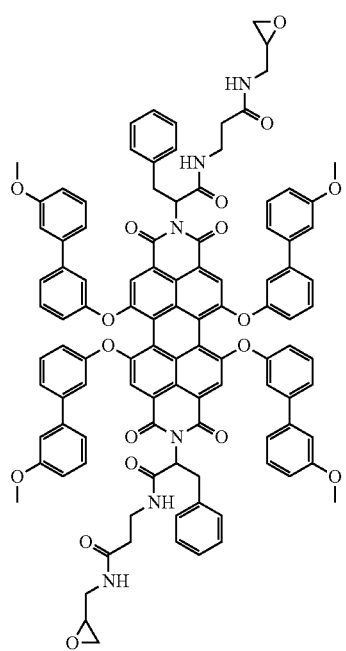
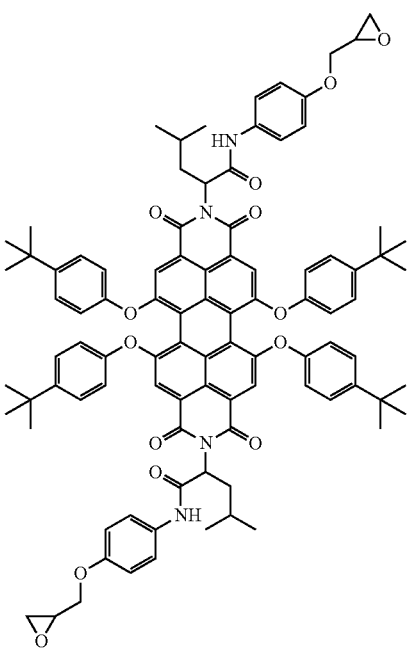

215
-continued
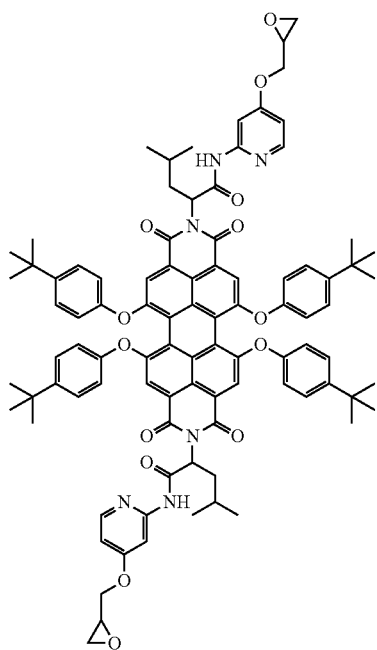
216
-continued
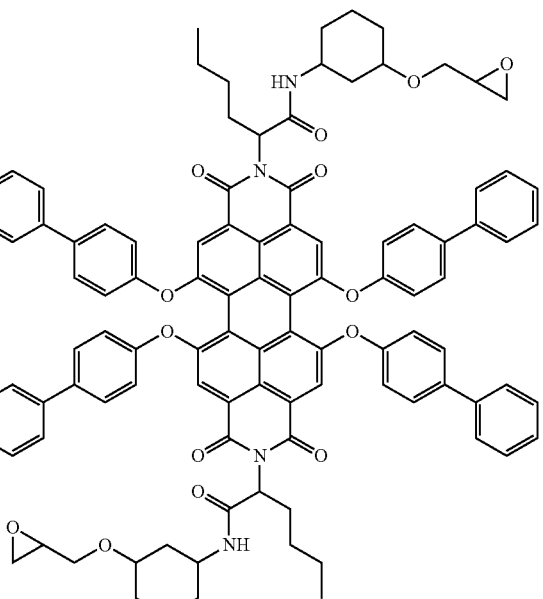
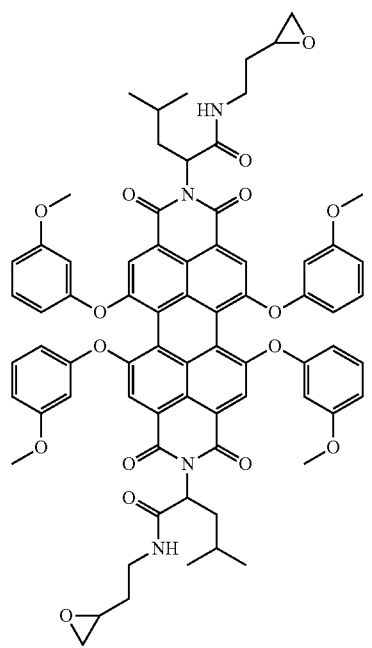
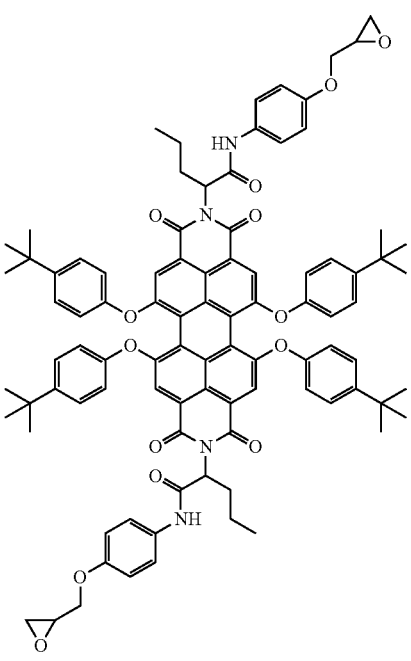

217
-continued
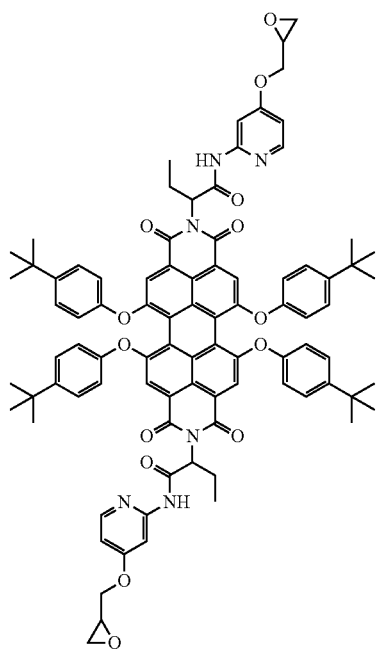
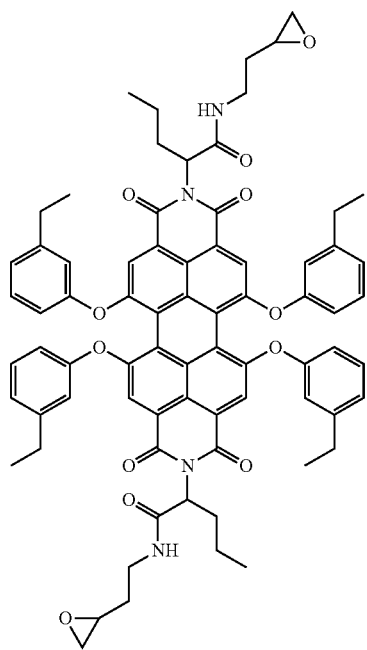
218
-continued
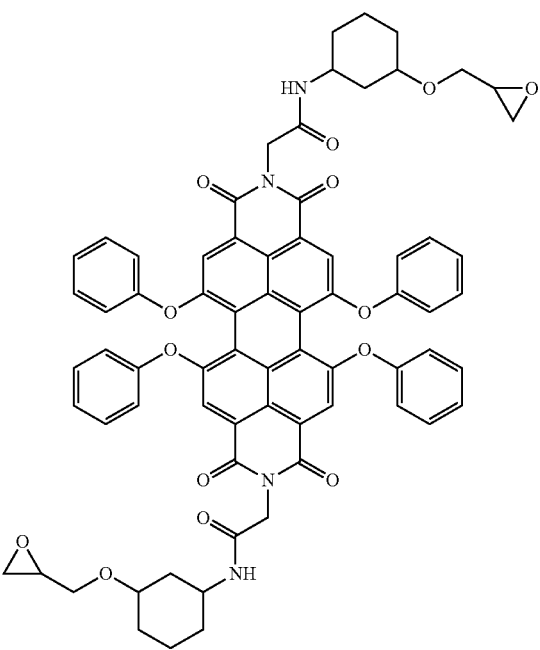
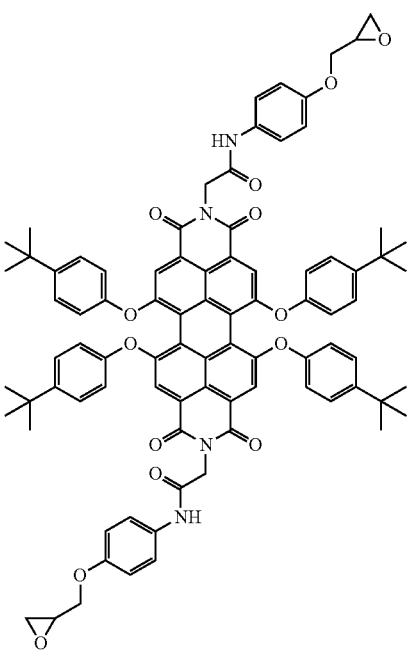

219
-continued
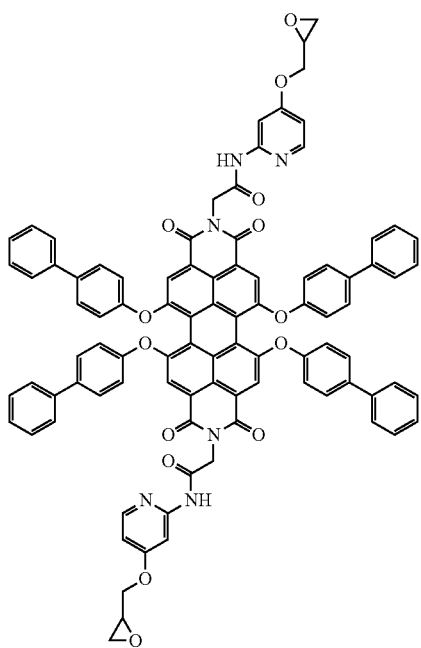
220
-continued
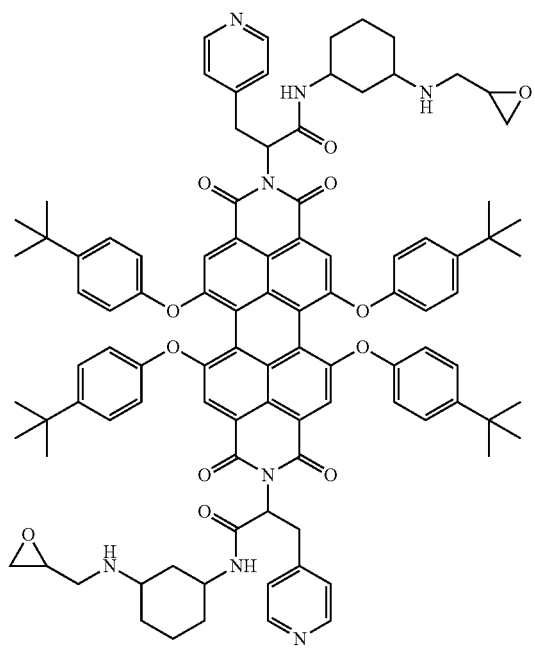
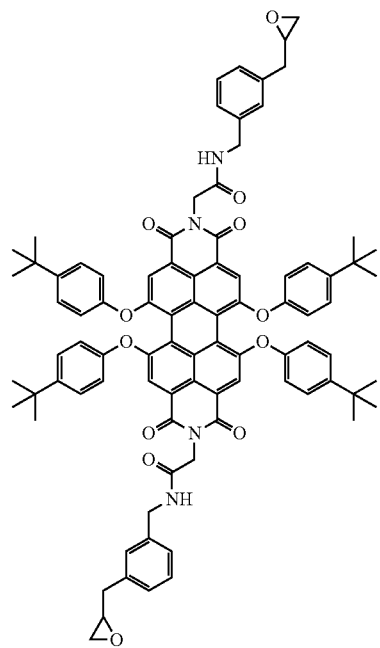
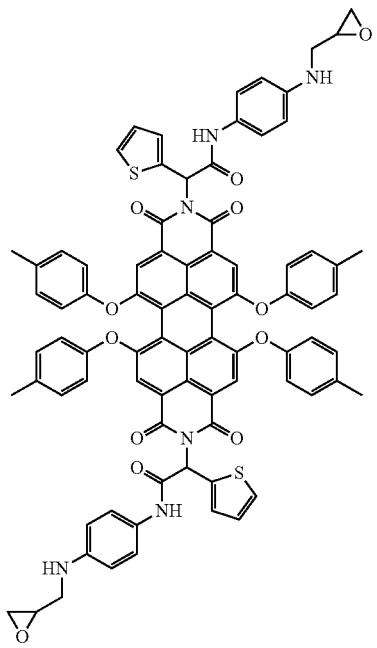

221
-continued
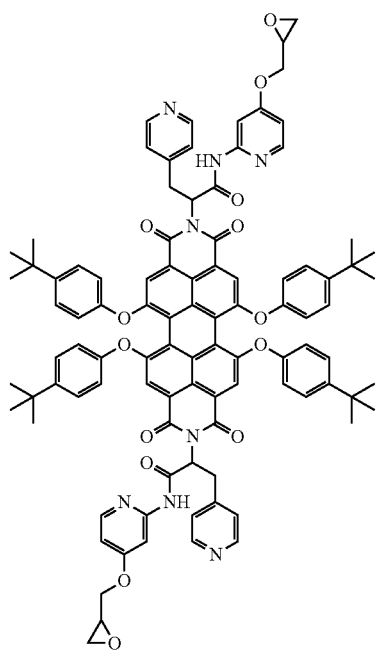
222
-continued
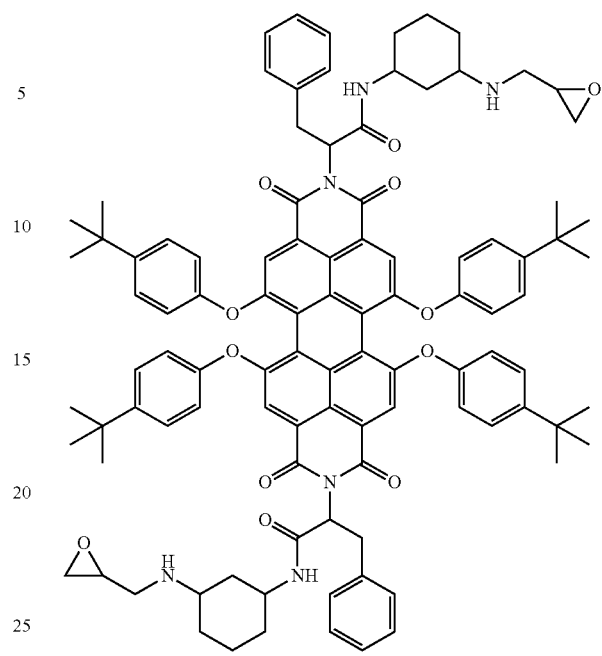
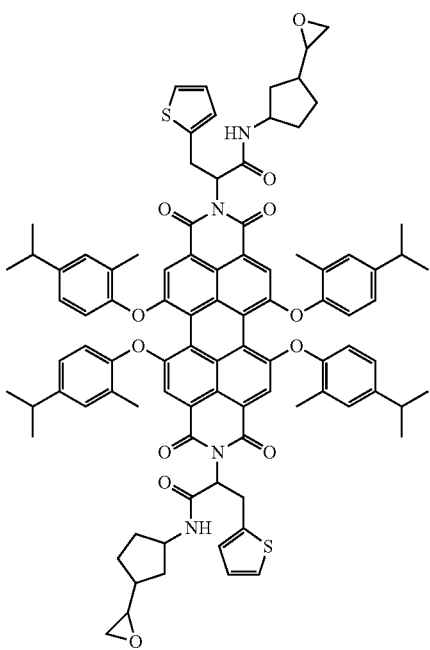
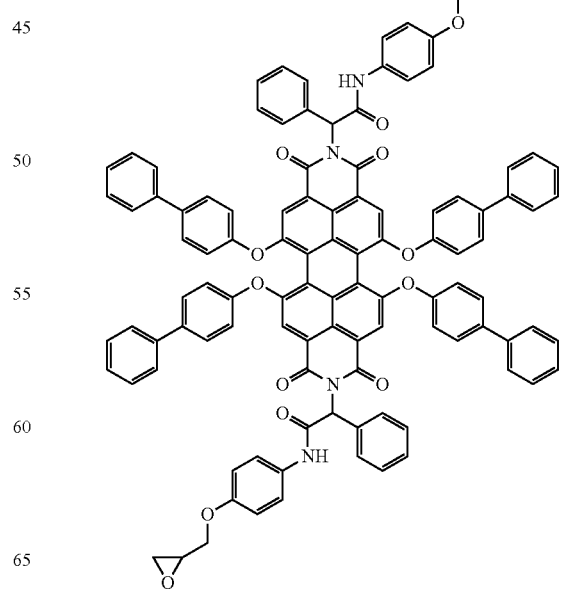

223
-continued
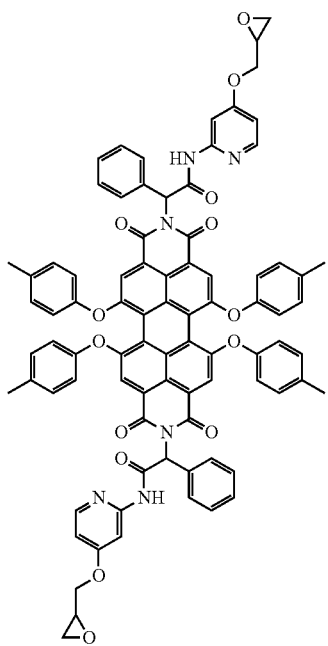
224
-continued
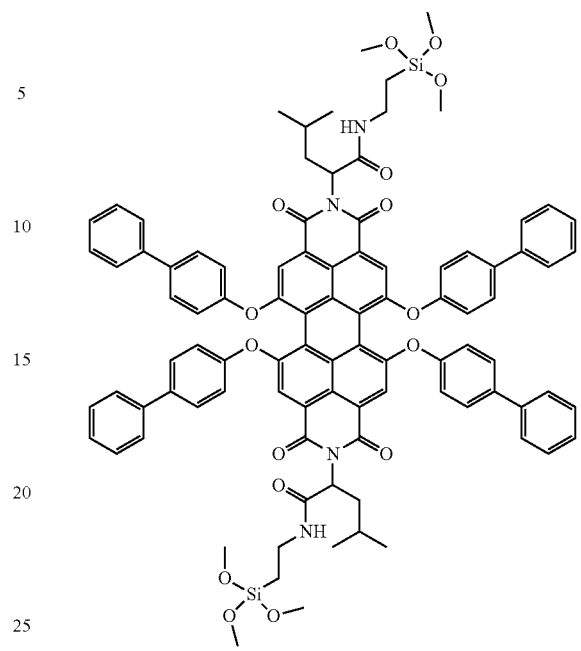
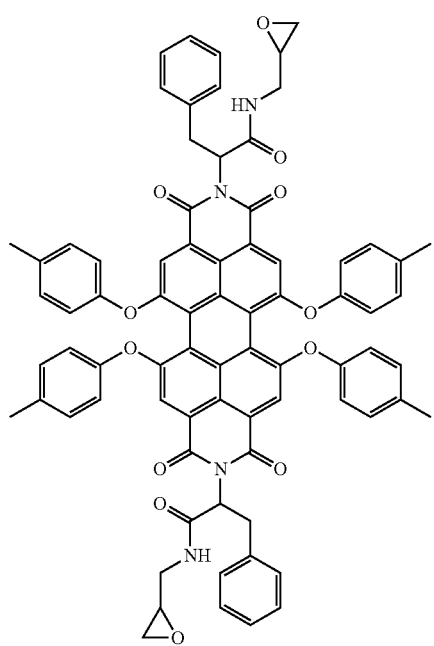
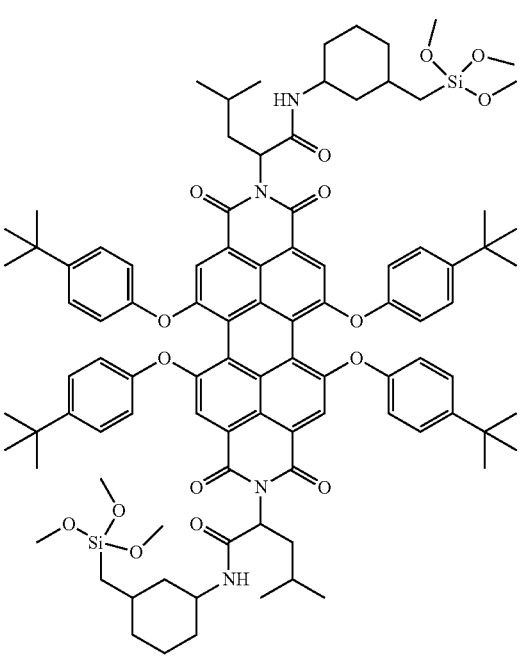

225
-continued
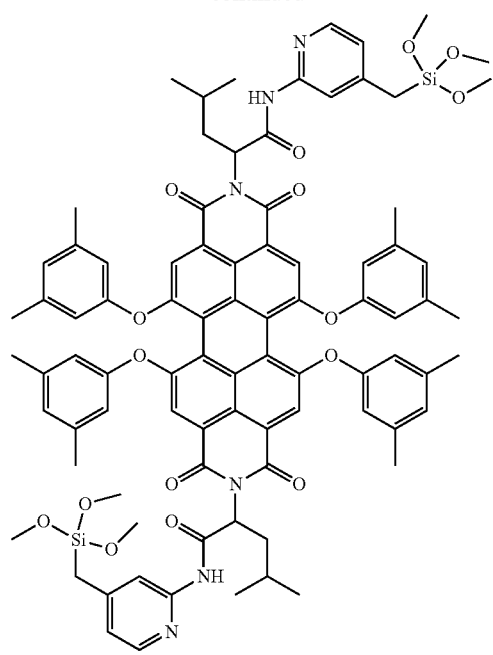
226
-continued
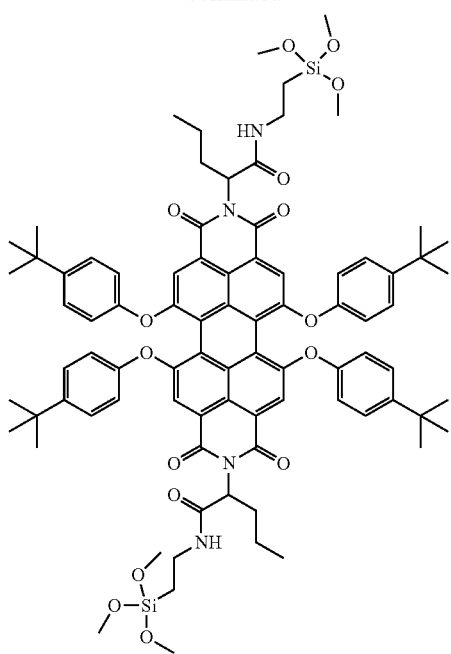
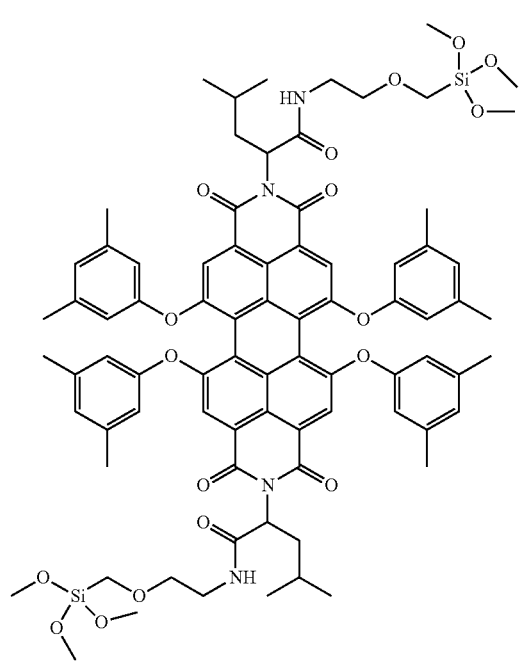
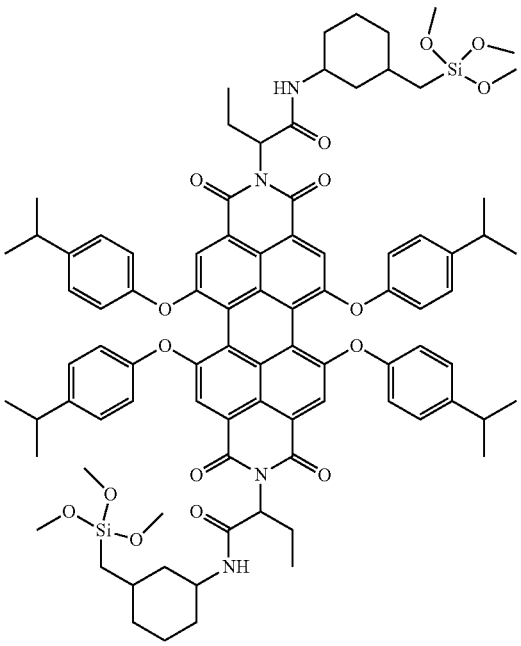

227
-continued
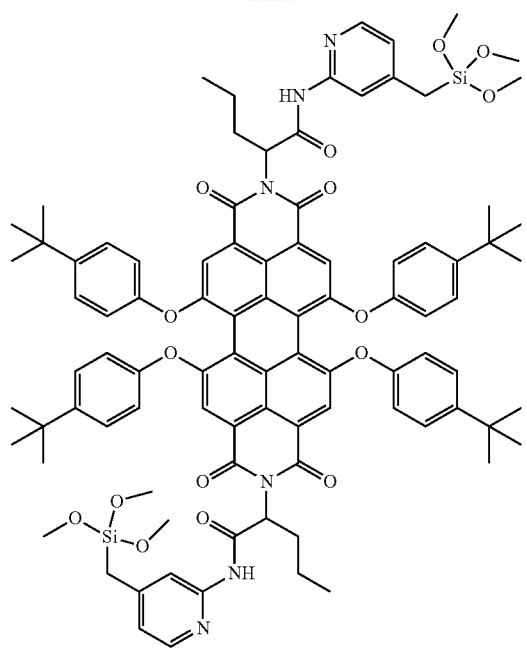
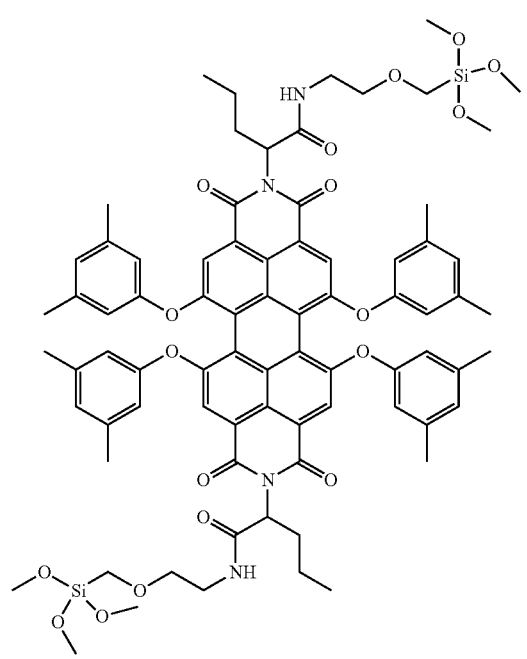
228
-continued
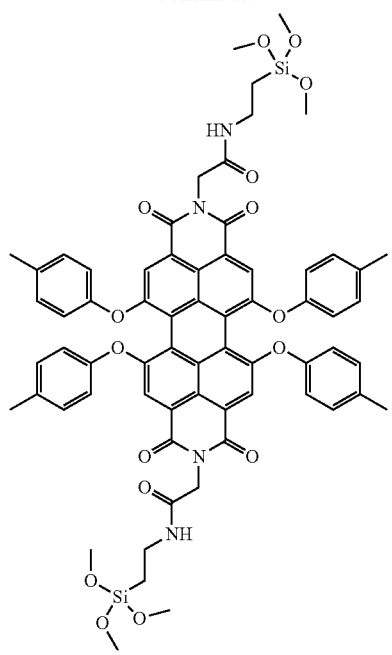
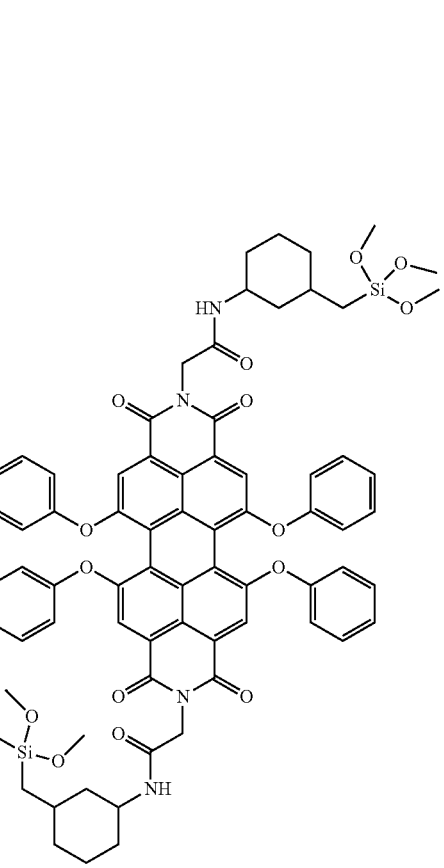

229
-continued
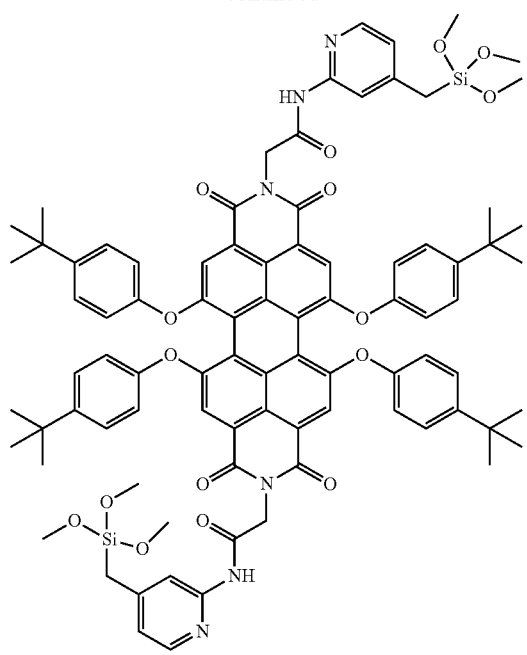
230
-continued
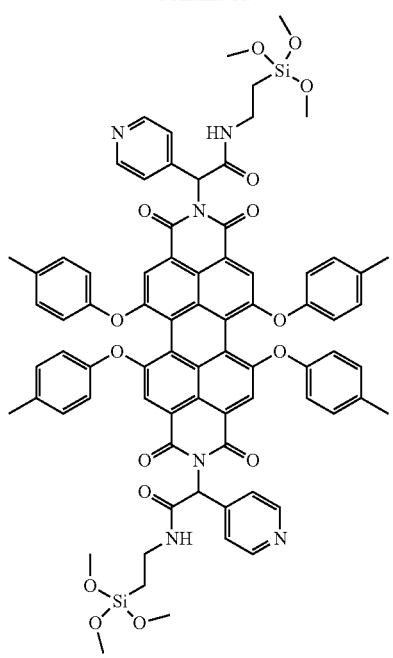
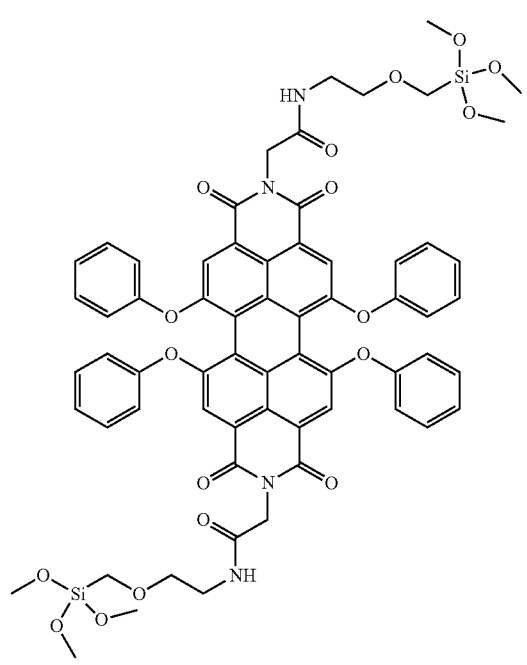
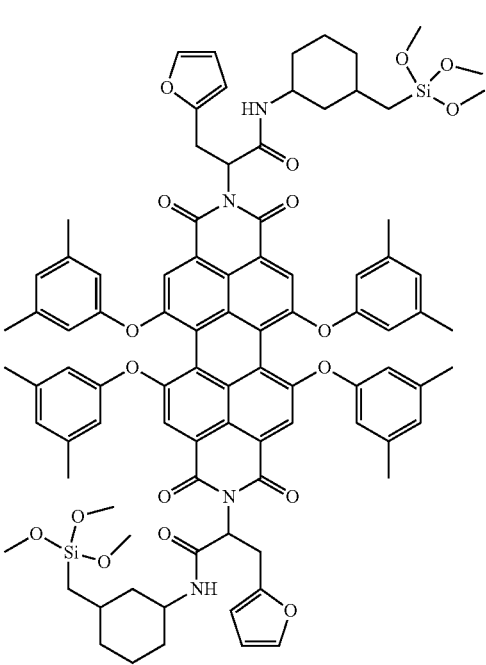

231
-continued
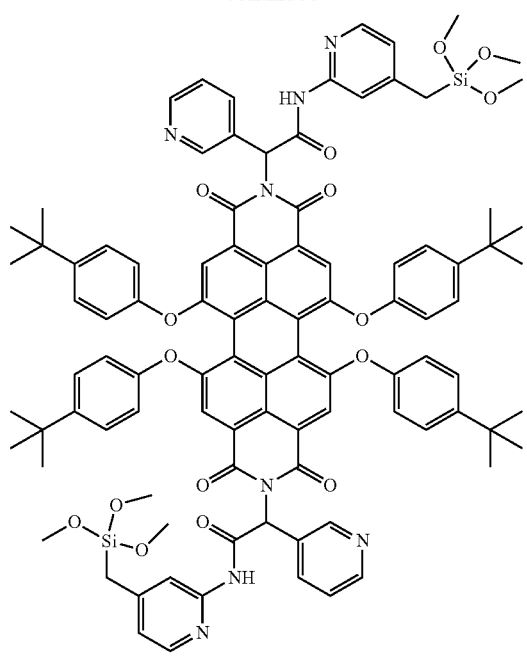
232
-continued
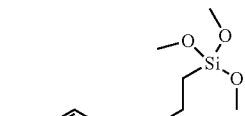
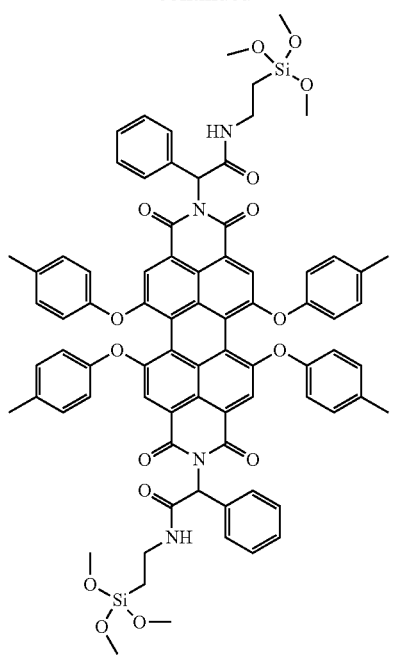
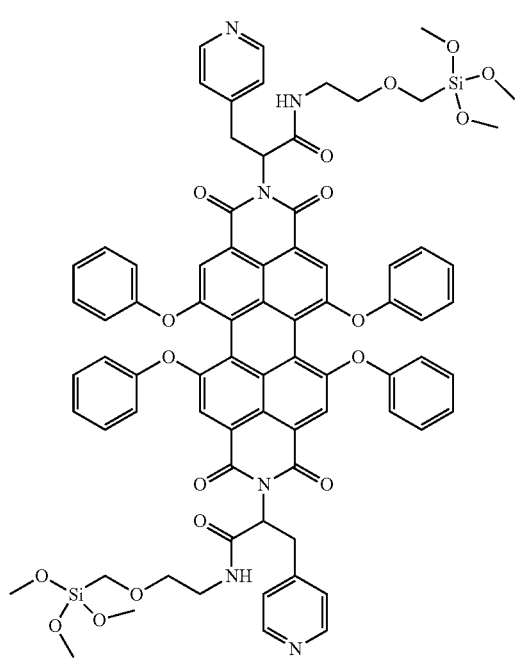
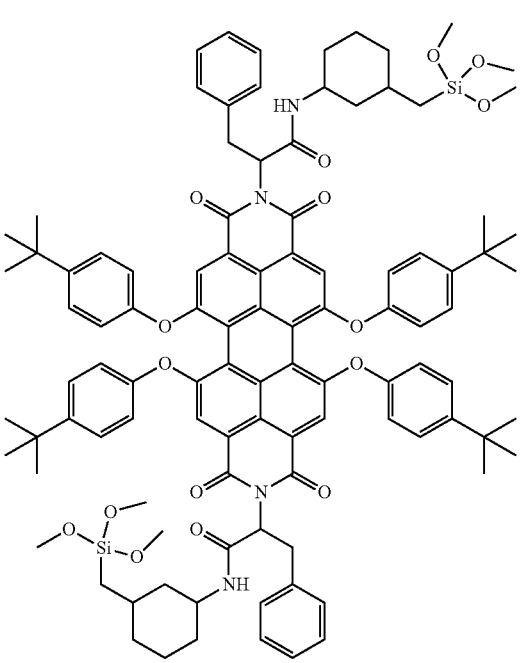

233
-continued
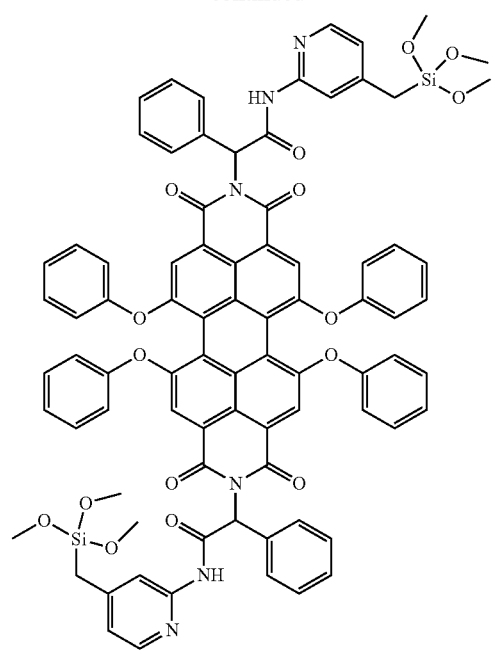
234
-continued
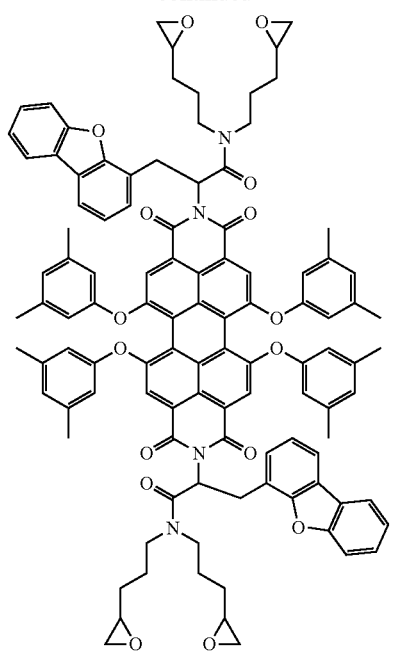
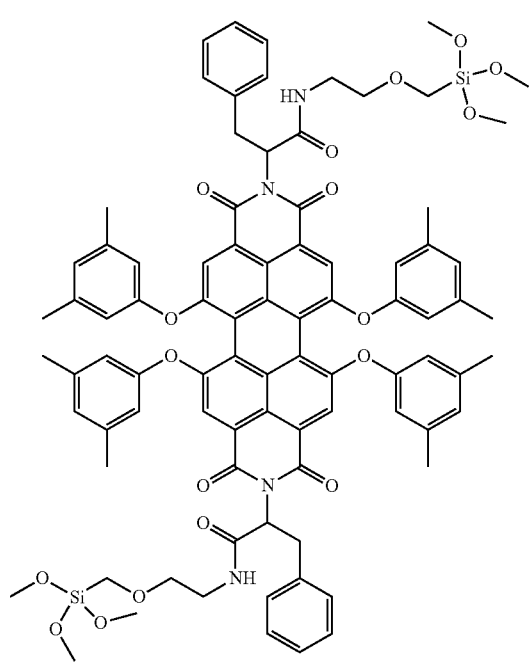
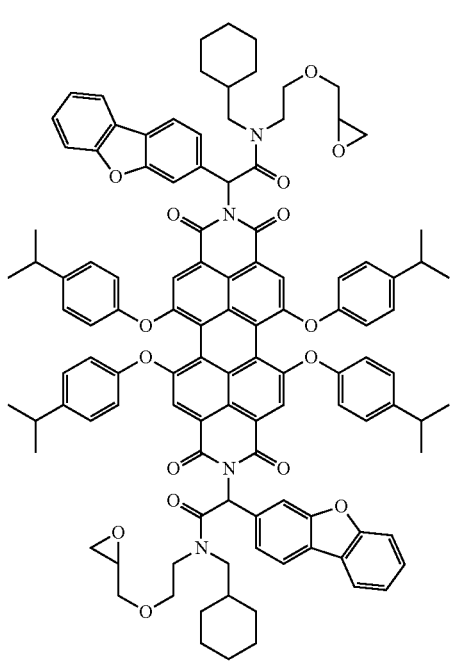

235
-continued
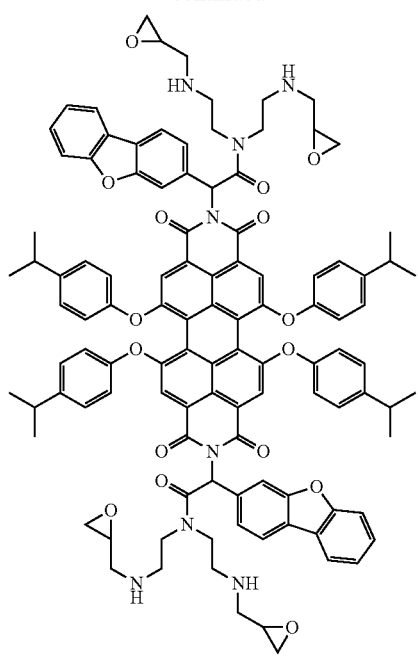
236
-continued
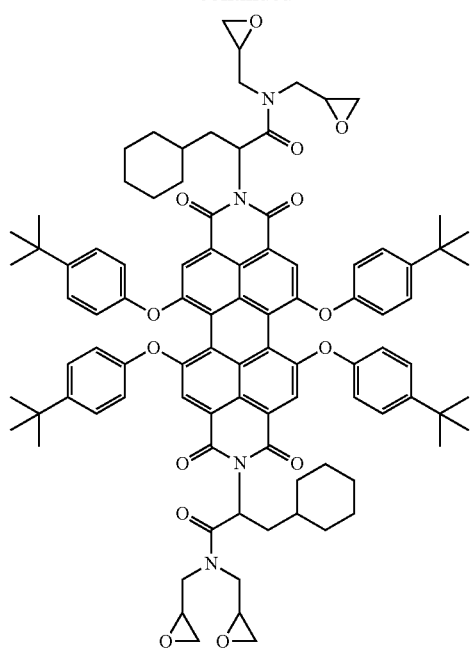
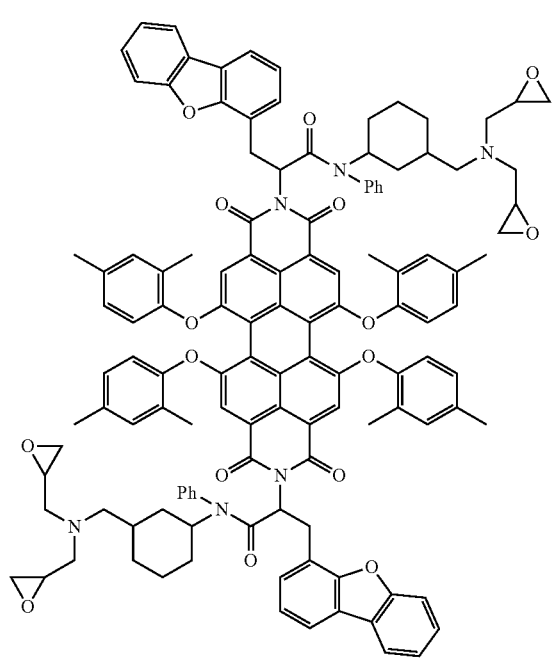
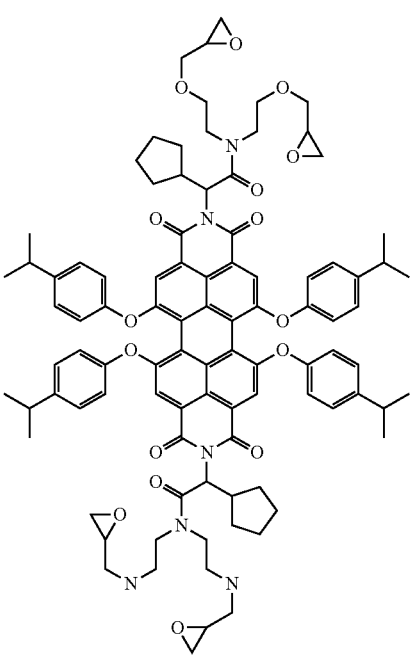

237
-continued
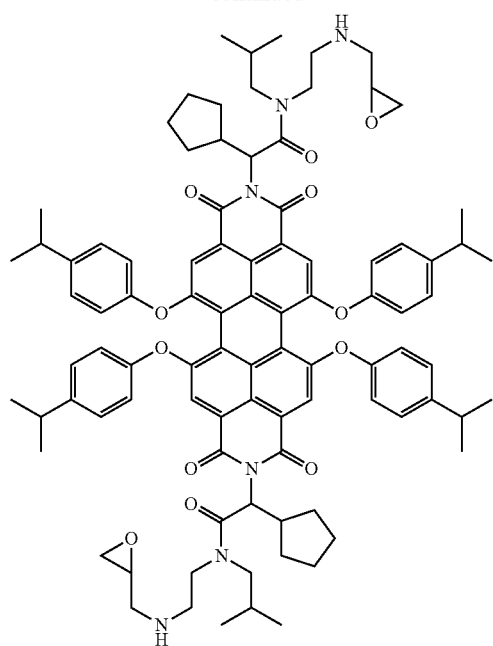
238
-continued
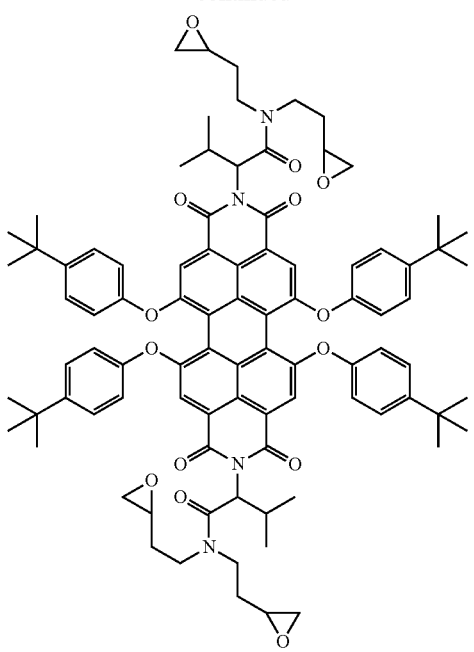
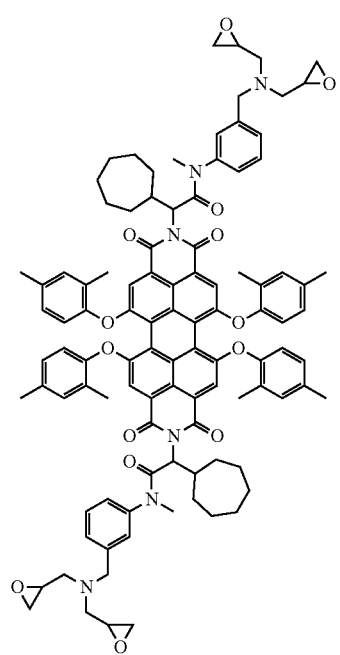
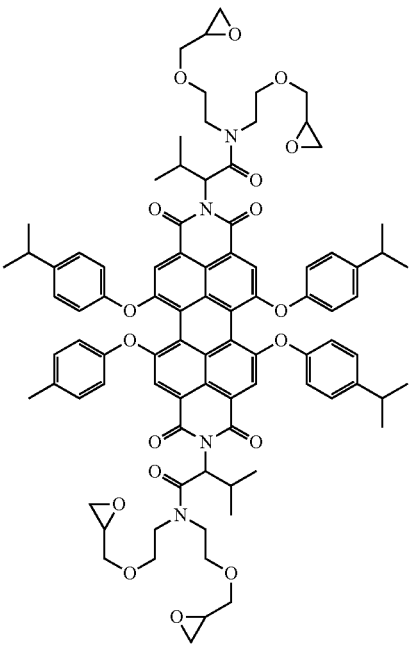

239
-continued
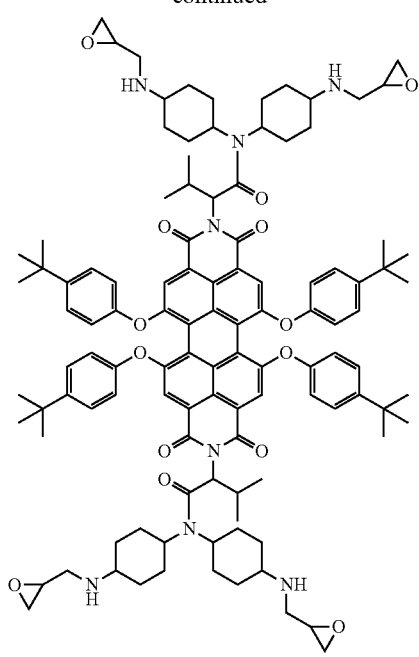
240
-continued
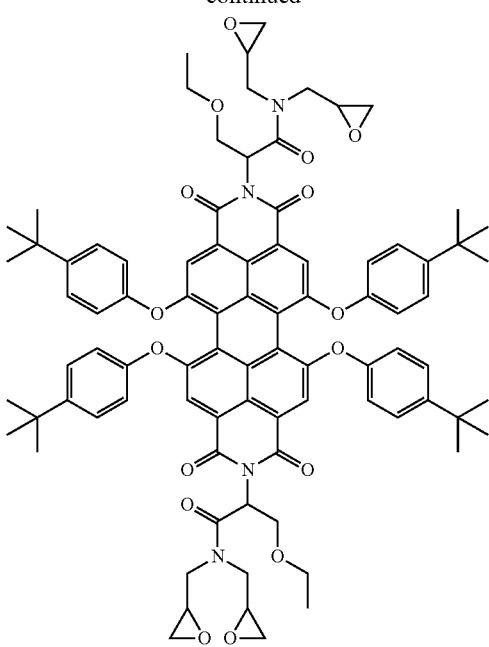
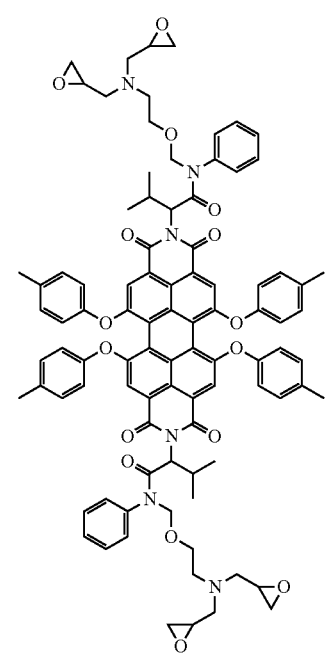

241
-continued
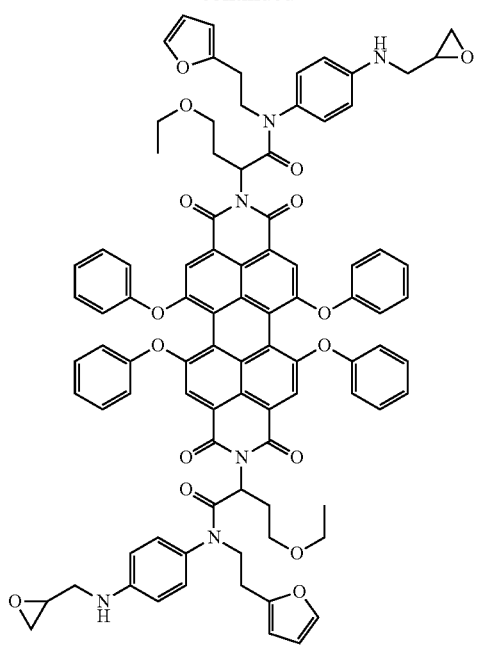
242
-continued
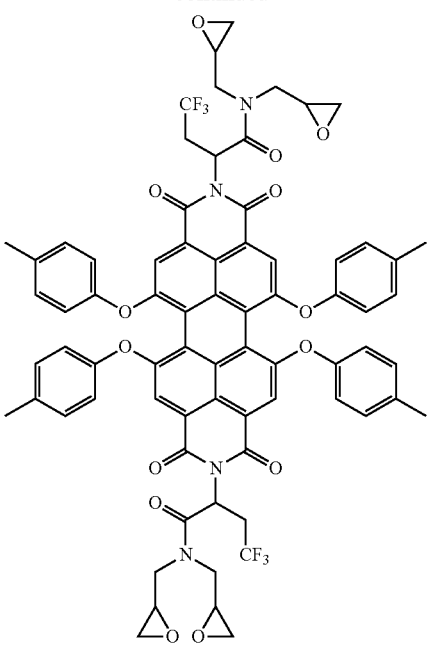
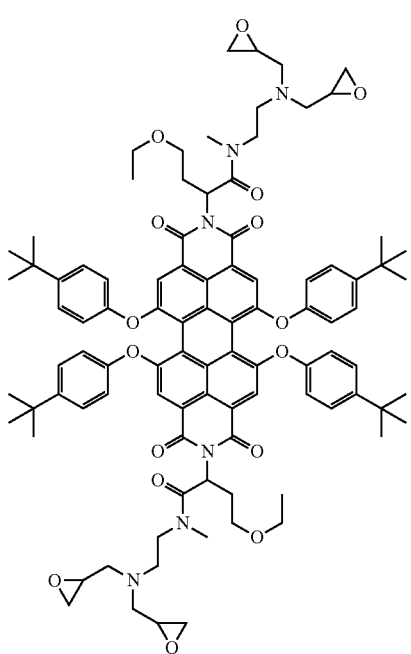
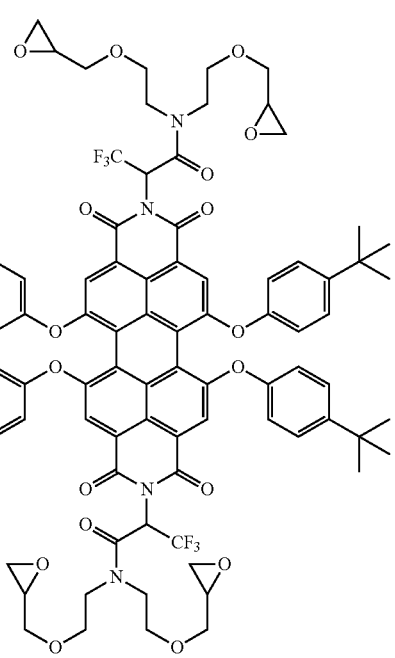

243
-continued
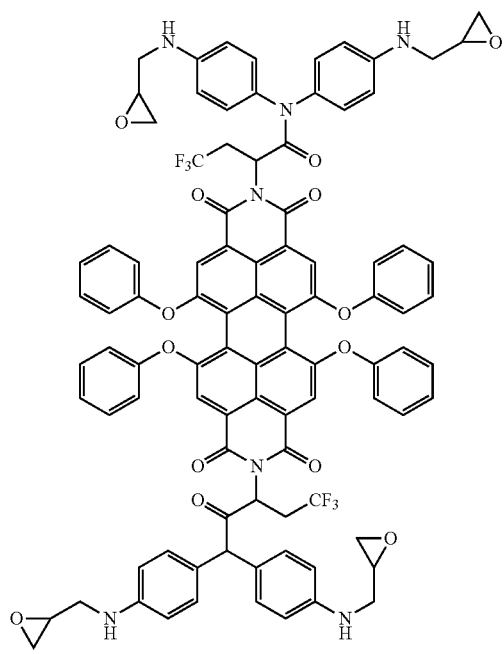
244
-continued
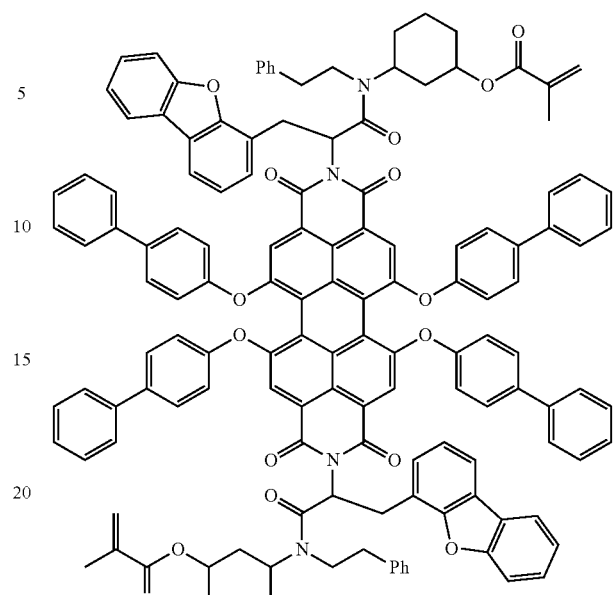
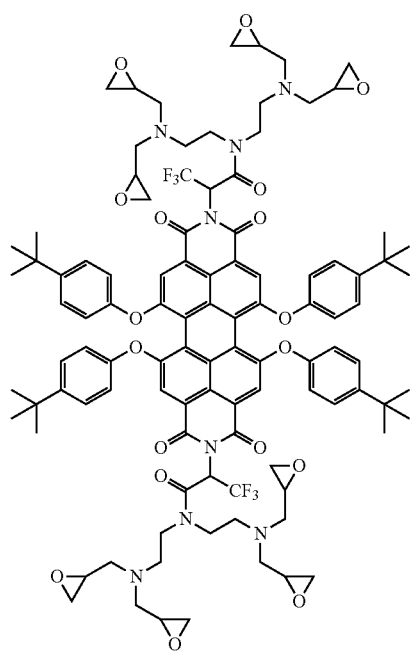
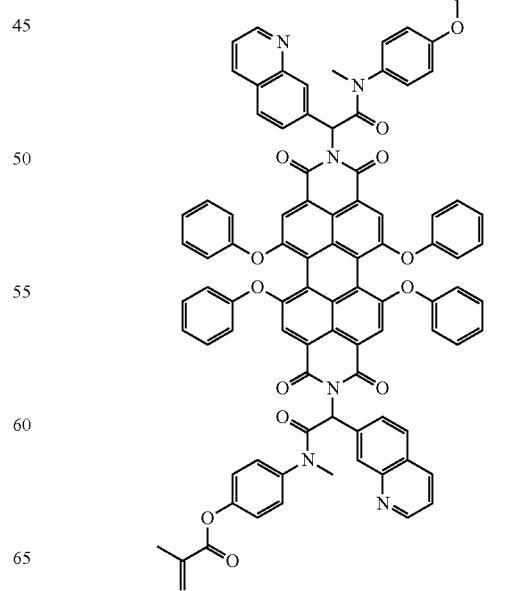

245
-continued
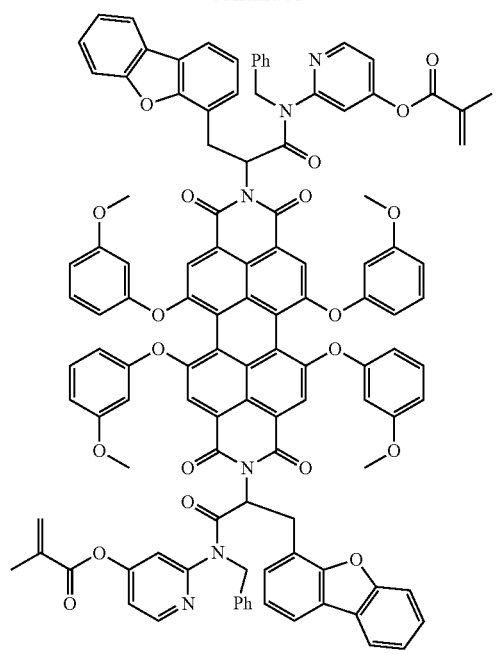
246
-continued
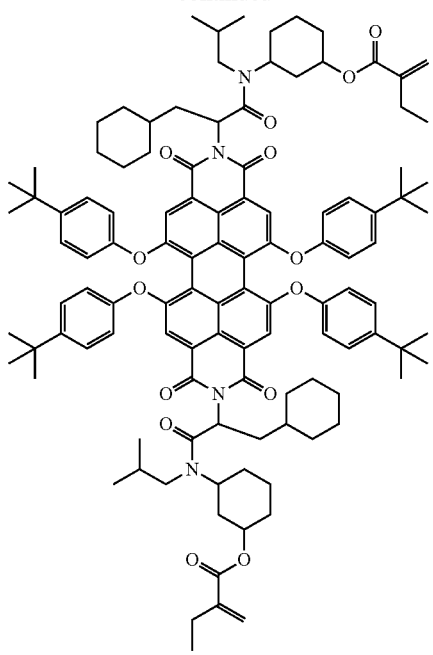
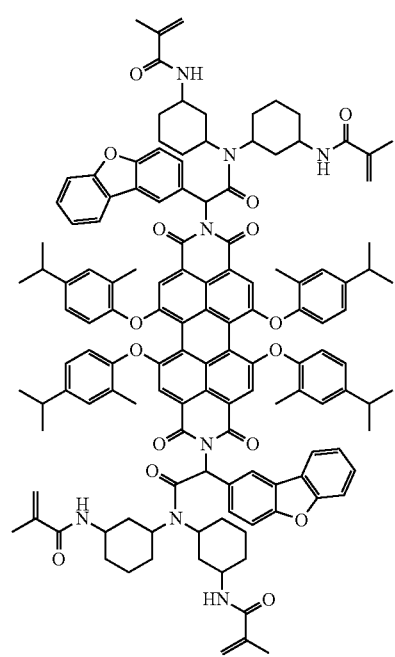
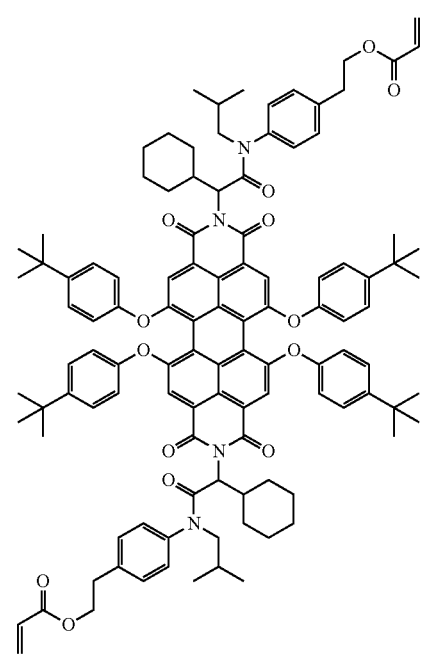

247
-continued
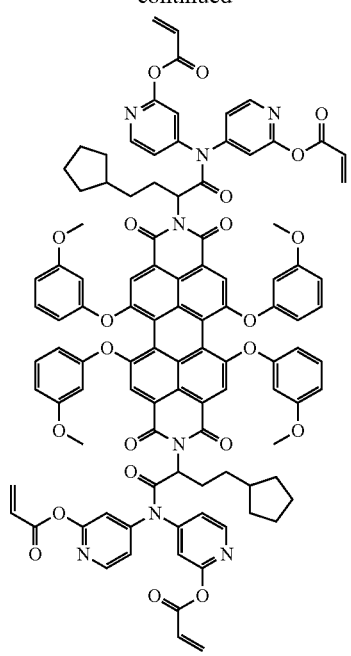
248
-continued
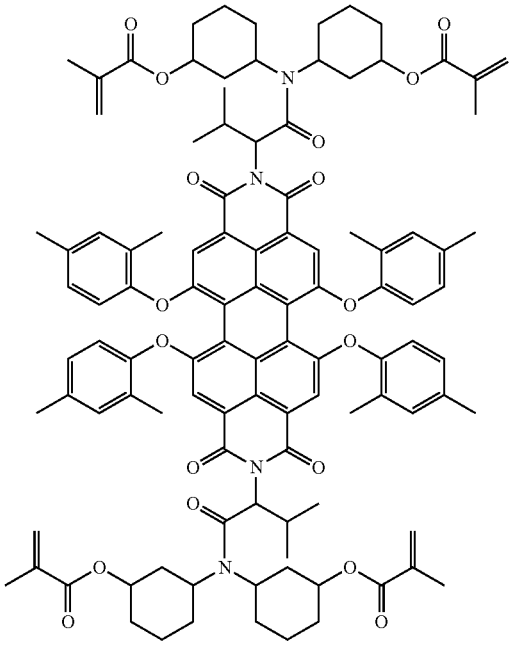
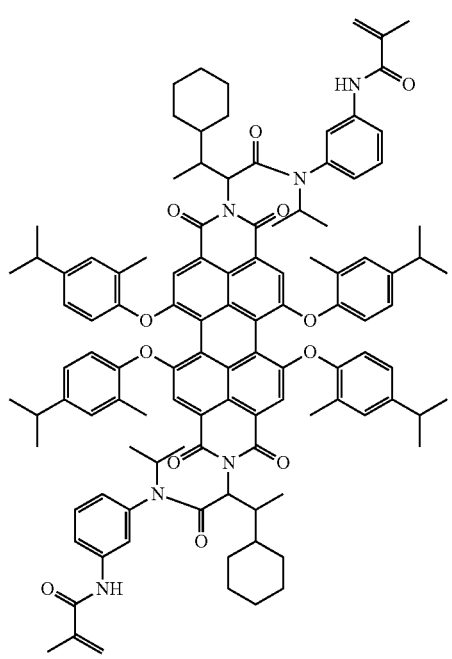
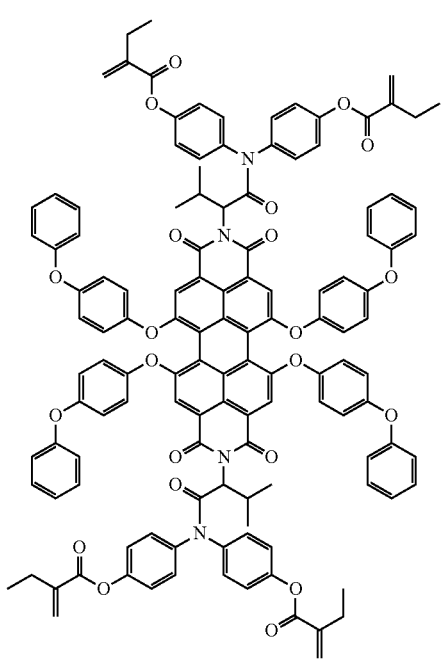

249
-continued
250
-continued
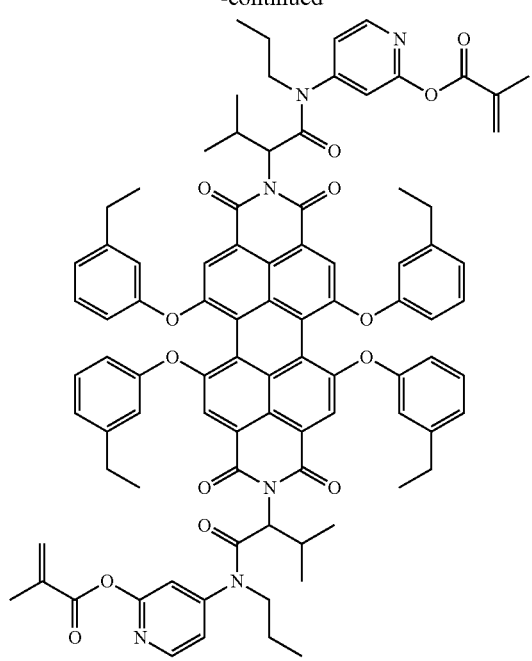
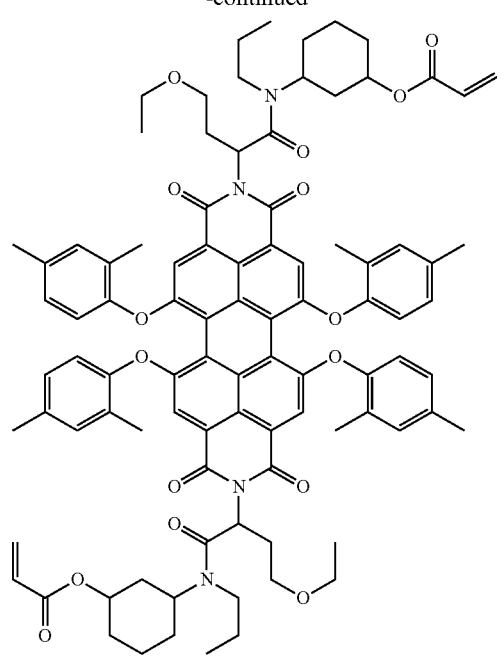
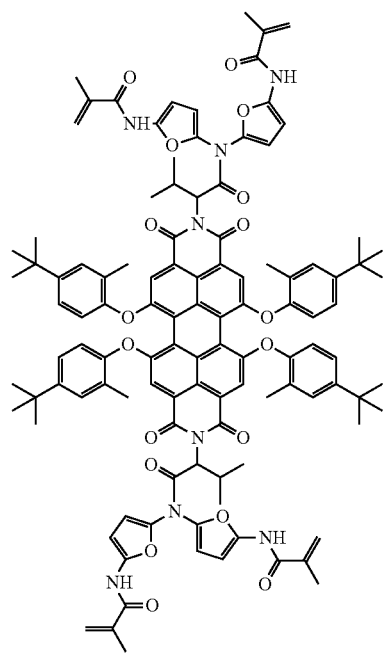
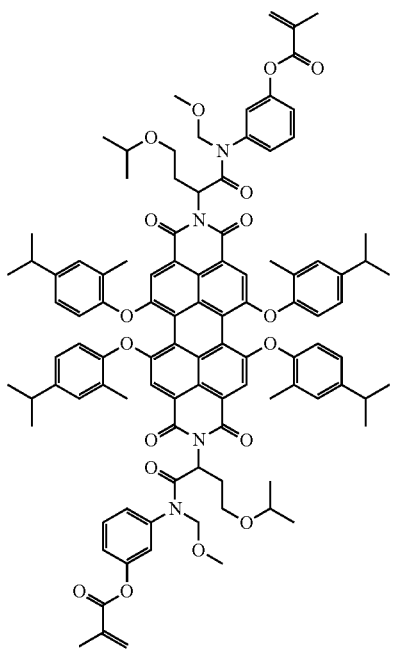

251
-continued
252
-continued
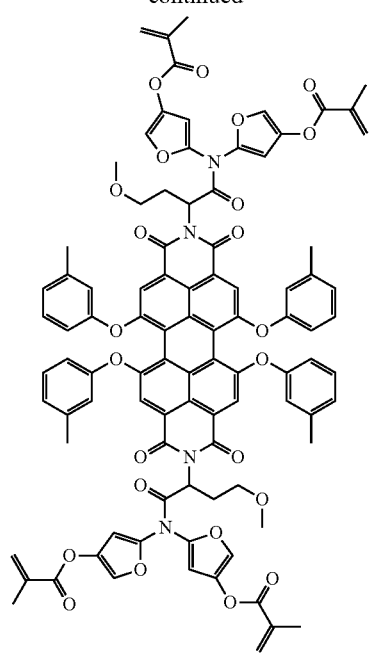
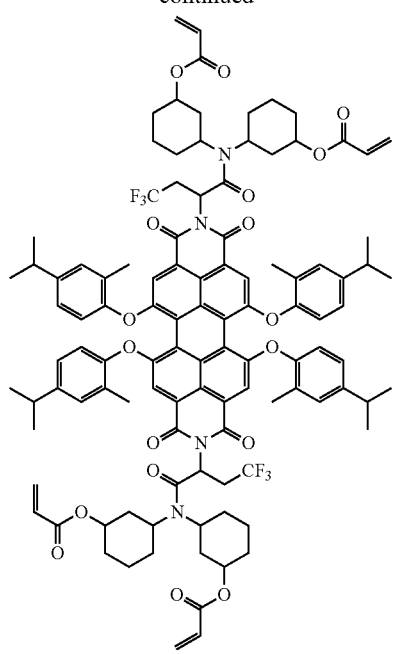
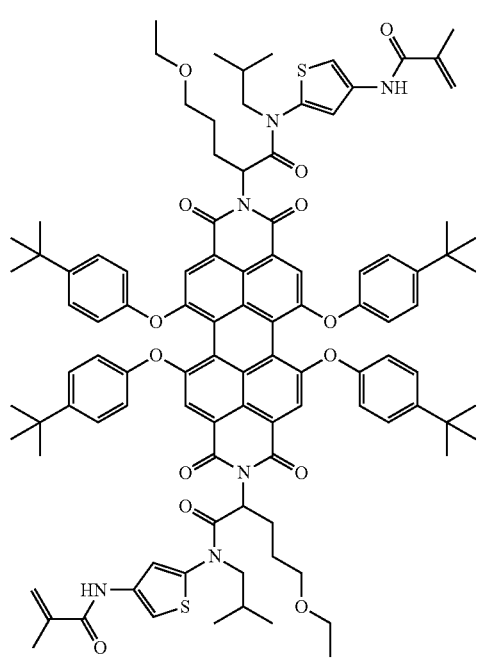

253
-continued
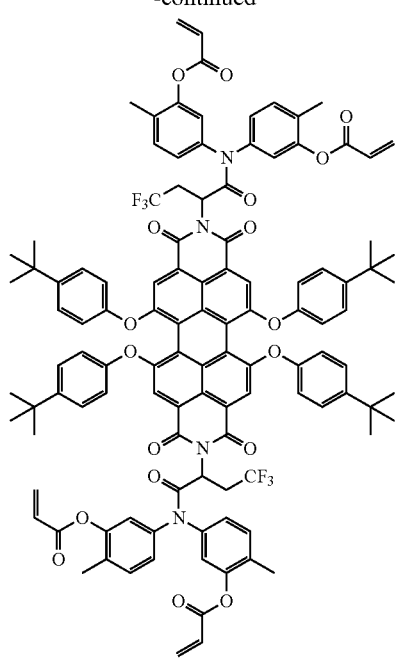
254
-continued
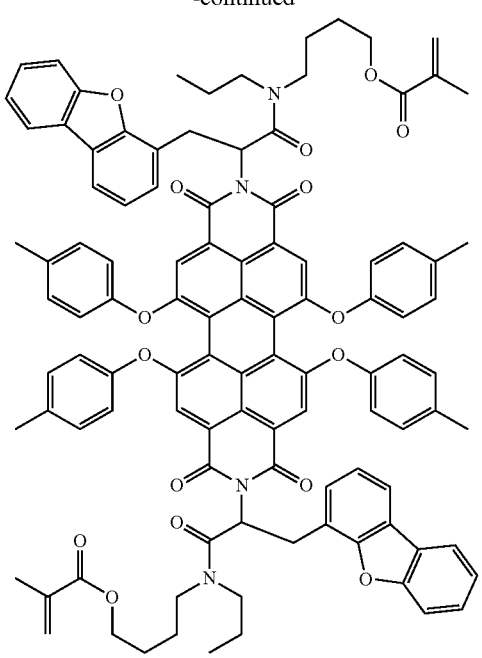
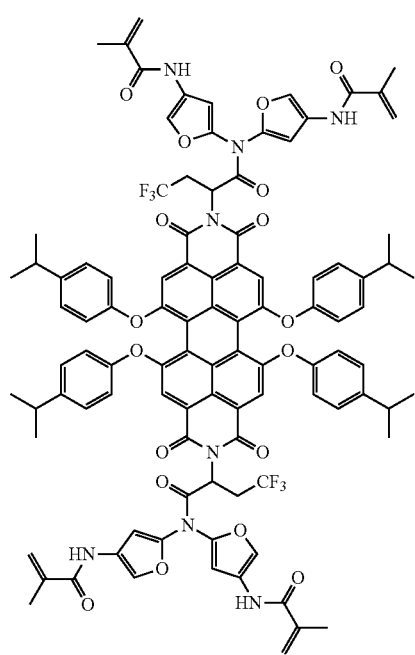
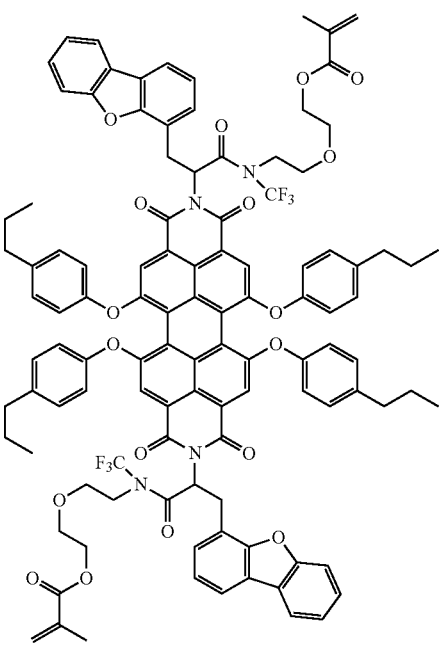

255
-continued
256
-continued
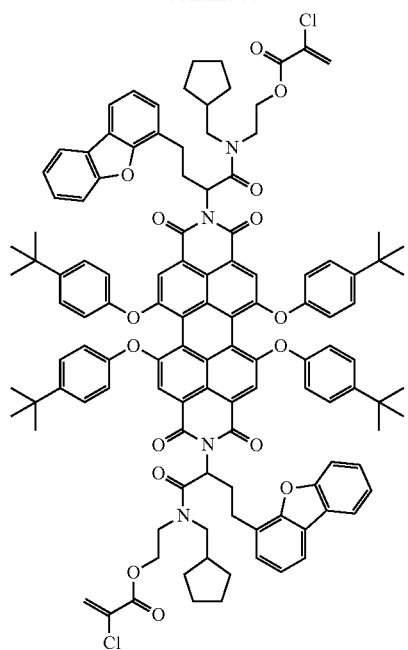
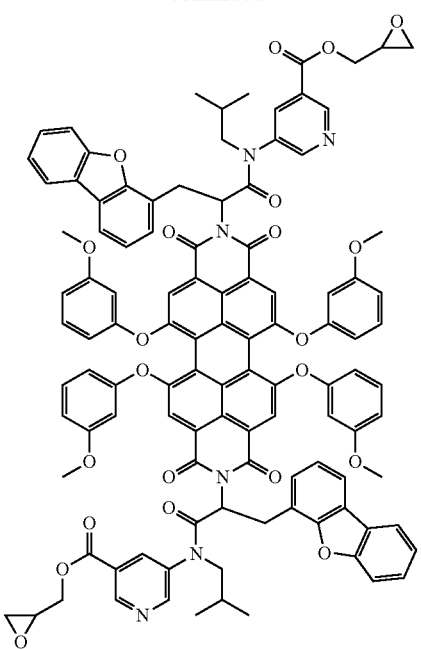

257
-continued
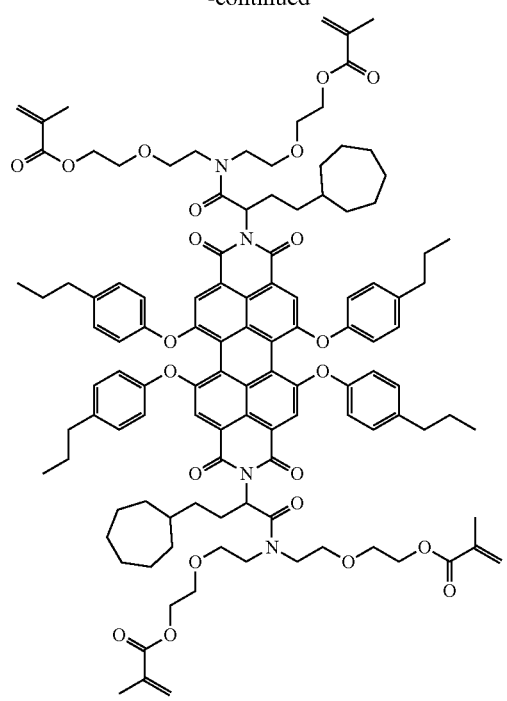
258
-continued
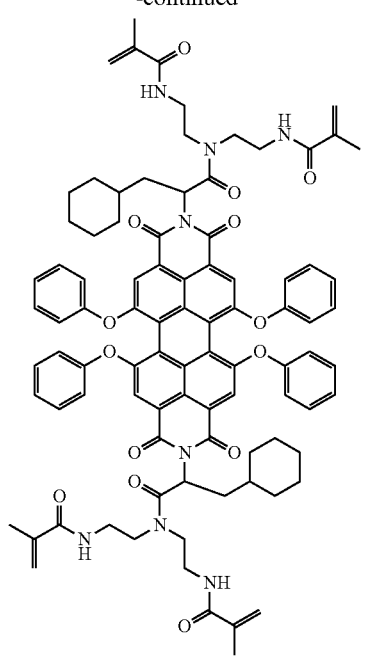
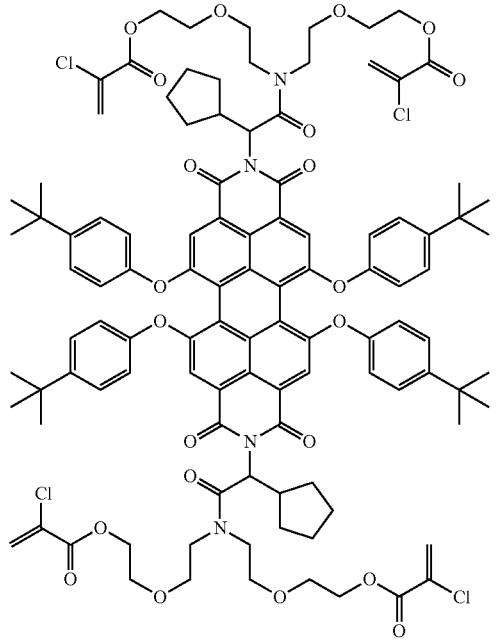
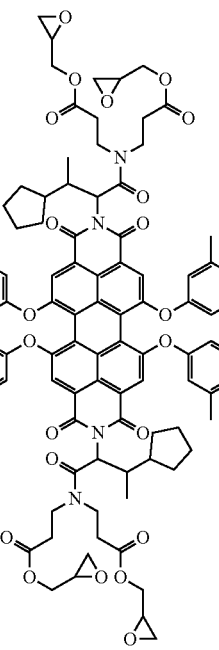

259
-continued
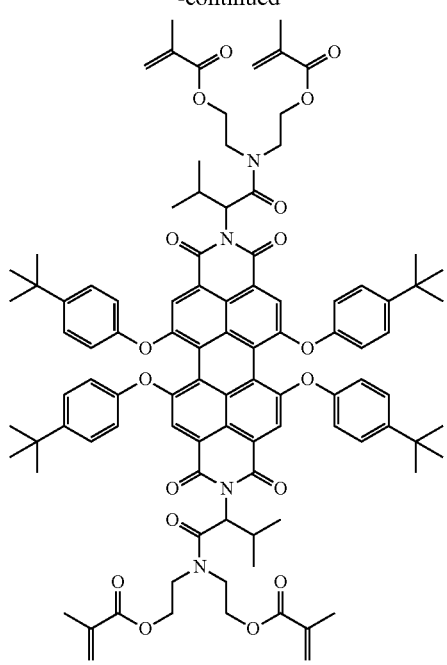
260
-continued
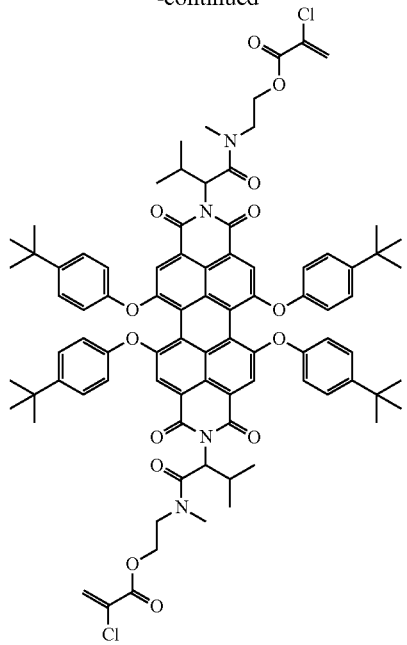
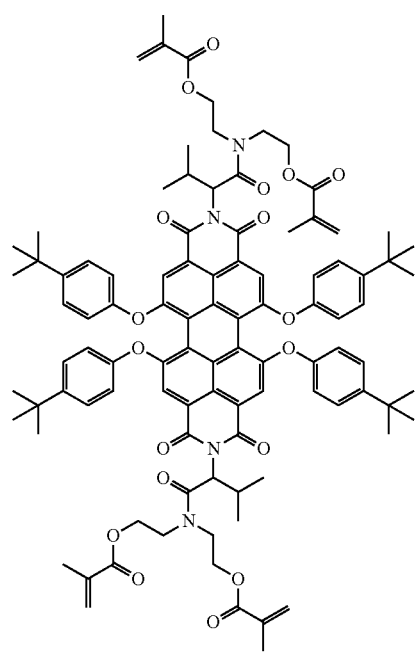
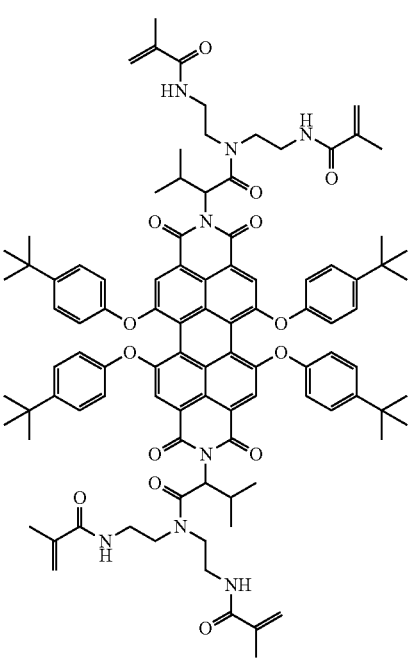

261
-continued
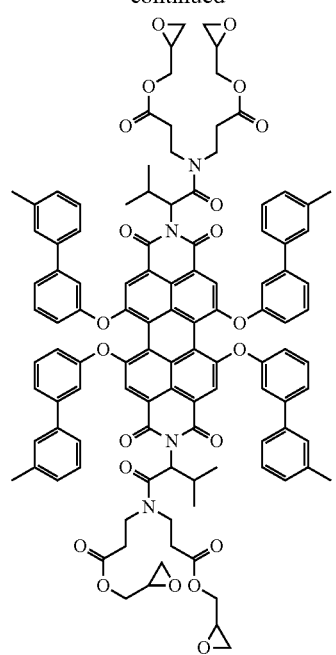
262
-continued
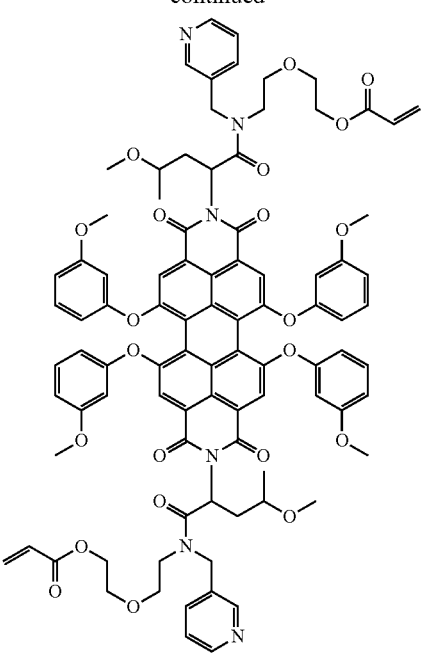
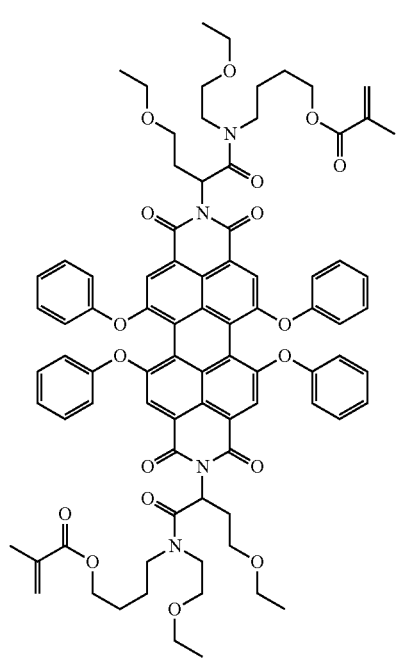
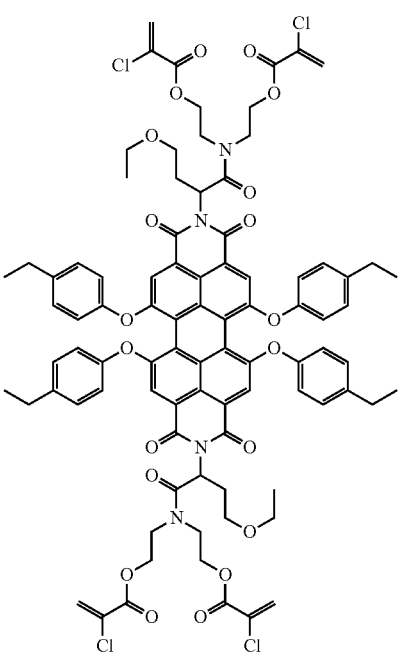

263
-continued
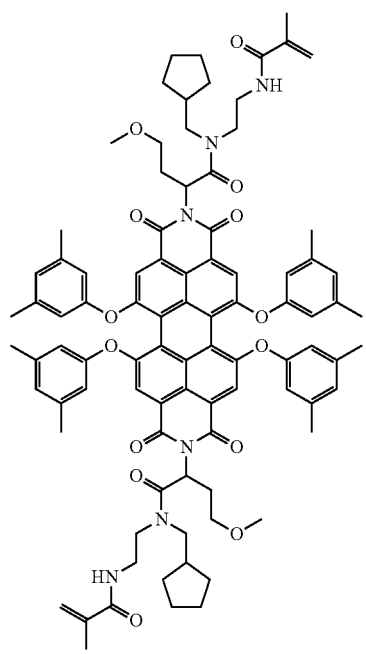
264
-continued
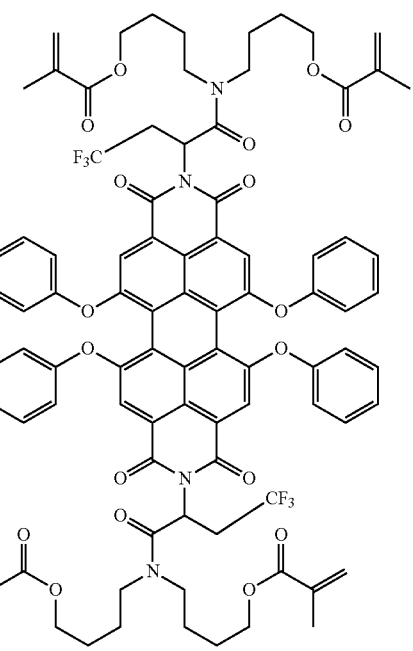
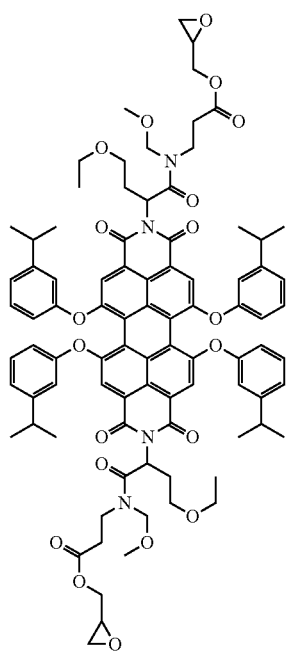
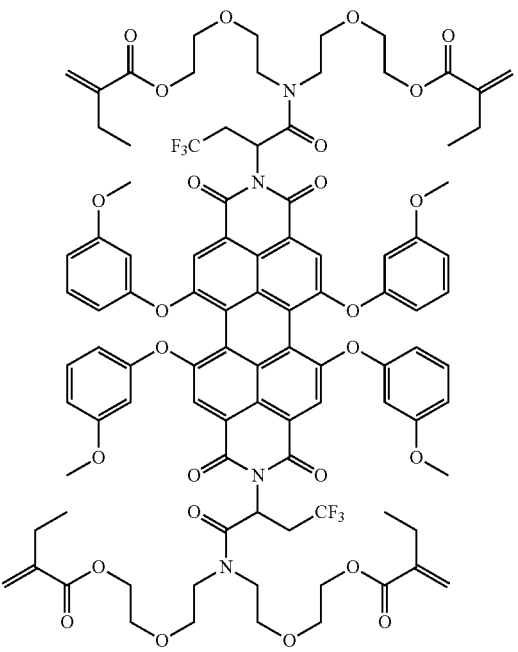

265
-continued
266
-continued
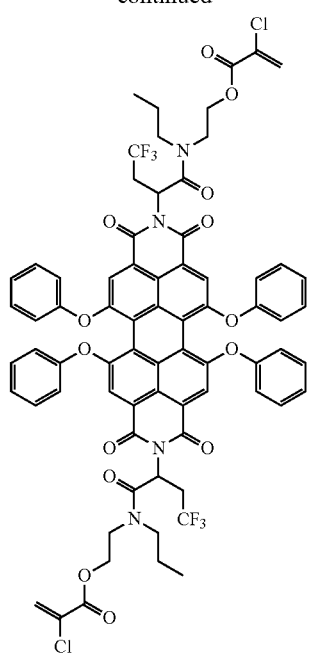
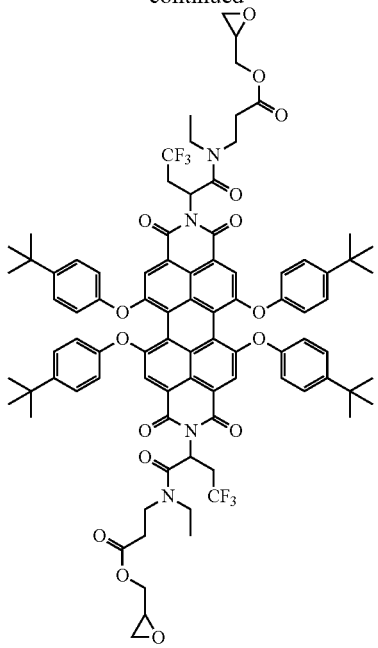

267
-continued
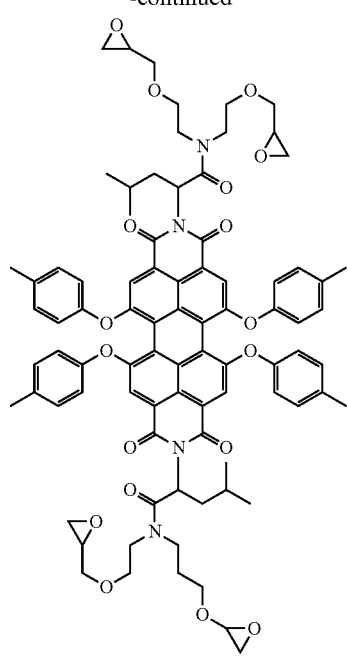
268
-continued
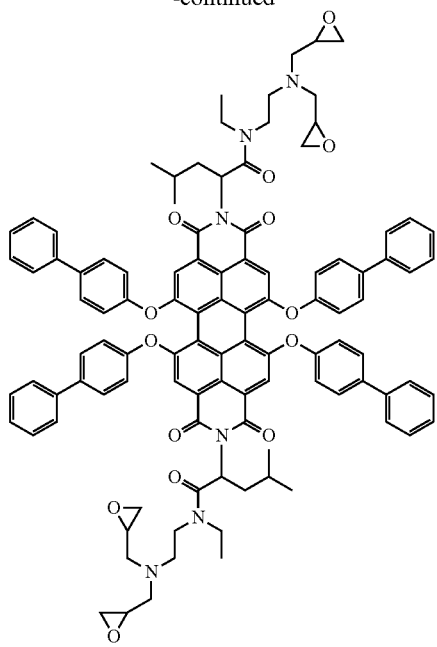
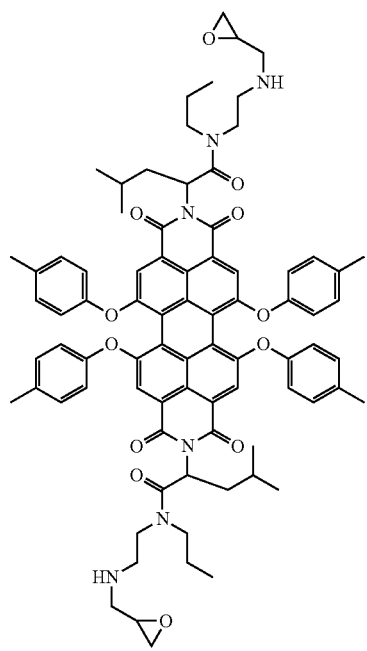

269
-continued
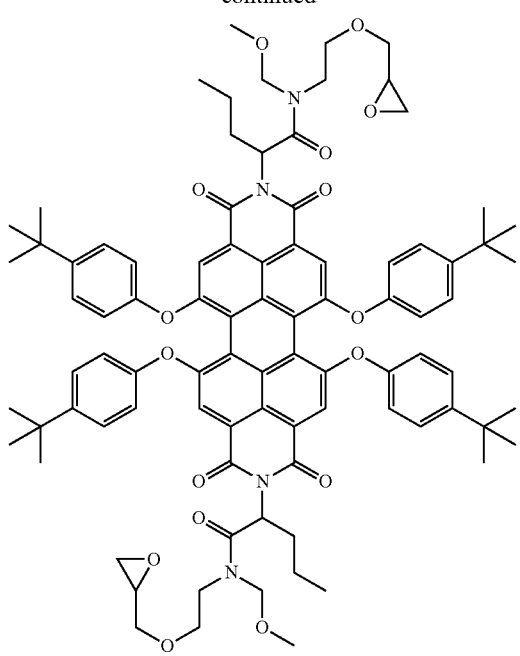
270
-continued
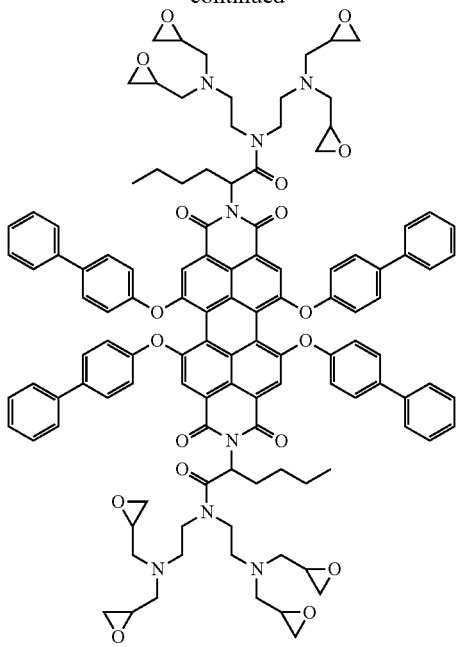
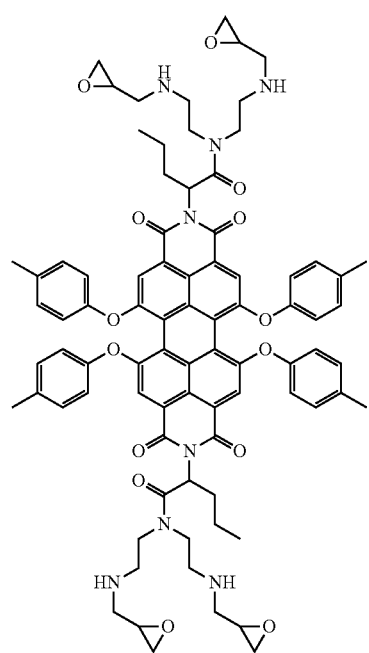
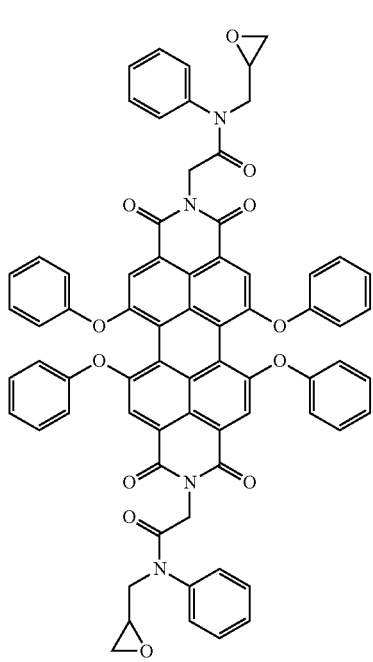

271
-continued
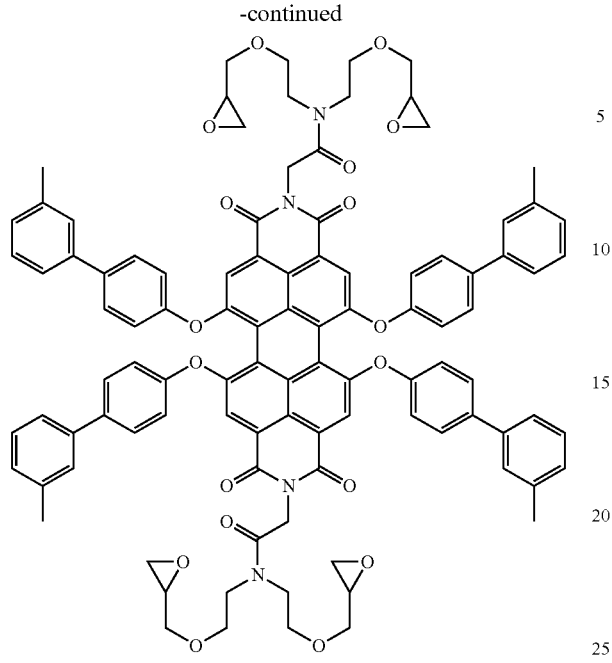
272
-continued
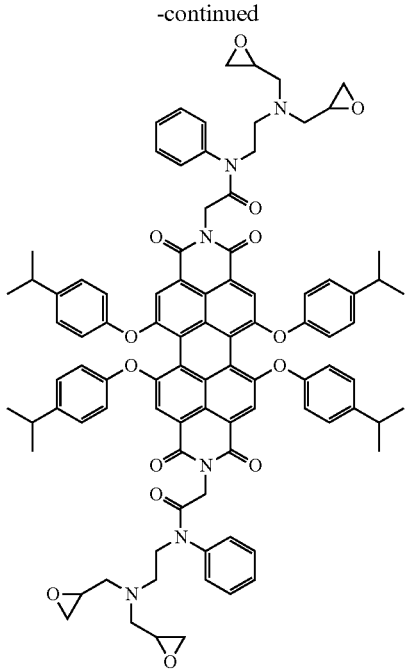
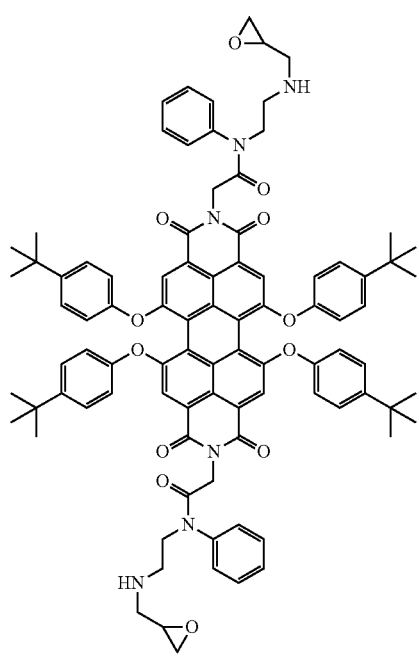
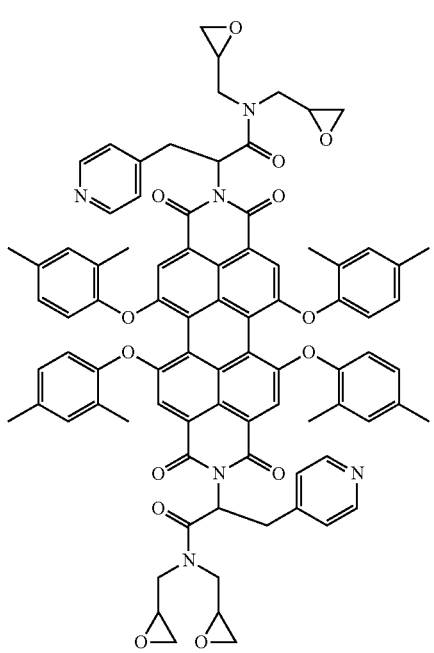

273
-continued
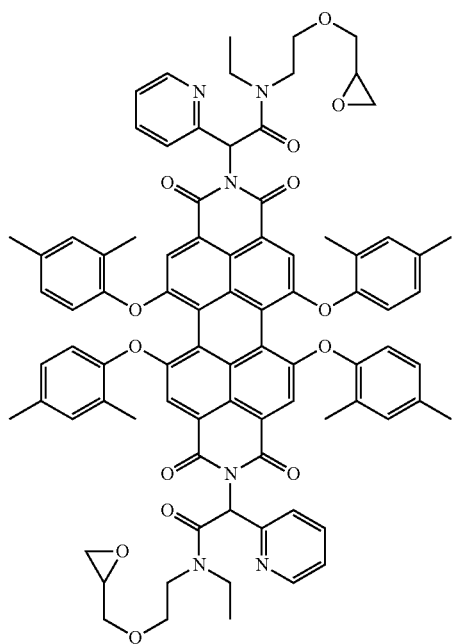
274
-continued
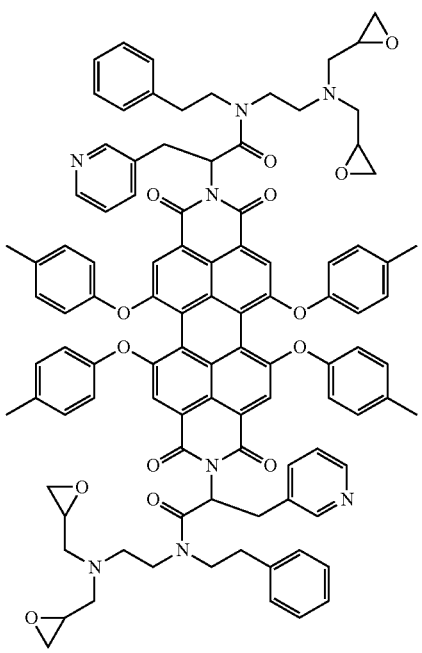
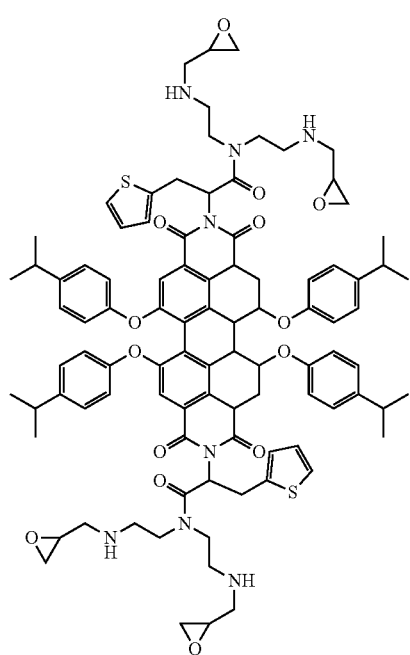
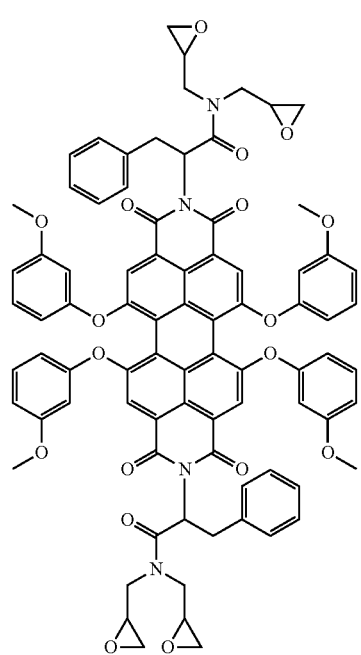

275
-continued
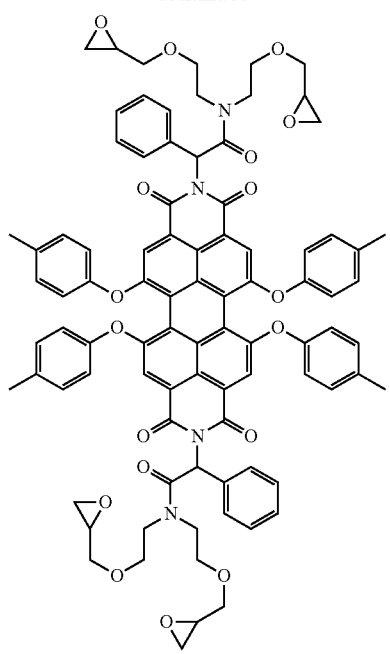
276
-continued
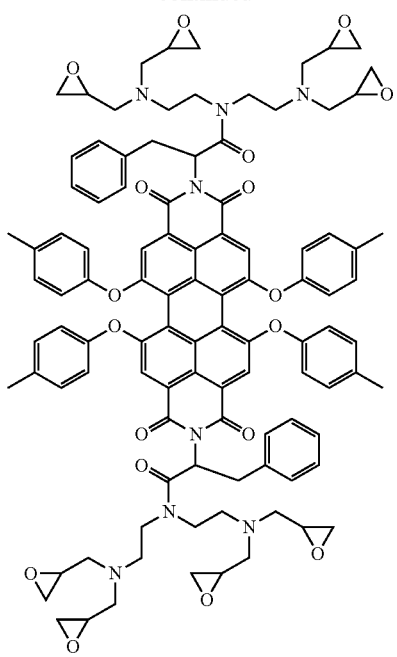
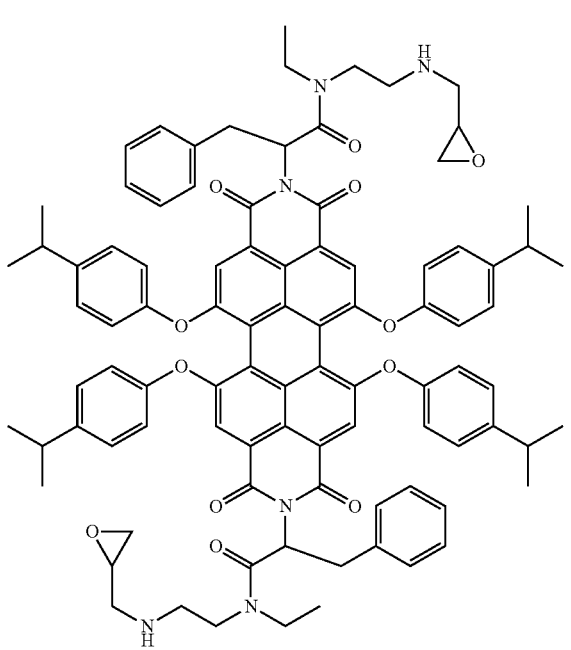
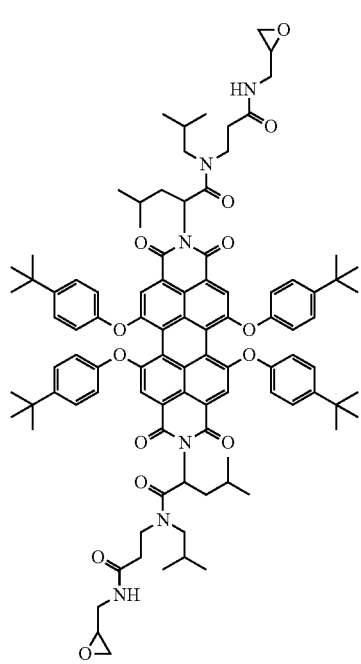

277
-continued
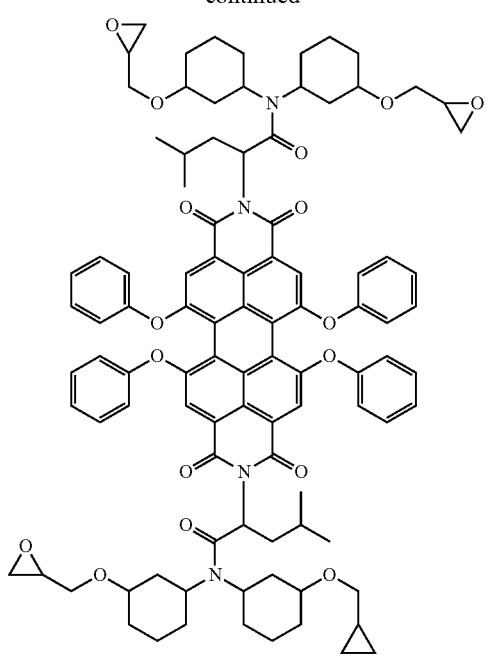
278
-continued
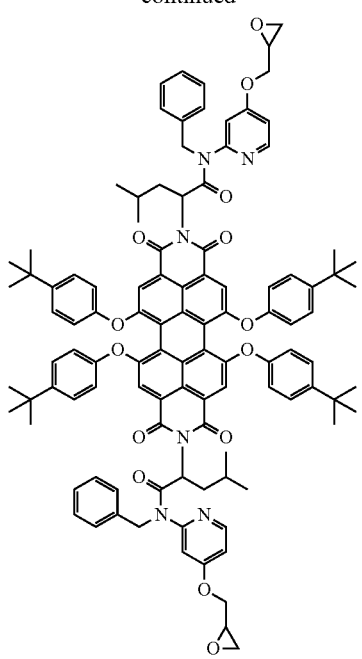
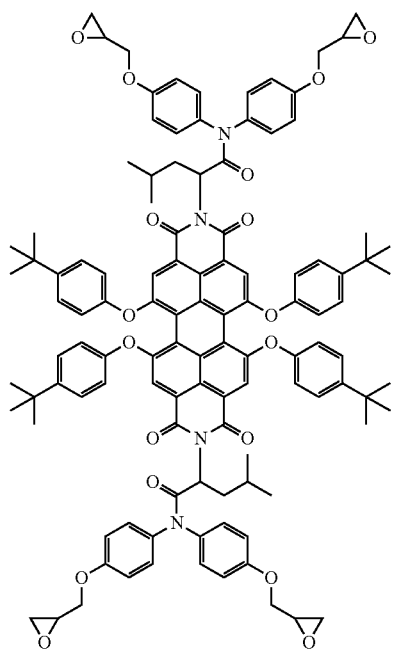
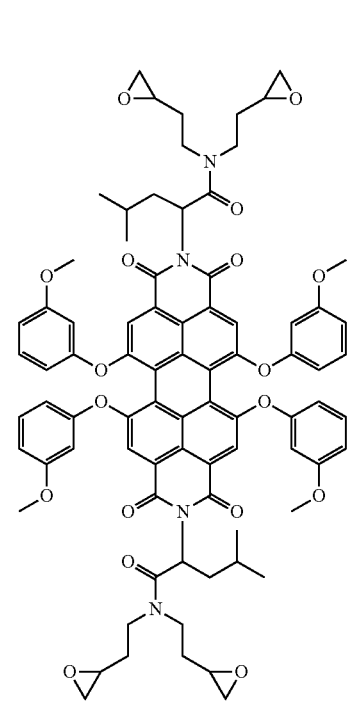 [SMILES: COc1cccc(Oc2cc3c4c(cc(Oc5cccc(OC)c5)c5c6c(Oc7cccc(OC)c7)cc7c8c(cc(Oc9cccc(OC)c9)c(c2c45)c86)C(=O)N(C(CC(C)C)C(=O)N(CCC2CO2)CCC2CO2)C7=O)C(=O)N(C(CC(C)C)C(=O)N(CCC2CO2)CCC2CO2)C3=O)c1]

279
-continued
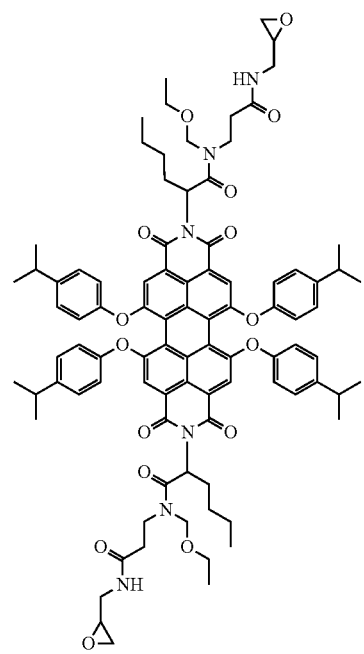
280
-continued
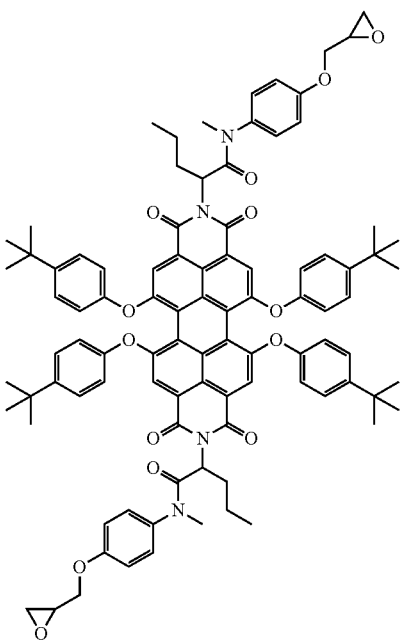
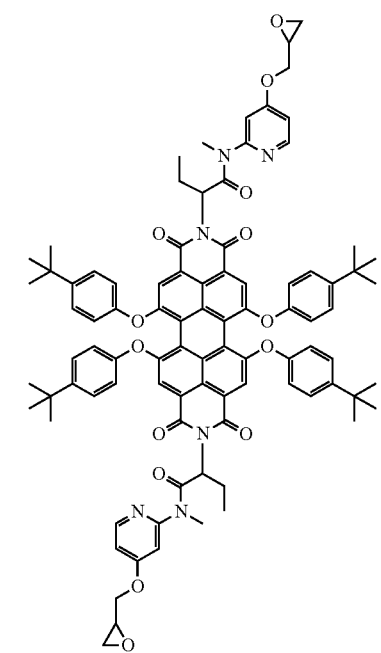

281
-continued
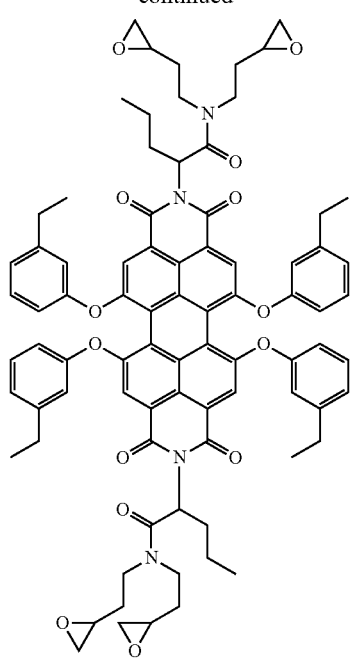
282
-continued
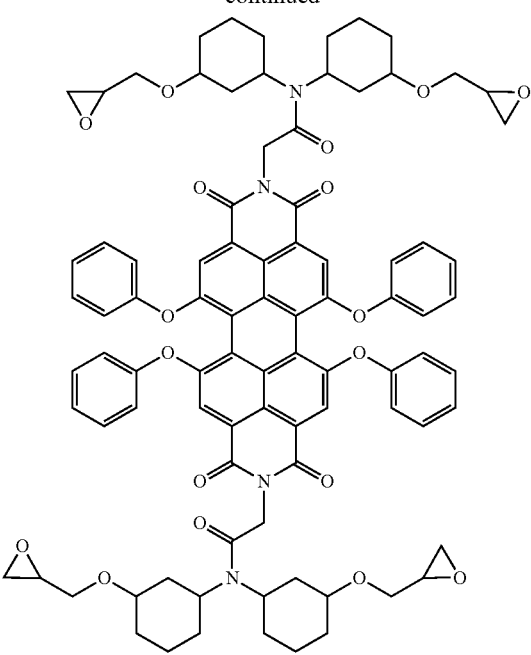
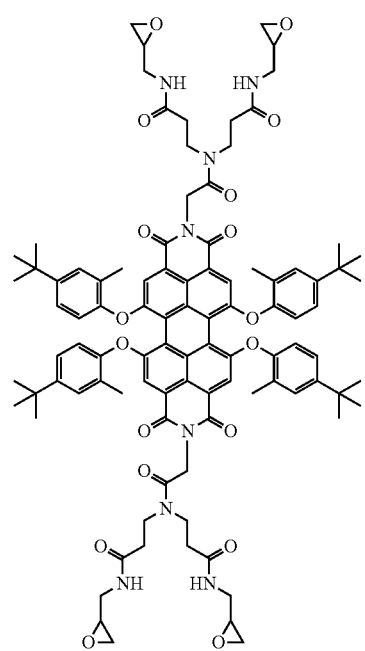
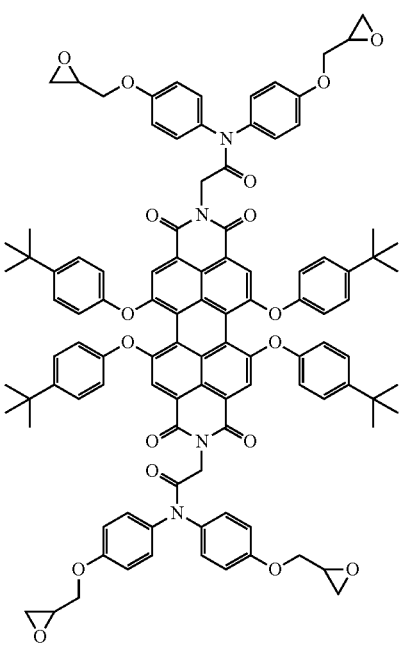

283
-continued
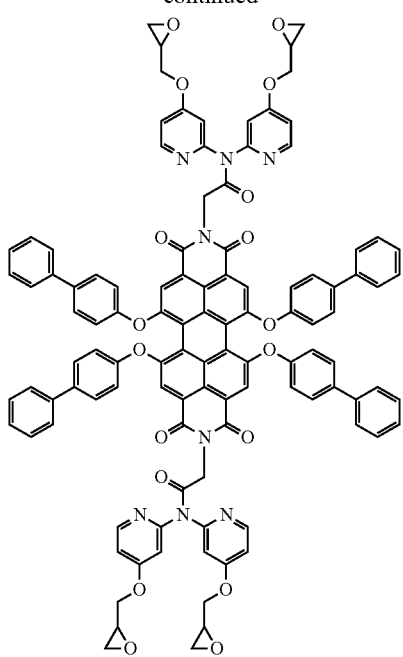
284
-continued
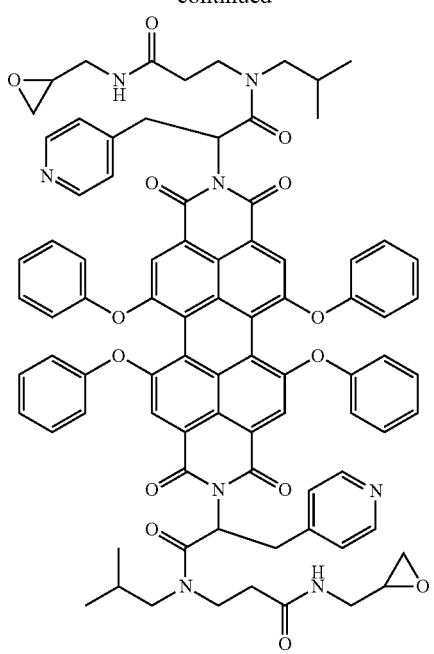
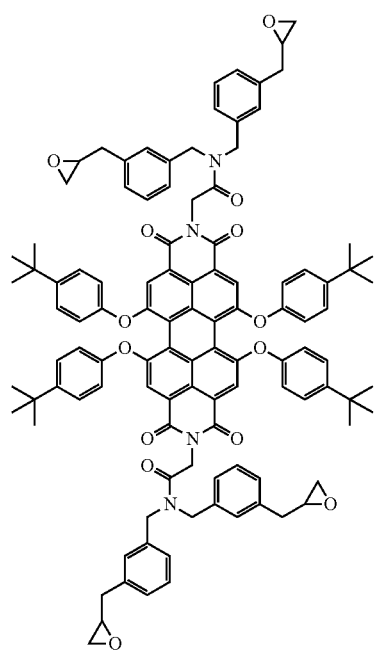
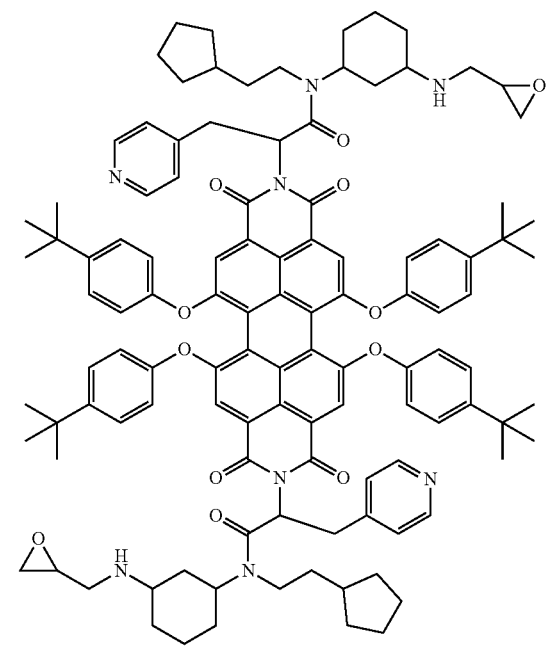

285
-continued
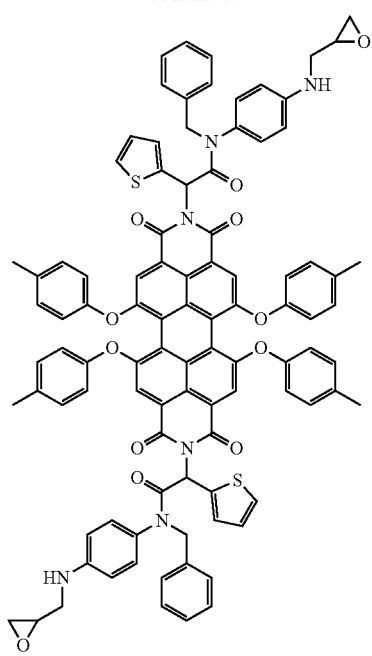
286
-continued
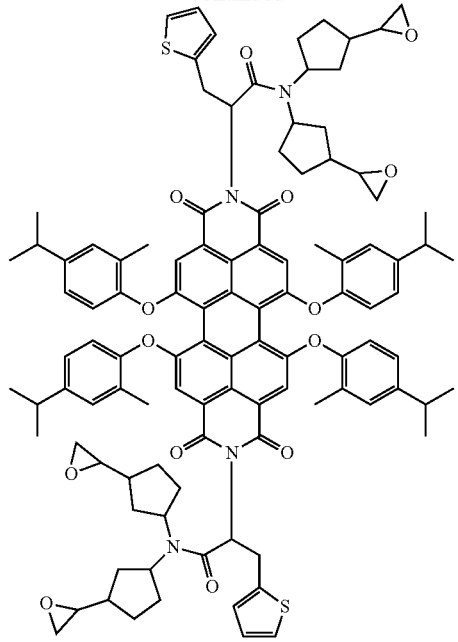
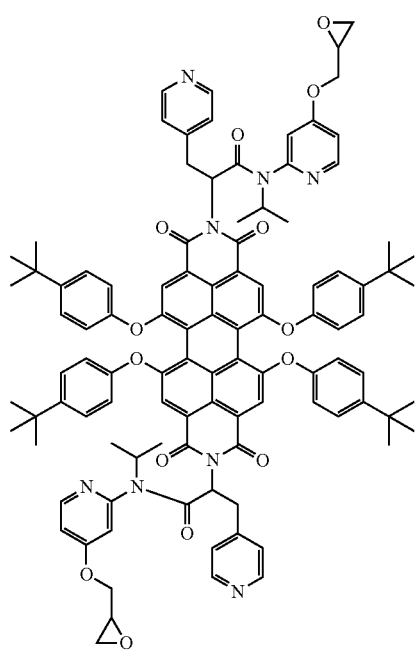
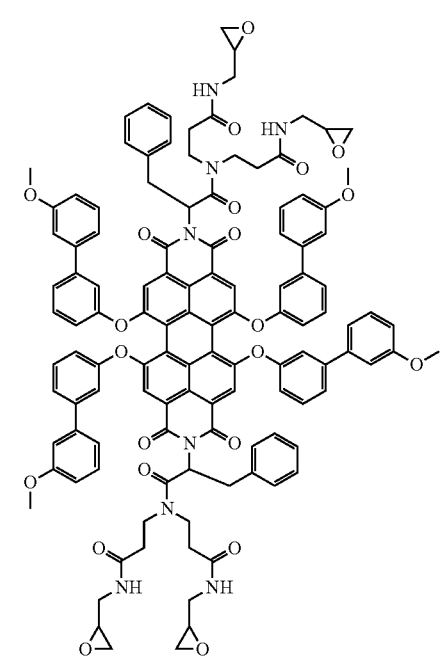

287
-continued
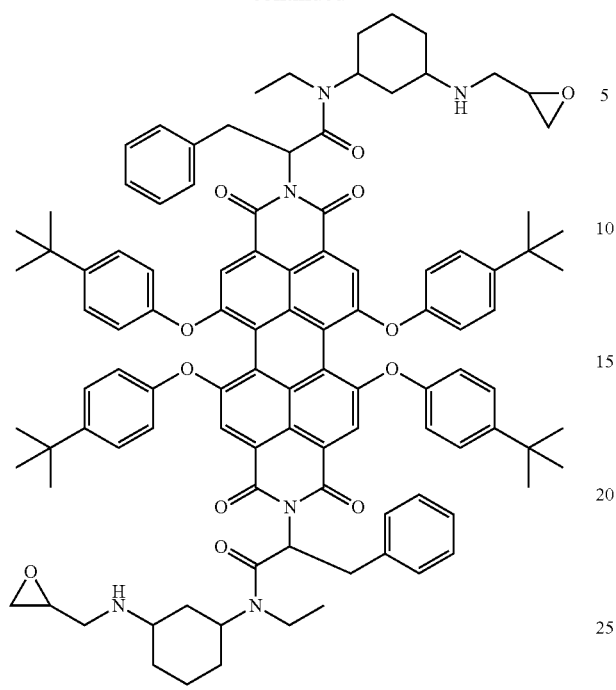
288
-continued
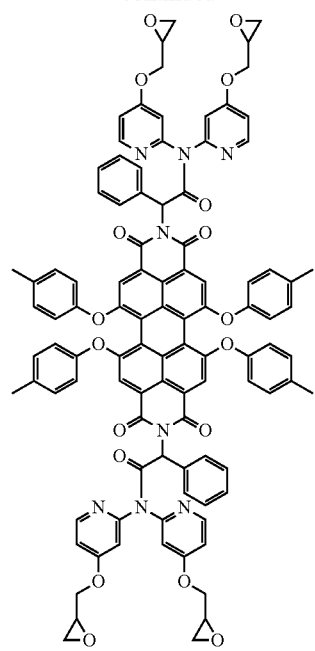
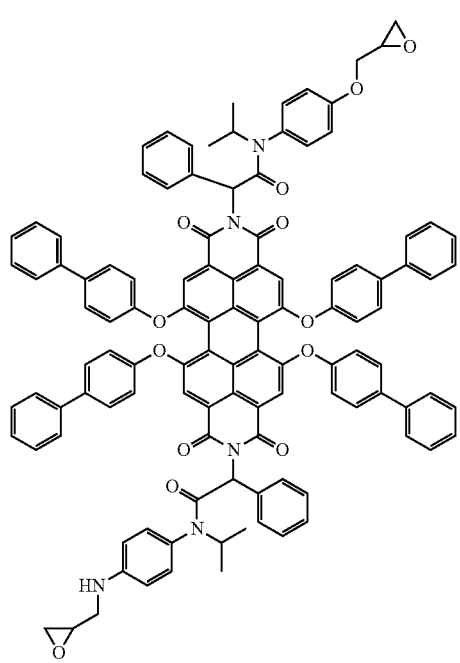
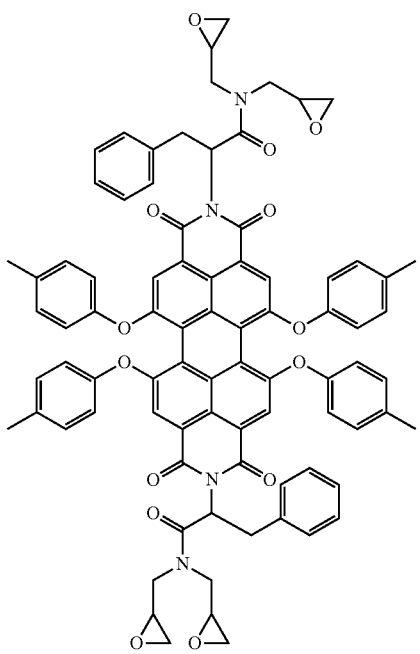

289
-continued
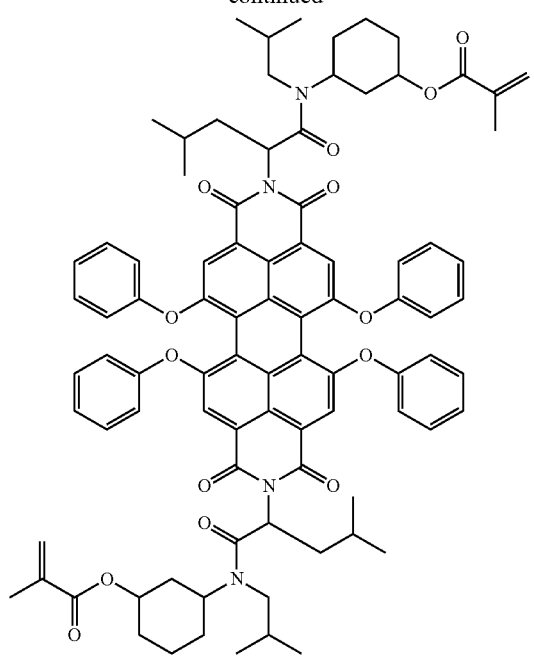
290
-continued
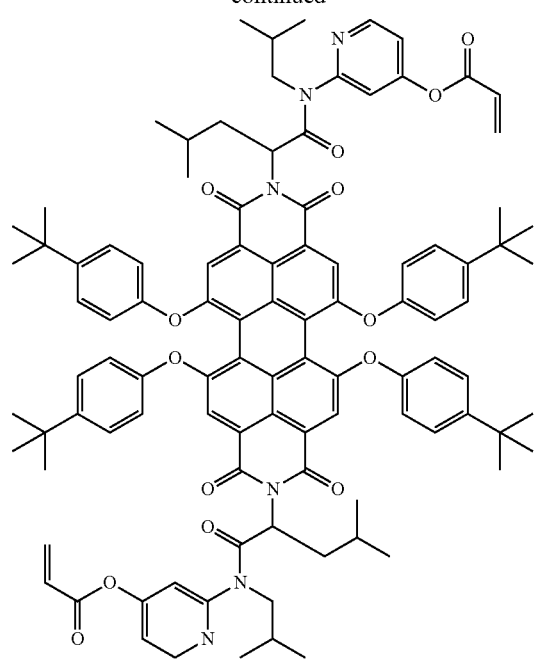
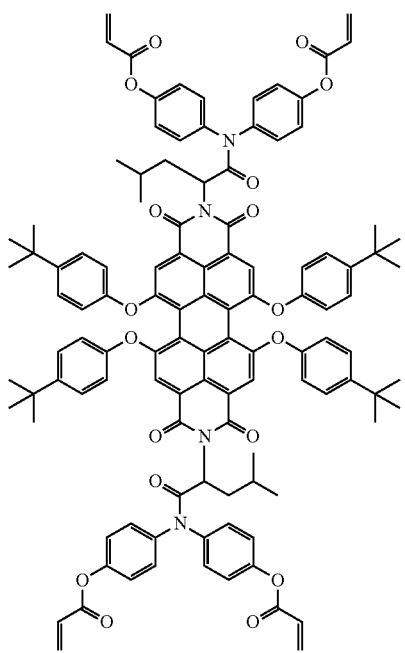
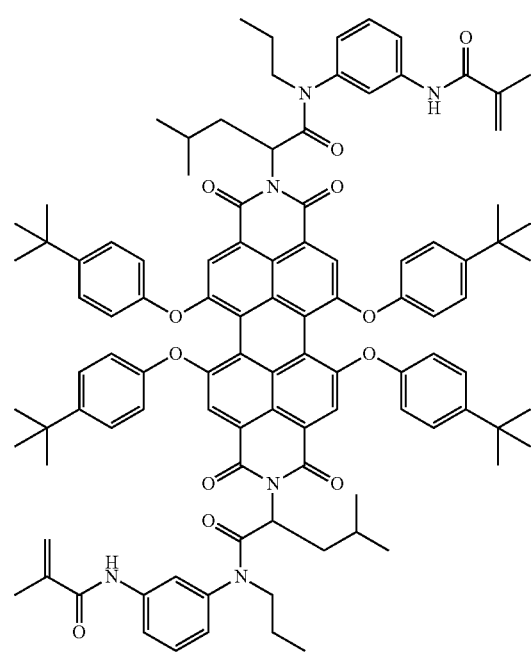

291
-continued
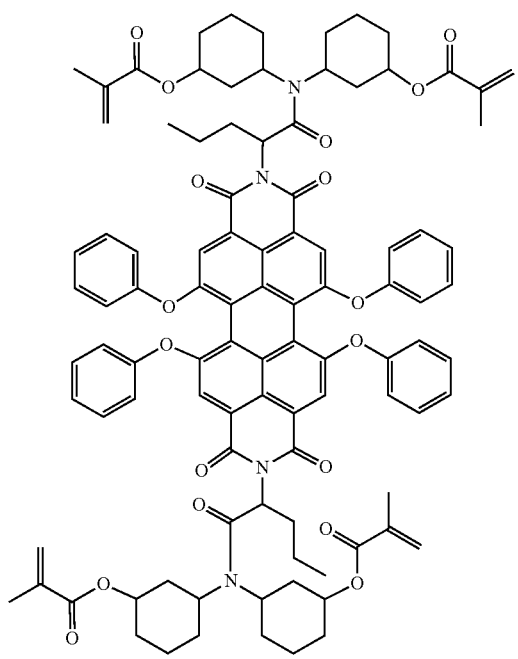
292
-continued
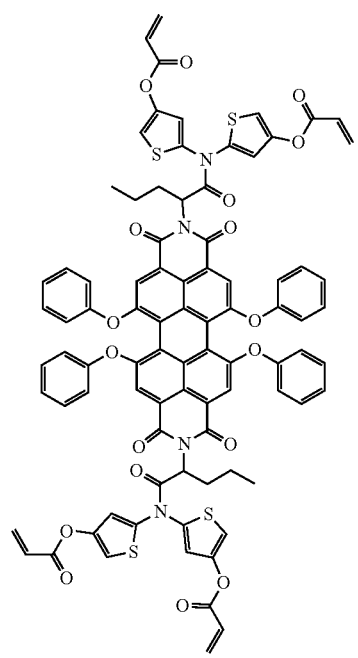
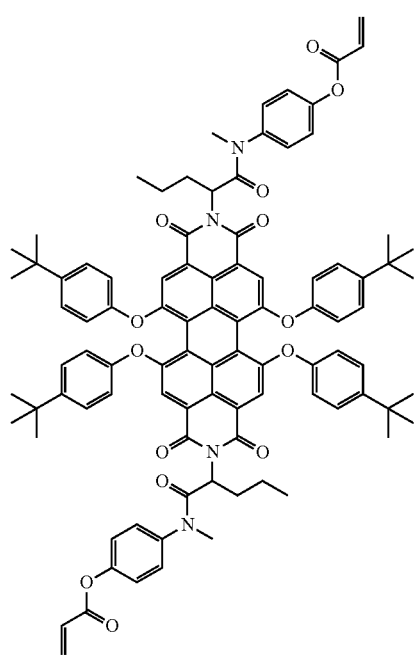
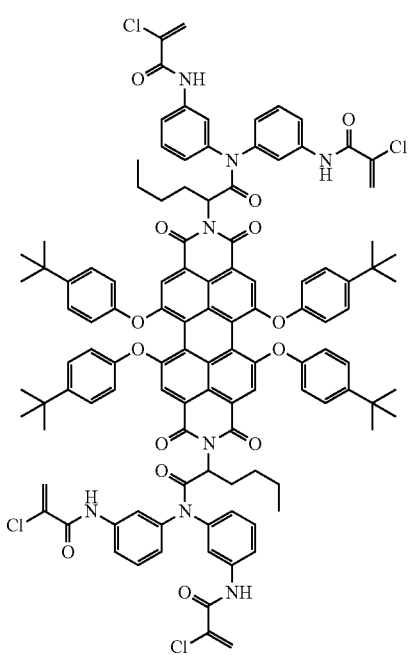

293
-continued
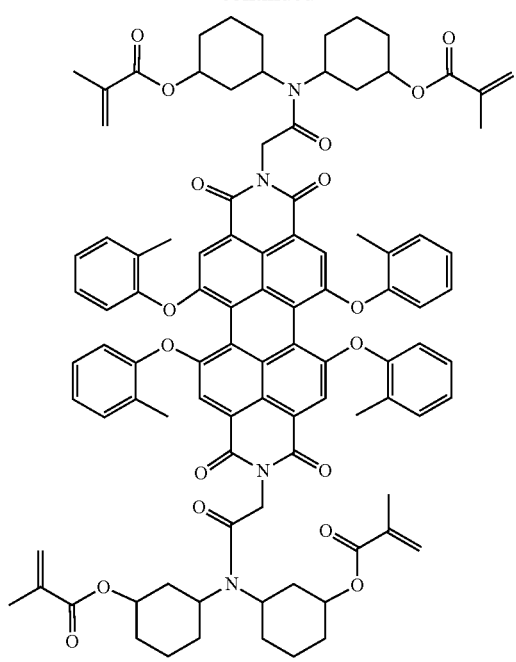
294
-continued
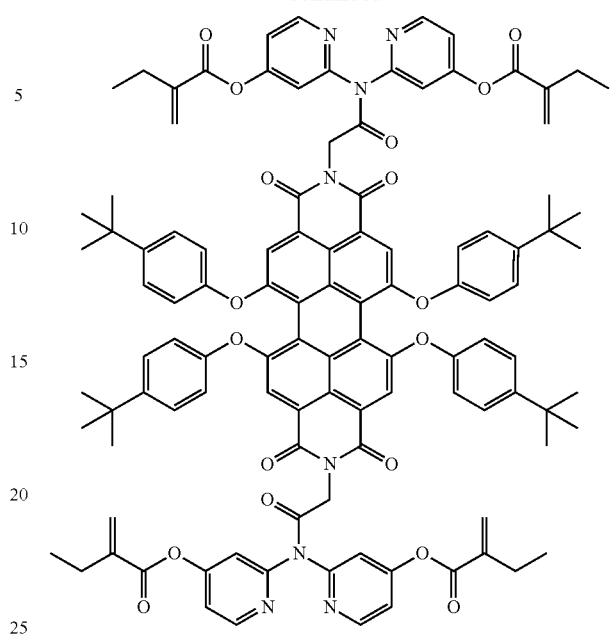
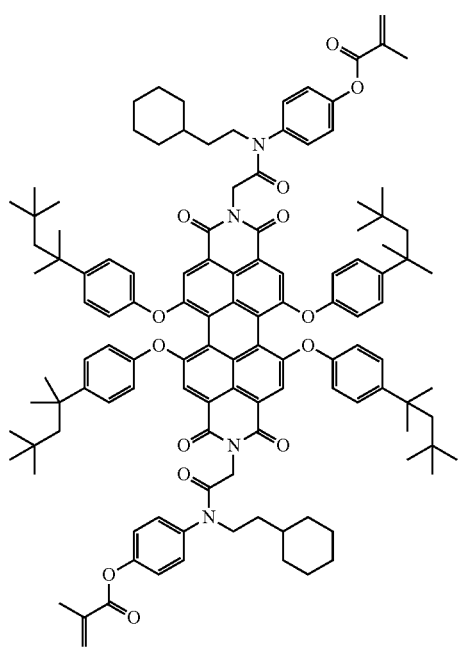
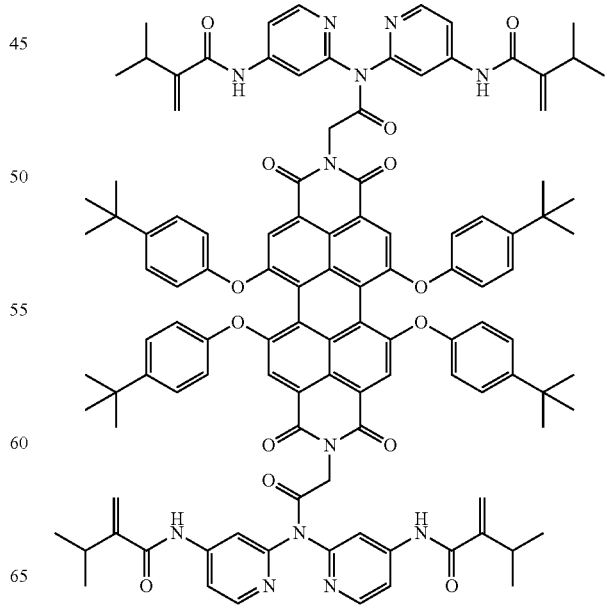

295
-continued
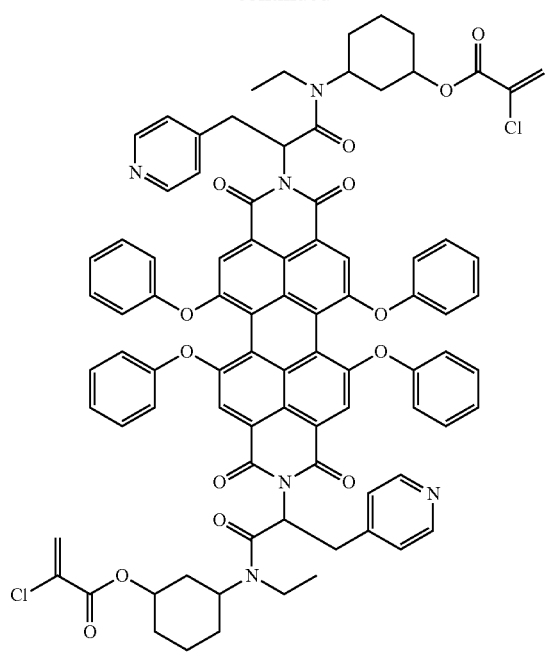
296
-continued
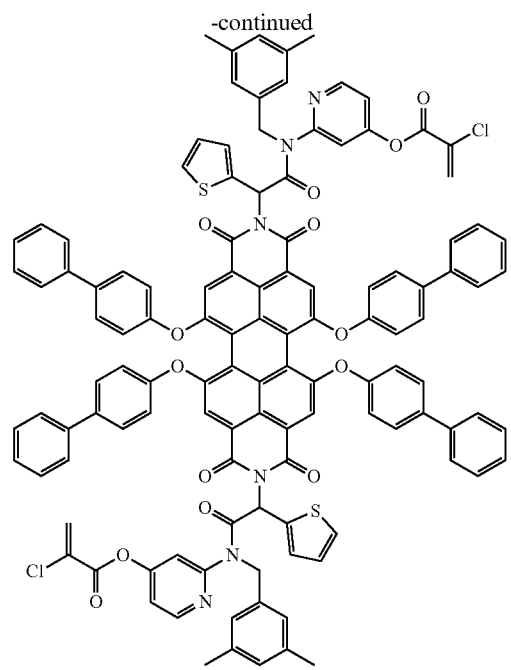
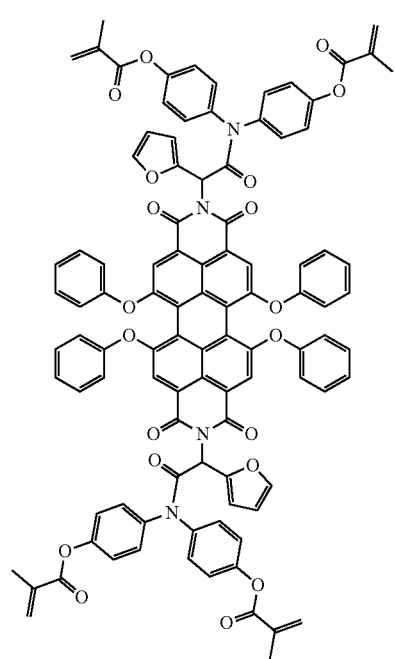
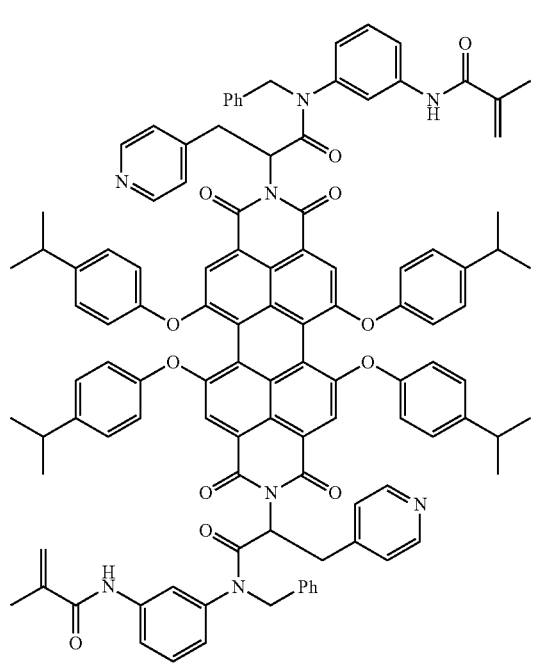

297
-continued
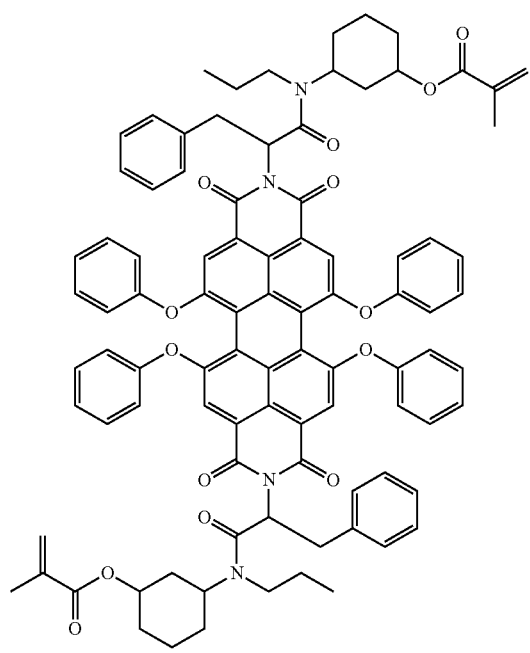
298
-continued
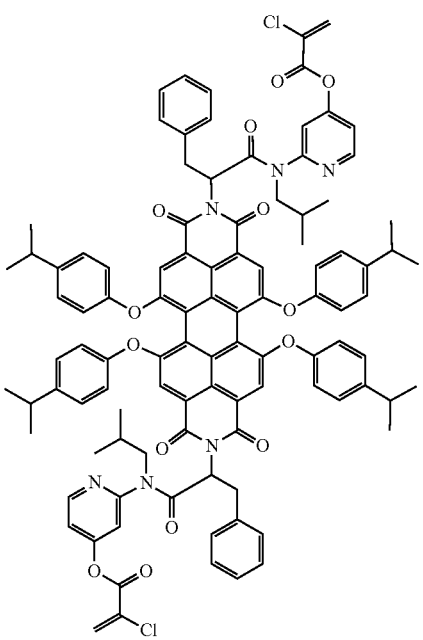
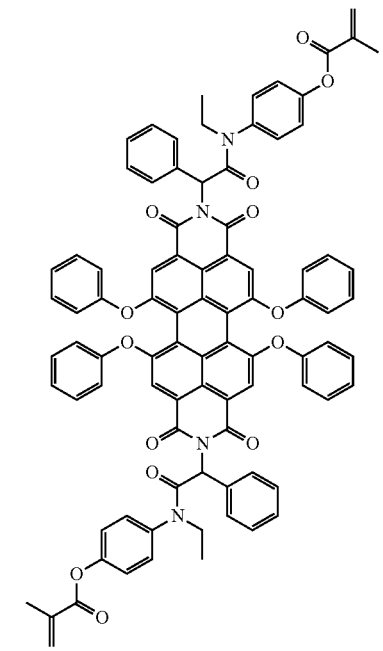

| 299 | 300 |
|---|---|
| -continued | -continued |
| 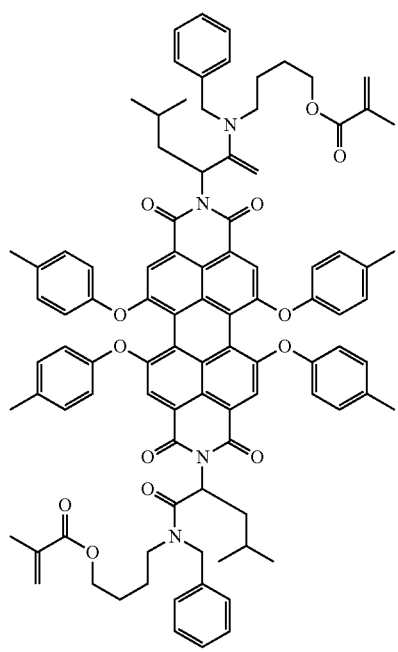 | 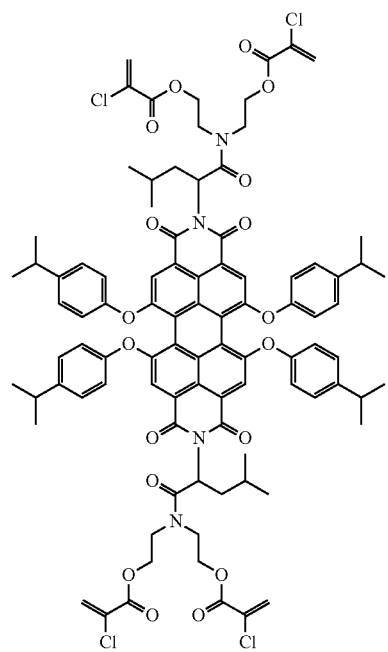 |

301
-continued
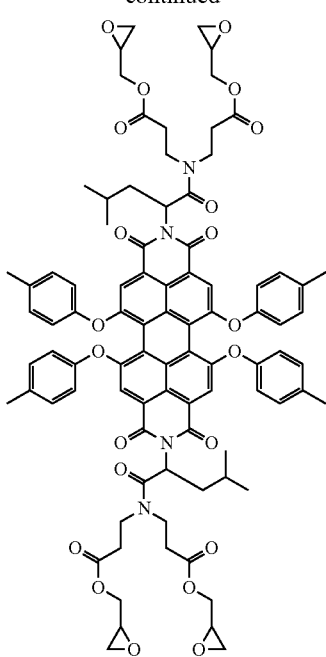
302
-continued
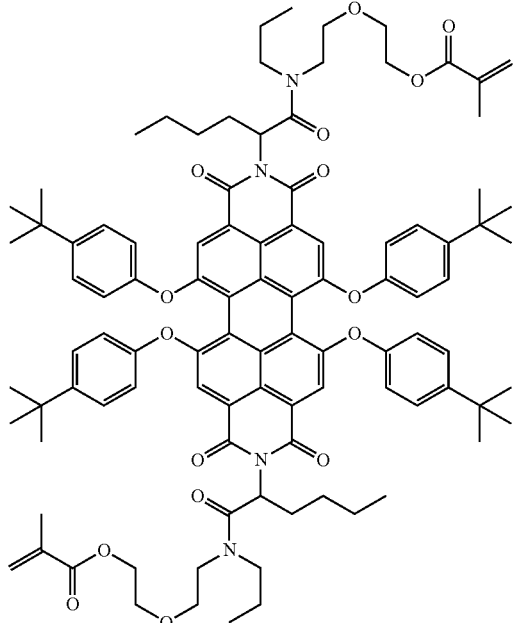

303
-continued
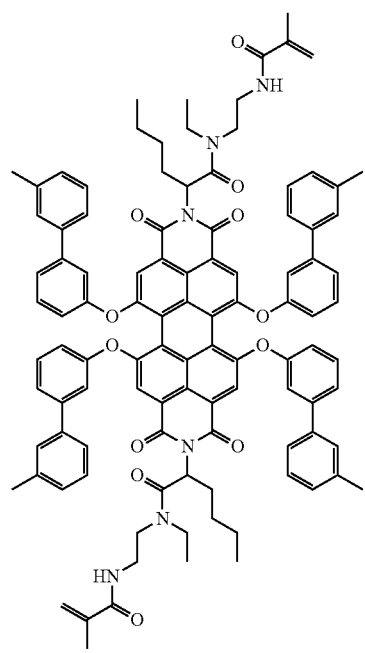
304
-continued
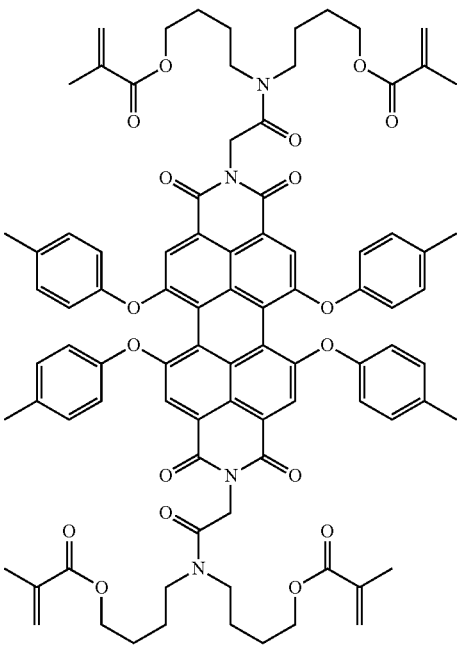
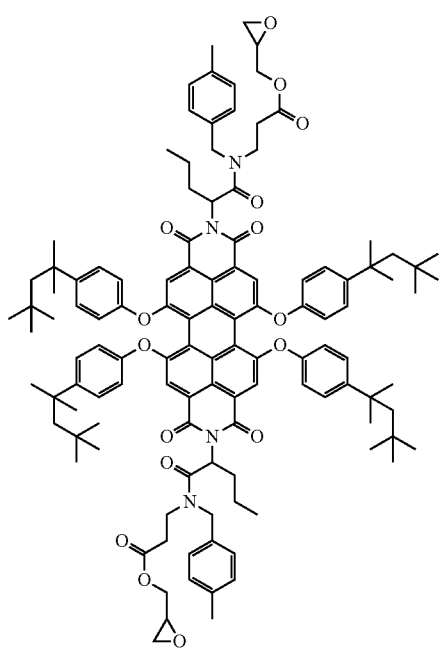
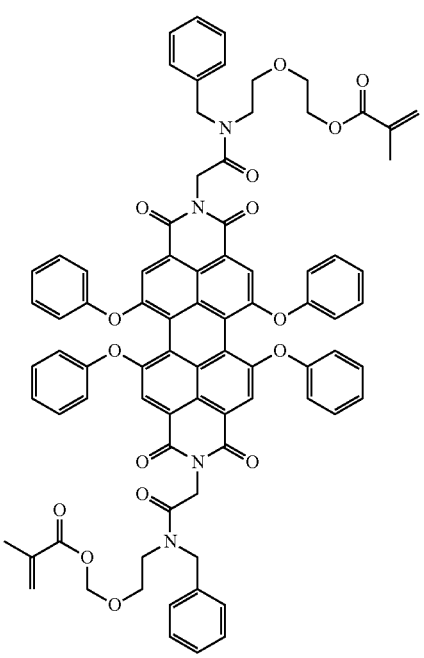

305
-continued
306
-continued
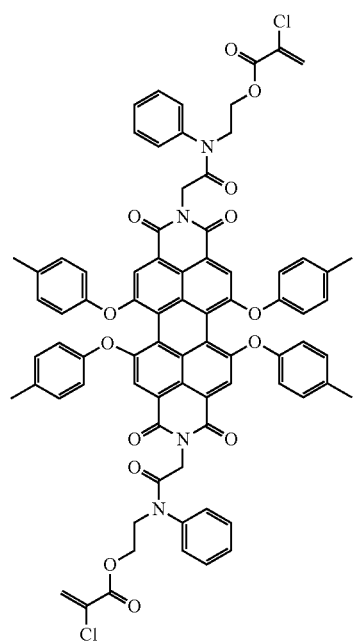
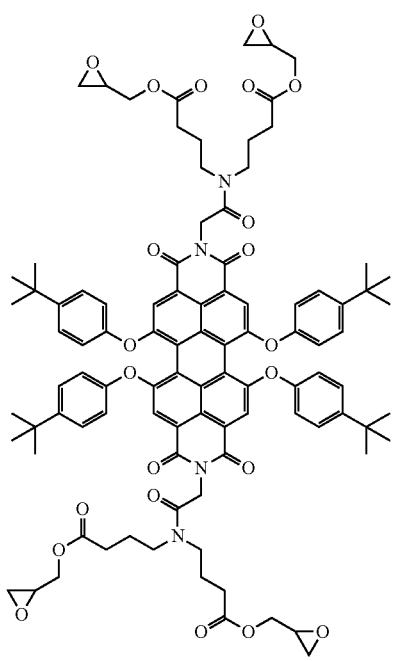

307
-continued
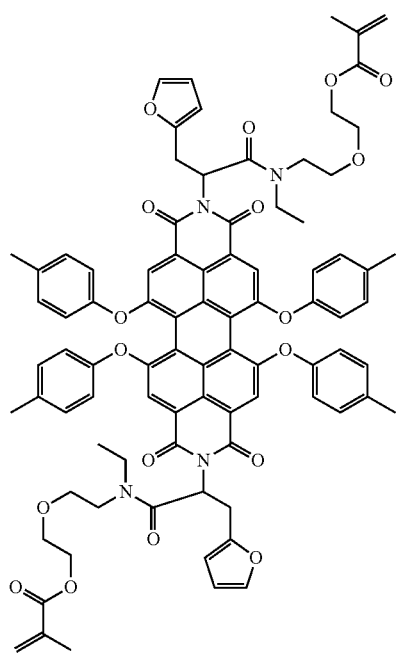
308
-continued
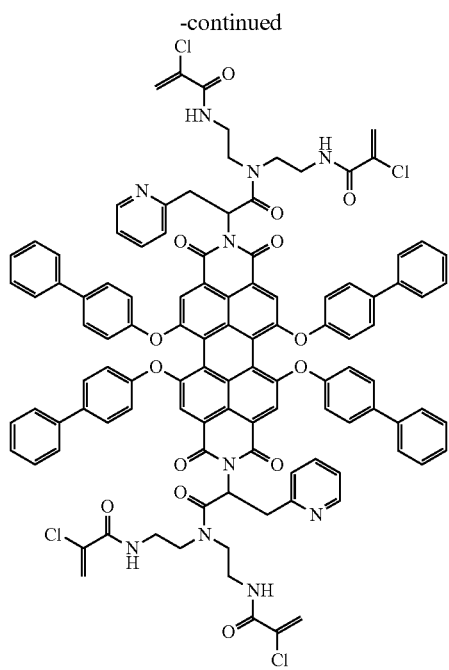
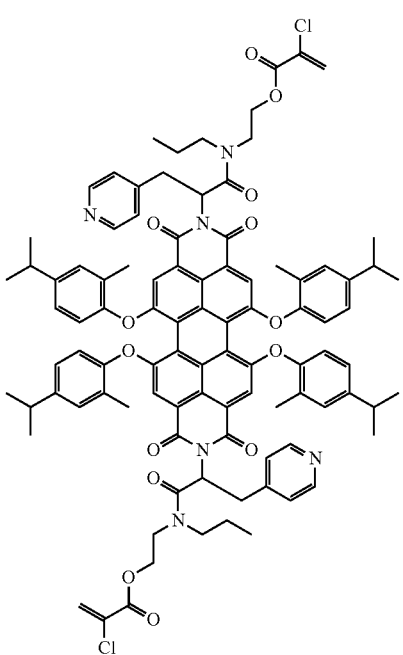
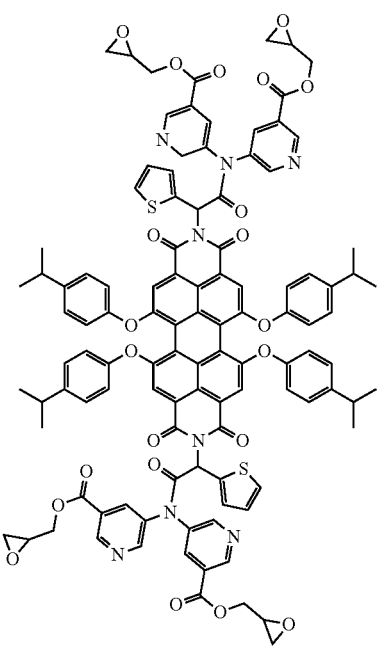

309
-continued
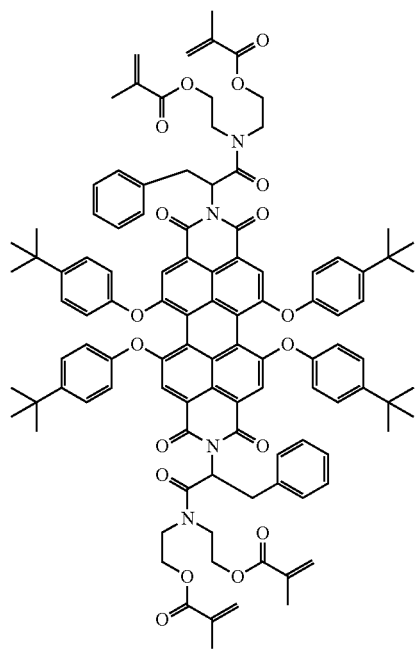
310
-continued
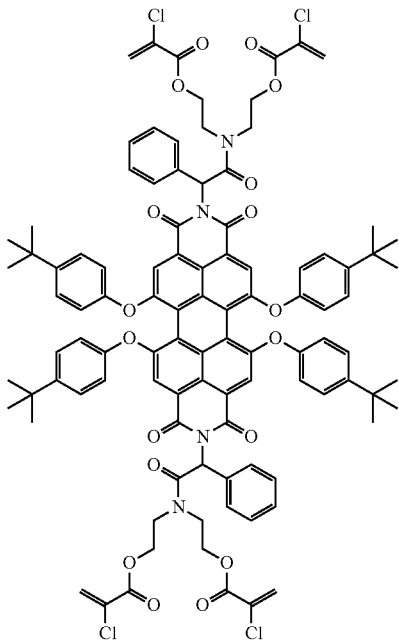
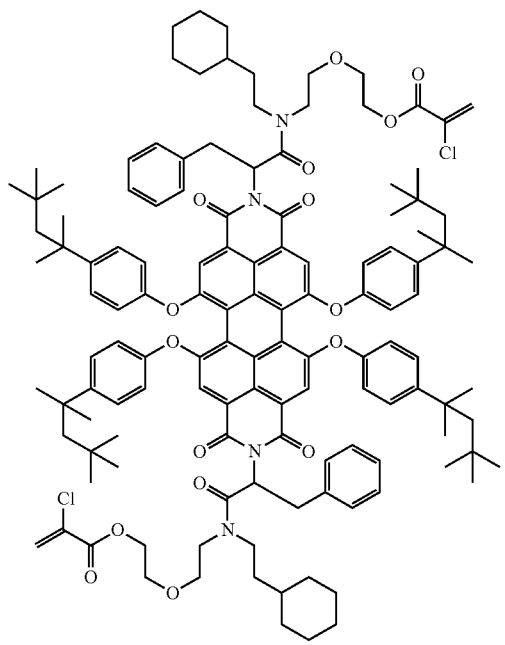
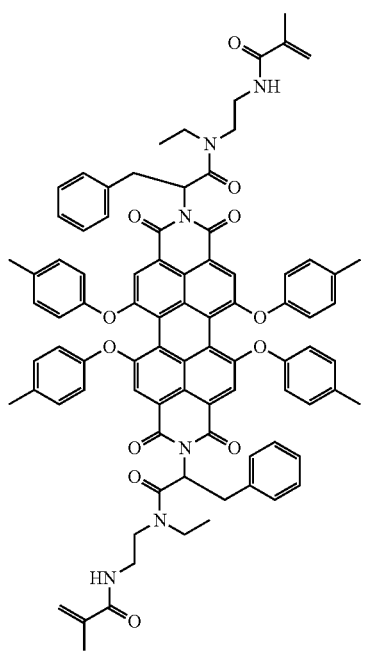

311
-continued
312
-continued
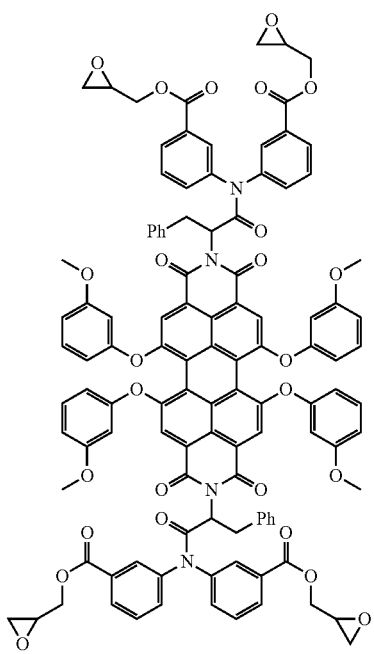 [SMILES: COc1cccc(Oc2cc3c4c(cc(Oc5cccc(OC)c5)c5c6c(Oc7cccc(OC)c7)cc7c8c(cc(Oc9cccc(OC)c9)c(c2c45)c86)C(=O)N(C(Cc2ccccc2)C(=O)N(c2cccc(C(=O)OCC4CO4)c2)c2cccc(C(=O)OCC4CO4)c2)C7=O)C(=O)N(C(Cc2ccccc2)C(=O)N(c2cccc(C(=O)OCC4CO4)c2)c2cccc(C(=O)OCC4CO4)c2)C3=O)c1]
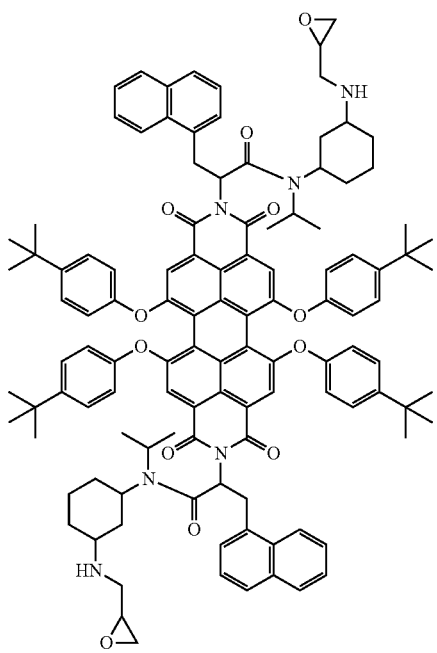

313
-continued
314
-continued
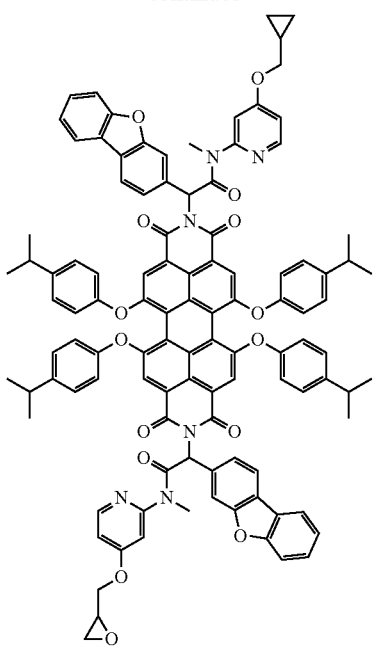
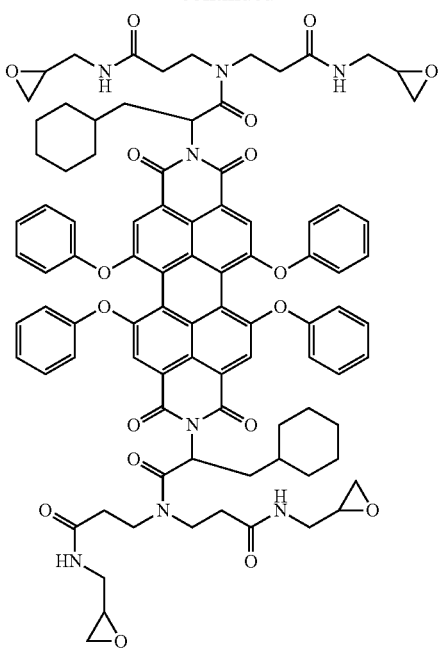

315
-continued
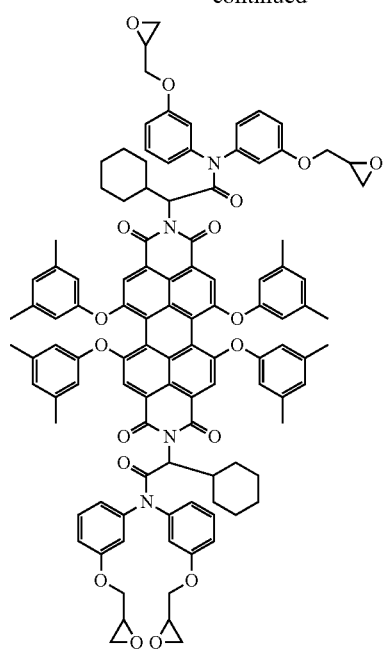
316
-continued
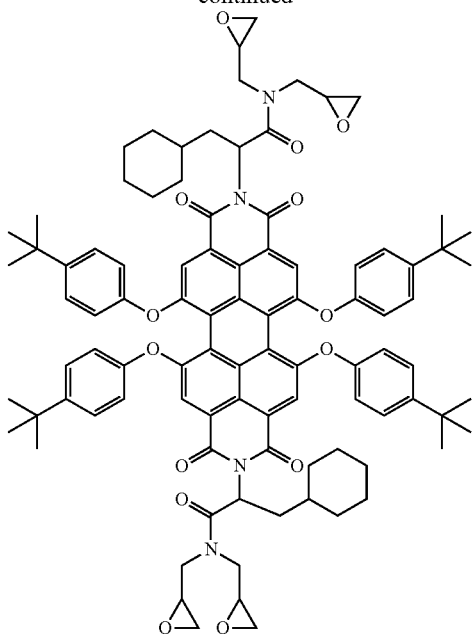
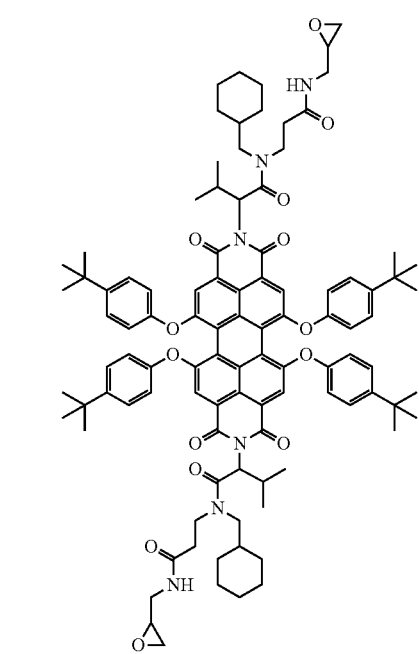

317
-continued
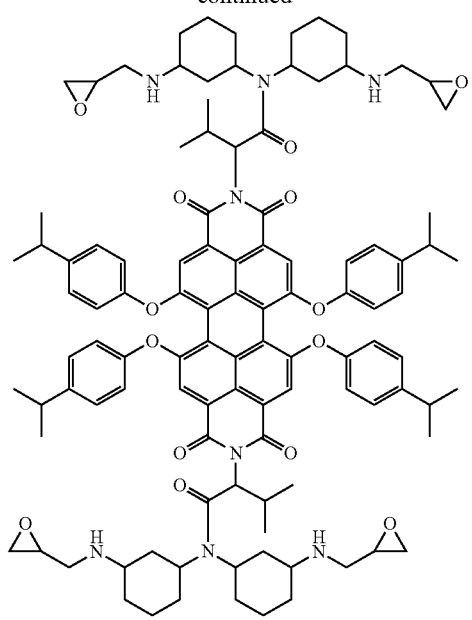
318
-continued
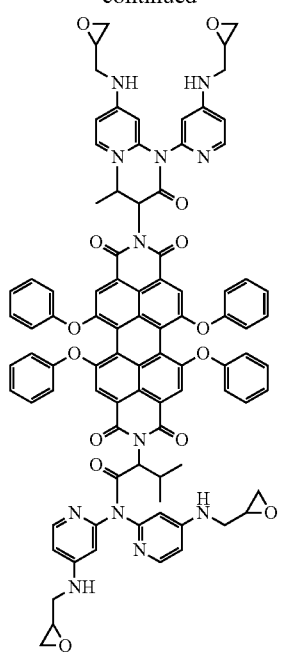
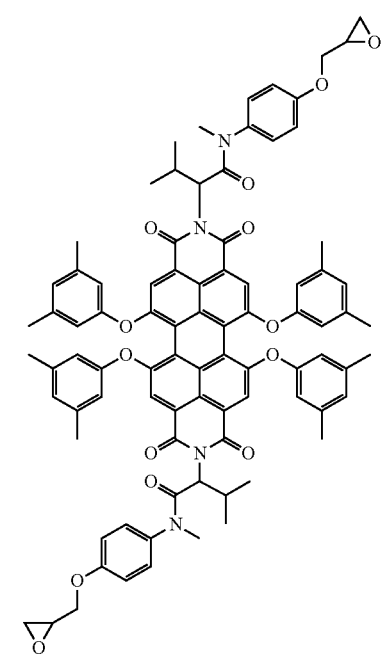
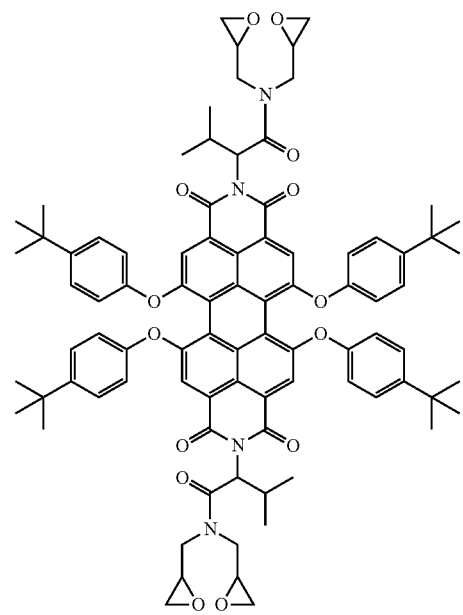

319
-continued
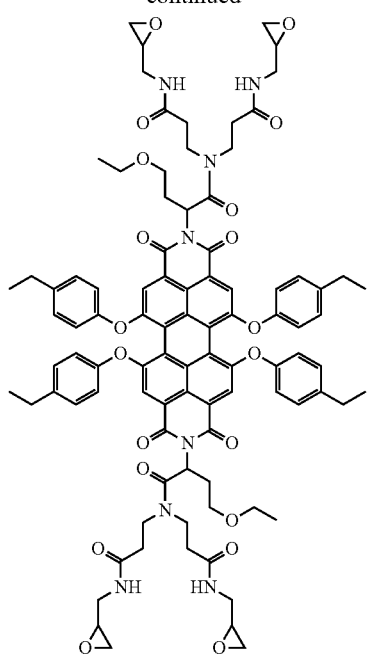
320
-continued
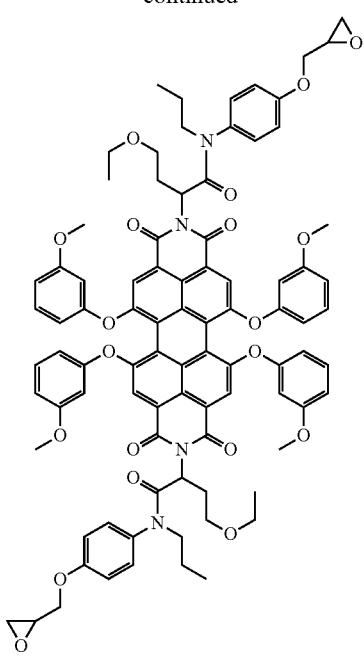
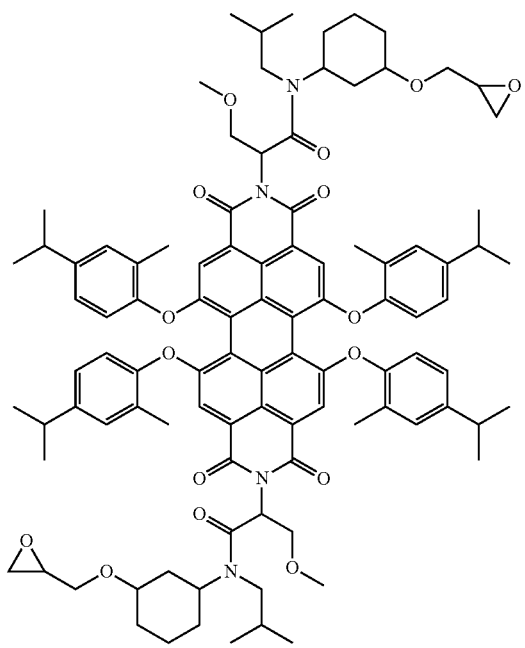
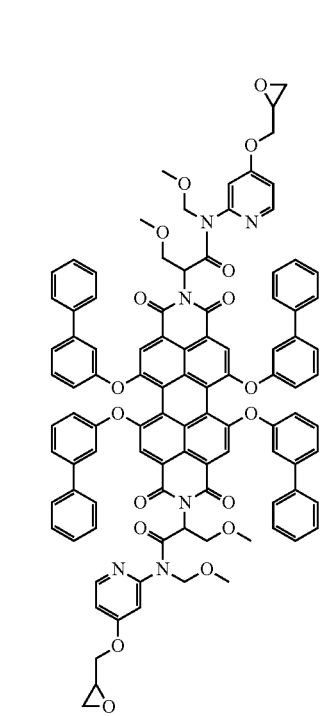

321
-continued
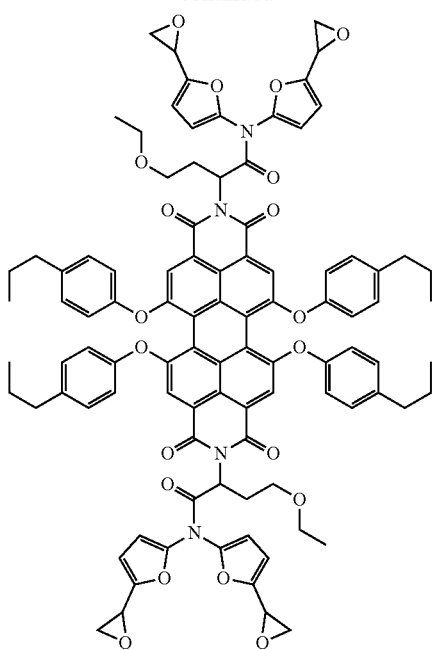
322
-continued
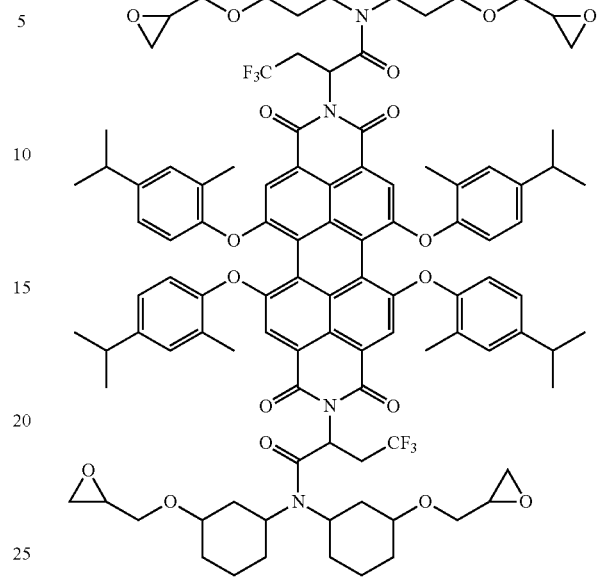
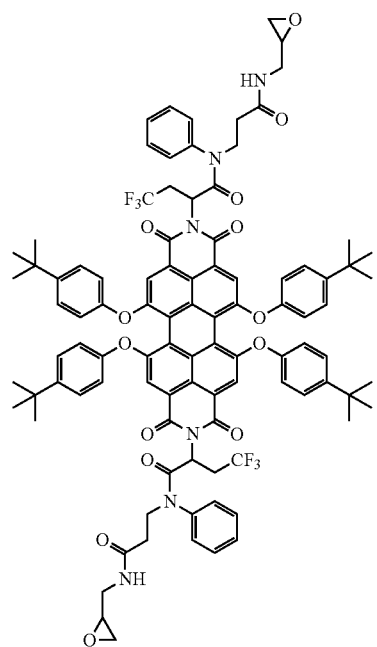
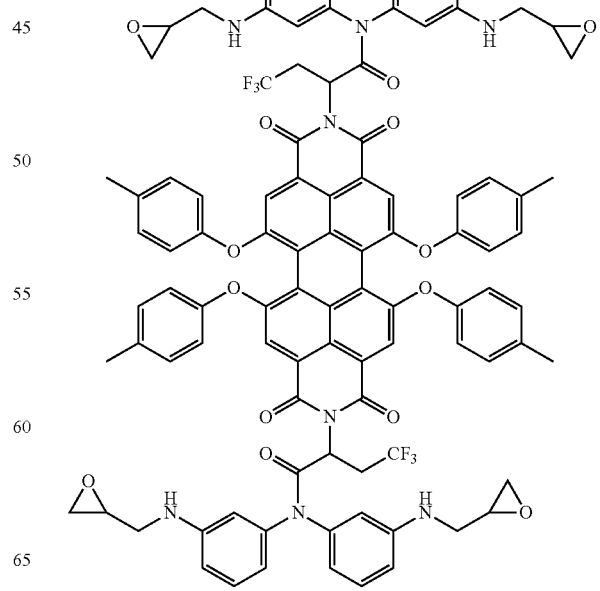

323
-continued
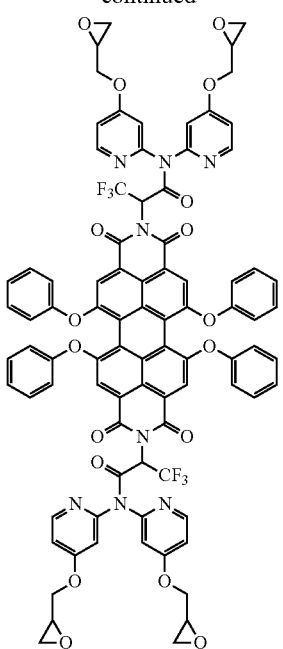
324
-continued
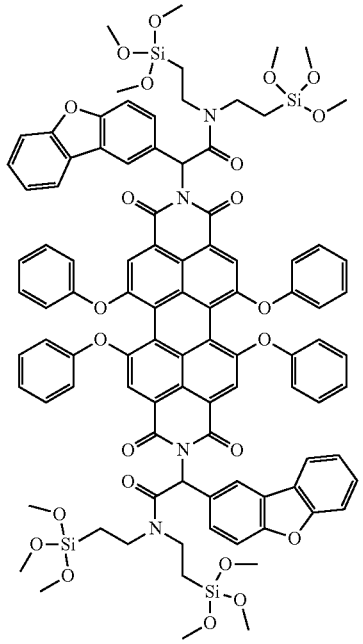

325
-continued
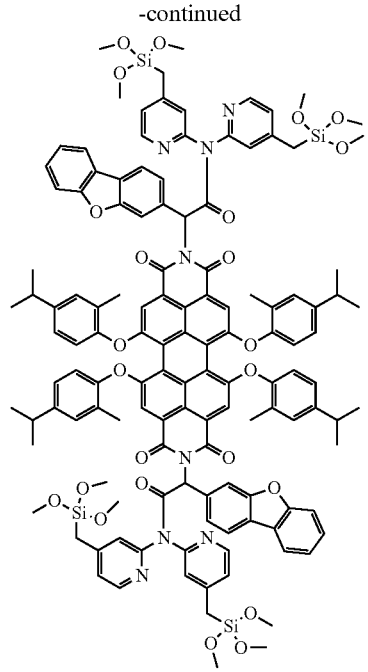
326
-continued
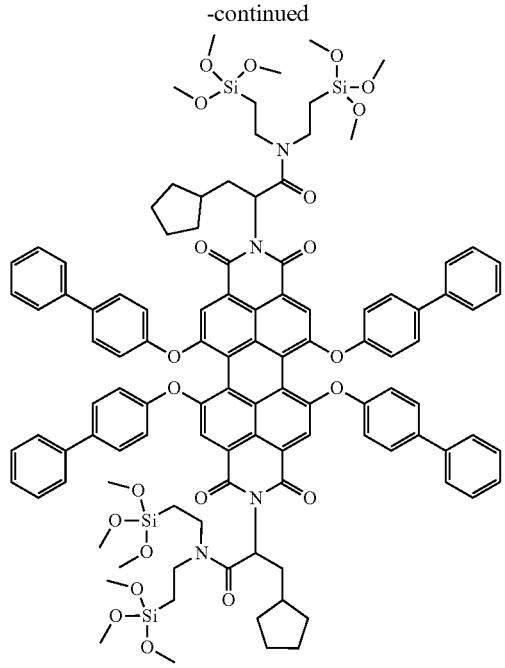
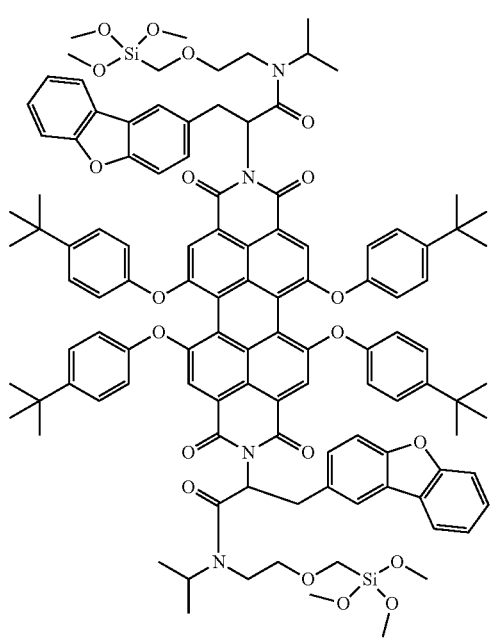
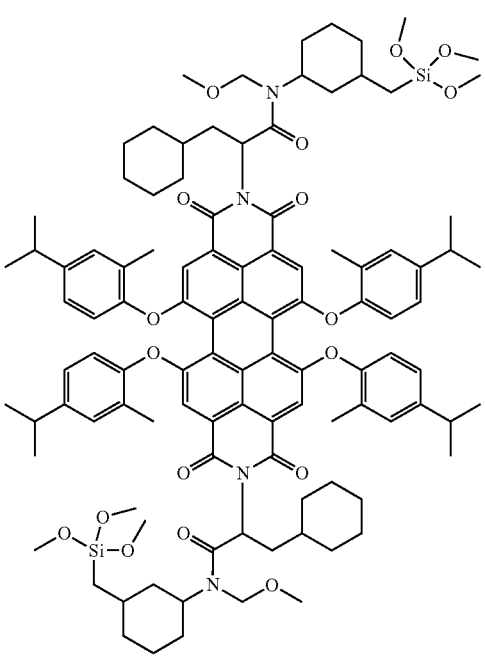

327
-continued
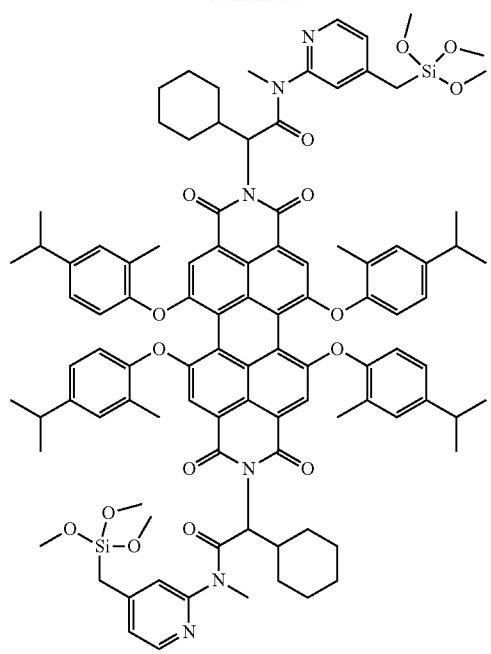
328
-continued
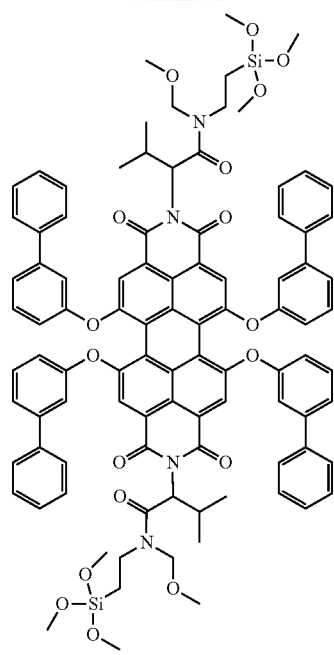
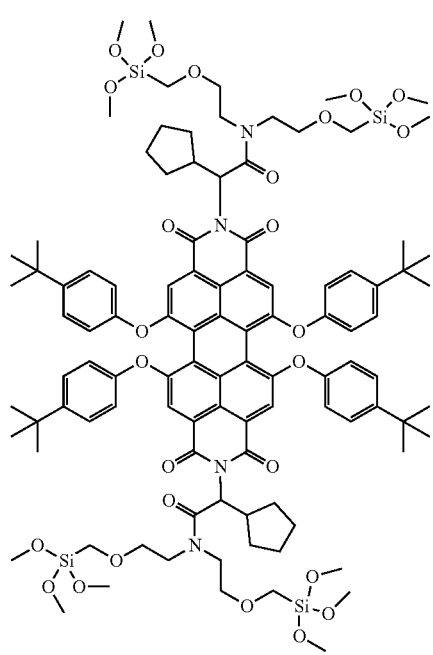
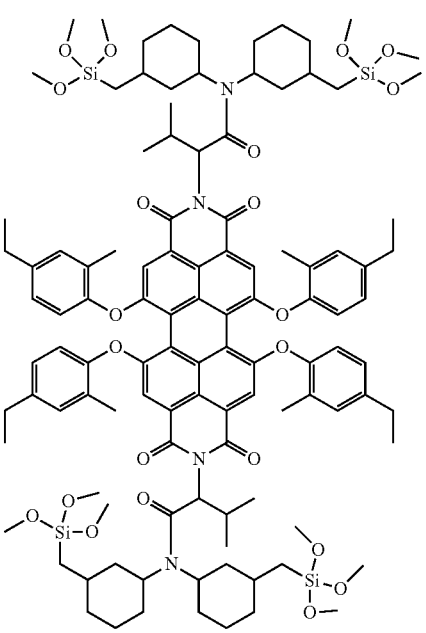

329
-continued
330
-continued
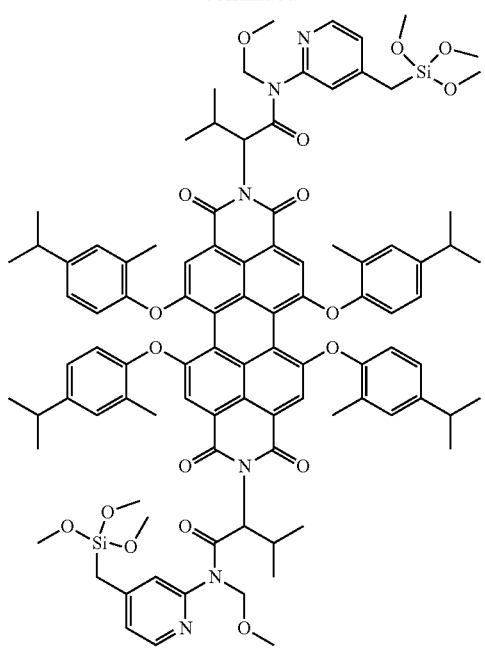
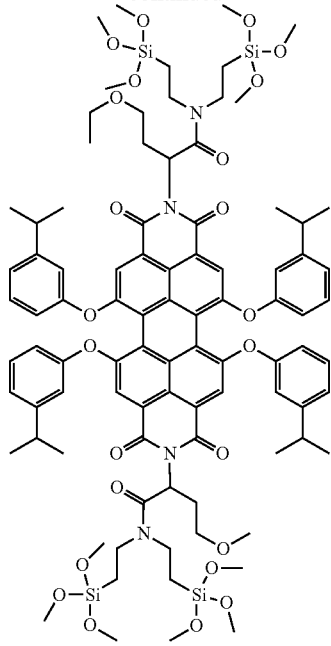
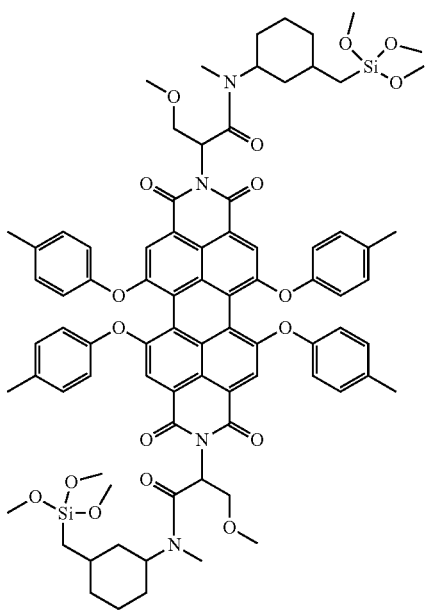

331
-continued
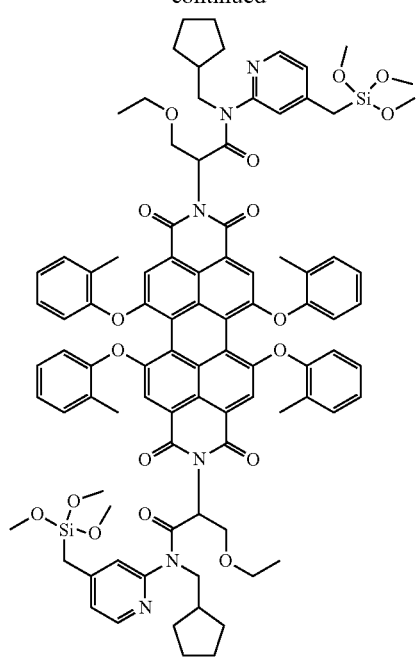
332
-continued
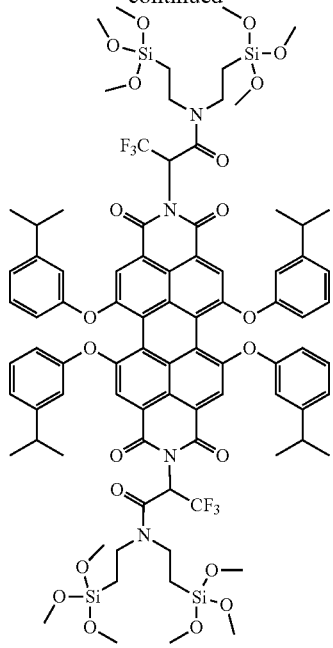
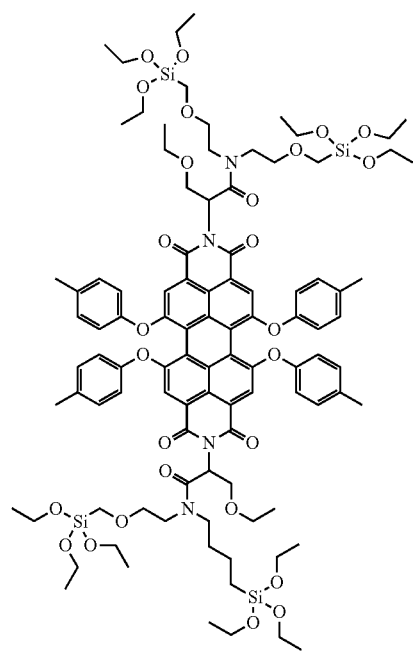
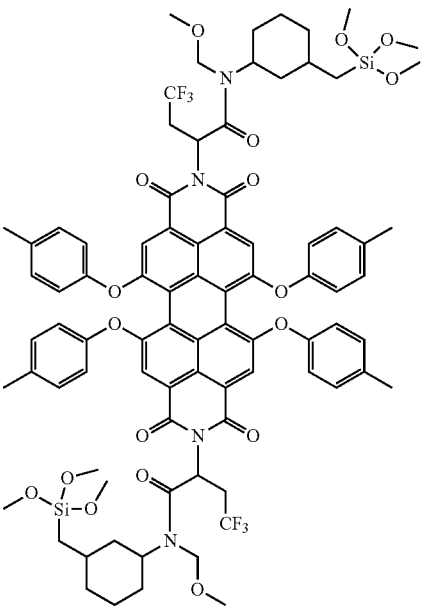

333
-continued
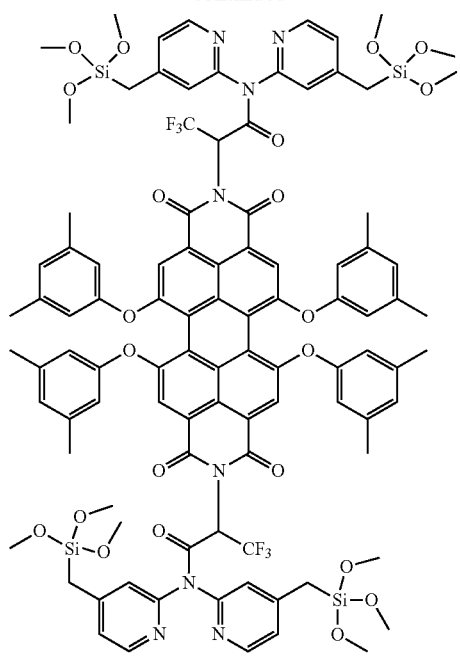
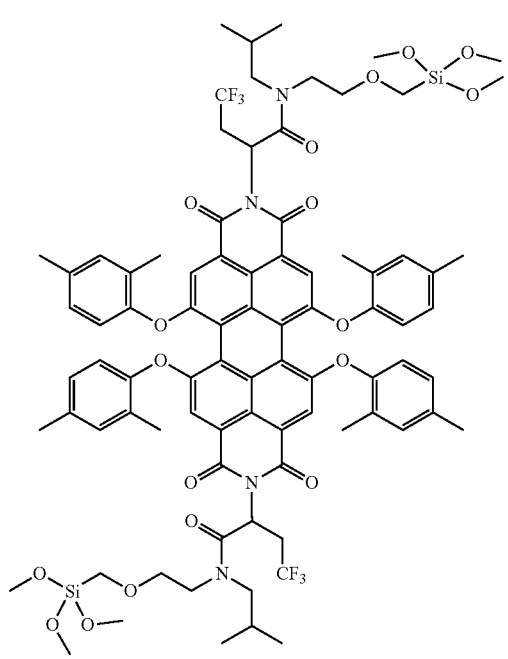
334
-continued
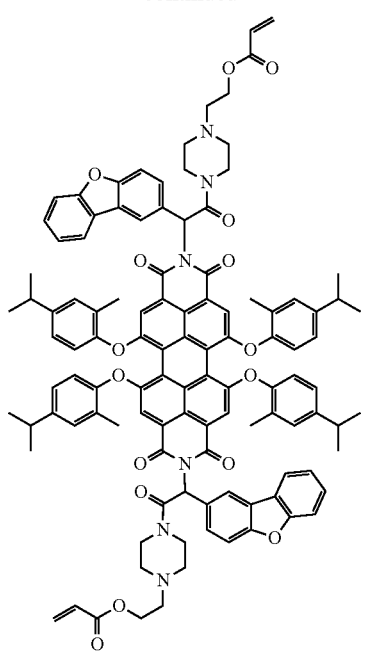
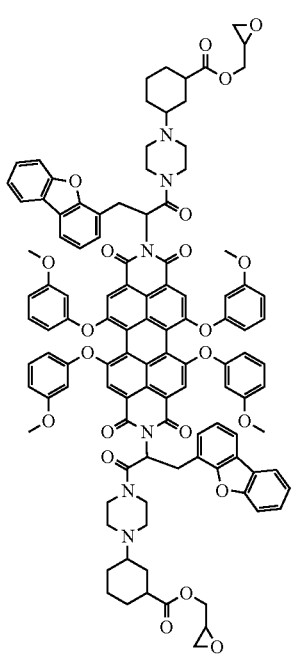

335
-continued
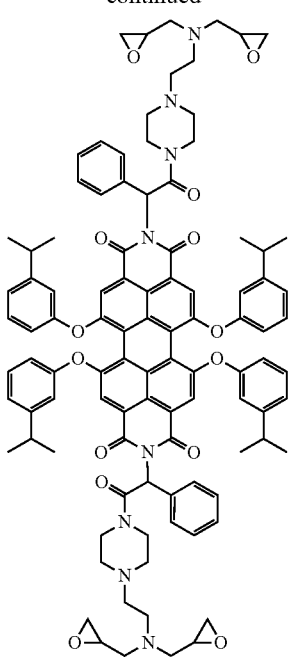
336
-continued
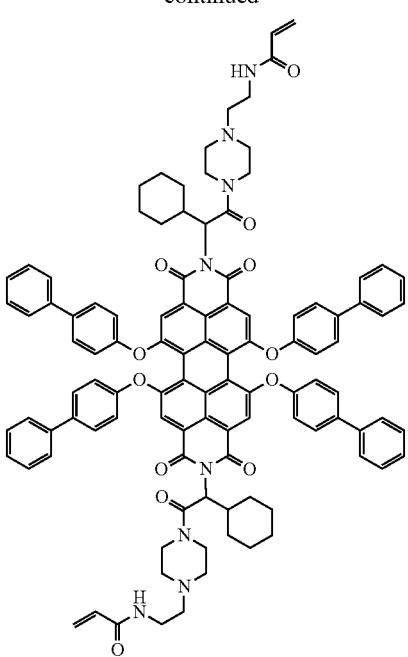
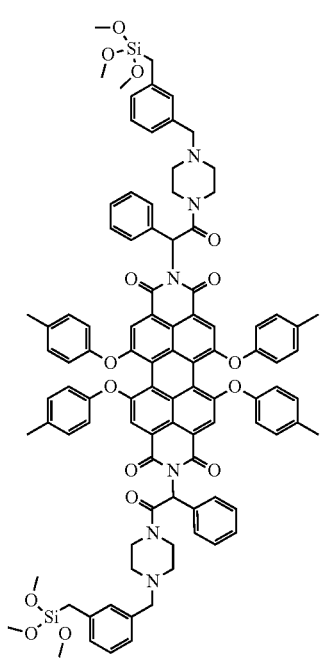
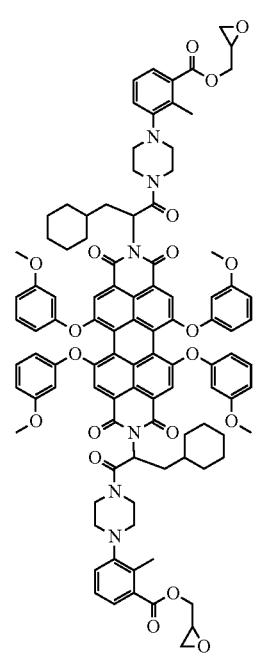

337
-continued
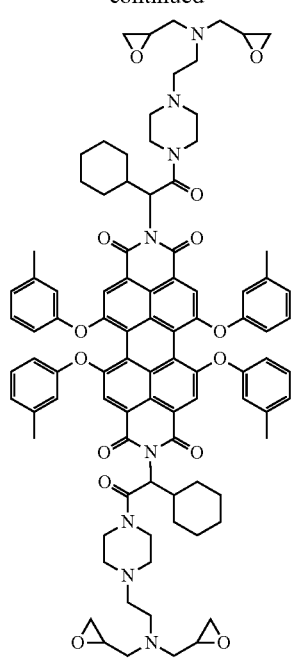
338
-continued

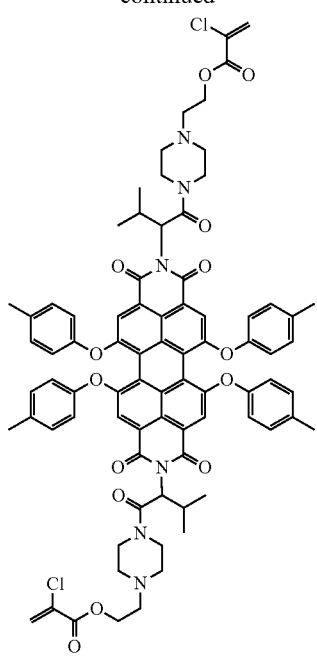

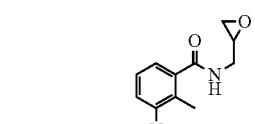
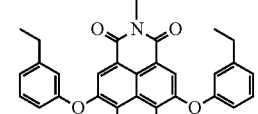
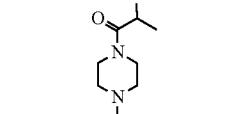

339
-continued
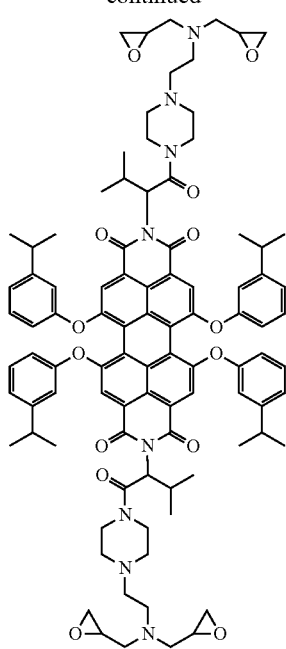
340
-continued
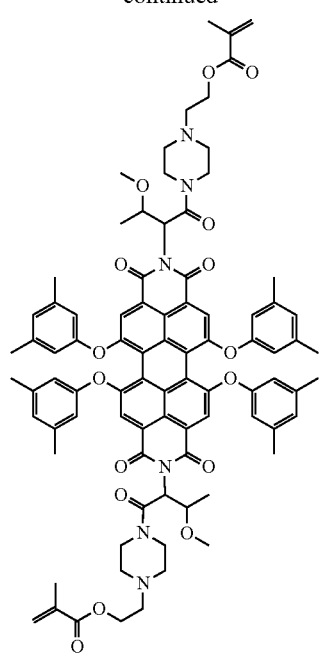
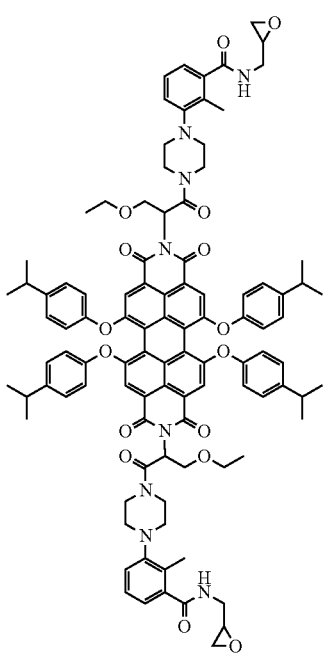

341
-continued
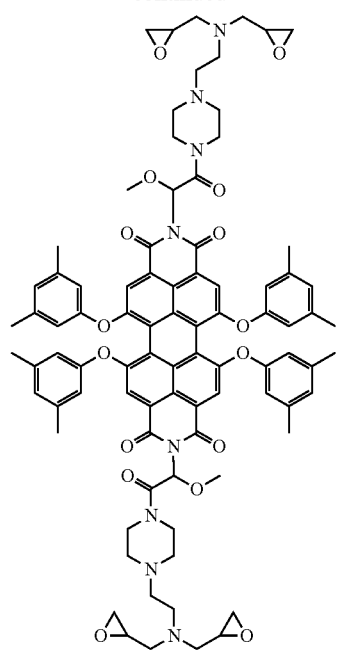
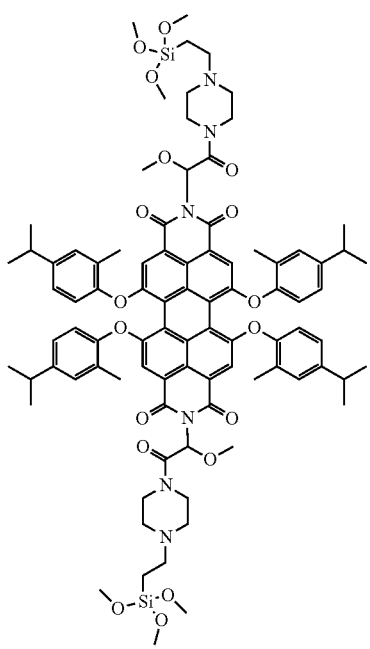
342
-continued
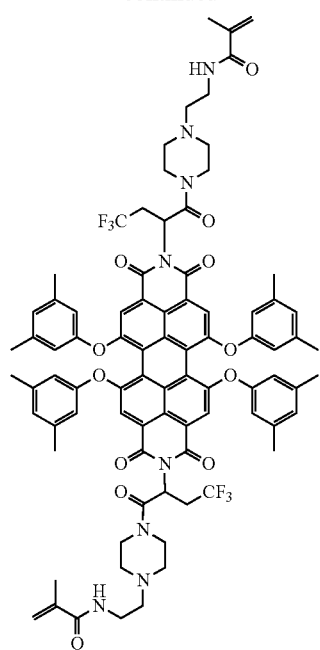
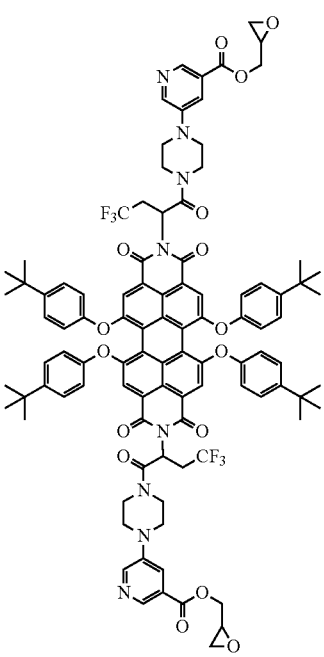

343
-continued
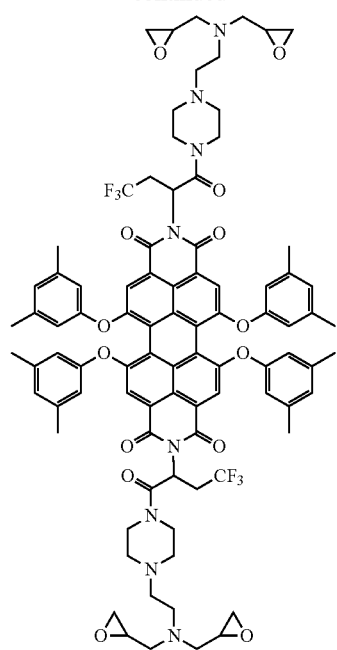
344
-continued
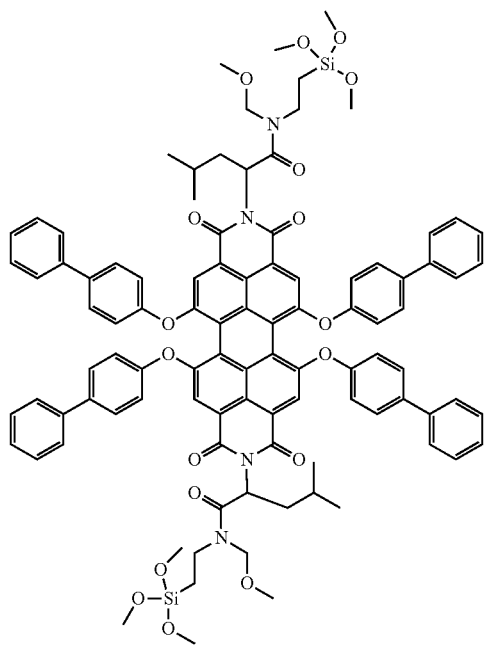
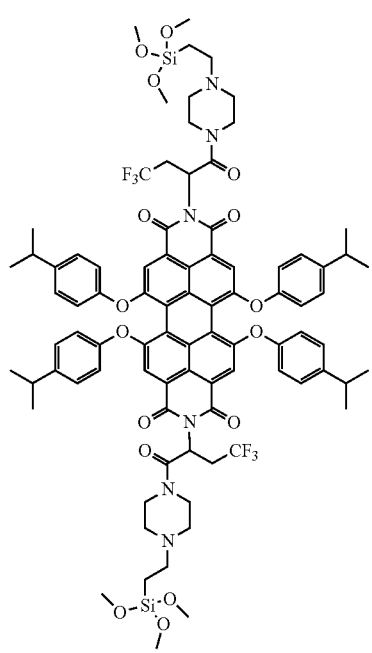
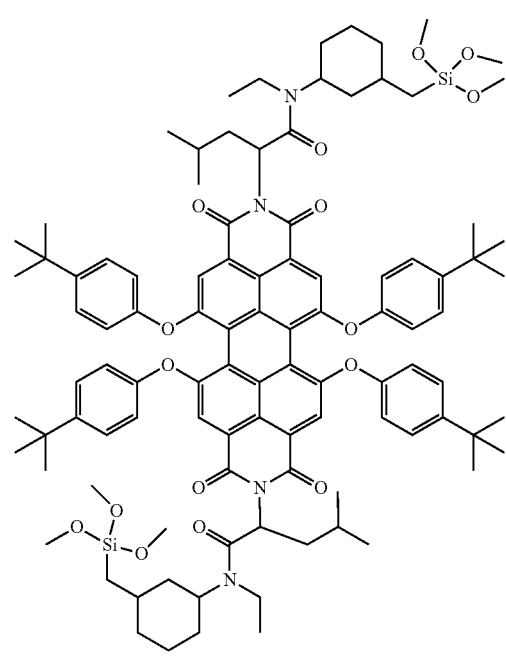

345
-continued
346
-continued
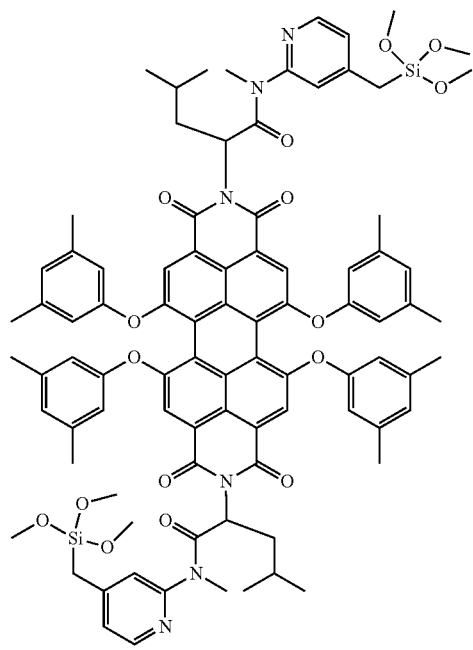
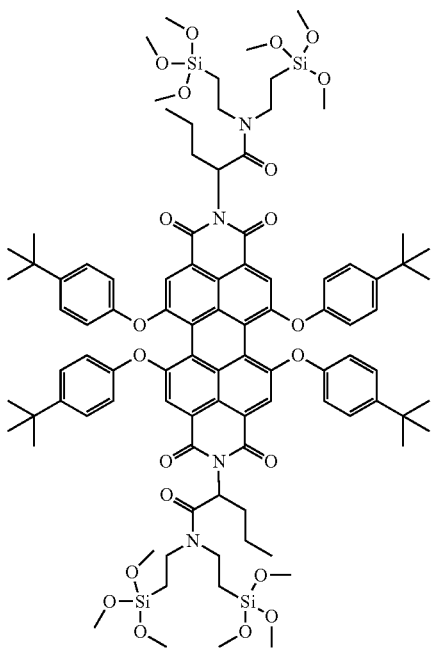

347
-continued
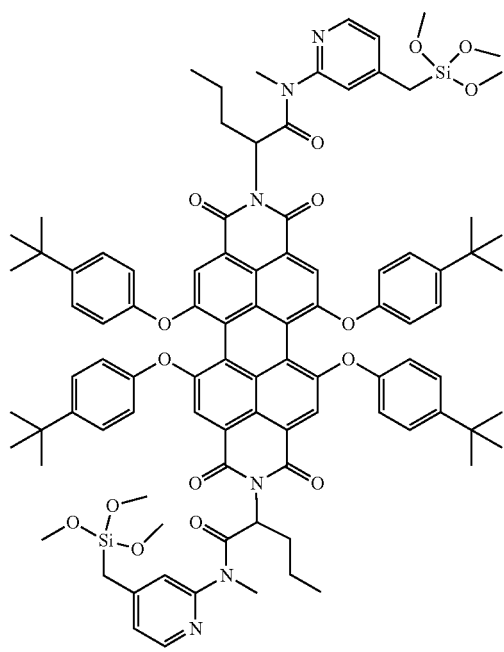
348
-continued
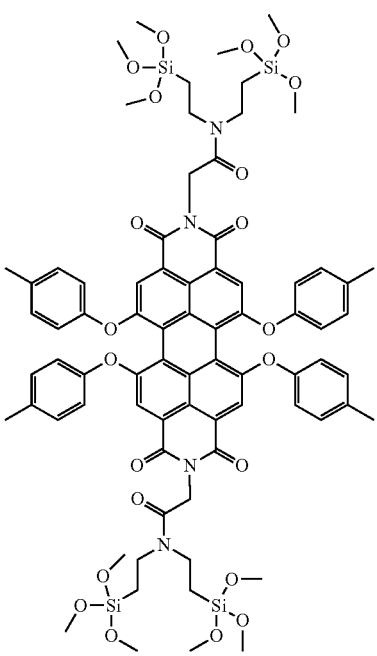
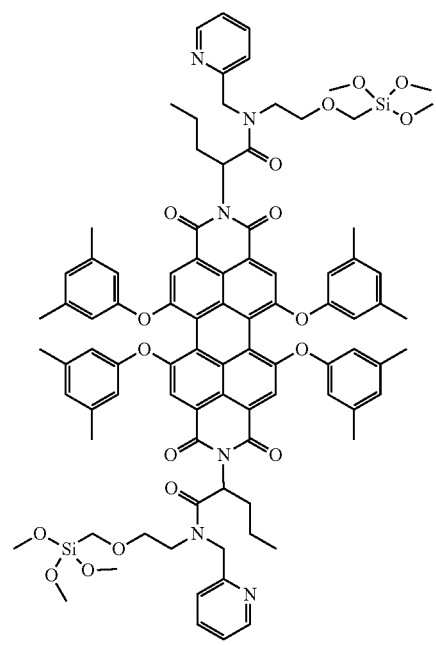
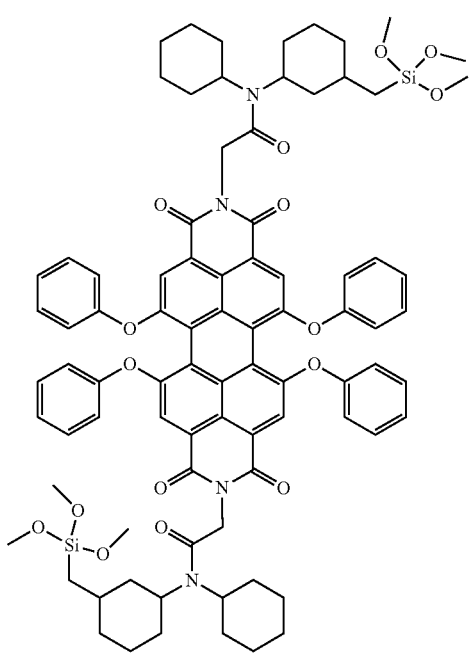

349
-continued
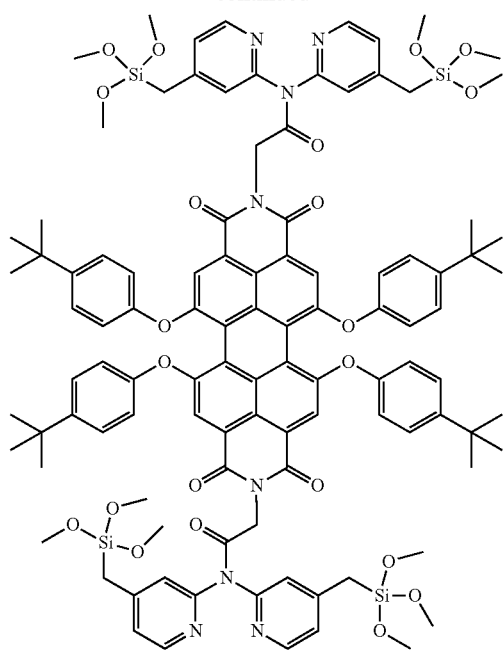
350
-continued
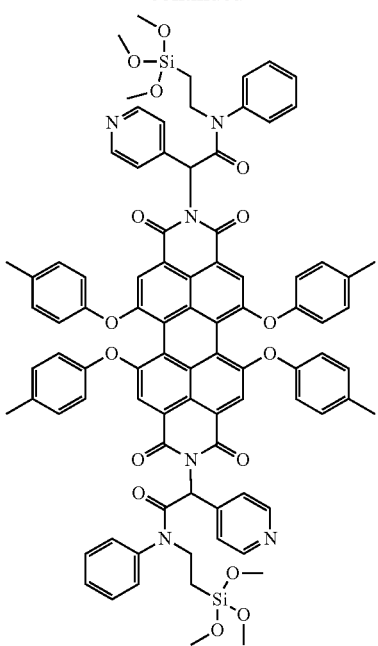
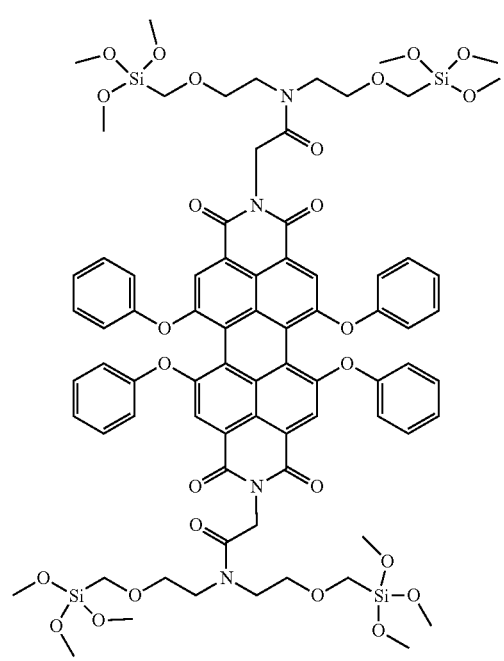
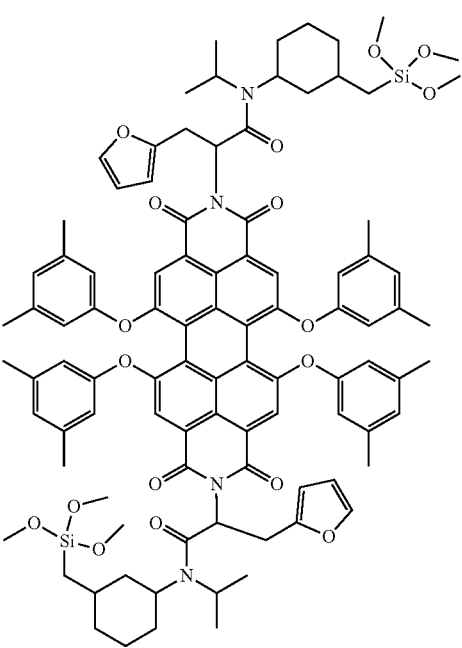

351
-continued
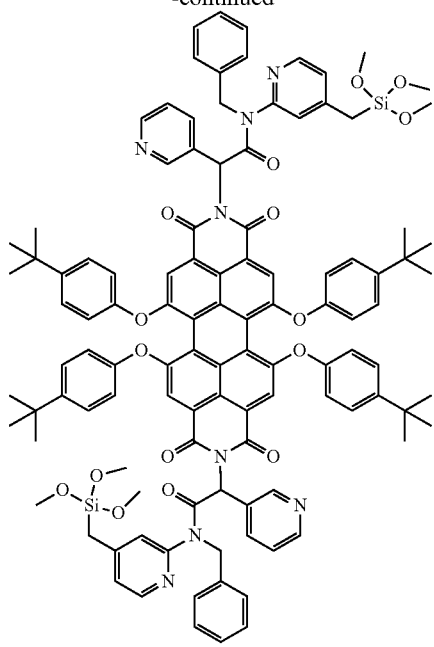
352
-continued
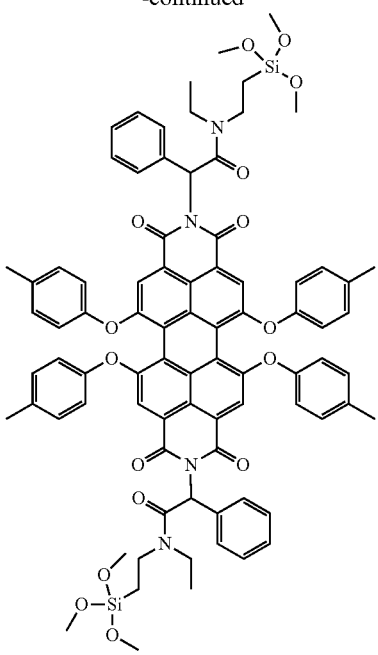
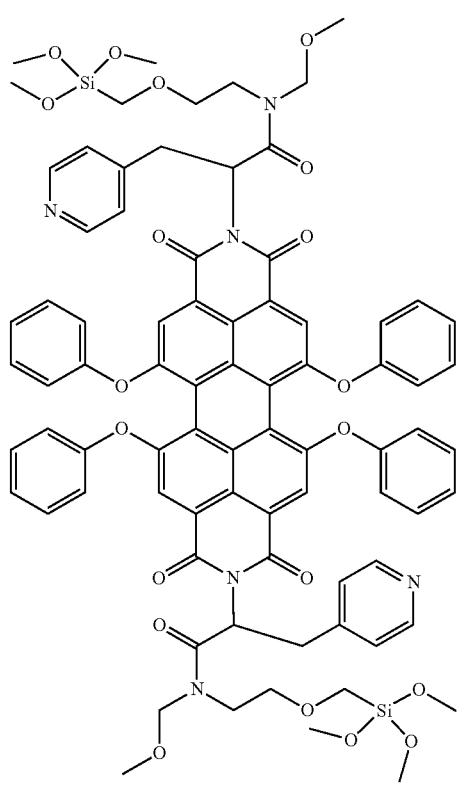
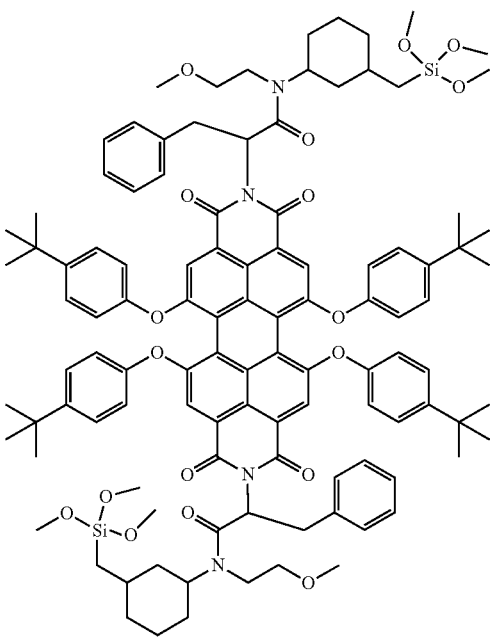

353
-continued
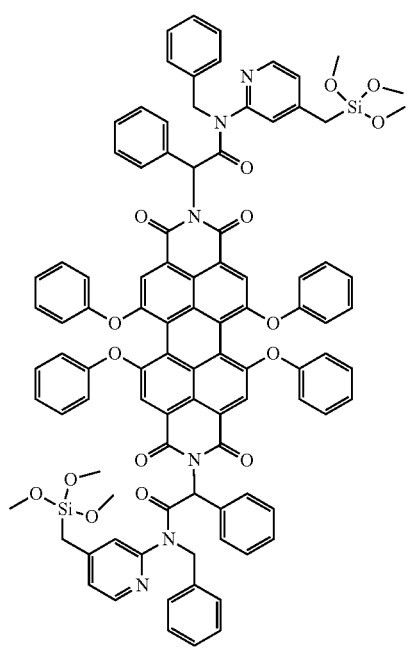
354
-continued
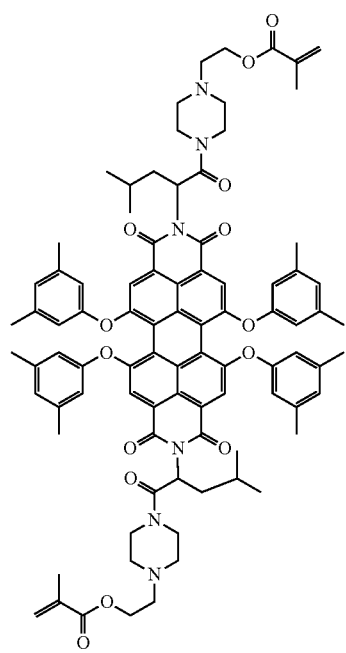
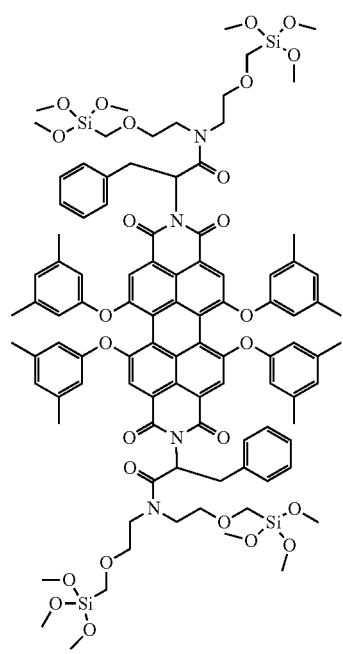
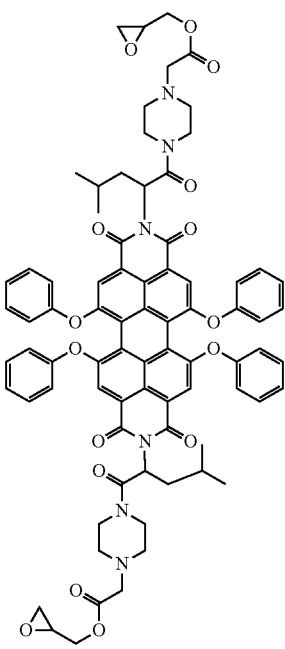

355
-continued
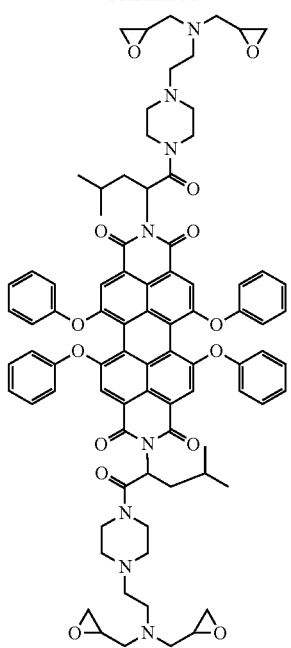
356
-continued
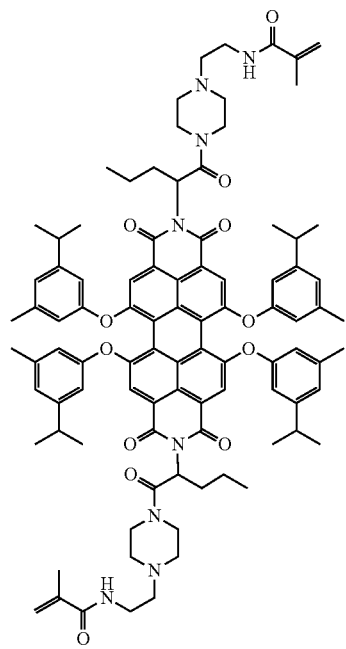
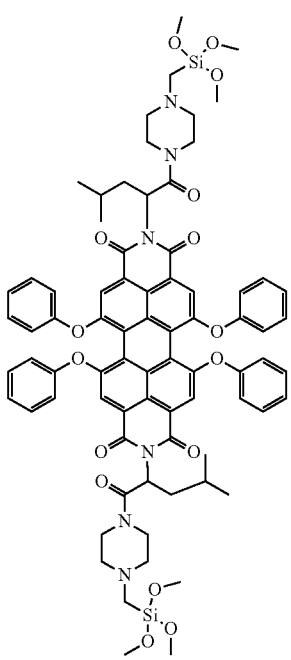
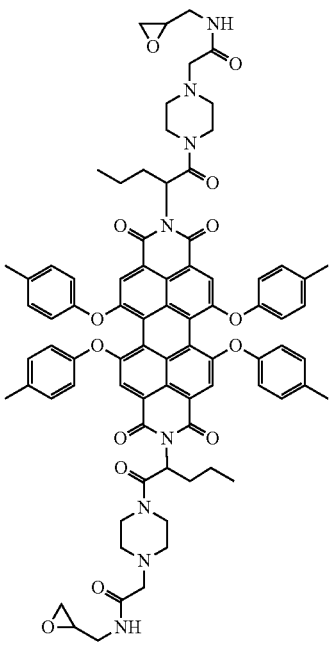

357
-continued
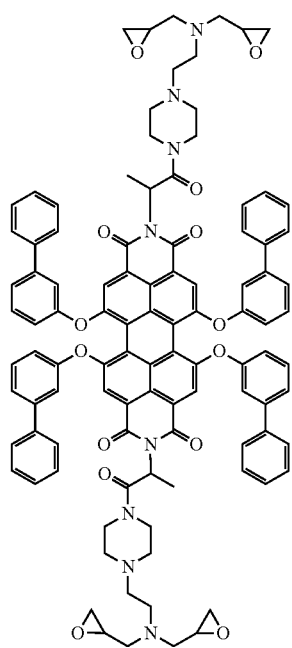
358
-continued
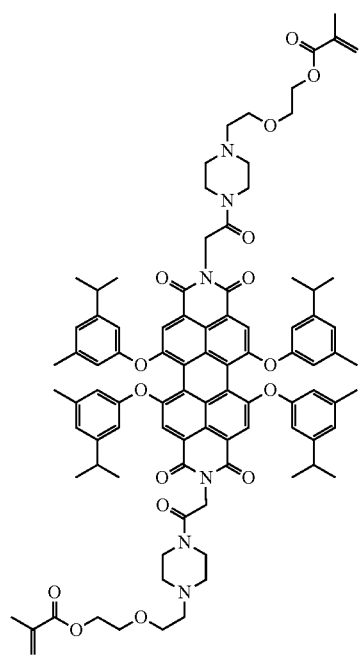
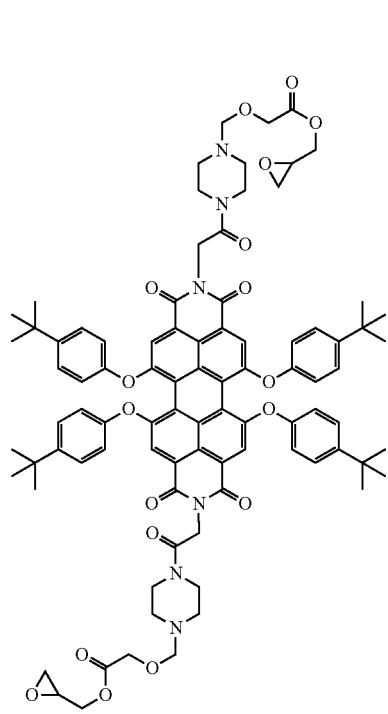

359
-continued
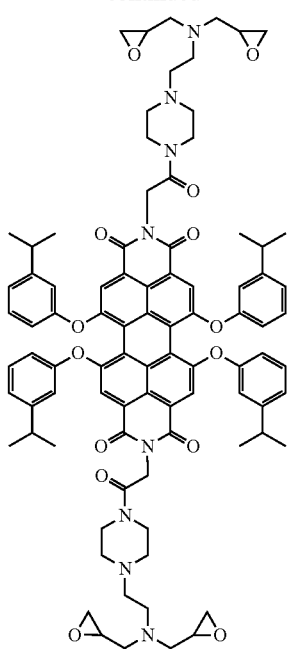
360
-continued
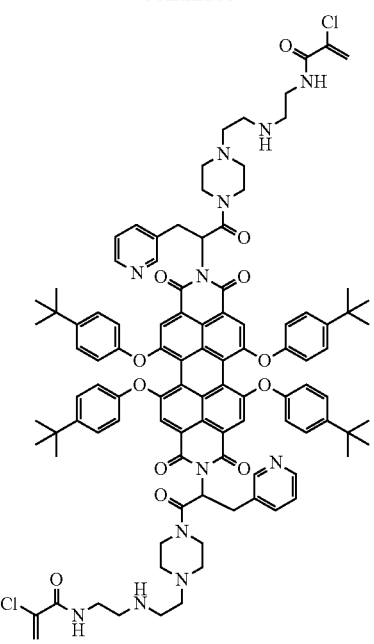
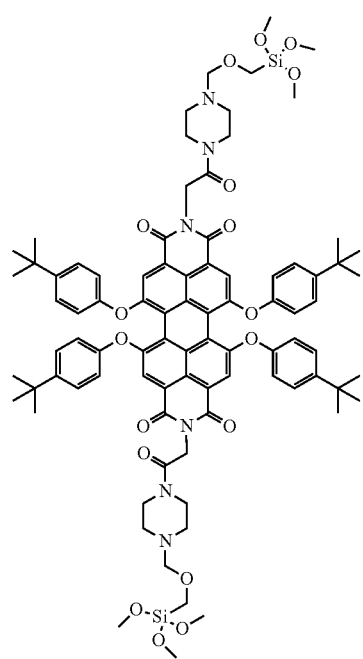
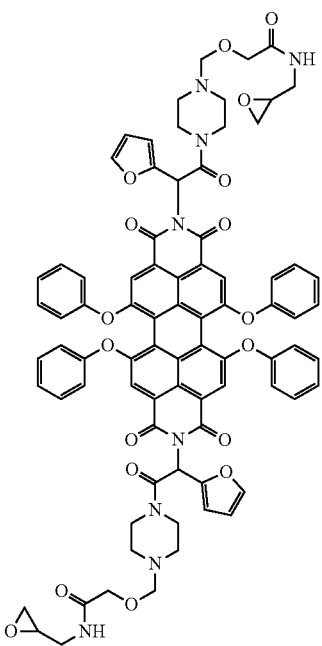

361
-continued
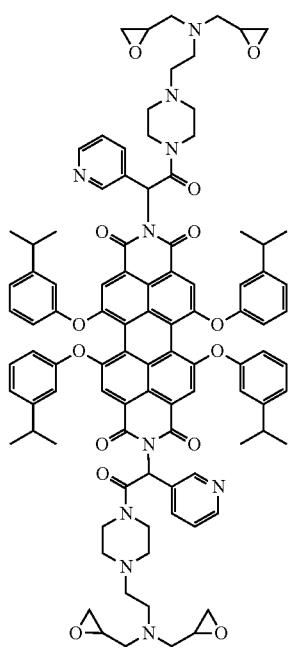
362
-continued
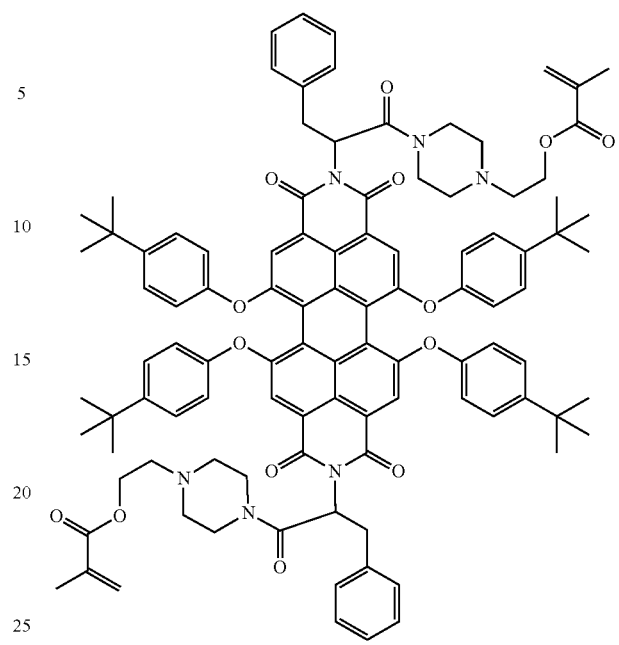
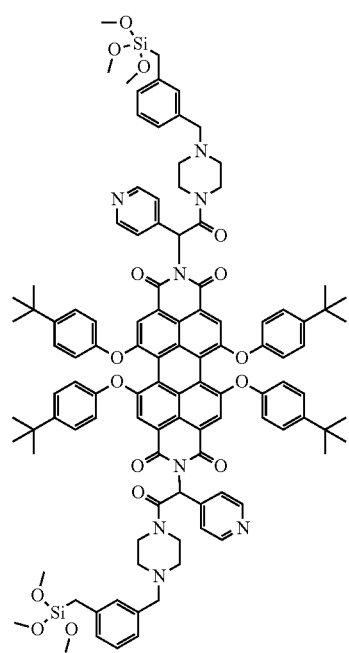
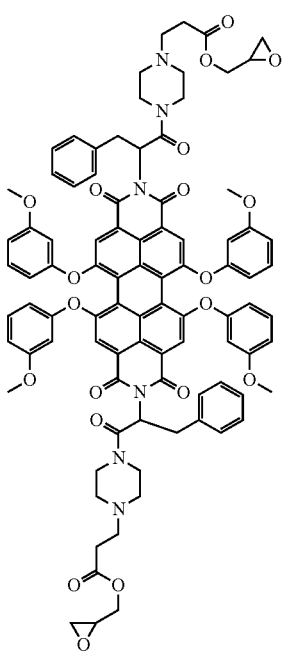

363
-continued
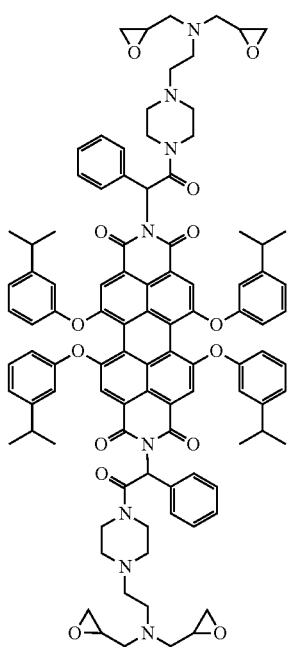
364
-continued
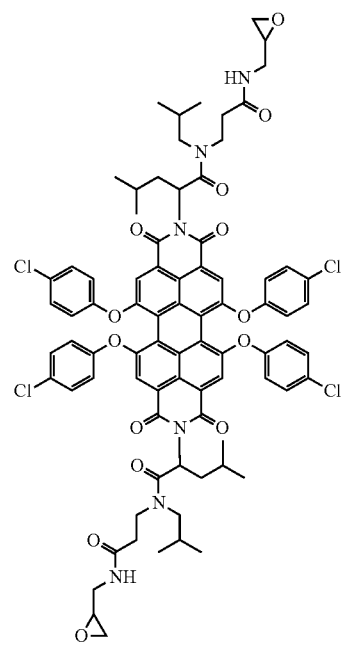
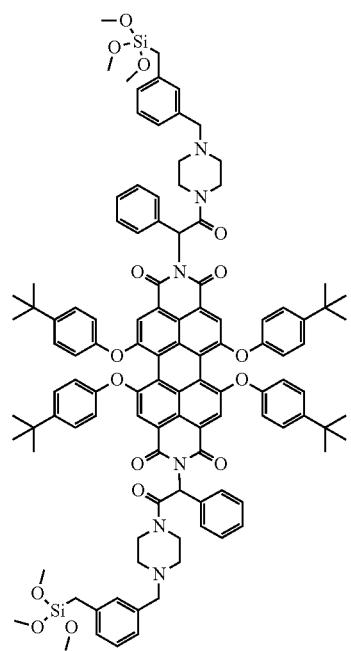
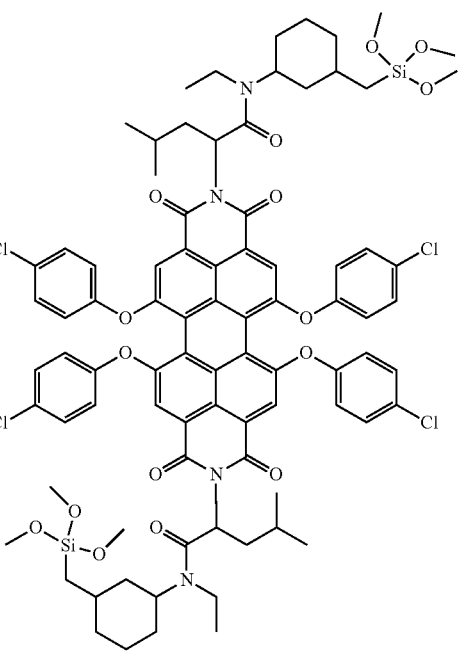

365
-continued
366
-continued
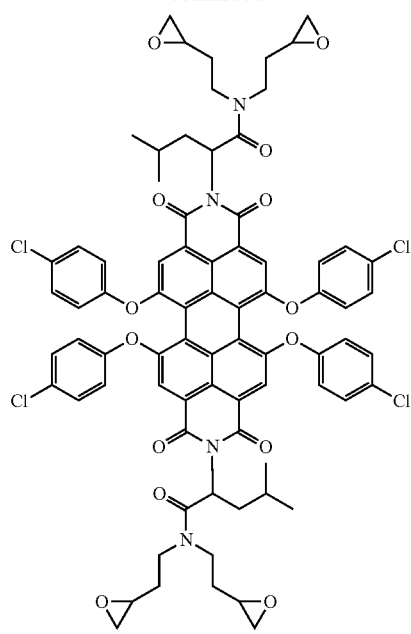
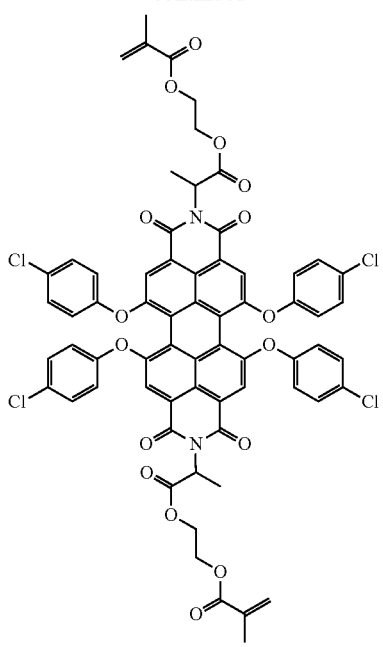 [SMILES: C=C(C)C(=O)OCCOC(=O)C(C)N1C(=O)c2cc(Oc3ccc(Cl)cc3)c3c4c(Oc5ccc(Cl)cc5)cc5c6c(cc(Oc7ccc(Cl)cc7)c(c7c(Oc8ccc(Cl)cc8)cc(c2c37)C1=O)c64)C(=O)N(C(C)C(=O)OCCOC(=O)C(=C)C)C5=O]
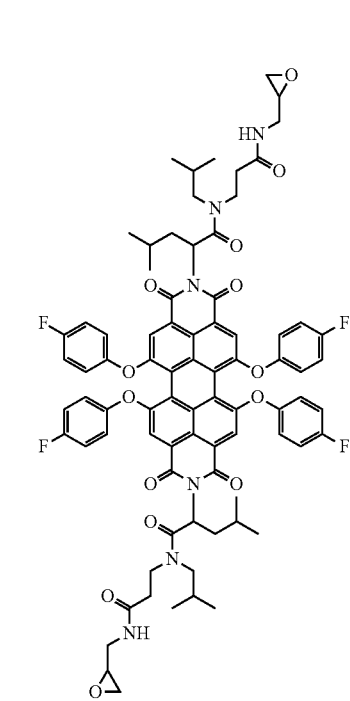

367
-continued
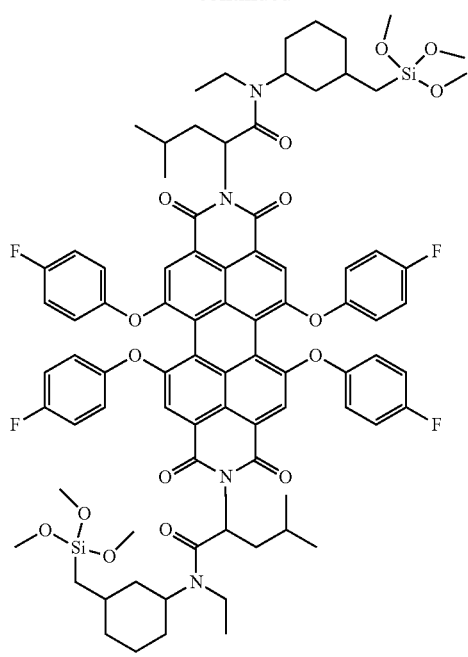
368
-continued
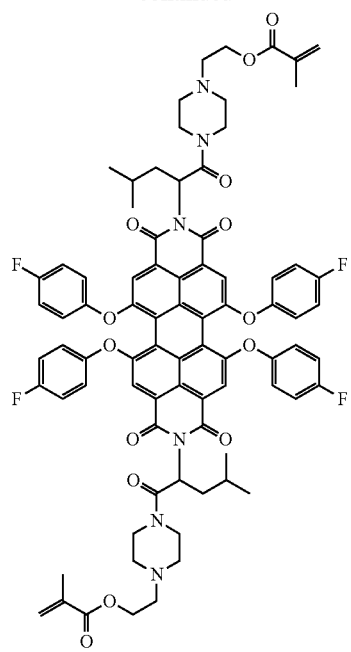
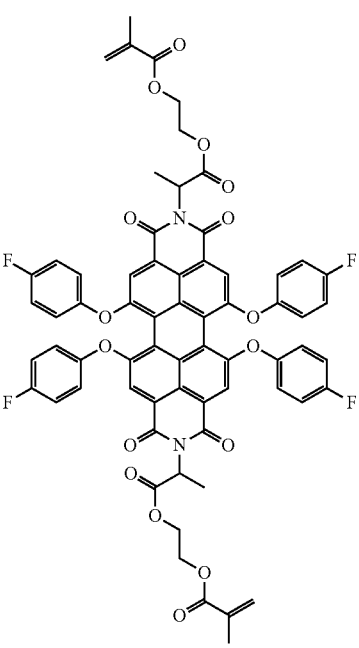 [SMILES: C=C(C)C(=O)OCCOC(=O)C(C)N1C(=O)c2cc(Oc3ccc(F)cc3)c3c4c(Oc5ccc(F)cc5)cc5c6c(cc(Oc7ccc(F)cc7)c(c7c(Oc8ccc(F)cc8)cc(c2c37)C1=O)c64)C(=O)N(C(C)C(=O)OCCOC(=O)C(=C)C)C5=O]

369
-continued
370
-continued
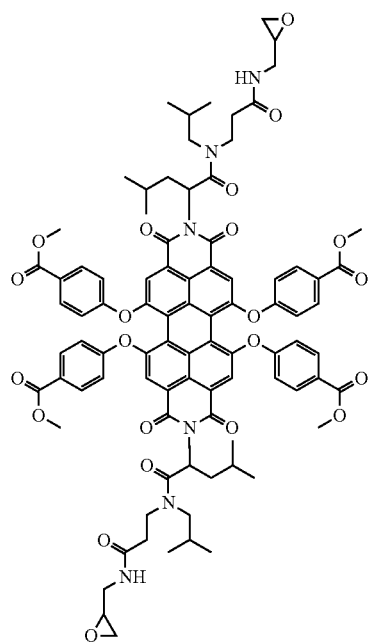
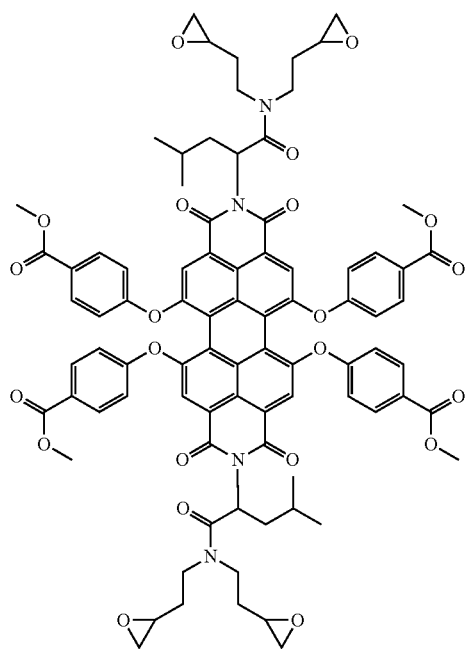
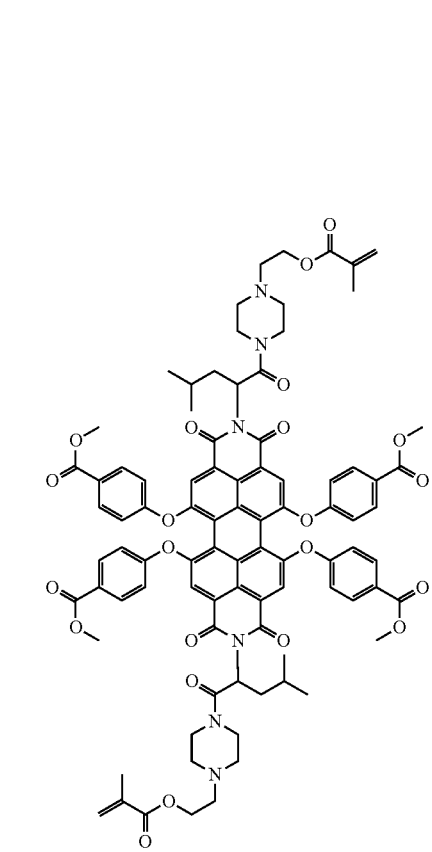

371
-continued
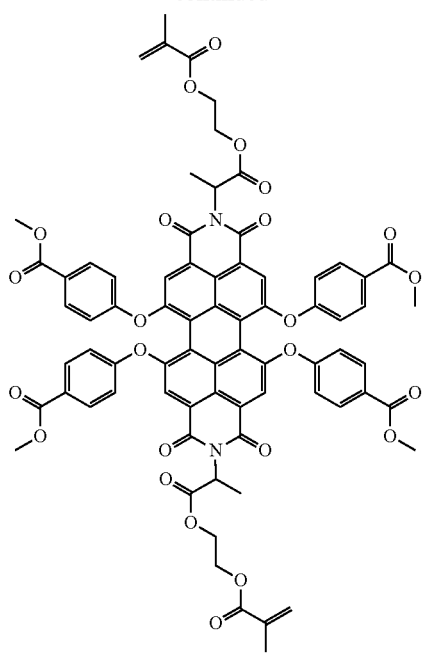 [SMILES: C=C(C)C(=O)OCCOC(=O)C(C)N1C(=O)c2cc(Oc3ccc(C(=O)OC)cc3)c3c4c(Oc5ccc(C(=O)OC)cc5)cc5c6c(cc(Oc7ccc(C(=O)OC)cc7)c(c7c(Oc8ccc(C(=O)OC)cc8)cc(c2c37)C1=O)c64)C(=O)N(C(C)C(=O)OCCOC(=O)C(=C)C)C5=O]
372
-continued
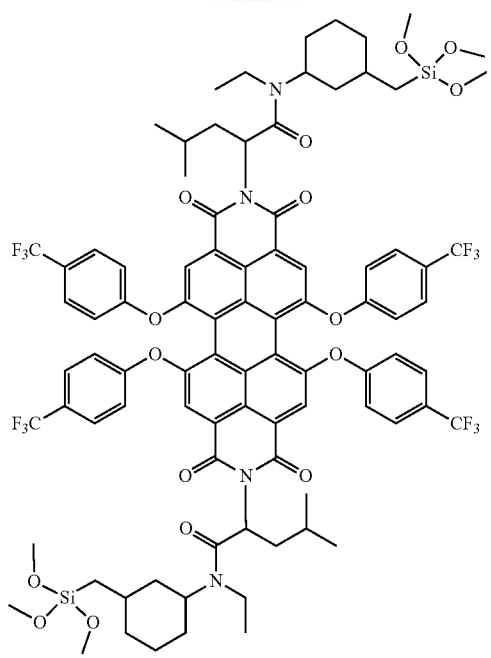
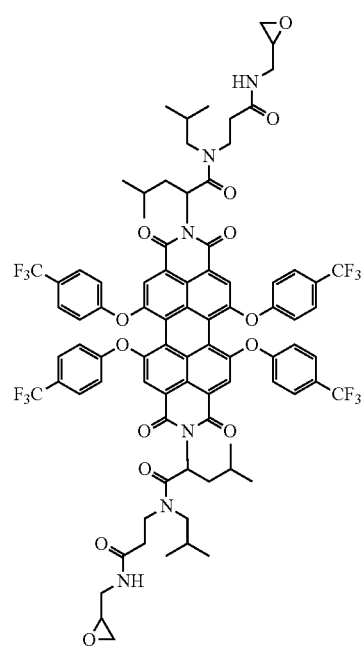
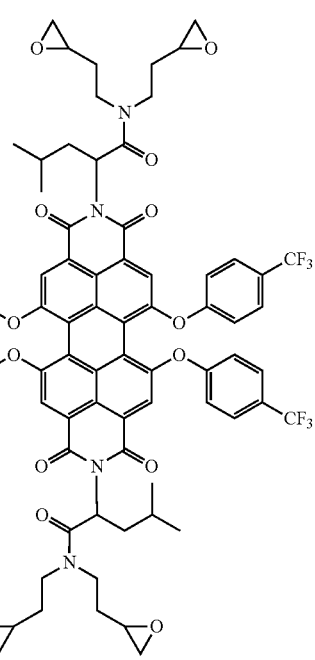

373
-continued
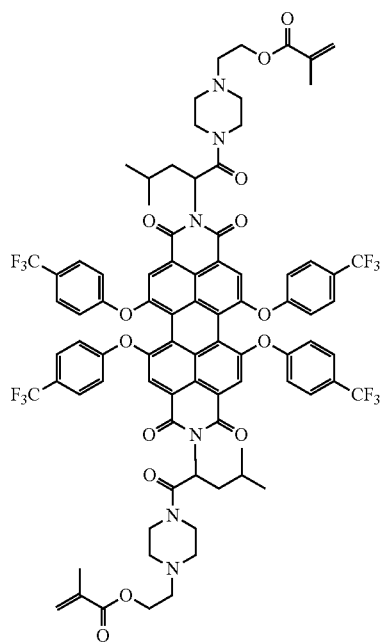
374
-continued
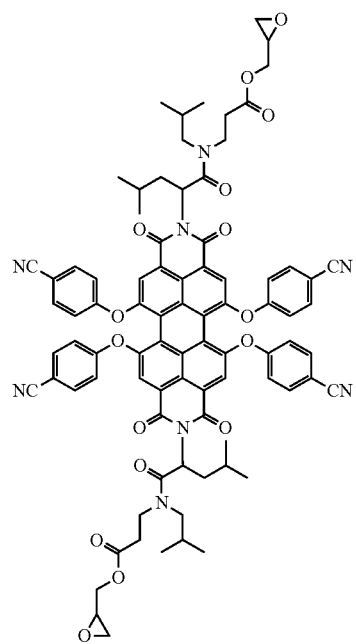
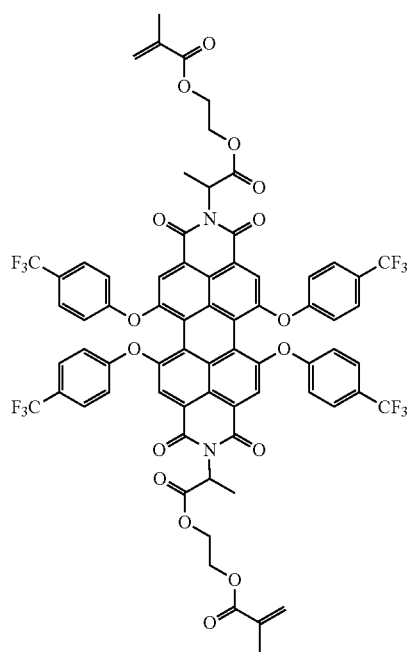
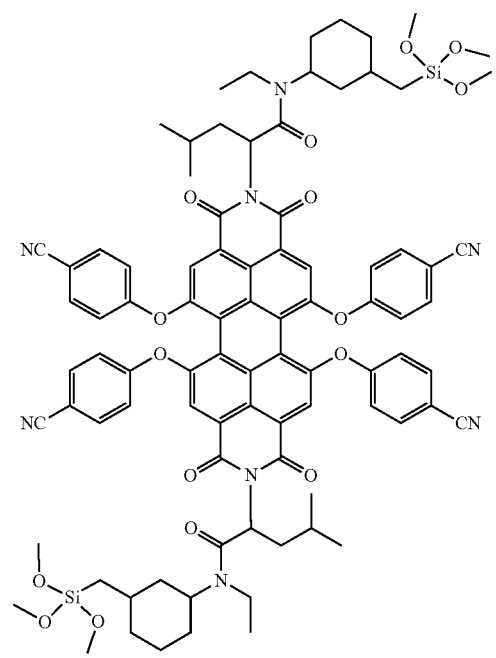

375
-continued
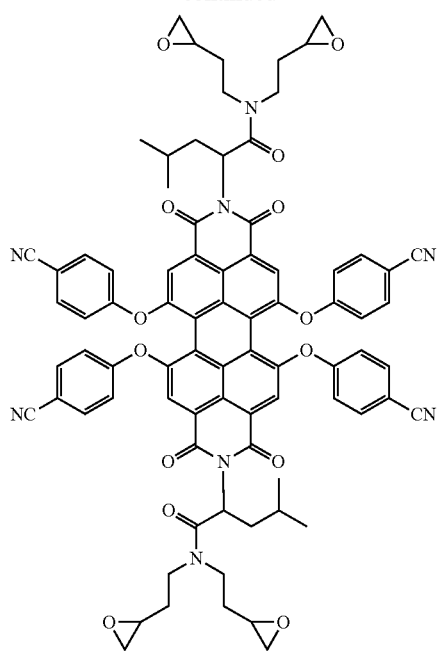
376
-continued
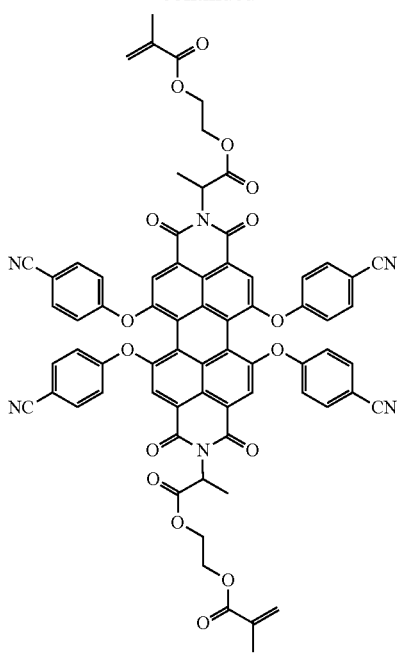 [SMILES: C=C(C)C(=O)OCCOC(=O)C(C)N1C(=O)c2cc(Oc3ccc(C#N)cc3)c3c4c(Oc5ccc(C#N)cc5)cc5c6c(cc(Oc7ccc(C#N)cc7)c(c7c(Oc8ccc(C#N)cc8)cc(c2c37)C1=O)c64)C(=O)N(C(C)C(=O)OCCOC(=O)C(=C)C)C5=O]
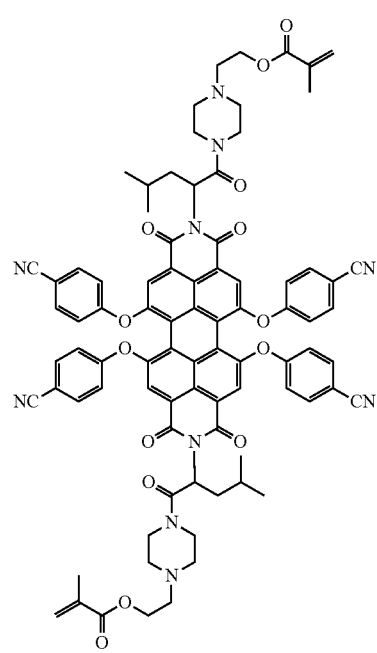
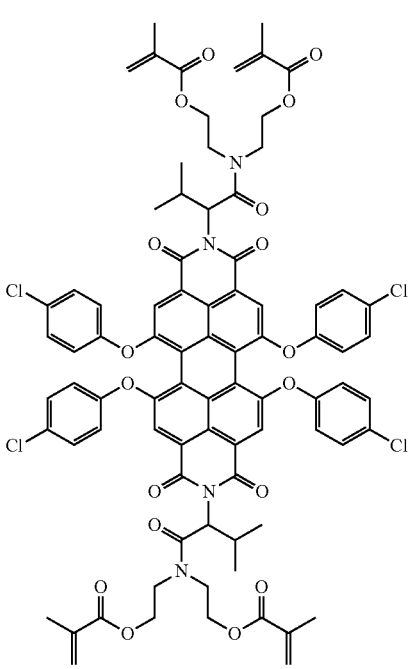

377
-continued
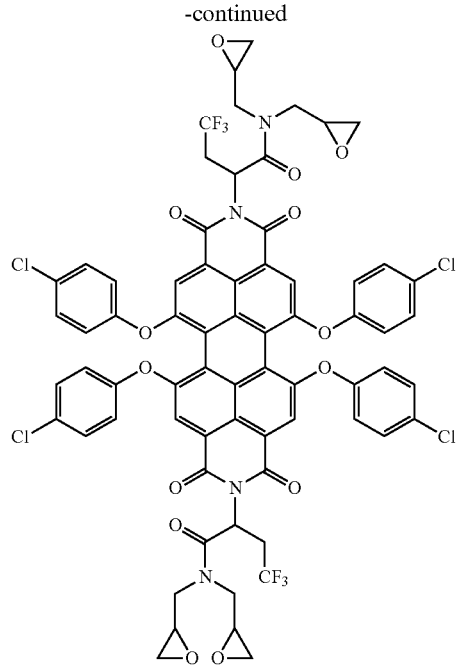
378
-continued
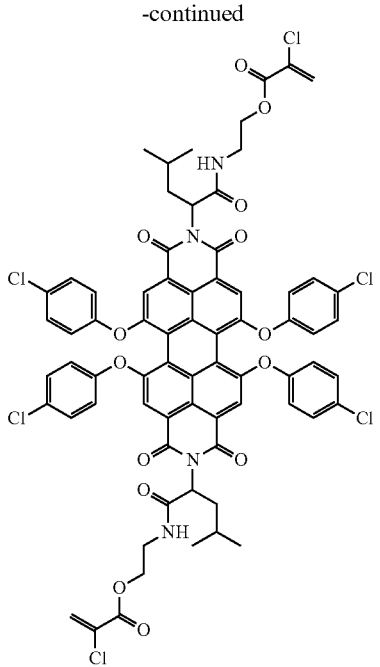
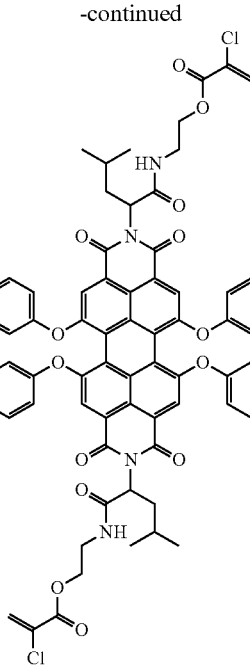
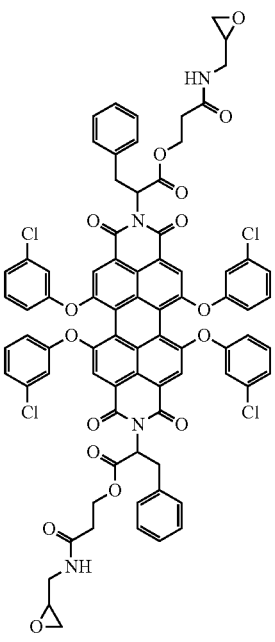

379
-continued
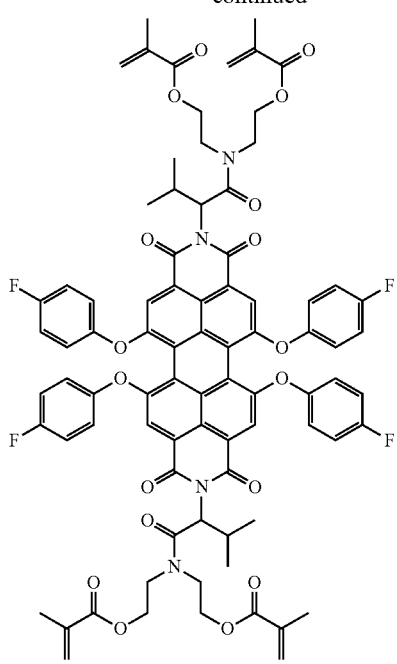
380
-continued
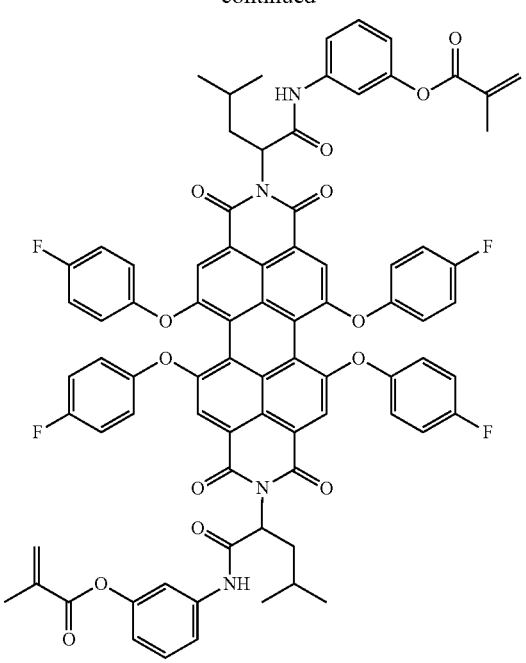
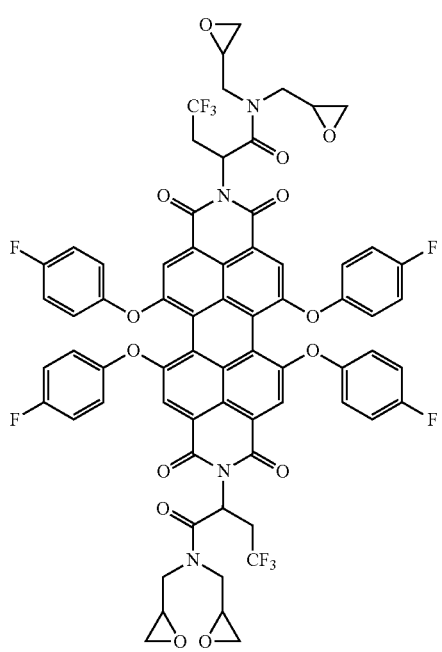
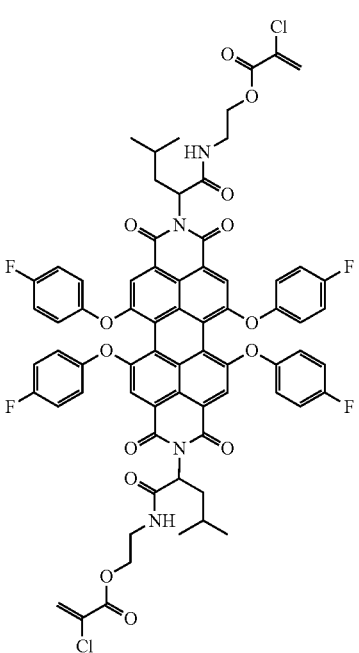

381
-continued
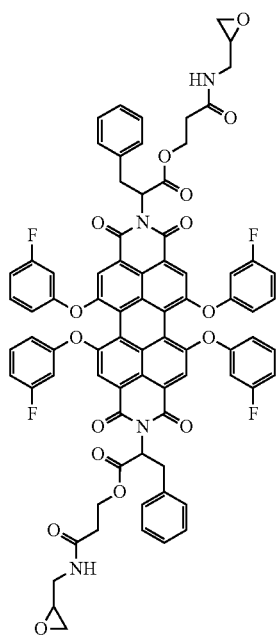 [SMILES: O=C(CCOC(=O)C(Cc1ccccc1)N1C(=O)c2cc(Oc3cccc(F)c3)c3c4c(Oc5cccc(F)c5)cc5c6c(cc(Oc7cccc(F)c7)c(c7c(Oc8cccc(F)c8)cc(c2c37)C1=O)c64)C(=O)N(C(Cc1ccccc1)C(=O)OCCC(=O)NCC1CO1)C5=O)NCC1CO1]
382
-continued
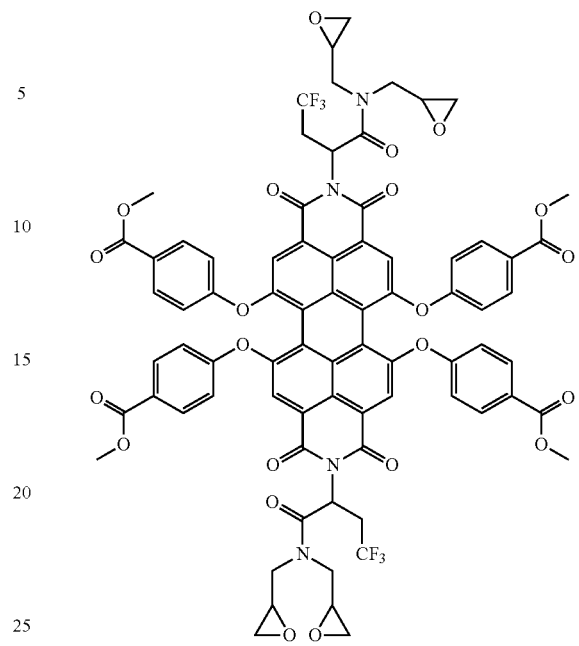
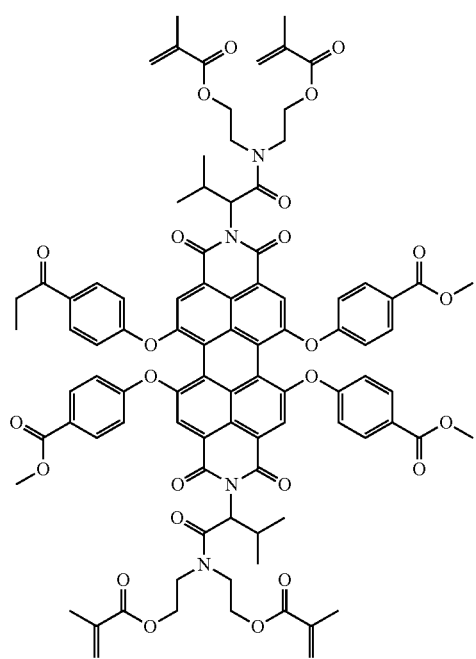
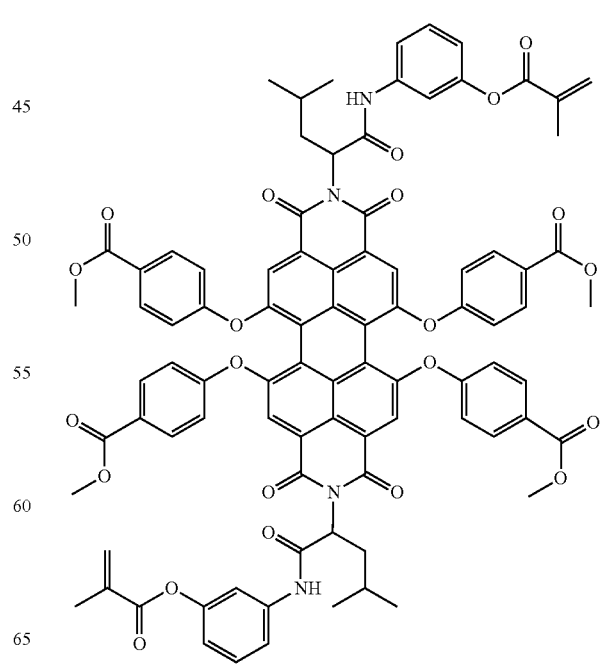

383
-continued
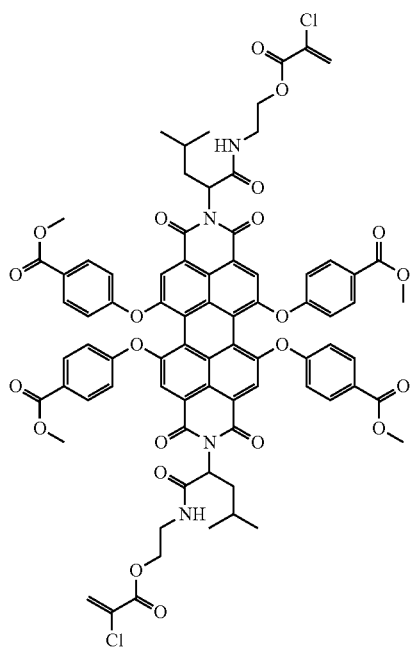
384
-continued
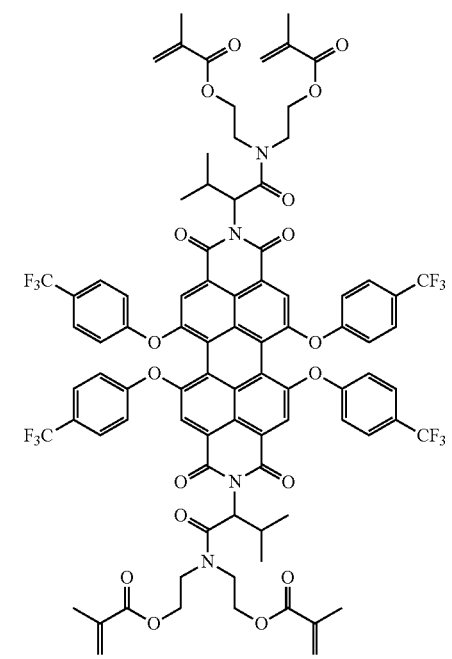
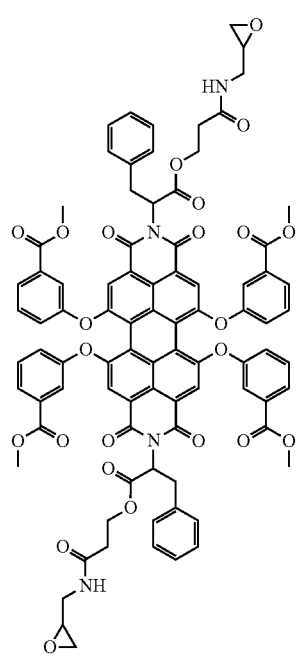 [SMILES: COC(=O)c1cccc(Oc2cc3c4c(cc(Oc5cccc(C(=O)OC)c5)c5c6c(Oc7cccc(C(=O)OC)c7)cc7c8c(cc(Oc9cccc(C(=O)OC)c9)c(c2c45)c86)C(=O)N(C(Cc2ccccc2)C(=O)OCCC(=O)NCC2CO2)C7=O)C(=O)N(C(Cc2ccccc2)C(=O)OCCC(=O)NCC2CO2)C3=O)c1]
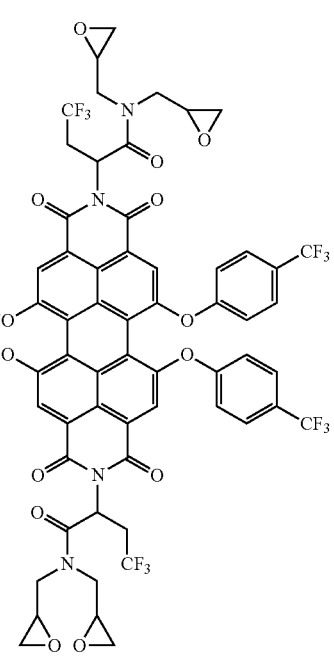

385
-continued
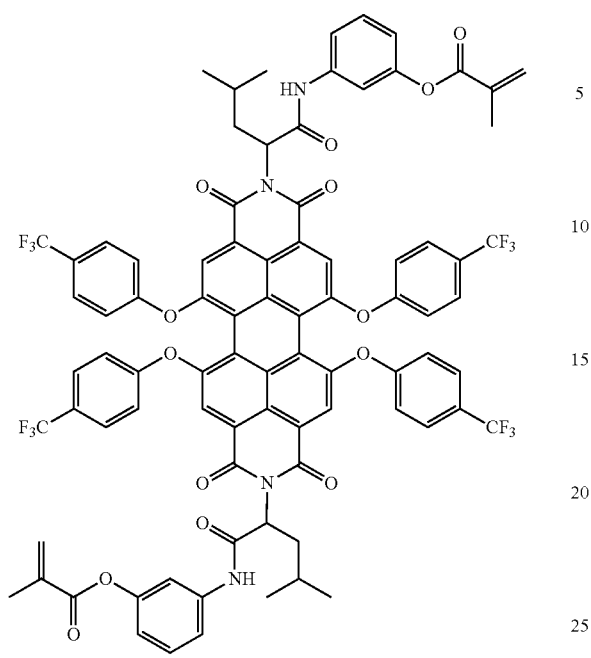
386
-continued
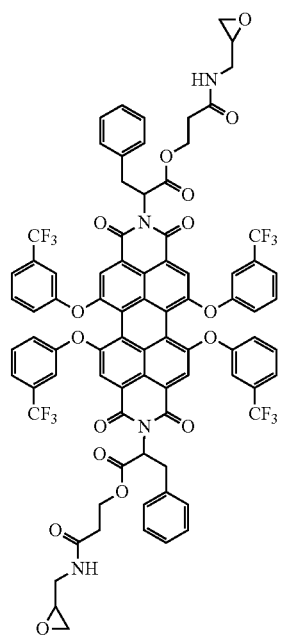
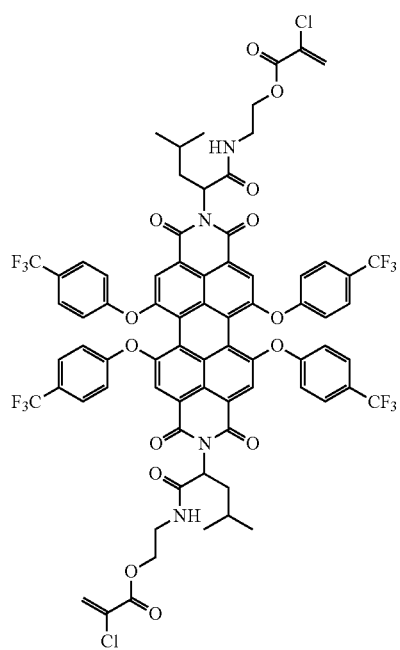
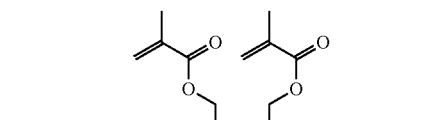

387
-continued
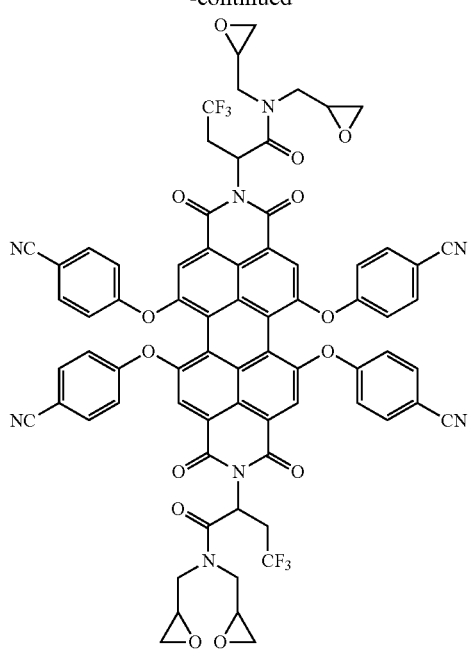
388
-continued
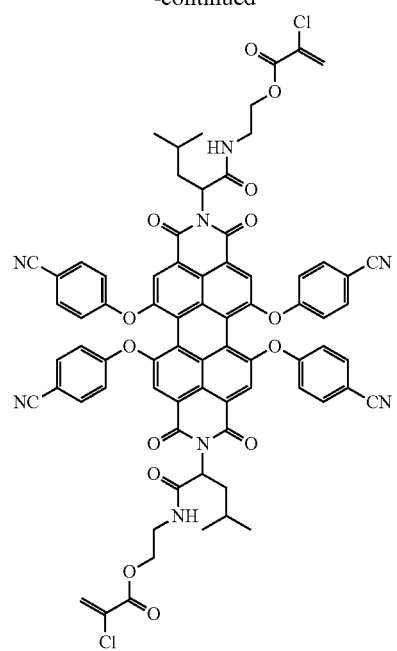
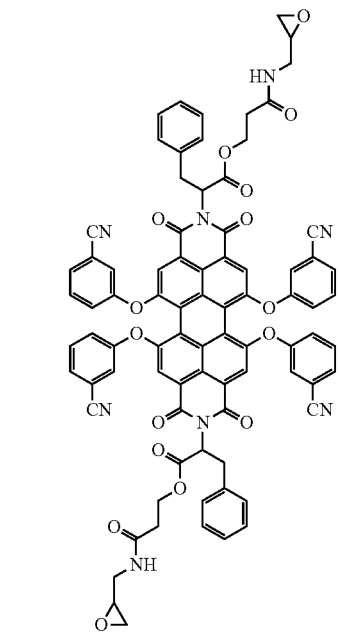 [SMILES: O=C(CCOC(=O)C(Cc1ccccc1)N1C(=O)c2cc(Oc3cccc(C(F)(F)F)c3)c3c4c(Oc5cccc(C(F)(F)F)c5)cc5c6c(cc(Oc7cccc(C(F)(F)F)c7)c(c7c(Oc8cccc(C(F)(F)F)c8)cc(c2c37)C1=O)c64)C(=O)N(C(Cc1ccccc1)C(=O)OCCC(=O)NCC1CO1)C5=O)NCC1CO1]

389
-continued
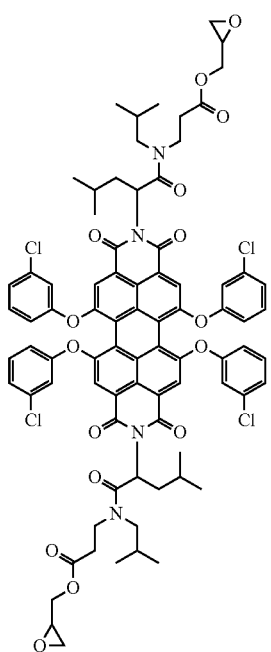
390
-continued
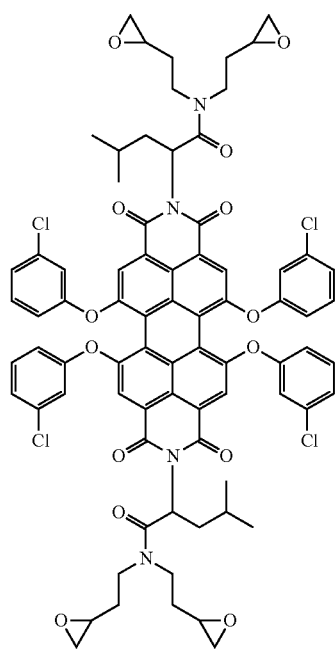
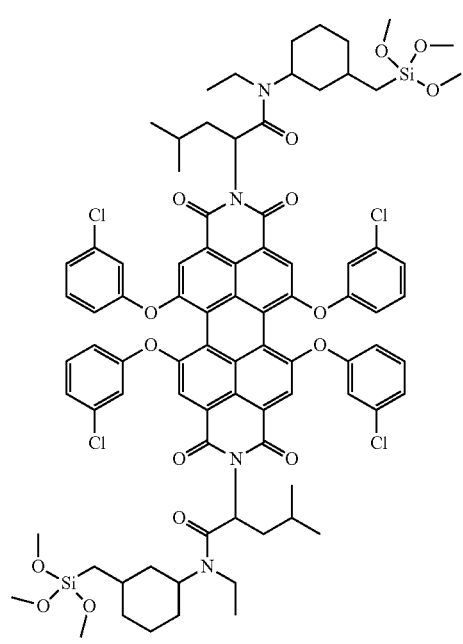
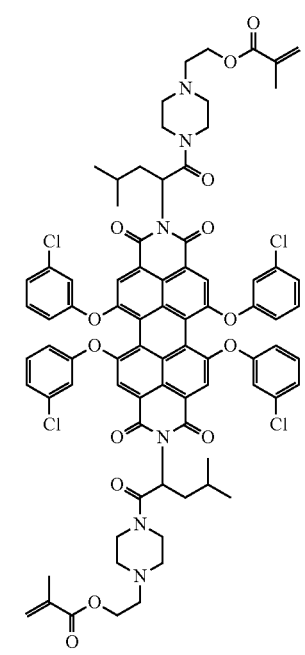

391
-continued
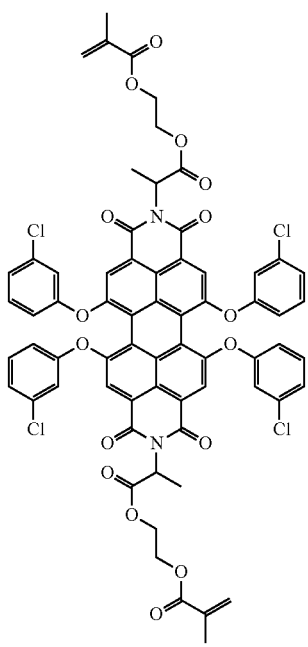 [SMILES: C=C(C)C(=O)OCCOC(=O)C(C)N1C(=O)c2cc(Oc3cccc(Cl)c3)c3c4c(Oc5cccc(Cl)c5)cc5c6c(cc(Oc7cccc(Cl)c7)c(c7c(Oc8cccc(Cl)c8)cc(c2c37)C1=O)c64)C(=O)N(C(C)C(=O)OCCOC(=O)C(=C)C)C5=O]
392
-continued
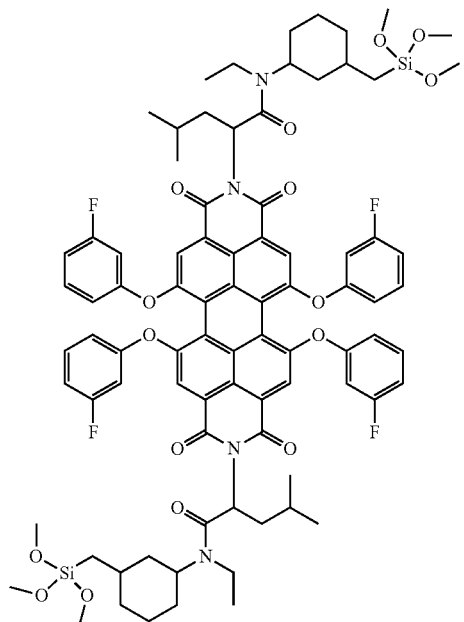
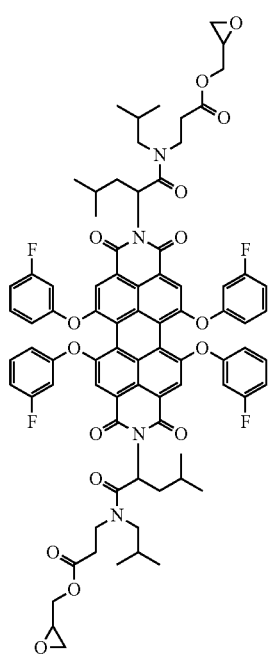
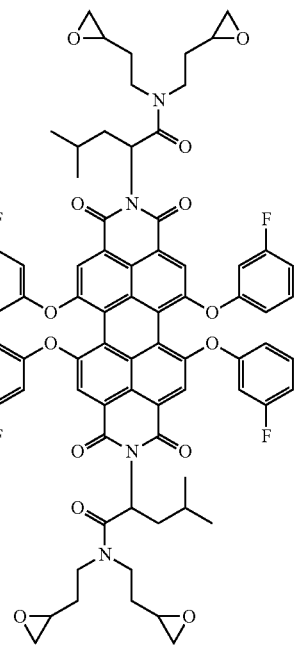

393
-continued
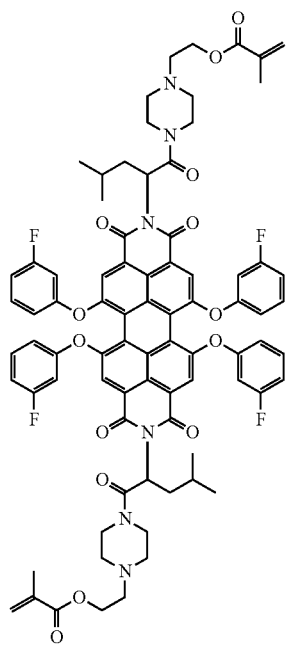
394
-continued
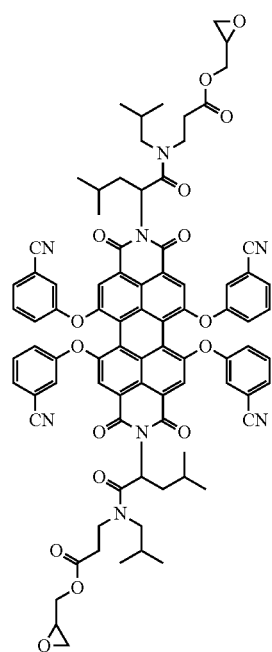
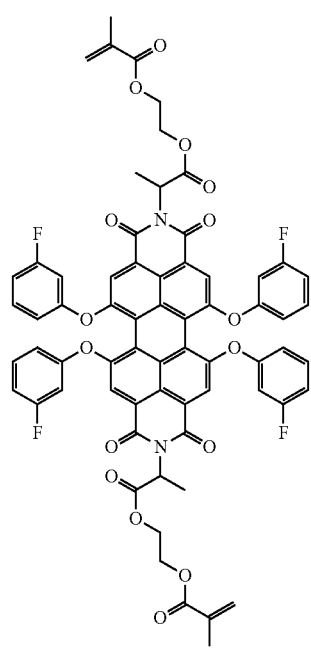 [SMILES: C=C(C)C(=O)OCCOC(=O)C(C)N1C(=O)c2cc(Oc3cccc(F)c3)c3c4c(Oc5cccc(F)c5)cc5c6c(cc(Oc7cccc(F)c7)c(c7c(Oc8cccc(F)c8)cc(c2c37)C1=O)c64)C(=O)N(C(C)C(=O)OCCOC(=O)C(=C)C)C5=O]
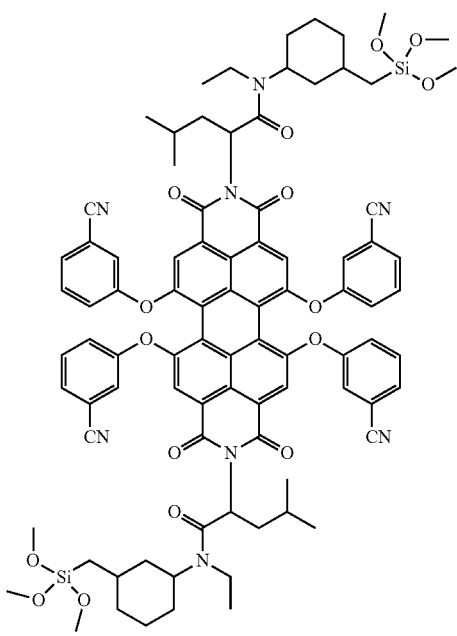

395
-continued
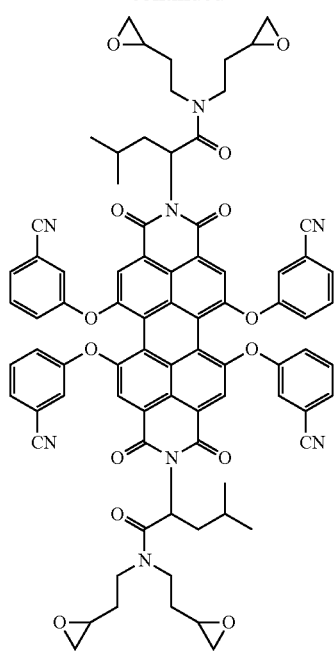
396
-continued
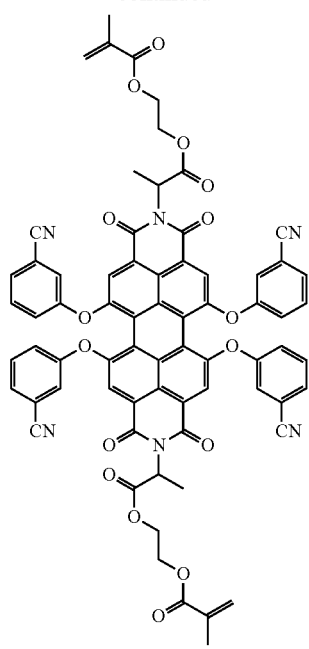 [SMILES: C=C(C)C(=O)OCCOC(=O)C(C)N1C(=O)c2cc(Oc3cccc(C#N)c3)c3c4c(Oc5cccc(C#N)c5)cc5c6c(cc(Oc7cccc(C#N)c7)c(c7c(Oc8cccc(C#N)c8)cc(c2c37)C1=O)c64)C(=O)N(C(C)C(=O)OCCOC(=O)C(=C)C)C5=O]
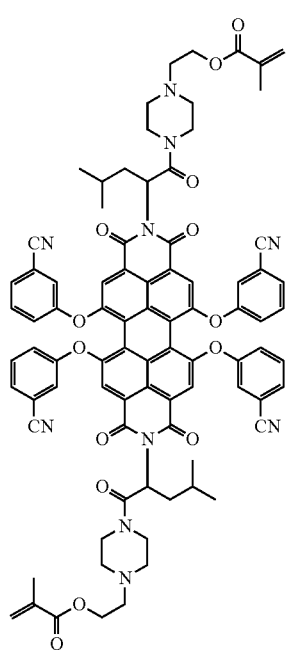

397
-continued
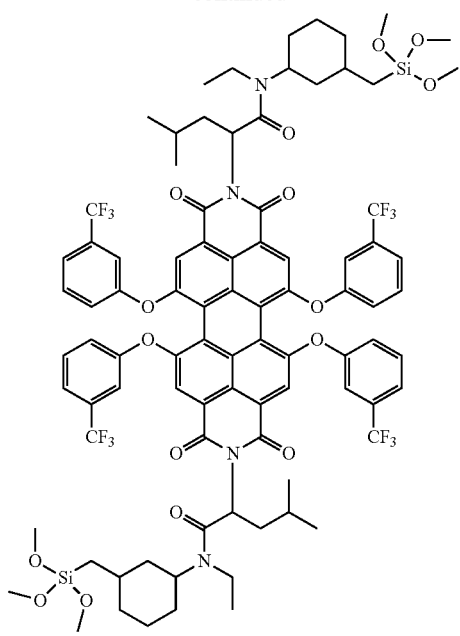
398
-continued
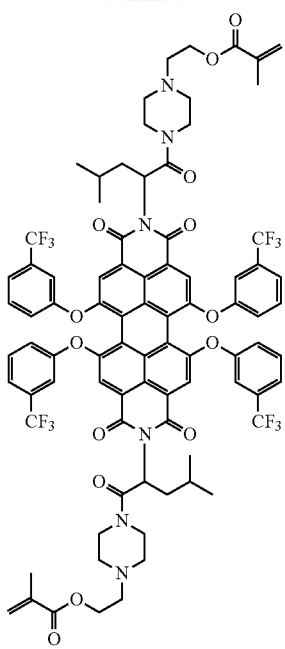
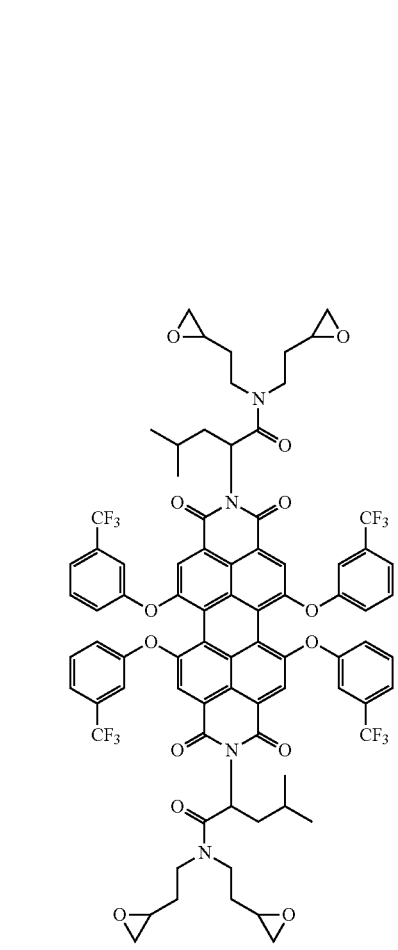
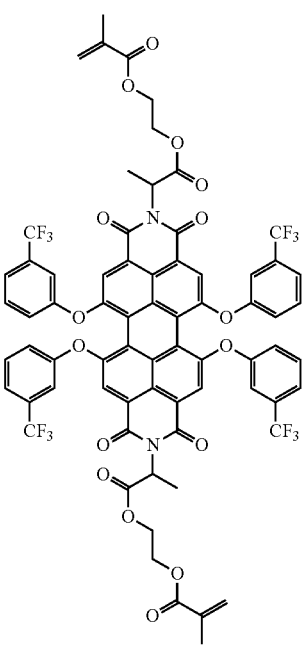

399
-continued
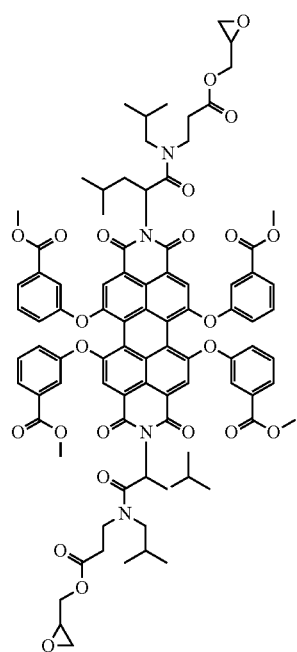
400
-continued
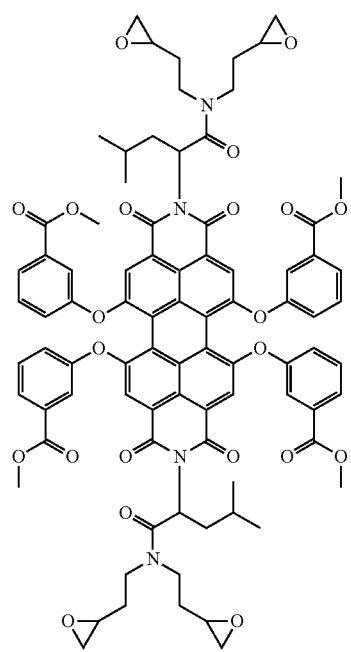
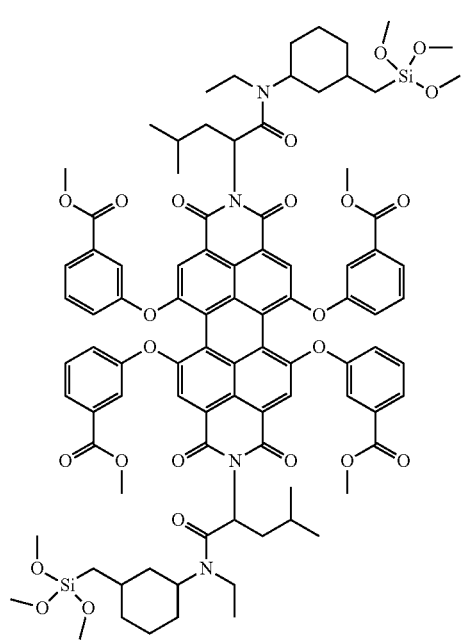
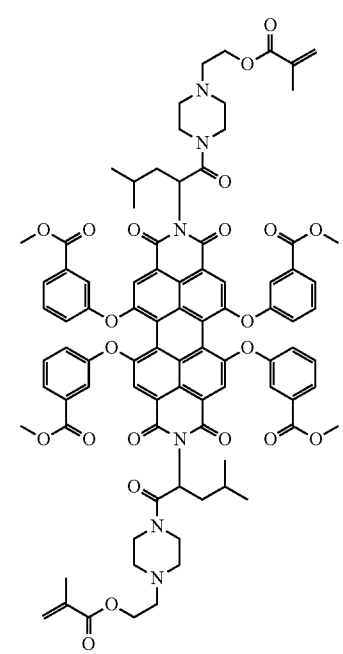

401
-continued
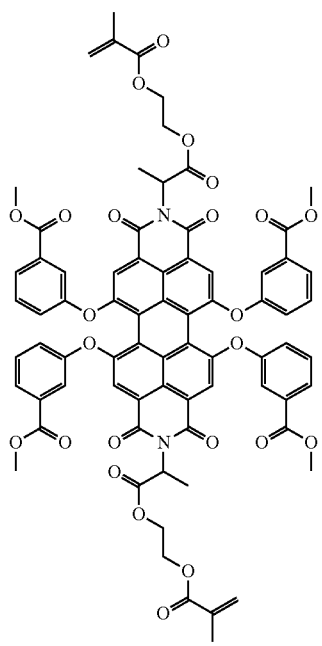 [SMILES: C=C(C)C(=O)OCCOC(=O)C(C)N1C(=O)c2cc(Oc3cccc(C(=O)OC)c3)c3c4c(Oc5cccc(C(=O)OC)c5)cc5c6c(cc(Oc7cccc(C(=O)OC)c7)c(c7c(Oc8cccc(C(=O)OC)c8)cc(c2c37)C1=O)c64)C(=O)N(C(C)C(=O)OCCOC(=O)C(=C)C)C5=O]
402
-continued
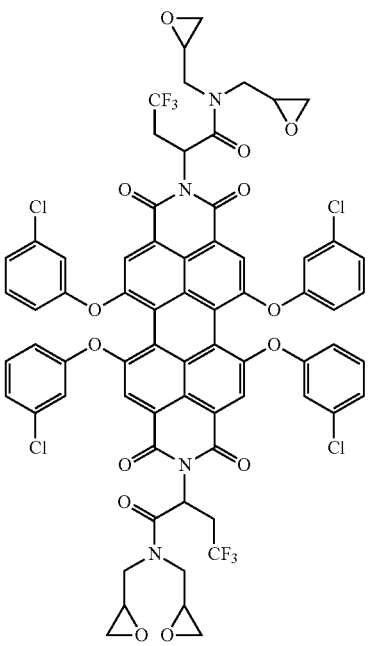
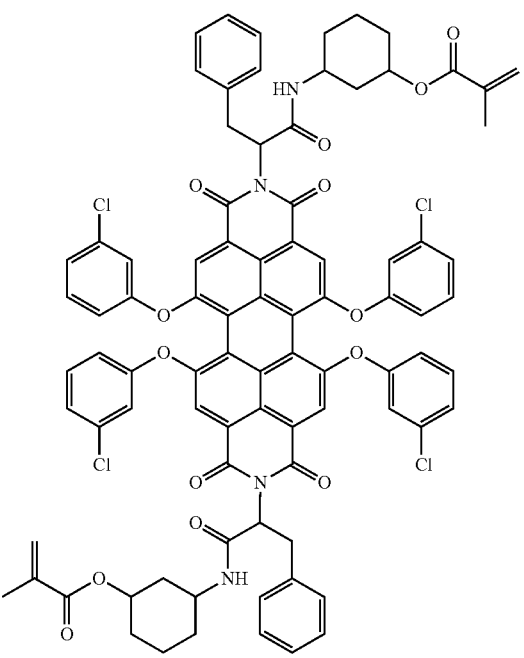

403
-continued
404
-continued
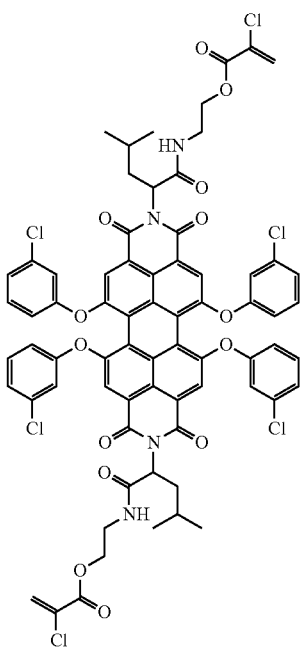
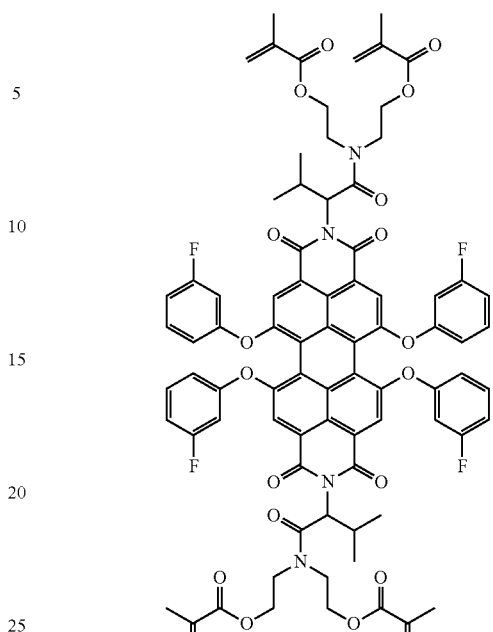
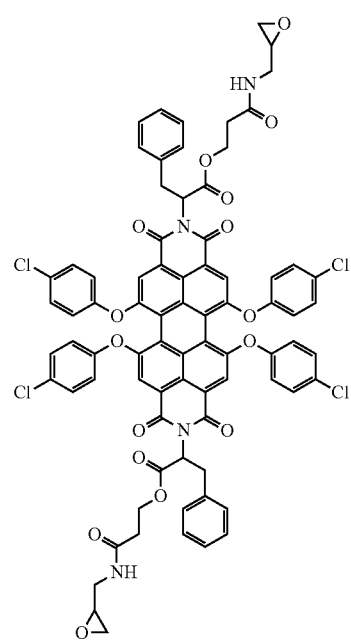 [SMILES: O=C(CCOC(=O)C(Cc1ccccc1)N1C(=O)c2cc(Oc3ccc(Cl)cc3)c3c4c(Oc5ccc(Cl)cc5)cc5c6c(cc(Oc7ccc(Cl)cc7)c(c7c(Oc8ccc(Cl)cc8)cc(c2c37)C1=O)c64)C(=O)N(C(Cc1ccccc1)C(=O)OCCC(=O)NCC1CO1)C5=O)NCC1CO1]
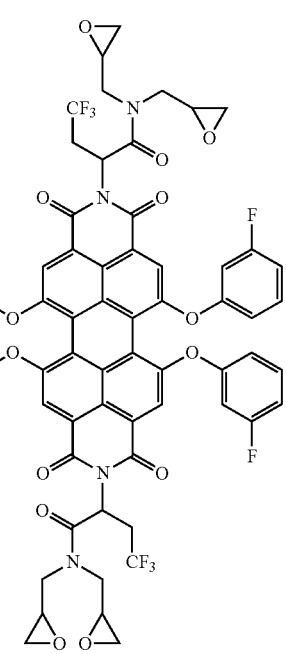

405
-continued
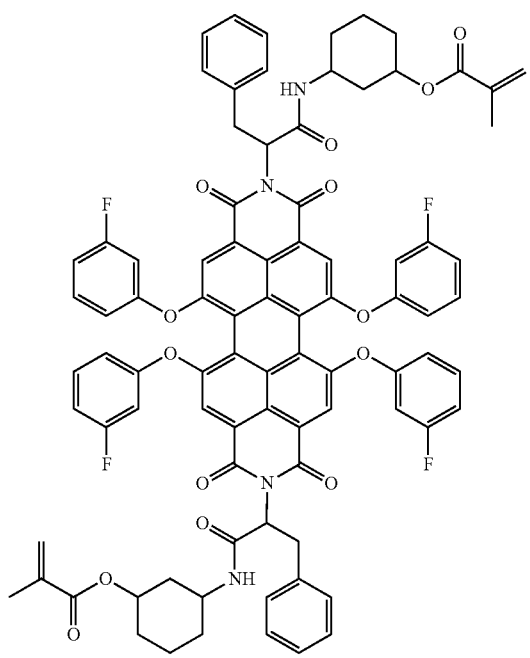
406
-continued
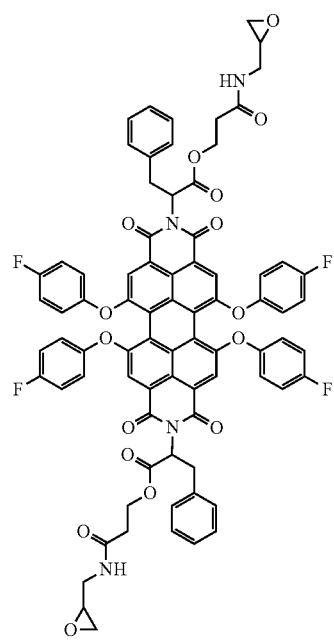 [SMILES: O=C(CCOC(=O)C(Cc1ccccc1)N1C(=O)c2cc(Oc3ccc(F)cc3)c3c4c(Oc5ccc(F)cc5)cc5c6c(cc(Oc7ccc(F)cc7)c(c7c(Oc8ccc(F)cc8)cc(c2c37)C1=O)c64)C(=O)N(C(Cc1ccccc1)C(=O)OCCC(=O)NCC1CO1)C5=O)NCC1CO1]
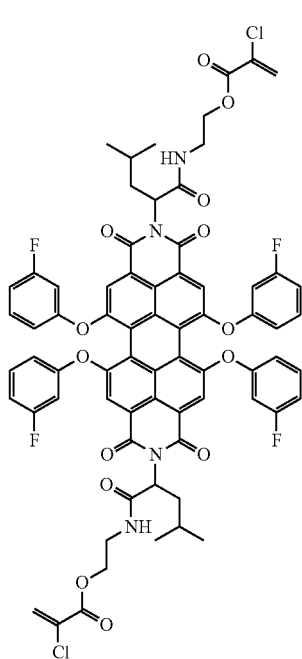
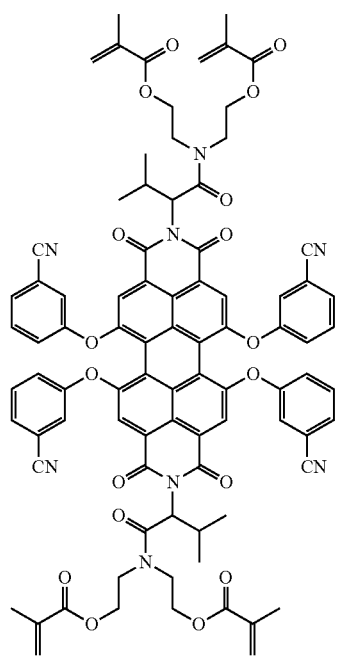

407
-continued
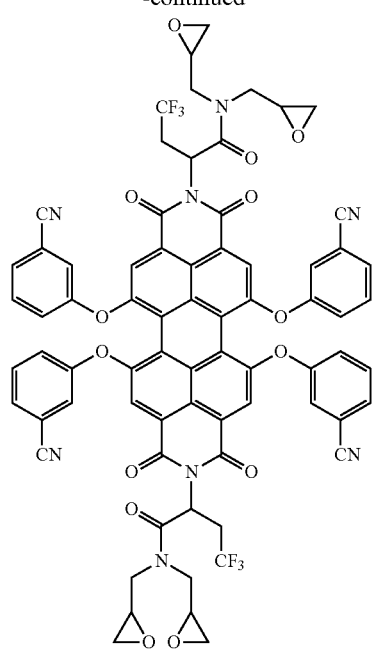
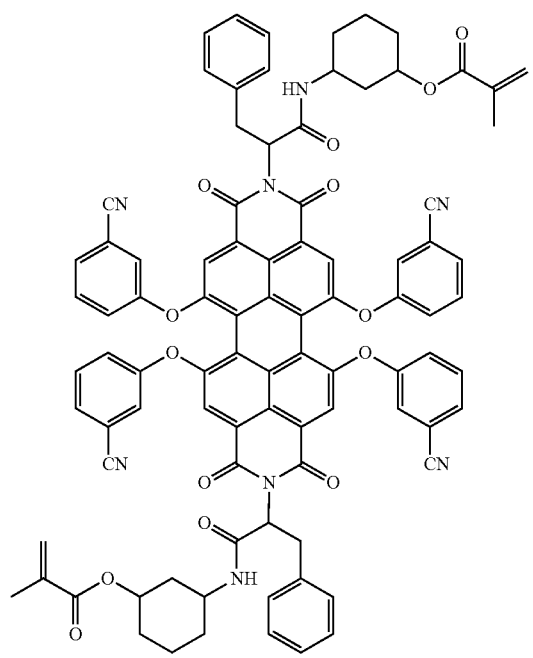
408
-continued
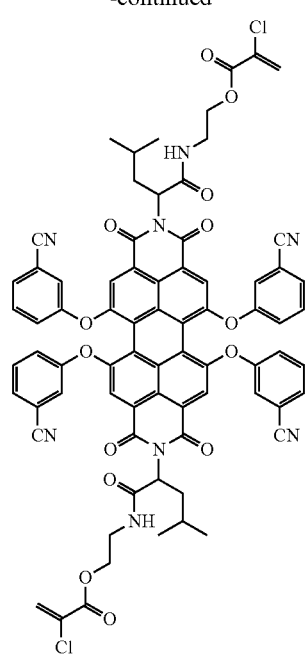
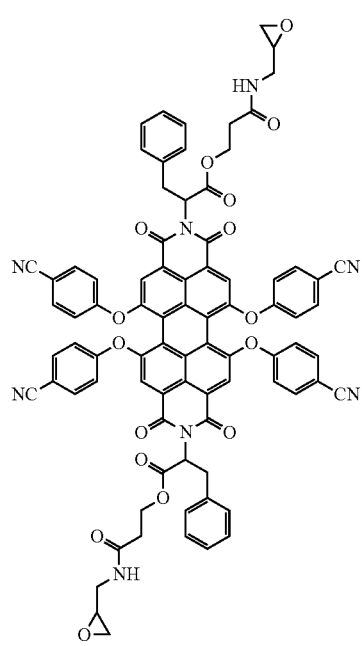 [SMILES: N#Cc1ccc(Oc2cc3c4c(cc(Oc5ccc(C#N)cc5)c5c6c(Oc7ccc(C#N)cc7)cc7c8c(cc(Oc9ccc(C#N)cc9)c(c2c45)c86)C(=O)N(C(Cc2ccccc2)C(=O)OCCC(=O)NCC2CO2)C7=O)C(=O)N(C(Cc2ccccc2)C(=O)OCCC(=O)NCC2CO2)C3=O)cc1]

409
-continued
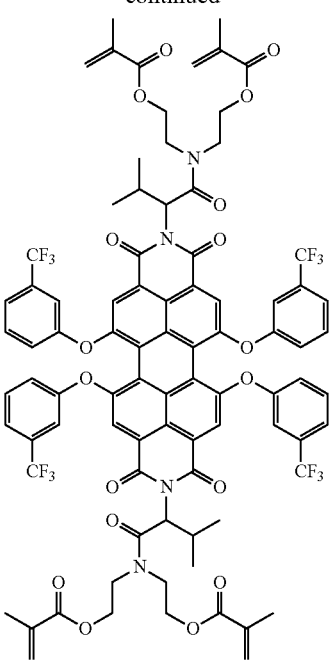
410
-continued
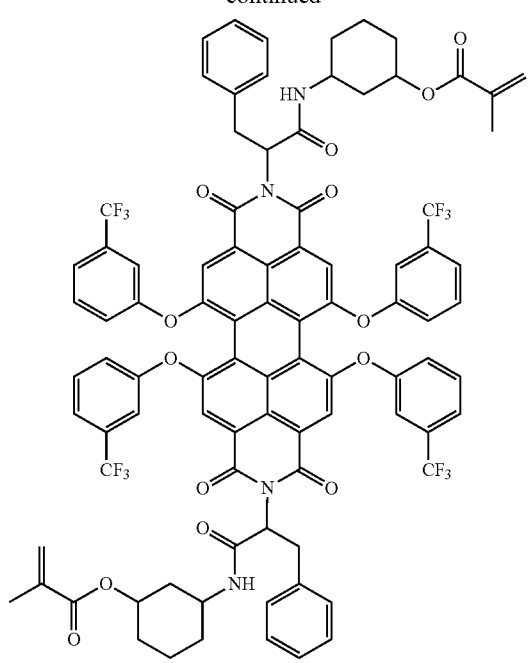
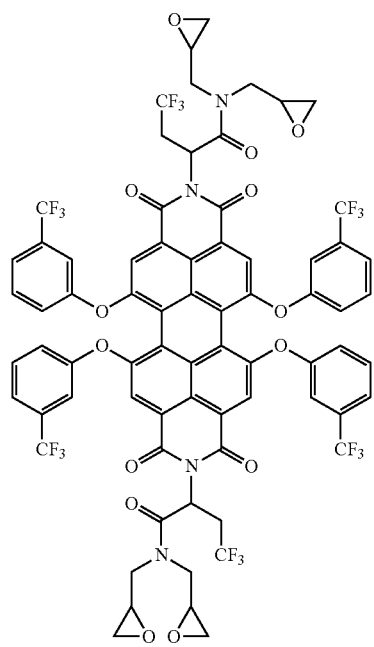
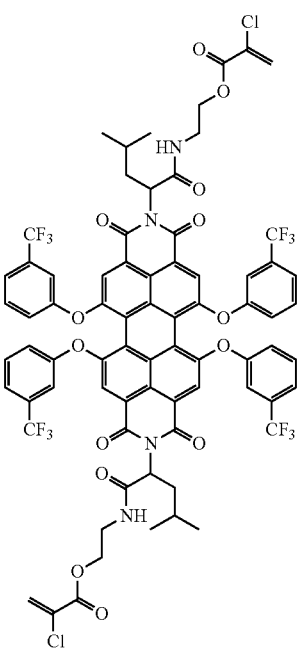

411
-continued
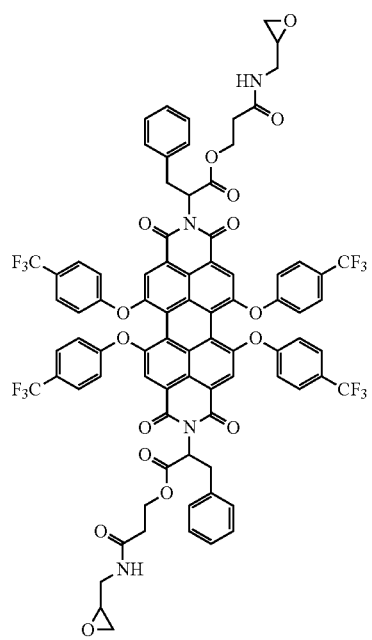 [SMILES: O=C(CCOC(=O)C(Cc1ccccc1)N1C(=O)c2cc(Oc3ccc(C(F)(F)F)cc3)c3c4c(Oc5ccc(C(F)(F)F)cc5)cc5c6c(cc(Oc7ccc(C(F)(F)F)cc7)c(c7c(Oc8ccc(C(F)(F)F)cc8)cc(c2c37)C1=O)c64)C(=O)N(C(Cc1ccccc1)C(=O)OCCC(=O)NCC1CO1)C5=O)NCC1CO1]
412
-continued
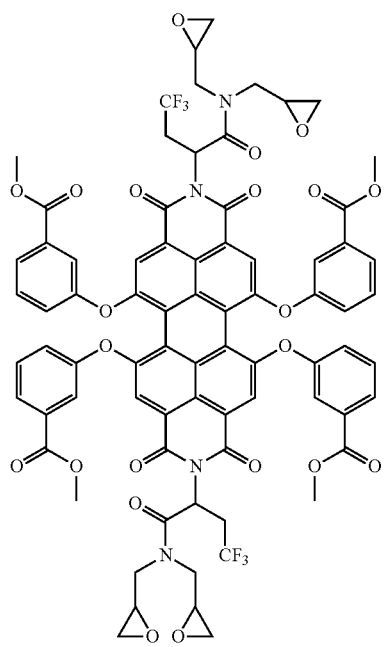
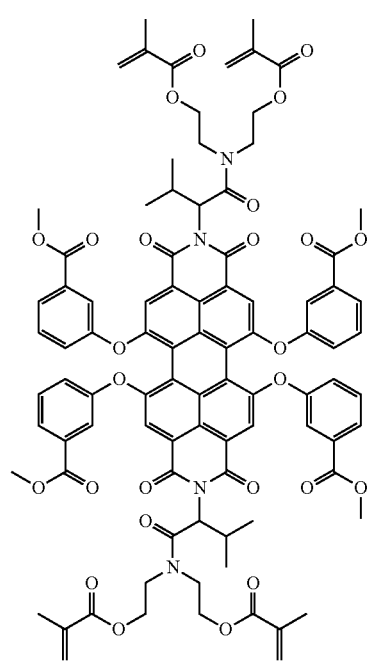
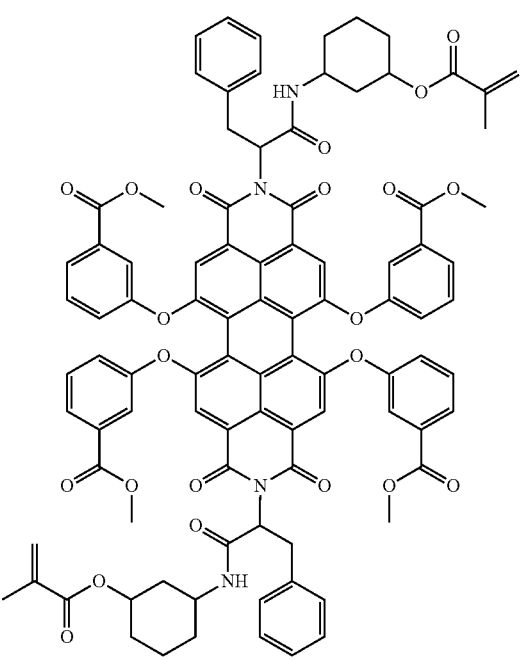

-continued

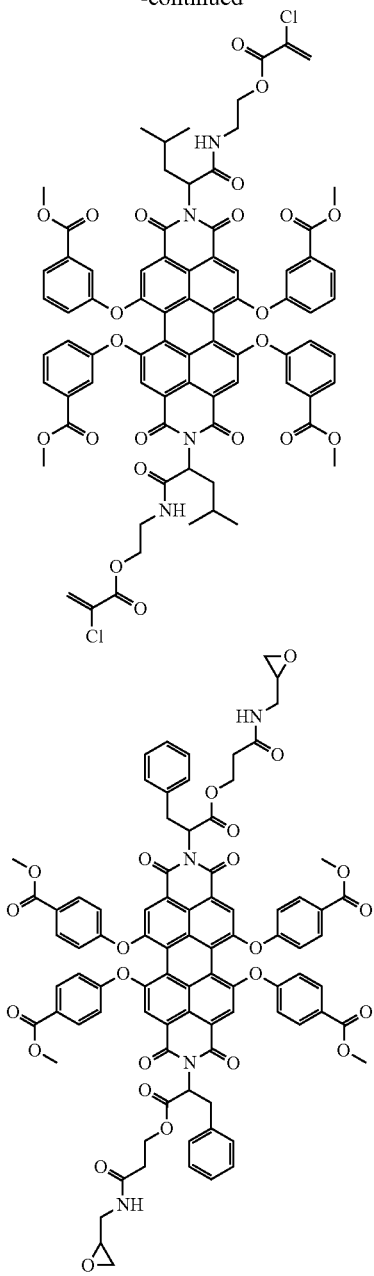

In the compounds, Ph is a phenyl group.

One embodiment of the present specification provides a photoresist fluorescent resin composition including a binder resin; a multifunctional monomer; and the compound described above.

A content of the compound may be from 0.005% by weight to 70% by weight based on a total solid weight of the photoresist fluorescent resin composition, but is not limited thereto.

A content of the compound may be from 0.001% by weight to 15% by weight based on a total weight of the photoresist fluorescent resin composition, but is not limited thereto.

The compound may have a maximum absorption wavelength ($\lambda_{max}$) of 570 nm to 590 nm, and specifically 580 nm to 590 nm.

As the binder resin, a copolymer resin of a monomer providing mechanical strength and a monomer providing alkali solubility may be used.

The monomer providing mechanical strength of the film may be any one or more of unsaturated carboxylic acid esters; aromatic vinyls; unsaturated ethers; unsaturated imides; and acid anhydrides.

Specific examples of the unsaturated carboxylic acid esters may be selected from the group consisting of benzyl (meth)acrylate, methyl (meth)acrylate, ethyl (meth)acrylate, butyl (meth)acrylate, dimethylaminoethyl (meth)acrylate, isobutyl (meth)acrylate, t-butyl (meth)acrylate, cyclohexyl (meth)acrylate, isobornyl (meth)acrylate, ethylhexyl (meth)acrylate, 2-phenoxyethyl (meth)acrylate, tetrahydrofurfuryl (meth)acrylate, hydroxyethyl (meth)acrylate, 2-hydroxypropyl (meth)acrylate, 2-hydroxy-3-chloropropyl (meth)acrylate, 4-hydroxybutyl (meth)acrylate, acyloctyloxy-2-hydroxypropyl (meth)acrylate, glycerol (meth)acrylate, 2-methoxyethyl (meth)acrylate, 3-methoxybutyl (meth)acrylate, ethoxy diethylene glycol (meth)acrylate, methoxy triethylene glycol (meth)acrylate, methoxy tripropylene glycol (meth)acrylate, poly(ethylene glycol)methyl ether (meth)acrylate, phenoxy diethylene glycol (meth)acrylate, p-nonylphenoxy polyethylene glycol (meth)acrylate, p-nonylphenoxy polypropylene glycol (meth)acrylate, glycidyl (meth)acrylate, tetrafluoropropyl (meth)acrylate, 1,1,1,3,3,3-hexafluoroisopropyl (meth)acrylate, octafluoropentyl (meth)acrylate, heptadecafluorodecyl (meth)acrylate, tribromophenyl (meth)acrylate, methyl α-hydroxynnethyl acrylate, ethyl α-hydroxynnethyl acrylate, propyl α-hydroxynnethyl acrylate and butyl α-hydroxynnethyl acrylate, but are not limited thereto.

Specific examples of the aromatic vinyls may be selected from the group consisting of styrene, α-methylstyrene, (o,m,p)-vinyl toluene, (o,m,p)-methoxystyrene and (o,m,p)-chlorostyrene, but are not limited thereto.

Specific examples of the unsaturated ethers may be selected from the group consisting of vinyl methyl ether, vinyl ethyl ether and allyl glycidyl ether, but are not limited thereto.

Specific examples of the unsaturated imides may be selected from the group consisting of N-phenylmaleimide, N-(4-chlorophenyl)maleimide, N-(4-hydroxyphenyl)maleimide and N-cyclohexylmaleimide, but are not limited thereto.

Specific examples of the acid anhydride may include maleic anhydride, methyl maleic anhydride, tetrahydrophthalic anhydride and the like, but are not limited thereto.

The monomer providing alkali solubility may be a monomer containing an acid group. The monomer containing an acid group may use one or more types selected from the group consisting of (meth)acrylic acid, crotonic acid, itaconic acid, maleic acid, fumaric acid, monomethyl maleic acid, isoprenesulfonic acid, styrenesulfonic acid, 5-norbornene-2-carboxylic acid and the like, but is not limited thereto.

A content of the binder resin may be greater than or equal to 1% by weight and less than or equal to 60% by weight based on a total solid weight of the photoresist fluorescent resin composition, but is not limited thereto.

A content of the binder resin may be greater than or equal to 1% by weight and less than or equal to 30% by weight based on a total weight of the photoresist fluorescent resin composition, but is not limited thereto.

The binder resin may have an acid value of greater than or equal to 50 KOH mg/g and less than or equal to 130 KOH mg/g, and a weight average molecular weight of greater than or equal to 1,000 g/mol and less than or equal to 40,000 g/mol, however, the acid value and the weight average molecular weight are not limited thereto.

The multifunctional monomer means a compound having two or more polymerizable functional groups, and acts as a crosslinking agent in the photoresist fluorescent resin composition. Herein, the polymerizable functional group is not particularly limited as long as it is capable of polymerization, and examples thereof may include an ethylenically unsaturated group, a siloxane group, a hydroxyl group, an epoxy group and the like. Specifically, the multifunctional monomer may include an ethylenically unsaturated bond.

The multifunctional monomer may be one or more types selected from among ethylene glycol di(meth)acrylate, polyethylene glycol di(meth)acrylate having 2 to 14 ethylene groups, trinnethylolpropane di(meth)acrylate, trinnethylolpropane tri(meth)acrylate, pentaerythritol tri(meth)acrylate, pentaerythritol tetra(meth)acrylate, propylene glycol di(meth)acrylate having 2 to 14 propylene groups, dipentaerythritol penta(meth)acrylate and dipentaerythritol hexa(meth)acrylate, but is not limited thereto.

A content of the multifunctional monomer may be from 1% by weight to 60% by weight based on a total solid weight of the photoresist fluorescent resin composition, but is not limited thereto.

A content of the multifunctional monomer may be from 1% by weight to 30% by weight based on a total weight of the photoresist fluorescent resin composition, but is not limited thereto.

The photoresist fluorescent resin composition may further include a photoinitiator.

In the photoresist fluorescent resin composition according to the present disclosure, the photoinitiator may be any one or more selected from among acetophenone-based compounds; biimidazole-based compounds; triazine-based compounds; and oxime-based compounds.

Examples of the acetophenone-based compound may include 2-hydroxy-2-methyl-1-phenyl propan-1-one, 1-(4-isopropylphenyl)-2-hydroxy-2-methylpropan-1-one, 4-(2-hydroxyethoxy)-phenyl-(2-hydroxy-2-propyl)ketone, 1-hydroxycyclohexylphenyl ketone, benzoin methyl ether, benzoin ethyl ether, benzoin isobutyl ether, benzoin butyl ether, 2,2-dimethoxy-2-phenylacetophenone, 2-methyl-(4-methylthio)phenyl-2-morpholino-1-propan-1-one, 2-benzyl-2-dimethylamino-1-(4-morpholinophenyl)-butan-1-one, 2-methyl-1-[4-(methylthio)phenyl]2-morpholinopropan-1-one or the like, but are not limited thereto.

Examples of the biimidazole-based compound may include 2,2'-bis(2-chlorophenyl)-4,4',5,5'-tetraphenyl biimidazole, 2,2'-bis(o-chlorophenyl)-4,4',5,5'-tetrakis(3,4,5-trimethoxyphenyl)-1,2'-biimidazole, 2,2'-bis(2,3-dichlorophenyl)-4,4',5,5'-tetra phenyl biimidazole, 2,2'-bis(o-chlorophenyl)-4,4',5,5'-tetraphenyl-1,2'-biimidazole or the like, but are not limited thereto.

Examples of the triazine-based compound may include 3-{[2,4-bis(trichloromethyl)-s-triazin-6-yl]phenylthio}propionic acid, 1,1,1,3,3,3-hexafluoroisopropyl-3-{4-[2,4-bis(trichloromethyl)-s-triazin-6-yl]phenylthio}propionate, ethyl-2-{4-[2,4-bis(trichloromethyl)-s-triazin-6-yl]phenylthio}acetate, 2-epoxyethyl-2-{4-[2,4-bis(trichloromethyl)-s-triazin-6-yl]phenylthio}acetate, cyclohexyl-2-{4-[2,4-bis(trichloromethyl)-s-triazin-6-yl]phenylthio}acetate, benzyl-2-{4-[2,4-bis(trichloromethyl)-s-triazin-6-yl]phenylthio}acetate, 3-{chloro-4-[2,4-bis(trichloromethyl)-s-triazin-6-yl]phenylthio}propionic acid, 3-{4-[2,4-bis(trichloromethyl)-s-triazin-6-yl]phenylthio}propionamide, 2,4-bis(trichloromethyl)-6-p-methoxystyryl-s-triazine, 2,4-bis(trichloromethyl)-6-(1-p-dimethylaminophenyl)-1,3-butadienyl-s-triazine, 2-trichloromethyl-4-amino-6-p-methoxystyryl-s-triazine or the like, but are not limited thereto.

Examples of the oxime-based compound may include CGI-242, CGI-124 of Ciba Specialty Chemicals, and the like, but are not limited thereto.

A content of the photoinitiator may be from 0.1% by weight to 20% by weight based on a total solid content of the photoresist fluorescent resin composition, but is not limited thereto.

A content of the photoinitiator may be from 0.1% by weight to 15% by weight based on a total weight of the photoresist fluorescent resin composition, but is not limited thereto.

The photoresist fluorescent resin composition according to one embodiment of the present disclosure may further include a solvent.

The solvent may be one or more types selected from the group consisting of acetone, methyl ethyl ketone, methyl isobutyl ketone, methyl cellosolve, ethyl cellosolve, tetrahydrofuran, 1,4-dioxane, ethylene glycol dimethyl ether, ethylene glycol diethyl ether, propylene glycol dimethyl ether, propylene glycol diethyl ether, diethylene glycol dimethyl ether, diethylene glycol diethyl ether, diethylene glycol methylethyl ether, chloroform, methylene chloride, 1,2-dichloroethane, 1,1,1-trichloroethane, 1,1,2-trichloroethane, 1,1,2-trichloroethene, hexane, heptane, octane, cyclohexane, benzene, toluene, xylene, methanol, ethanol, isopropanol, propanol, butanol, t-butanol, 2-ethoxypropanol, 2-methoxypropanol, 3-methoxybutanol, cyclohexanone, cyclopentanone, propylene glycol methyl ether acetate, propylene glycol ethyl ether acetate, 3-methoxybutyl acetate, ethyl 3-ethoxypropionate, ethyl cellosolve acetate, methyl cellosolve acetate, butyl acetate, propylene glycol monomethyl ether and dipropylene glycol monomethyl ether, but is not limited thereto.

A content of the total solid may be from 10% by weight to 50% by weight, and a content of the solvent may be from 50% by weight to 90% by weight based on a total weight of the photoresist fluorescent resin composition, however, the content is not limited thereto.

The photoresist composition according to one embodiment of the present disclosure may further include one or more types of additives selected from the group consisting of a dispersant, a curing accelerator, a thermal polymerization inhibitor, a surfactant, a photosensitizer, a plasticizer, an adhesion promoter, a filler and an adhesion aid.

As the photosensitizer, the plasticizer, the adhesion promoter, the filler and the like, all compounds that may be included in existing photoresist fluorescent resin compositions may be used.

The additives may be each independently included in 0.01% by weight to 5% by weight based on a total weight of the photoresist fluorescent resin composition, however, each content is not limited thereto.

The additives may be each independently included in 0.01% by weight to 5% by weight based on a total solid weight of the photoresist fluorescent resin composition, however, each content is not limited thereto.

One embodiment of the present specification provides a color conversion film including the compound described above bonding to a binder resin.

More specifically, a thin-film type photoresist material is formed by coating the photoresist fluorescent resin composition of the present disclosure on a substrate using a proper method.

The coating method is not particularly limited, and a spray method, a roll coating method, a spin coating method and the like may be used, and a spin coating method is generally widely used. In addition, after forming the coated film, some of the residual solvent may be removed under vacuum in some cases.

Examples of a light source for curing the photoresist fluorescent resin composition according to the present disclosure include mercury vapor arc, carbon arc, Xe arc, which emit light with a wavelength of 250 nm to 450 nm, and the like, but are not limited thereto.

When curing the photoresist fluorescent resin composition, the compound represented by Chemical Formula 1 has a polymerizable group capable of binding with a binder resin. In this case, an advantage of having no dyeing in the process is obtained.

The color conversion film of the present specification has a maximum emission peak in a 610 nm to 640 nm region, and specifically, has a maximum emission peak in a 615 nm to 640 nm region and preferably in a 620 nm to 640 nm region. In this case, an advantage of high color reproduction is obtained.

In the color conversion film of the present specification, the maximum emission peak may have a full width at half maximum of 41 nm or less, and specifically greater than or equal to 35 nm and less than or equal to 41 nm. The full width at half maximum means, when converting light absorbed from an external light source to light having another wavelength and emitting the light, a width of the emission peak at half the maximum height in the maximum emission peak of the emitted light, and color gamut is excellent as the full width at half maximum is smaller.

The color conversion film may further include additional fluorescent materials in addition to the compound represented by Chemical Formula 1. When using a light source emitting blue light, the color conversion film preferably includes both a green light emitting fluorescent material and a red light emitting fluorescent material. In addition, when using a light source emitting blue light and green light, the color conversion film may only include a red light emitting fluorescent material. However, the color conversion film is not limited thereto, and even when using a light source emitting blue light, the color conversion film may only include a red light emitting compound when a separate film including a green light emitting fluorescent material is laminated. On the other hand, even when using a light source emitting blue light, the color conversion film may only include a green light emitting compound when a separate film including a red light emitting fluorescent material is laminated.

The color conversion film may further include an additional layer including a resin matrix; and a compound dispersed into the resin matrix and emitting light in a wavelength different from the wavelength of the compound represented by Chemical Formula 1. The compound emitting light in a wavelength different from the wavelength of the compound represented by Chemical Formula 1 may also be the compound represented by Chemical Formula 1, or may be other known fluorescent materials.

The resin matrix material is preferably a thermoplastic polymer or a thermocurable polymer. Specifically, a poly (meth)acryl-based such as polymethyl methacrylate (PMMA), a polycarbonate (PC)-based, a polystyrene (PS)-based, a polyarylene (PAR)-based, a polyurethane (PU)-based, a styrene-acrylonitrile (SAN)-based, a polyvinylidene fluoride (PVDF)-based, a modified polyvinylidene fluoride (modified-PVDF)-based and the like may be used as the resin matrix material.

According to one embodiment of the present specification, the color conversion film according to the embodiments described above additionally includes light diffusing particles. By dispersing light diffusing particles into the color conversion film instead of a light diffusing film used in the art for enhancing luminance, higher luminance may be exhibited compared to using a separate light diffusing film, and an adhering process may be skipped as well.

As the light diffusing particles, particles having a high refractive index with the resin matrix may be used, and examples thereof may include $TiO_2$, silica, borosilicate, alumina, sapphire, air or other gas-filled hollow beads or particles (for example, air/gas-filled glass or polymers); polystyrene, polycarbonate, polymethyl methacrylate, acryl, methyl methacrylate, styrene, a melamine resin, a formaldehyde resin, or polymer particles including melamine and formaldehyde resins, or any suitable combination thereof.

The light diffusing particles may have particle diameters in a range of 0.1 μm to 5 μm, for example, in a range of 0.3 μm to 1 μm. The content of the light diffusing particles may be determined as necessary.

The color conversion film according to the embodiments described above may have a thickness of 2 μm to 200 μm. Particularly, the color conversion film may exhibit high luminance even with a small thickness of 2 μm to 20 μm. This is due to the fact that the content of the fluorescent material molecules included in the unit volume is higher compared to quantum dots.

The color conversion film according to the embodiments described above may have a substrate provided on one surface. This substrate may function as a support when preparing the color conversion film. Types of the substrate are not particularly limited, and the material or thickness is not limited as long as it is transparent and is capable of functioning as the support. Herein, being transparent means having visible light transmittance of 70% or higher. For example, a PET film may be used as the substrate.

One embodiment of the present specification provides a backlight unit including the color conversion film. The backlight unit may have backlight unit constitutions known in the art except for including the color conversion film. FIG. 1 illustrates a mimetic diagram of a backlight unit structure according to one embodiment. According to FIG. 1, the color conversion film including the compound represented by Chemical Formula 1 is provided on a surface opposite to a surface facing a reflecting plate of a light guide plate. FIG. 1 illustrates a constitution including a light source and a reflecting plate surrounding the light source, however, the constitution is not limited to such a structure, and may vary depending on the backlight unit structure known in the art. In addition, as the light source, a direct type as well as a side chain type may be used, and the reflecting plate or the reflective layer may not be included or may be replaced with other constituents as necessary, and as necessary, additional films such as a light diffusing film, a light concentrating film and a luminance enhancing film may be further provided. Preferably, a prism sheet, a multilayer reflective polarizer film, a light concentrating film or a luminance enhancing film is further provided on the color conversion film.

In the constitution of the backlight unit as in FIG. 1, a scattering pattern may be provided as necessary on an upper surface or a lower surface of the light guide plate. Light introduced into the light guide plate has non-uniform light distribution due to repetition of optical processes such as reflection, total reflection, refraction or transmission, and the scattering pattern may be used to induce the non-uniform light distribution to uniform brightness.

One embodiment of the present specification provides a display apparatus including the backlight unit. The display apparatus is not particularly limited as long as it includes the backlight unit. For example, the display apparatus includes a display module and a backlight unit. FIG. 2 illustrates a structure of the display apparatus. However, the structure is not limited thereto, and between the display module and the backlight unit, additional films such as a light diffusing film, a light concentrating film and a luminance enhancing film may be further provided as necessary.

Hereinafter, the present specification will be described in more detail with reference to examples. However, the following examples are for illustrative purposes only, and are not to limit the present specification.

The compound according to one embodiment of the present application may be prepared using preparation methods to describe later.

For example, the core structure of the compound having the structure of Chemical Formula 1 may be prepared through the following Reaction Formula 1. Substituents may bond using methods known in the art, and types, positions and the number of the substituents may vary depending on technologies known in the art.

[Reaction Formula 1]
<Step 1>

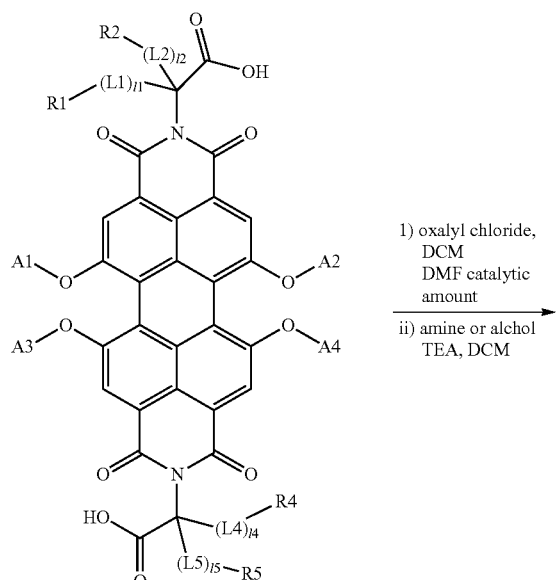

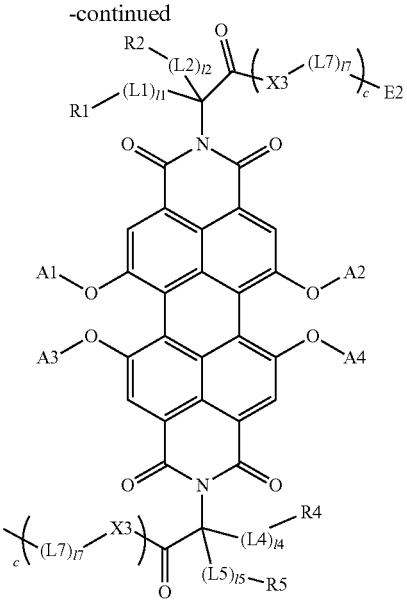

Herein, A1 to A4, L1, I1, L2, I2, L4, I4, L5, I5, R1, R2, R4 and R5 have the same definitions as in Chemical Formula 1, and X3, L7, I7, E2 and c have the same definitions as in the following Chemical Formula 8.

After dissolving 1 equivalent of Compound 1 and a catalytic amount of dimethylformamide (DMF) in a dichloromethane (DCM) solvent in a reaction container, 4 equivalents of oxalyl chloride was slowly introduced thereto in an ice bath. The result was stirred at room temperature under nitrogen. Then, dichloromethane was evaporated using a rotary evaporator. An acyl chloride in which a hydroxyl group is replaced with a chlorine group in the carboxyl group of Compound 1 was synthesized.

After dissolving 4 equivalents of an amine or an alcohol represented by the following Chemical Formula 8 and 10 equivalents of triethylamine (TEA) in a dichloromethane solvent in another reaction container, the synthesized acyl chloride was dissolved in dichloromethane in an ice bath, and then the solution described above was slowly introduced thereto. The mixture was stirred at room temperature under nitrogen. After the reaction was completed, the result was extracted using dichloromethane and water, and water was removed from the separated organic layer using anhydrous magnesium sulfate ($MgSO_4$). The water-removed organic layer was concentrated through vacuum distillation, and then recrystallized using dichloromethane and hexane to obtain Compound 2 by suction filtration. Compound 2 was dried under a vacuum condition at 80° C.

[Chemical Formula 8]

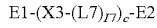

In Chemical Formula 8,
X3, L7, I7 and c respectively have the same definitions as X1, L3, I3 and a of Chemical Formula 1,
E1 is hydrogen, and
E2 is a hydroxyl group, a halogen group, a carboxyl group, an amine group, a vinyl group, —C(=O)$NH_2$ or a polymerizable group.

In Compound 2, when E2 is not a polymerizable group, that is, when E2 is a hydroxyl group, a halogen group, a carboxyl group, an amine group, a vinyl group or —C(=O)NH$_2$, the polymerizable group may react through the following Step 2.

<Step 2>

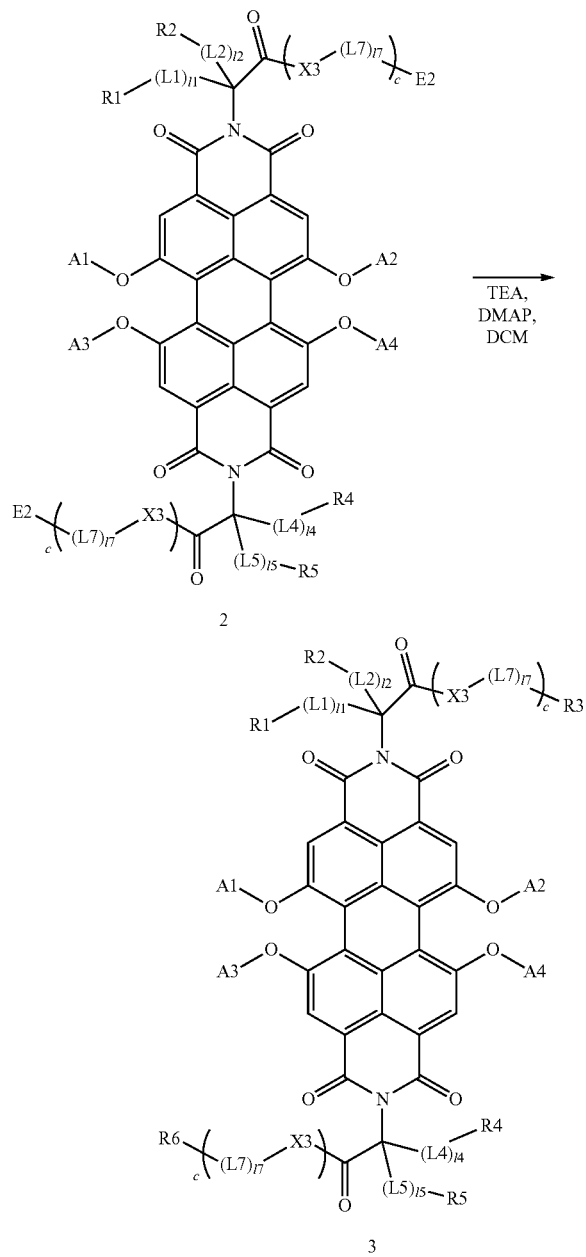

Herein, A1 to A4, L1, l1, L2, l2, L4, l4, L5, l5 and R1 to R6 have the same definitions as in Chemical Formula 1, and X3, L7, l7, E2 and c have the same definitions as in Chemical Formula 8.

After dissolving 1 equivalent of Compound 2 and 6 equivalents of triethylamine (TEA) in a dichloromethane (DCM) solvent in a reaction container, the result was stirred in an ice bath. In this reaction container, a compound, which has a polymerizable group and capable of reacting with E2 of Compound 2, dissolved in dichloromethane was slowly introduced thereto, then 4-dimethylaminopyridine (DMAP) was introduced thereto, and the result was stirred at room temperature under nitrogen. After the reaction was completed, the result was extracted using dichloromethane and water, and water was removed from the separated organic layer using anhydrous magnesium sulfate (MgSO$_4$). The water-removed organic layer was concentrated through vacuum distillation, and then recrystallized using methyl tertiary-butyl ether and hexane to obtain Compound 3 by suction filtration. Compound 3 was dried under a vacuum condition at 80° C.

EXAMPLE

[Preparation Example 1] Synthesis of Compound A

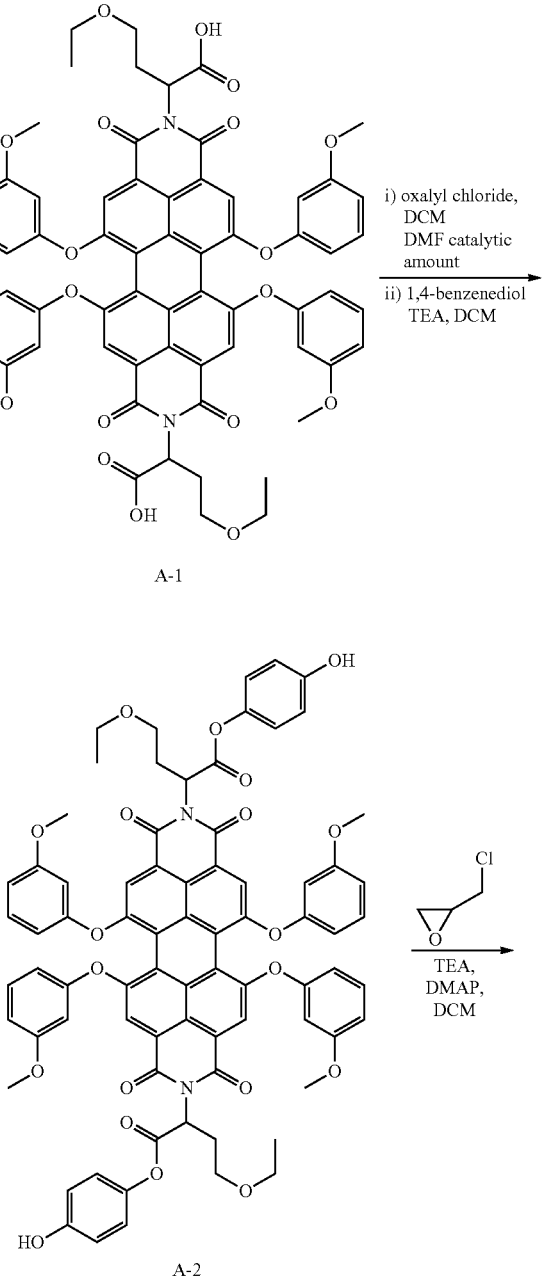

-continued

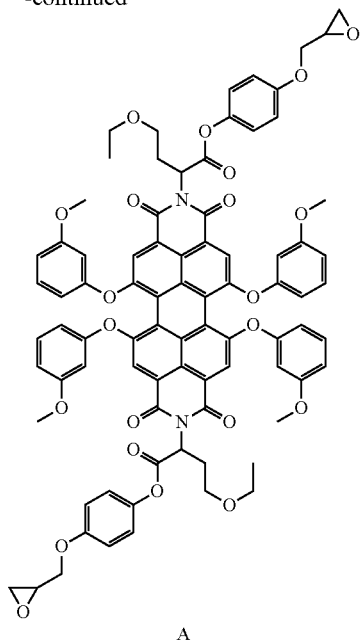

A

A. Synthesis of Compound A-2

After dissolving 1 equivalent of Compound A-1 and a catalytic amount of dimethylformamide (DMF) in a dichloromethane (DCM) solvent in a reaction container, 4 equivalents of oxalyl chloride was slowly introduced thereto in an ice bath. The result was stirred at room temperature under nitrogen, and dichloromethane was evaporated using a rotary evaporator. An acyl chloride in which a hydroxyl group is replaced with a chlorine group in the carboxyl group of Compound A-1 was synthesized.

After dissolving 4 equivalents of 1,4-benzenediol and 10 equivalents of triethylamine (TEA) in a dichloromethane solvent in another reaction container, the synthesized acyl chloride was dissolved in dichloromethane in an ice bath, and the above-described solution was slowly introduced thereto. The mixture was stirred at room temperature under nitrogen. After the reaction was completed, the result was extracted using dichloromethane and water, and water was removed from the separated organic layer using anhydrous magnesium sulfate (MgSO₄). The water-removed organic layer was concentrated through vacuum distillation, and then recrystallized with dichloromethane and hexane to obtain Compound A-2 by suction filtration. Compound A-2 was dried under a vacuum condition at 80° C.

B. Synthesis of Compound A

After dissolving 1 equivalent of Compound A-2 and 6 equivalents of triethylamine in a dichloromethane solvent in a reaction container, the result was stirred in an ice bath. In this reaction container, 6 equivalents of epichlorohydrin dissolved in dichloromethane was slowly introduced. 4-Dimethylaminopyridine was further introduced thereto, and the result was stirred at room temperature under nitrogen. After the reaction was completed, the result was extracted using dichloromethane and water, and water was removed from the separated organic layer using anhydrous magnesium sulfate (MgSO₄). The water-removed organic layer was concentrated through vacuum distillation, and then recrystallized with methyl tertiary-butyl ether and hexane to obtain Compound A by suction filtration. Compound A was dried under a vacuum condition at 80° C.

HR LC/MS/MS m/z calculated for C82H70N2O22 (M+): 1434.4420; found: 1434.4421.

[Preparation Example 2] Synthesis of Compound B

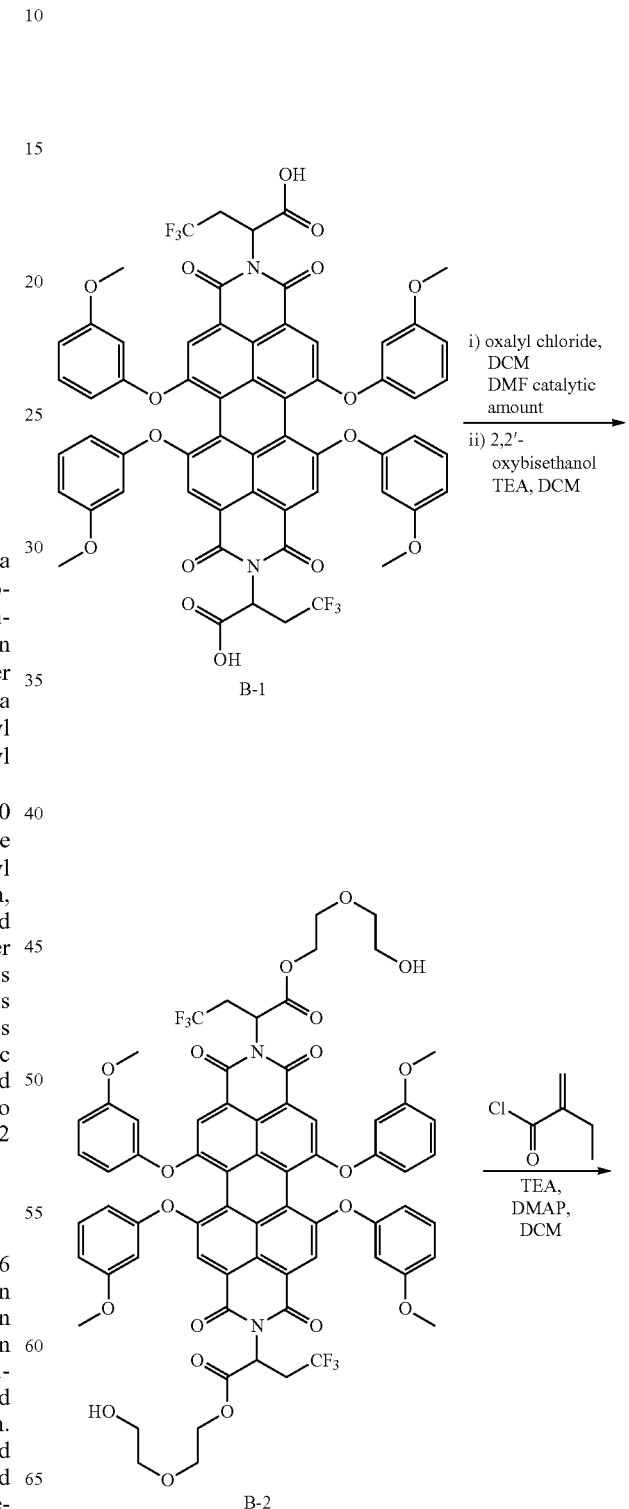

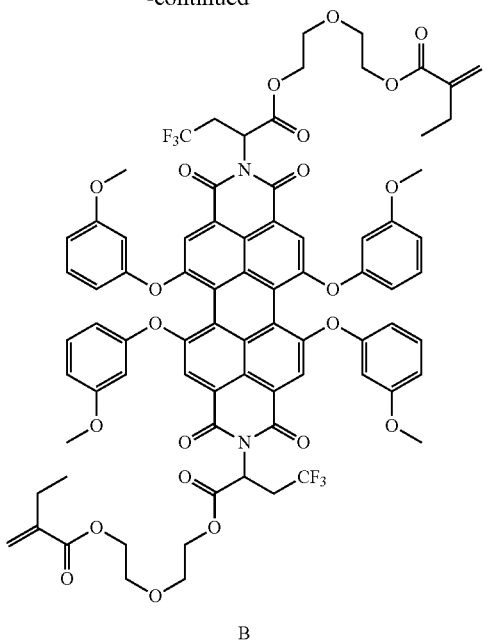

B

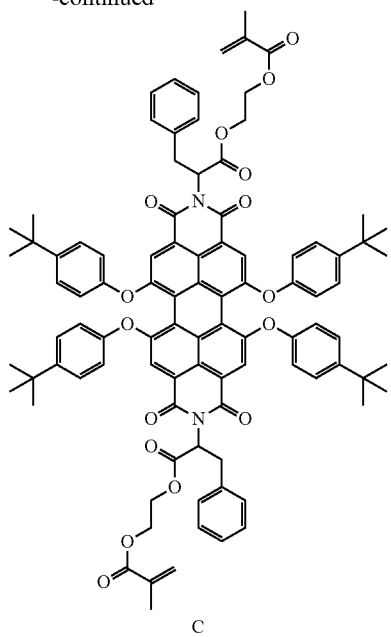

C

Synthesis was conducted in the same manner as in Preparation Example 1 except that Compound B-1 and 2,2'-oxybisethanol were used instead of Compound A-1 and 1,4-benzenediol in Synthesis of Compound A-2, and Compound B-2 and 2-methylene-butyryl chloride were used instead of Compound A-2 and epichlorohydrin in Synthesis of Compound A, and Compound B was synthesized therethrough.

HR LC/MS/MS m/z calculated for C78H68F6N2O22 (M+): 1498.4168; found: 1498.4164.

[Preparation Example 3] Synthesis of Compound C

Synthesis was conducted in the same manner as in Synthesis of Compound A-2 except that Compound C-1 and 2-hydroxyethyl methacrylate (HEMA) were used instead of Compound A-1 and 1,4-benzenediol, and Compound C was synthesized therethrough.

HR LC/MS/MS m/z calculated for C94H90N2O16 (M+): 1502.6290; found: 1502.6280.

[Preparation Example 4] Synthesis of Compound D

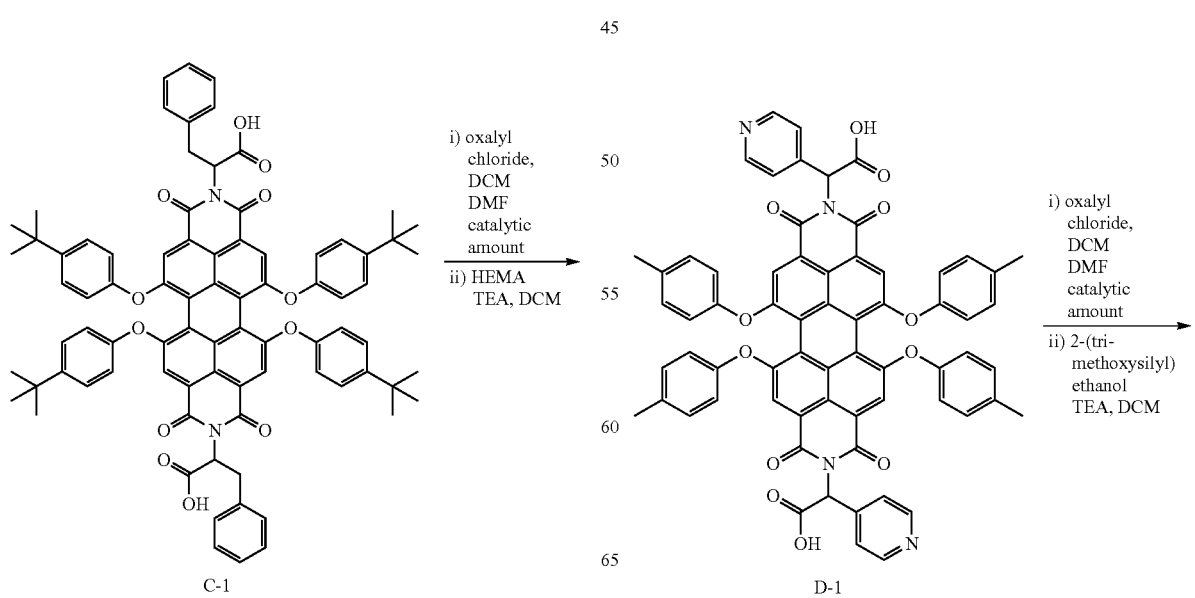

C-1

D-1

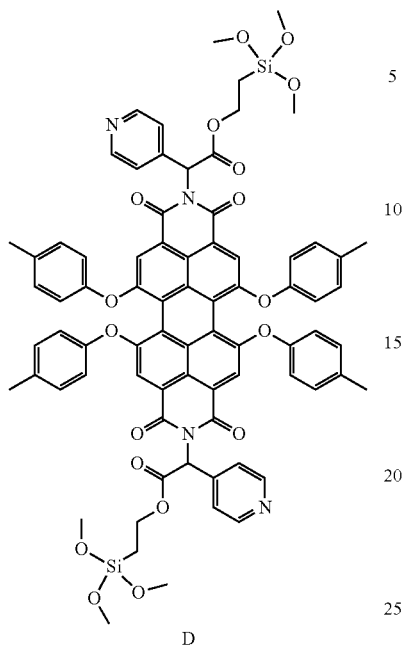
D
Synthesis was conducted in the same manner as in Synthesis of Compound A-2 except that Compound D-1 and 2-(trimethoxysilyl)ethanol were used instead of Compound A-1 and 1,4-benzenediol, and Compound D was synthesized therethrough.
HR LC/MS/MS m/z calculated for C76H68N4O18Si2 (M+): 1380.4067; found: 1380.4067.
[Preparation Example 5] Synthesis of Compound E
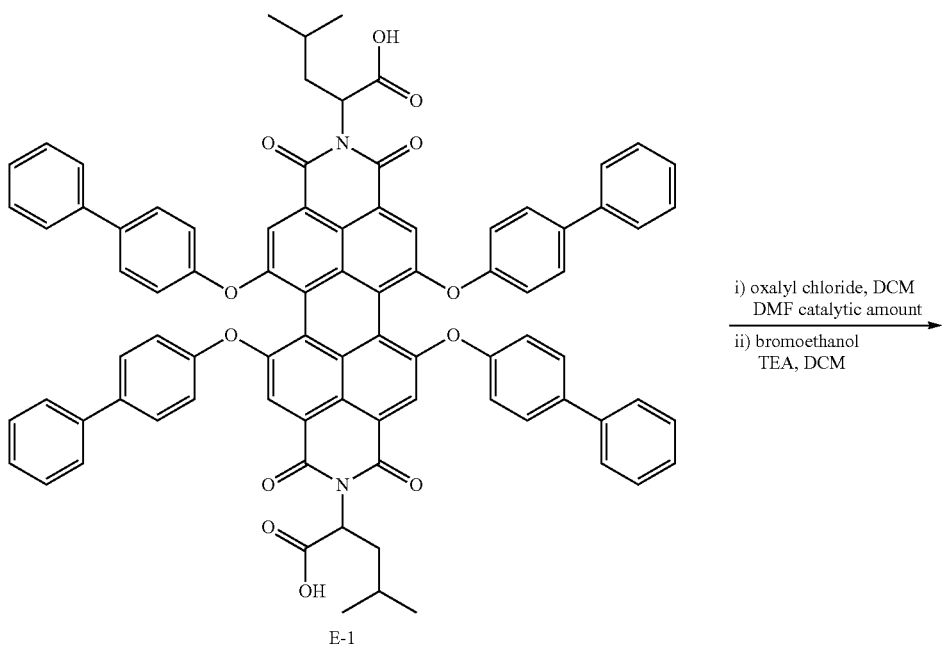
E-1

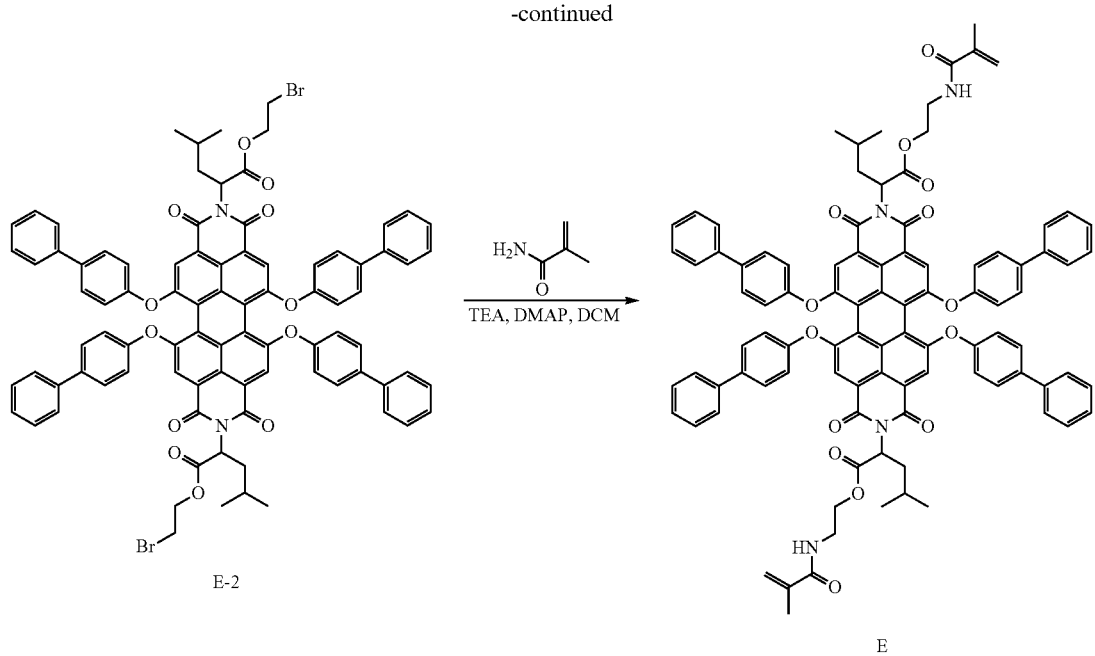

Synthesis was conducted in the same manner as in Preparation Example 1 except that Compound E-1 and bromoethanol were used instead of Compound A-1 and 1,4-benzenediol in Synthesis of Compound A-2, and Compound E-2 and methacrylamide were used instead of Compound A-2 and epichlorohydrin in Synthesis of Compound A, and Compound E was synthesized therethrough.

HR LC/MS/MS m/z calculated for $C_{96}H_{80}N_4O_{14}$ (M+): 1512.5671; found: 1516.5671.

[Preparation Example 6] Synthesis of Compound F

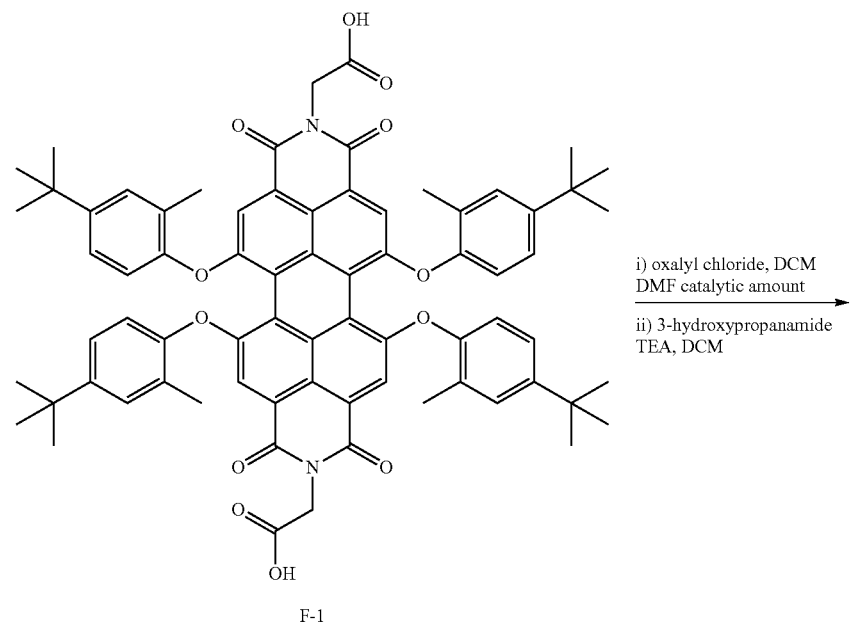

-continued

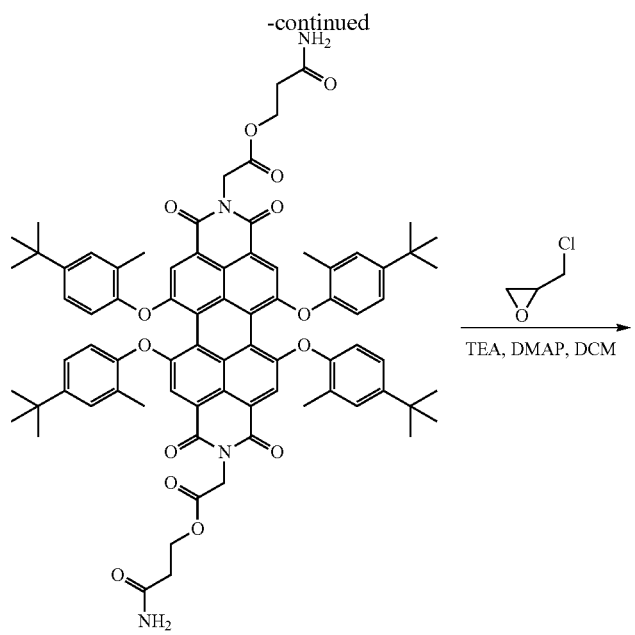

F-2

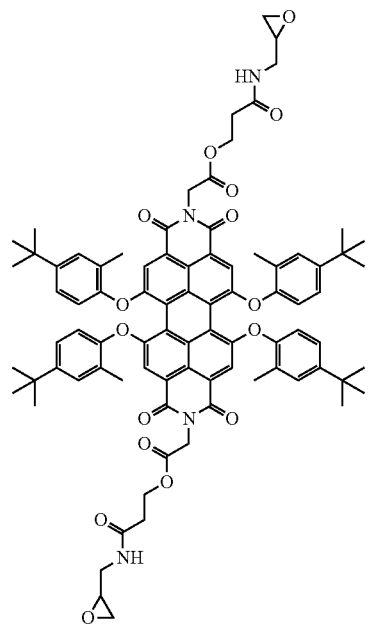

F

Synthesis was conducted in the same manner as in Preparation Example 1 except that Compound F-1 and 3-hydroxypropanamide were used instead of Compound A-1 and 1,4-benzenediol in Synthesis of Compound A-2, and Compound F-2 was used instead of Compound A-2 in Synthesis of Compound A, and Compound F was synthesized therethrough.

HR LC/MS/MS m/z calculated for $C_{84}H_{88}N_4O_{16}$ (M+): 1408.6195; found: 1408.6199.

[Preparation Example 7] Synthesis of Compound G
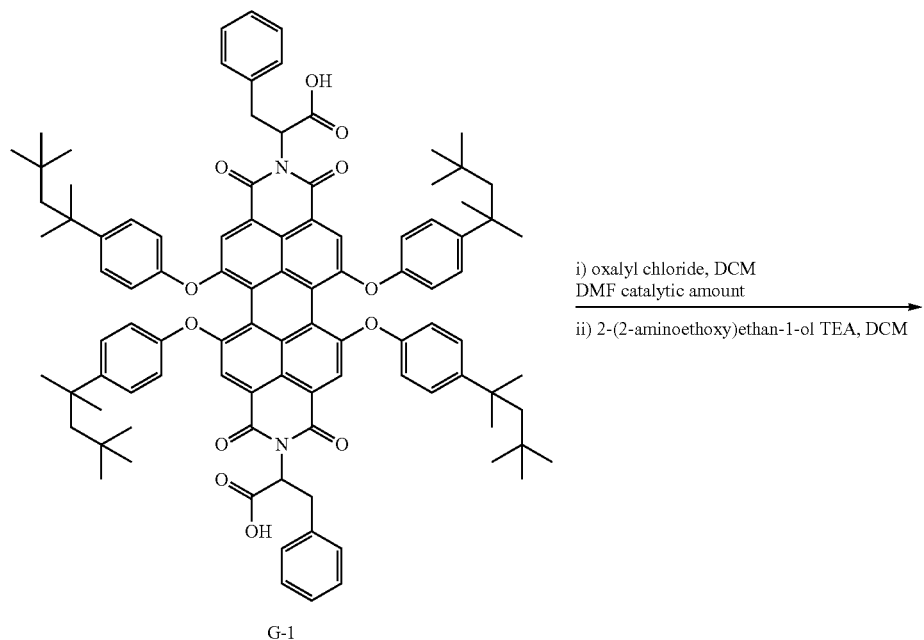
G-1
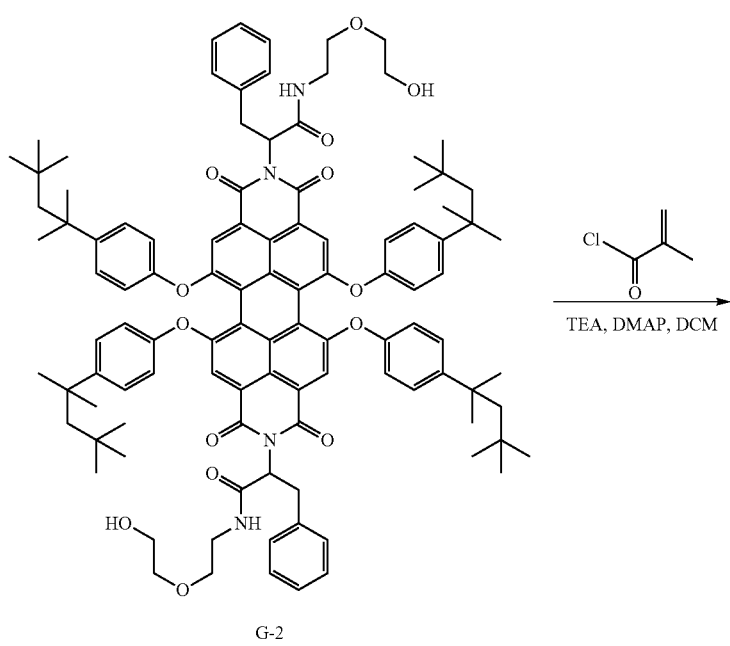
G-2

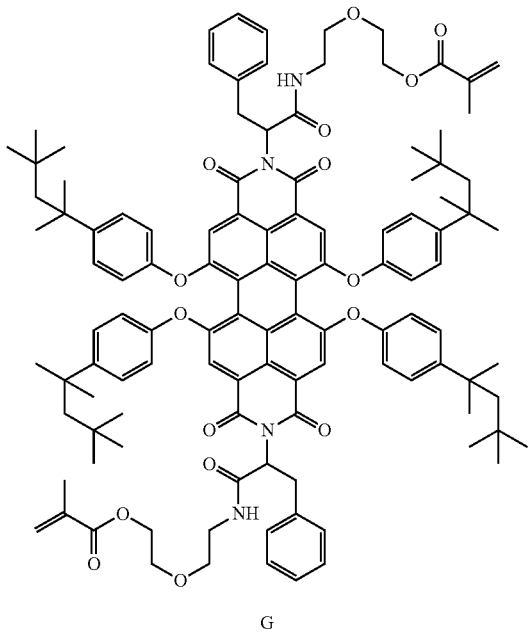 [SMILES: C=C(C)C(=O)OCCOCCNC(=O)C(Cc1ccccc1)N1C(=O)c2cc(Oc3ccc(C(C)(C)CC(C)(C)C)cc3)c3c4c(Oc5ccc(C(C)(C)CC(C)(C)C)cc5)cc5c6c(cc(Oc7ccc(C(C)(C)CC(C)(C)C)cc7)c(c7c(Oc8ccc(C(C)(C)CC(C)(C)C)cc8)cc(c2c37)C1=O)c64)C(=O)N(C(Cc1ccccc1)C(=O)NCCOCCOC(=O)C(=C)C)C5=O]

G

Synthesis was conducted in the same manner as in Preparation Example 1 except that Compound G-1 and 2-(2-aminoethoxy)ethan-1-ol were used instead of Compound A-1 and 1,4-benzenediol in Synthesis of Compound A-2, and Compound G-2 and methacryloyl chloride were used instead of Compound A-2 and epichlorohydrin in Synthesis of Compound A, and Compound G was synthesized therethrough.

HR LC/MS/MS m/z calculated for C114H132N4O16 (M+): 1812.9638; found: 1812.9640.

[Preparation Example 8] Synthesis of Compound H

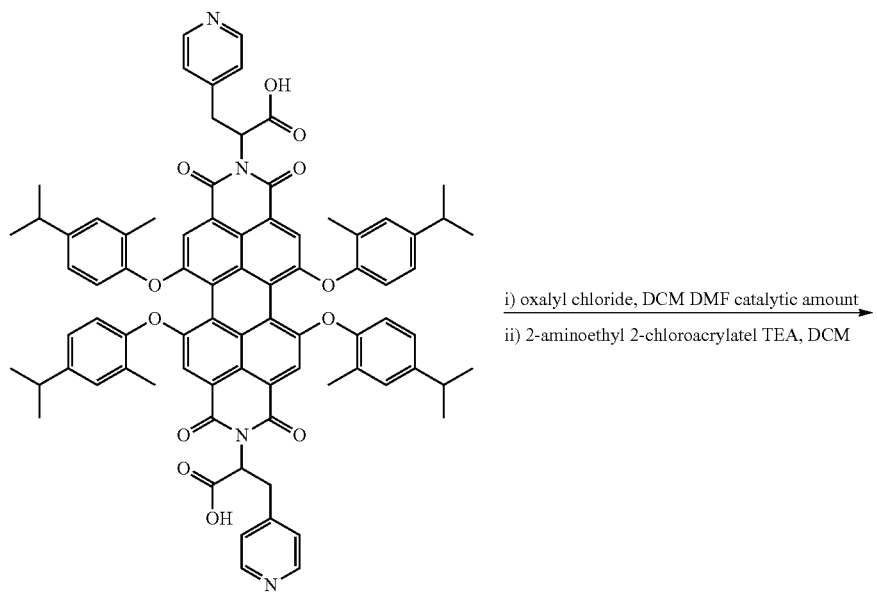

H-1

-continued
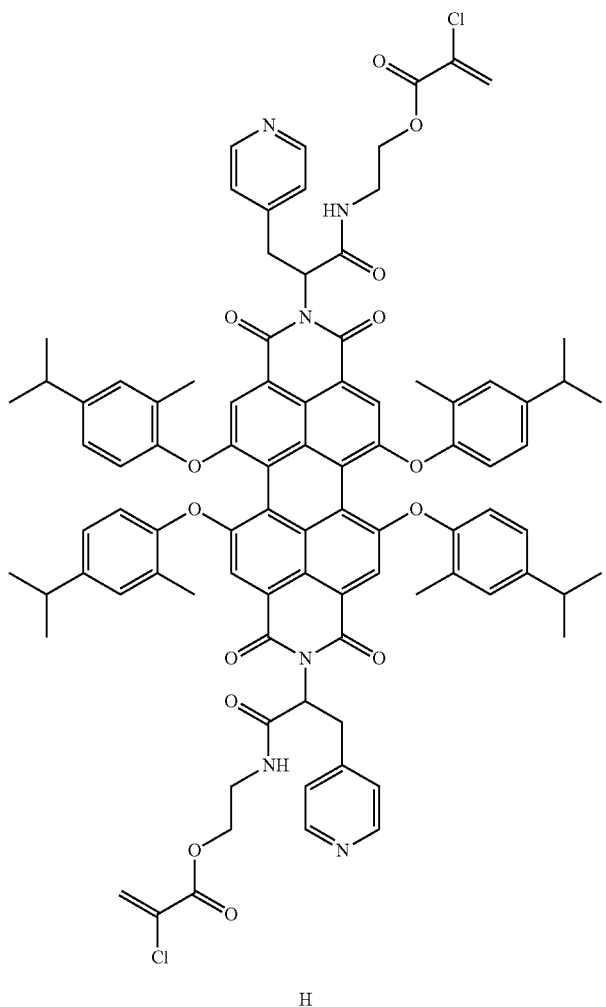
H
Synthesis was conducted in the same manner as in Synthesis of Compound A-2 except that Compound H-1 and 2-aminoethyl 2-chloroacrylate were used instead of Compound A-1 and 1,4-benzenediol, and Compound H was synthesized therethrough.
HR LC/MS/MS m/z calculated for $C_{90}H_{84}Cl_2N_6O_{14}$ (M+): 1542.5423; found: 1542.5424.

[Preparation Example 9] Synthesis of Compound I
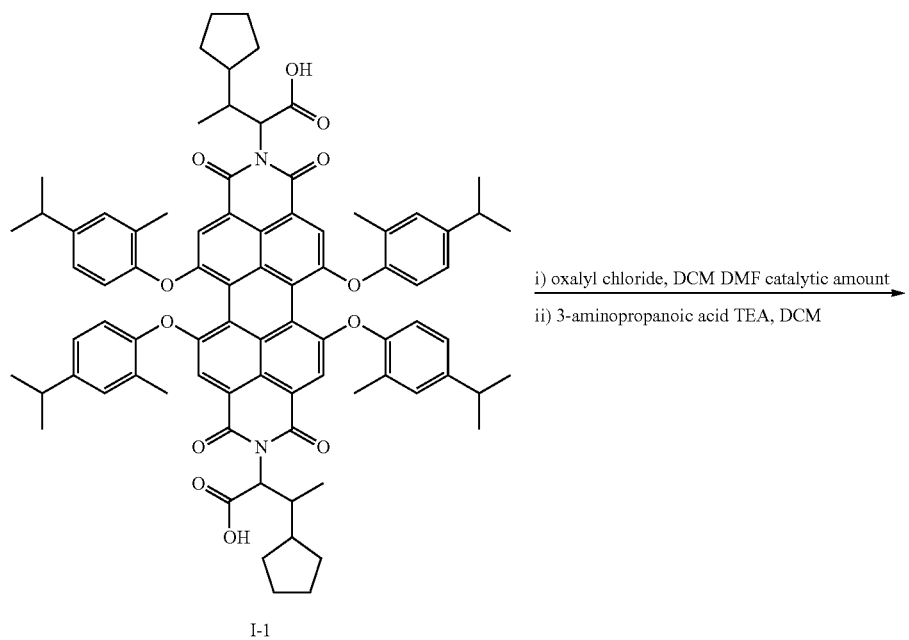
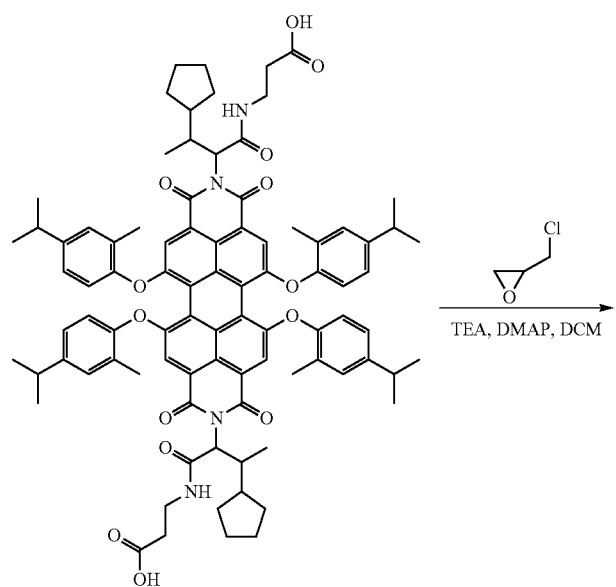

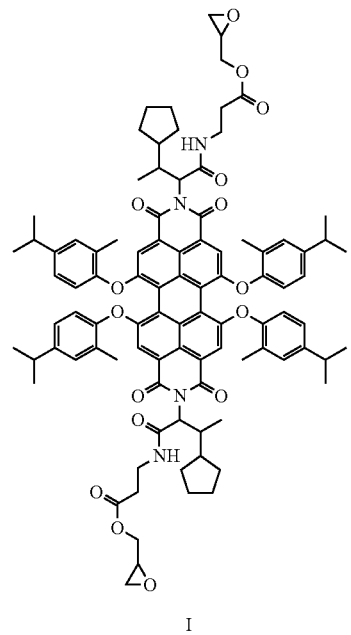

I

Synthesis was conducted in the same manner as in Preparation Example 1 except that Compound I-1 and 3-aminopropionic acid were used instead of Compound A-1 and 1,4-benzenediol in Synthesis of Compound A-2, and Compound I-2 was used instead of Compound A-2 in Synthesis of Compound A, and Compound I was synthesized therethrough.

HR LC/MS/MS m/z calculated for C94H104N4O16 (M+): 1544.7447; found: 1544.7447.

[Preparation Example 10] Synthesis of Compound J

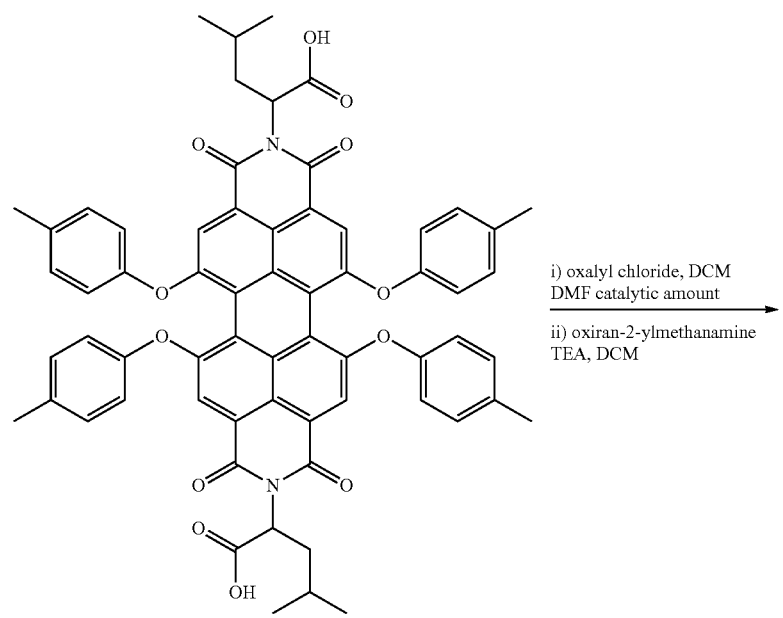

i) oxalyl chloride, DCM
DMF catalytic amount ii) oxiran-2-ylmethanamine
TEA, DCM

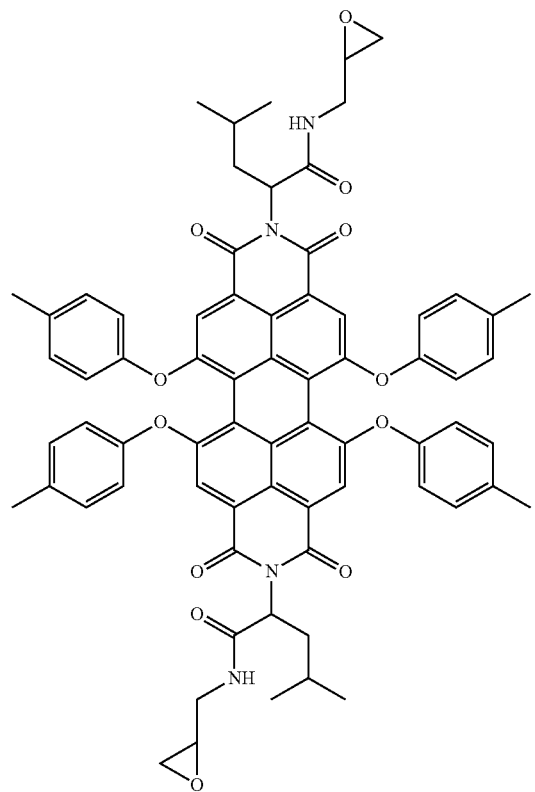
J
Synthesis was conducted in the same manner as in Synthesis of Compound A-2 except that Compound J-2 and oxiran-2-ylmethanamine were used instead of Compound A-1 and 1,4-benzenediol, and Compound J was synthesized therethrough.
HR LC/MS/MS m/z calculated for C70H64N4O12 (M+): 1152.4521; found: 1152.4525.

[Preparation Example 11] Synthesis of Compound K
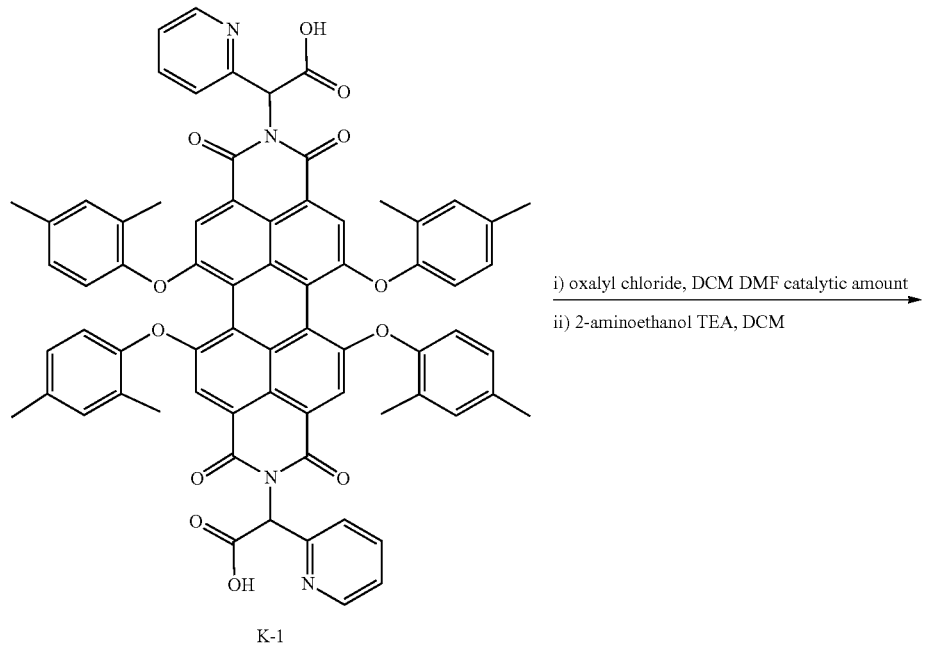
i) oxalyl chloride, DCM DMF catalytic amount
ii) 2-aminoethanol TEA, DCM
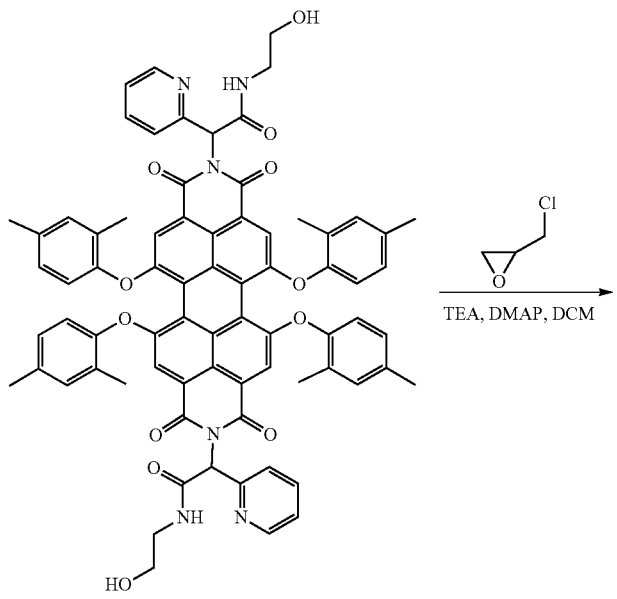
TEA, DMAP, DCM

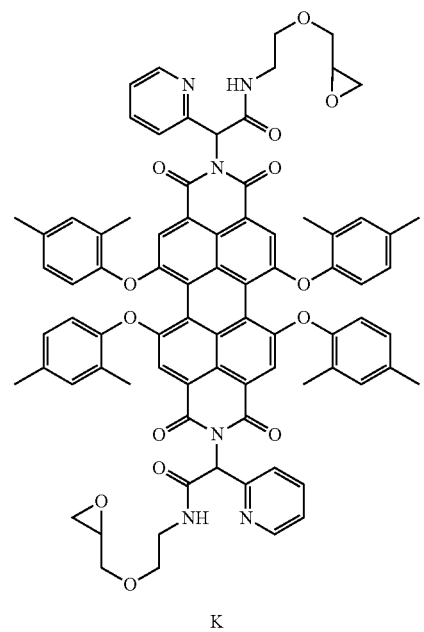

K

Synthesis was conducted in the same manner as in Preparation Example 1 except that Compound K-1 and 2-aminoethanol were used instead of Compound A-1 and 1,4-benzenediol in Synthesis of Compound A-2, and Compound K-2 was used instead of Compound A-2 in Synthesis of Compound A, and Compound K was synthesized therethrough.

HR LC/MS/MS m/z calculated for C80H70N6O14 (M+): 1338.4950; found: 1338.4950.

[Preparation Example 12] Synthesis of Compound L

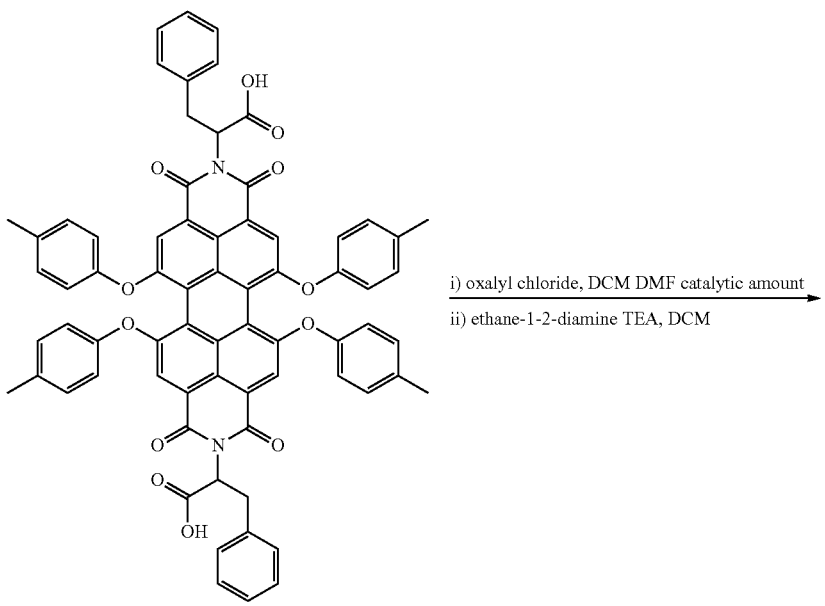

L-1 i) oxalyl chloride, DCM DMF catalytic amount
ii) ethane-1-2-diamine TEA, DCM

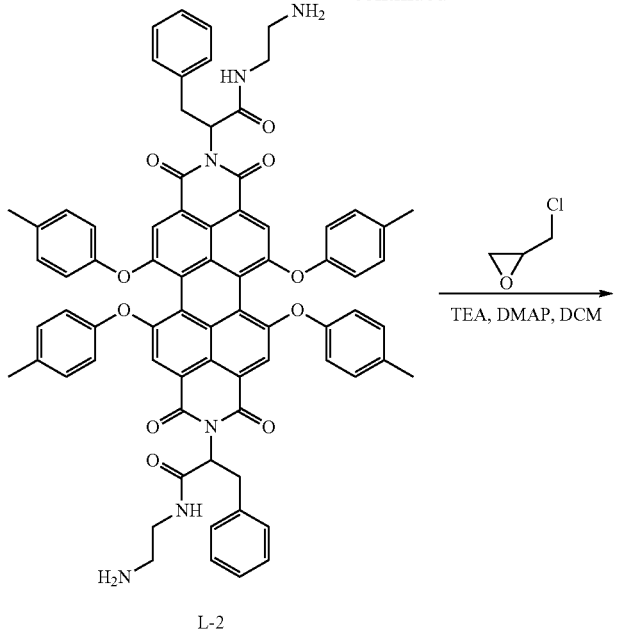

L-2

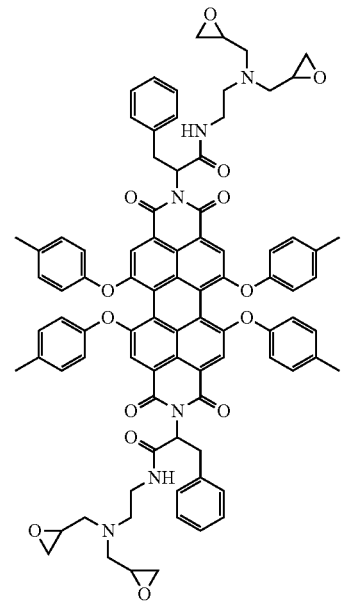

L

Synthesis was conducted in the same manner as in Preparation Example 1 except that Compound L-1 and ethylenediamine were used instead of Compound A-1 and 1,4-benzenediol in Synthesis of Compound A-2, and Compound L-2 and 12 equivalents of epichlorohydrin were used instead of Compound A-2 and 6 equivalents of epichlorohydrin in Synthesis of Compound A, and Compound L was synthesized therethrough.

HR LC/MS/MS m/z calculated for $C_{86}H_{78}N_6O_{14}$ (M+): 1418.5576; found: 1418.5572.

[Preparation Example 13] Synthesis of Compound M
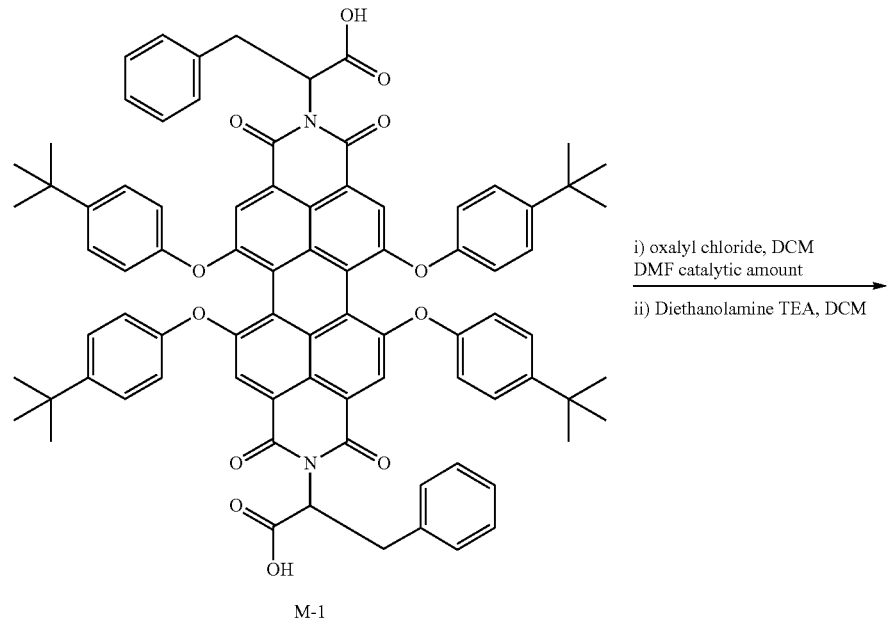
M-1
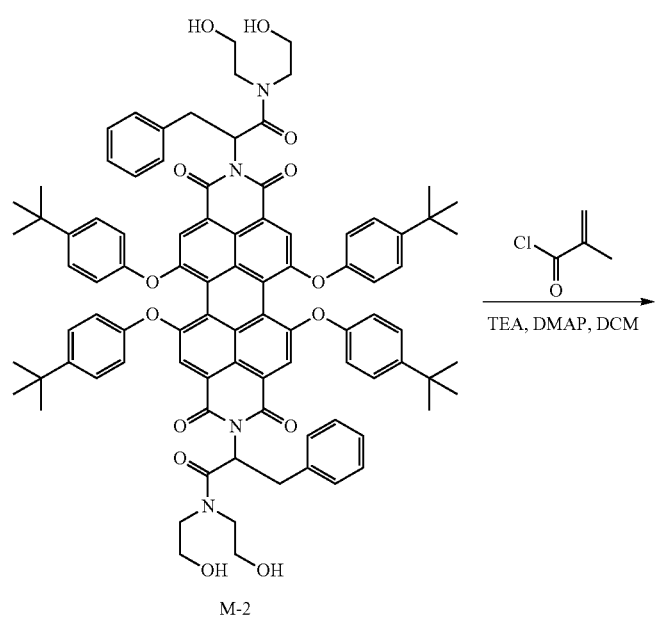
M-2

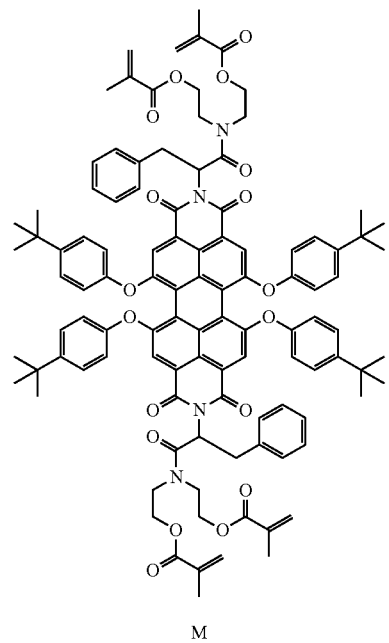

M

Synthesis was conducted in the same manner as in Preparation Example 1 except that Compound M-1 and diethanolamine were used instead of Compound A-1 and 1,4-benzenediol in Synthesis of Compound A-2, and Compound M-2 and 12 equivalents of methacryloly chloride were used instead of Compound A-2 and 6 equivalents of epichlorohydrin in Synthesis of Compound A, and Compound M was synthesized therethrough.

HR LC/MS/MS m/z calculated for C106H108N4O18 (M+): 1724.7659; found: 1724.7660.

[Preparation Example 14] Synthesis of Compound N

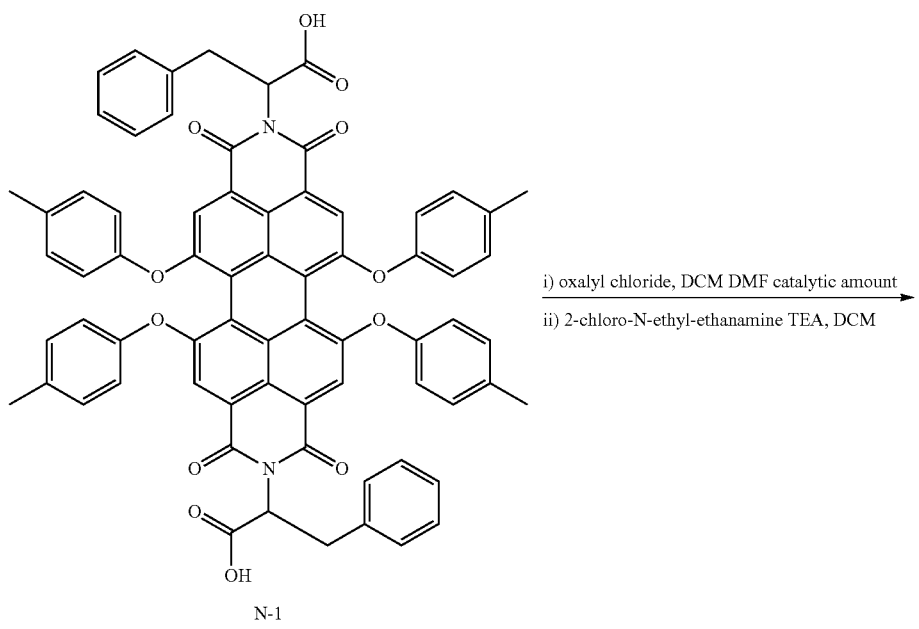

i) oxalyl chloride, DCM DMF catalytic amount
ii) 2-chloro-N-ethyl-ethanamine TEA, DCM

N-1

-continued

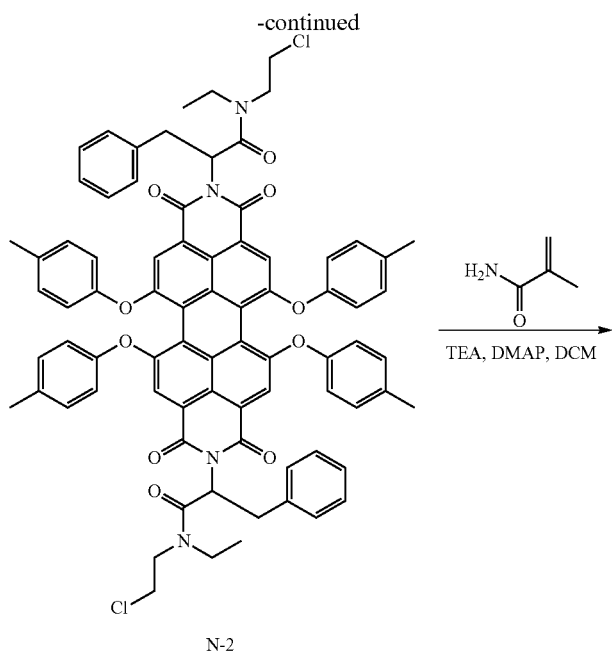

N-2

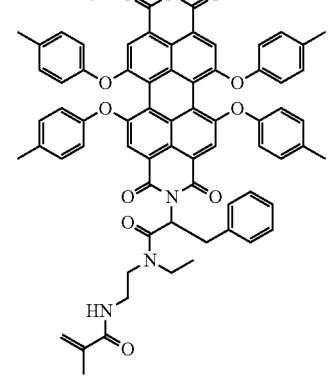

N

Synthesis was conducted in the same manner as in Preparation Example 1 except that Compound N-1 and 2-chloro-N-ethyl-ethanamine were used instead of Compound A-1 and 1,4-benzenediol in Synthesis of Compound A-2, and Compound N-2 and methacrylamide were used instead of Compound A-2 and epichlorohydrin in Synthesis of Compound A, and Compound N was synthesized therethrough.

HR LC/MS/MS m/z calculated for $C_{86}H_{78}N_6O_{12}$ (M+): 1386.5678; found: 1386.5678.

[Preparation Example 15] Synthesis of Compound O
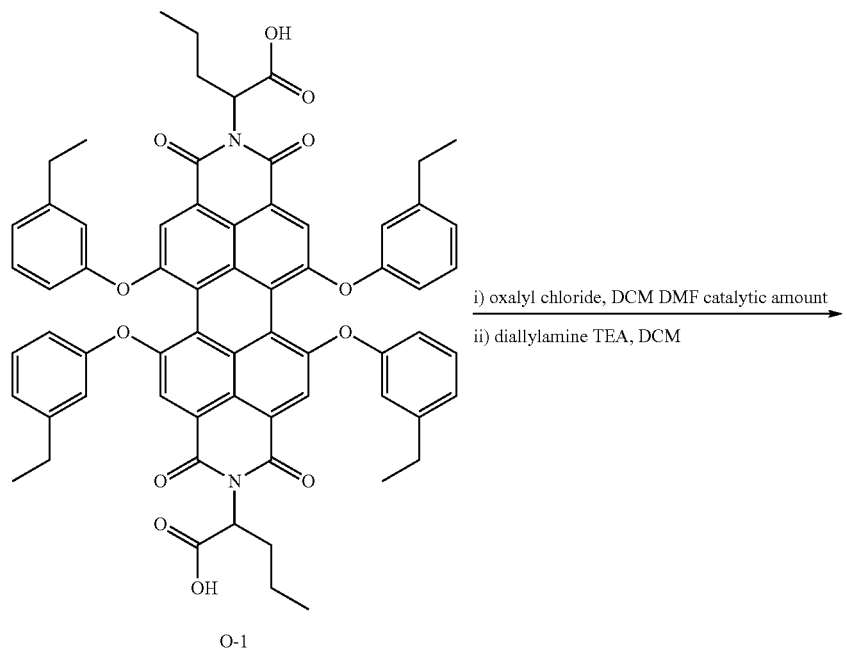
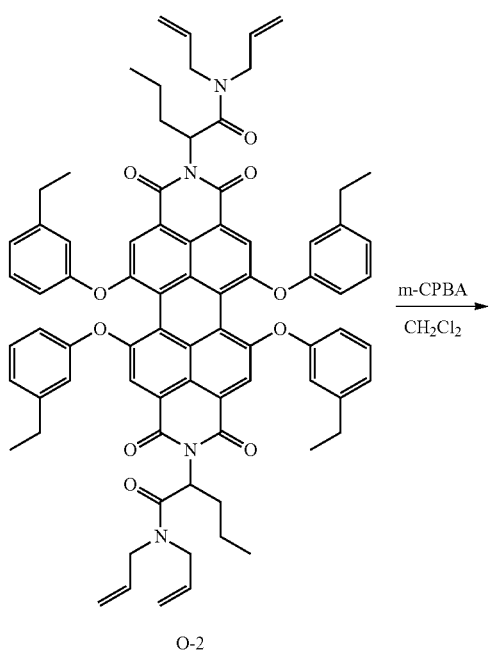

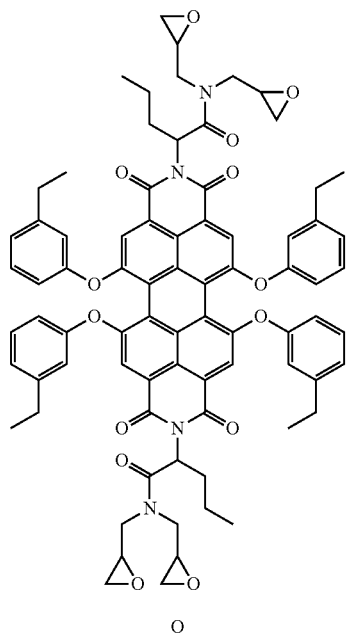 [SMILES: CCCC(C(=O)N(CC1CO1)CC1CO1)N1C(=O)c2cc(Oc3cccc(CC)c3)c3c4c(Oc5cccc(CC)c5)cc5c6c(cc(Oc7cccc(CC)c7)c(c7c(Oc8cccc(CC)c8)cc(c2c37)C1=O)c64)C(=O)N(C(CCC)C(=O)N(CC1CO1)CC1CO1)C5=O ; O]

Synthesis was conducted in the same manner as in Synthesis of Compound A-2, except that Compound O-1 and diallylamine were used instead of Compound A-1 and 1,4-benzenediol, and Compound O-2 was synthesized therethrough.

After dissolving 1 equivalent of Compound O-2 and 10 equivalents of meta-chloroperoxybenzoic acid (m-CPBA) in dichloromethane, the reaction was progressed at room temperature under nitrogen, and Compound 0 was synthesized therethrough.

HR LC/MS/MS m/z calculated for C78H76N4O14 (M+): 1292.5358; found: 1292.5358.

[Preparation Example 16] Synthesis of Compound P

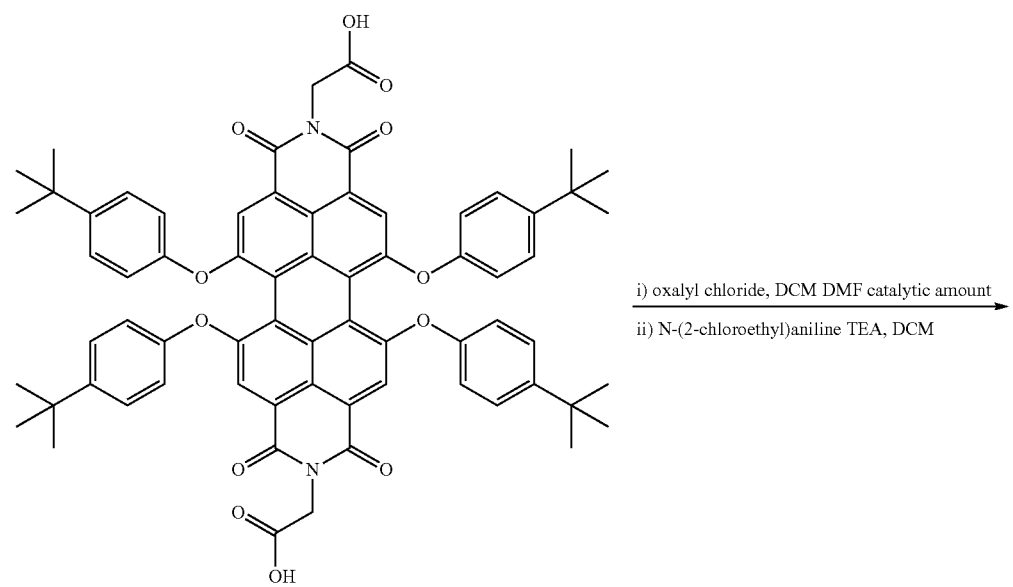

i) oxalyl chloride, DCM DMF catalytic amount
ii) N-(2-chloroethyl)aniline TEA, DCM

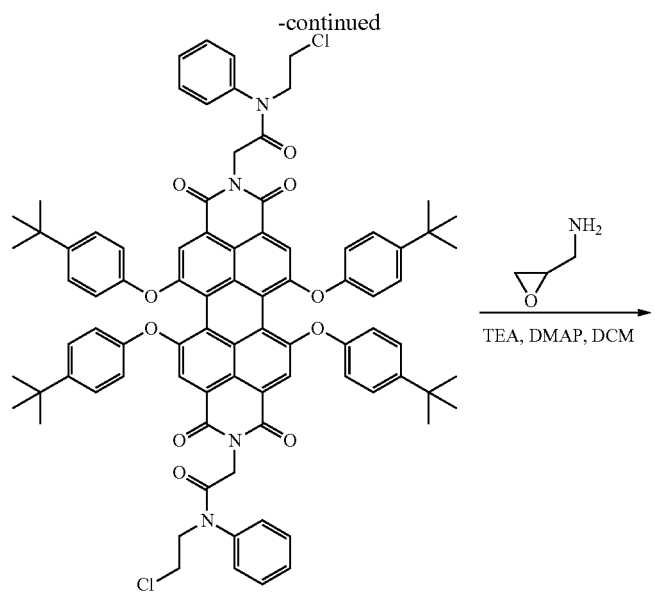

P-2

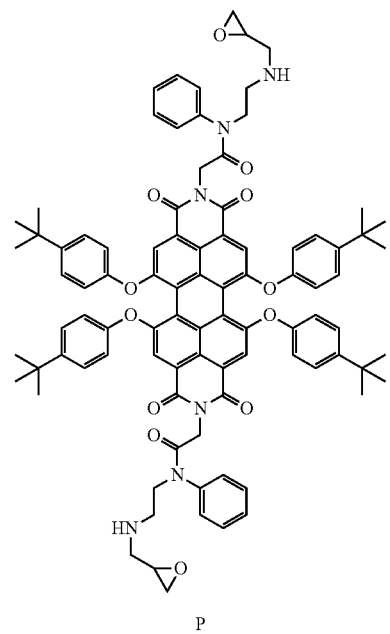

P

Synthesis was conducted in the same manner as in Preparation Example 1 except that Compound P-1 and N-(2-chloroethyl)aniline were used instead of Compound A-1 and 1,4-benzenediol in Synthesis of Compound A-2, and Compound P-2 and oxiran-2-ylmethanamine were used instead of Compound A-2 and epichlorohydrin in Synthesis of Compound A, and Compound P was synthesized therethrough.

HR LC/MS/MS m/z calculated for $C_{90}H_{90}N_6O_{12}$ (M+): 1446.6617; found: 1446.6618.

[Preparation Example 17] Synthesis of Compound Q
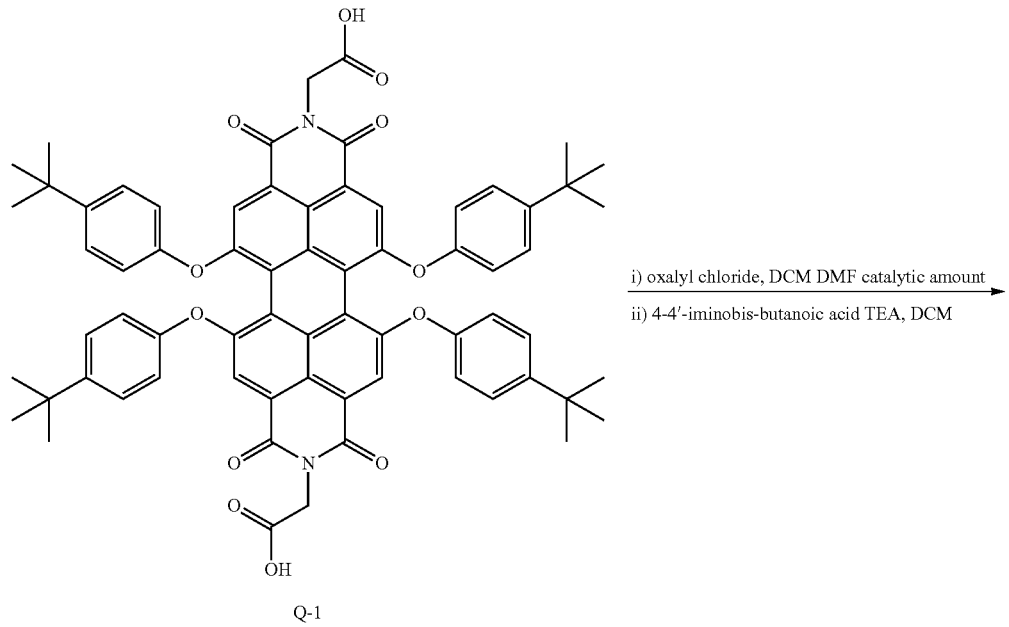
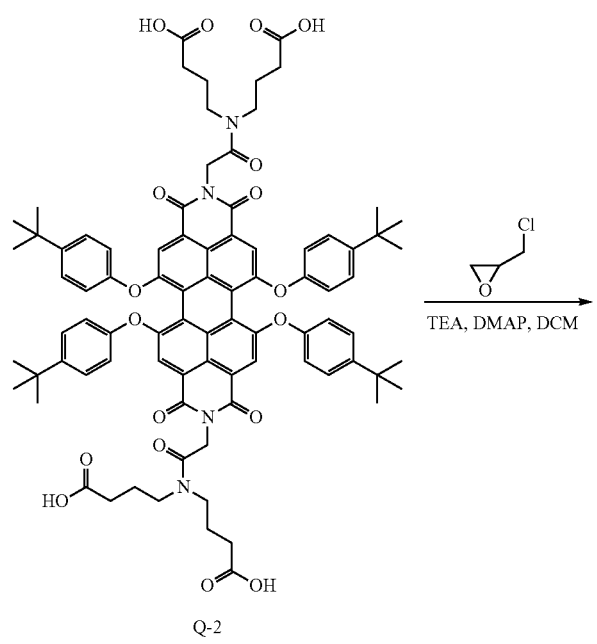

-continued

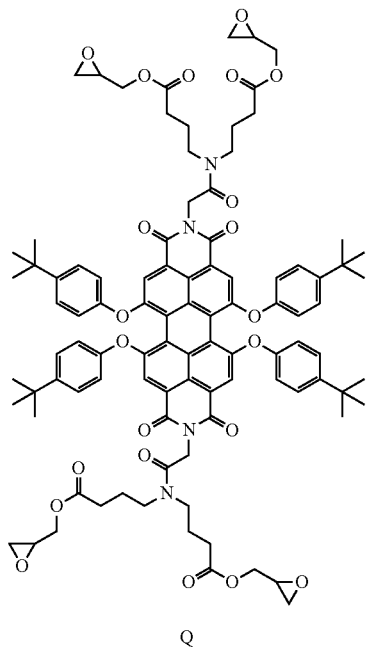

Q

Synthesis was conducted in the same manner as in Preparation Example 1 except that Compound Q-1 and 4,4'-iminobis-butanoic acid were used instead of Compound A-1 and 1,4-benzenediol in Synthesis of Compound A-2, and Compound Q-2 and 12 equivalents of epichlorohydrin were used instead of Compound A-2 and 6 equivalents of epichlorohydrin in Synthesis of Compound A, and Compound Q was synthesized therethrough.

HR LC/MS/MS m/z calculated for $C_{96}H_{104}N_4O_{22}$ (M+): 1664.7142; found: 1664.7142.

[Preparation Example 18] Synthesis of Compound R

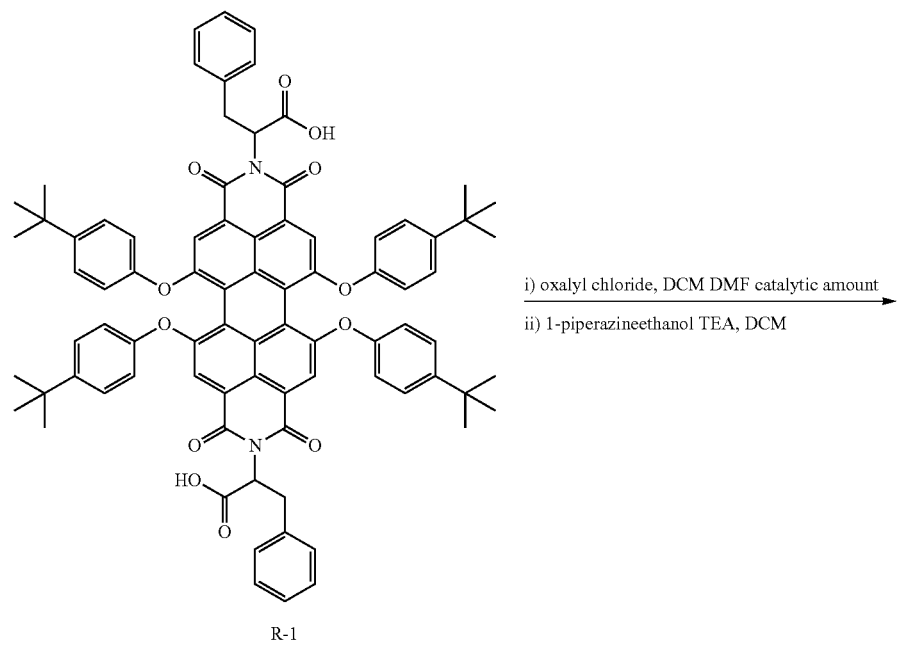

R-1 i) oxalyl chloride, DCM DMF catalytic amount
ii) 1-piperazineethanol TEA, DCM

-continued

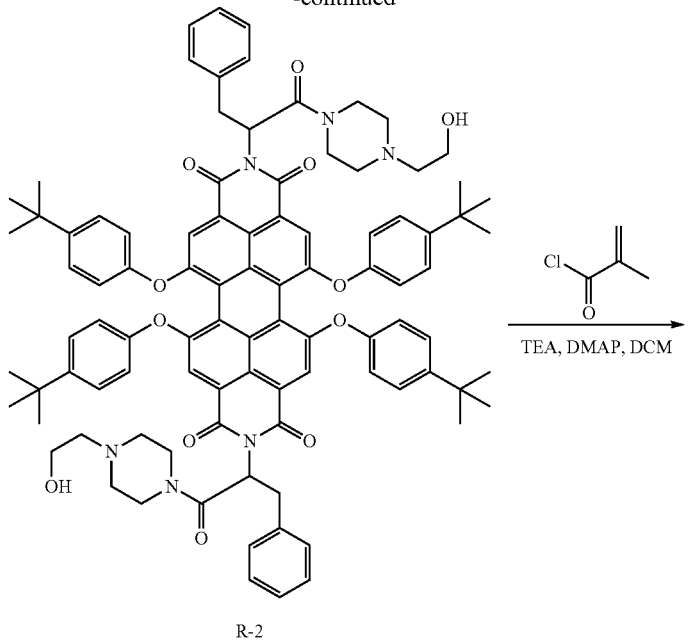

R-2

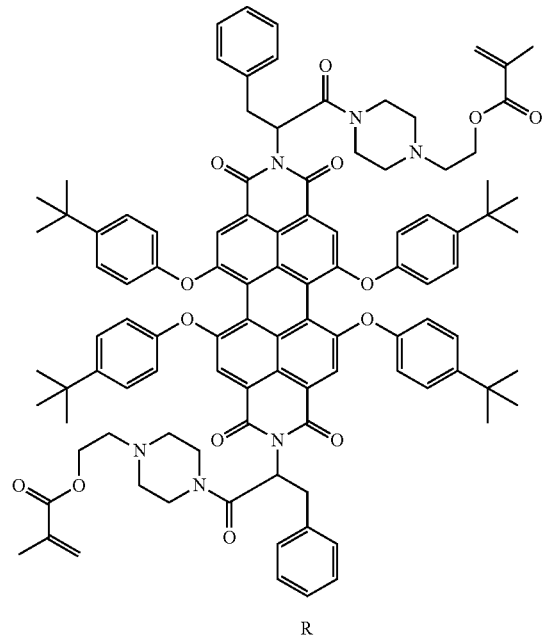

R

Synthesis was conducted in the same manner as in Preparation Example 1 except that Compound R-1 and 1-piperazineethanol were used instead of Compound A-1 and 1,4-benzenediol in Synthesis of Compound A-2, and Compound R-2 and methacryloyl chloride were used instead of Compound A-2 and epichlorohydrin in Synthesis of Compound A, and Compound R was synthesized therethrough.

HR LC/MS/MS m/z calculated for $C_{102}H_{106}N_6O_{14}$ (M+): 1664.7142; found: 1664.7142.

[Comparative Preparation Example 1] Synthesis of Compound S

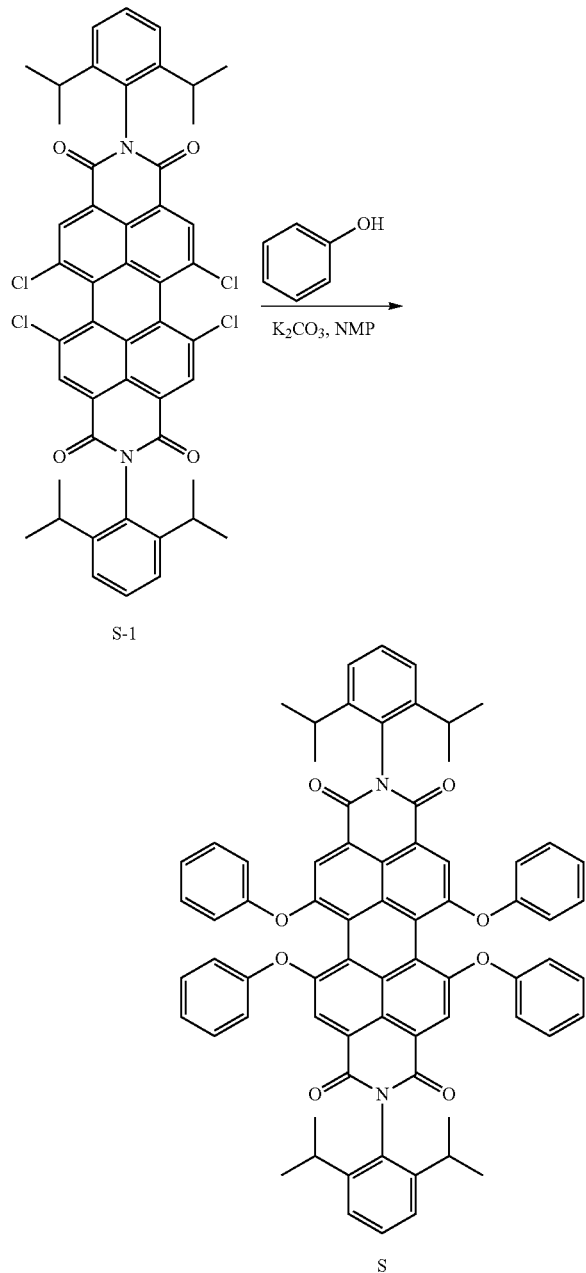

After dissolving 1 equivalent of Compound S-1, 8 equivalents of phenol and 6 equivalents of potassium carbonate in a methylpyrrolidone (NMP) solvent in a reaction container, the result was stirred at 110° C. After the reaction was completed, a compound was obtained using water and then suction filtration. The obtained compound was extracted using dichloromethane and water, and then water was removed from the separated organic layer using anhydrous magnesium sulfate. The water-removed organic layer was concentrated through vacuum distillation, and then recrystallized using dichloromethane and ethanol to obtain Compound S by suction filtration. Compound S was dried under a vacuum condition at 80° C.

HR LC/MS/MS m/z calculated for C72H58N2O8 (M+): 1078.4193; found: 1078.4195.

[Comparative Preparation Example 2] Synthesis of Compound T

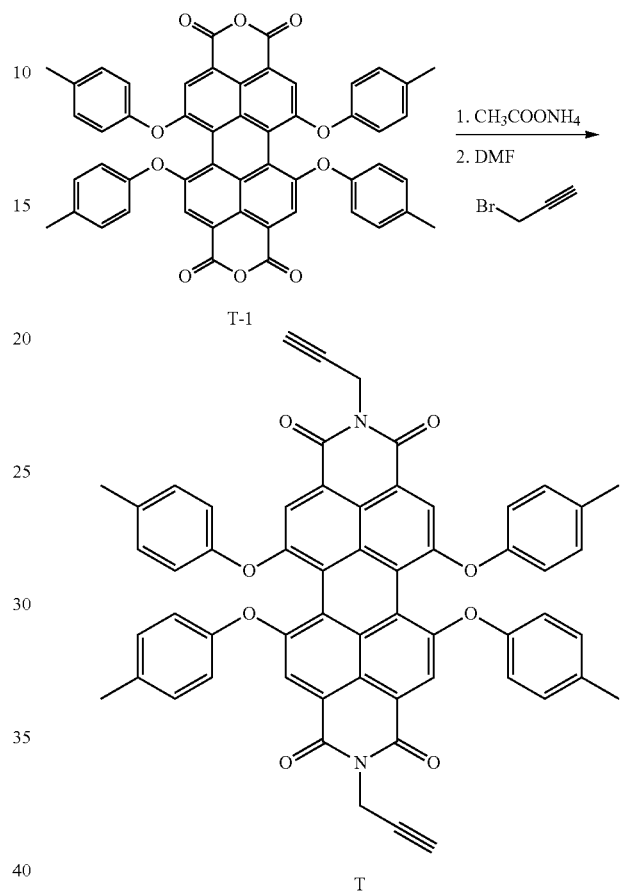

After dissolving 1 equivalent of Compound T-1 and 10 equivalents of ammonium acetate in a propionic acid solvent in a reaction container, the result was refluxed for 24 hours. After the reaction was completed, precipitates were collected using water. The precipitates were obtained by suction filtration, and used in a next reaction without separate purification. After dissolving 1 equivalent of the precipitates in a dimethylformamide (DMF) solvent, 1 equivalent of sodium methoxide was introduced thereto, and the result was stirred for 4 hours. After that, 6 equivalents of 3-bromo-1-propyne was introduced thereto, and the result was stirred for 24 hours. After the reaction was completed, the result was extracted using water, and water was removed from the separated organic layer using anhydrous magnesium sulfate. The water-removed organic layer was concentrated through vacuum distillation, and then recrystallized using dichloromethane and ethanol to obtain Compound T by suction filtration. Compound T was dried under a vacuum condition at 80° C.

HR LC/MS/MS m/z calculated for C58H38N2O8 (M+): 890.2628; found: 890.2628.

Example 1

A solution was prepared by dissolving 1.5 parts by weight of Compound C (maximum absorption wavelength 583 nm and maximum emission wavelength 611 nm in toluene solution) prepared in Preparation Example 3, 33.9 parts by weight of an acryl-based binder (VS12A80, LG Chem.), 59.3 parts by weight of a multifunctional monomer (pentaerythritol triacrylate, Nippon Kayaku), 2.3 parts by weight of an adhesive aid and surfactant (KBM 503, Shinetsu) and 3.0 parts by weight of a photoinitiator (Tinuvin® 477, BASF) in a propylene glycol monomethyl ether acetate (PGMEA) solvent so that the solid content became 21% by weight. The mixed solution was sufficiently stirred, and coated as a thin film on a glass substrate, and then dried to prepare a color conversion film.

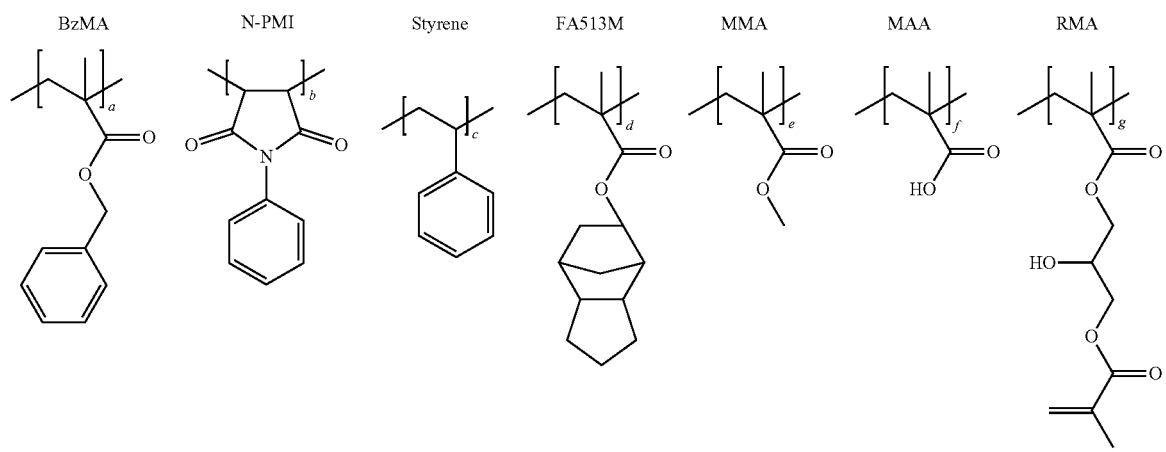

VS12A80 BINDER

Herein, a to g are each independently the number of repeating units in the parentheses, and for example, a to g are each independently an integer of 2 to 10,000.

Example 2

Preparation was made in the same manner as in Example 1 except that Compound E (maximum absorption wavelength 584 nm and maximum emission wavelength 611 nm in toluene solution) was used instead of Compound C.

Example 3

Preparation was made in the same manner as in Example 1 except that Compound F (maximum absorption wavelength 581 nm and maximum emission wavelength 609 nm in toluene solution) was used instead of Compound C.

Example 4

Preparation was made in the same manner as in Example 1 except that Compound H (maximum absorption wavelength 583 nm and maximum emission wavelength 612 nm in toluene solution) was used instead of Compound C.

Example 5

Preparation was made in the same manner as in Example 1 except that Compound M (maximum absorption wavelength 586 nm and maximum emission wavelength 614 nm in toluene solution) was used instead of Compound C.

Example 6

Preparation was made in the same manner as in Example 1 except that Compound R (maximum absorption wavelength 583 nm and maximum emission wavelength 612 nm in toluene solution) was used instead of Compound C.

Comparative Example 1

Preparation was made in the same manner as in Example 1 except that Compound S (maximum absorption wavelength 572 nm and maximum emission wavelength 601 nm in toluene solution) was used instead of Compound C.

Comparative Example 2

Preparation was made in the same manner as in Example 1 except that Compound T (maximum absorption wavelength 570 nm and maximum emission wavelength 599 nm in toluene solution) was used instead of Compound C.

Experimental Example 1

1) Measurement of Absorption and Emission Spectra in Thin Film State

A luminance spectrum of each of the color conversion films prepared in Examples 1 to 6 and Comparative Examples 1 and 2 was measured using a spectroradiometer (SR series of TOPCON Corporation). Specifically, the prepared color conversion film was laminated on one surface of a light guide plate of a backlight unit including an LED blue backlight (maximum emission wavelength 450 nm) and the light guide plate, and after laminating a prism sheet and a double brightness enhance film (DBEF) on the color conversion film, an initial value was set so that the brightness of the blue LED light was 600 nit based on the film.

2) Measurement of Absorption and Emission Spectra in Solution State

In order to measure absorption and emission wavelengths, the sample was dissolved to a concentration of $10^{-5}$ M using toluene as a solvent, and absorption and emission spectra thereof were measured.

3) Checking of Degree of Dyeing

A photoresist fluorescent resin composition was prepared by dissolving, based on 100 wt % of the photoresist fluorescent resin composition, 0.63 wt % (3.0 wt % in solid content) of a dye subject to measurement (compound of Table 1), 7.37 wt % of a binder (VS12A80, LG Chem.) and 13 wt % of a polyfunctional monomer (dipentaerythritol hexaacrylate) in 79 wt % of propylene glycol monomethyl ether acetate (PGMEA).

The prepared photoresist fluorescent resin composition was spin coated on 5 cm×5 cm glass (Corning Incorporated), and pre-baked for 70 seconds at 110° C. to form a coating film. Then, the distance between the coating film and a photo mask was set to 200 μm, and an exposure dose of 40 mJ/cm² was irradiated using an exposure device (Hoya-Schott). The exposed coating film was developed for 60 seconds using a developing solution (KOH, 0.04%) to form a pattern layer having a pattern width and a space width of 90 um and 180 um, respectively.

After forming the pattern layer, first post-bake (PB) was conducted for 20 minutes at 30° C. in an oven. After that, a solution obtained by dissolving 33 wt % of a photocurable epoxy acrylic resin in a solvent mixture of PGMEA, methyl-3-methoxy propionate (MMP) and methyl ethyl di glycol (MEDG), was overcoated on the pattern layer using a negative type coating method, and second post-bake (PB) was conducted for 30 minutes at 30° C. in an oven to complete the color conversion film. A colorimetric value of a pattern portion of the pattern layer without the overcoating layer and a colorimetric value of a pattern portion of the pattern layer after forming the overcoating layer were measured, and a degree of dyeing was checked through a difference between the two measured values (ΔEab).

Properties of the compounds used in Examples 1 to 6 and Comparative Examples 1 and 2 in the solution, and absorption and emission wavelengths in the thin film when used in the color conversion film, and a ΔEab value are as shown in Table 1.

TABLE 1

|  |  | Solution | | Thin Film | | |
| --- | --- | --- | --- | --- | --- | --- |
| Example | Compound | $\lambda_{max}$ (UV) | $\lambda_{max}$ (PL) | $\lambda_{max}$ (UV) | $\lambda_{max}$ (PL) | ΔEab |
| 1 | C | 583 | 611 | 584 | 625 | 2.23 |
| 2 | E | 584 | 611 | 584 | 623 | 2.54 |
| 3 | F | 581 | 609 | 585 | 621 | 2.98 |
| 4 | H | 583 | 612 | 585 | 625 | 2.12 |
| 5 | M | 586 | 614 | 586 | 627 | 1.91 |
| 6 | R | 583 | 612 | 585 | 625 | 1.95 |
| Comparative Example 1 | S | 572 | 601 | 575 | 612 | 4.81 |
| Comparative Example 2 | T | 570 | 599 | 572 | 610 | 3.99 |

Through Table 1, it was identified that the compound according to the disclosure of the present application had longer absorption and emission wavelengths in the solution and in the thin film compared to the comparative examples, and the ΔEab value was 3 or less, and as a result, it was seen that there was less dyeing compared to the comparative examples.

The invention claimed is:

1. A compound represented by the following Chemical Formula 1:

[Chemical Formula 1]

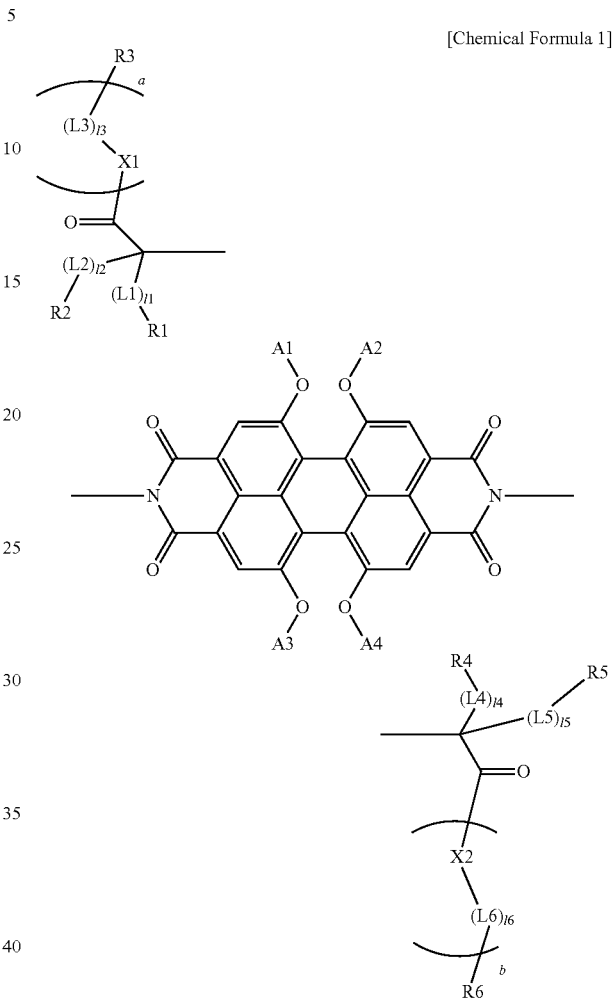

wherein, in the Chemical Formula 1,

A1 to A4 are each independently a substituted or unsubstituted aryl group, or a substituted or unsubstituted heterocyclic group;

X1 and X2 are each independently O, NH or NR';

R' is -(G1)$_{g1}$-E or -G2-O-G3-E, or forms a ring with adjacent groups;

R1, R2, R4 and R5 are each independently hydrogen, a halogen group, a substituted or unsubstituted alkyl group, a substituted or unsubstituted cycloalkyl group, a substituted or unsubstituted alkoxy group, a substituted or unsubstituted aryl group, or a substituted or unsubstituted heterocyclic group;

R3 and R6 are each independently a polymerizable group;

E is a halogen group, a substituted or unsubstituted alkyl group, a substituted or unsubstituted cycloalkyl group, a substituted or unsubstituted alkoxy group, a substituted or unsubstituted aryl group, a substituted or unsubstituted heterocyclic group, or a polymerizable group;

L1, L2, L4 and L5 are each independently a direct bond, or a substituted or unsubstituted alkylene group;

G1 to G3, L3 and L6 are each independently a direct bond, a substituted or unsubstituted alkylene group, a substituted or unsubstituted cycloalkylene group, a substituted or unsubstituted arylene group, or a substituted or unsubstituted divalent heterocyclic group;

a and b are each an integer of 0 to 3;

g1 and l1 to l6 are each an integer of 1 to 3; and when a, b, g1 and l1 to l6 are each 2 or greater, structures in the parentheses are the same as or different from each other, and wherein the polymerizable group is a group having at least one selected from the group consisting of a substituted or unsubstituted ethylenically unsaturated group, a substituted or unsubstituted siloxane group and a substituted or unsubstituted epoxy group.

2. The compound of claim 1, wherein the polymerizable group is any one of the following groups:

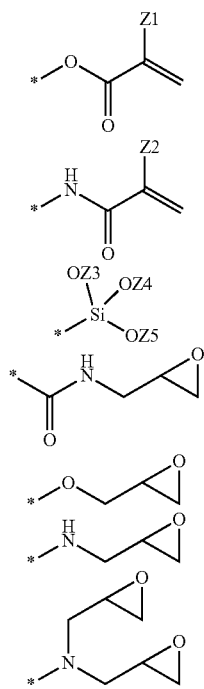

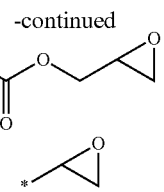

wherein,

Z1 and Z2 are each independently hydrogen, a halogen group, or a substituted or unsubstituted alkyl group;

Z3 to Z5 are each independently a substituted or unsubstituted alkyl group; and

* represents a bonding position.

3. The compound of claim 1, wherein the Chemical Formula 1 is represented by the following Chemical Formula 2:

[Chemical Formula 2]

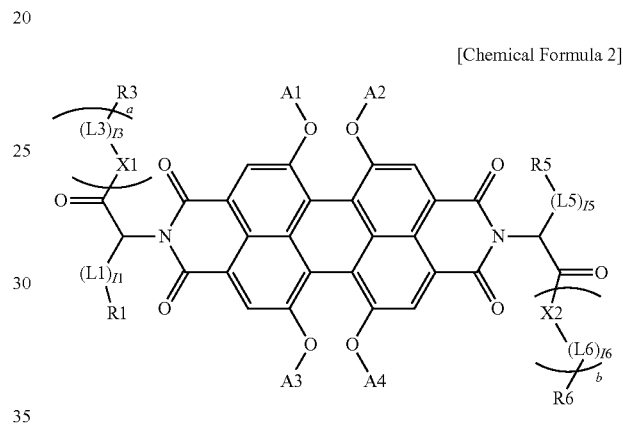

in the Chemical Formula 2,

A1 to A4, X1, X2, R1, R3, R5, R6, L1, L3, L5, L6, l1, l3, l5, l6, a and b have the same definitions as in the Chemical Formula 1.

4. The compound of claim 1, wherein the Chemical Formula 1 is represented by any one of the following Chemical Formulae 3 to 7:

[Chemical Formula 3]

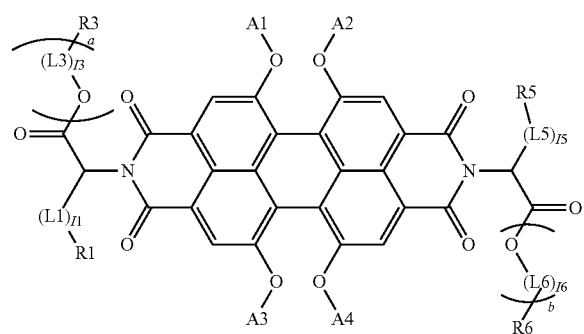

[Chemical Formula 4]

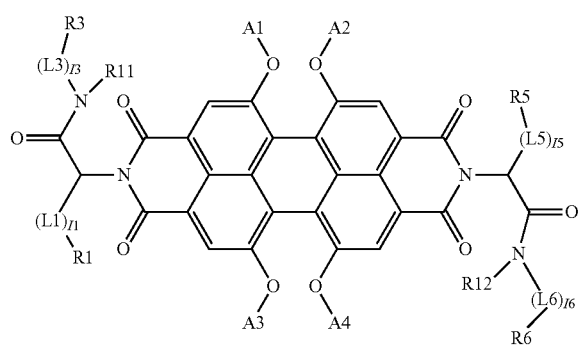

-continued

[Chemical Formula 5]

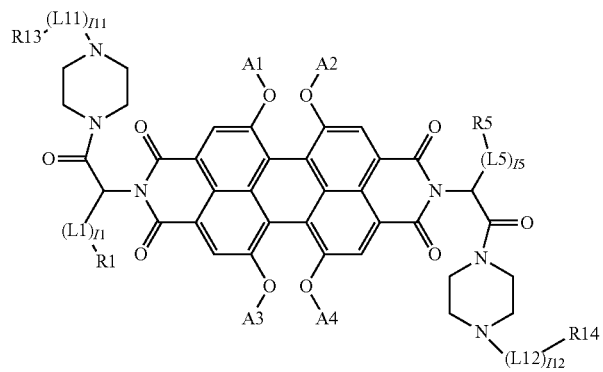

[Chemical Formula 6]

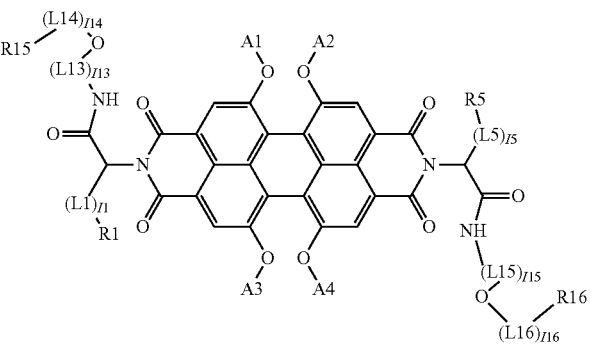

[Chemical Formula 7]

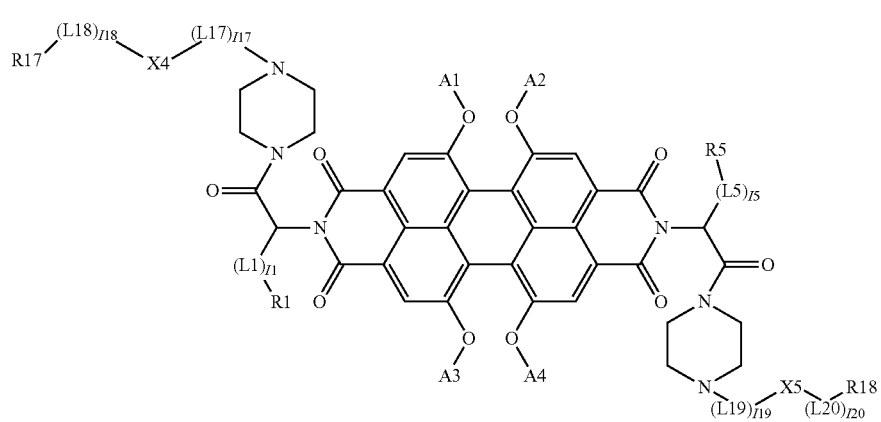

in the Chemical Formulae 3 to 7,

R11 and R12 are each independently -(G1)$_{g1}$-E or -G2-O-G3-E;

A1 to A4, R1, R3, R5, R6, L1, L3, L5, L6, G1 to G3, E, g1, l1, l3, l5, l6, a and b have the same definitions as in the Chemical Formula 1;

R13 to R18 are each independently a polymerizable group;

L11 to L20 are each independently a direct bond, or a substituted or unsubstituted alkylene group;

l11 to l20 are each an integer of 1 to 3;

when l11 to l20 are each 2 or greater, structures in the parentheses are the same as or different from each other; and X4 and X5 are each independently O or NH.

5. The compound of claim 1, wherein A1 to A4 in the Chemical Formula 1 are each independently a substituted or unsubstituted aryl group.

6. The compound of claim 1, wherein the compound represented by the Chemical Formula 1 is represented by any one of the following compounds:

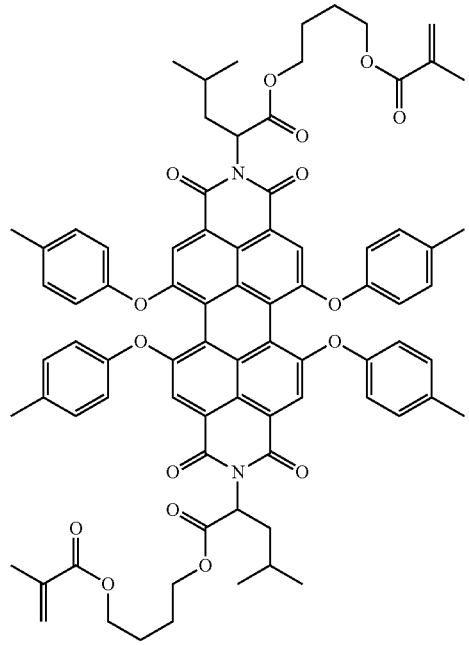

479
-continued
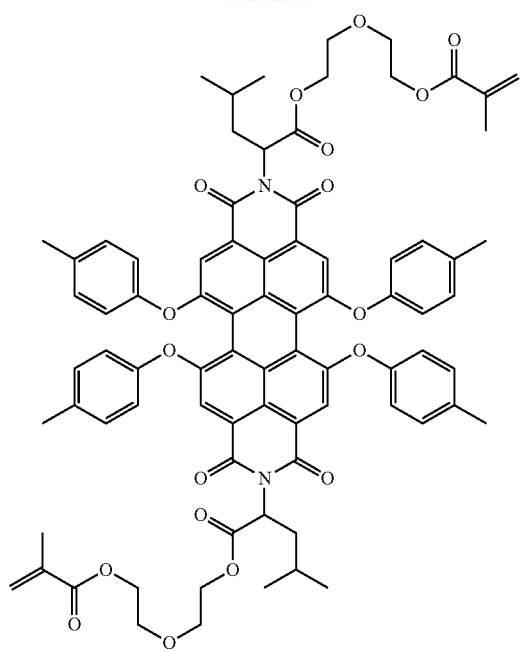
480
-continued
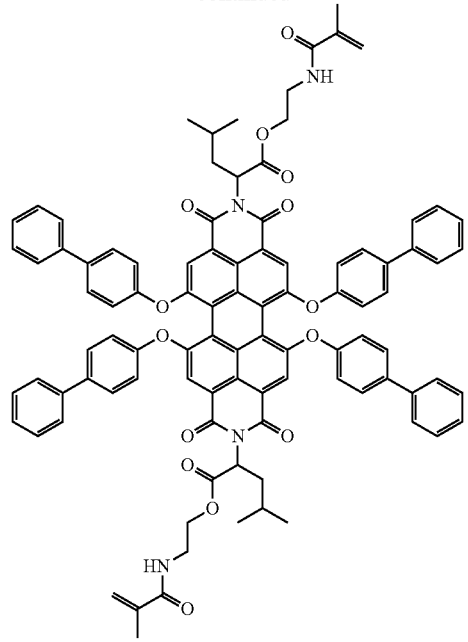
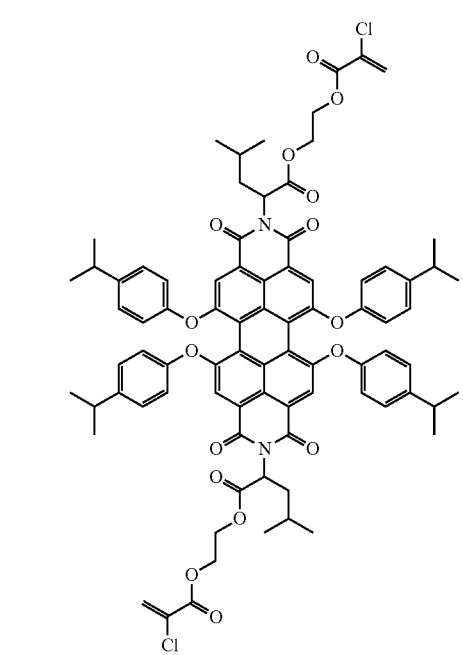
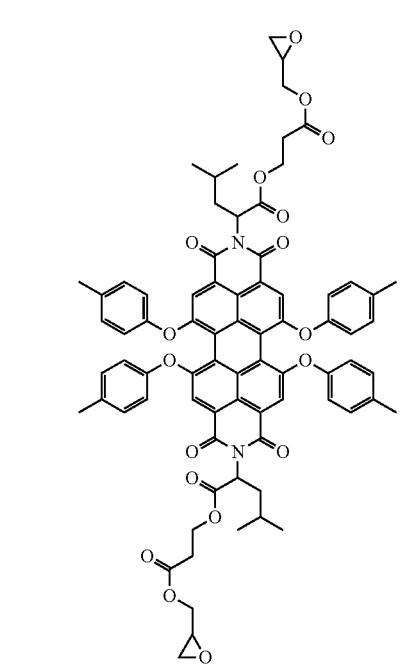

481
-continued
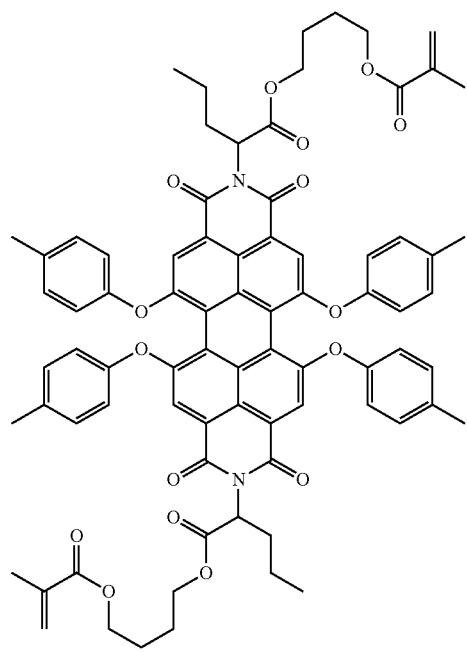
482
-continued
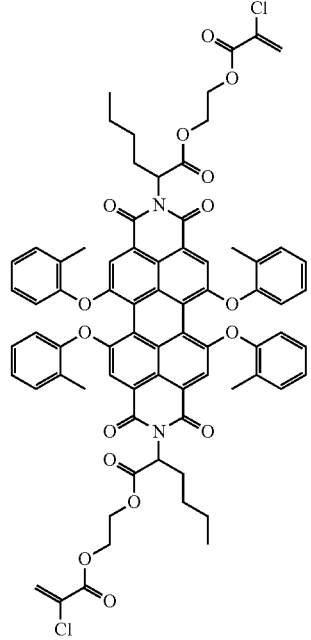
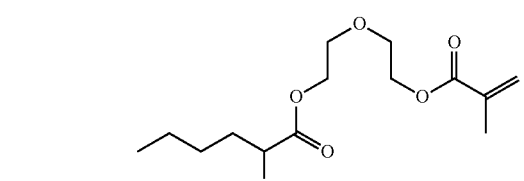
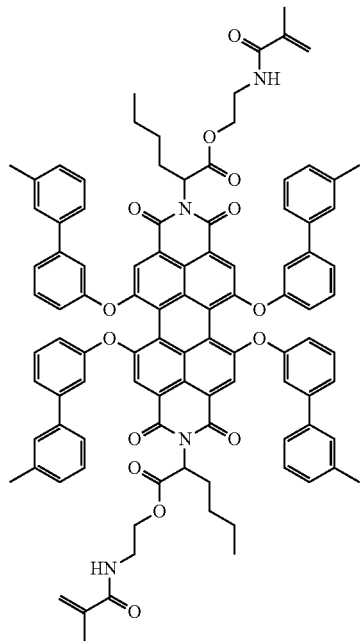

483
-continued
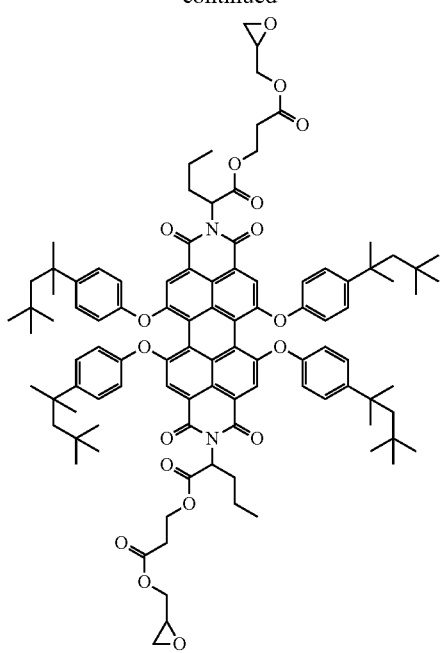
484
-continued
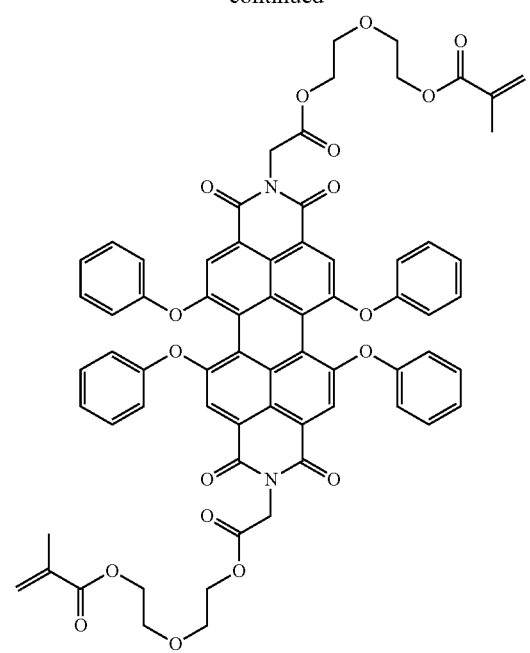
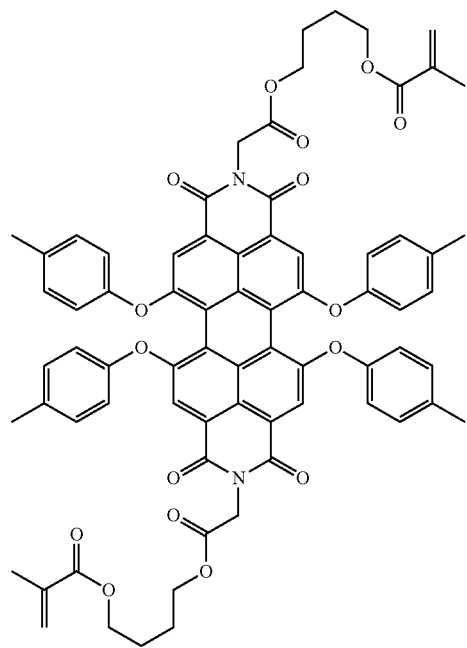
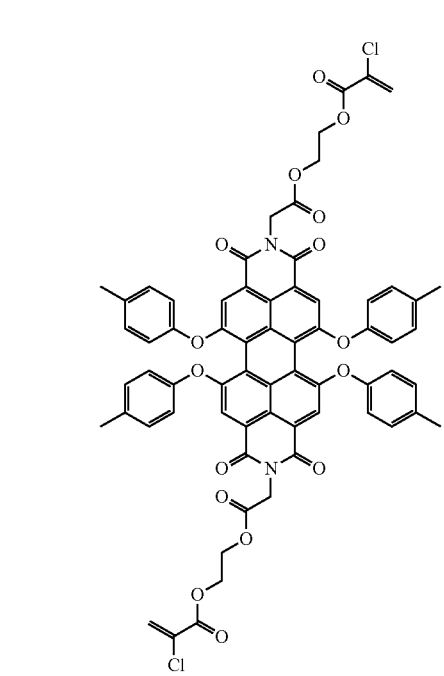

485
-continued
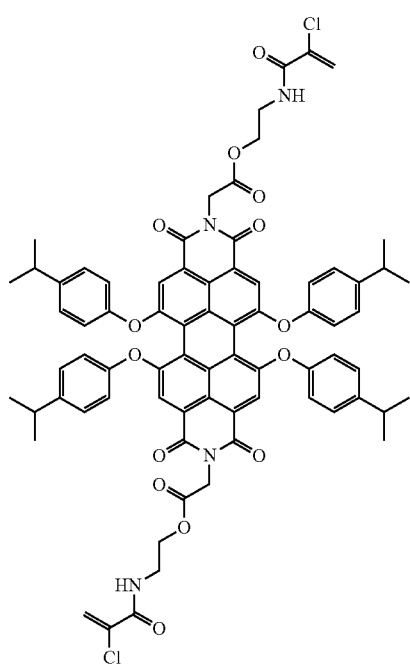
486
-continued
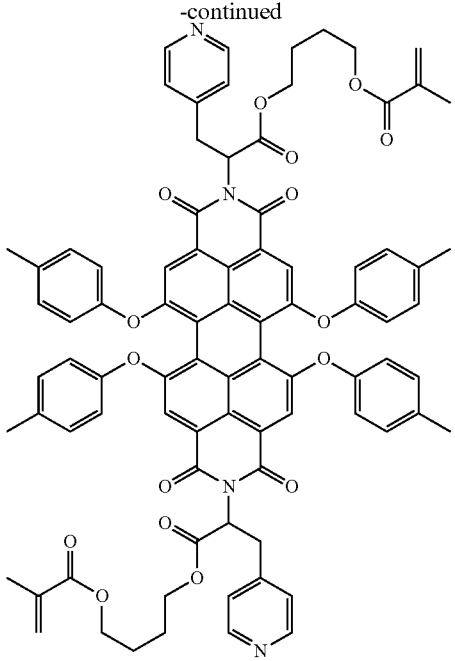
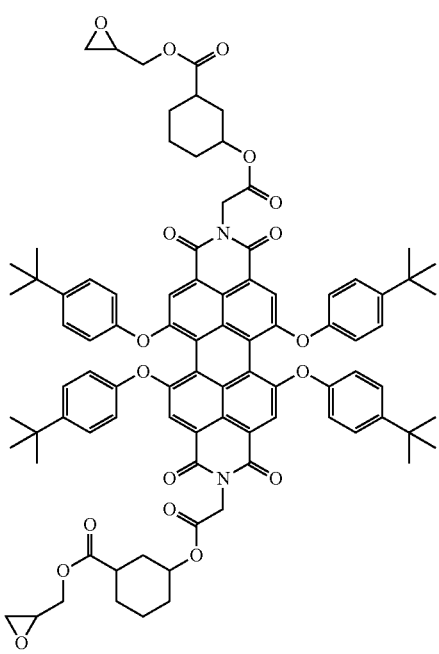
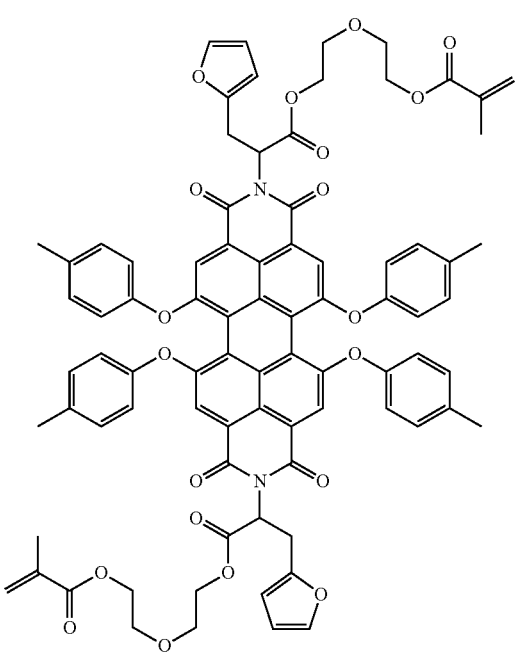

487
-continued
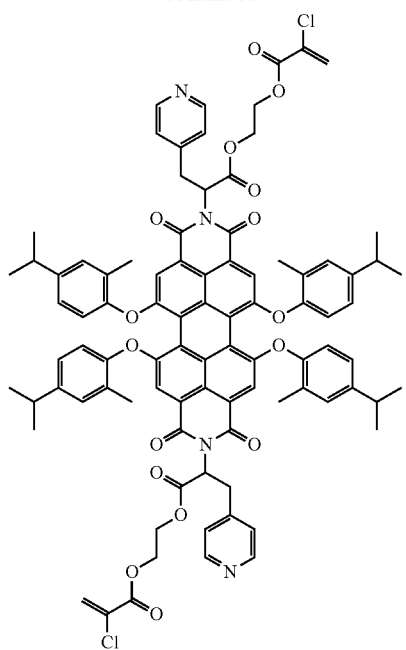
488
-continued
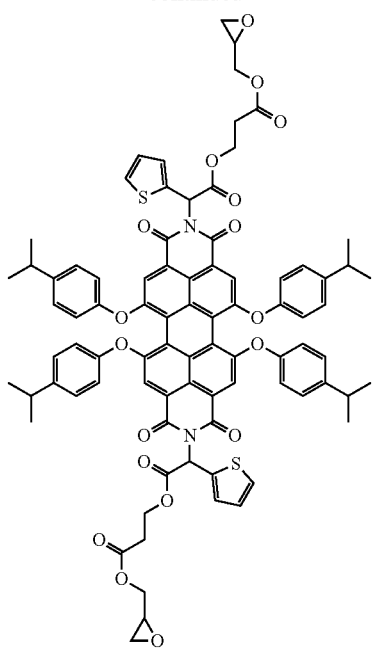
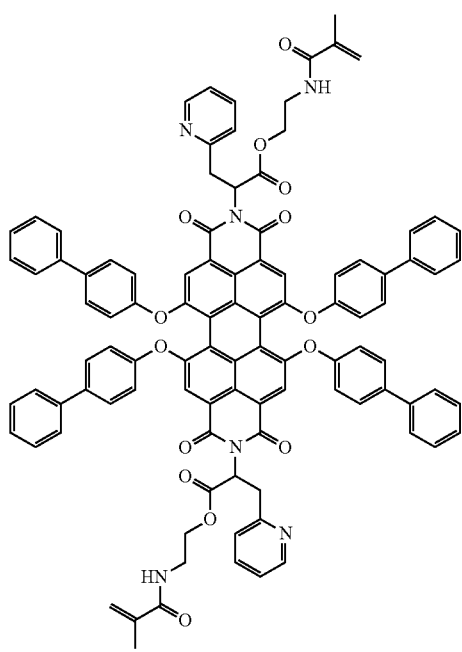

489
-continued
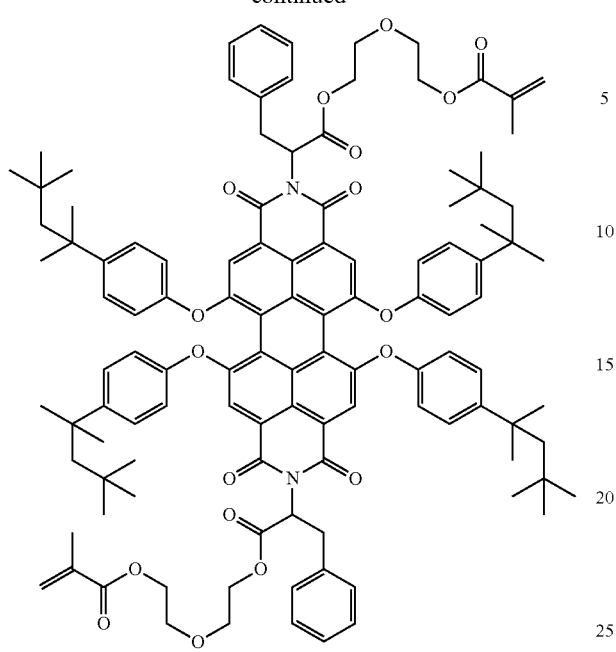
490
-continued
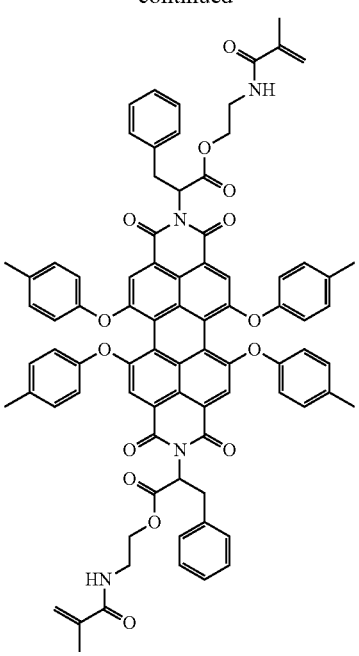
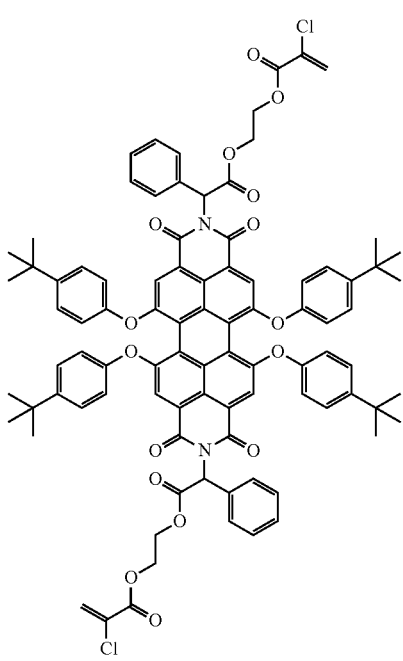
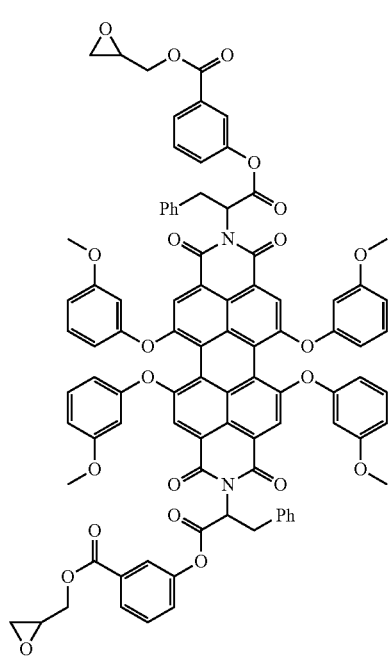

491
-continued
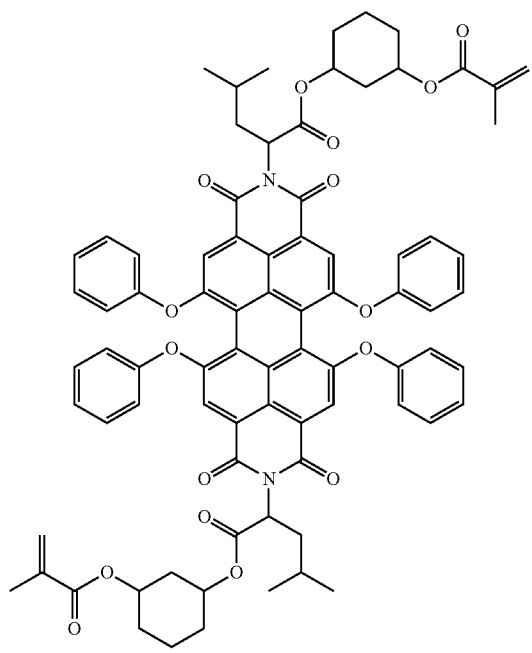
492
-continued
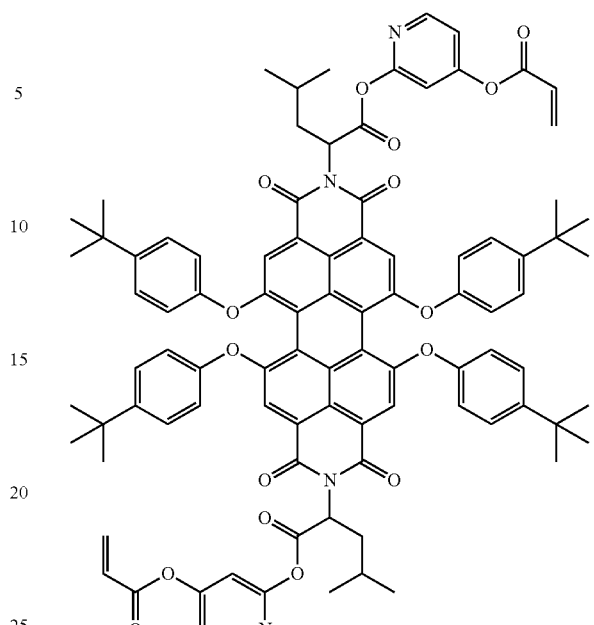
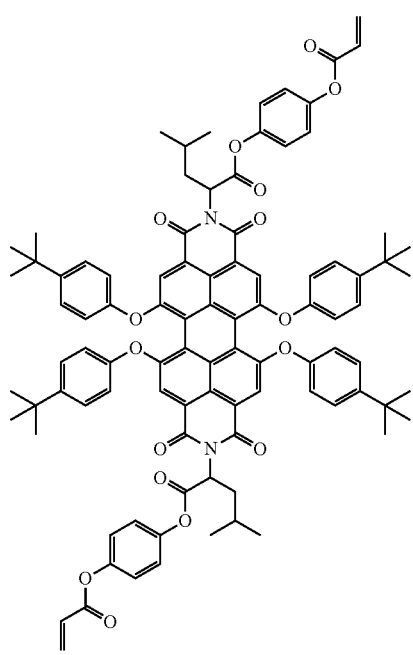
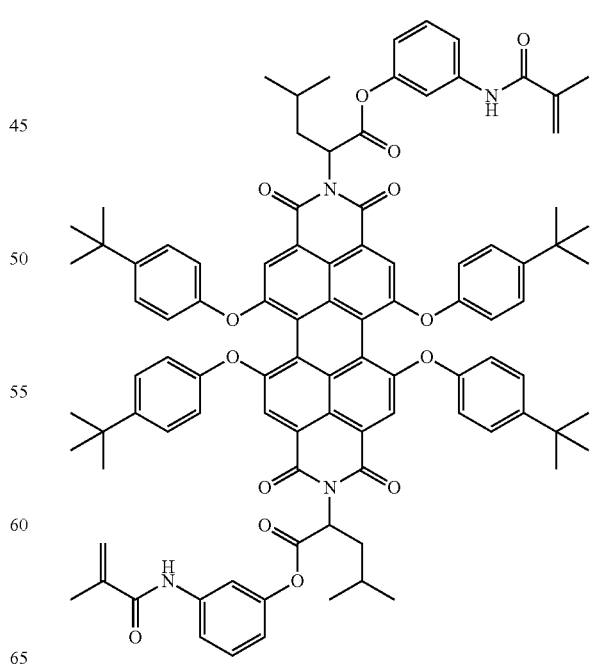

493
-continued
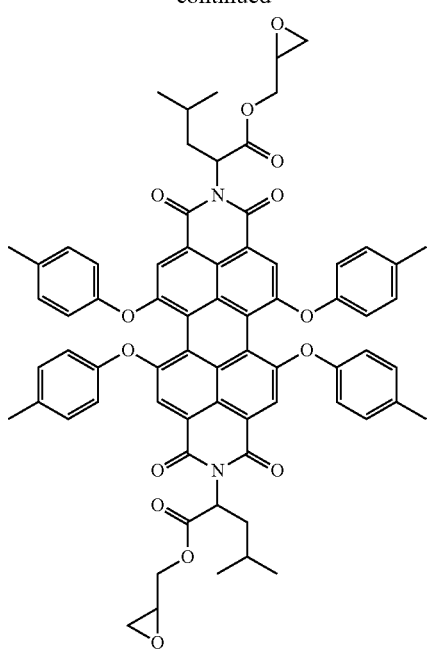
494
-continued
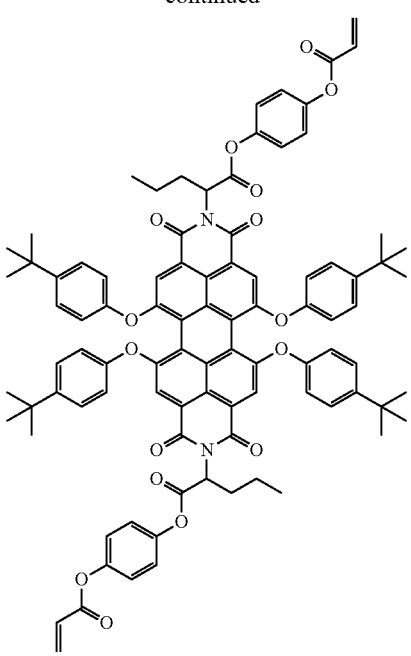
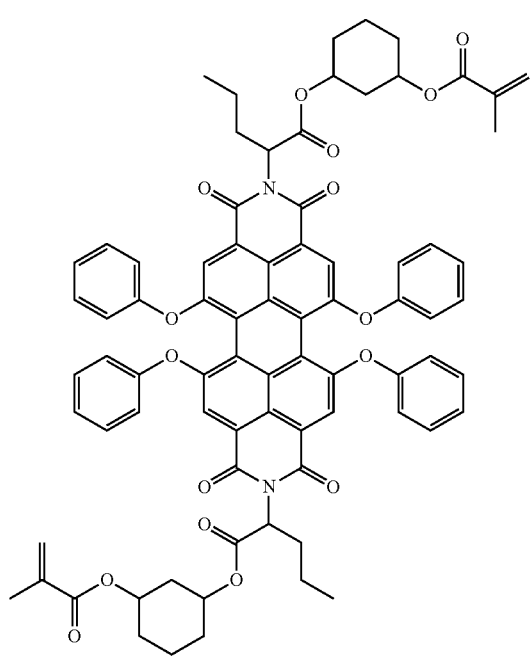
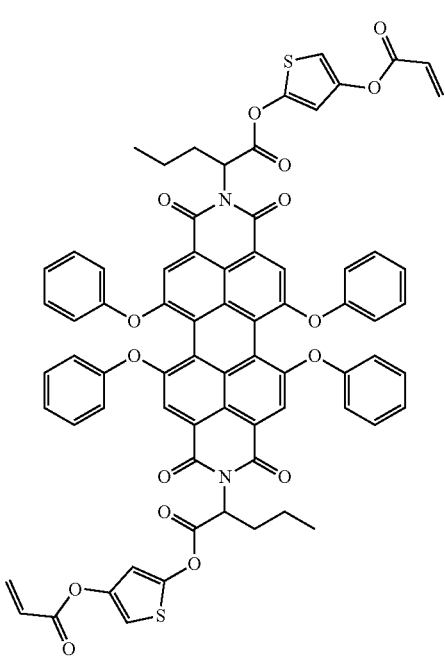

495
-continued
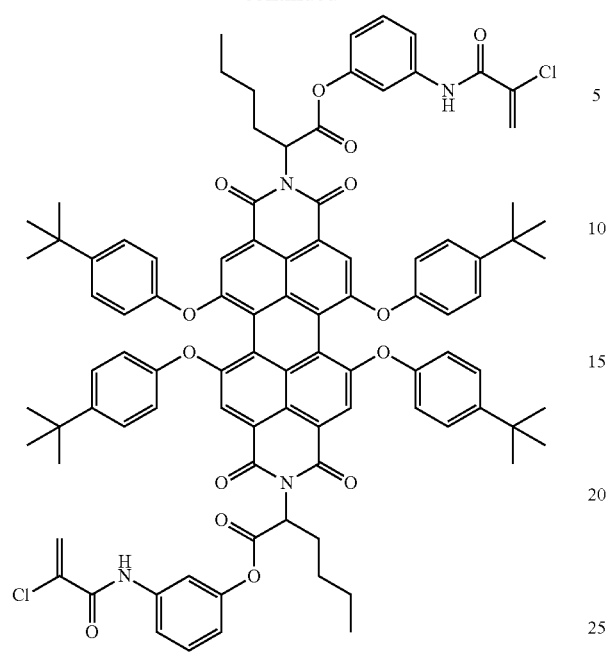
496
-continued
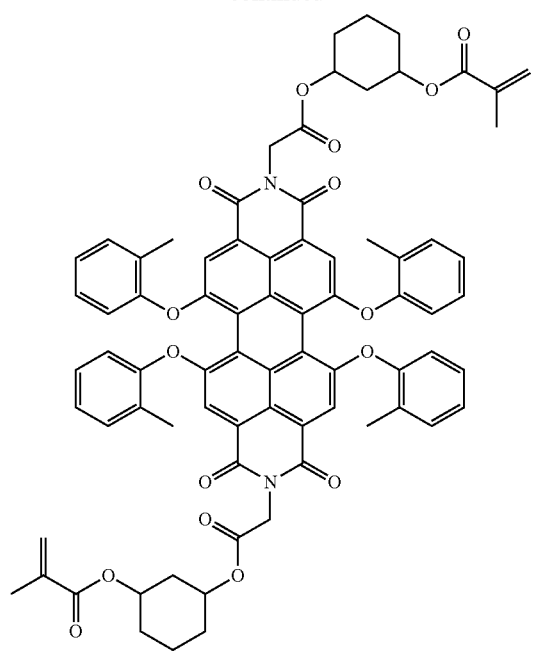
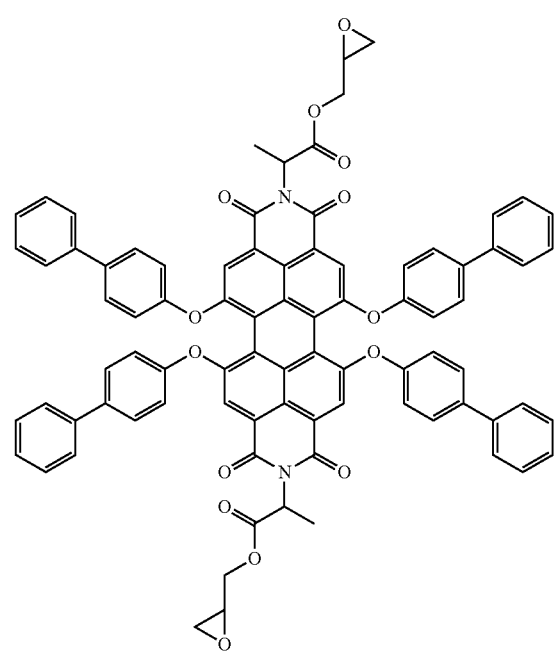
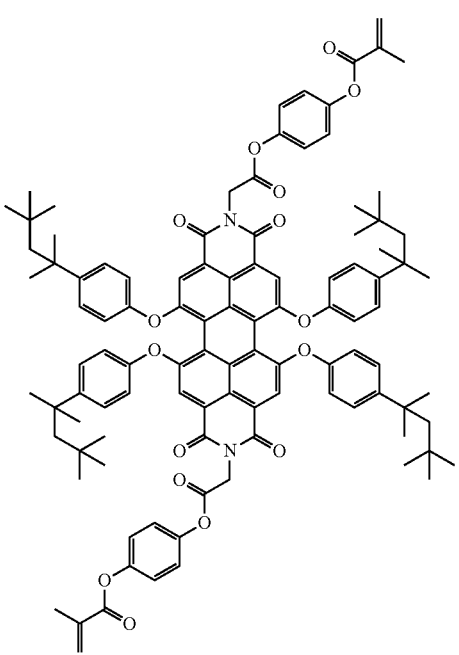

497
-continued

498
-continued
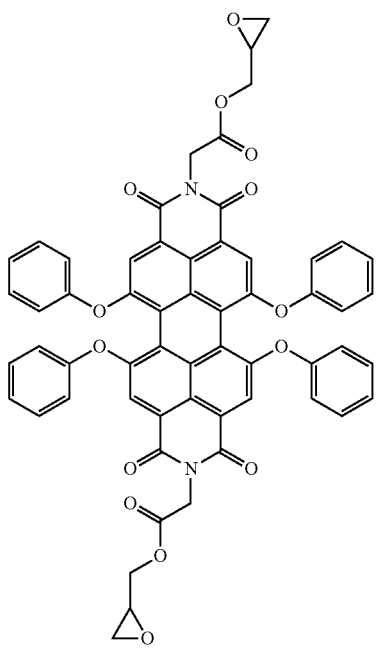
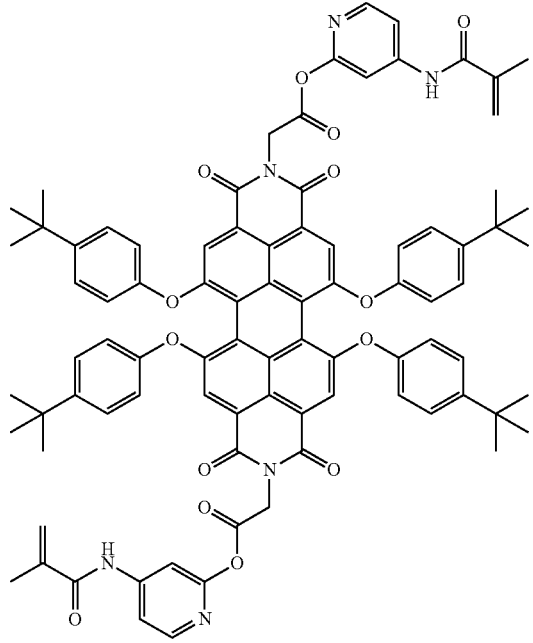
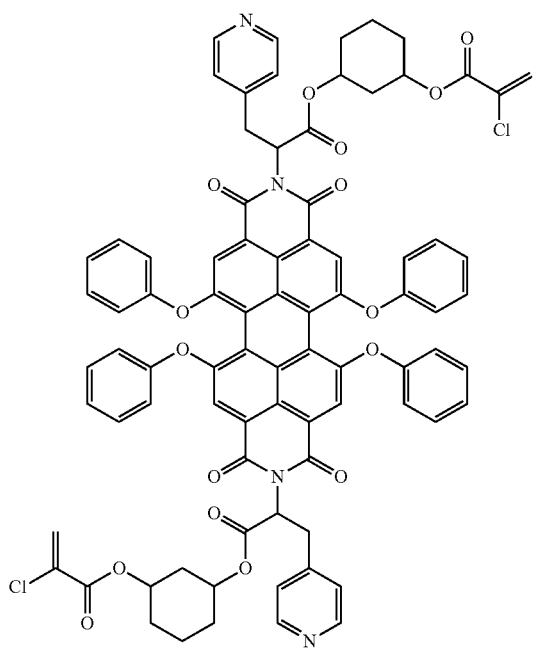

499
-continued
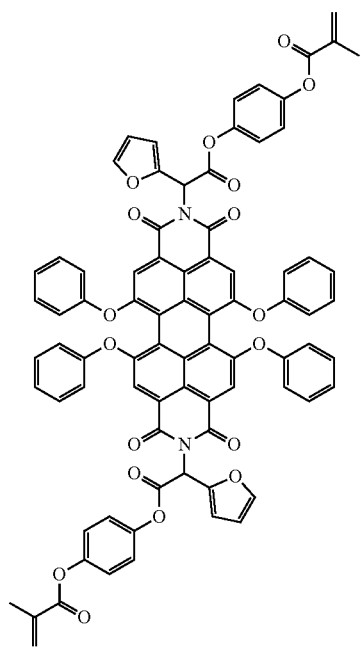
500
-continued
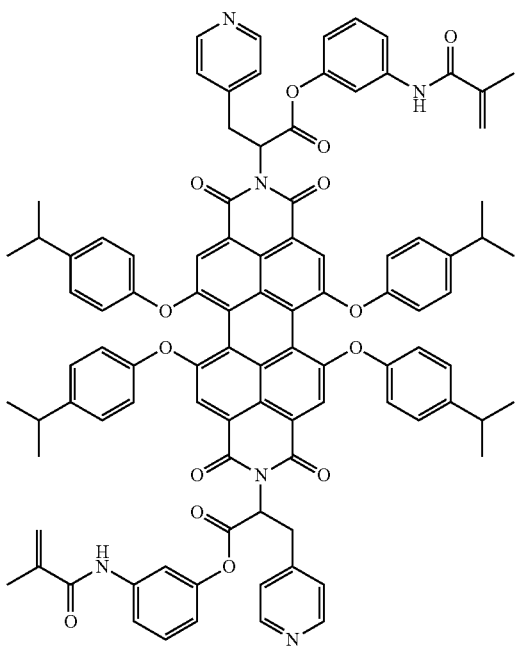
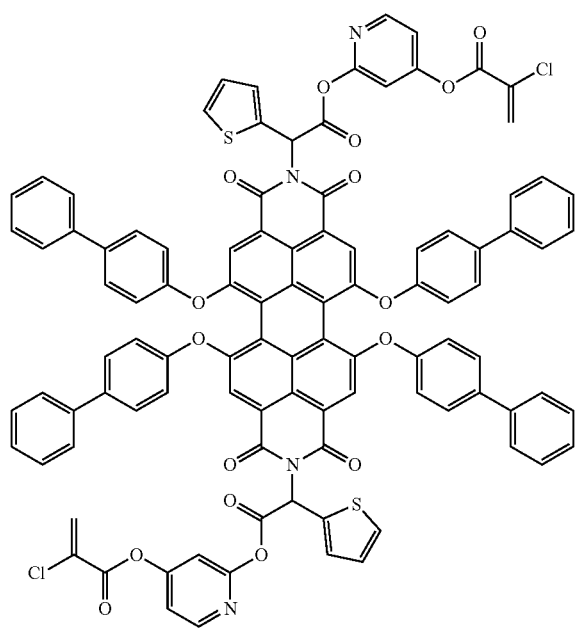
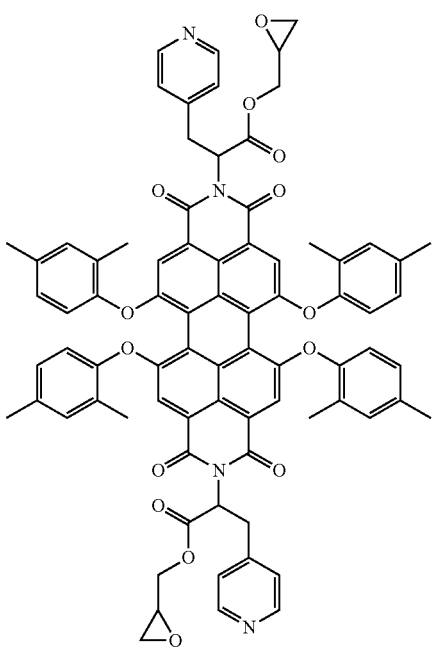

501
-continued
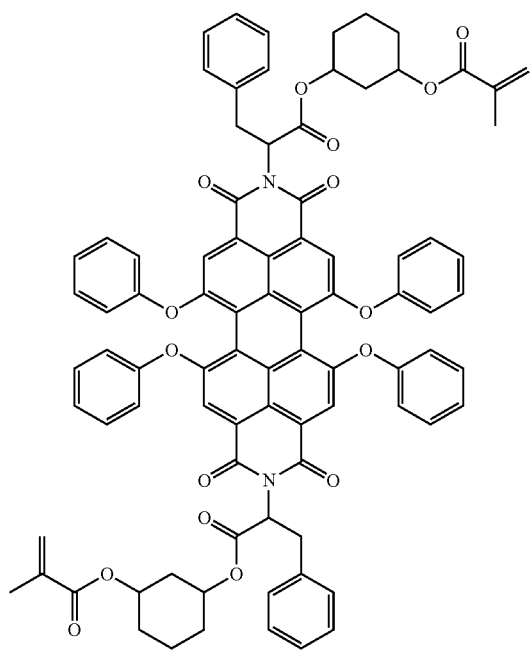
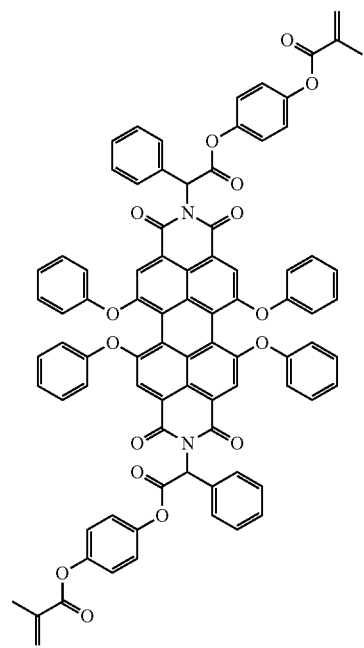
502
-continued
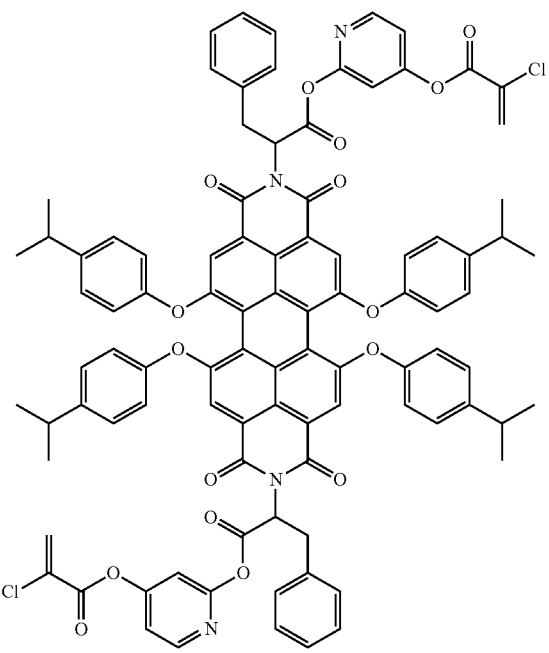
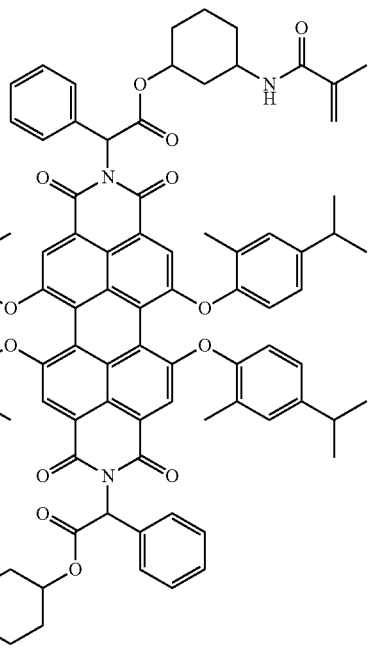

503
-continued
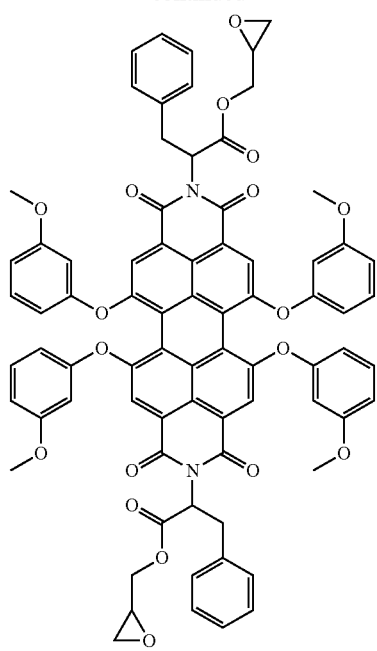
504
-continued
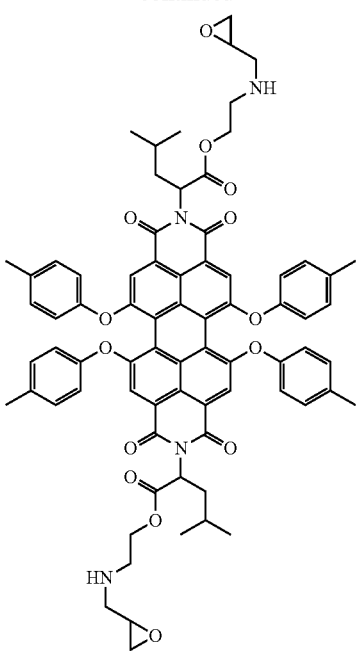
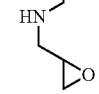
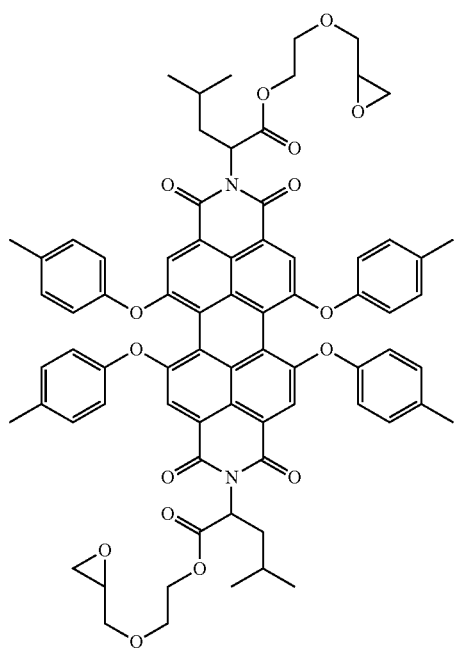

505
-continued
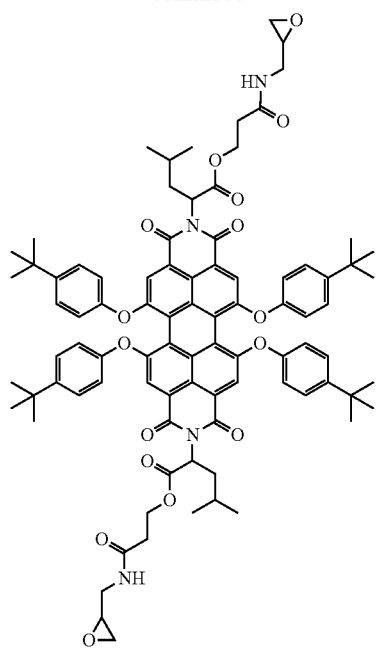
506
-continued
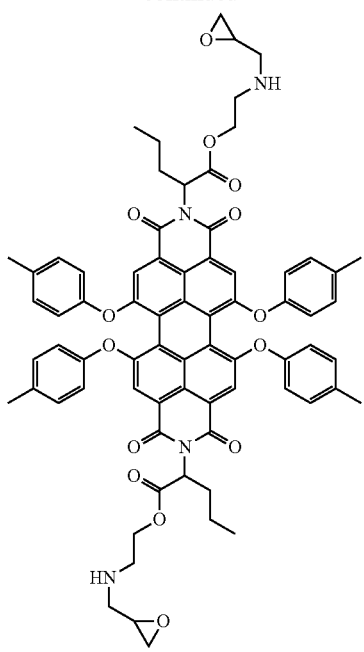
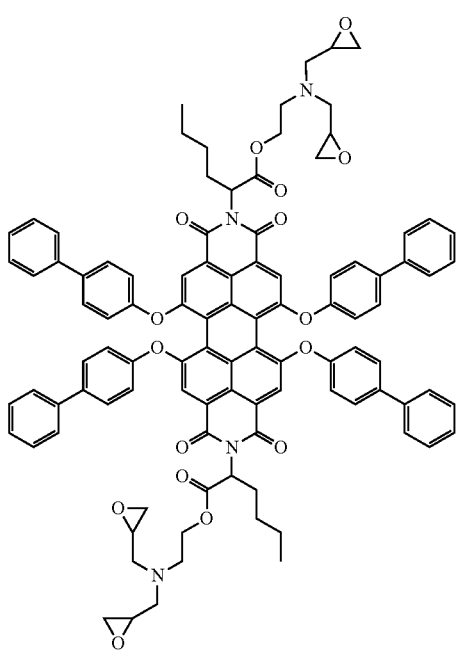

507
-continued
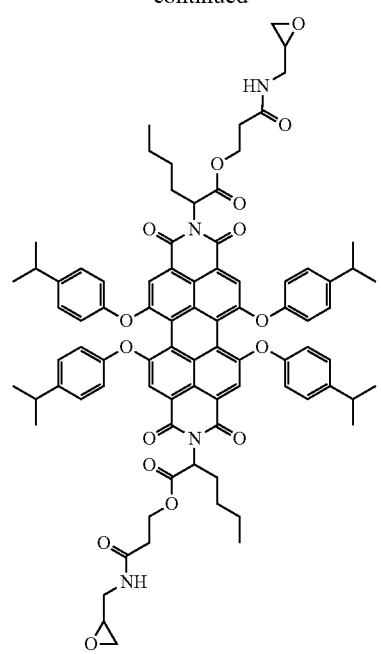
508
-continued
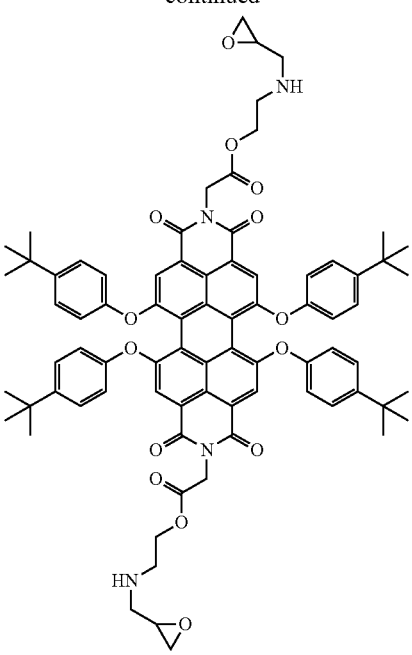
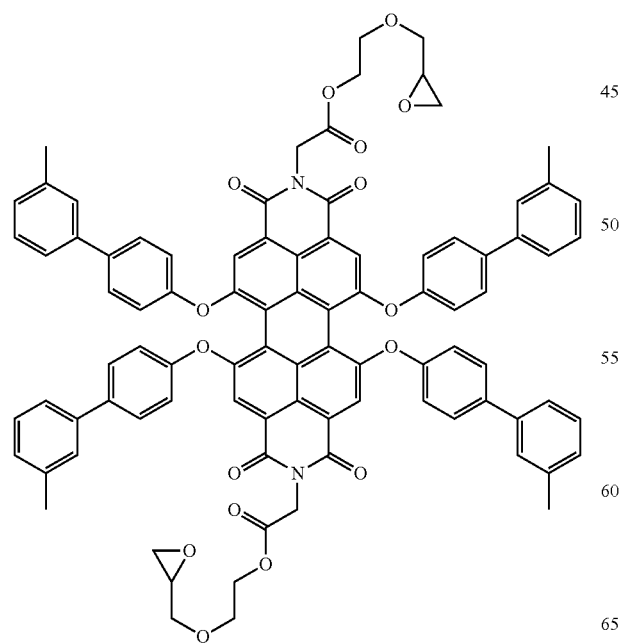
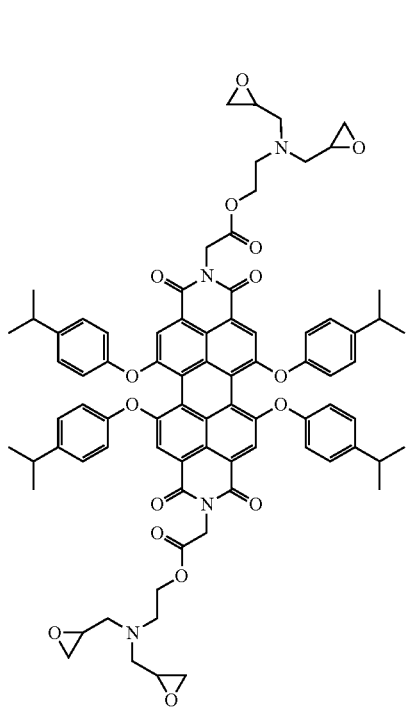

509
-continued
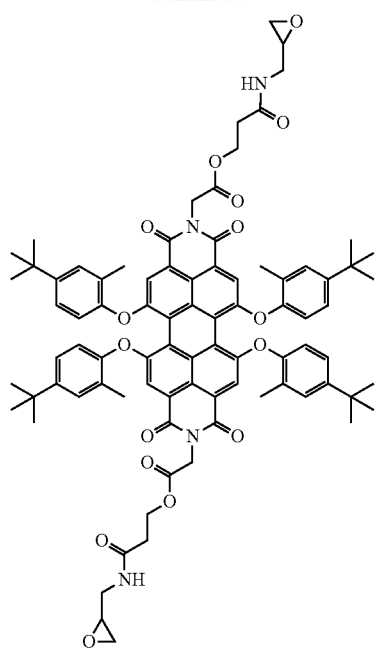
510
-continued
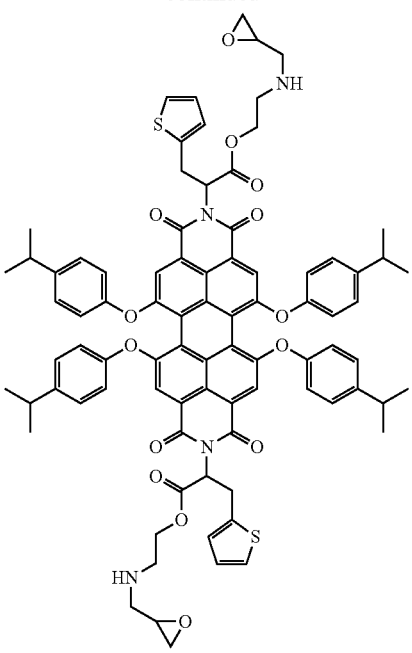
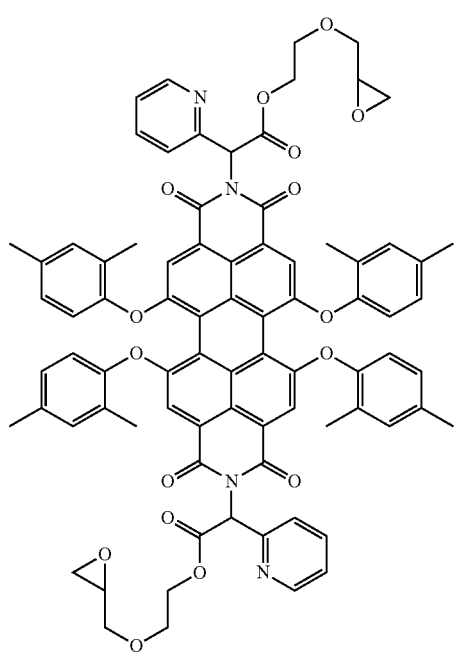
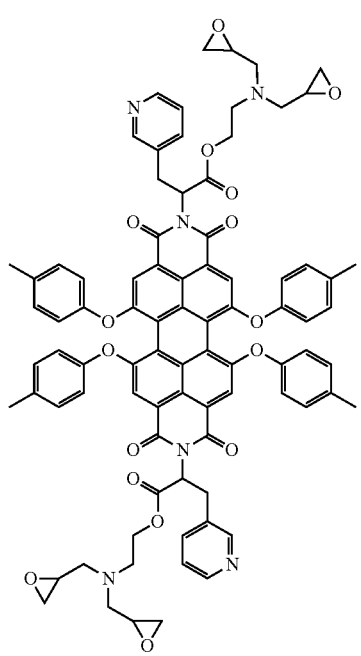

511
-continued
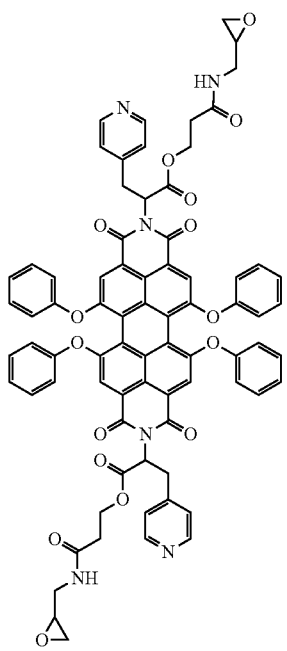
512
-continued
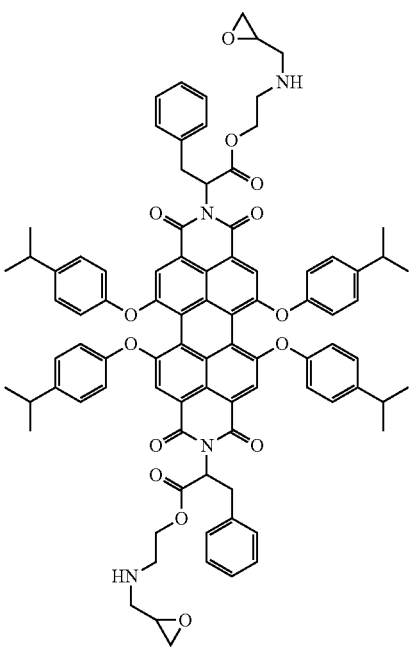
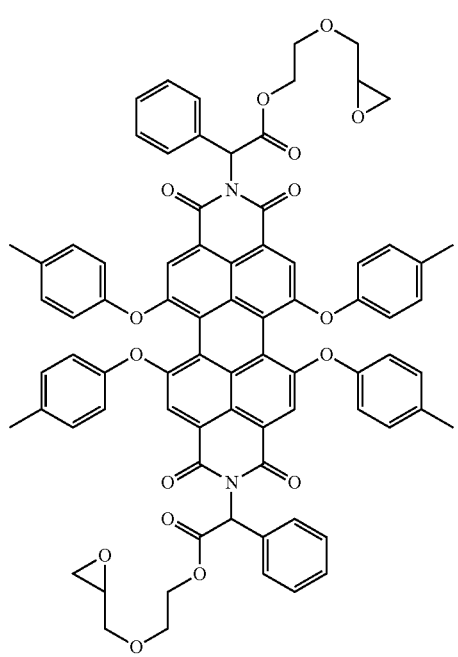
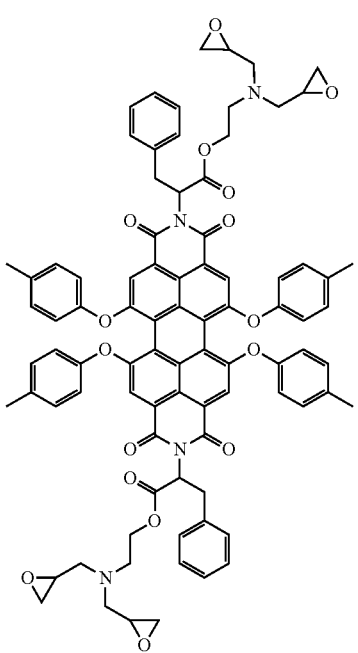

513
-continued
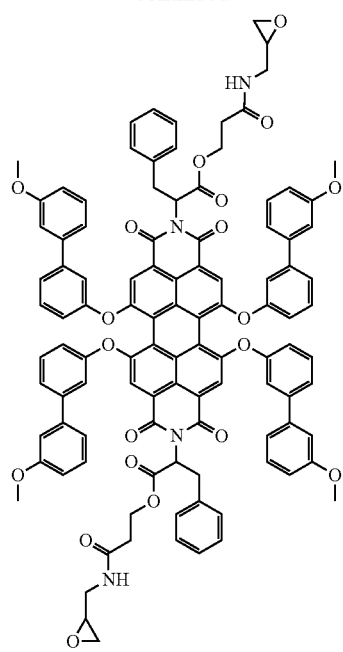
514
-continued
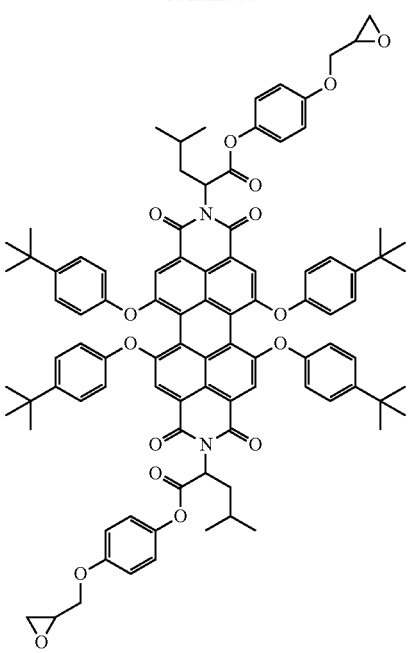
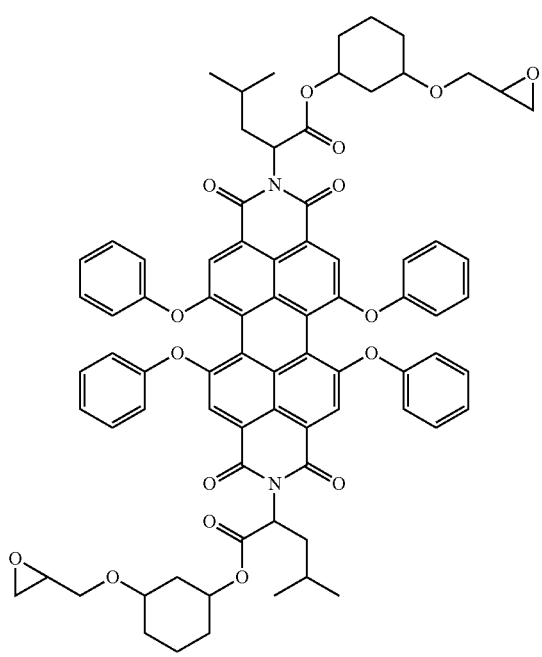
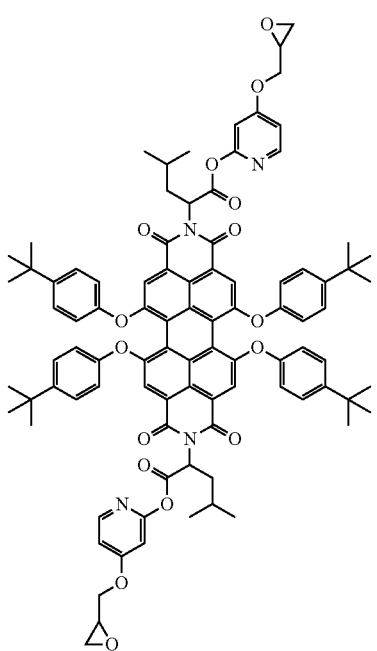

515
-continued
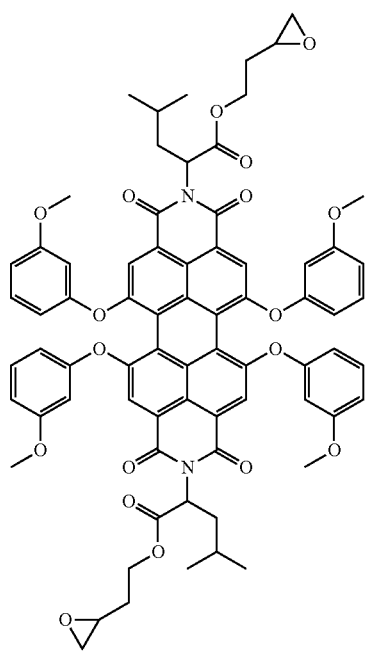
516
-continued
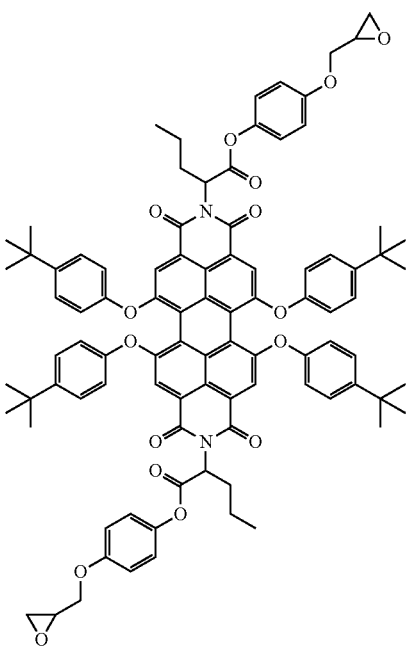
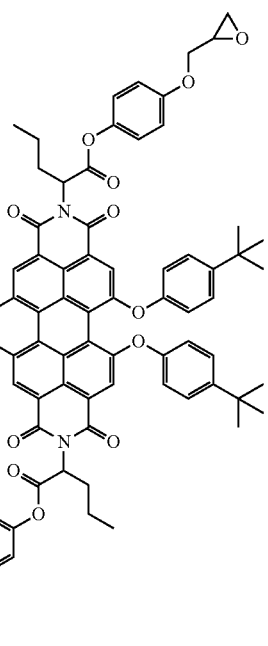
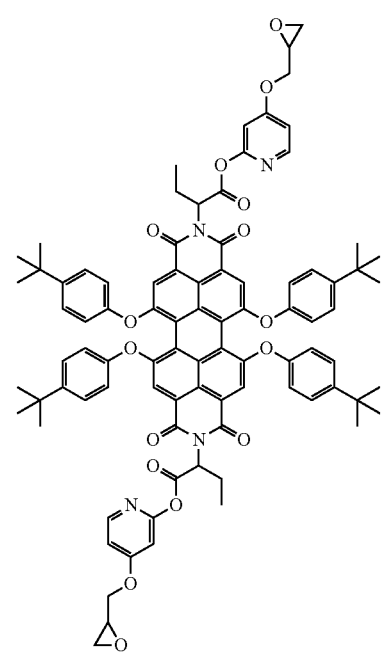

517
-continued
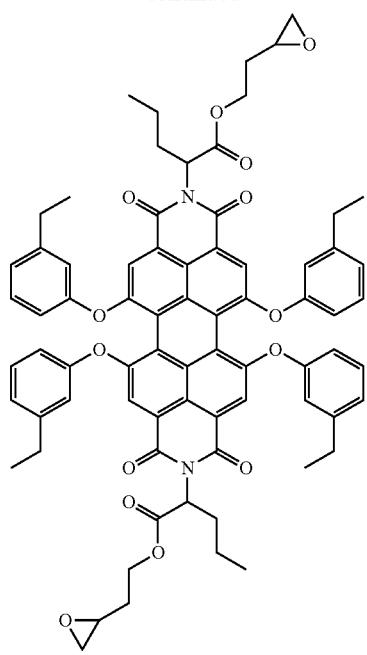
518
-continued
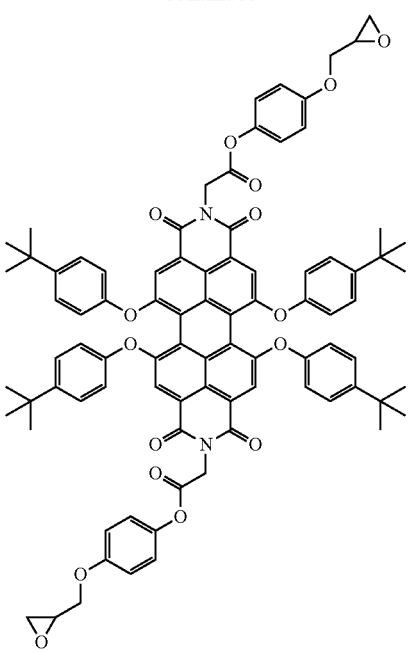
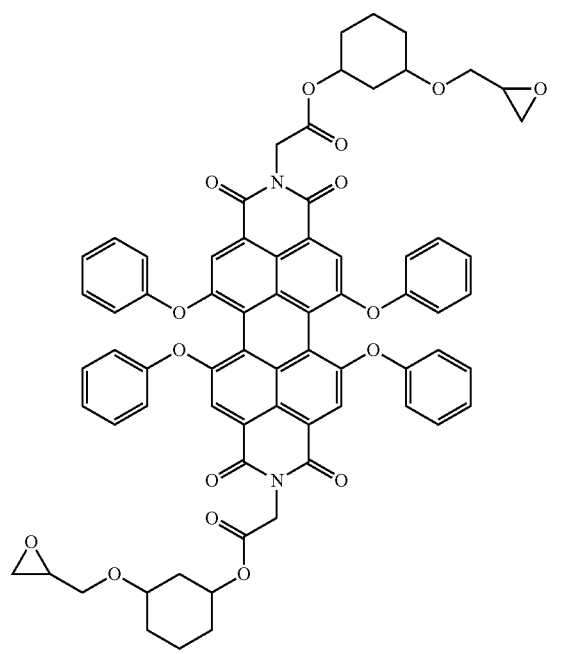
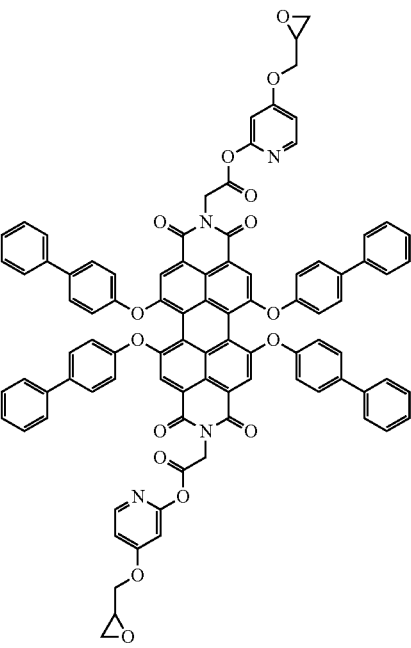

519
-continued
520
-continued
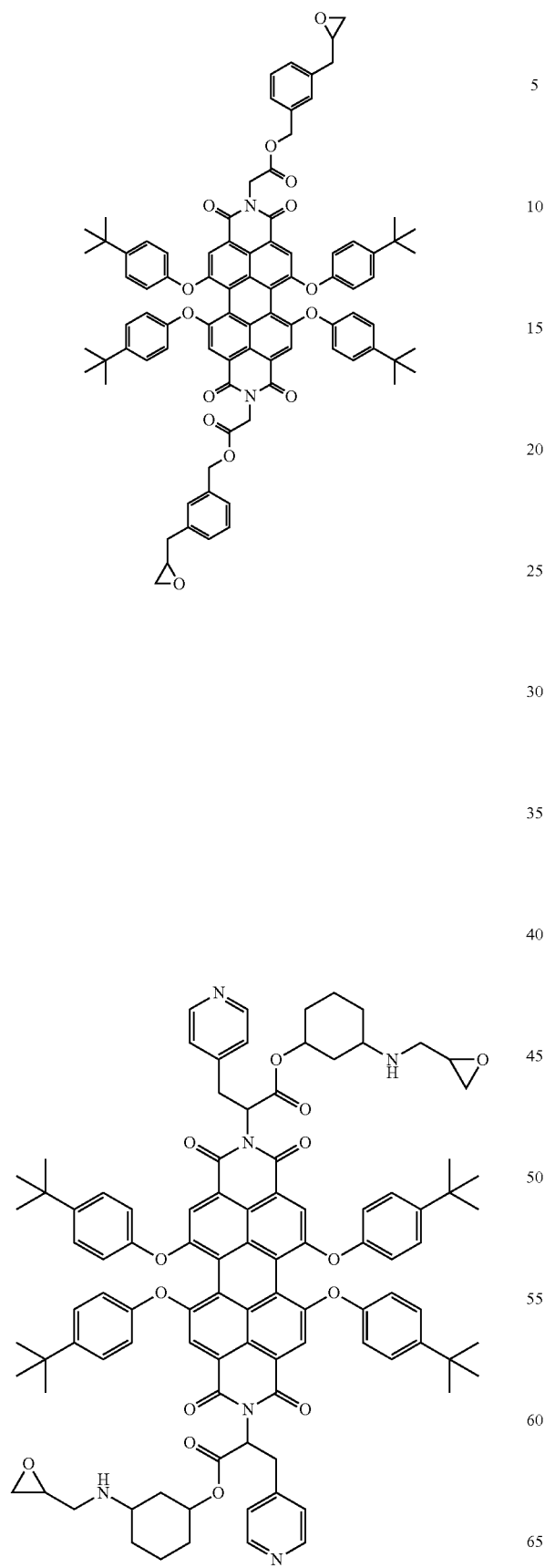

521
-continued
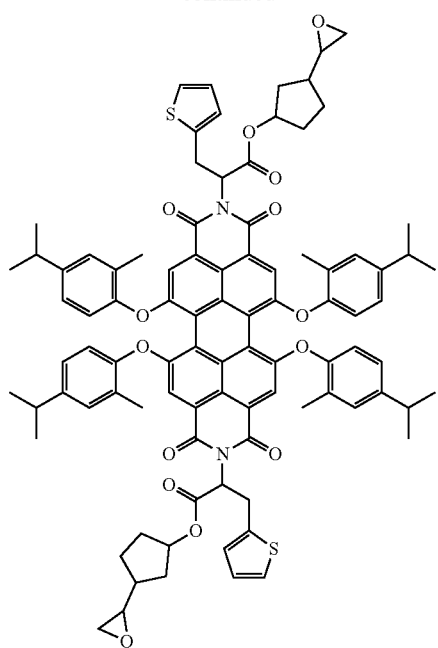
522
-continued
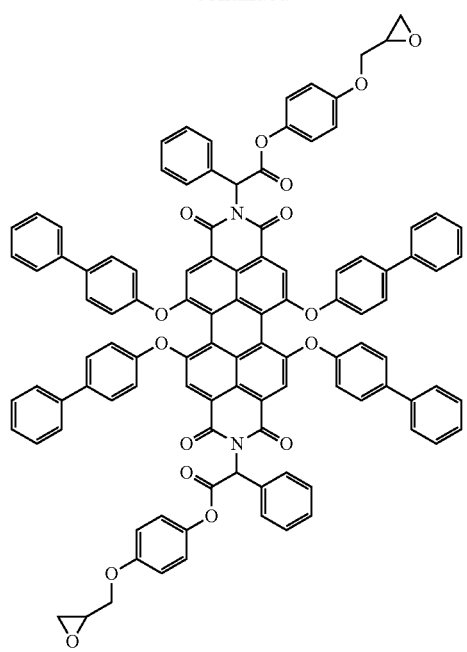
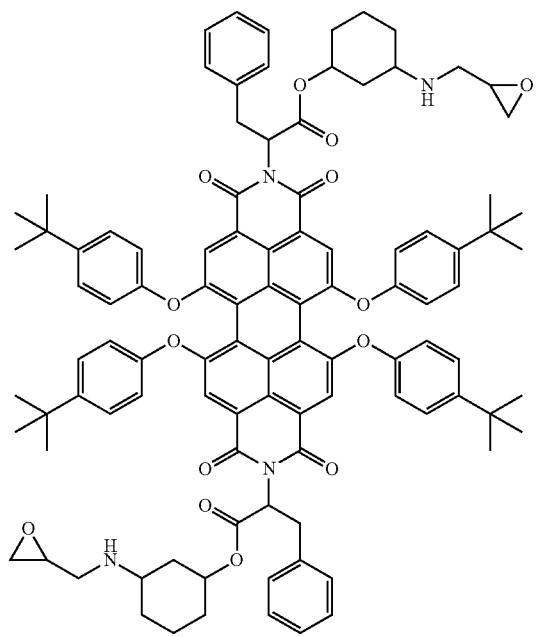
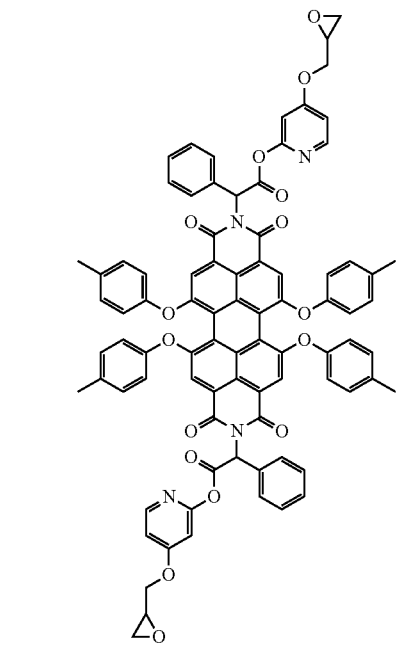

523
-continued
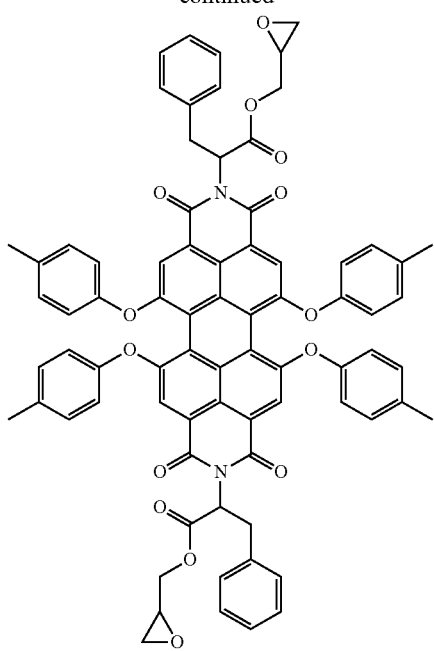
524
-continued
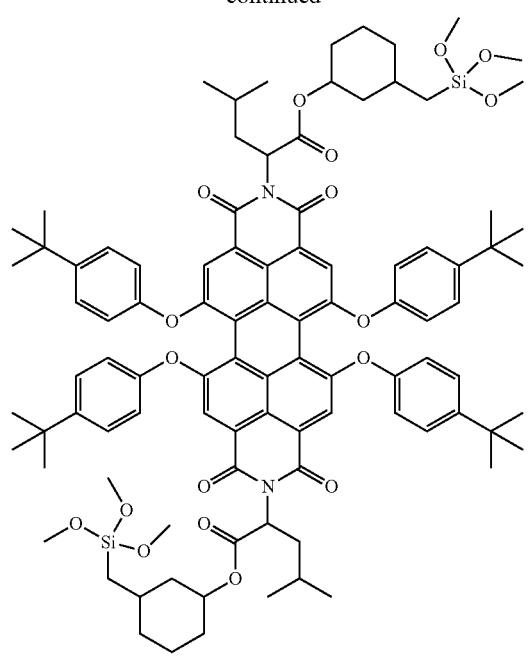

525
-continued
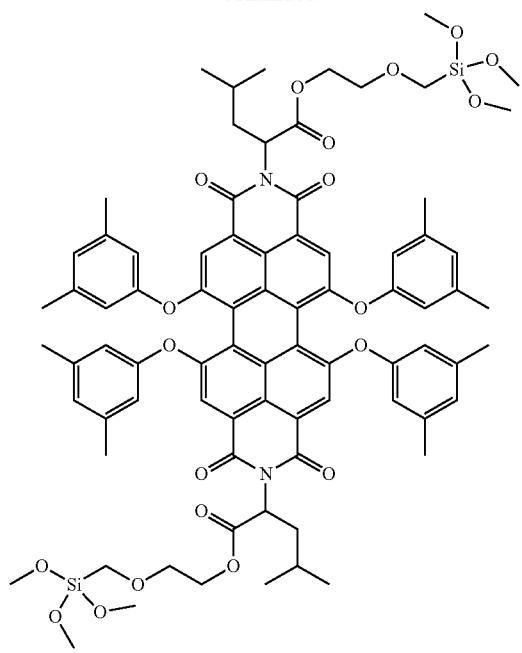
526
-continued
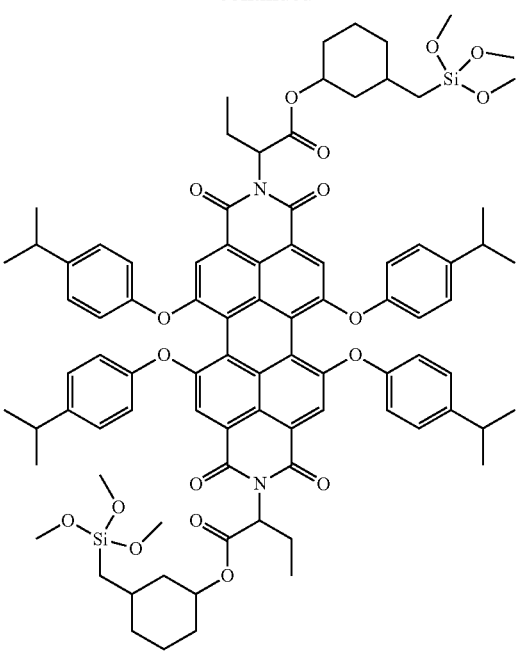
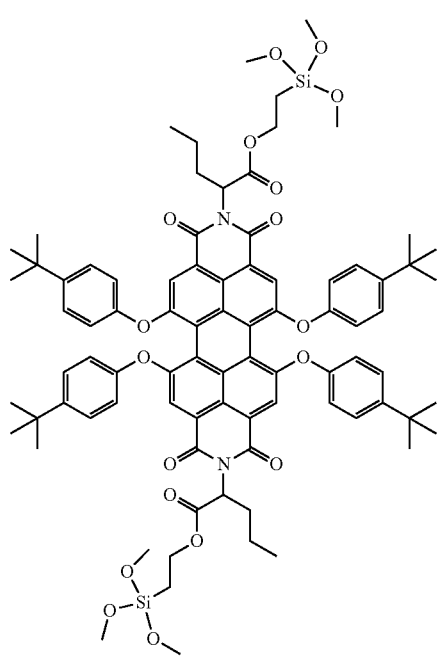
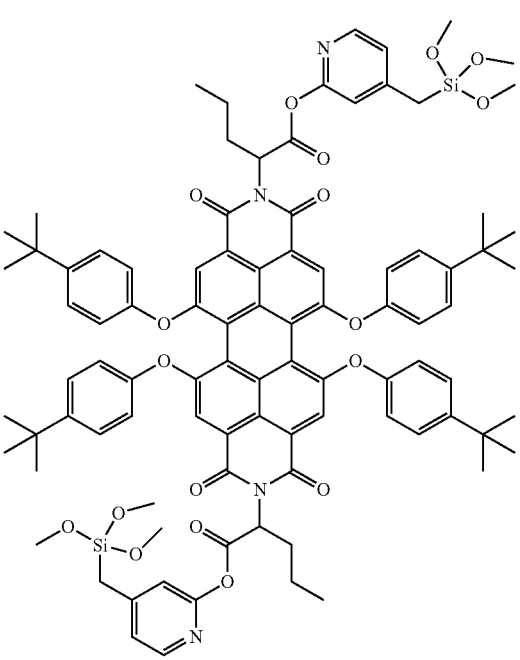

527
-continued
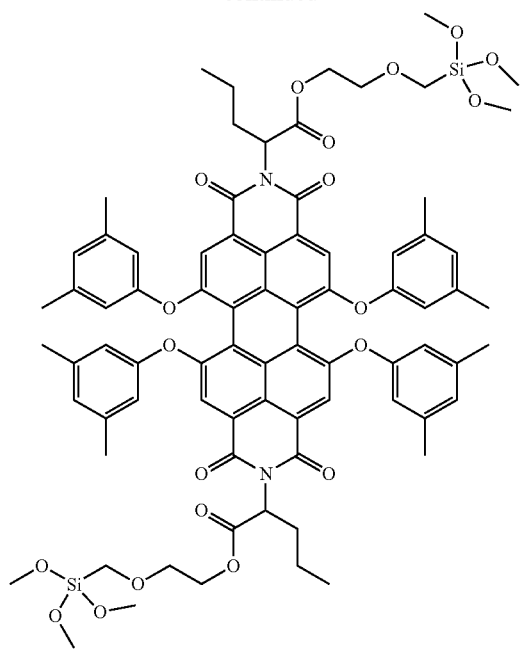
528
-continued
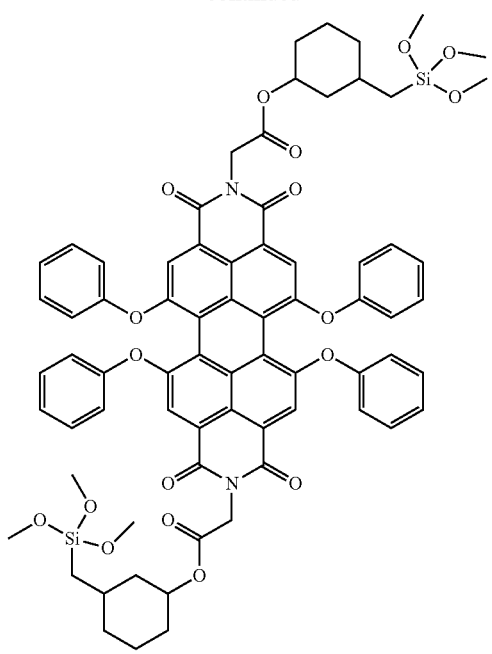
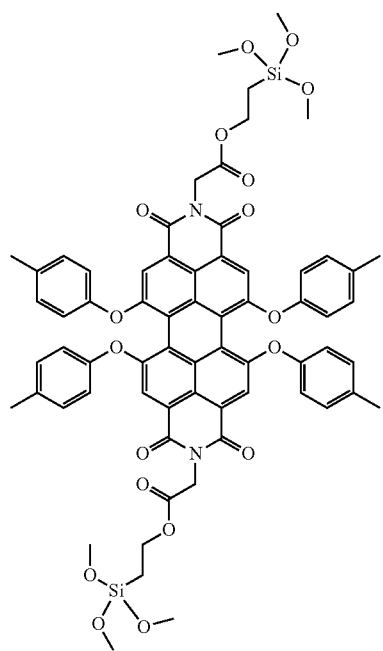
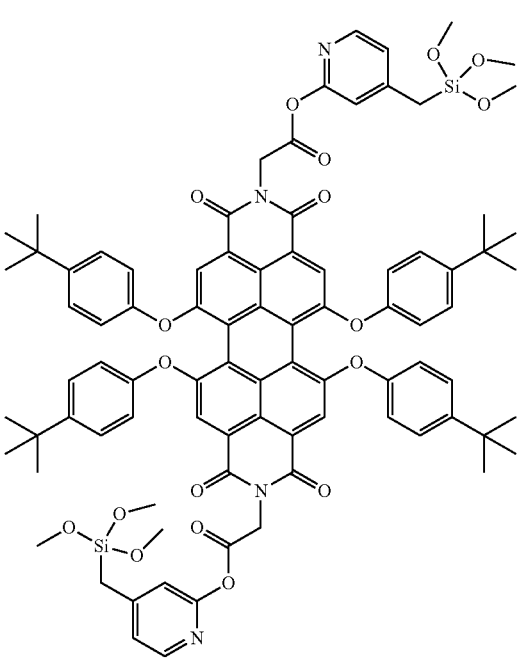

529
-continued
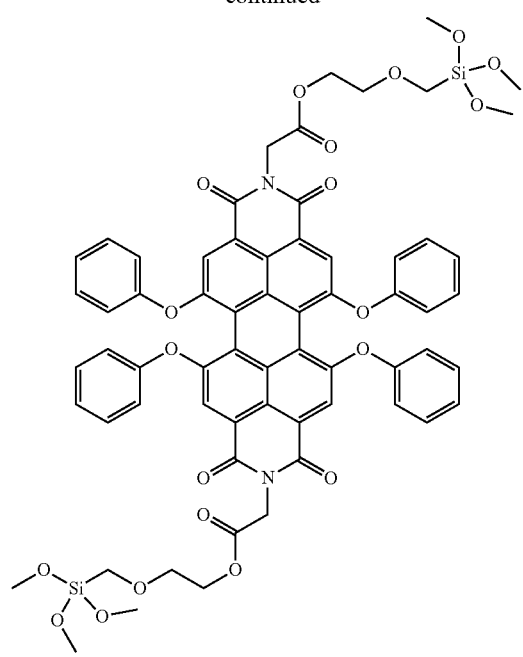
530
-continued
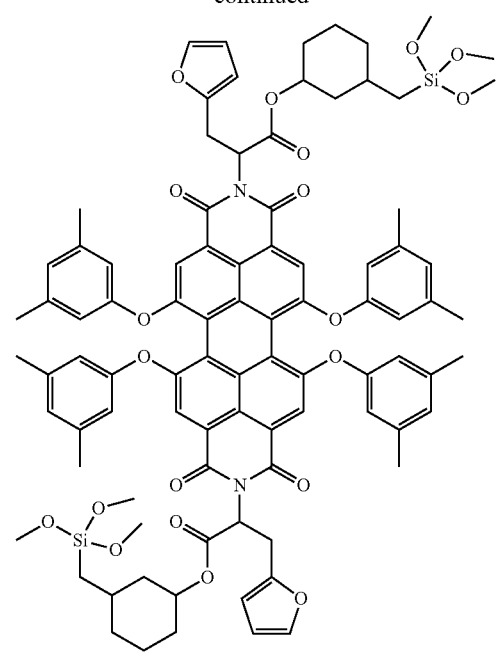
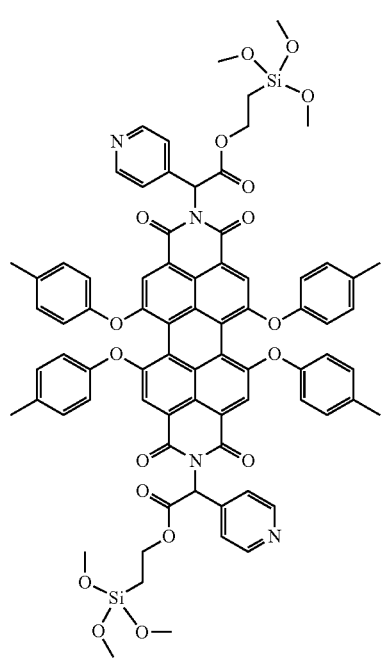
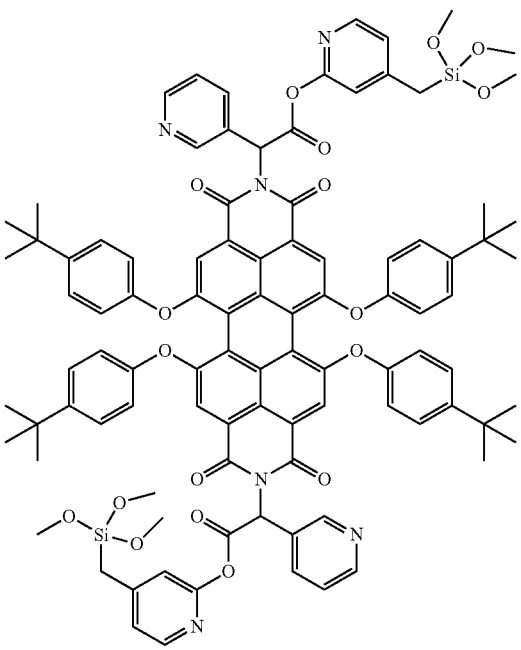

531
-continued
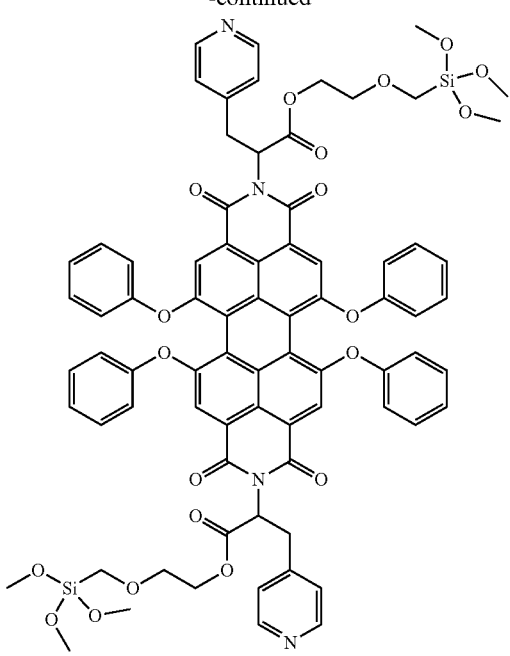
532
-continued
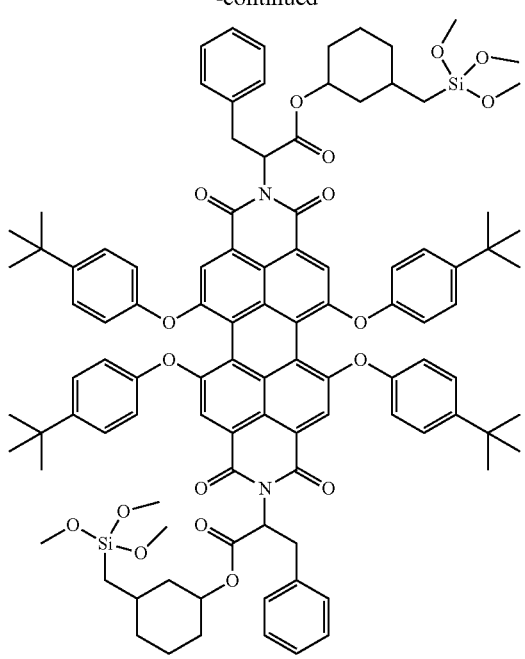
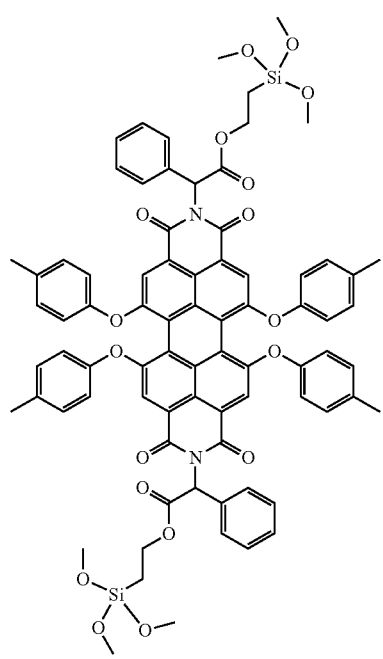
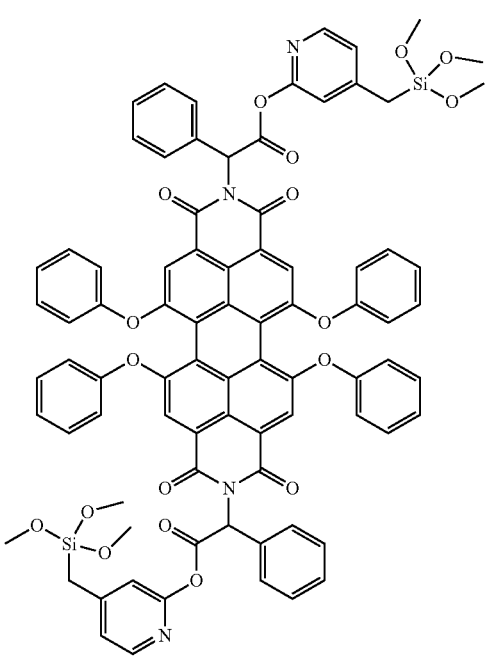

533
-continued
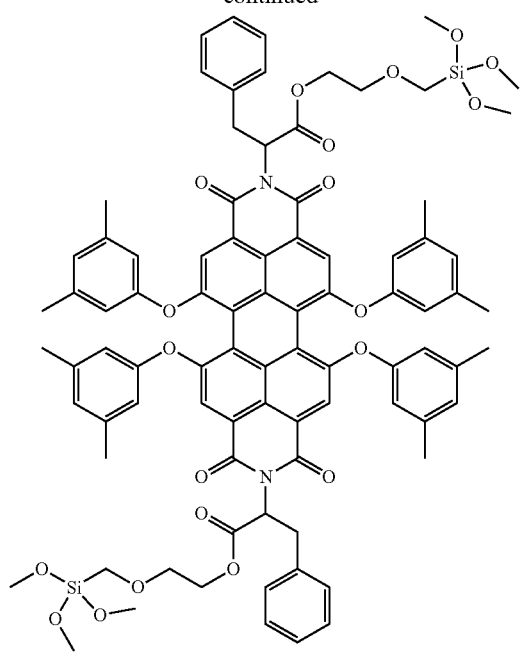
534
-continued
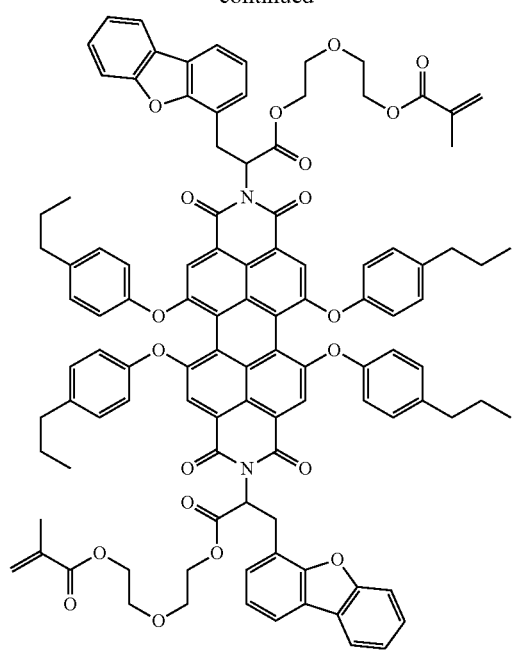
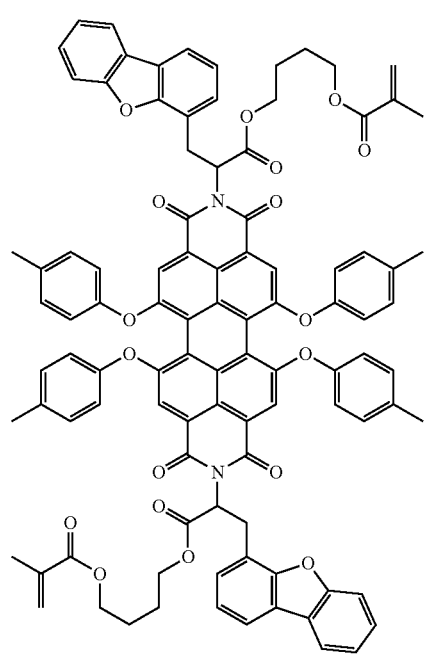
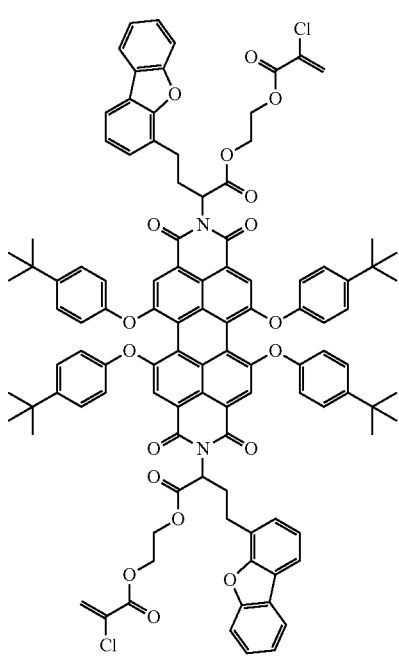

535
-continued
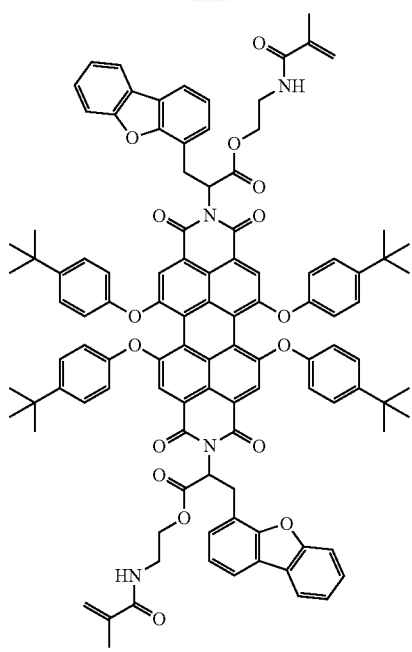
536
-continued
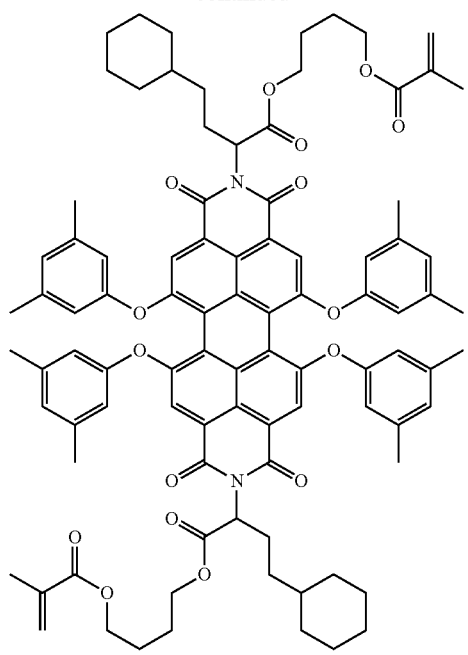
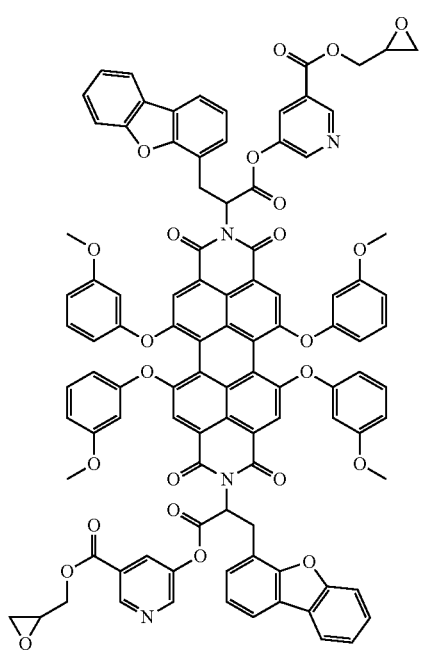
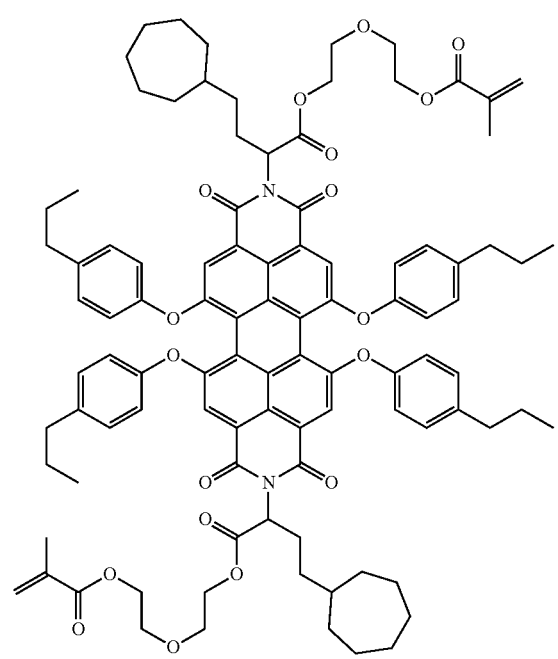

537
-continued
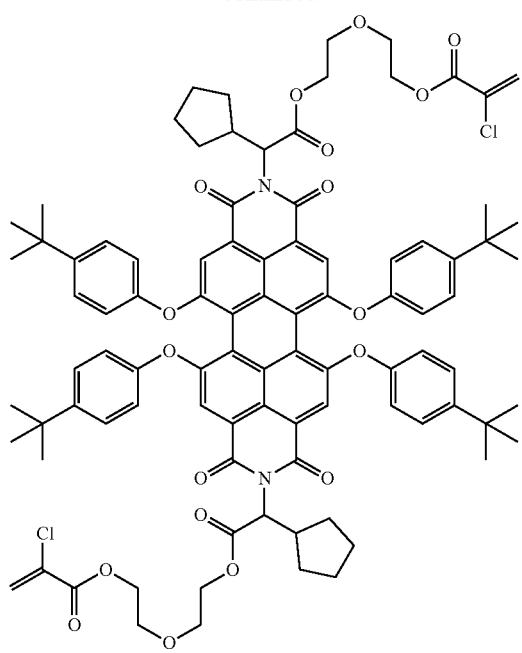
538
-continued
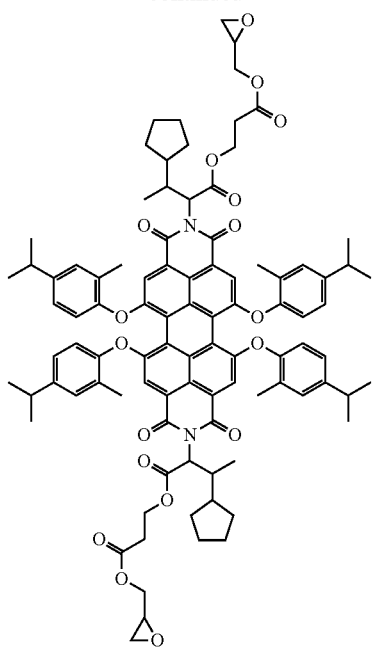
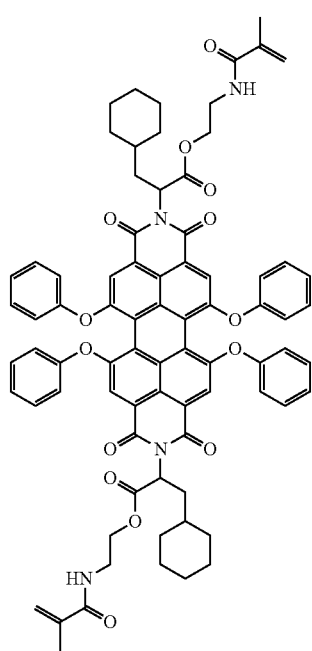
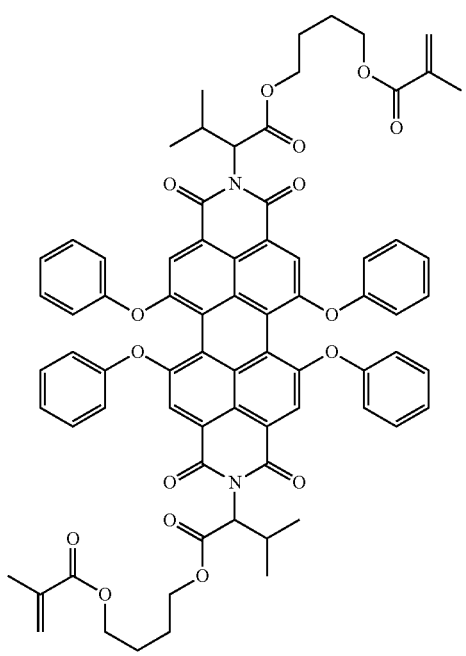

539
-continued
540
-continued
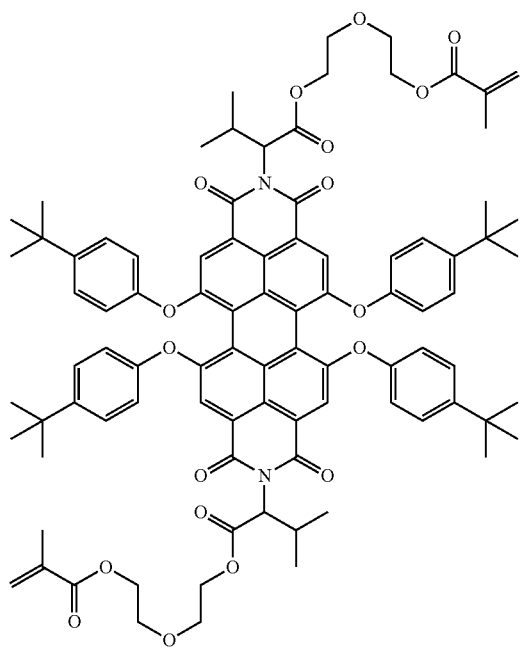
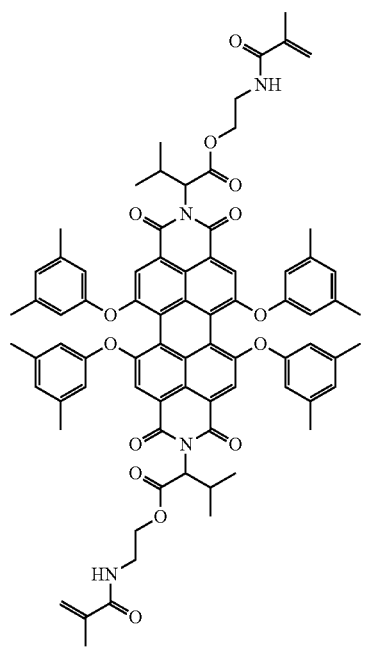
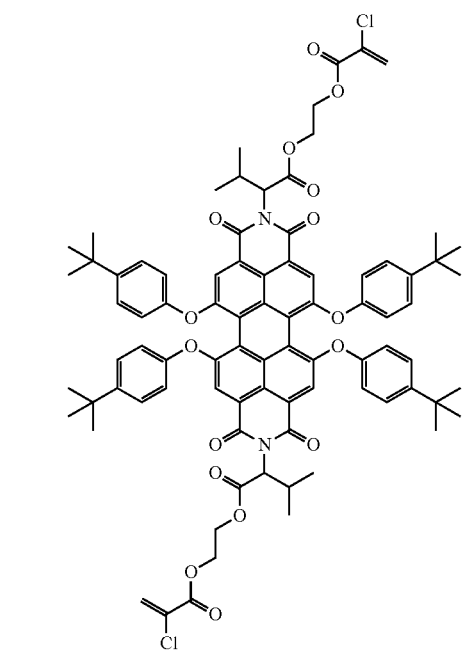
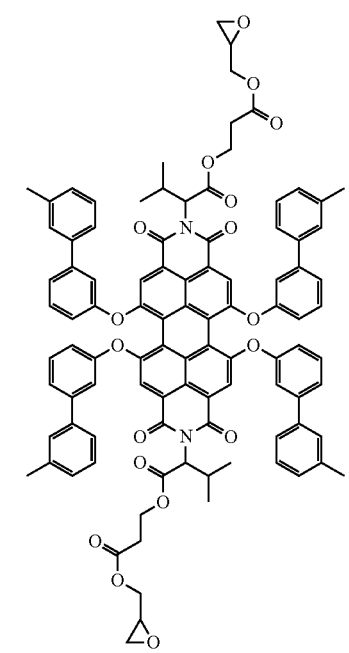

541
-continued
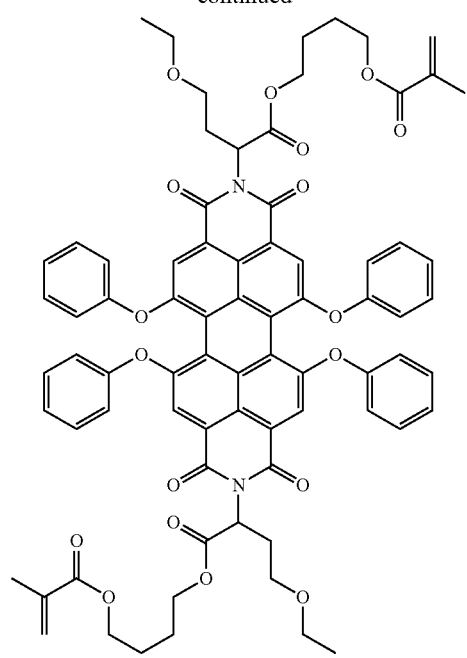
542
-continued
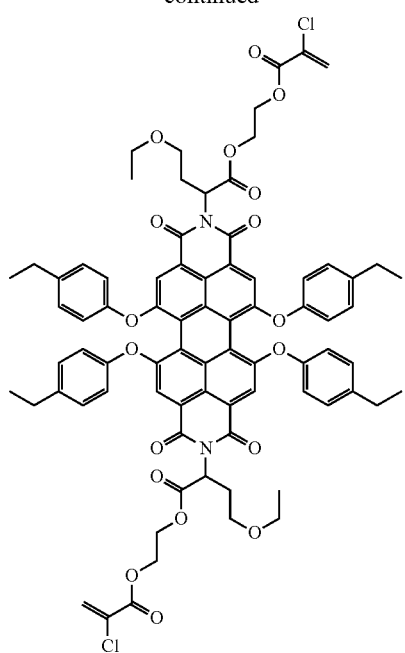
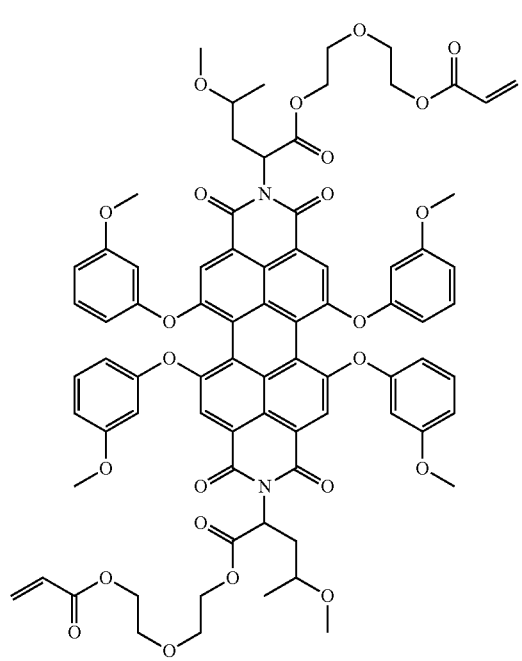
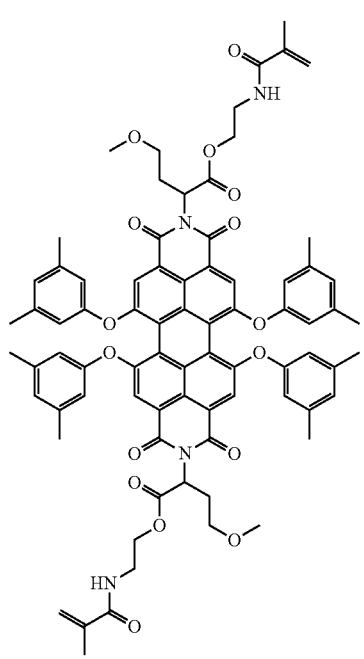

543
-continued
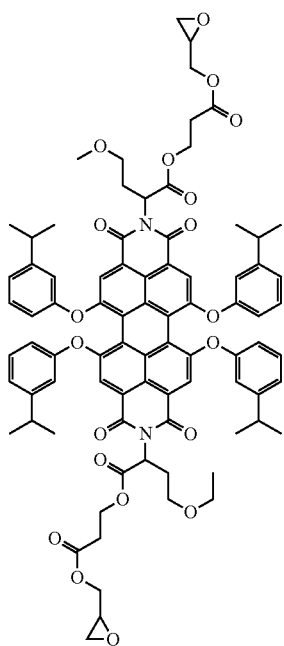
544
-continued
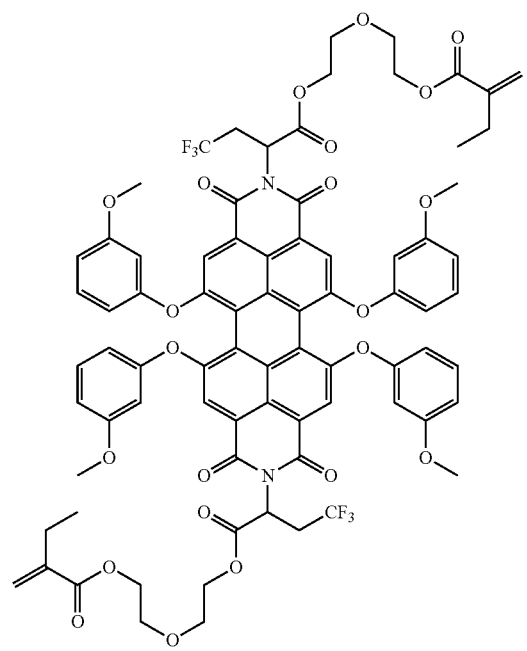
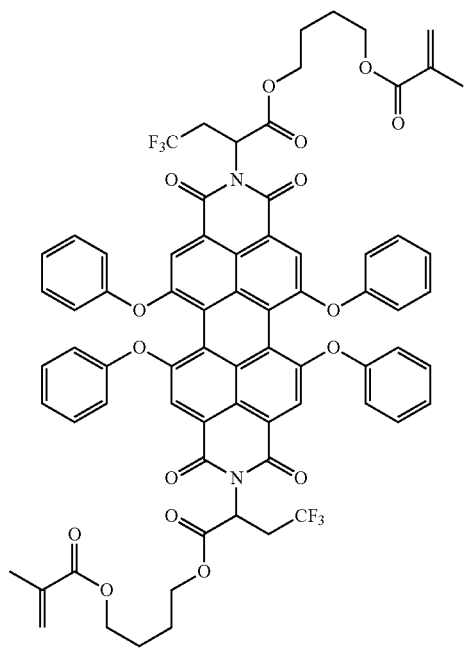
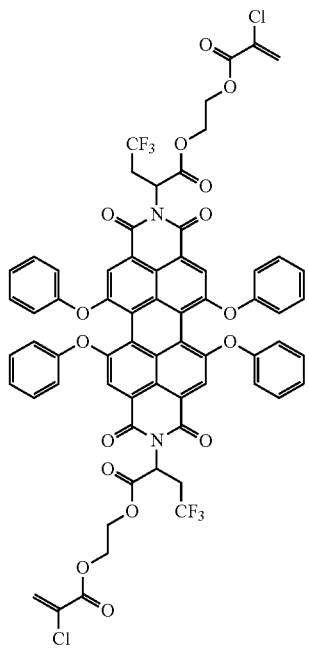

545
-continued
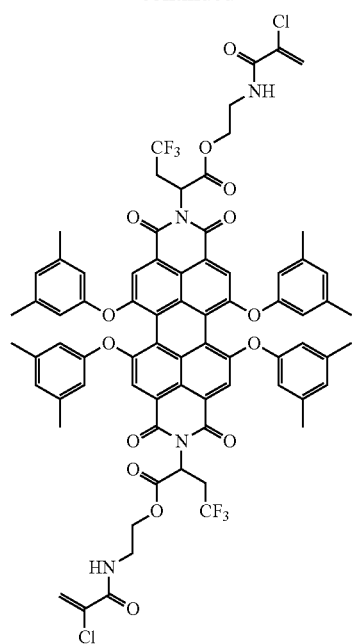
546
-continued
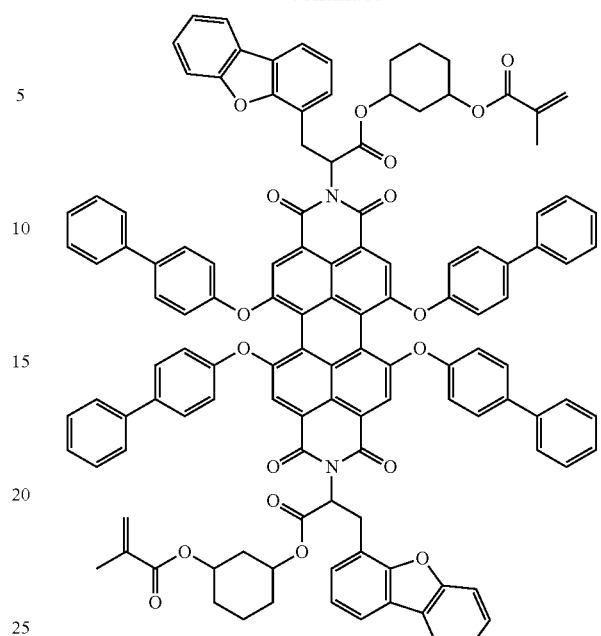
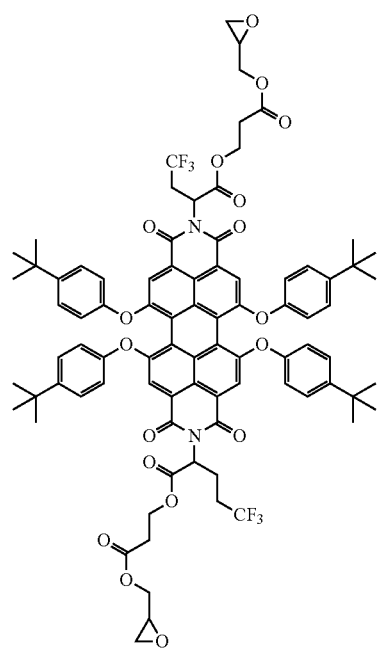
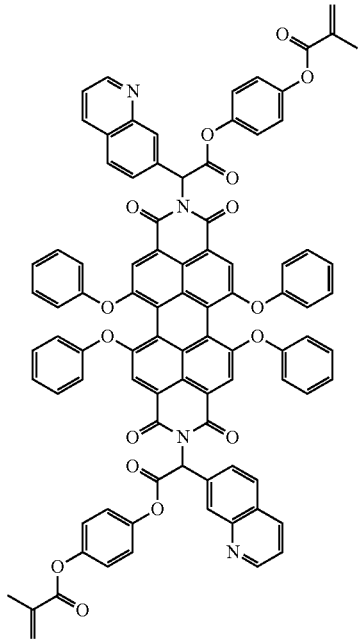

547
-continued
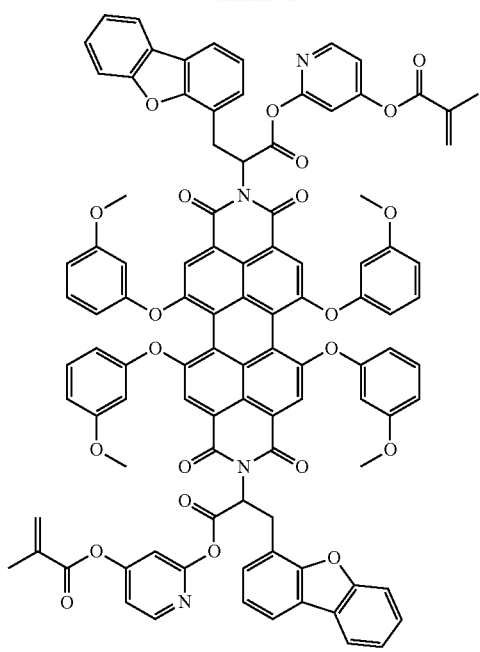
548
-continued
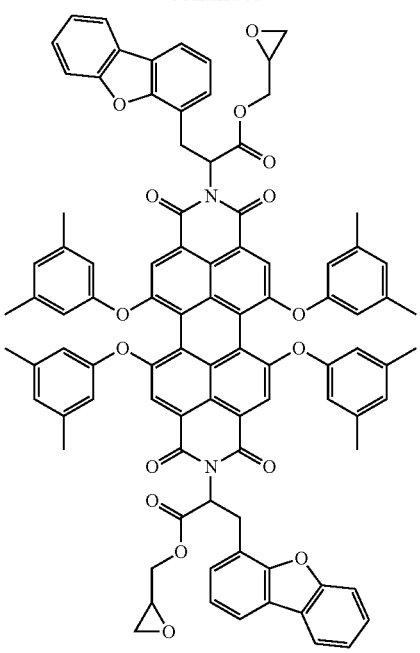
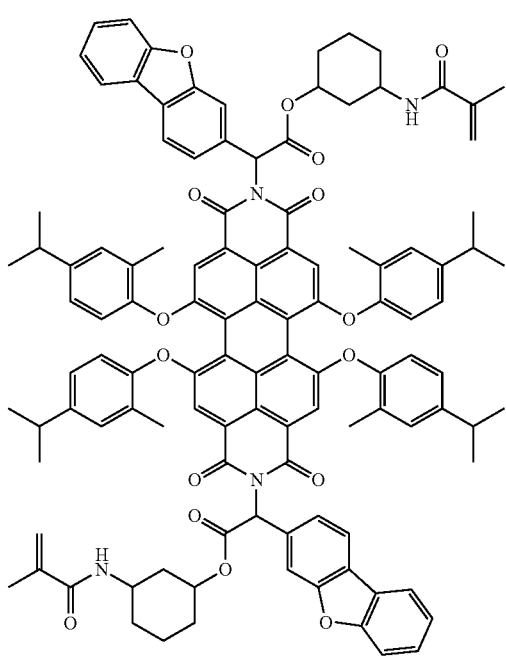
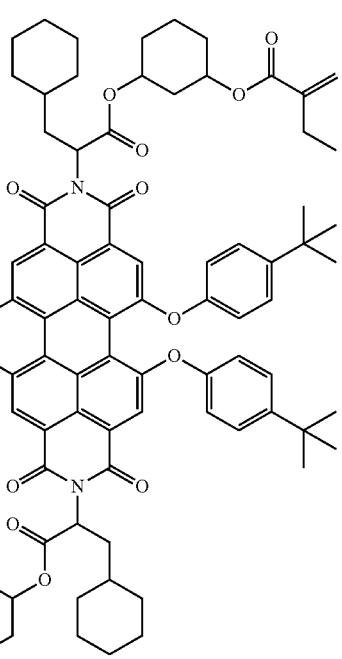

549
-continued
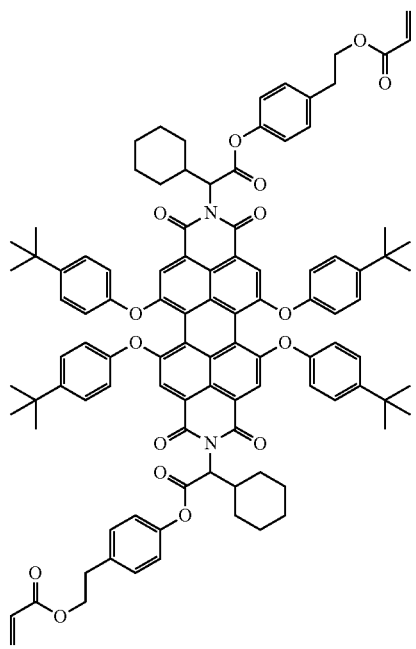
550
-continued
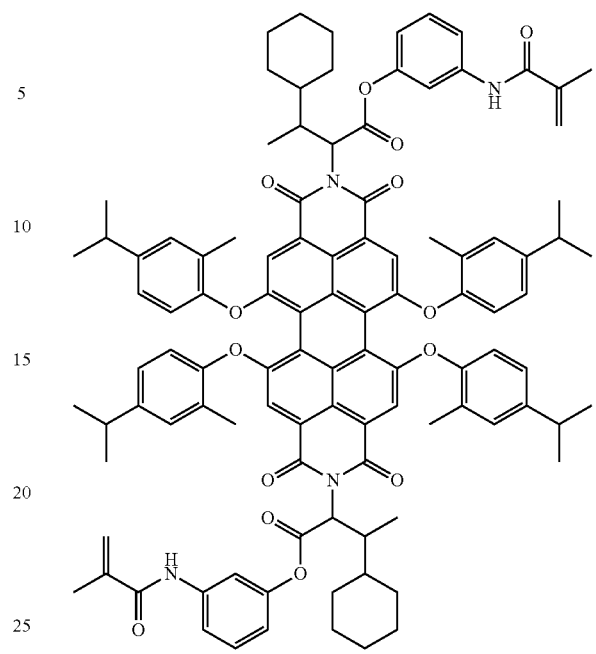
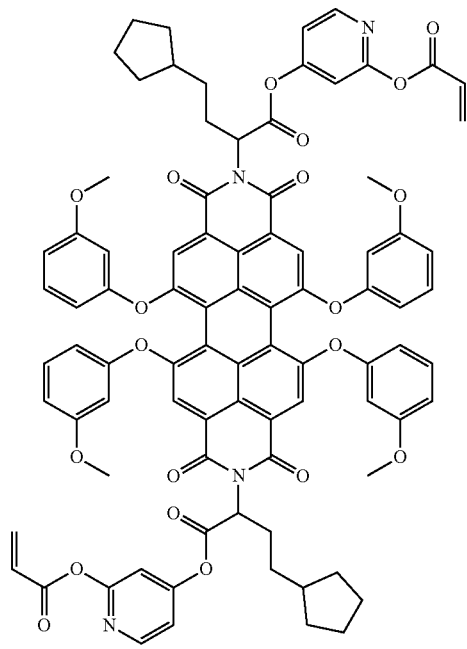
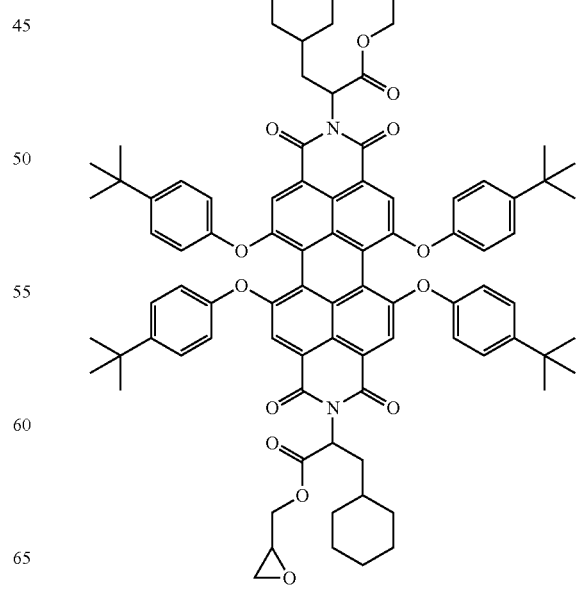

551
-continued
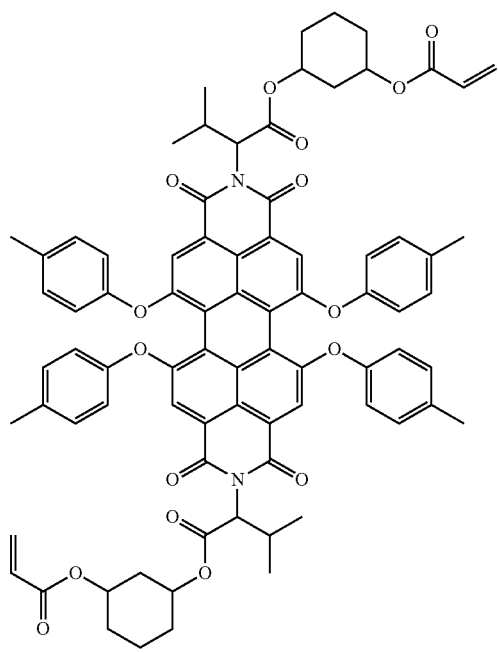
552
-continued
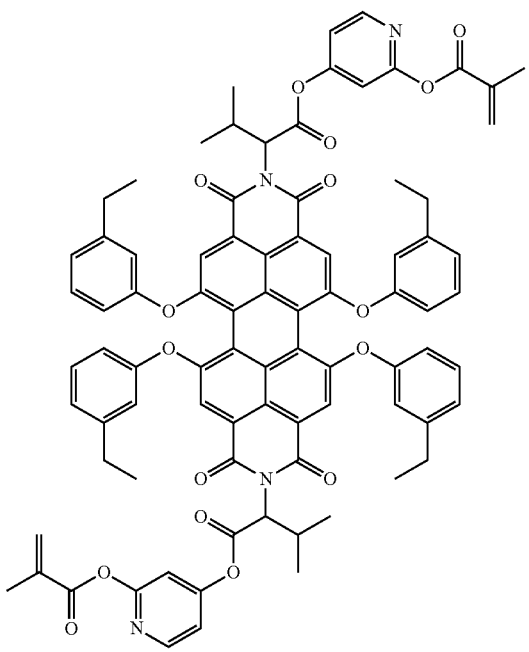
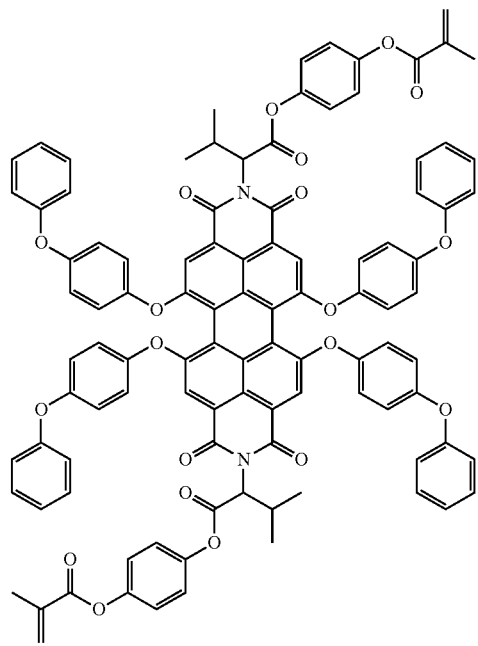
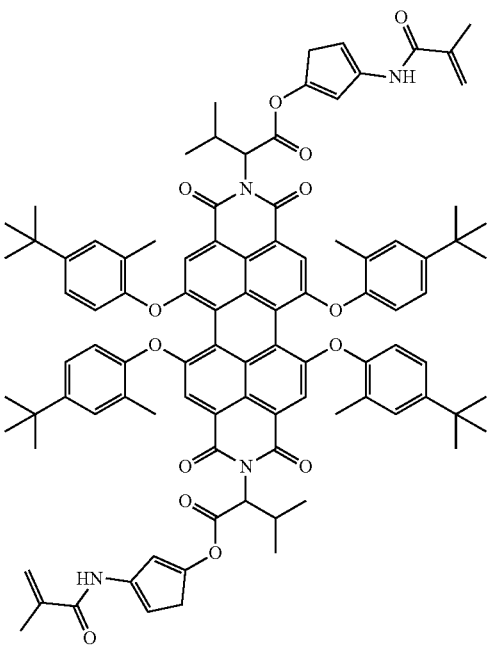

553
-continued
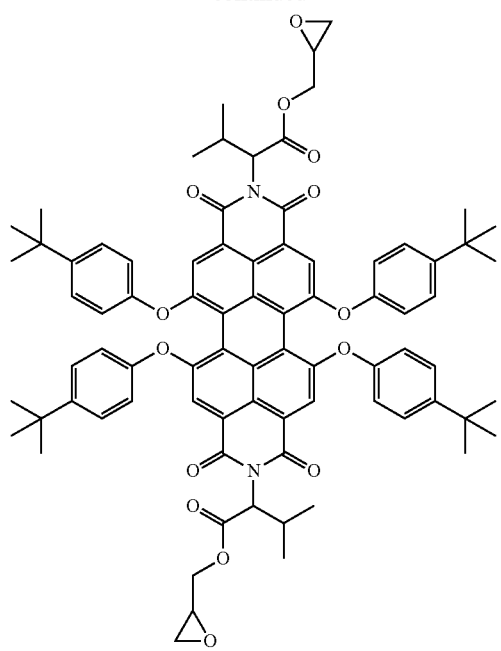
554
-continued
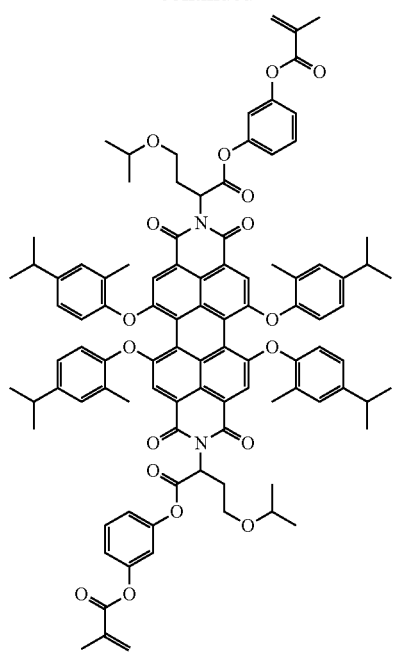
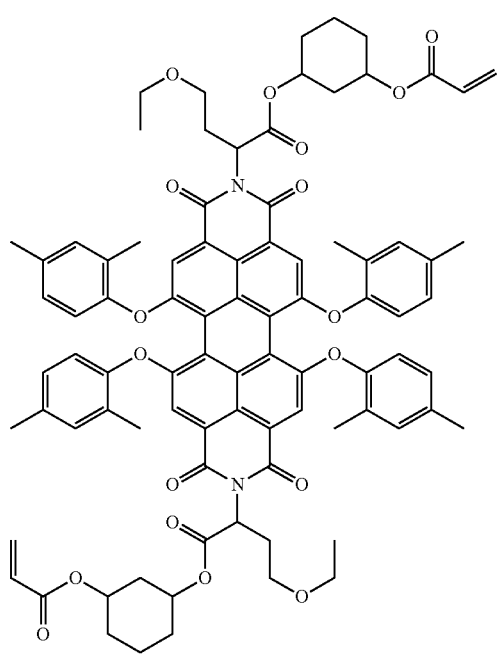
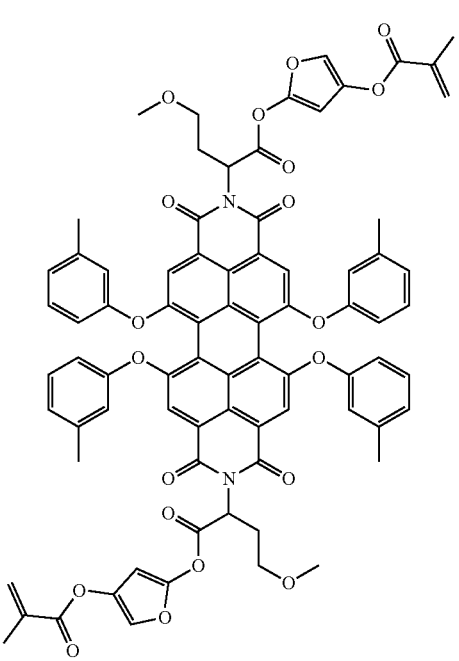

555
-continued
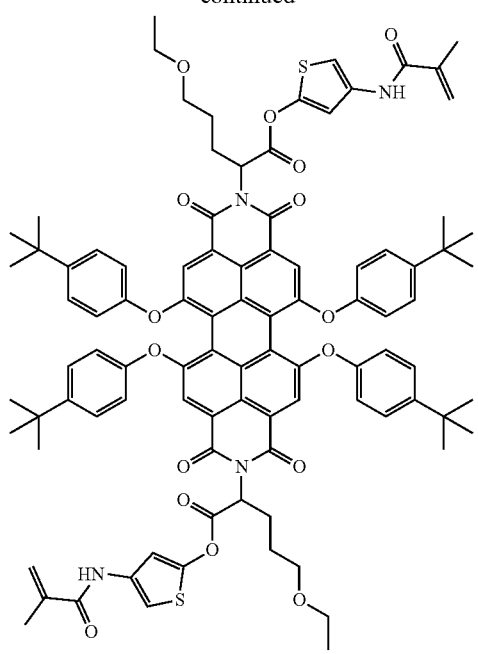
556
-continued
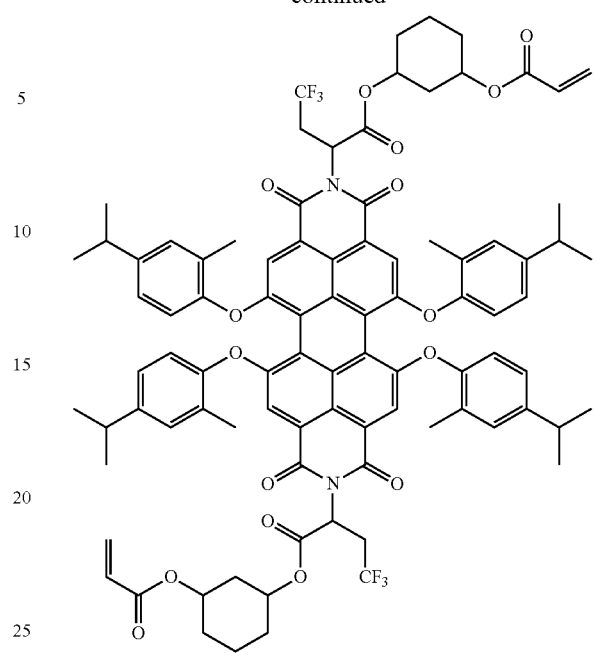
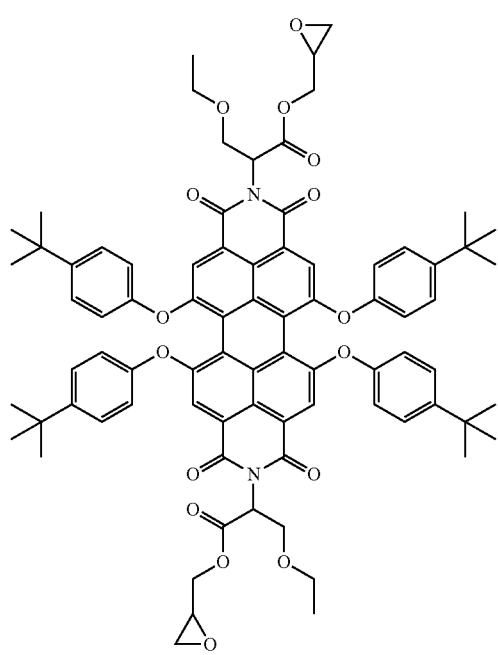
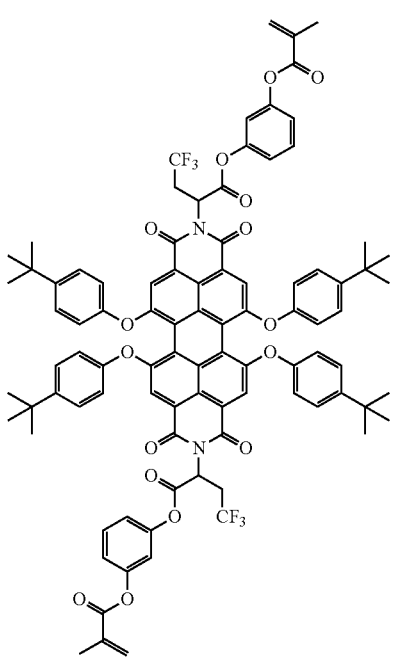

557
-continued
558
-continued
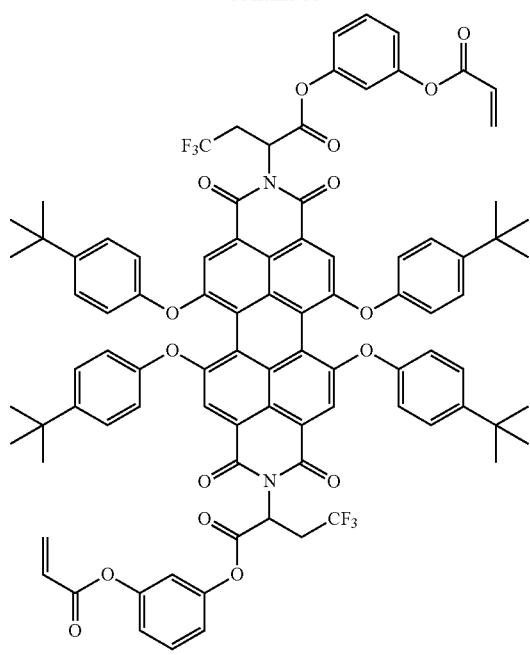
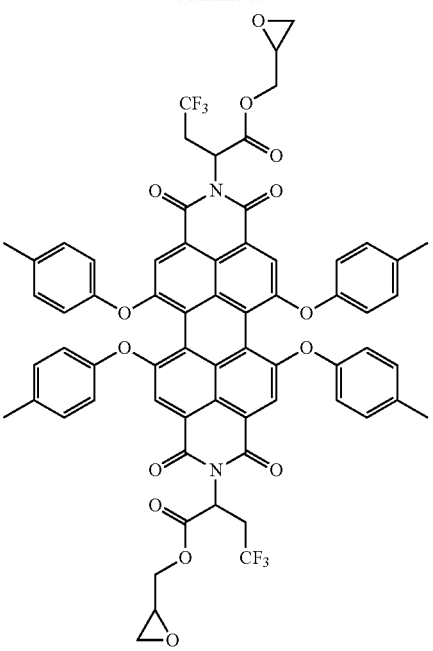
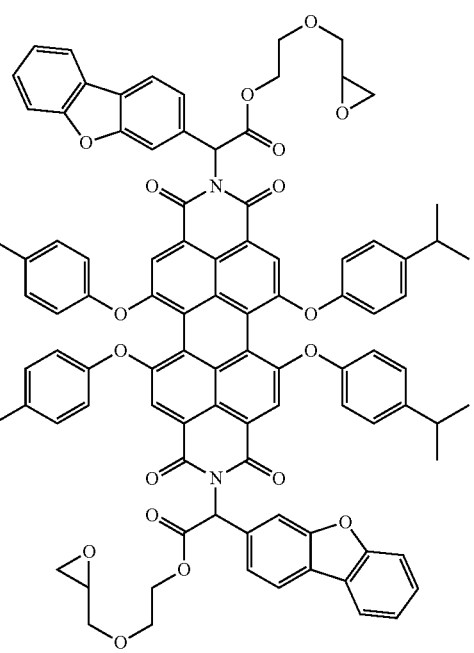

559
-continued
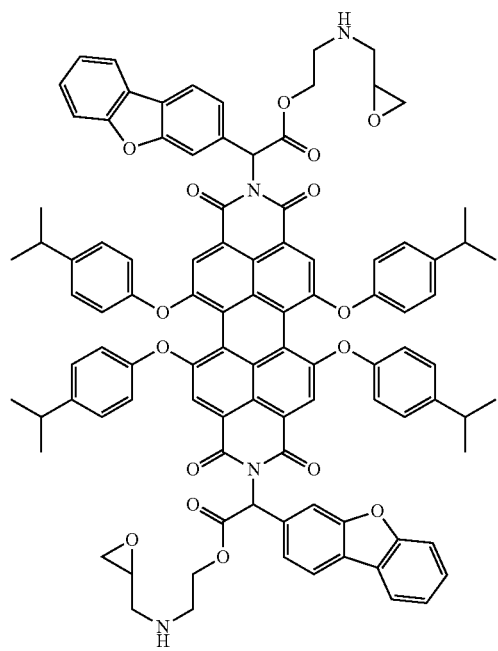
560
-continued
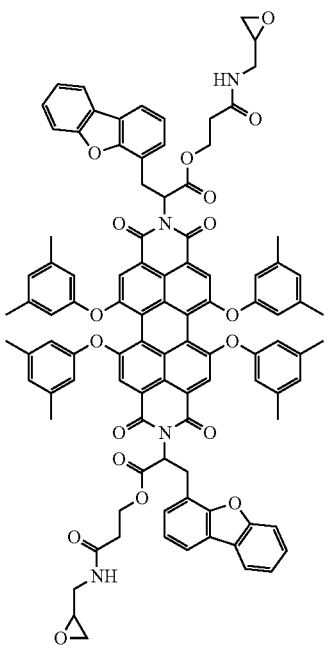
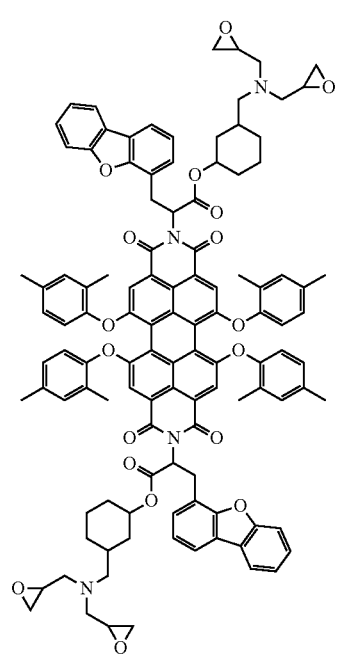
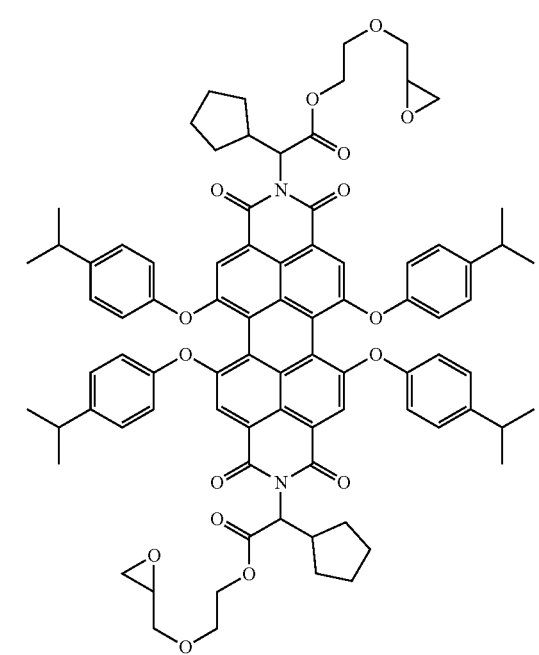

561
-continued
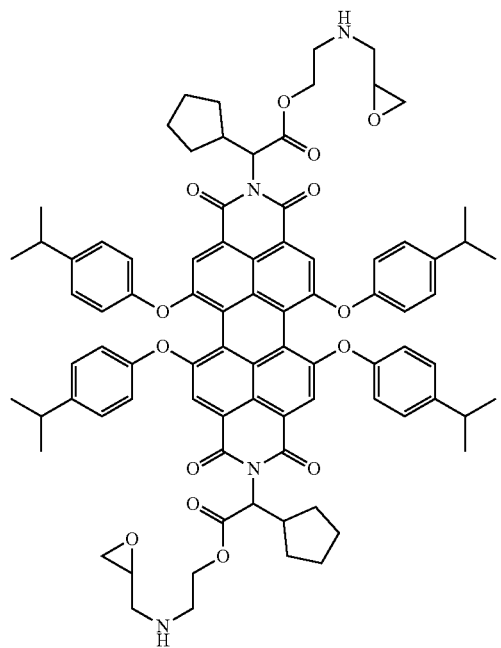
562
-continued
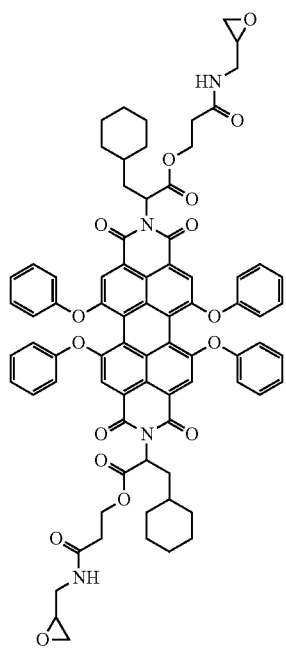
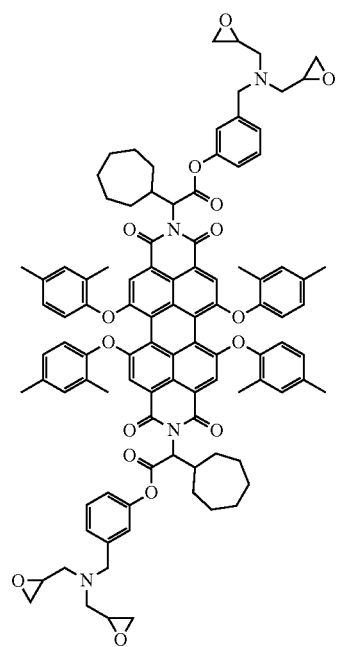
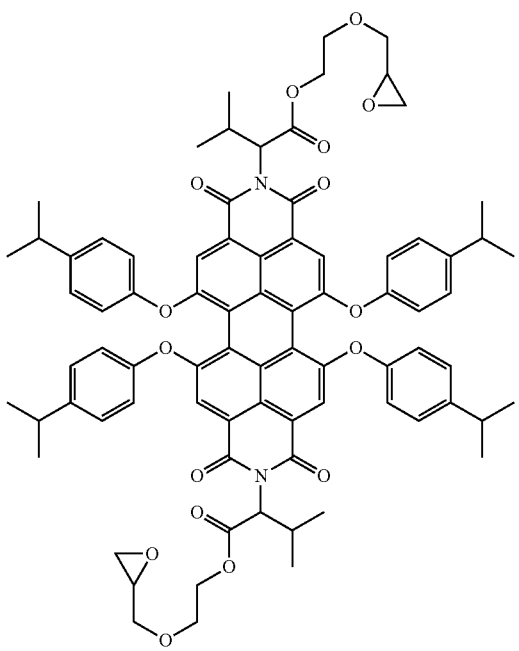

563
-continued
564
-continued
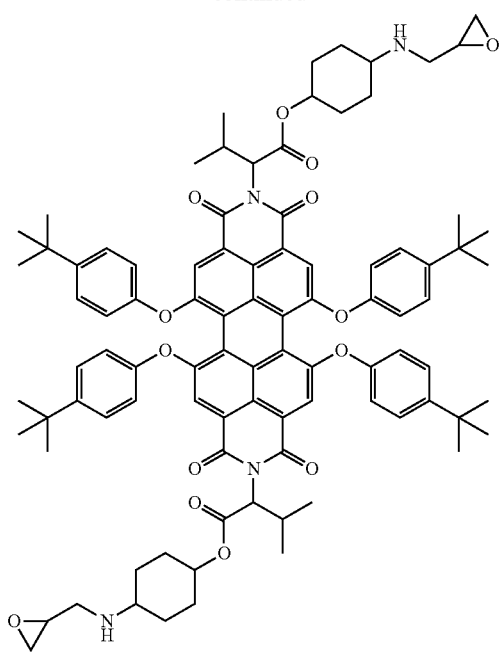
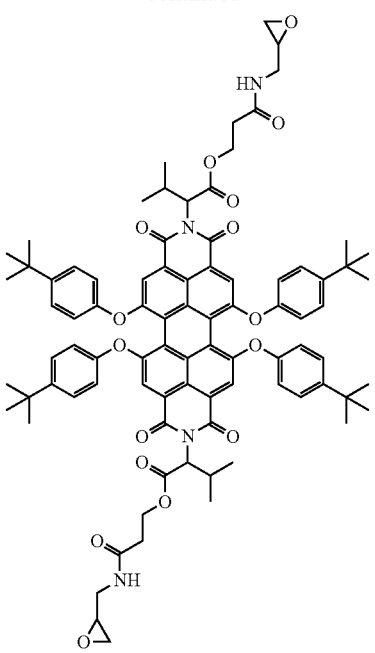

565
-continued
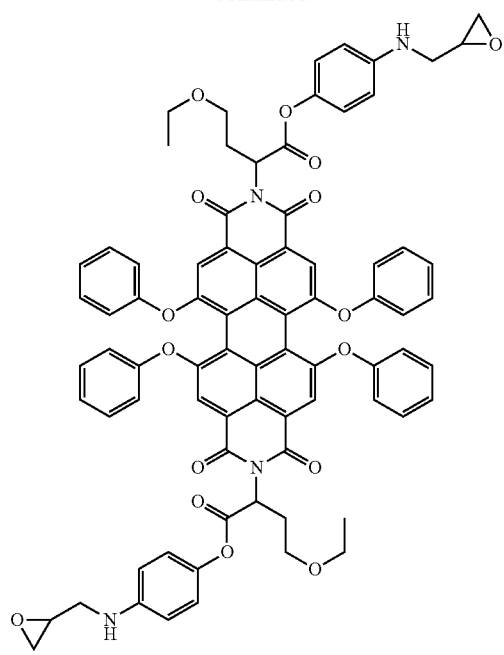
566
-continued
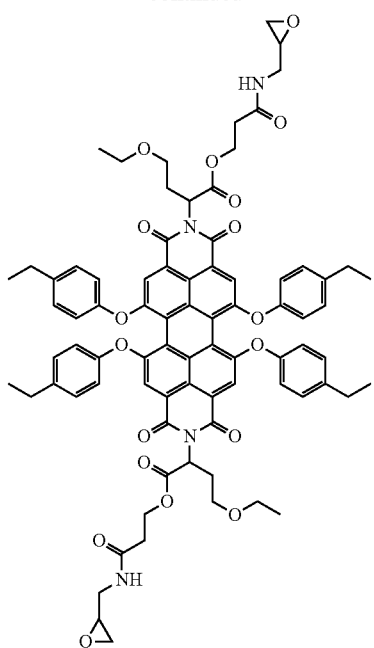
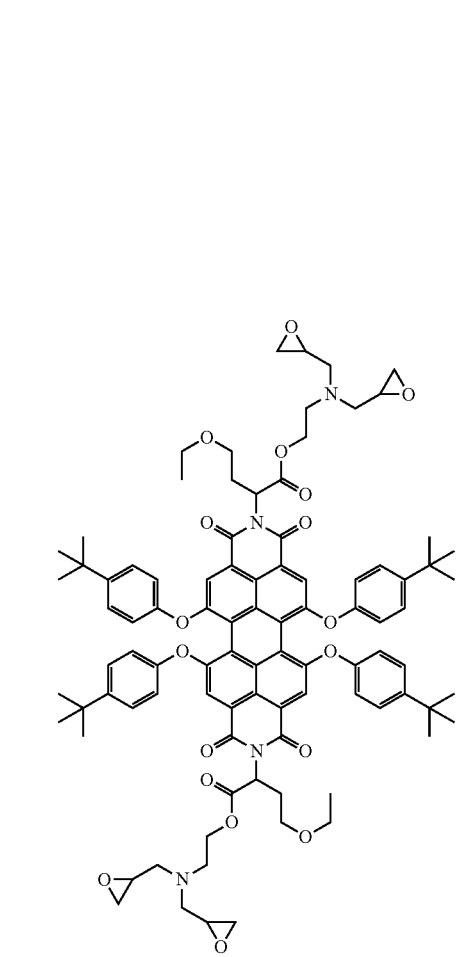
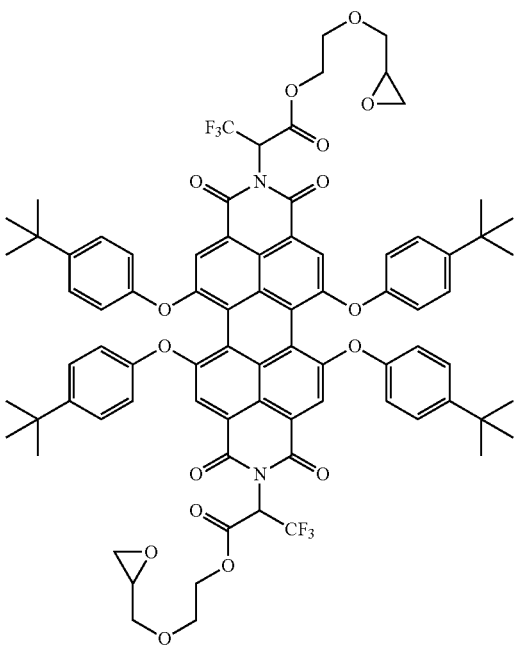

567
-continued
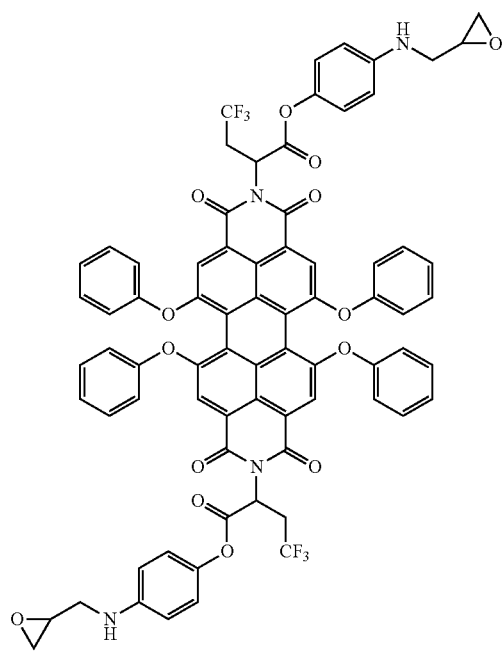
568
-continued
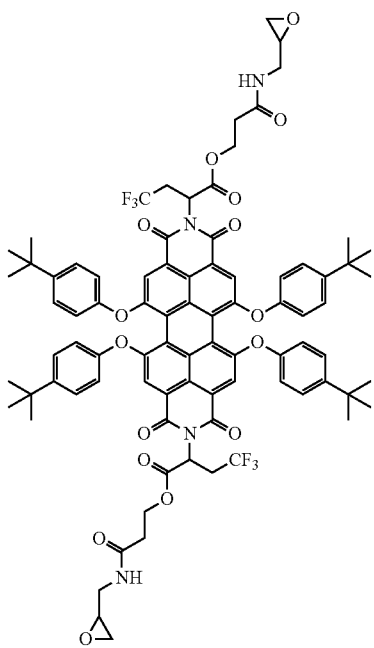
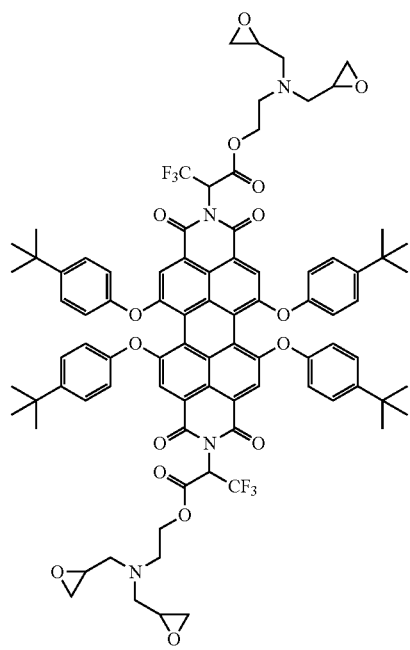
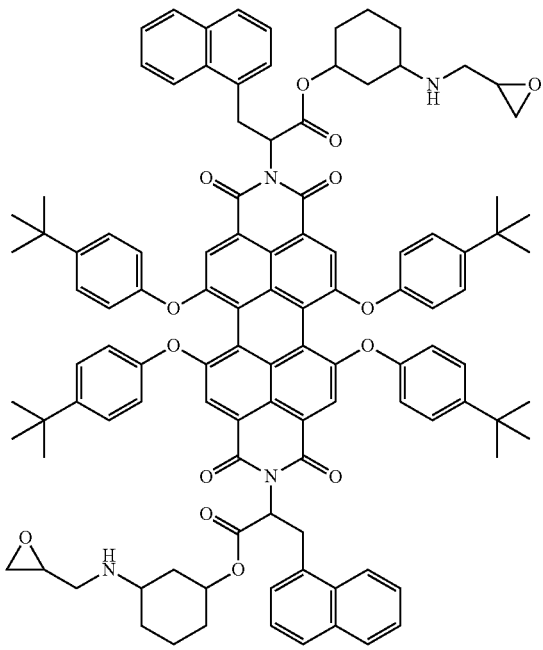

569
-continued
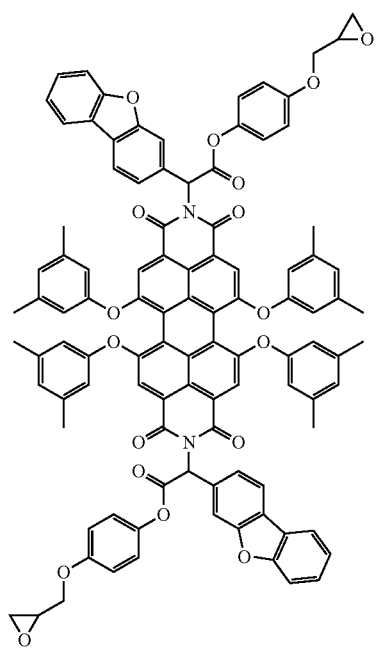
570
-continued
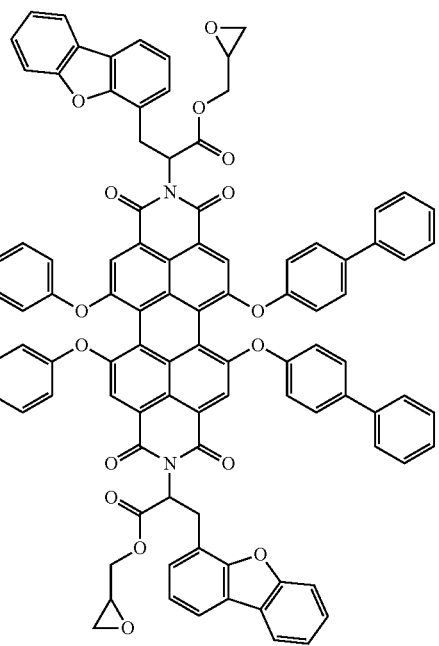
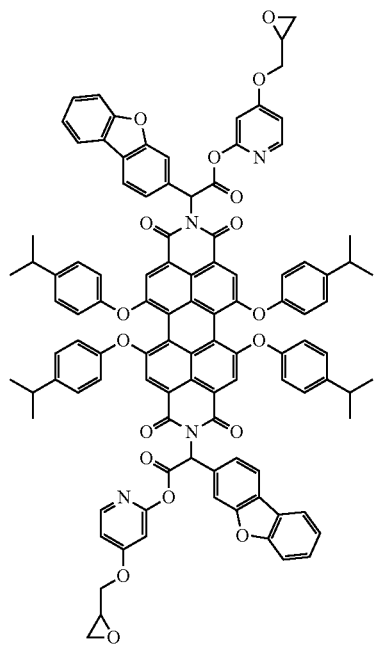
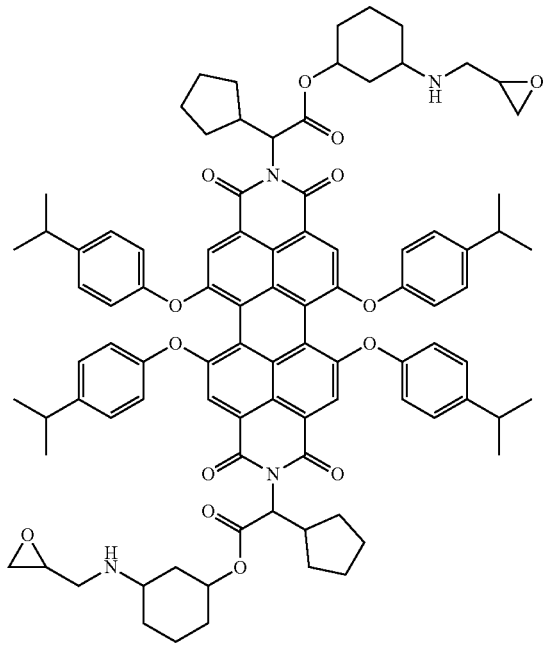

571
-continued
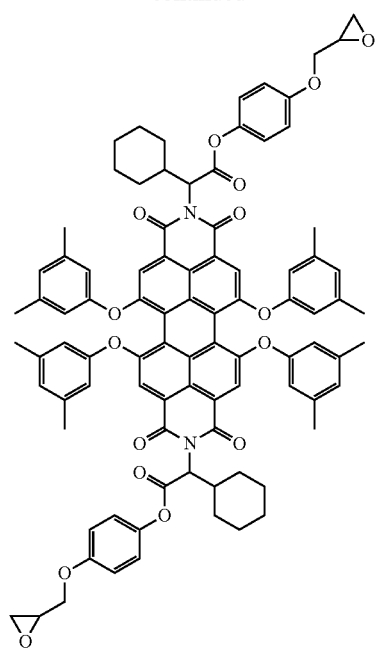
572
-continued
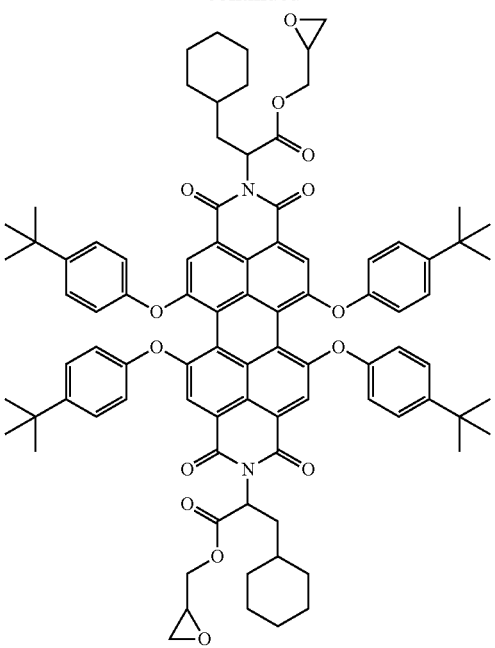
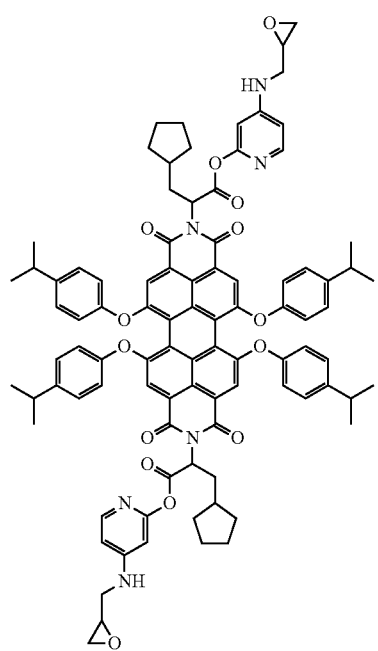
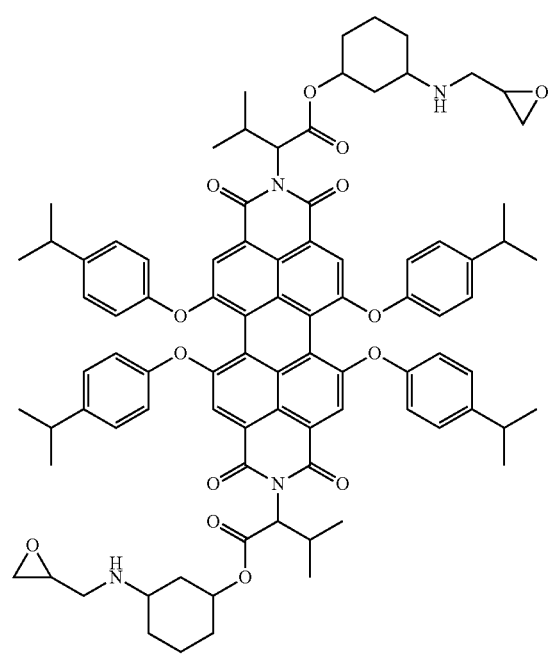

573
-continued
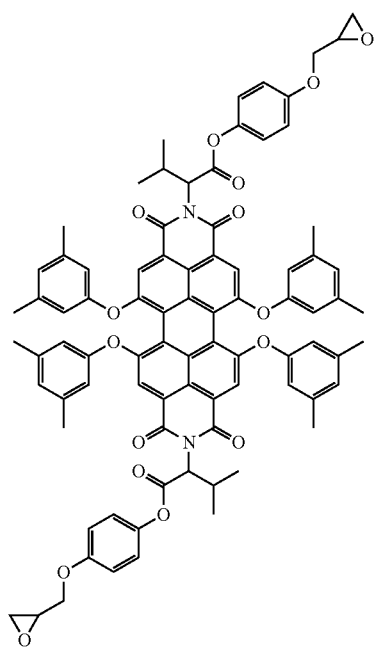
574
-continued
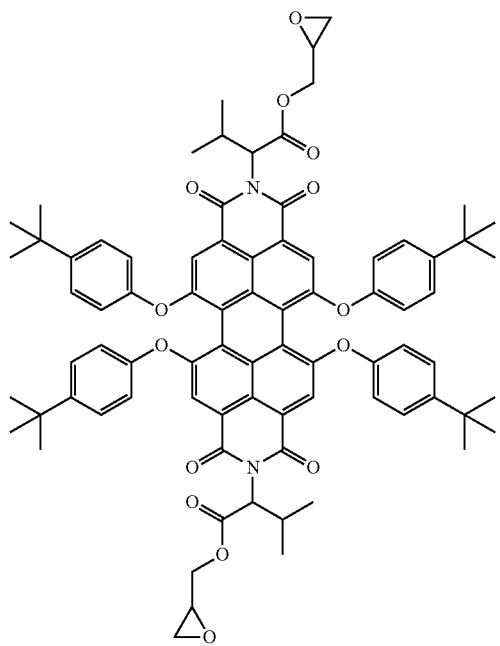
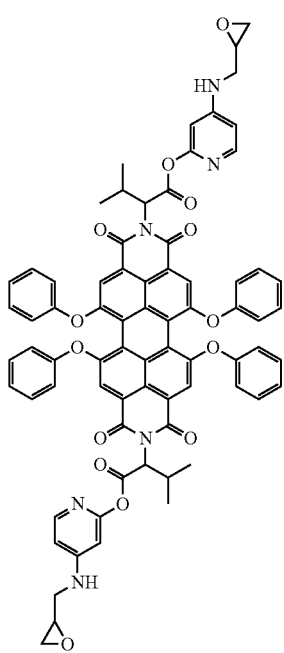
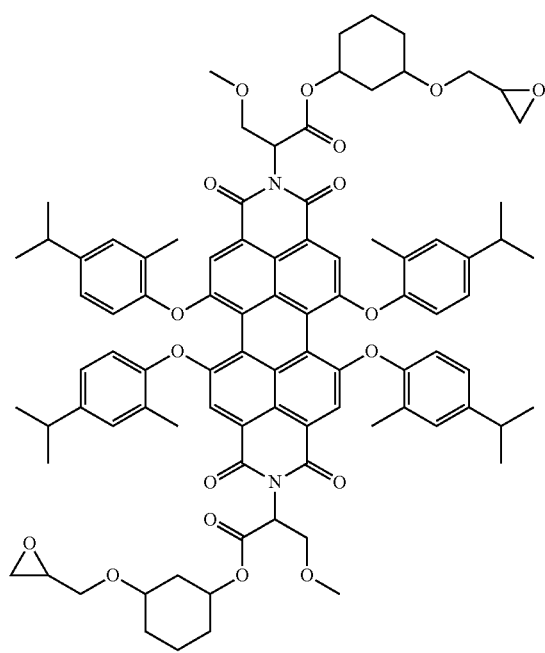

575
-continued
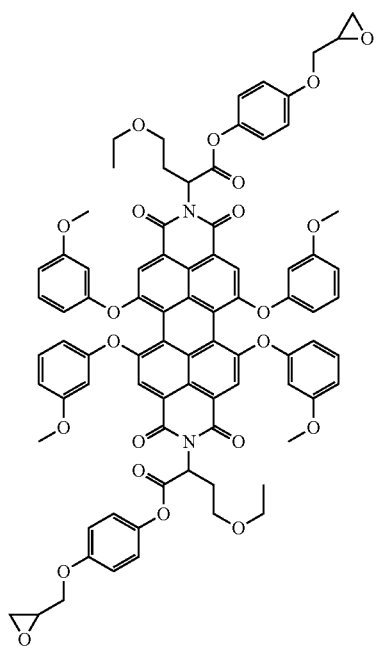
576
-continued
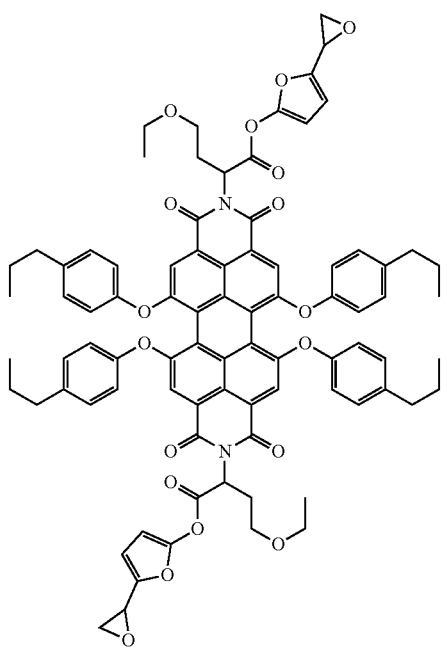
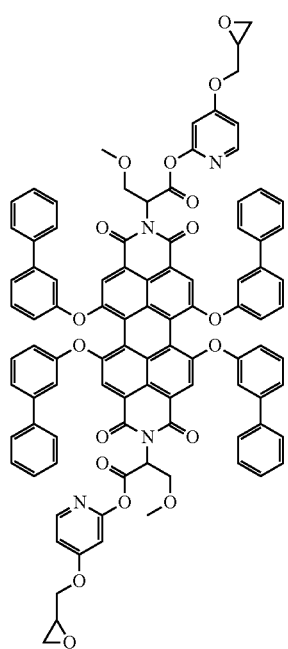
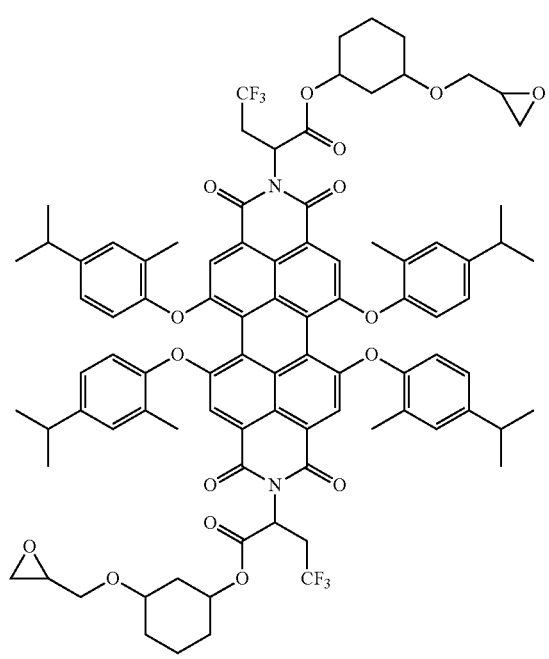

577
-continued
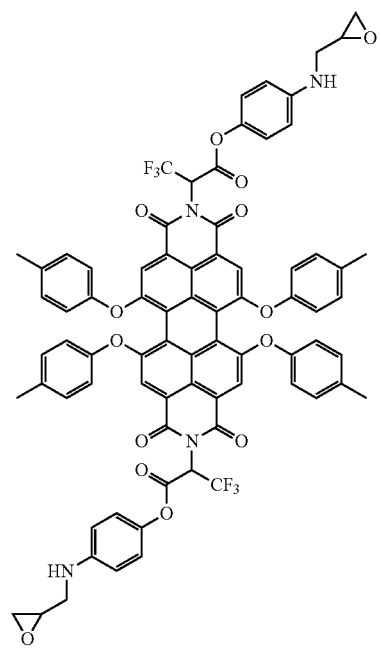
578
-continued
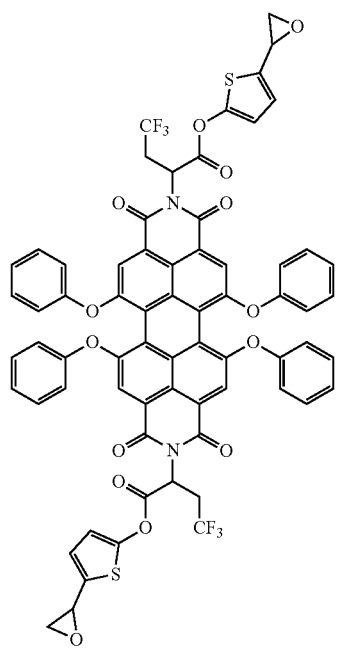
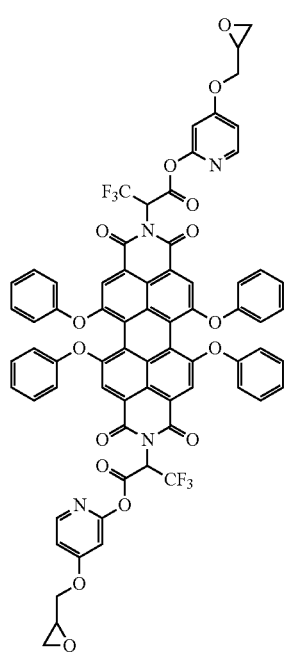
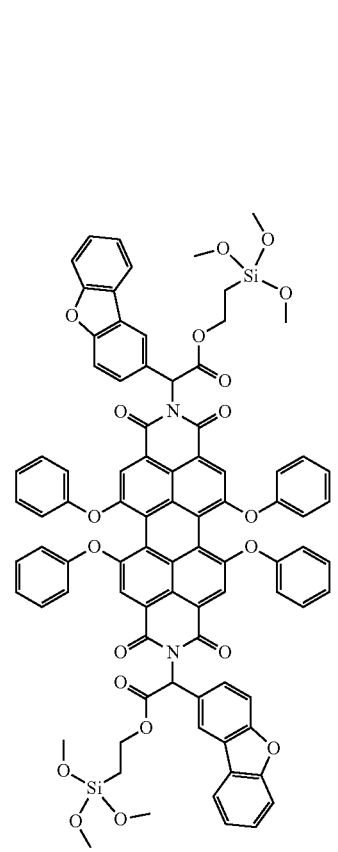

579
-continued
580
-continued
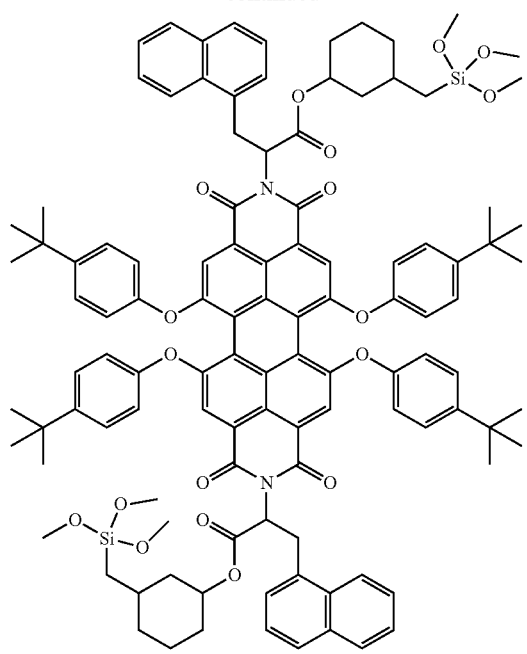
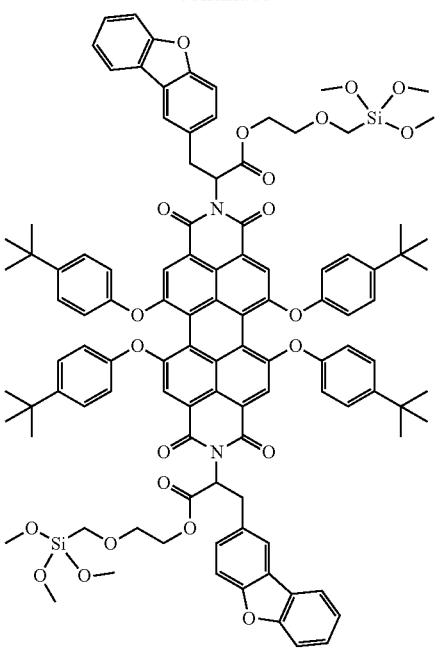

581
-continued
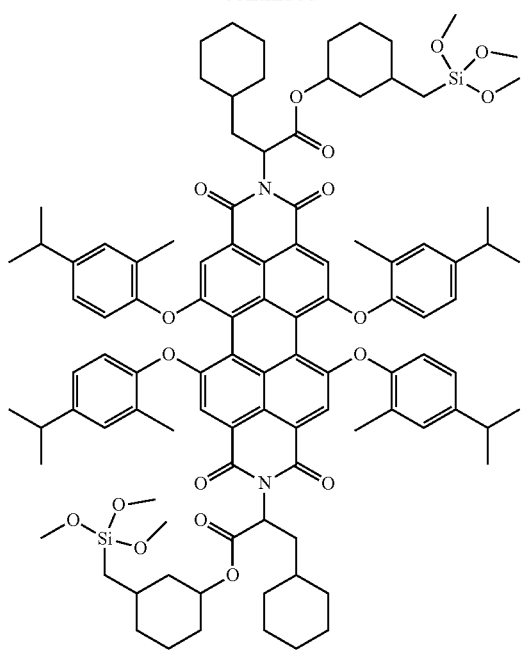
582
-continued
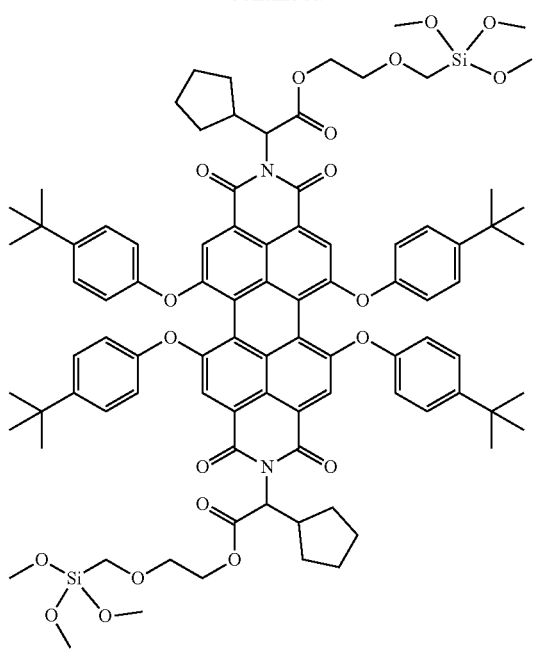
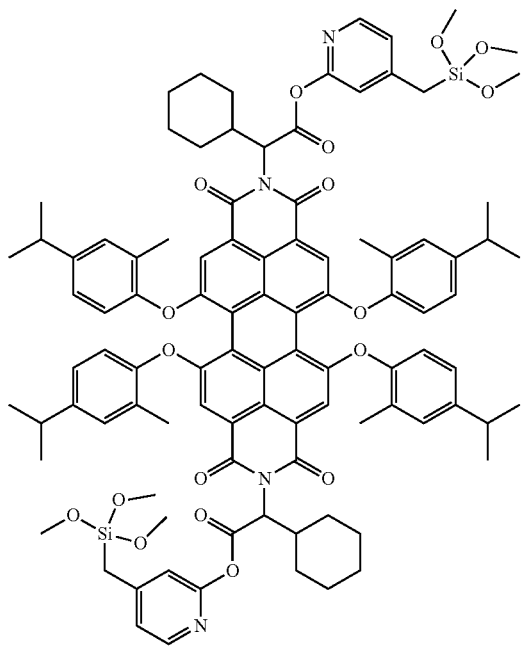
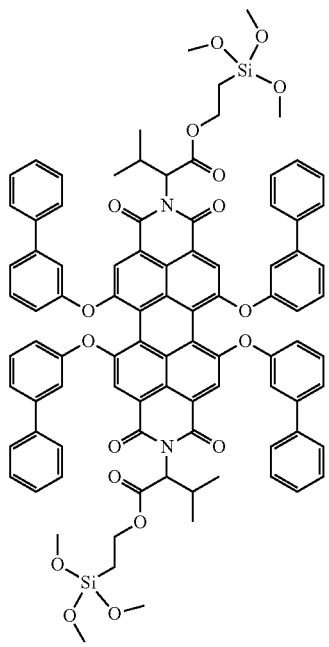

583
-continued
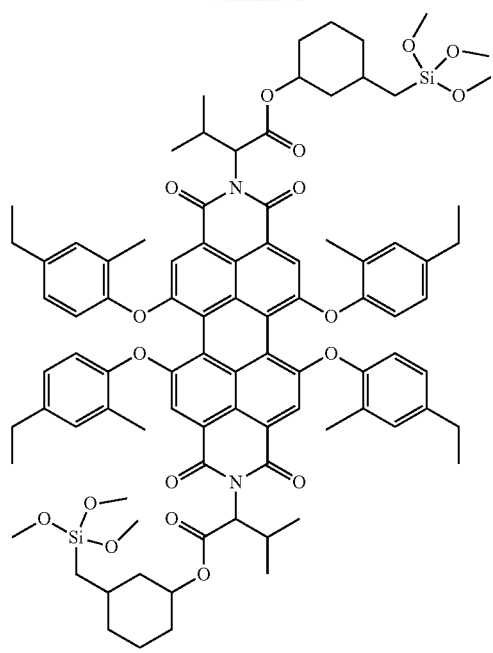
584
-continued
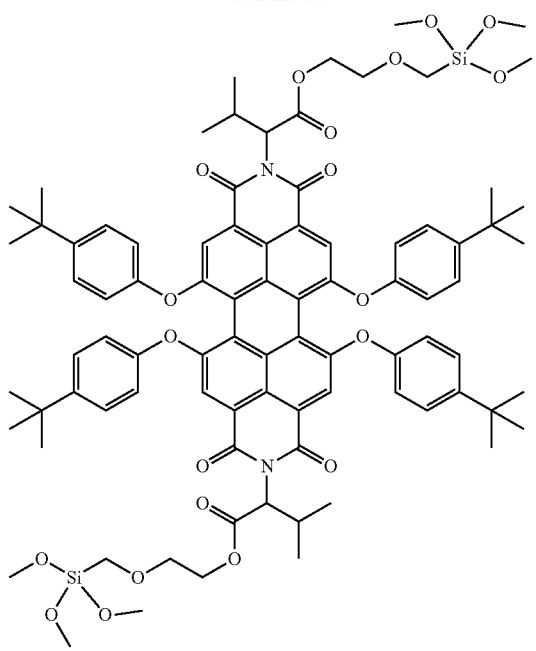
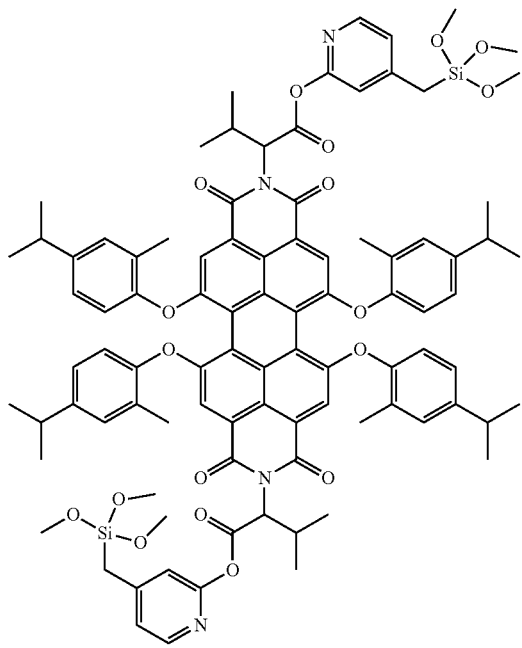
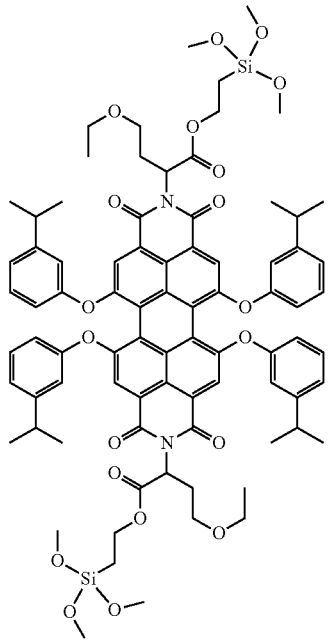

585
-continued
586
-continued
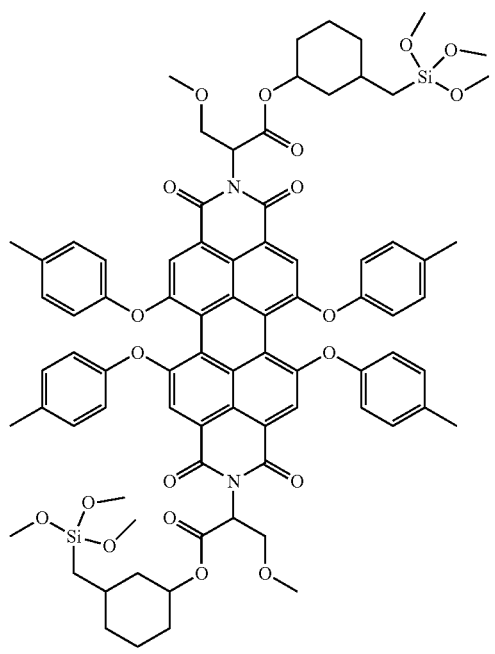
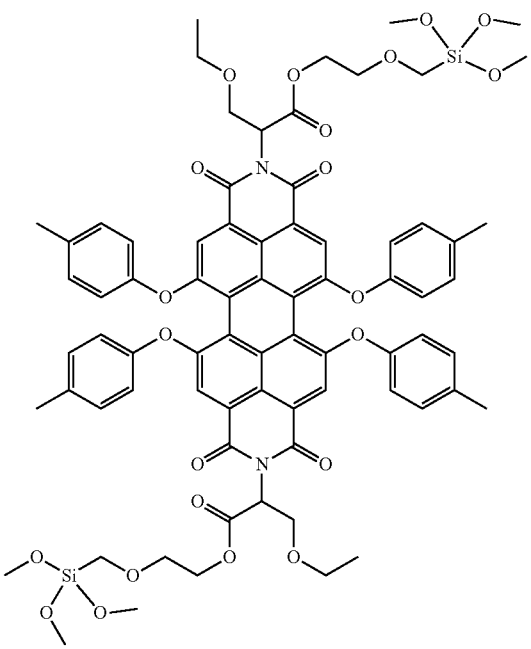
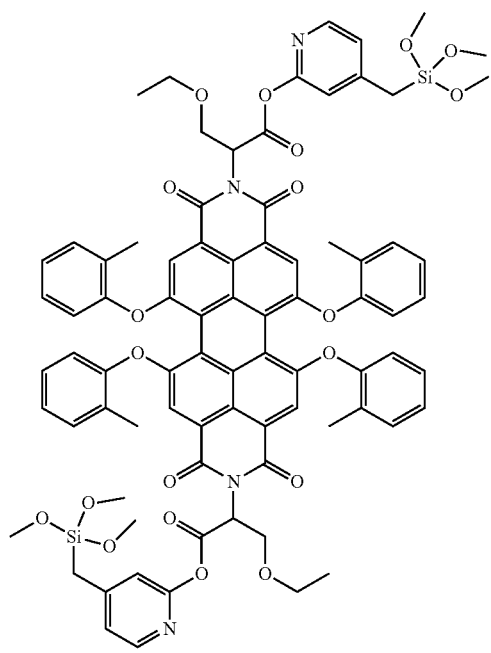
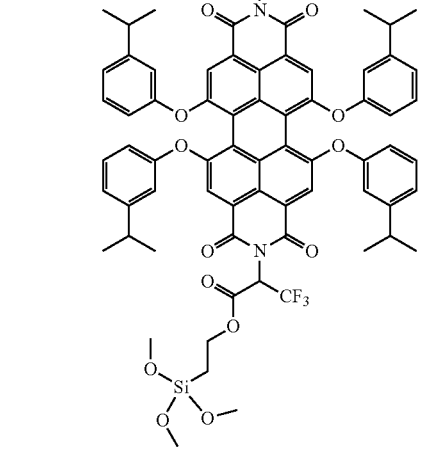

587
-continued
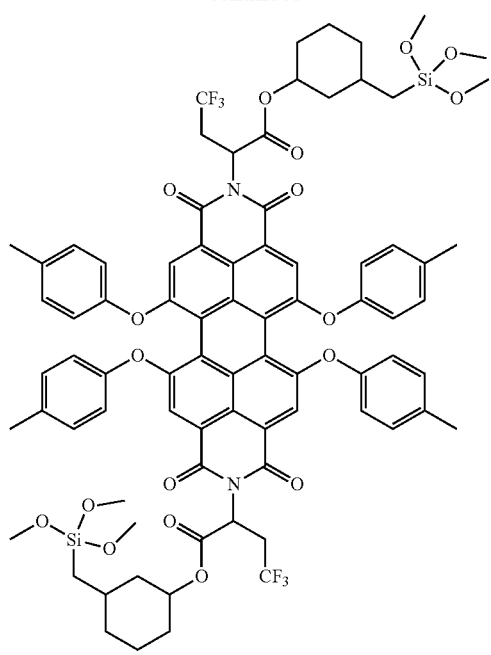
588
-continued
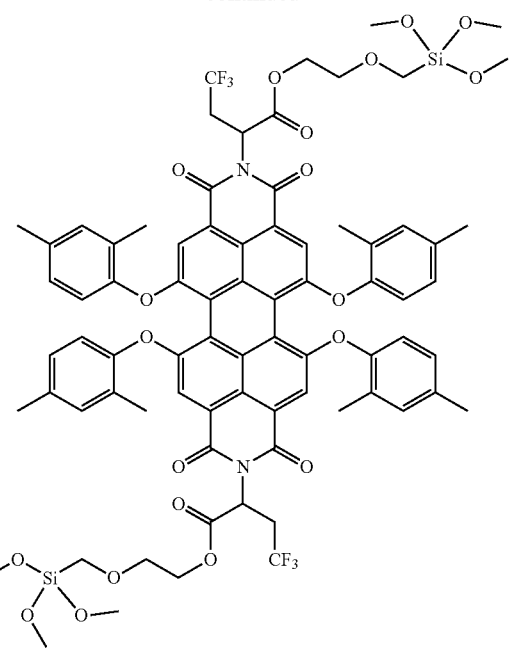
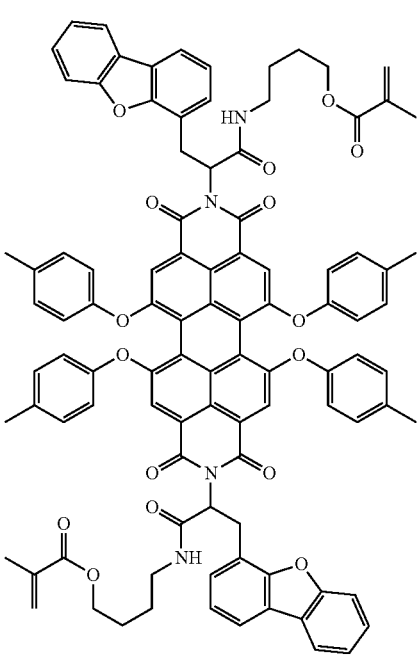

589
-continued
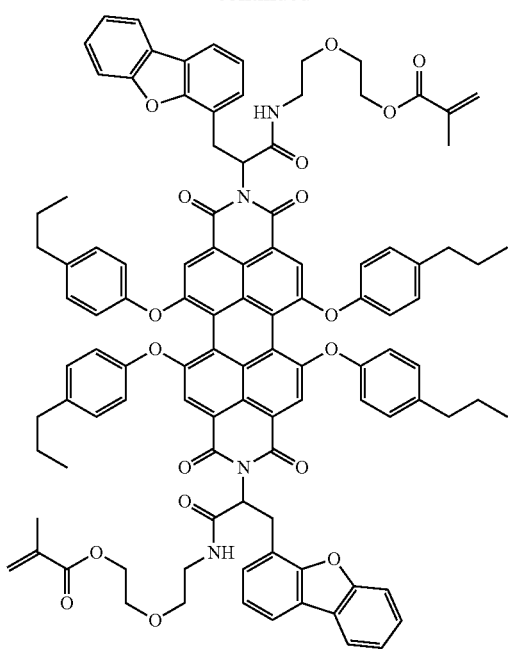
590
-continued
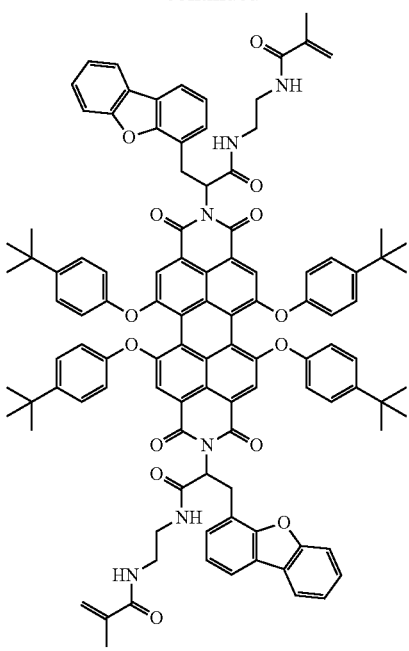
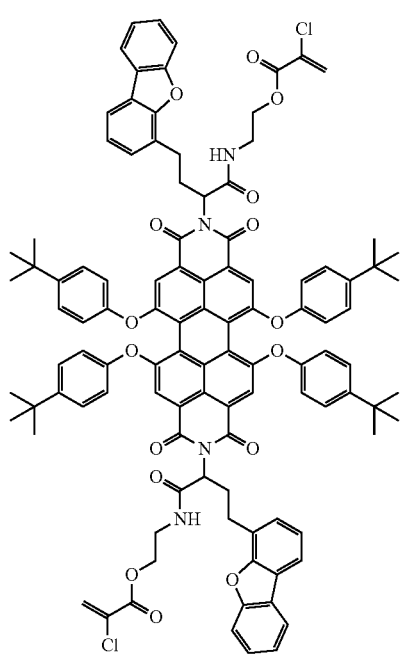
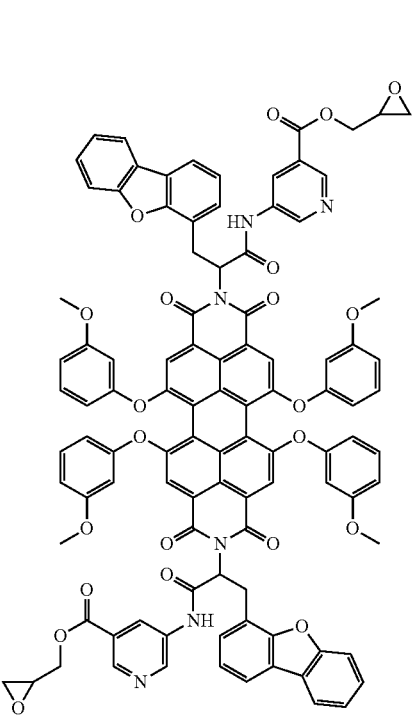

591
-continued
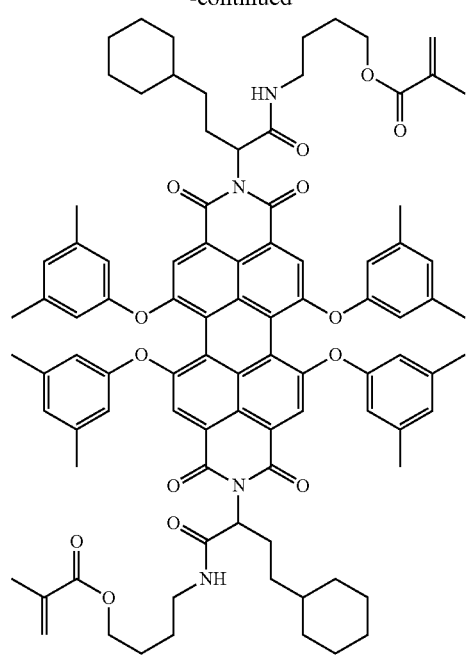
592
-continued
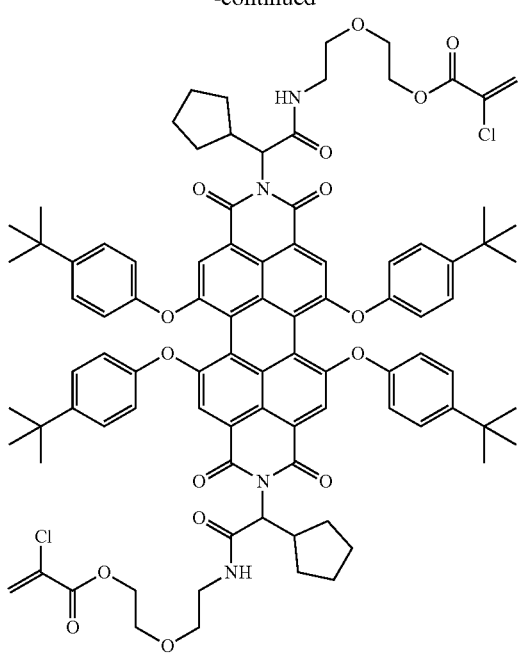
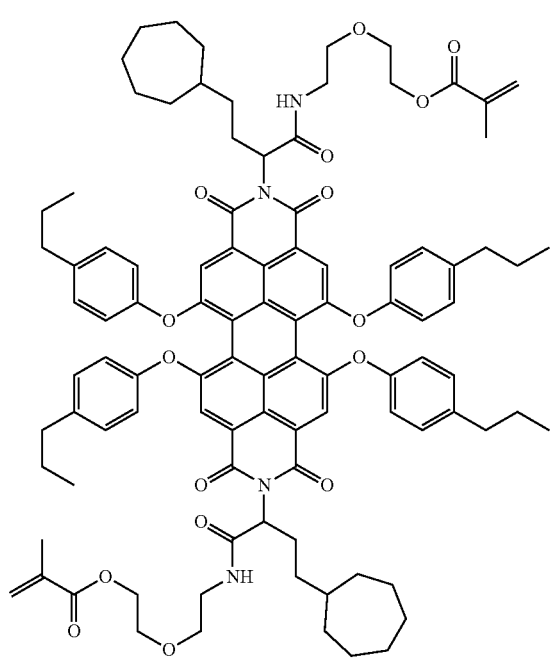
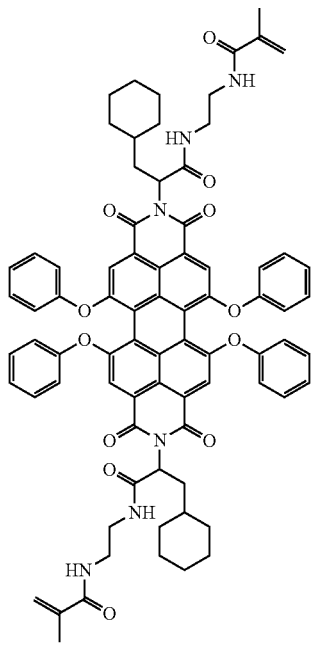

593
-continued
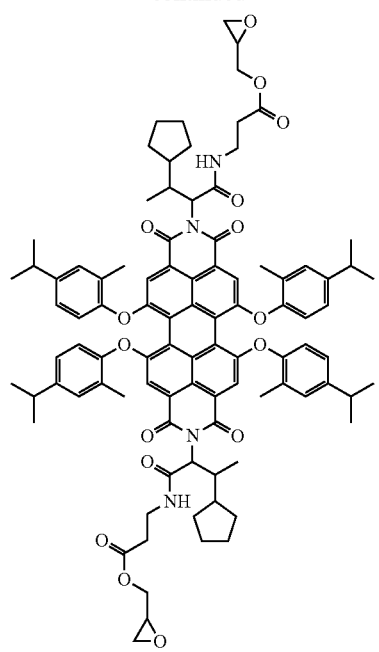
594
-continued
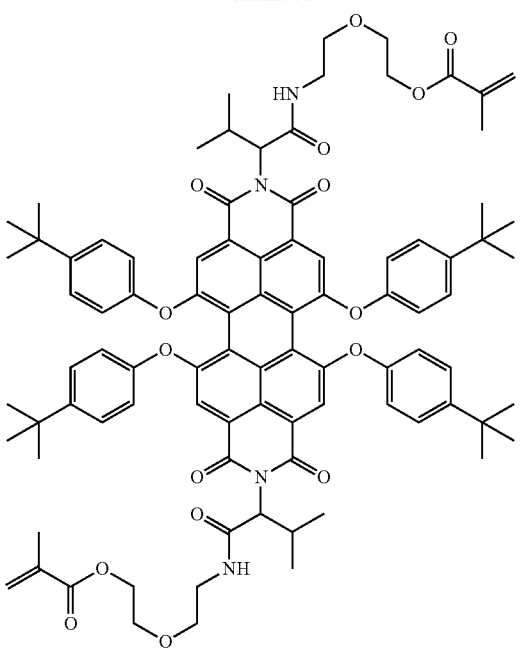
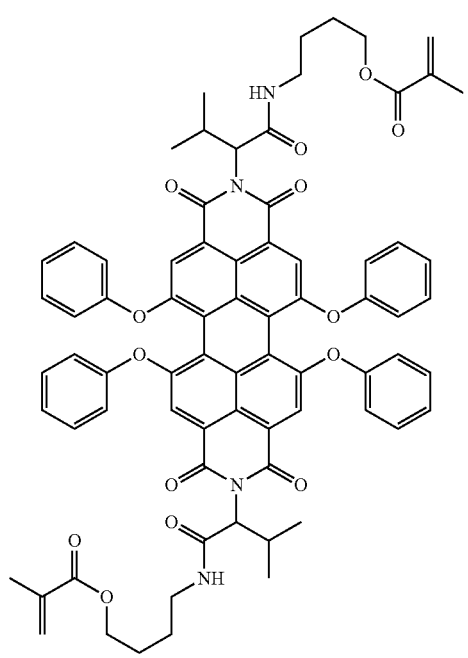
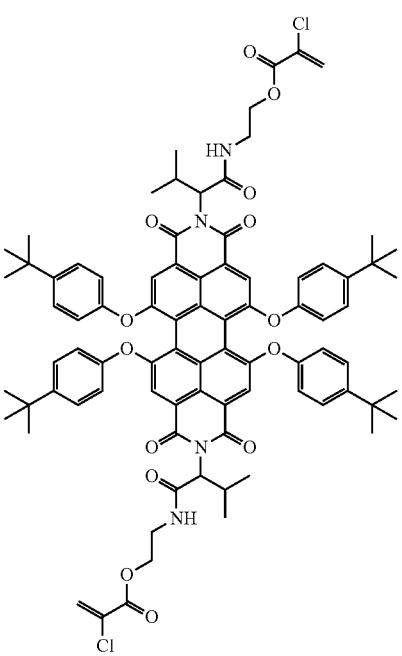

595
-continued
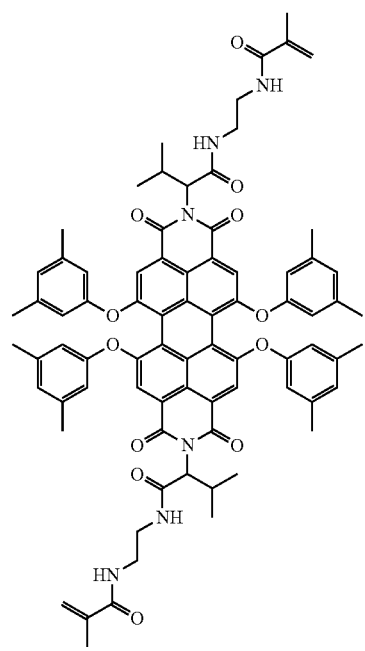
596
-continued
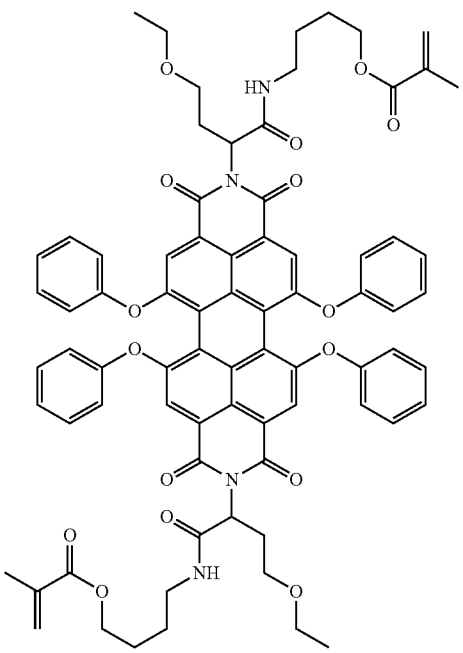
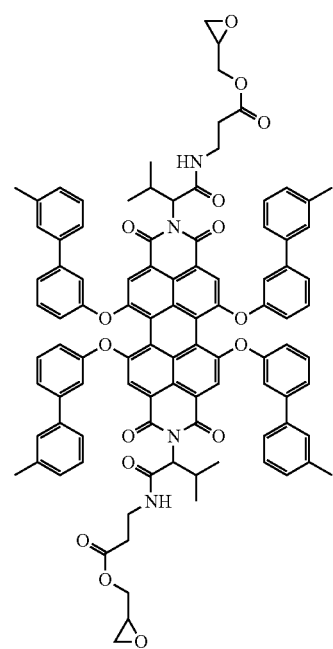
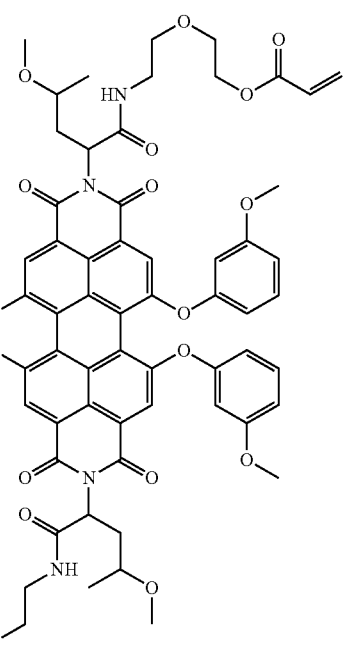

597
-continued
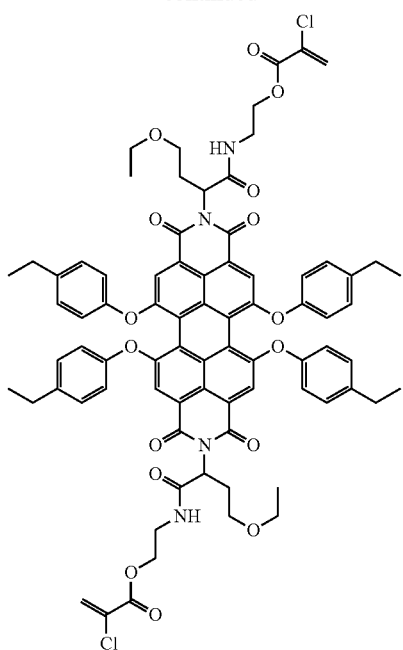
598
-continued
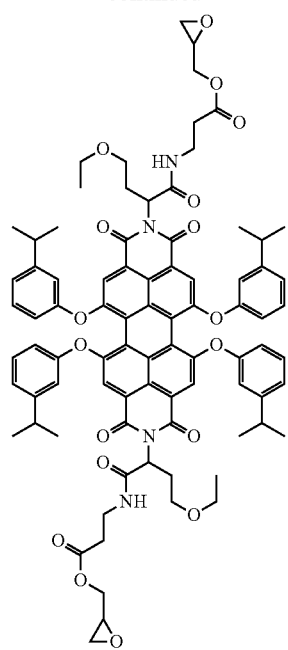
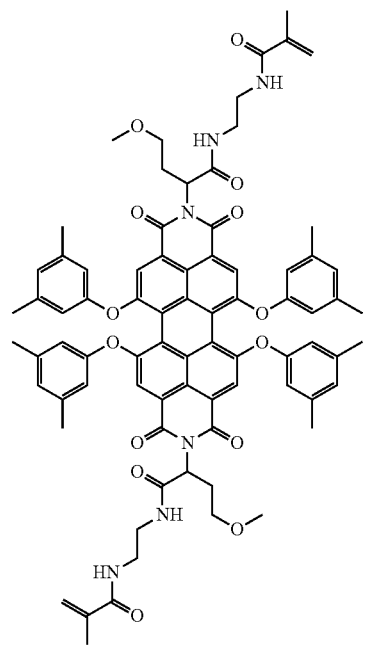
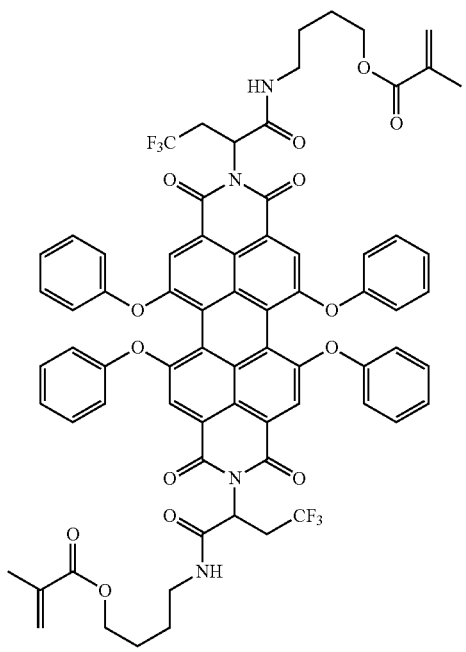

599
-continued
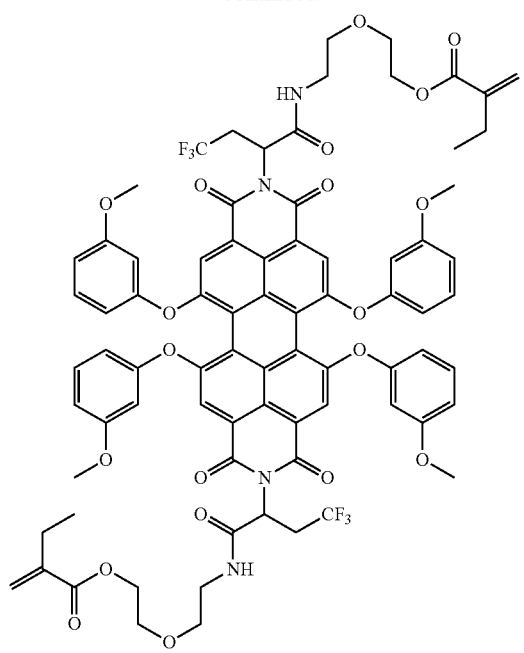
600
-continued
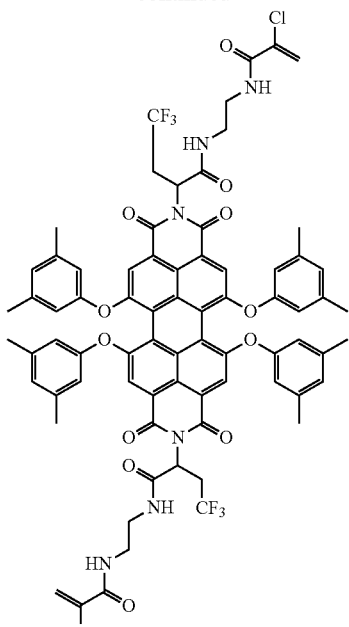
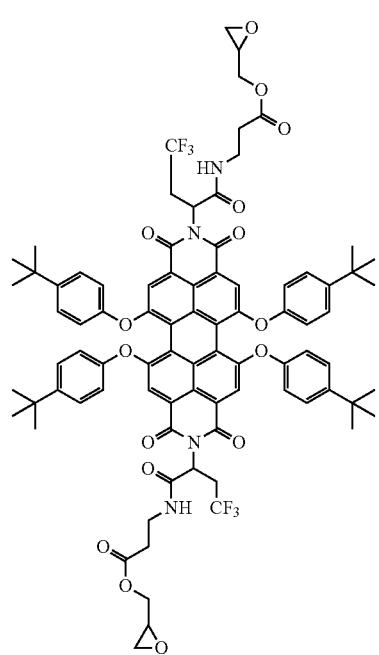 [SMILES: CC(C)(C)c1ccc(Oc2cc3c4c(cc(Oc5ccc(C(C)(C)C)cc5)c5c6c(Oc7ccc(C(C)(C)C)cc7)cc7c8c(cc(Oc9ccc(C(C)(C)C)cc9)c(c2c45)c86)C(=O)N(C(CC(F)(F)F)C(=O)NCCC(=O)OCC2CO2)C7=O)C(=O)N(C(CC(F)(F)F)C(=O)NCCC(=O)OCC2CO2)C3=O)cc1]

601
602
-continued
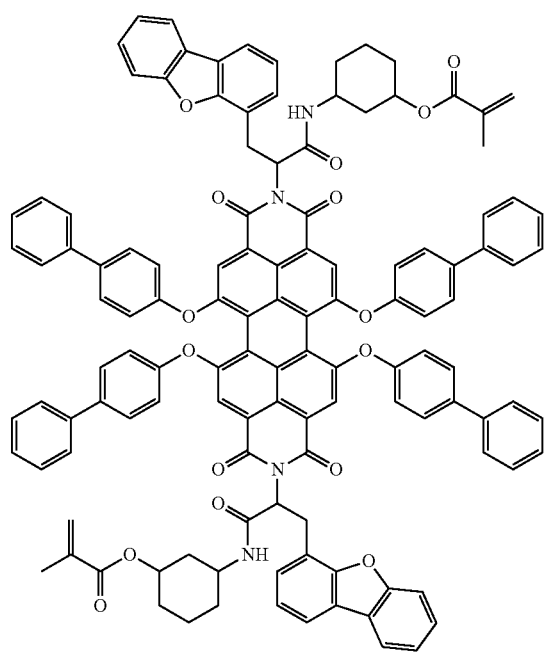
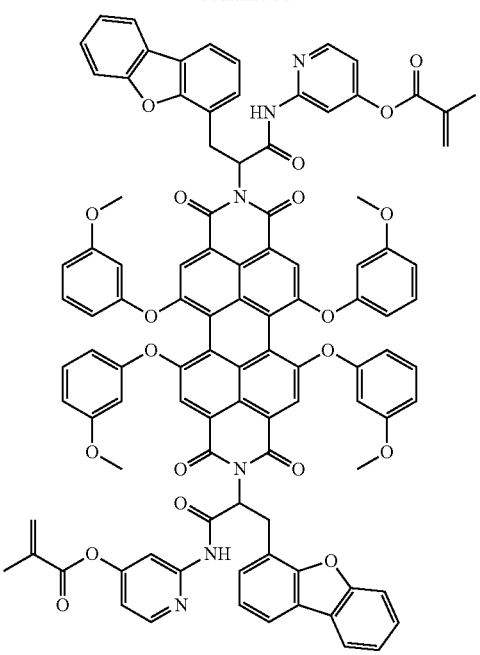
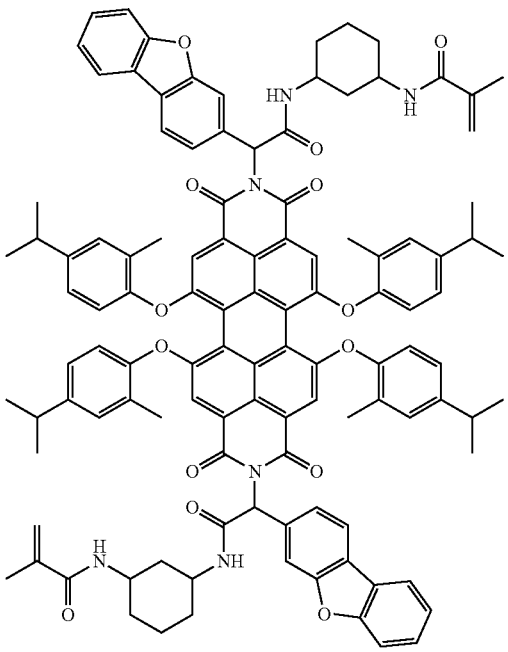

603
-continued
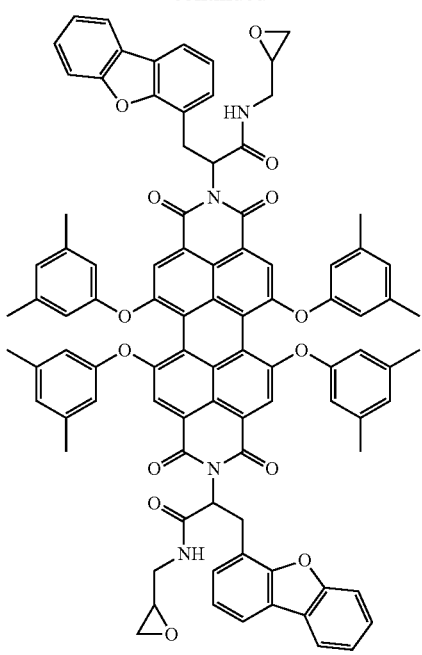
604
-continued
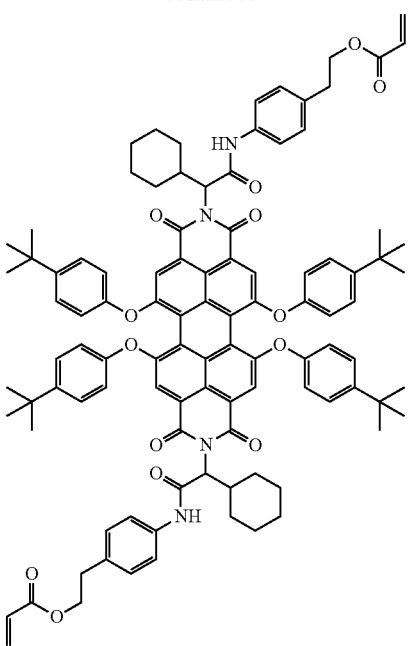
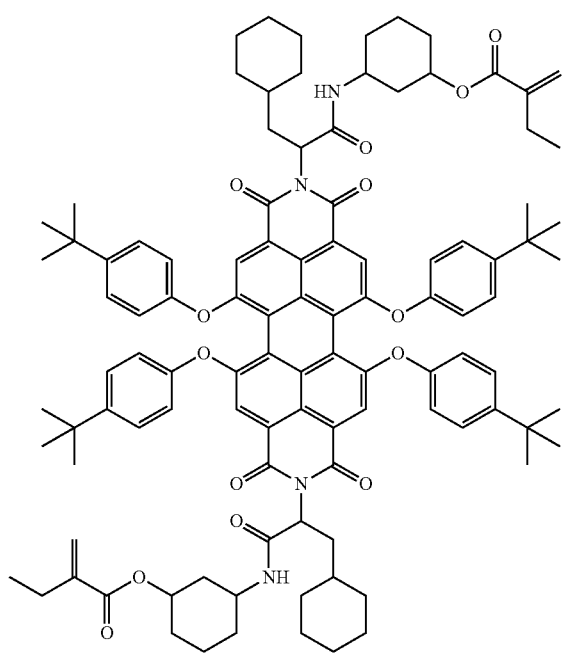
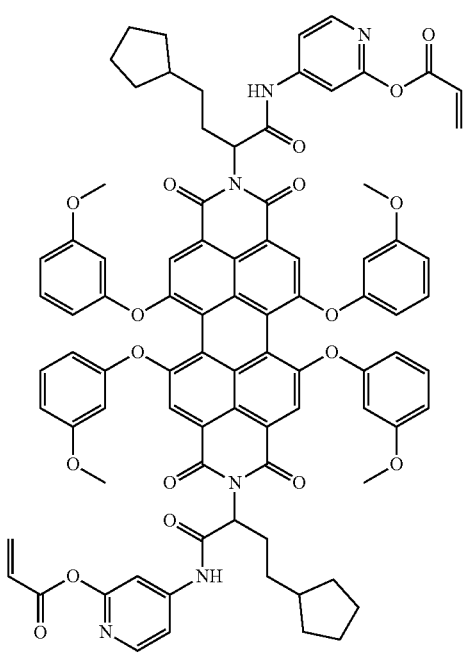

605
-continued
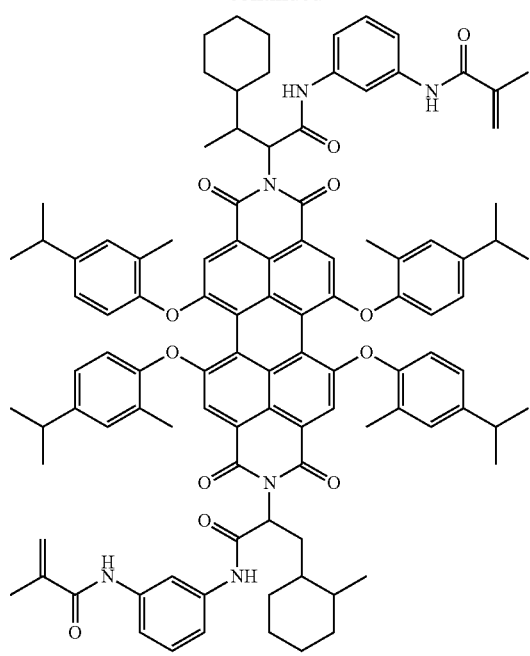
606
-continued
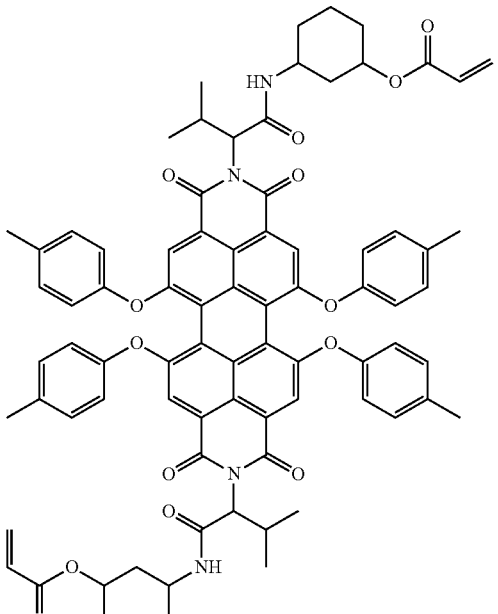
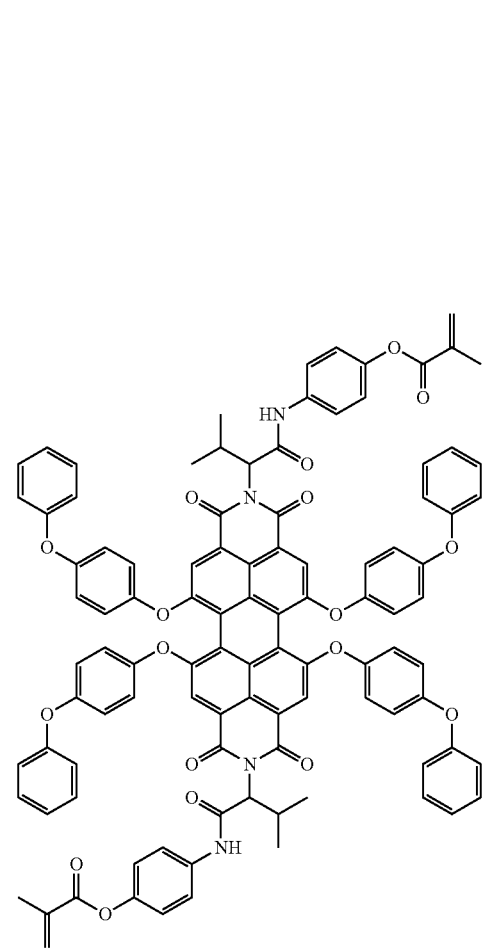

607
-continued
608
-continued
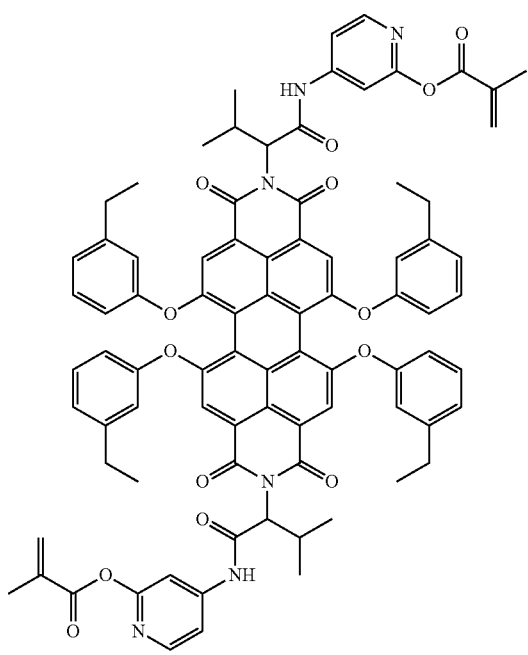
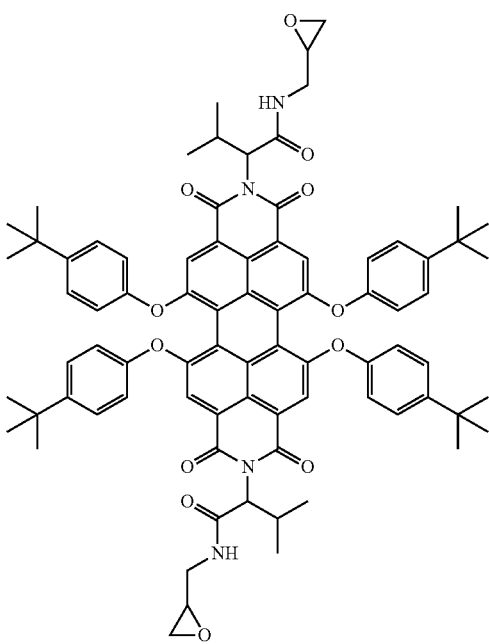
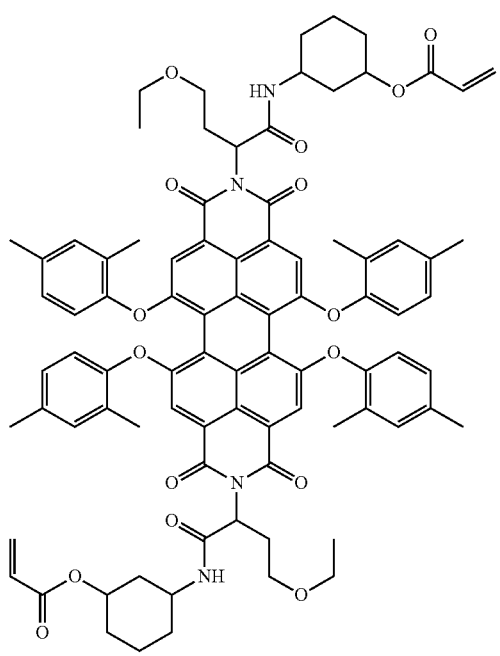

609
-continued
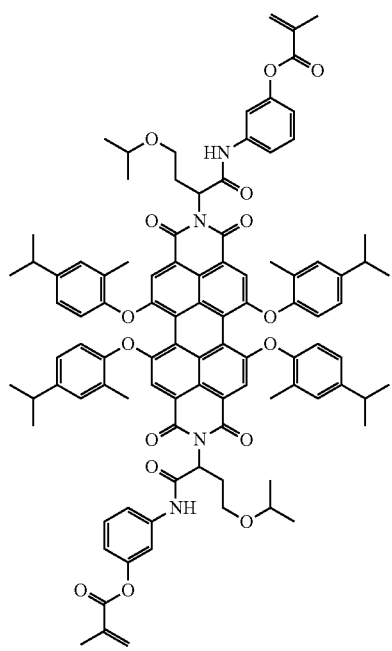
610
-continued
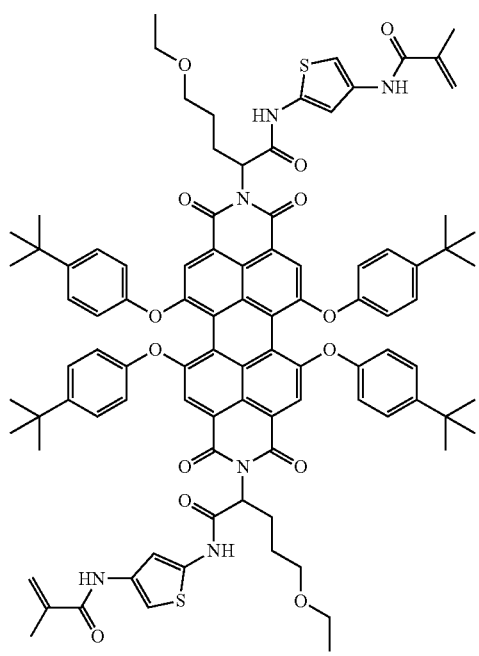
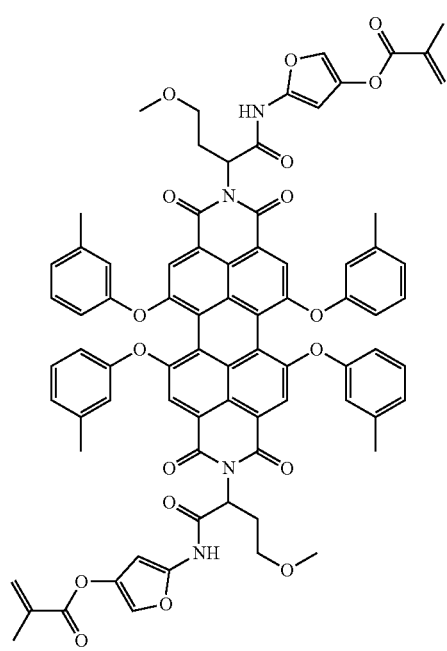
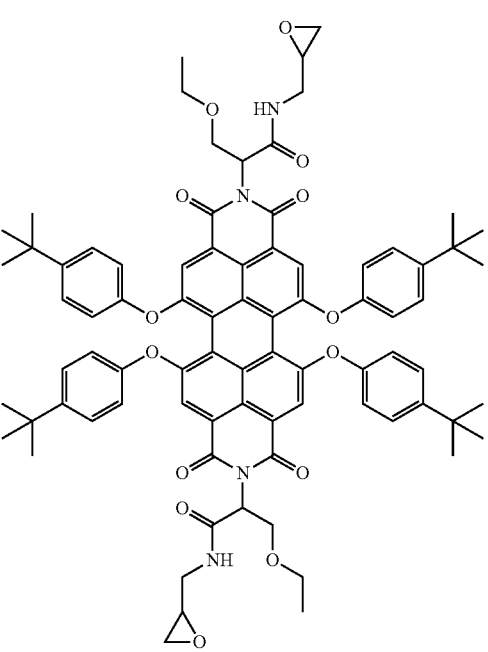

611
-continued
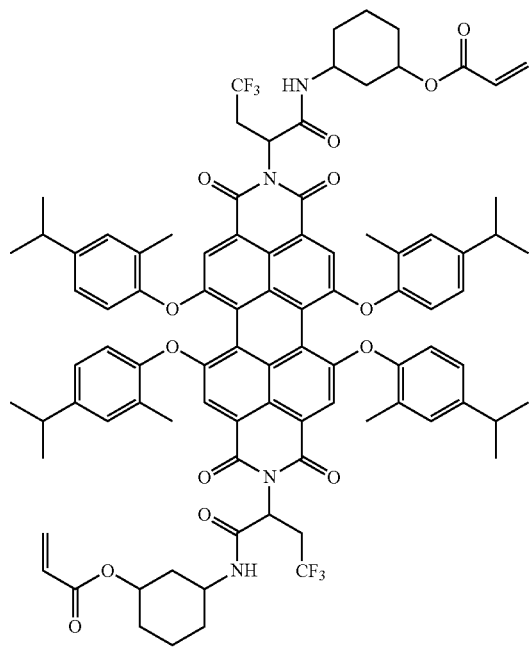
612
-continued
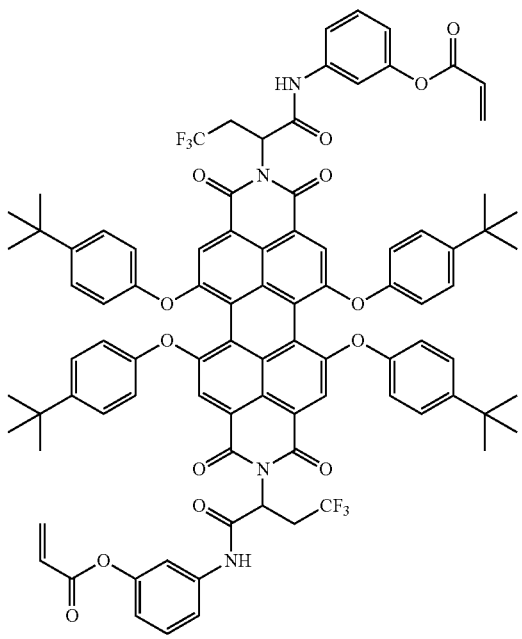
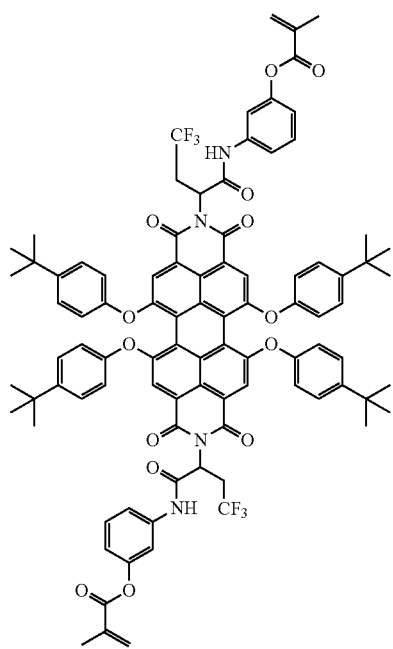

613
-continued
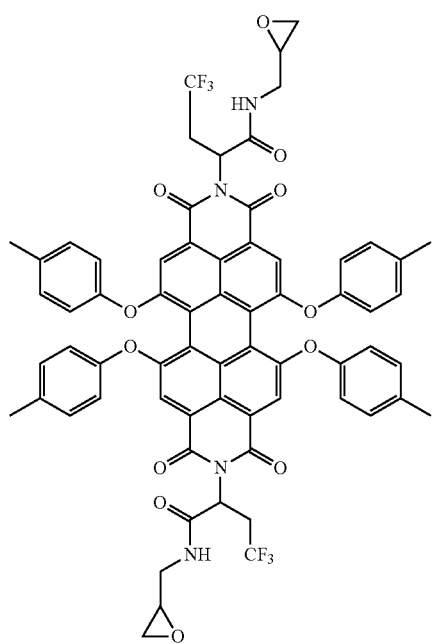
614
-continued
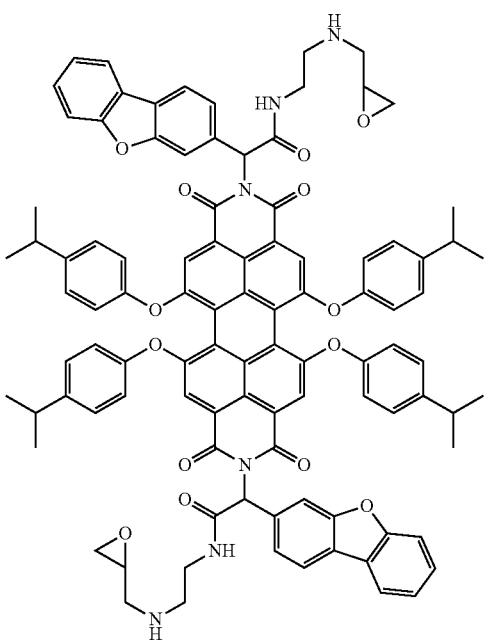
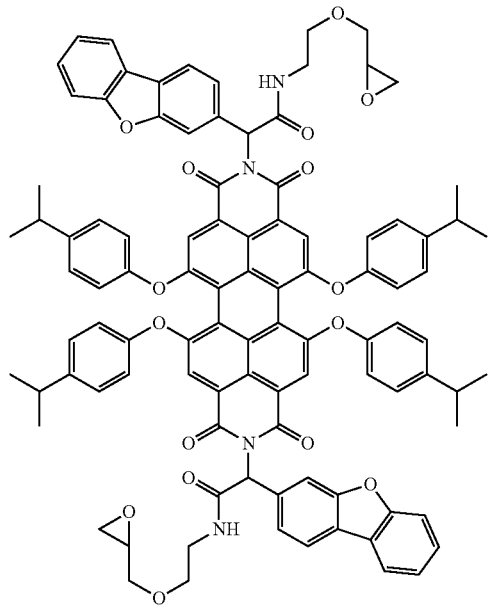
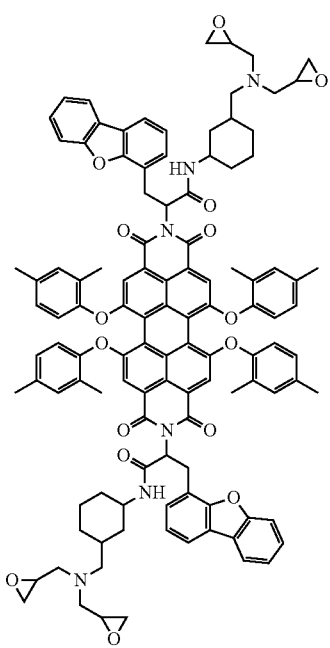

615
-continued
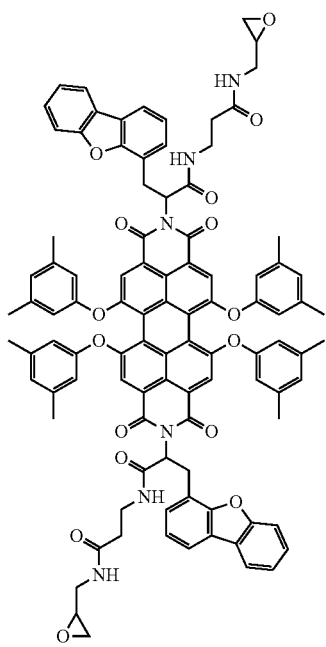
616
-continued
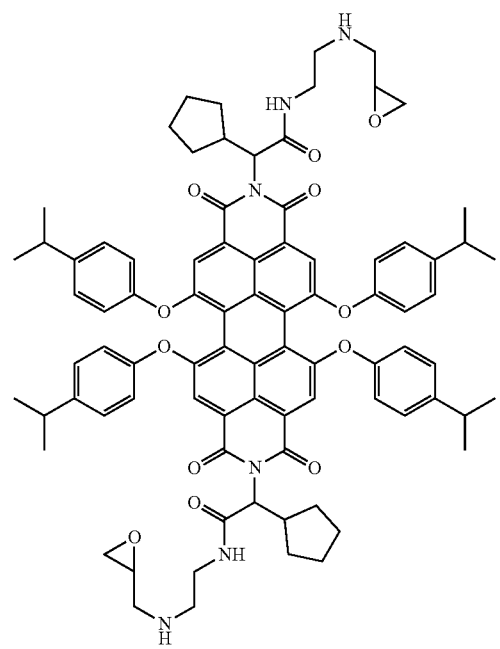
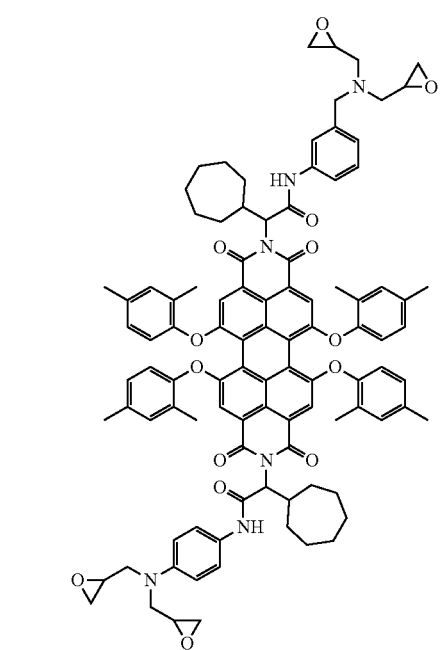

617
-continued
618
-continued
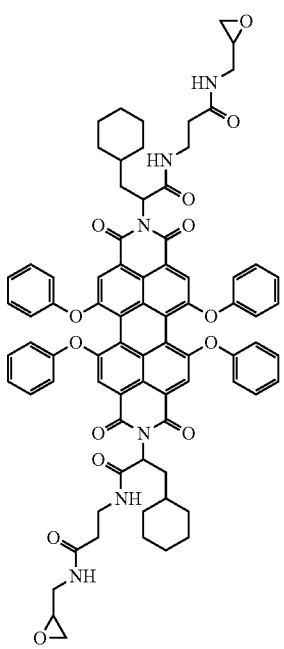
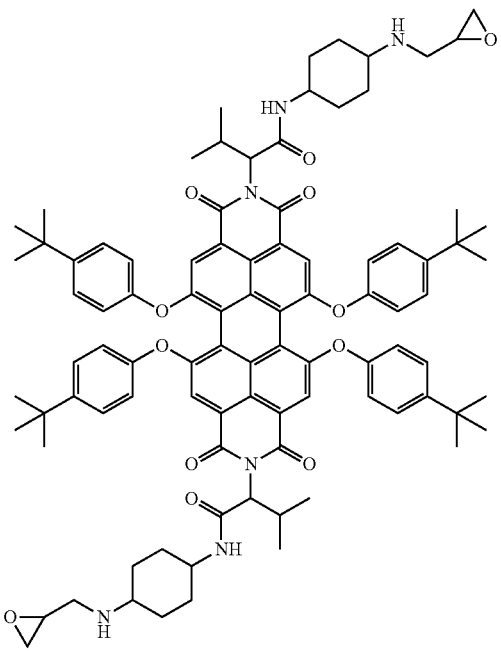
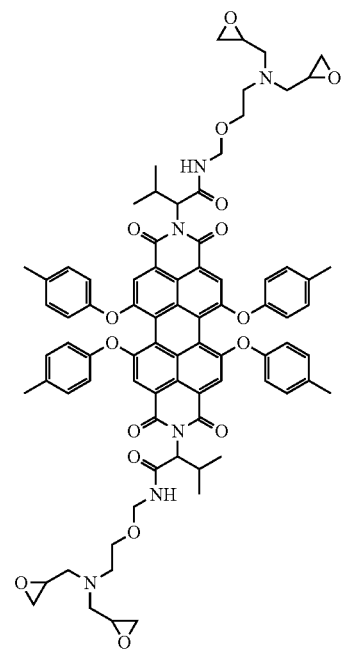

619
-continued
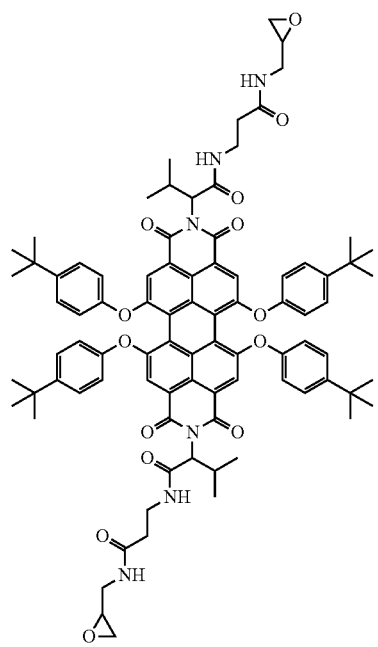
620
-continued
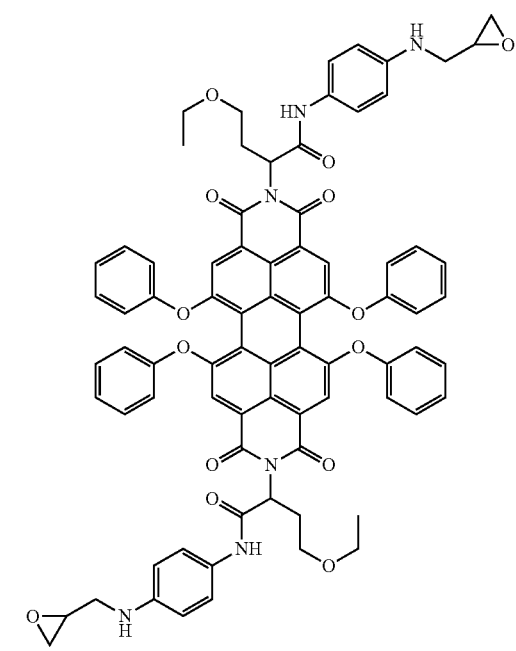
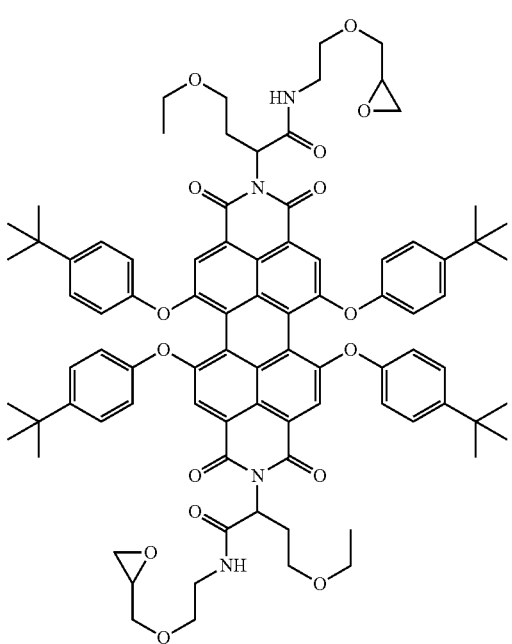
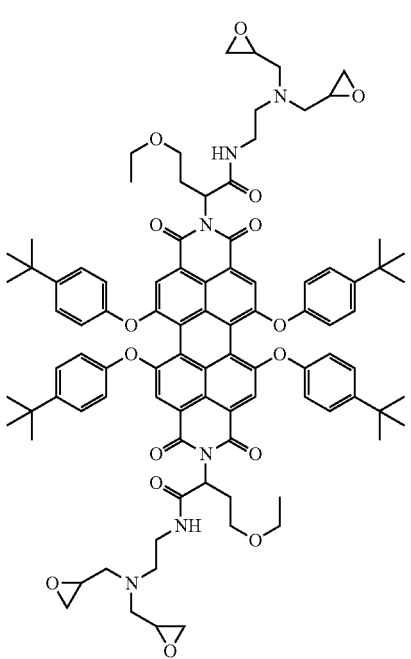

621
-continued
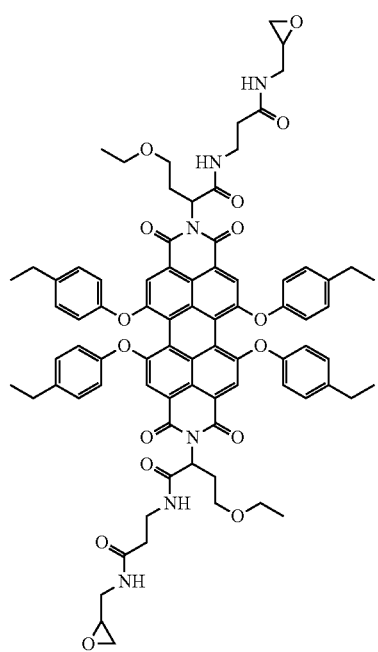
622
-continued
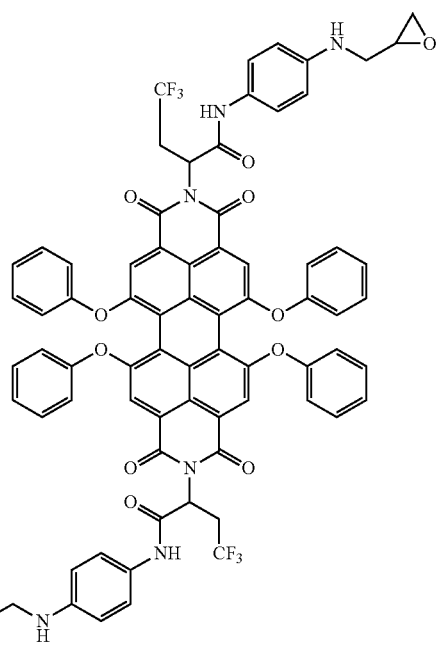
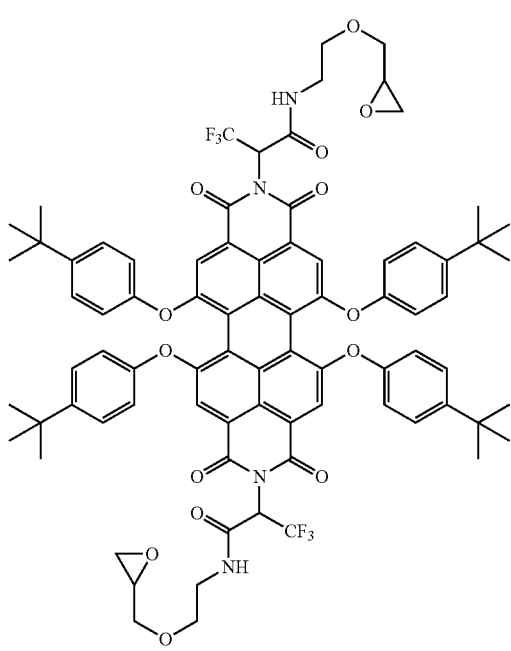
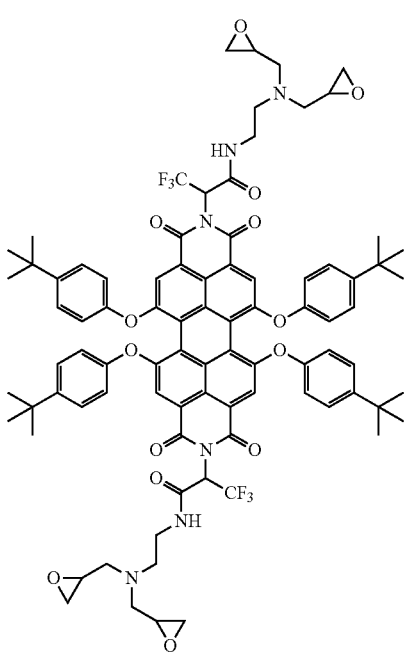

623
-continued
624
-continued
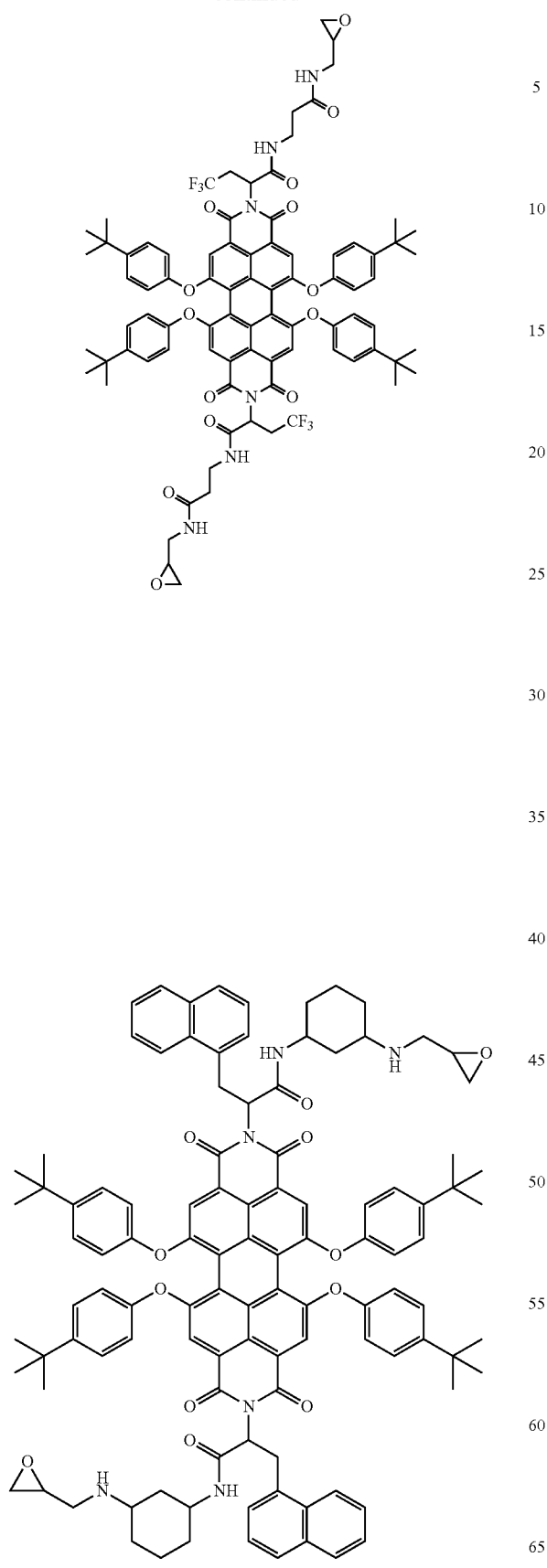

625
-continued
626
-continued
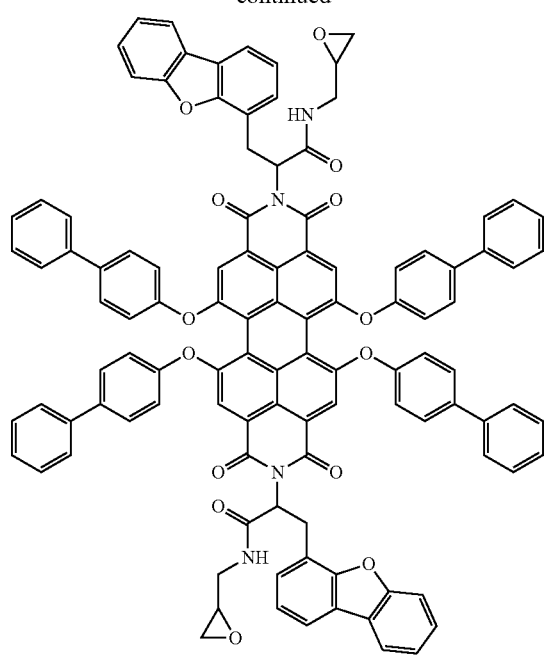
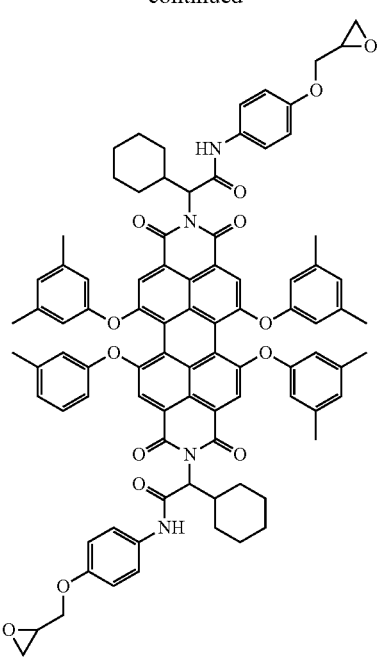
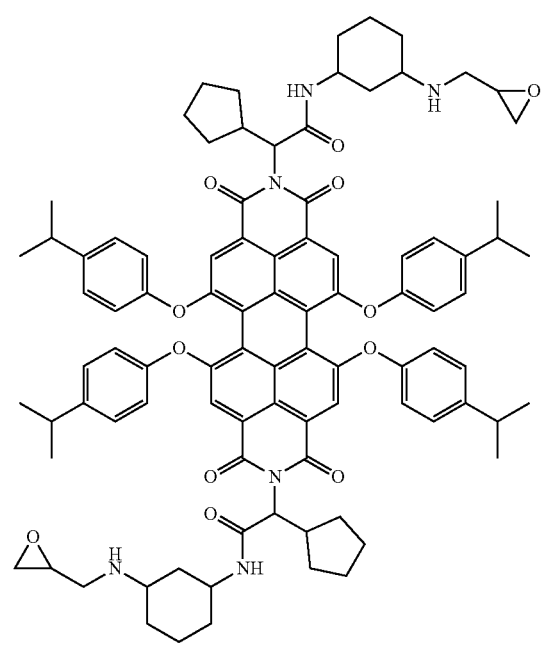
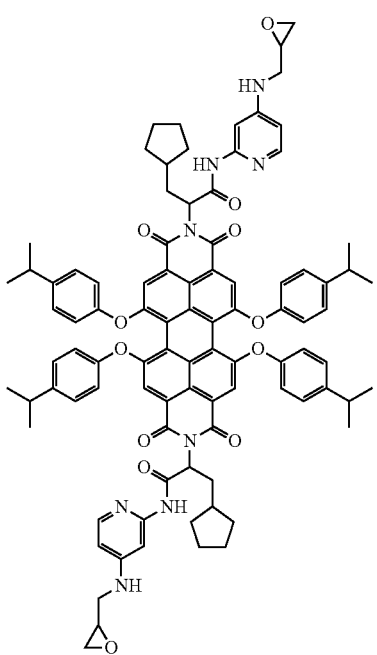

627
-continued
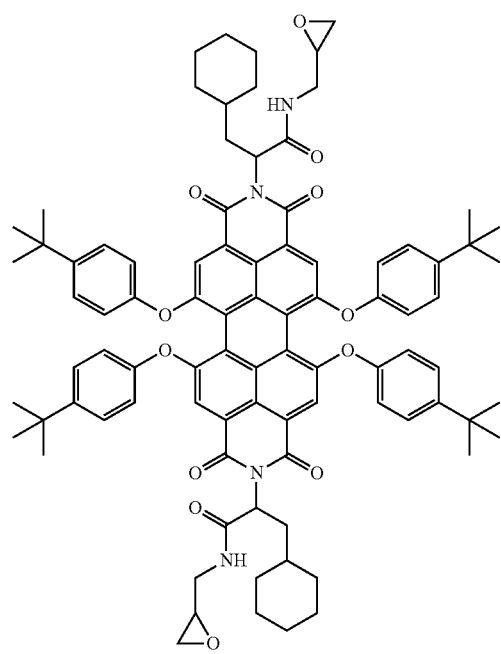
628
-continued
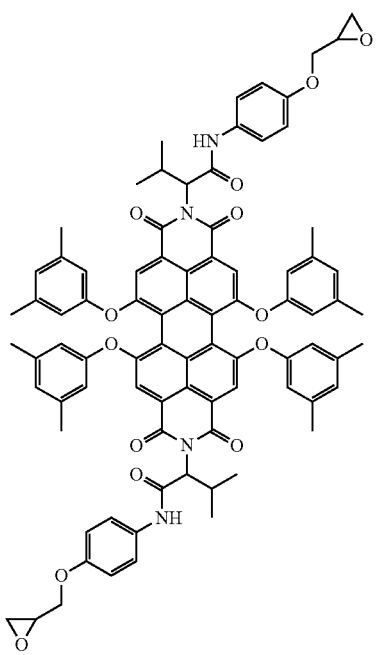
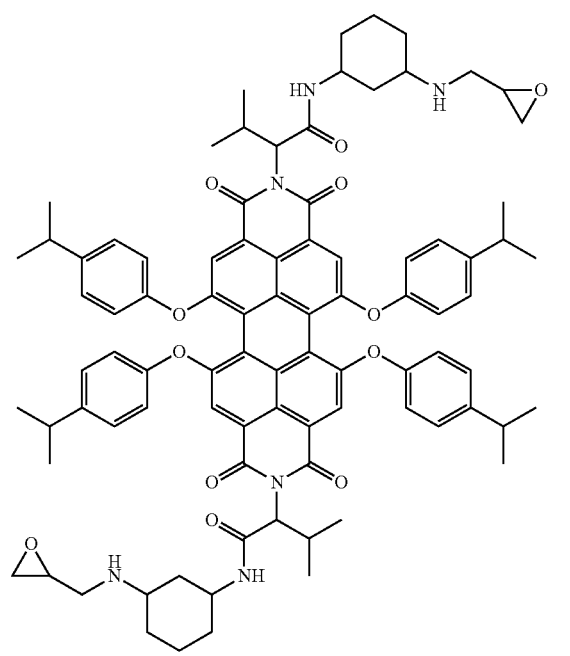
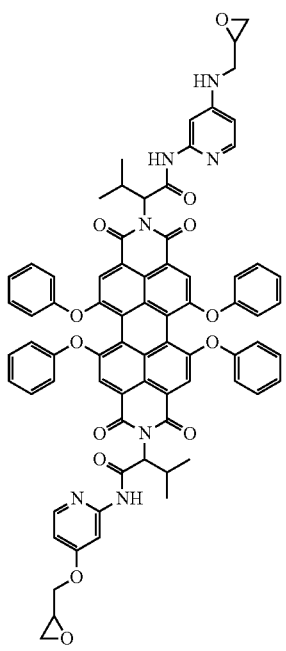

629
-continued
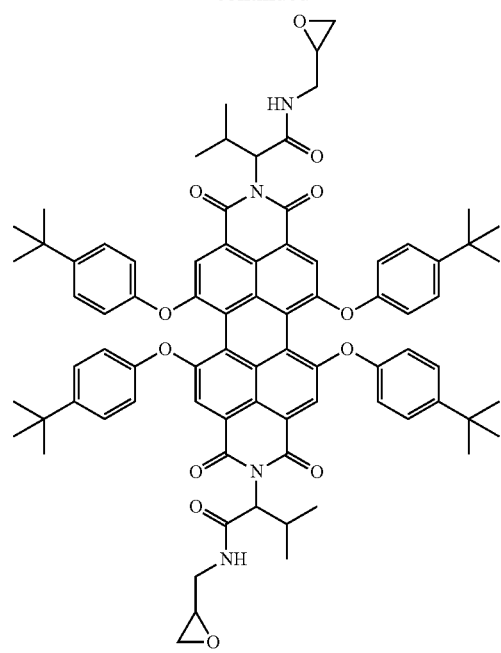
630
-continued
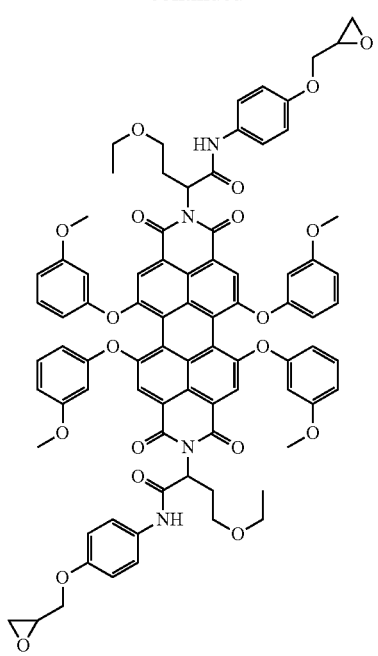
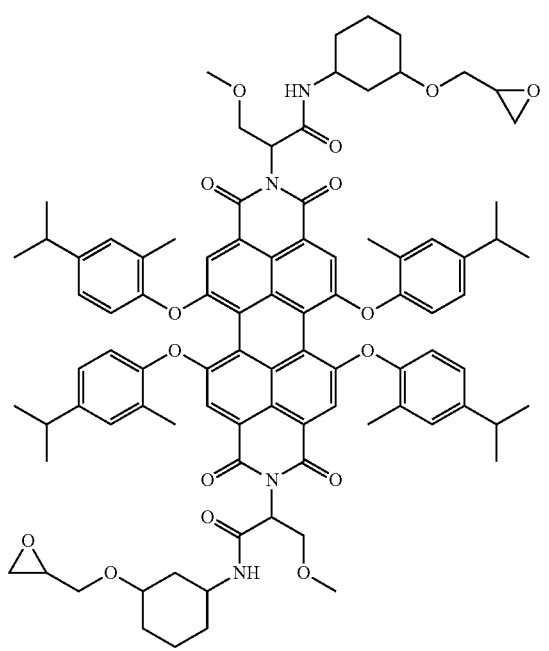
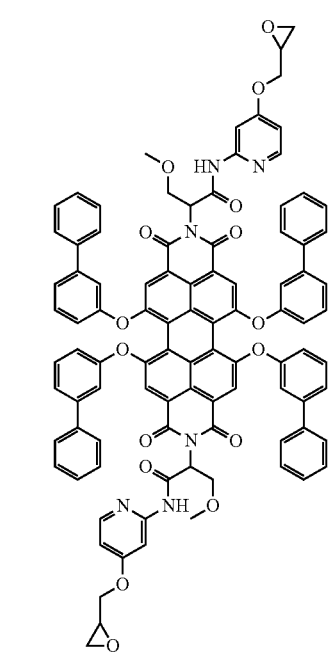

631
-continued
632
-continued
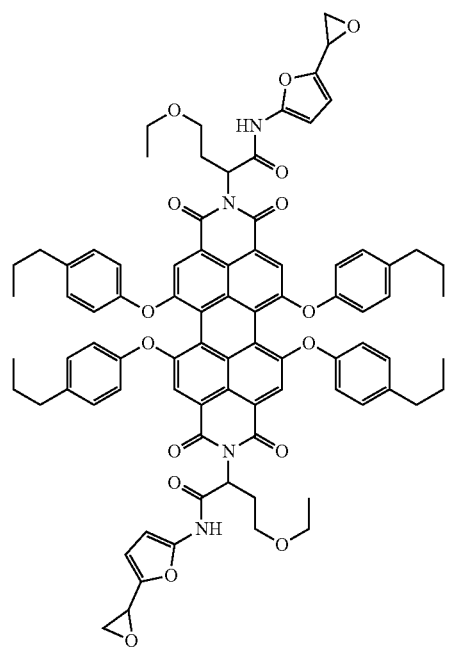
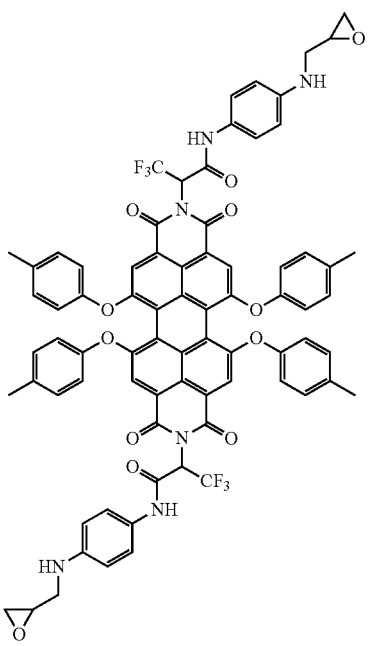
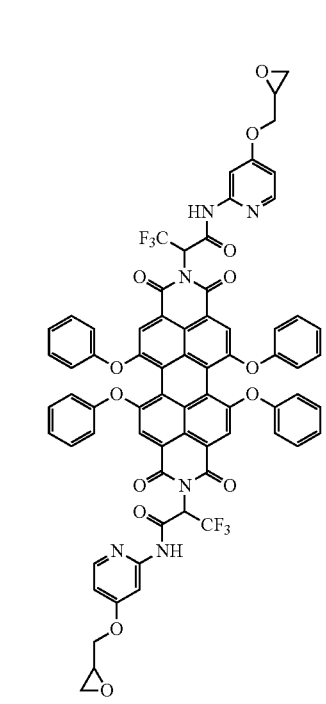

633
-continued
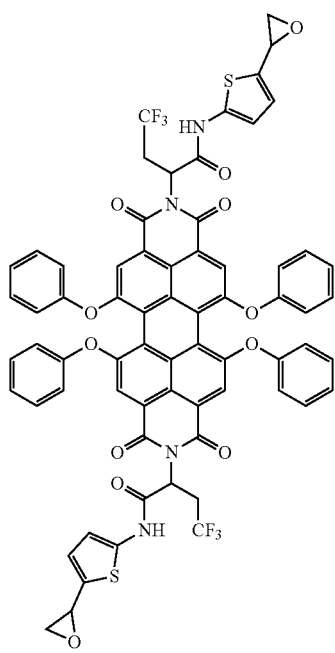
634
-continued
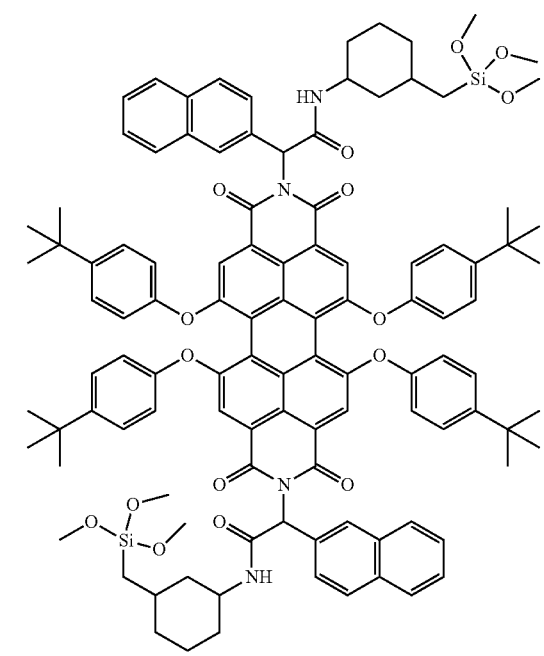
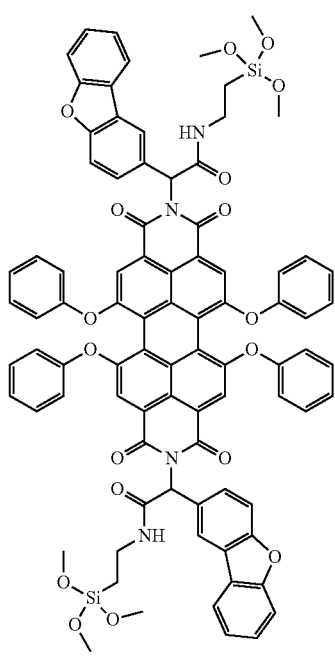
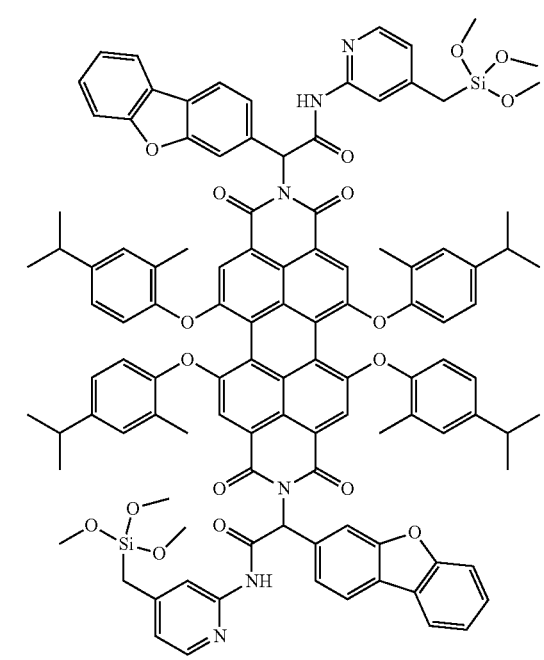

635
-continued
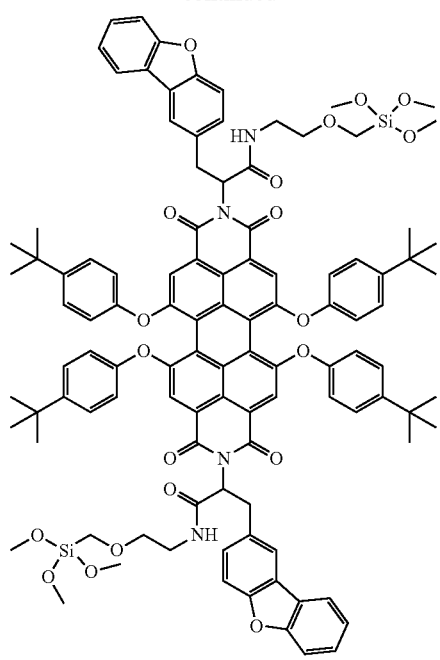
636
-continued
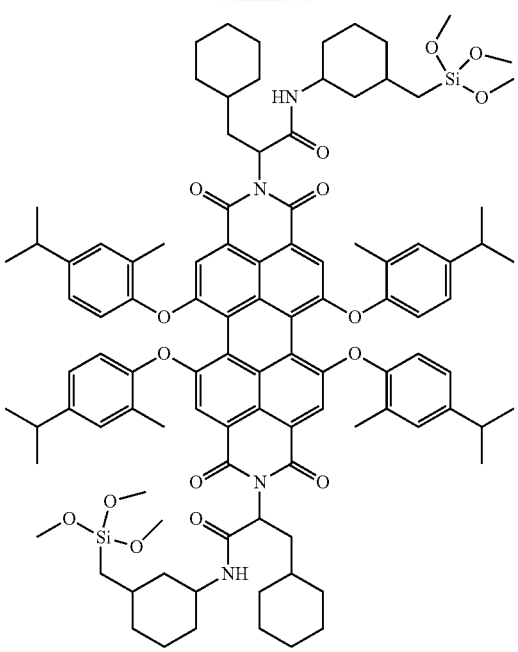
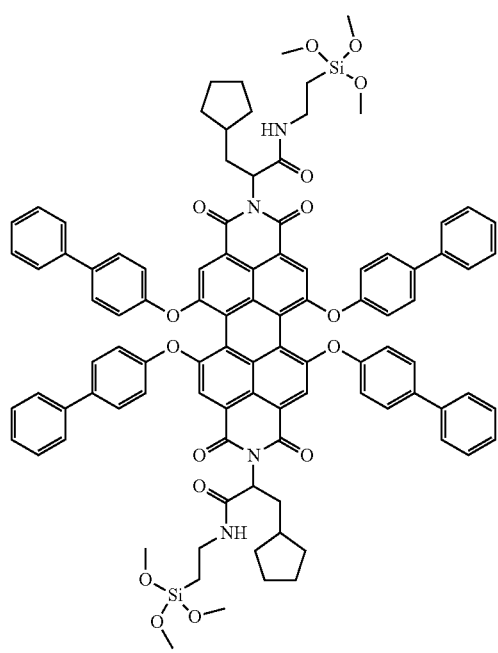
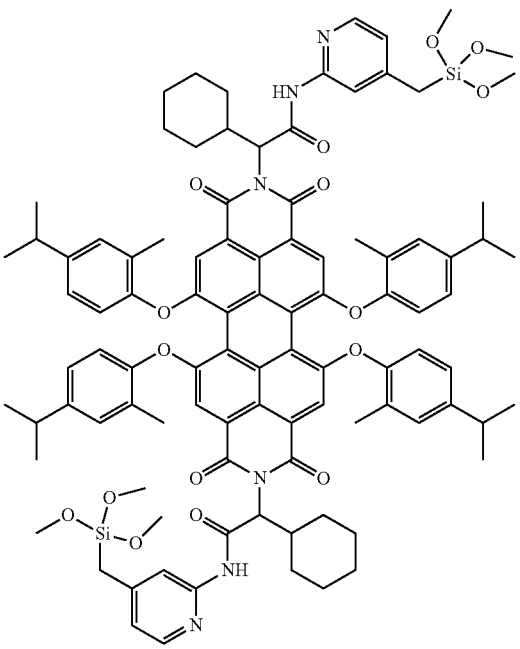

637
-continued
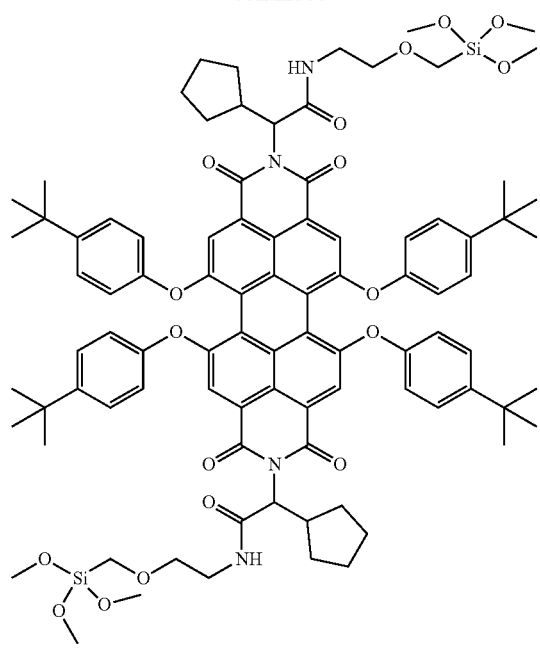
638
-continued
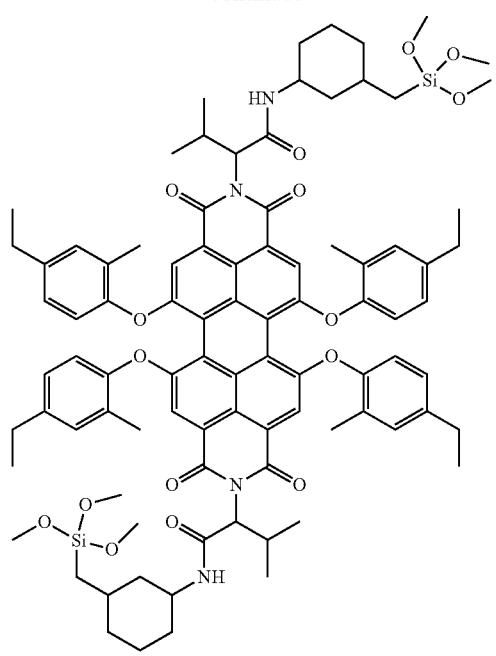
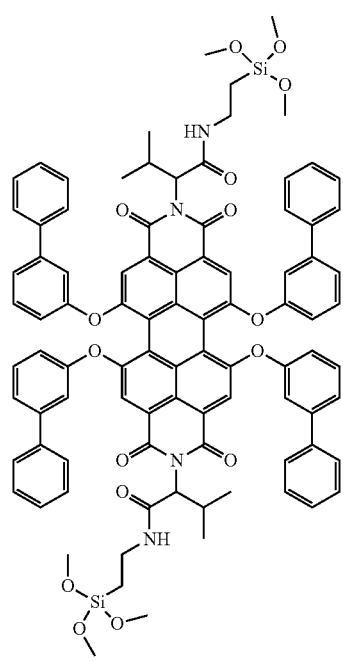
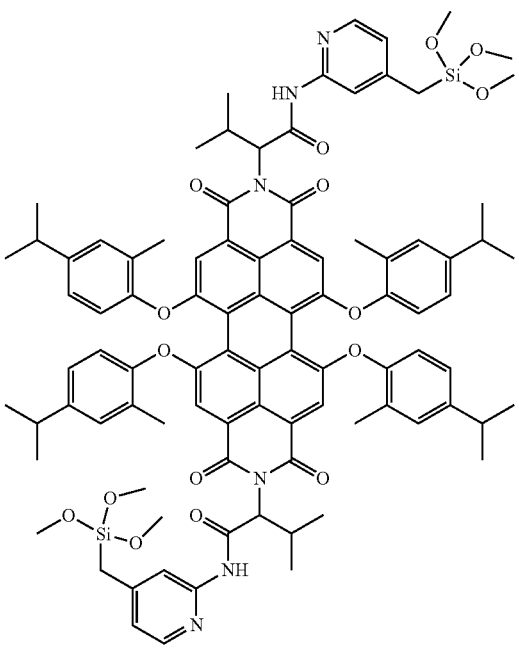

639
-continued
640
-continued
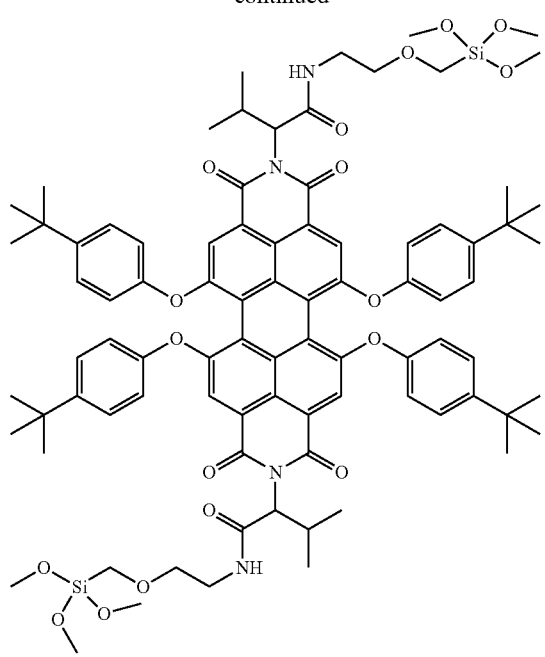
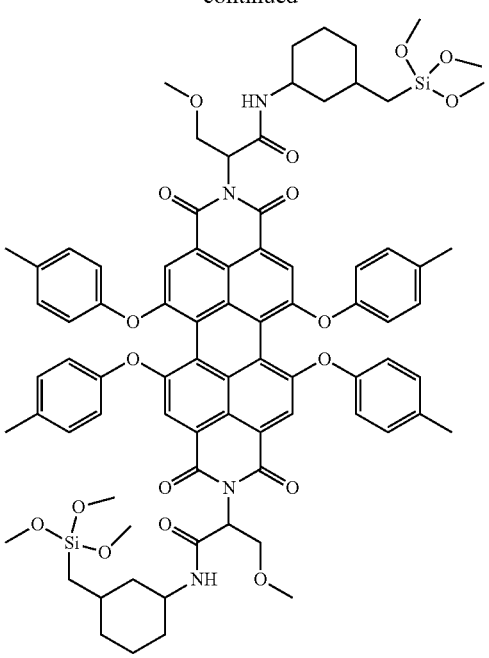
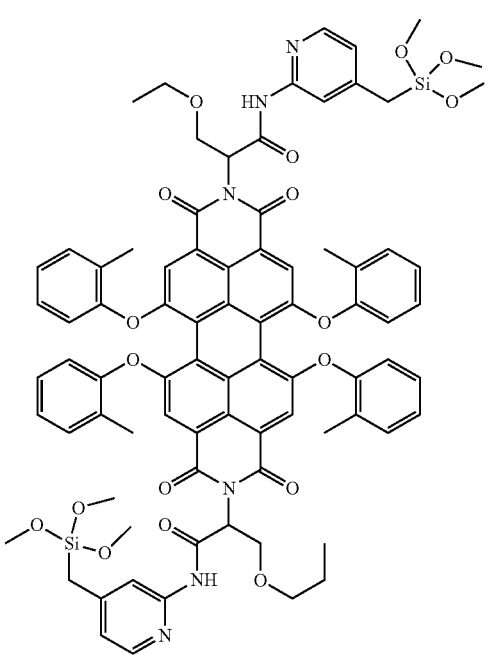

641
-continued
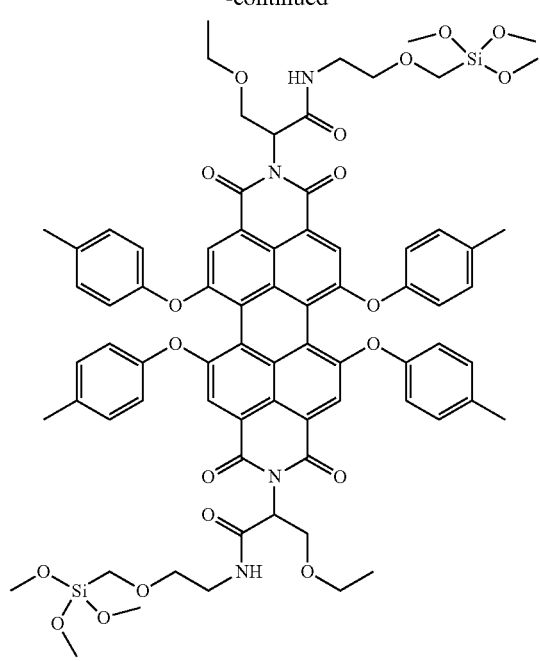
642
-continued
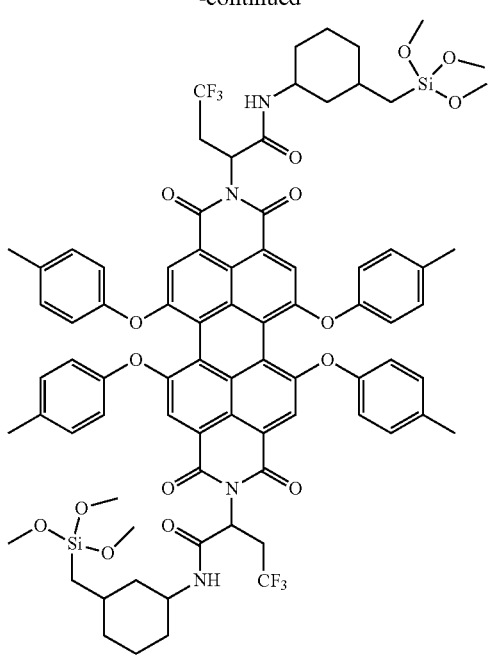
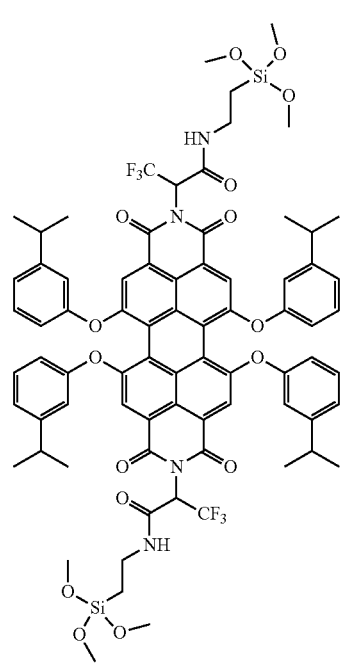
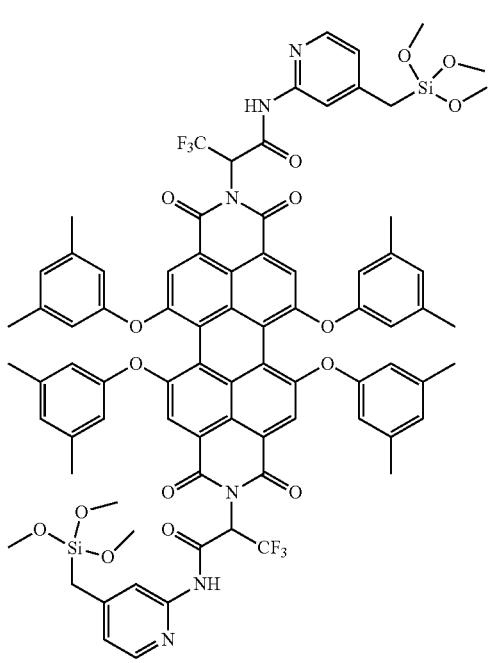

643
-continued
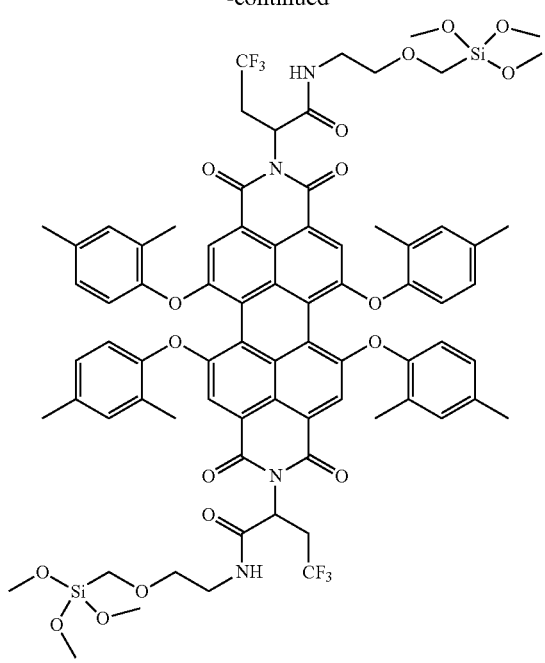
644
-continued
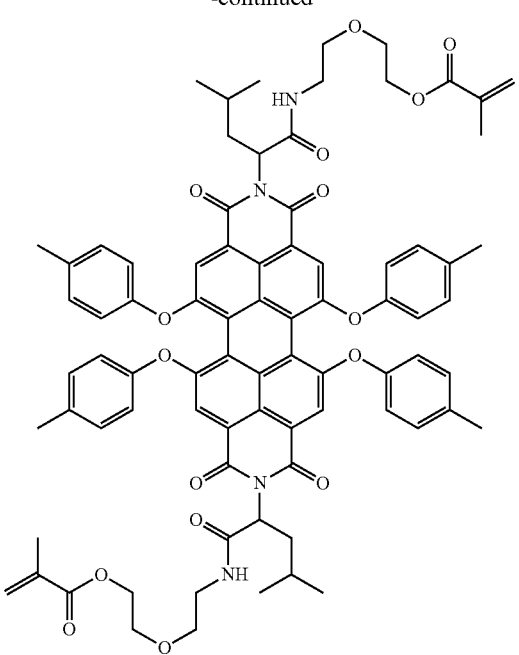
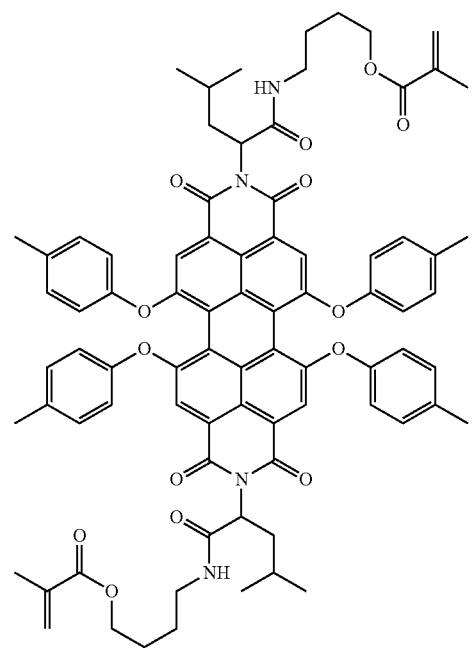
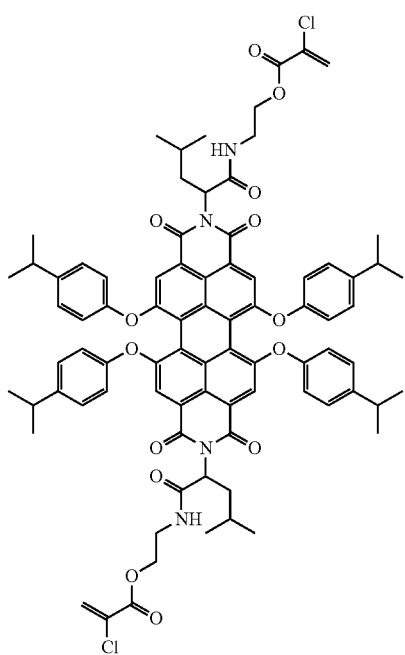

645
-continued
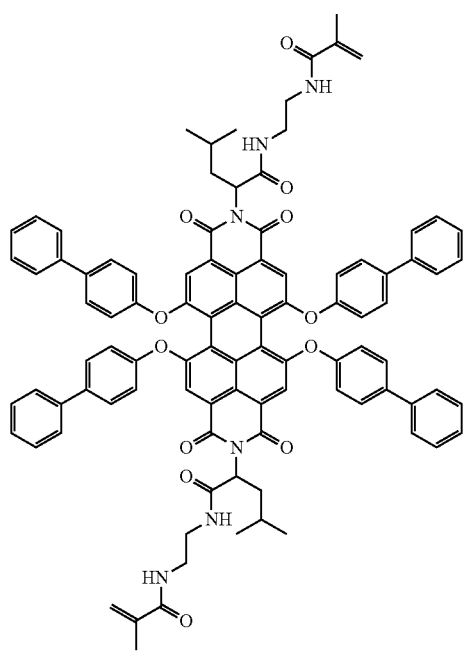
646
-continued
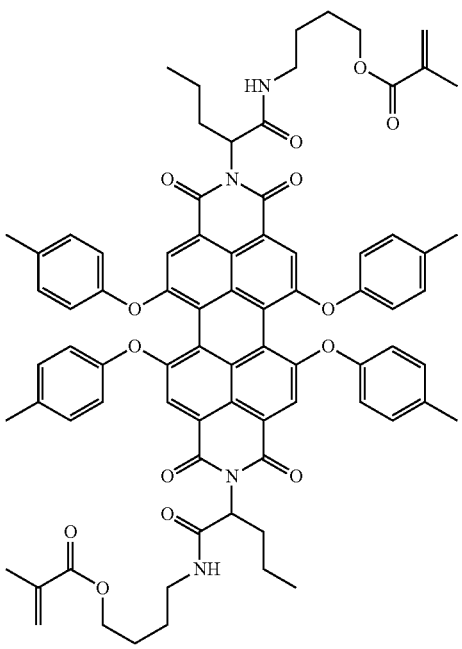
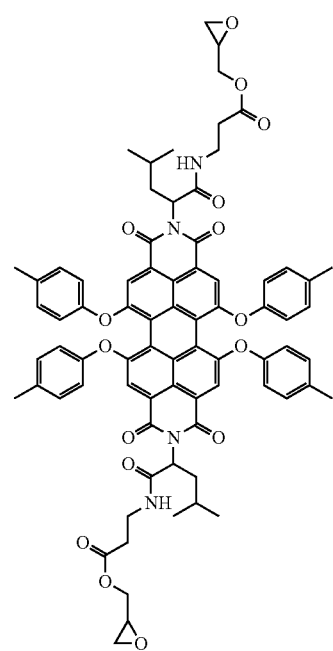
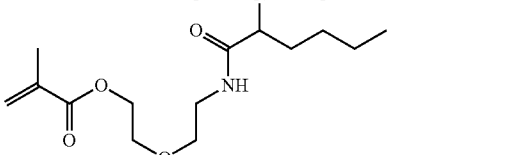

647
-continued
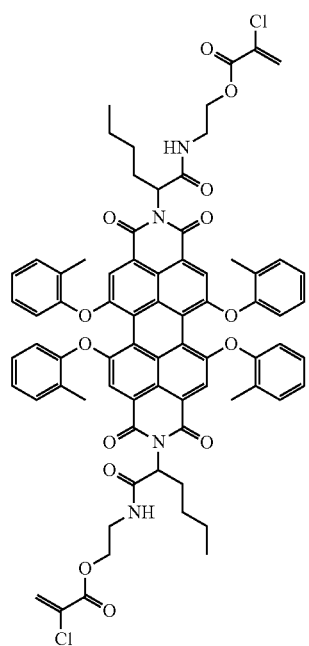
648
-continued
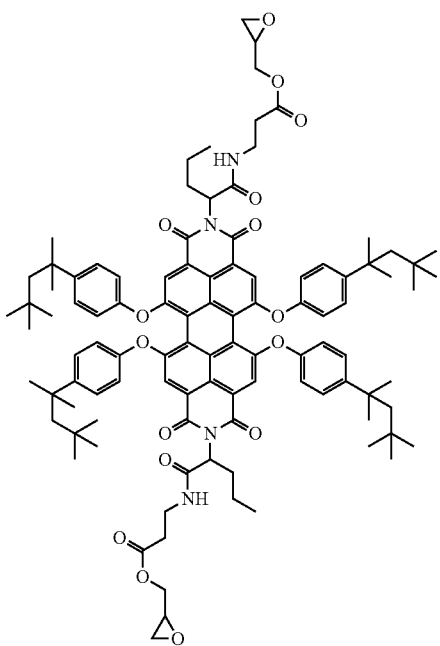
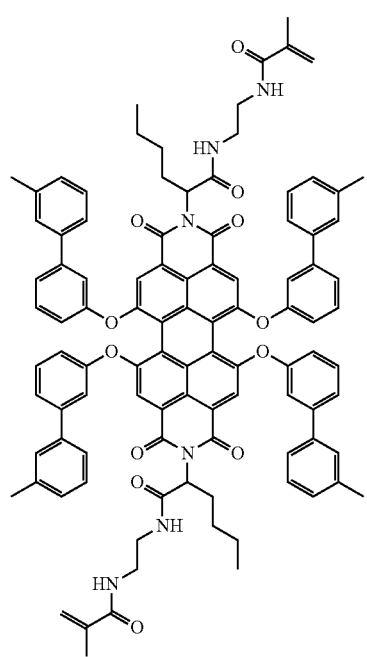
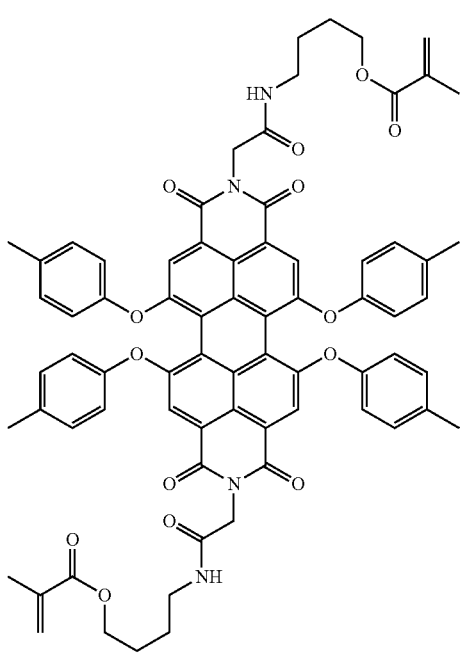

649
-continued
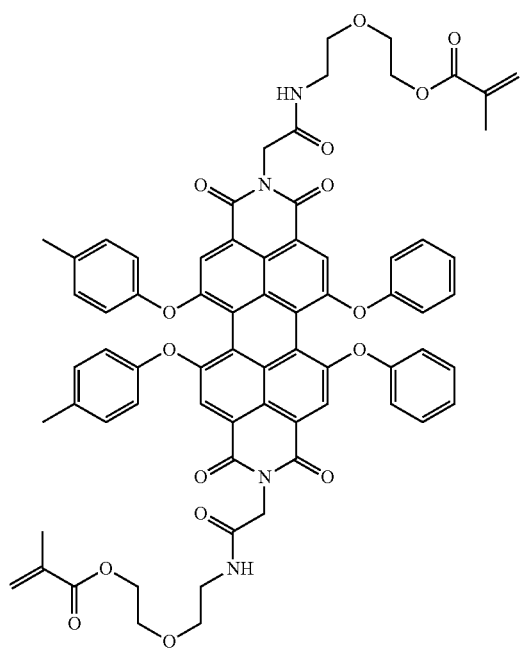
650
-continued
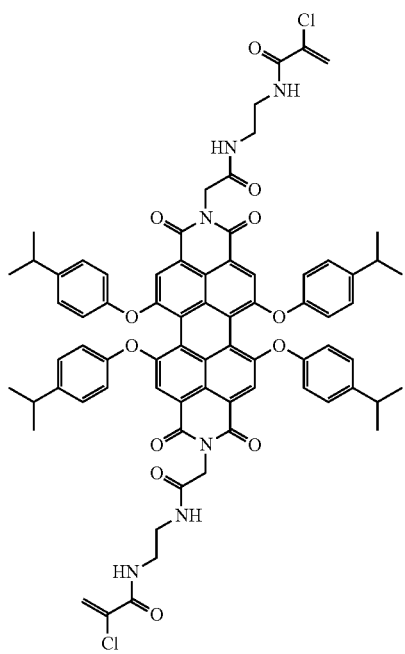
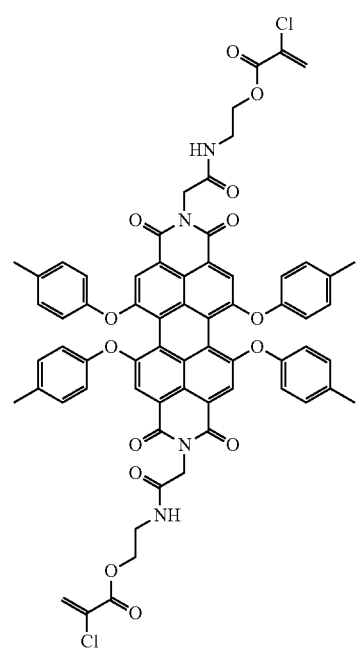
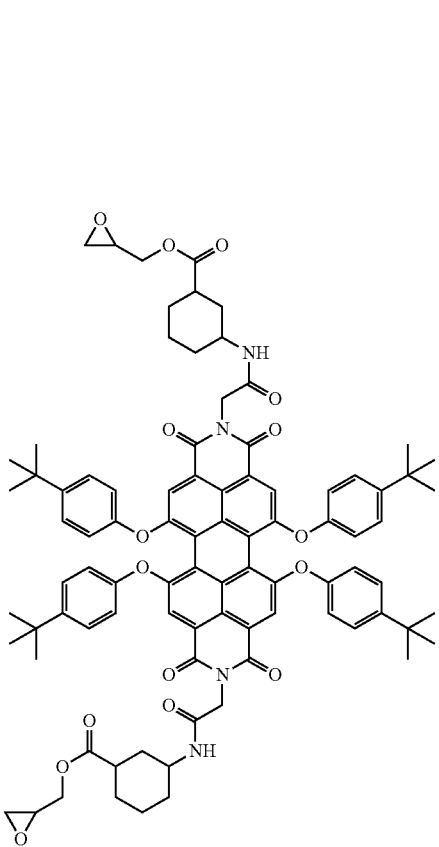

651
-continued
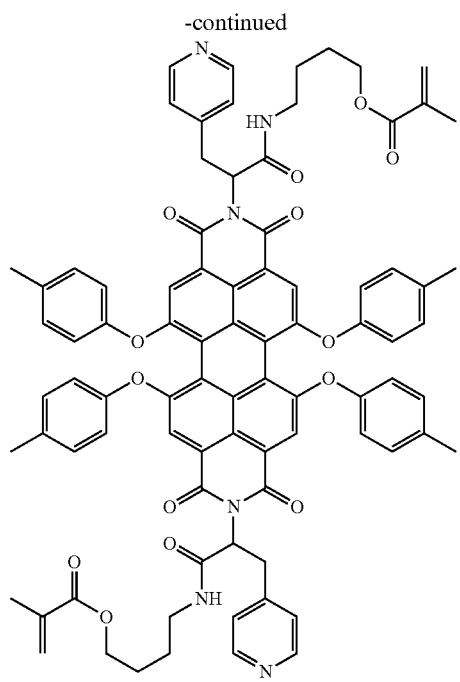
652
-continued
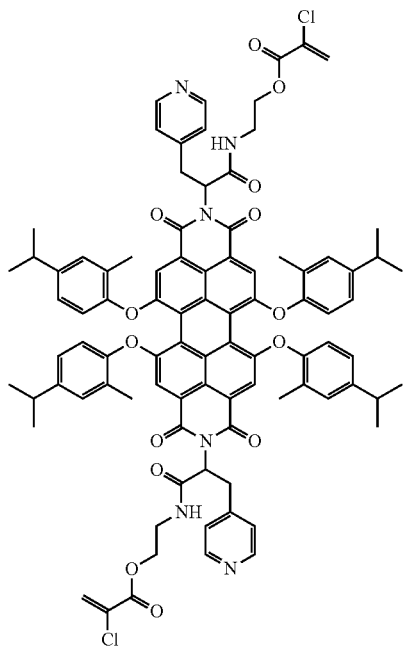
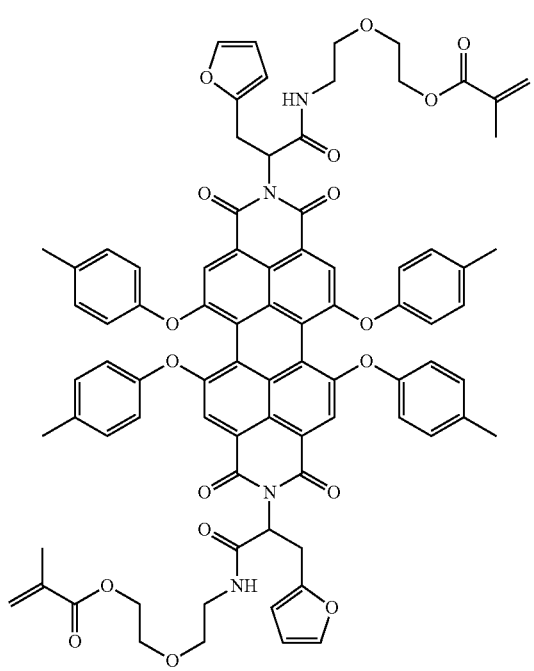
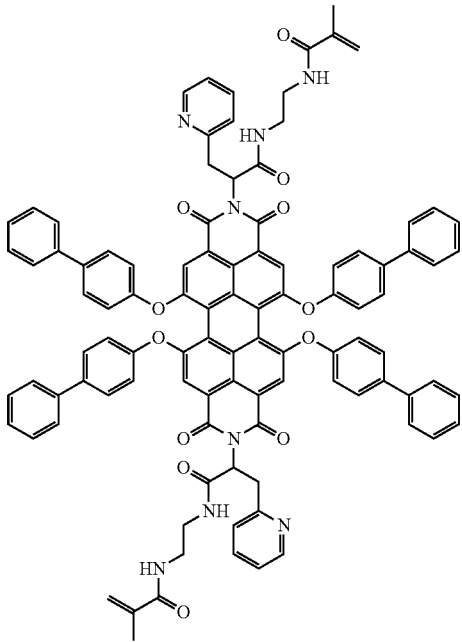

653
-continued
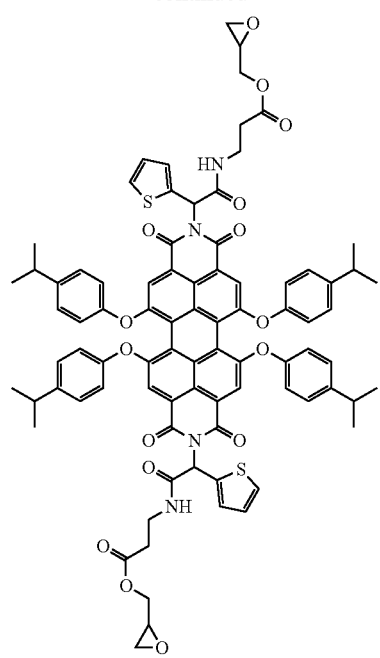
654
-continued
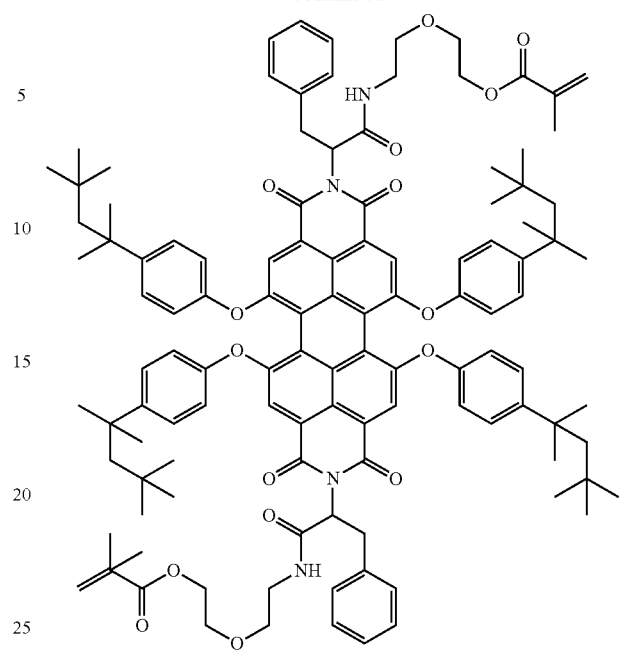
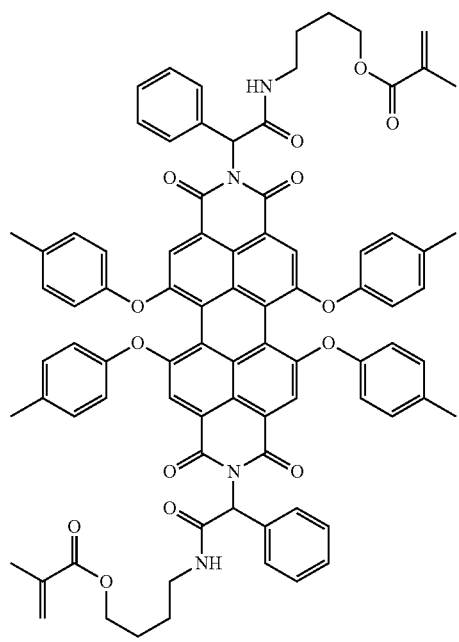
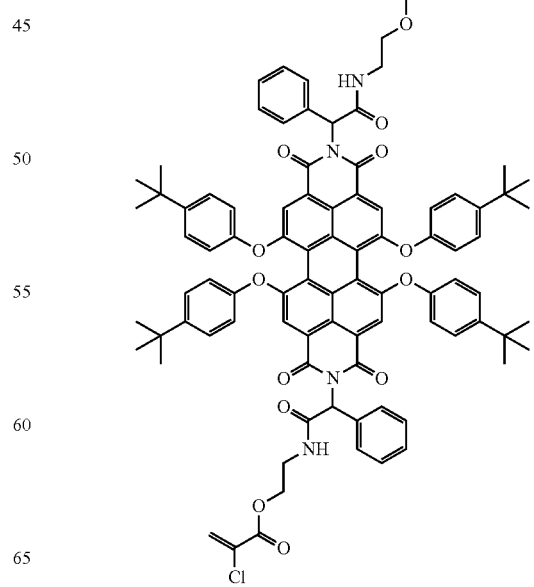

655
-continued
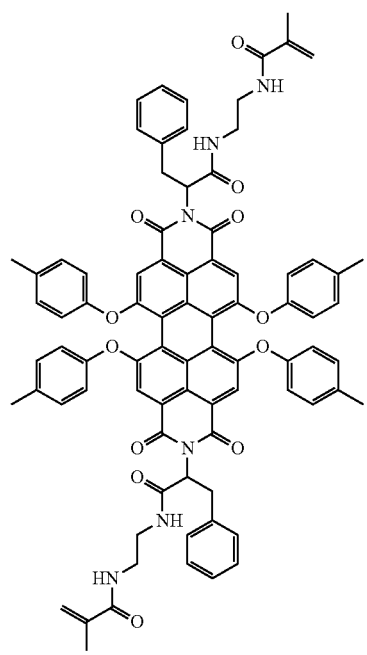
656
-continued
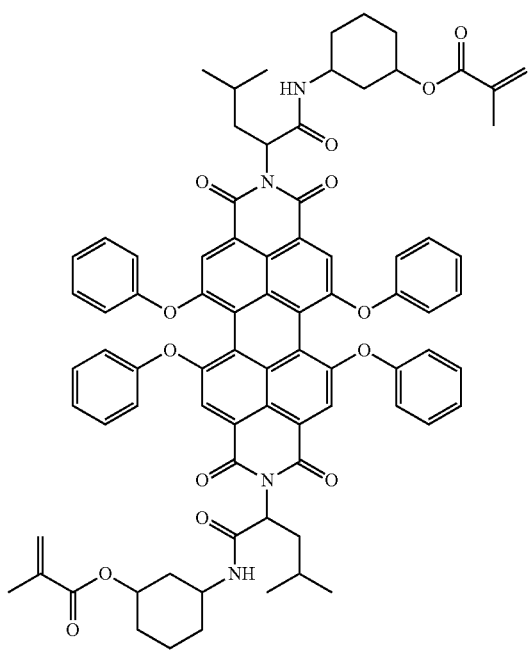
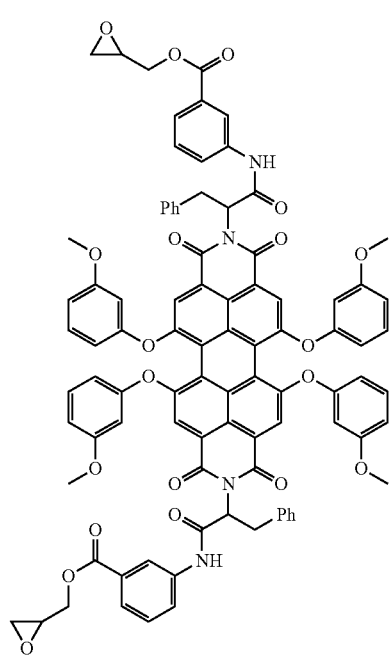
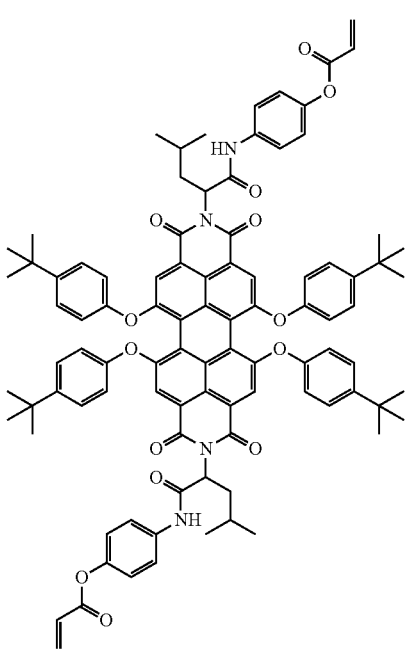

657
-continued
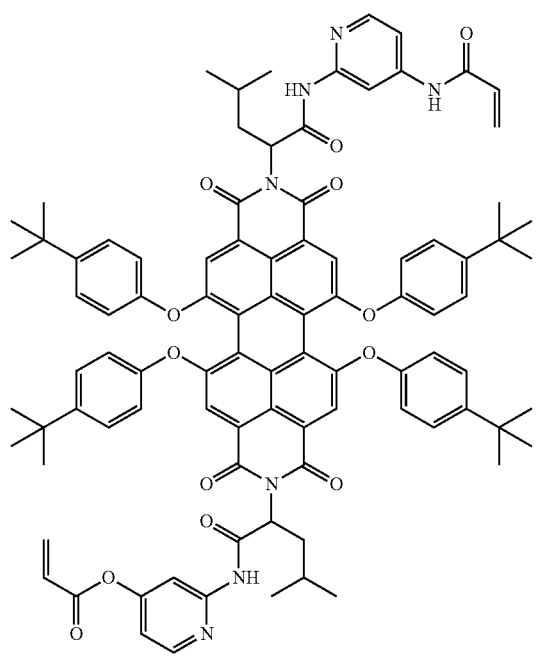
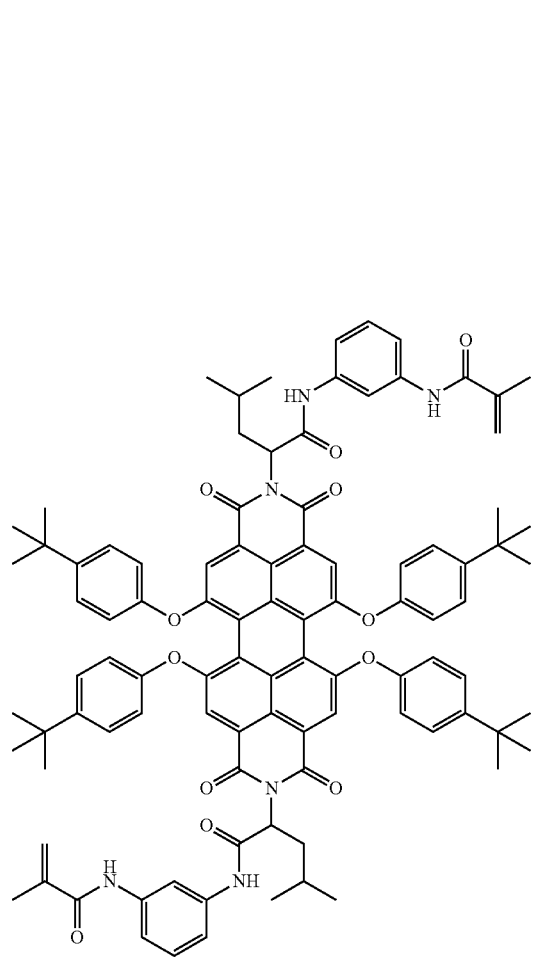
658
-continued
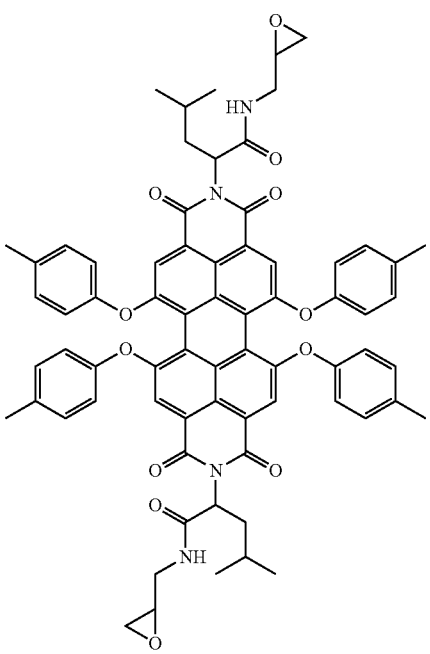
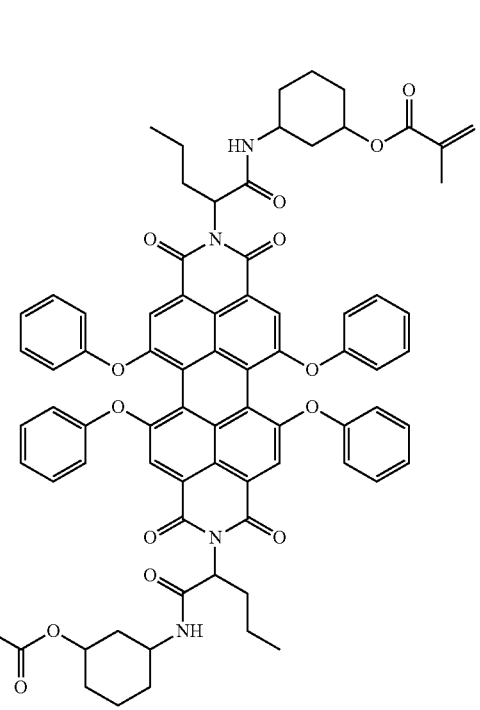

659
-continued
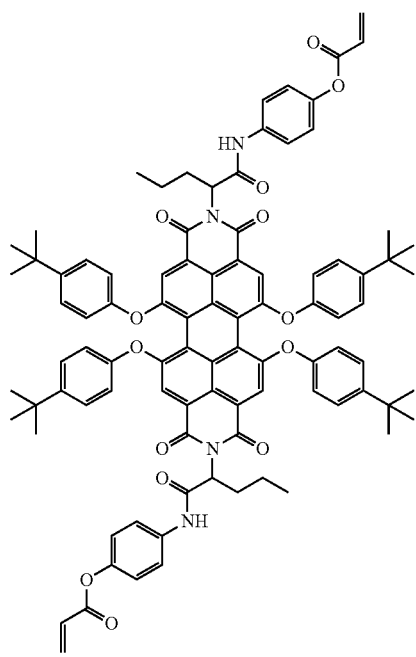
660
-continued
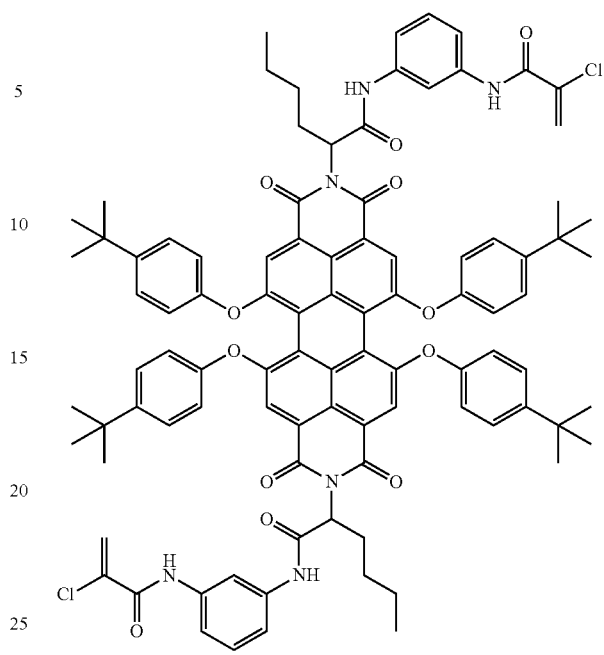
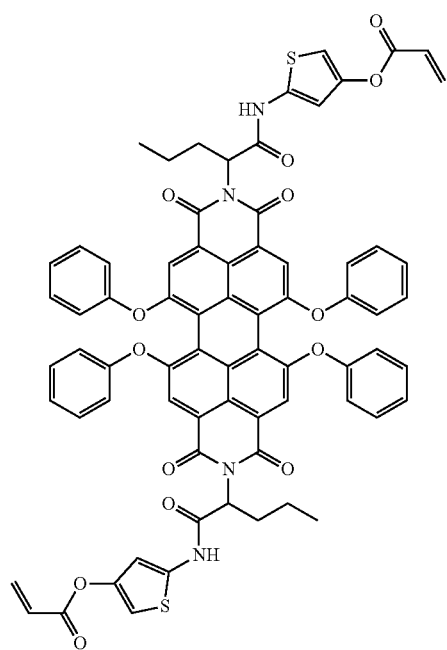
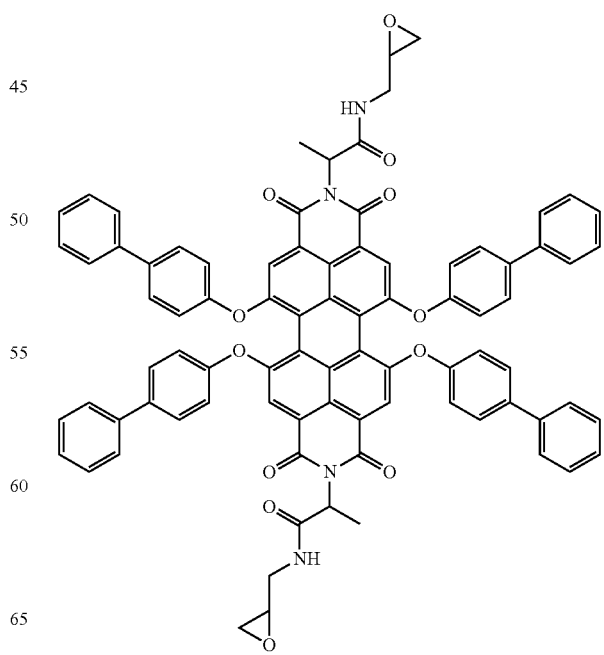

661
-continued
662
-continued
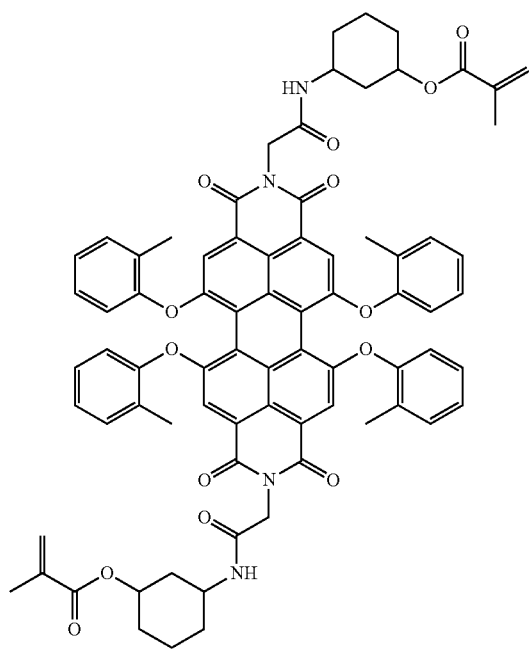
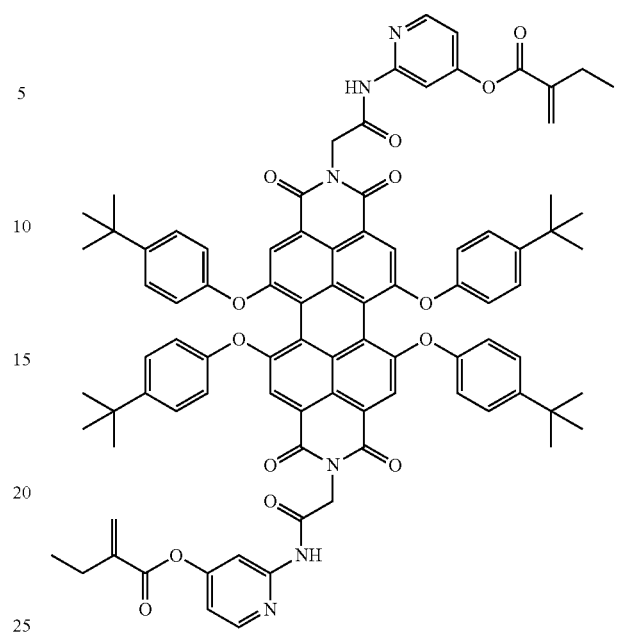
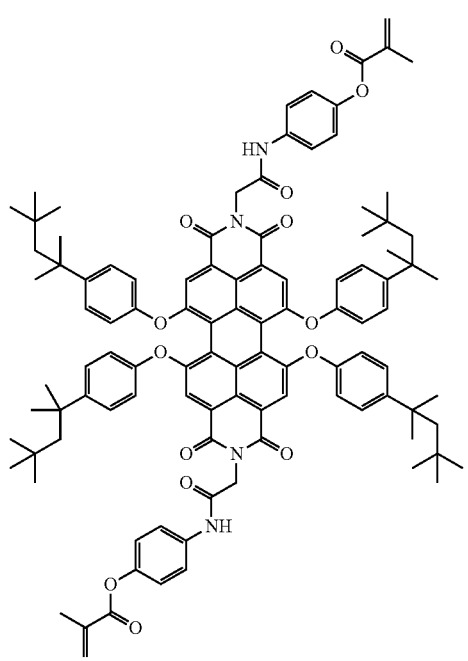
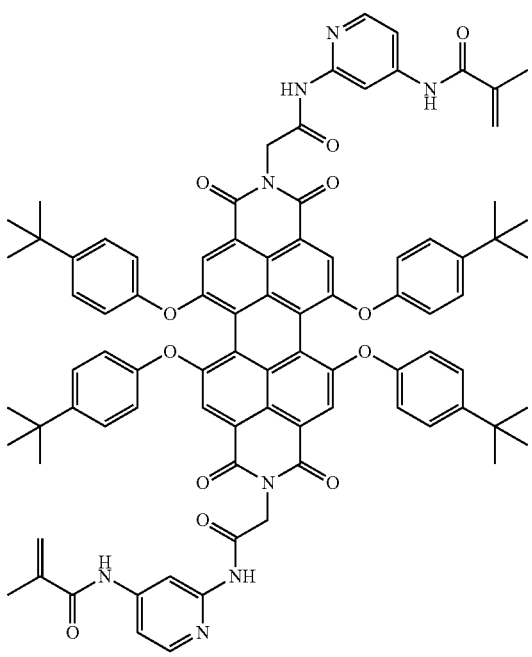

663
-continued
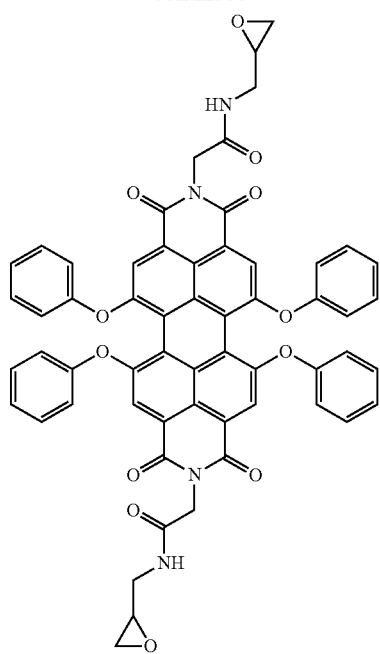
664
-continued
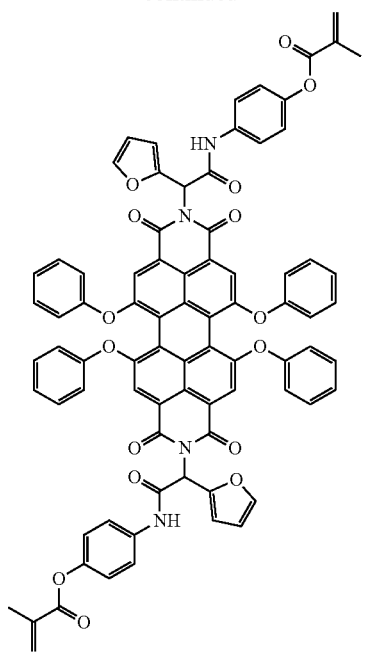
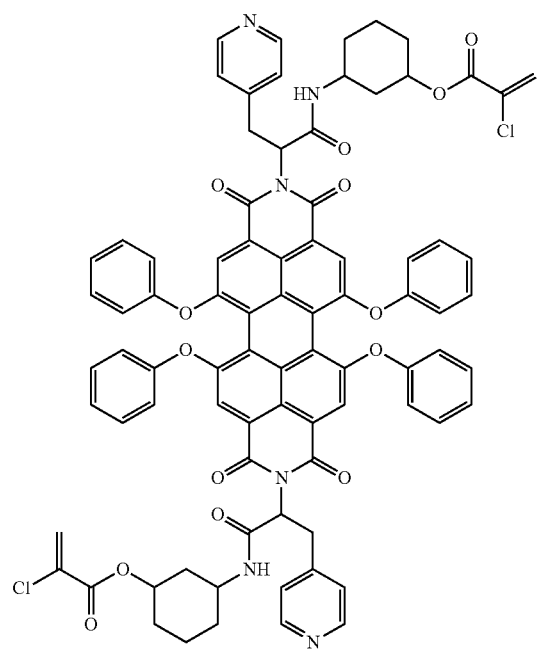
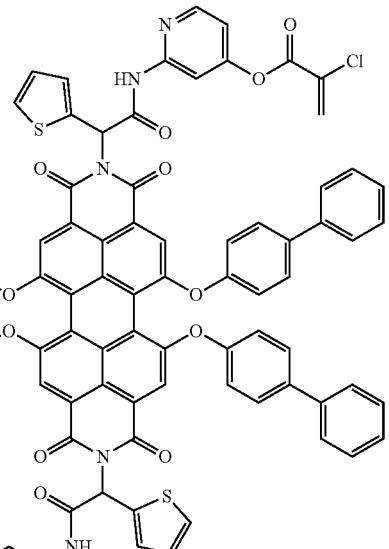

665
-continued
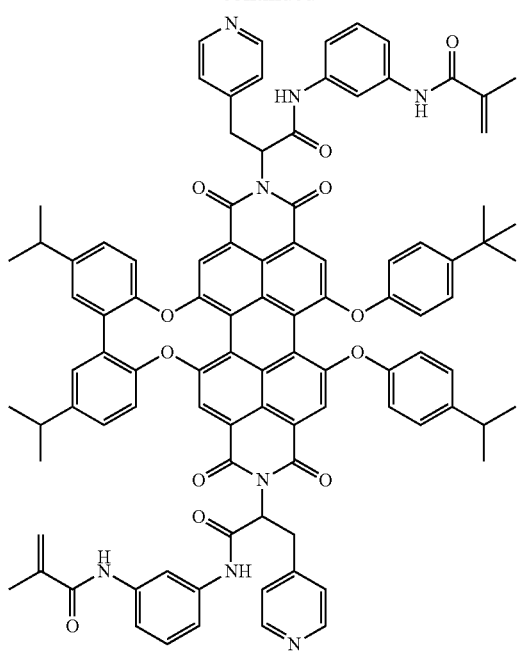
666
-continued
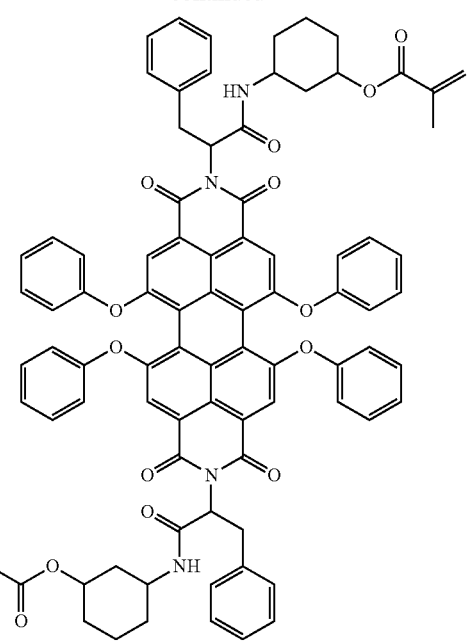
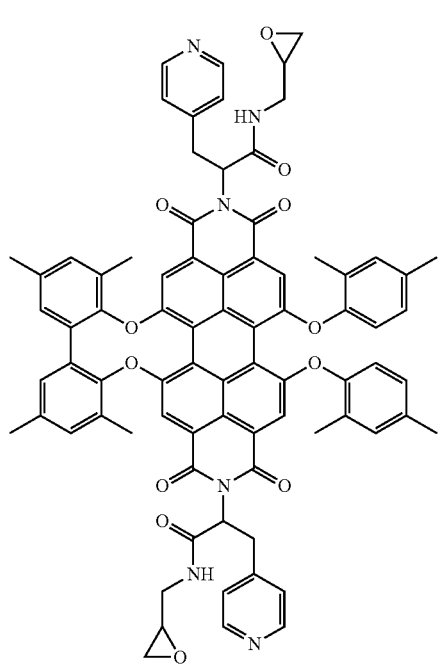
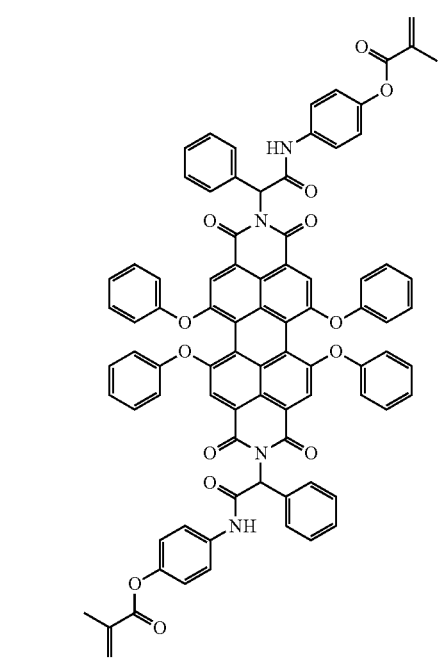

667
-continued
668
-continued
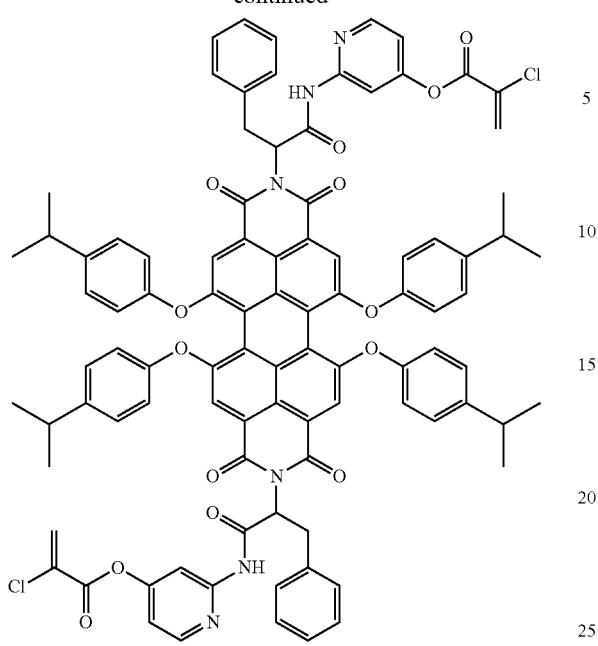
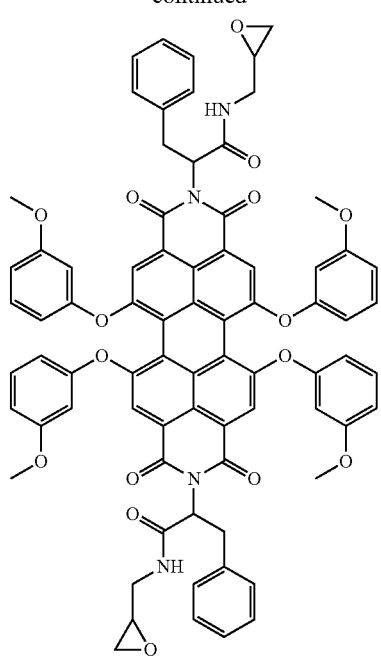
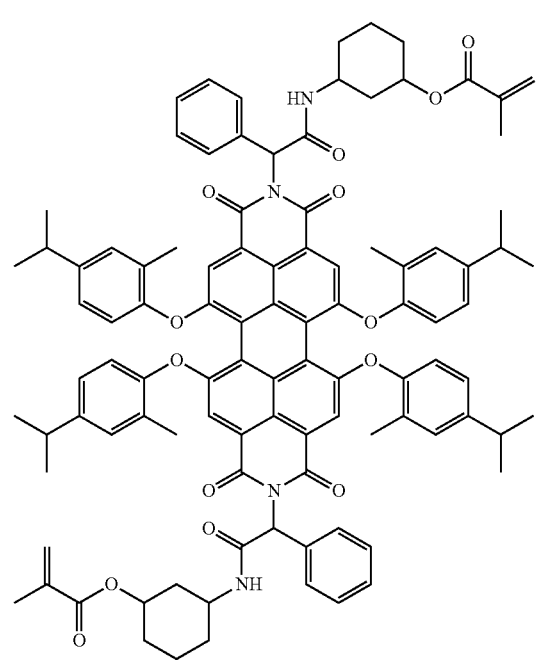
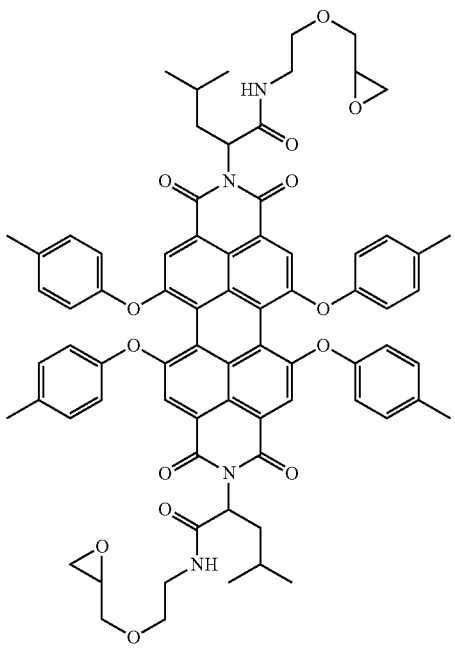

669
-continued
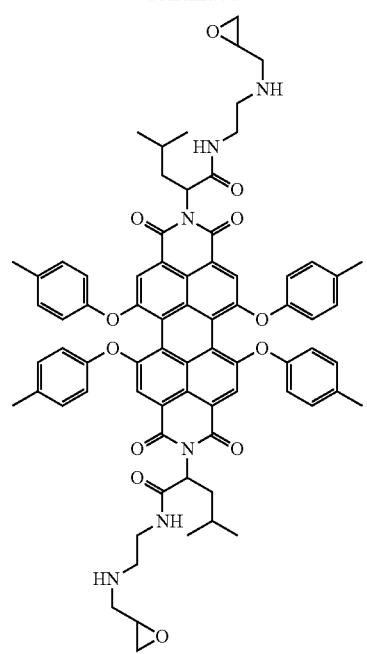
670
-continued
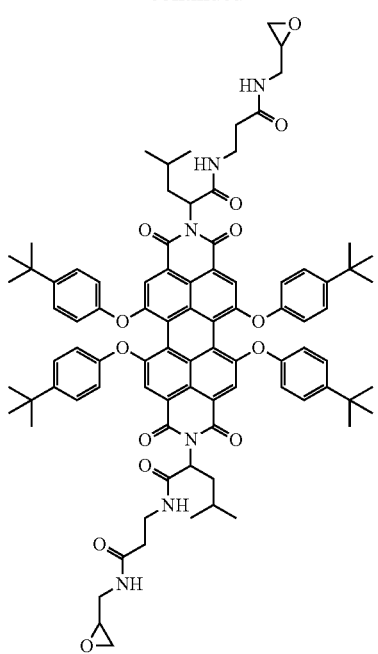
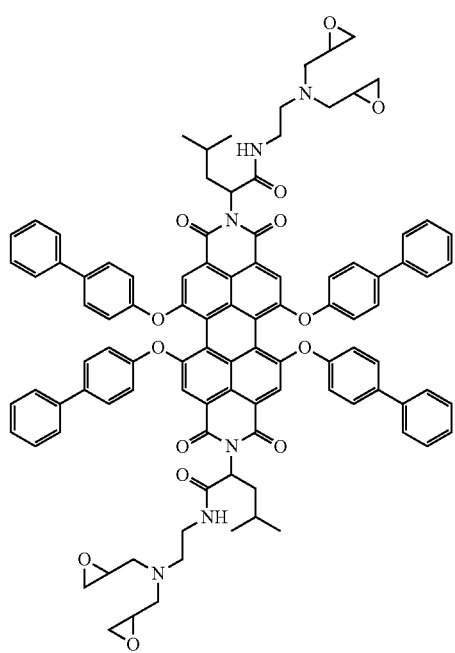
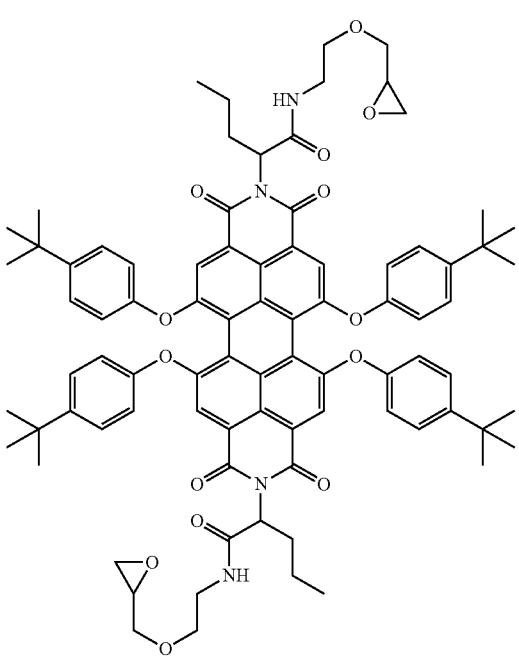

671
-continued
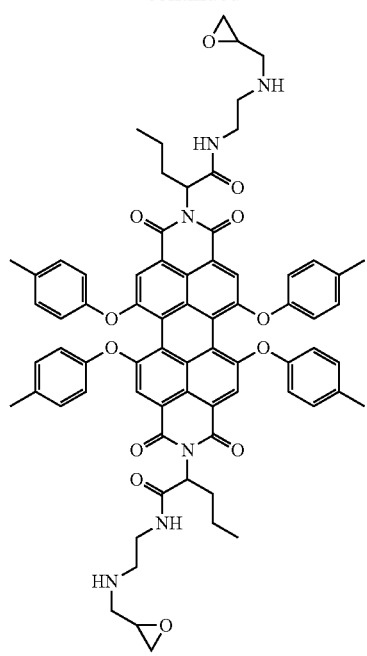
672
-continued
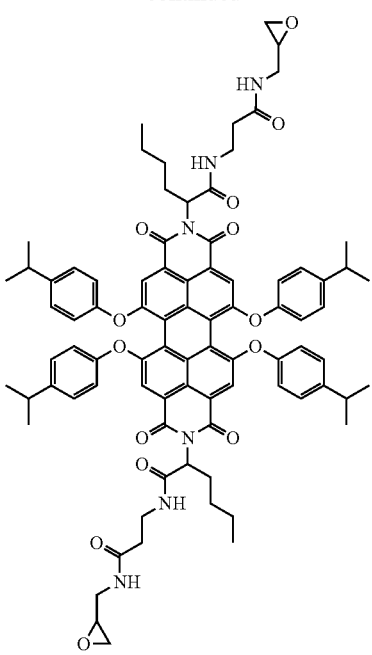
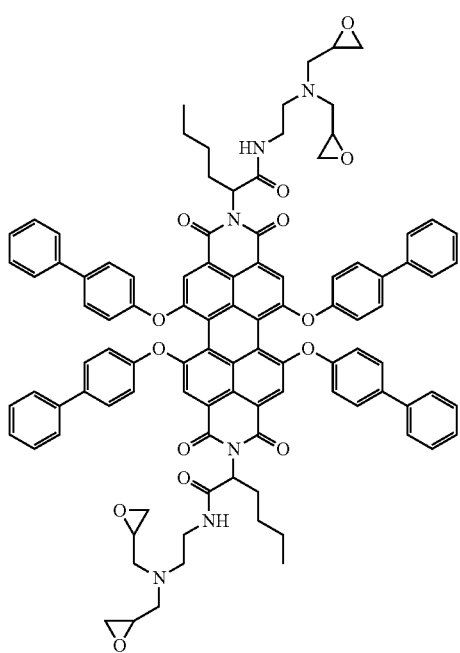
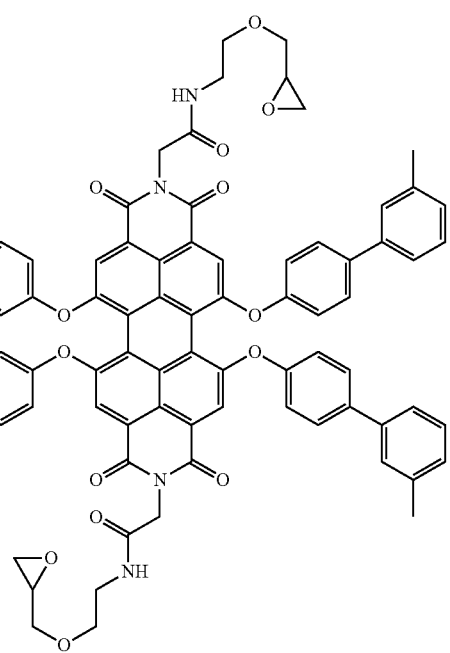

673
-continued
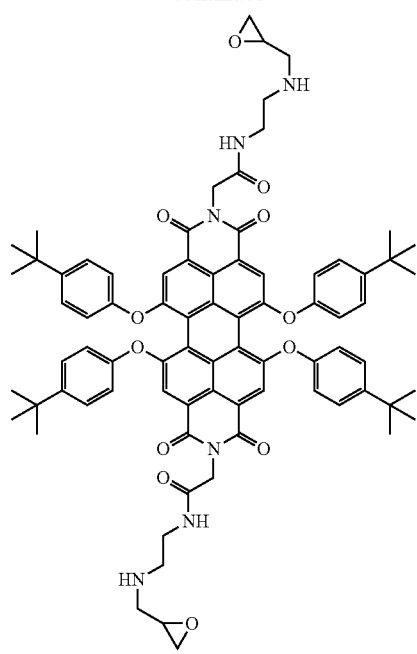
674
-continued
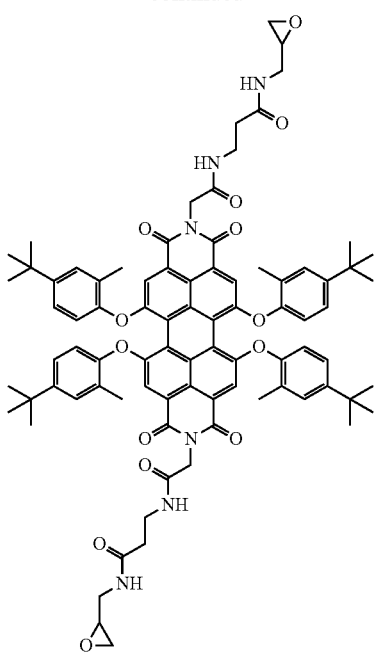
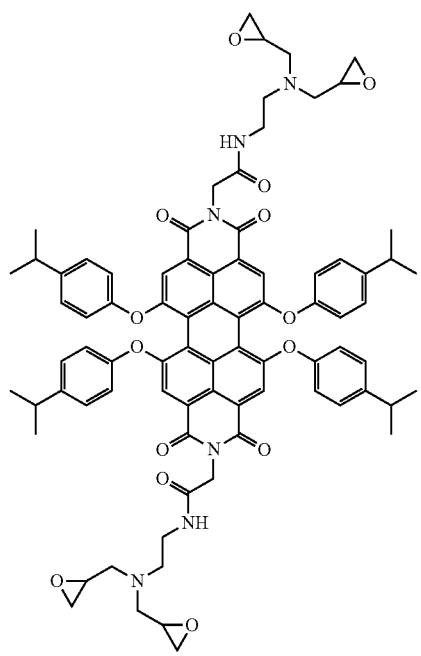
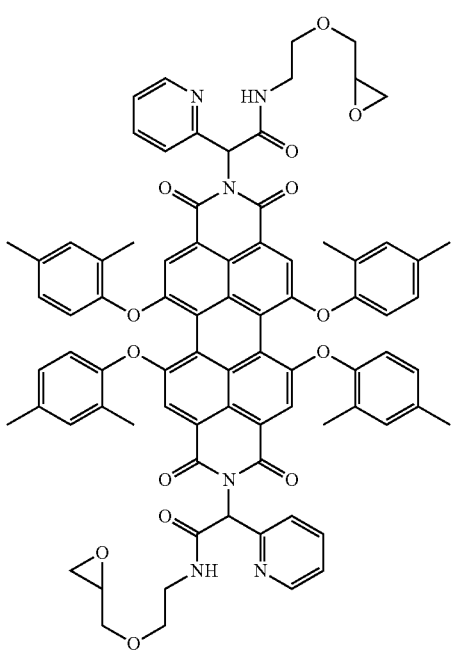

675
-continued
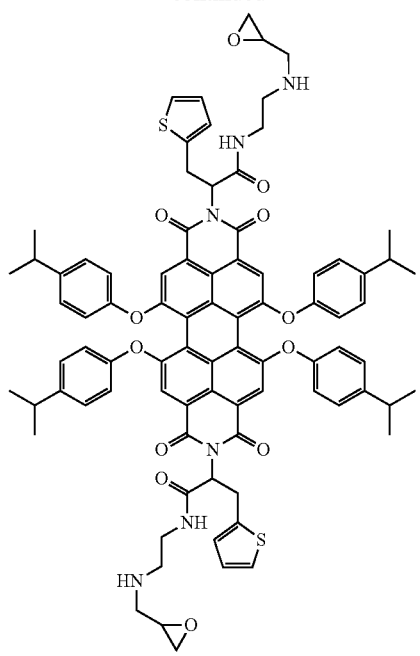
676
-continued
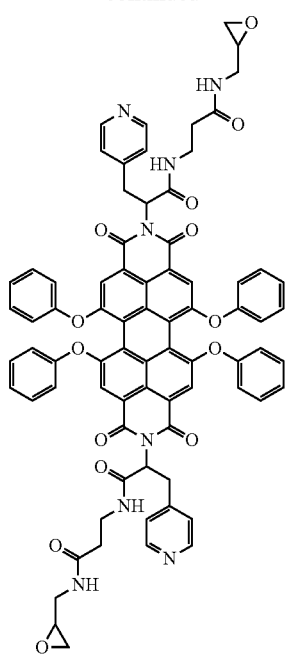
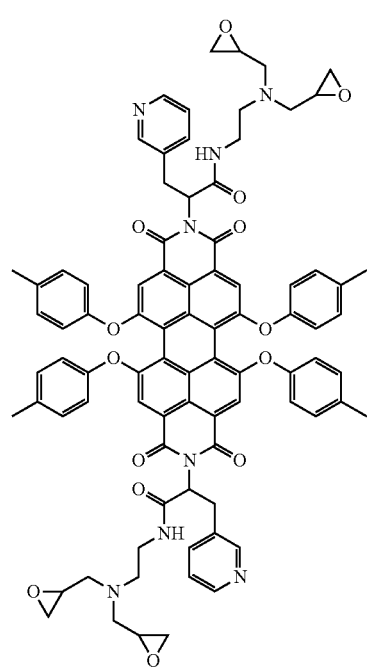
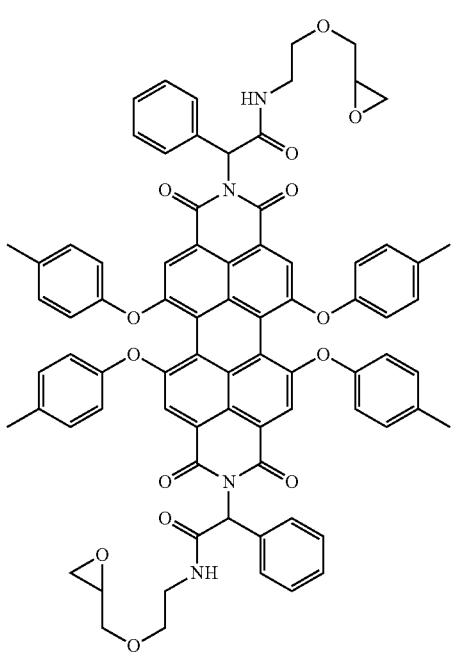

677
-continued
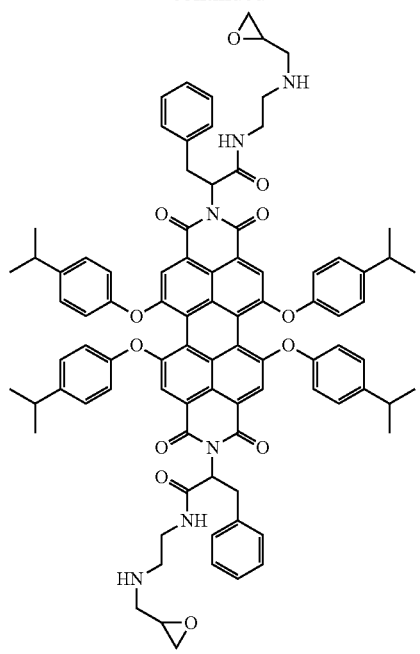
678
-continued
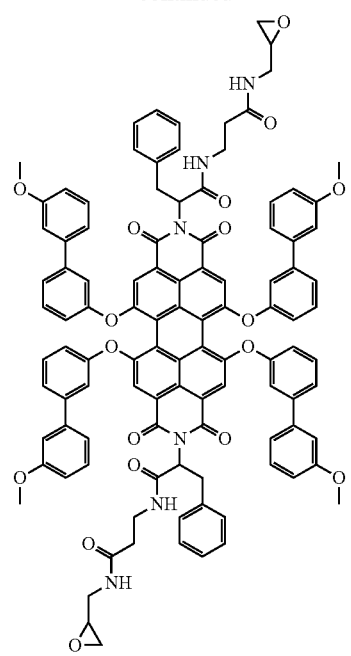
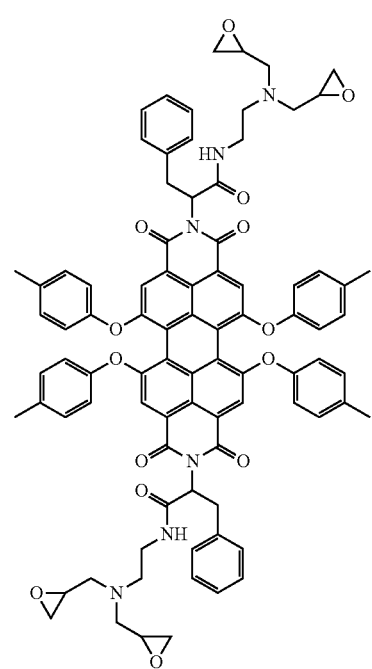
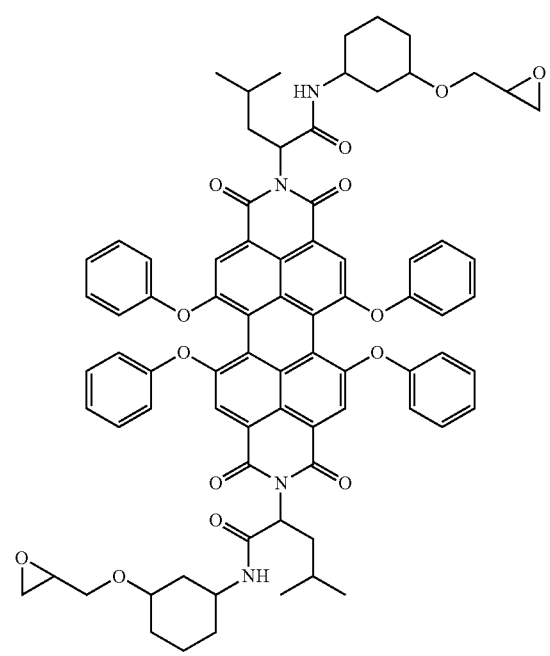

679
-continued
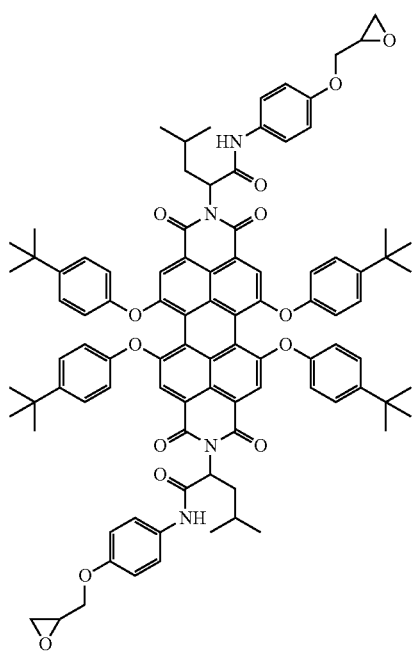
680
-continued
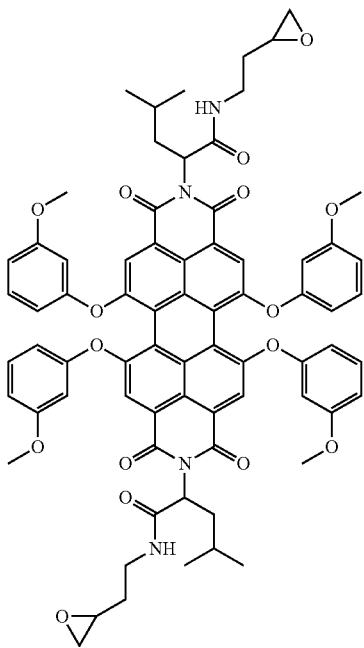
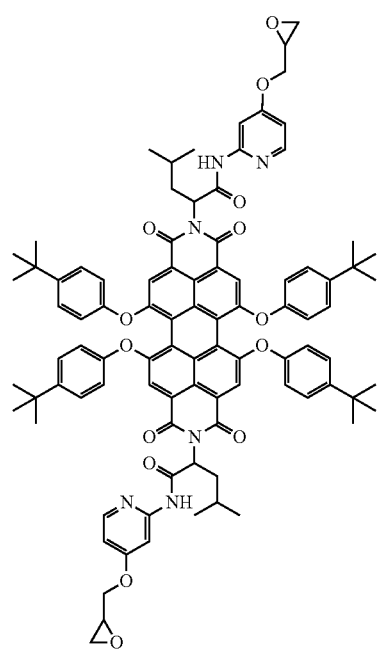

681
-continued
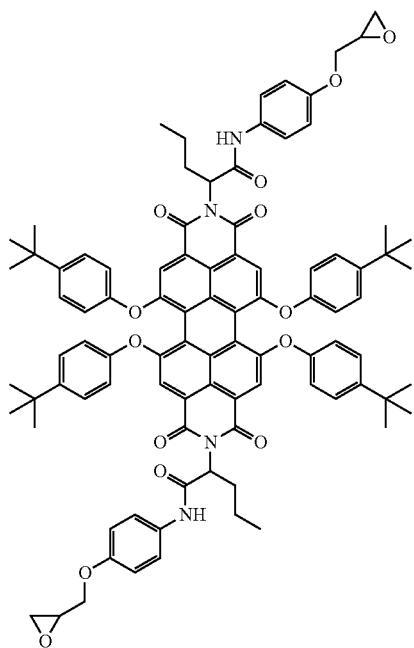
682
-continued
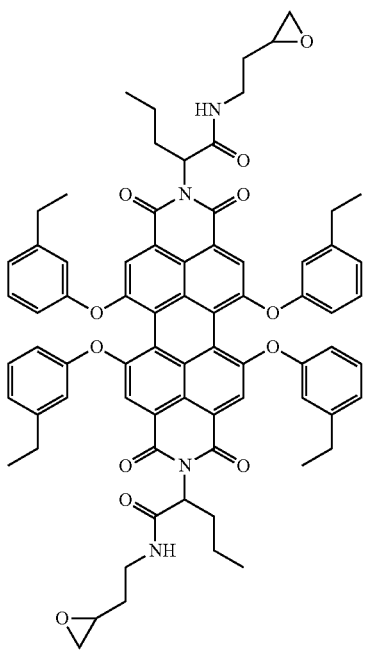
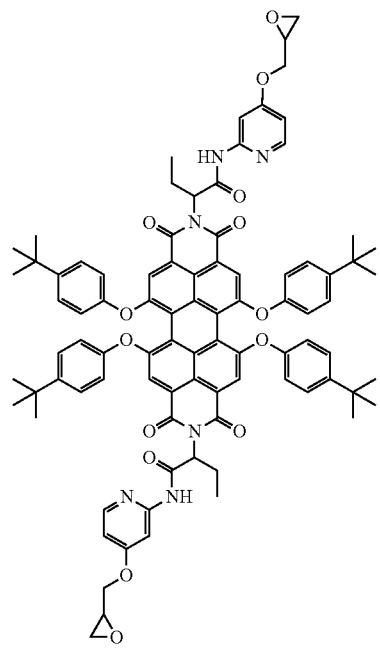
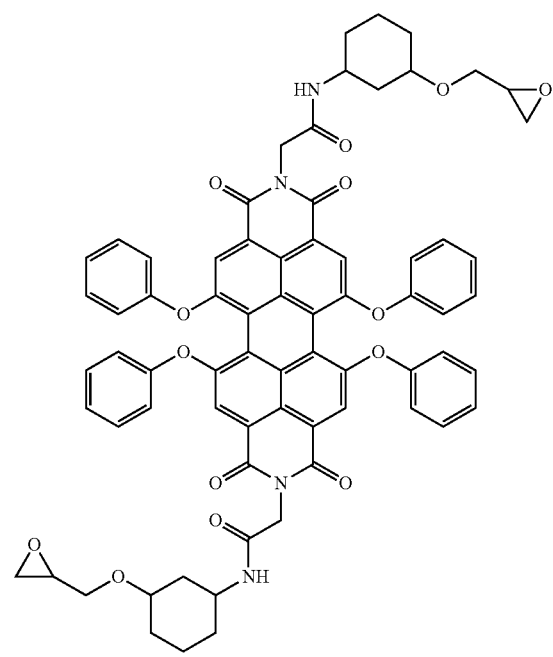

683
-continued
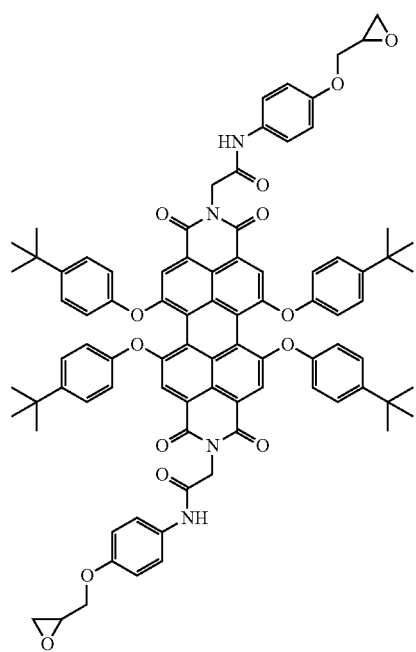
684
-continued
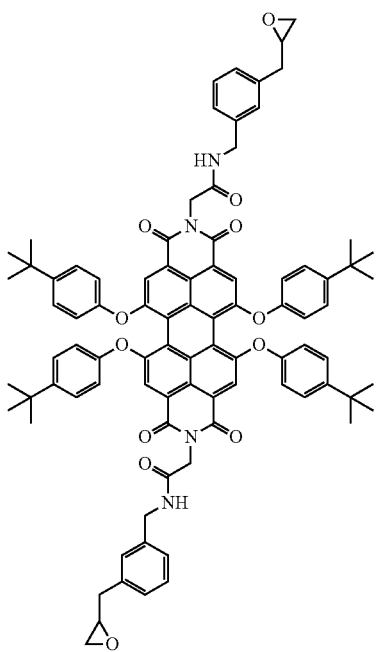
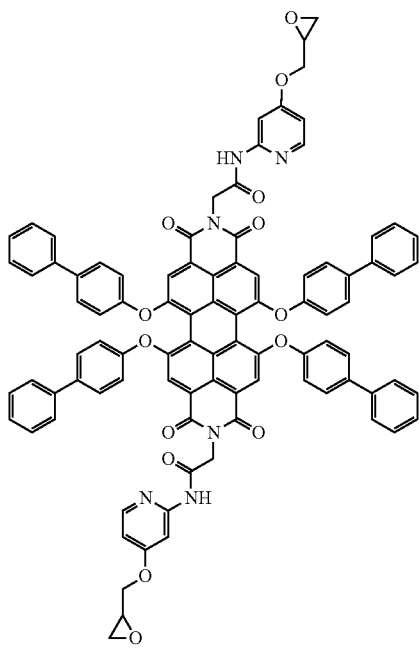
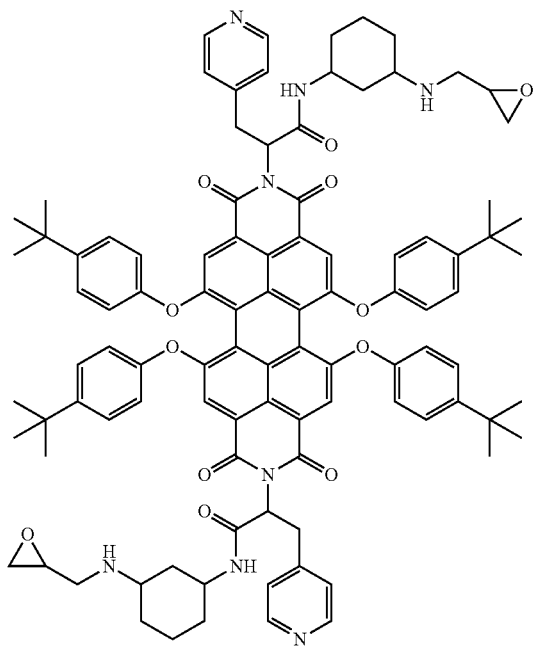

685
-continued
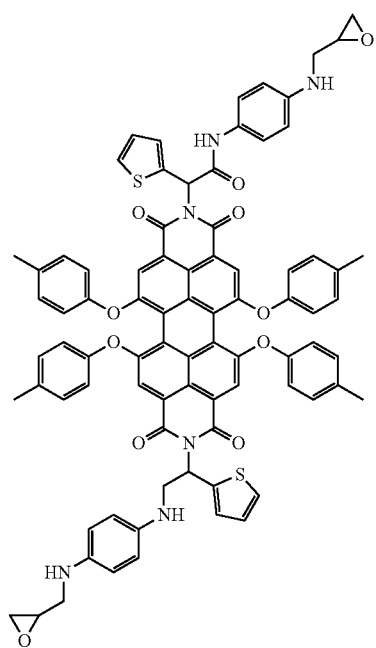
686
-continued
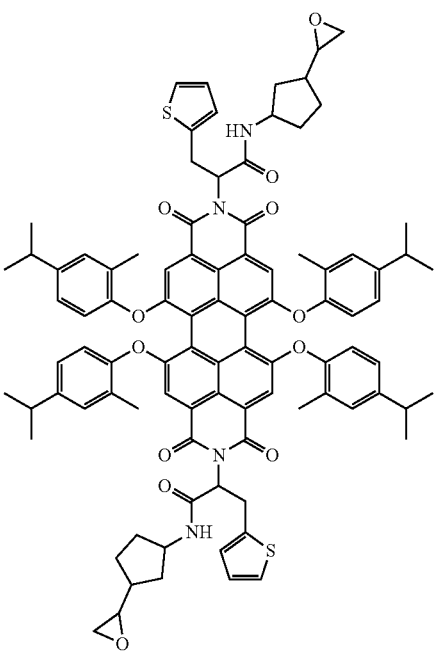
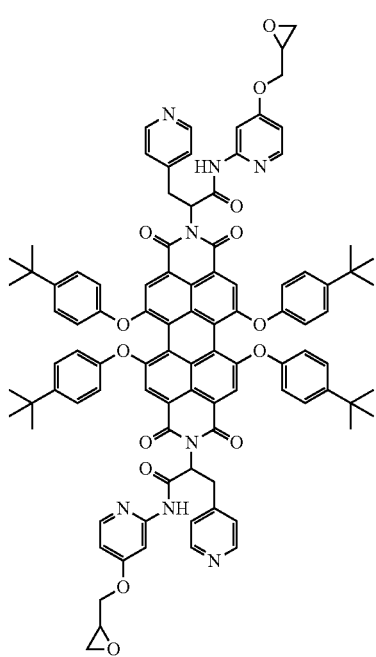
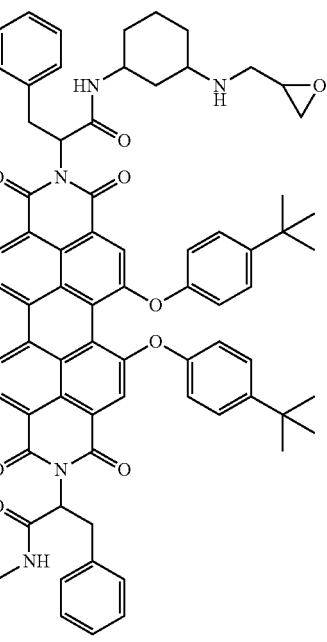

687
-continued
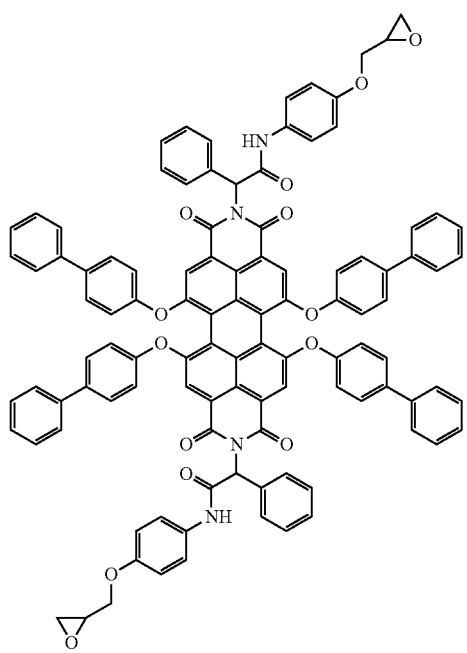
688
-continued
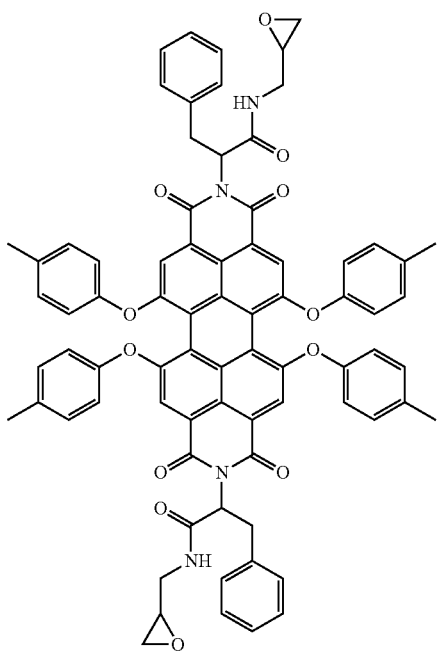
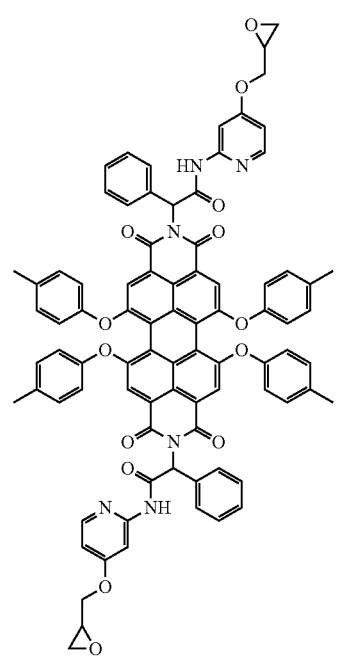
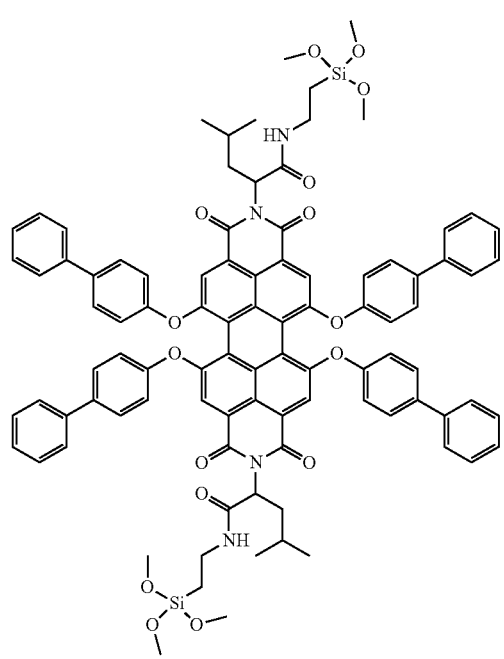

689
-continued
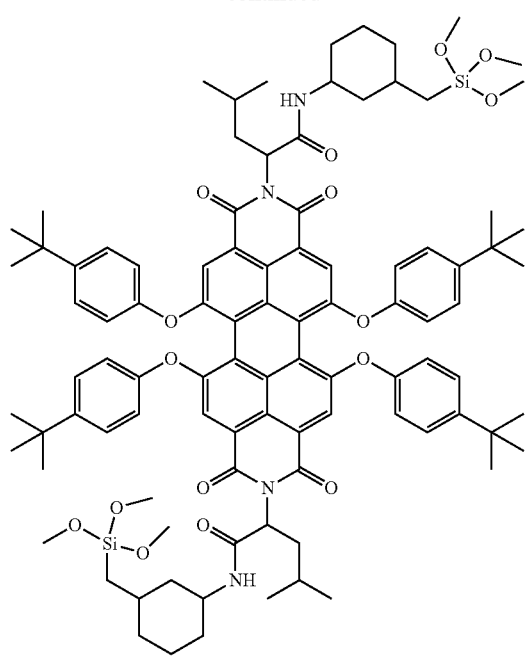
690
-continued
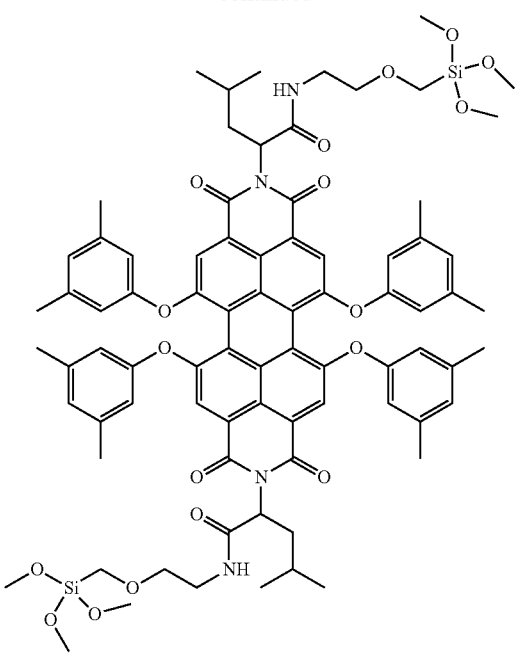
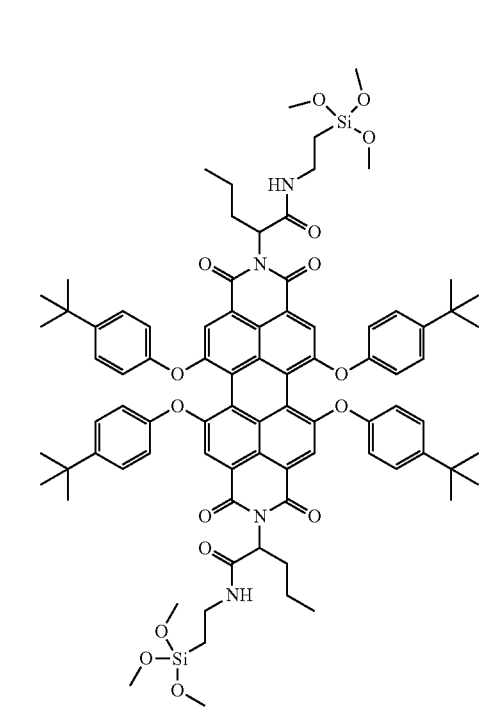

691
-continued
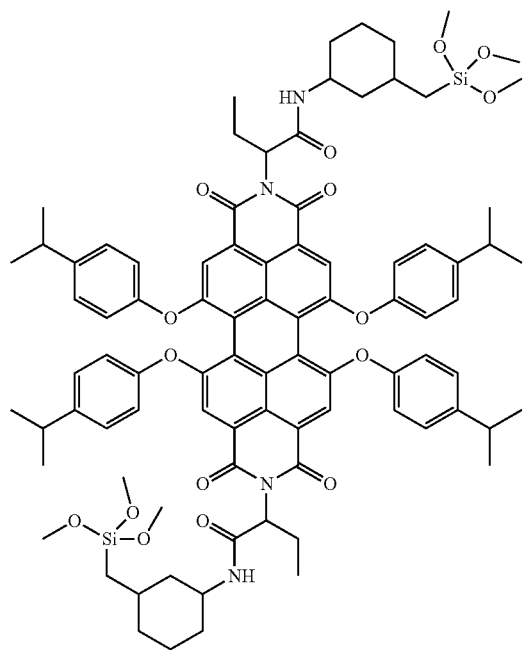
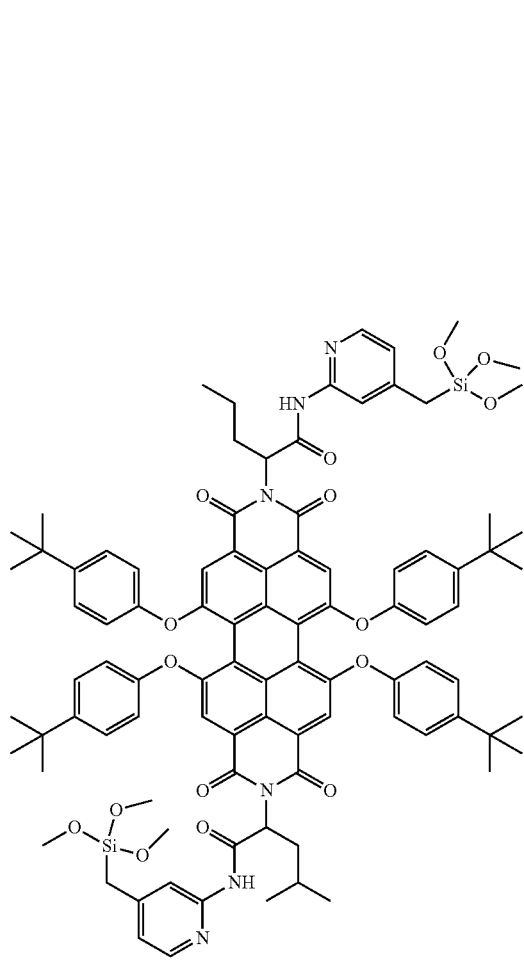
692
-continued
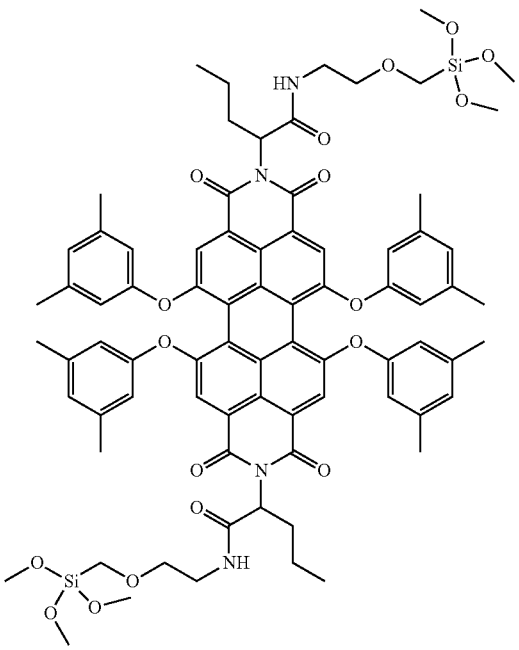
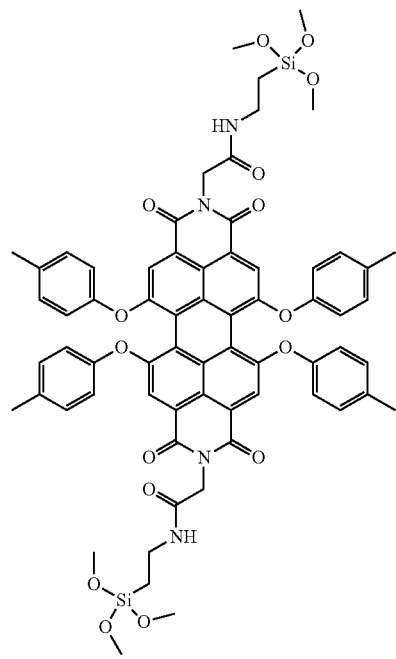

693
-continued
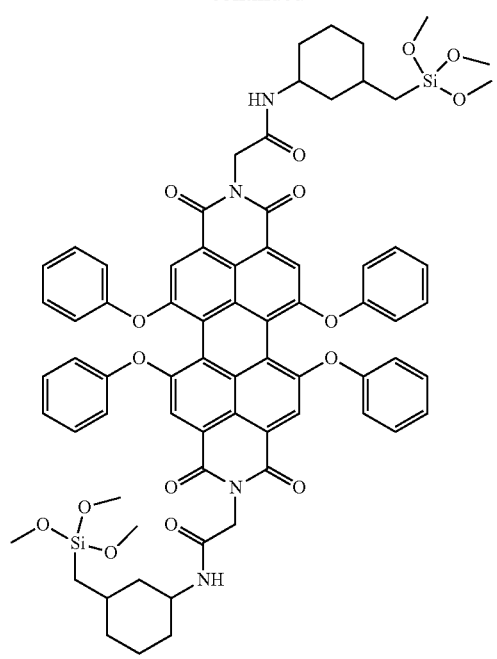
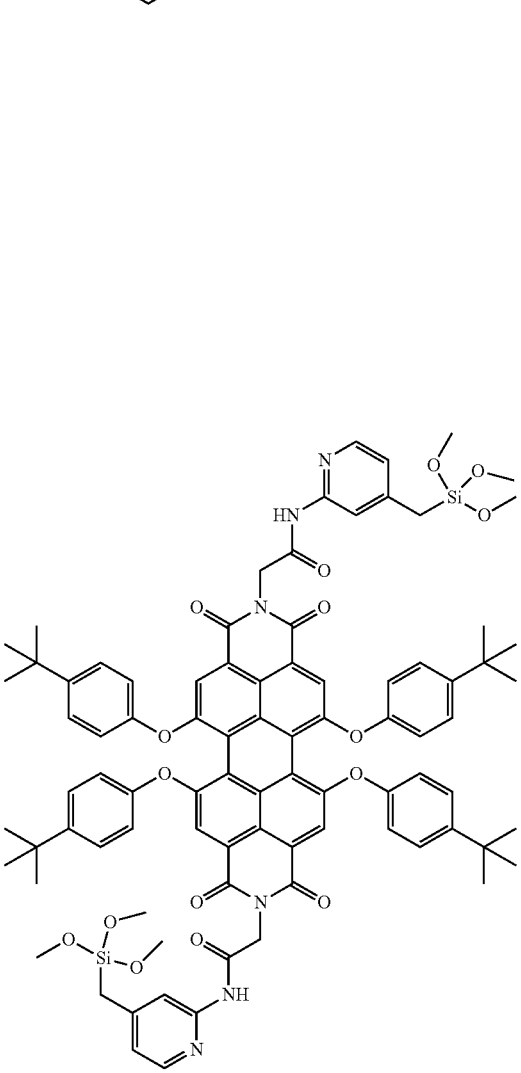
694
-continued
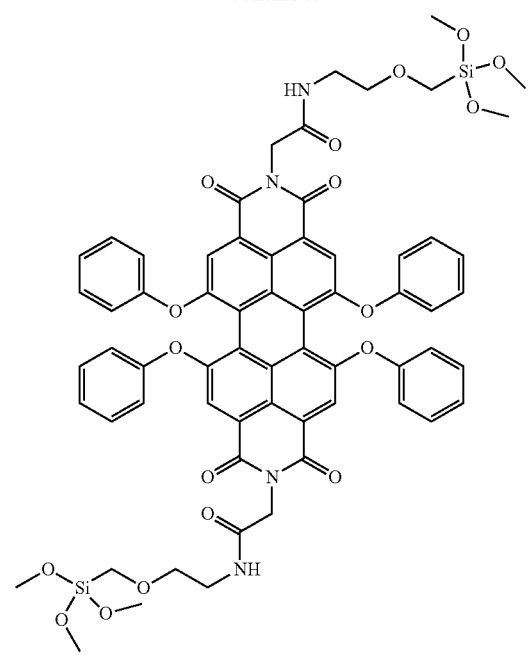
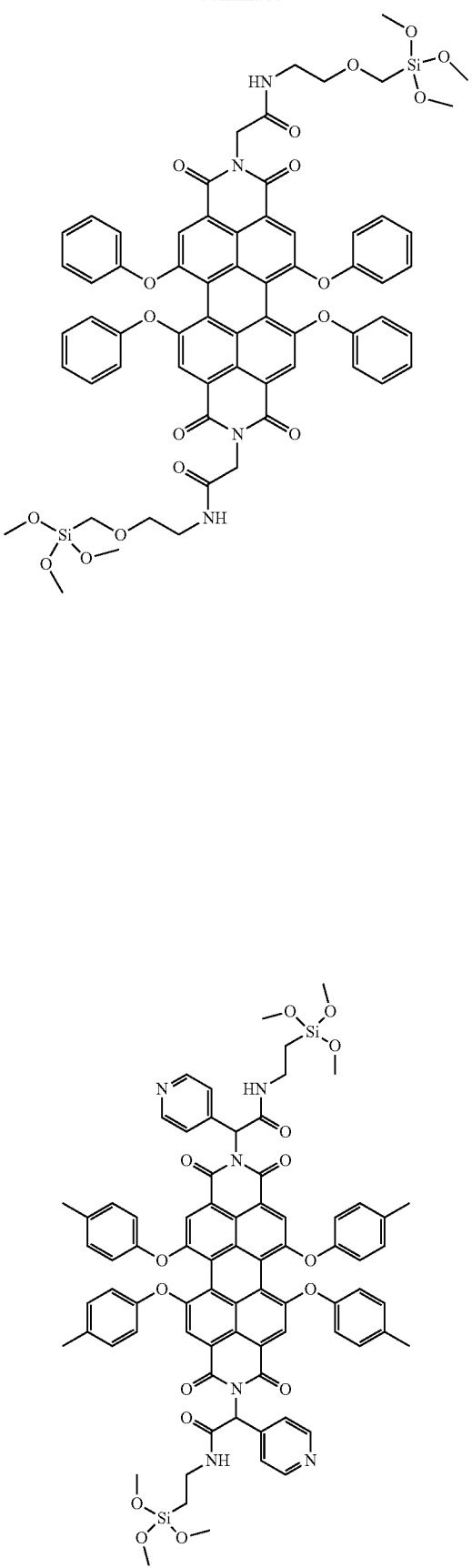

695
-continued
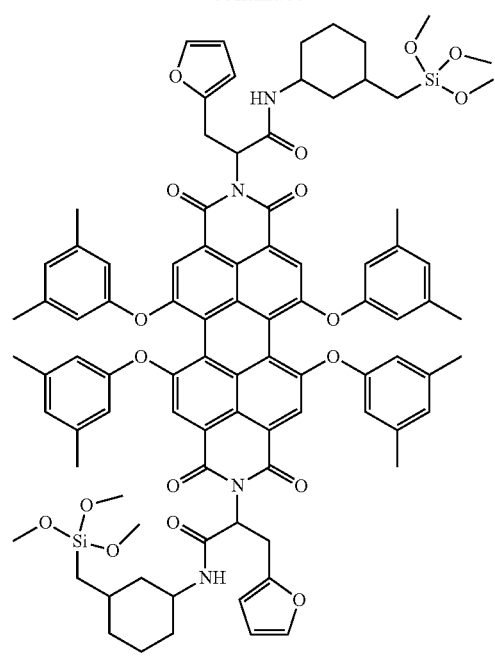
696
-continued
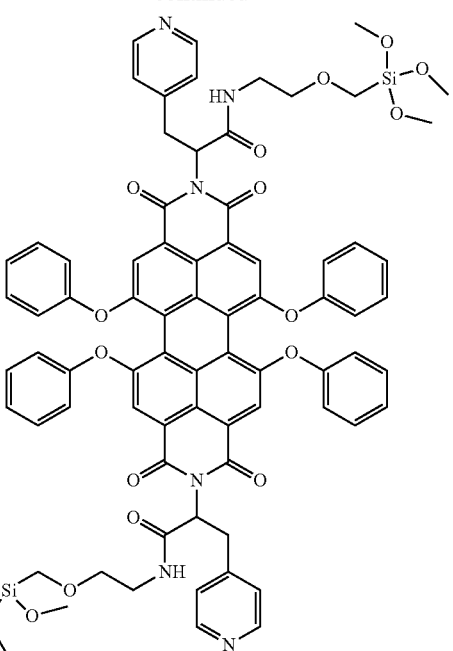
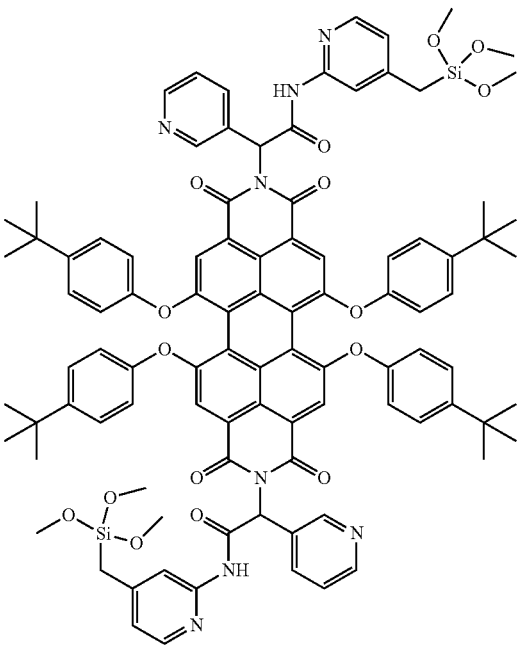

697
-continued
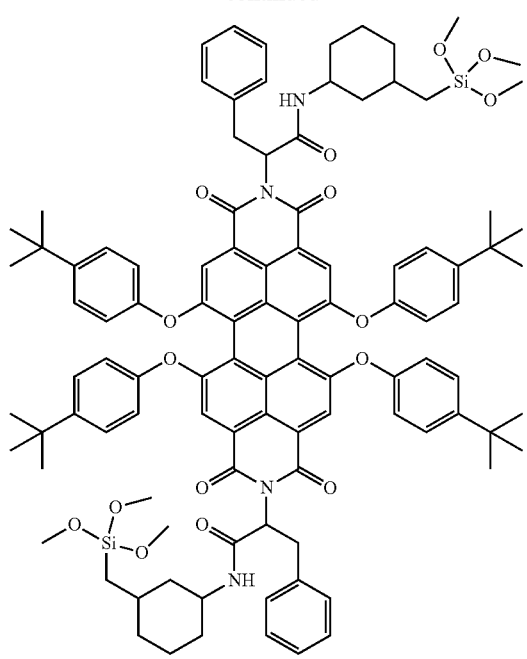
698
-continued
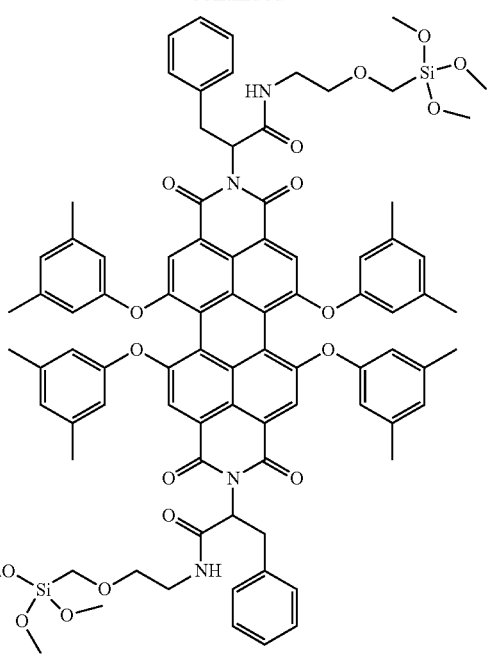
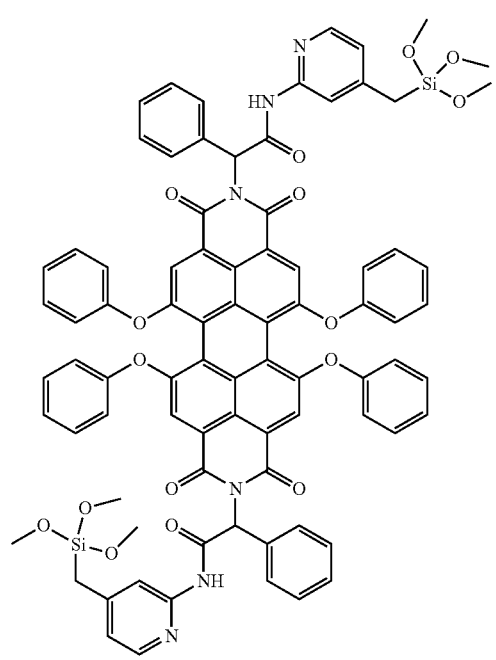
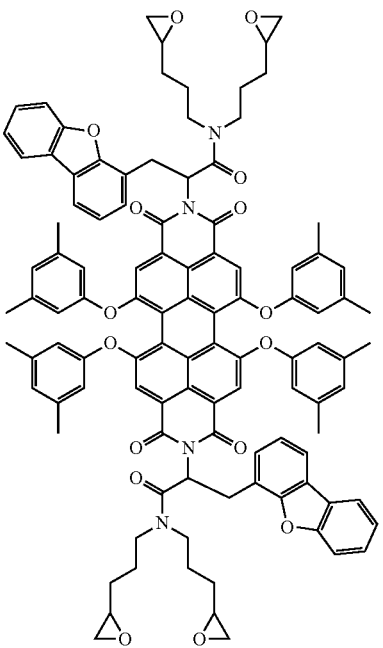

699
-continued
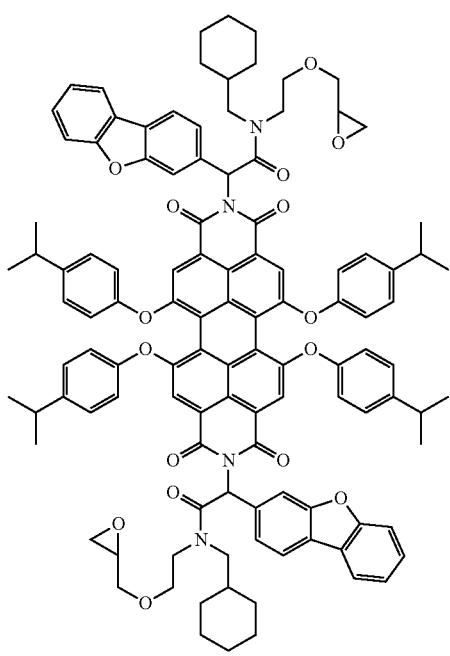
700
-continued
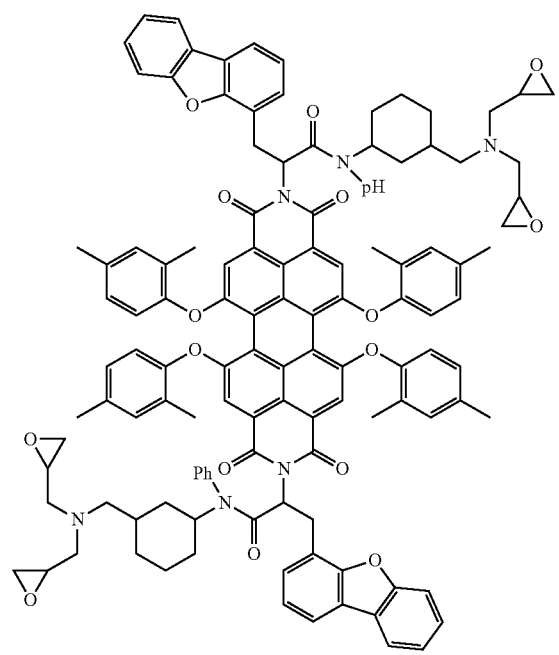
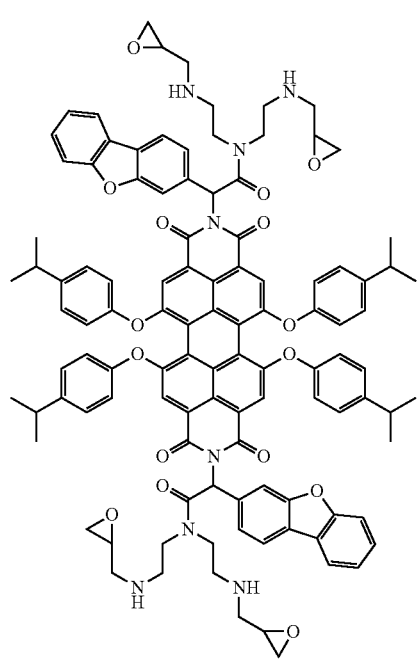
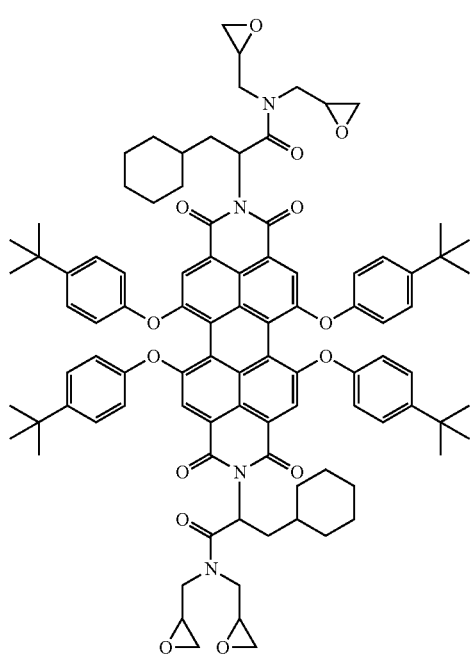

701
-continued
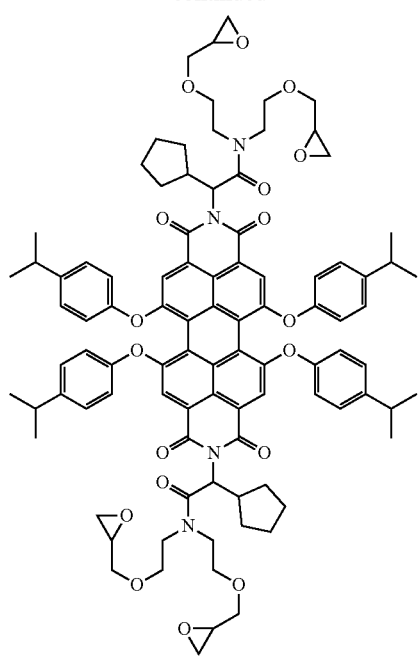
702
-continued
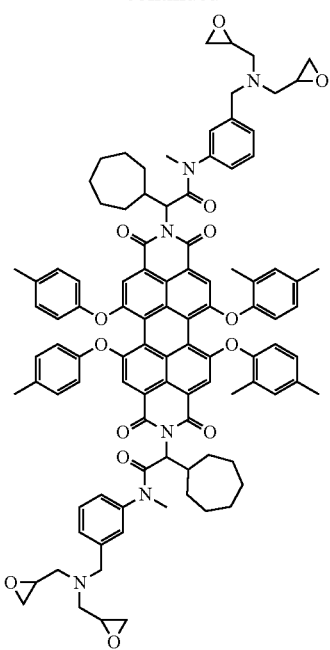
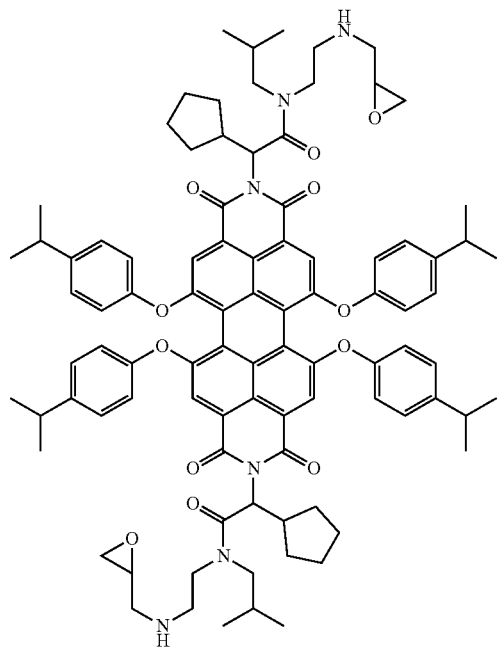
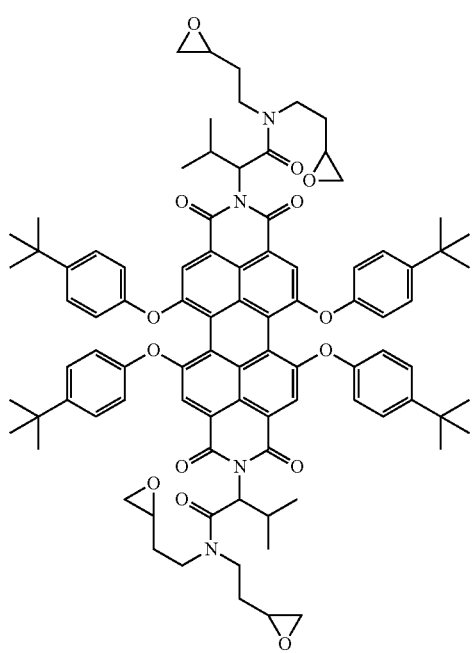

703
-continued
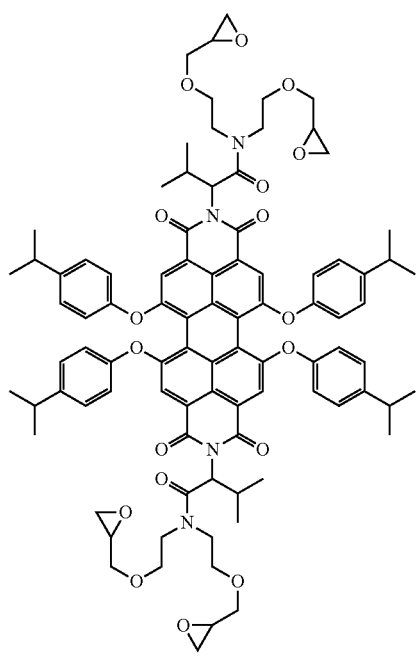
704
-continued
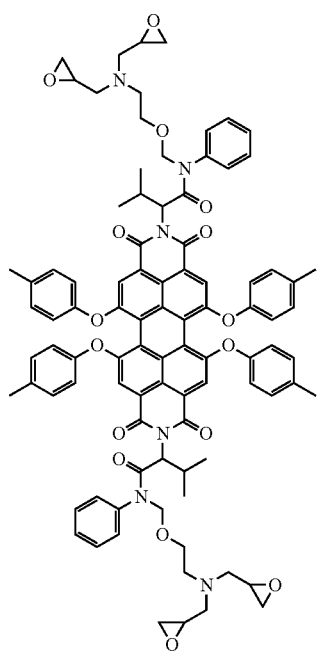
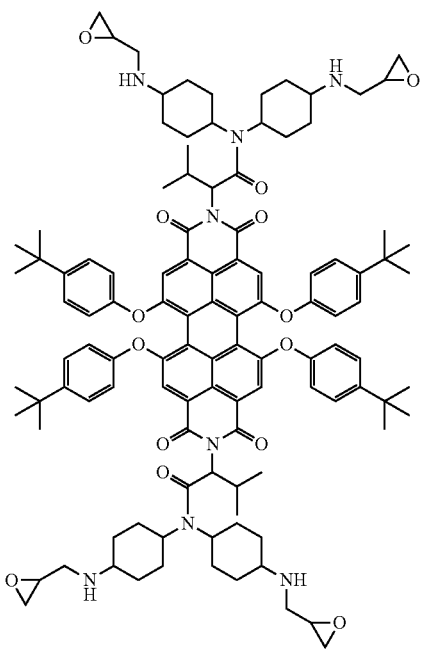
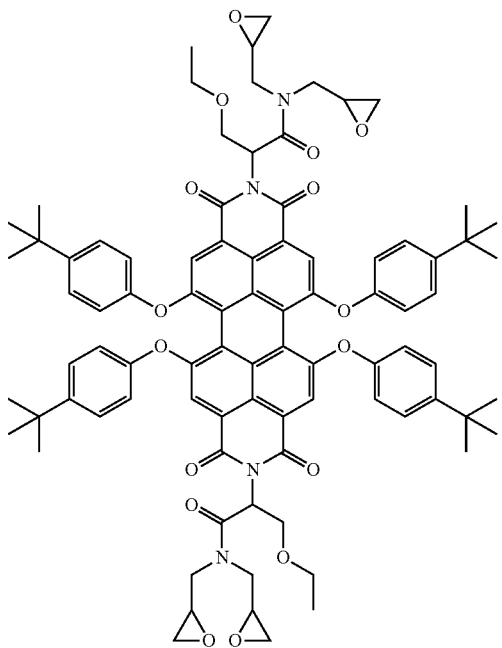

705
-continued
706
-continued
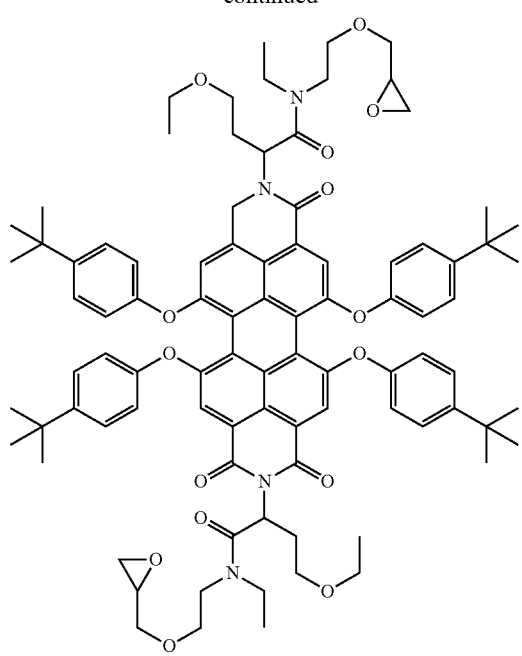
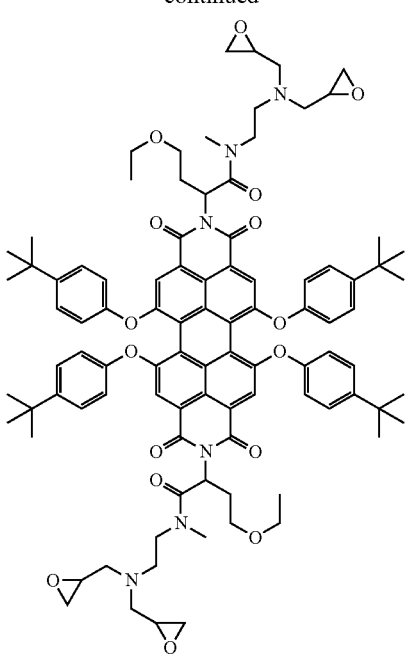
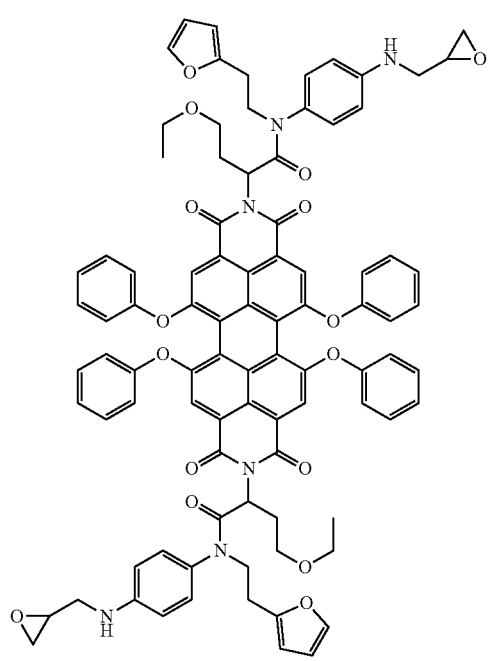

707
-continued
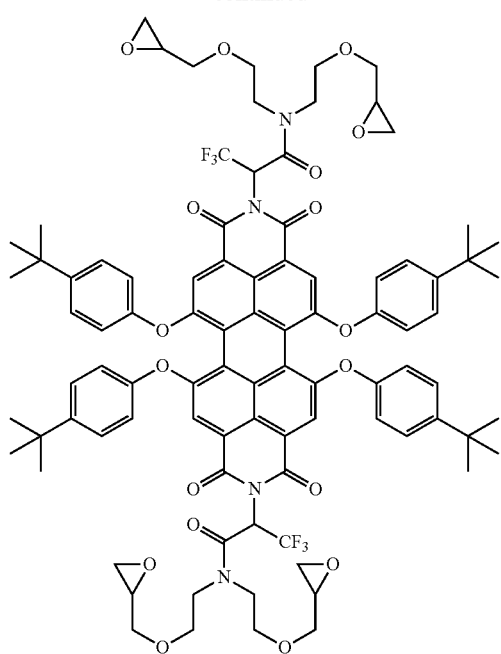
708
-continued
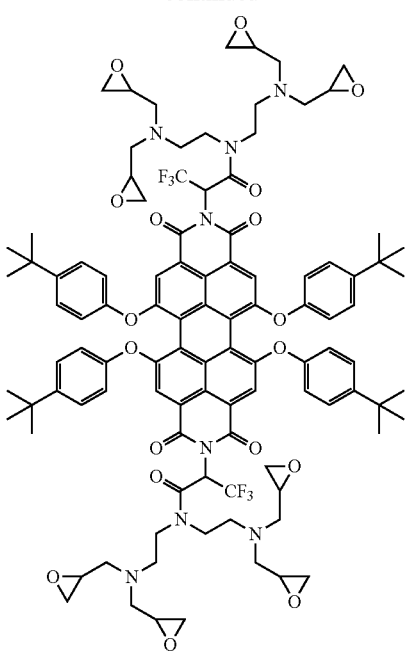
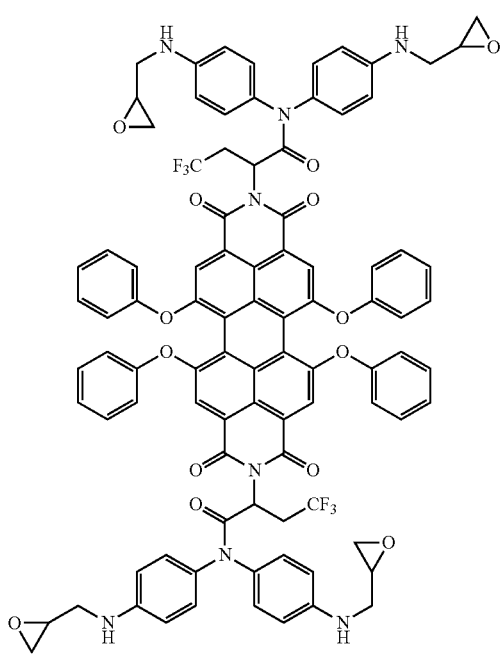
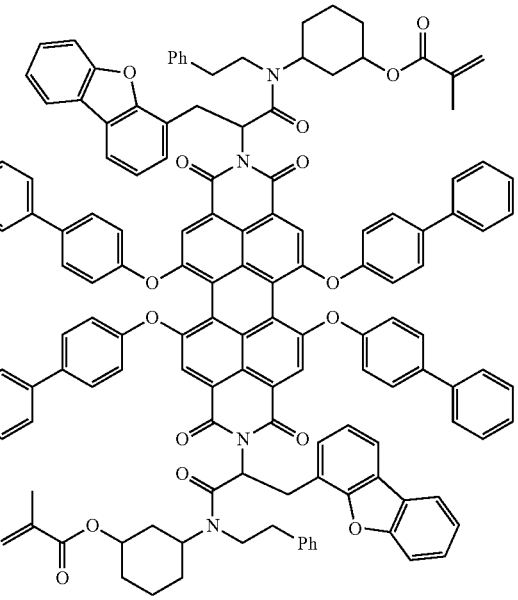

709
-continued
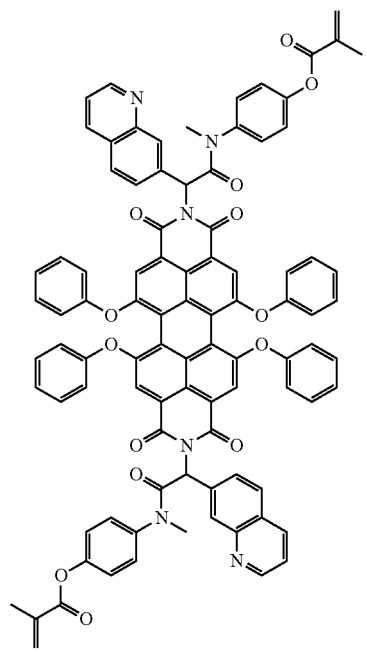
710
-continued
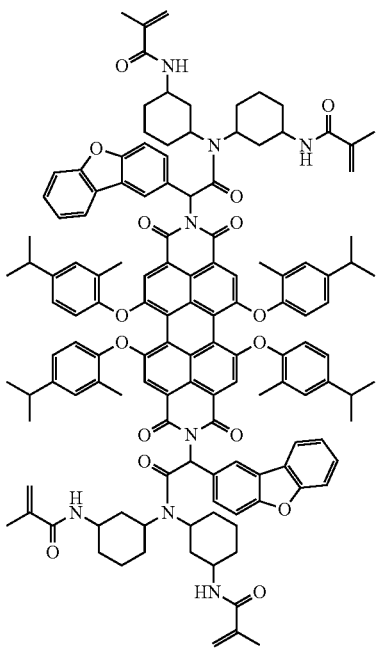
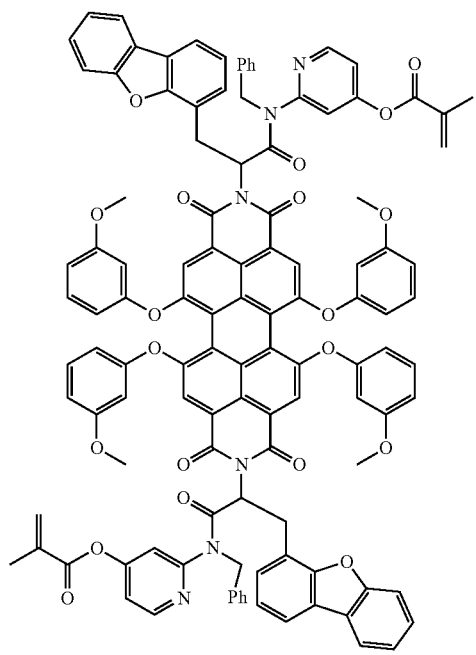
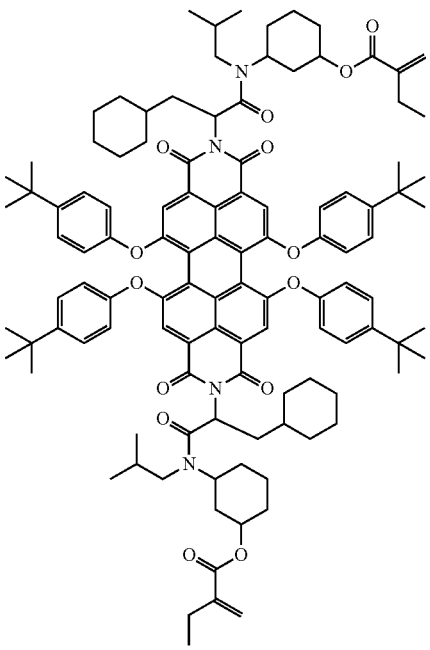

711
-continued
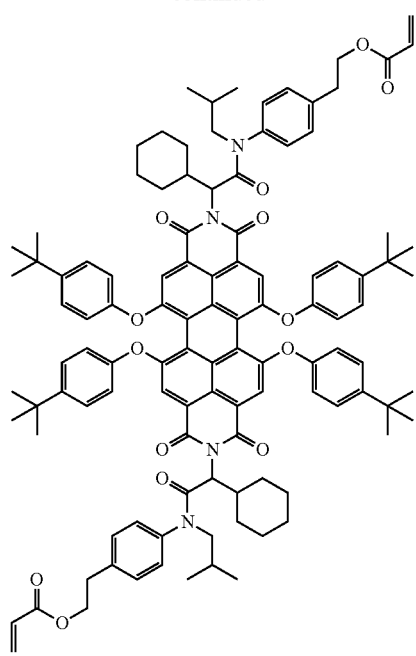
712
-continued
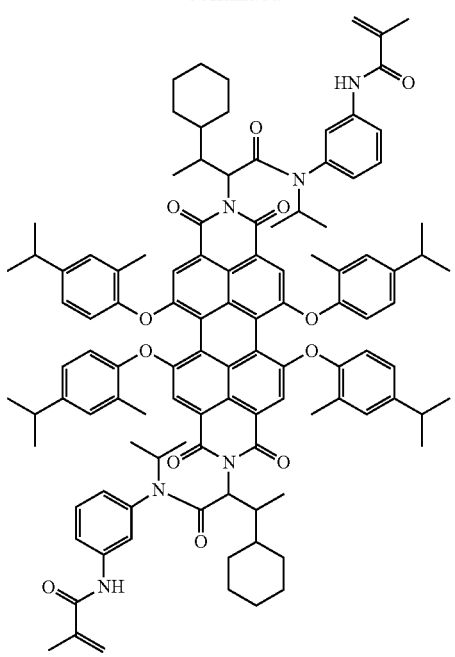
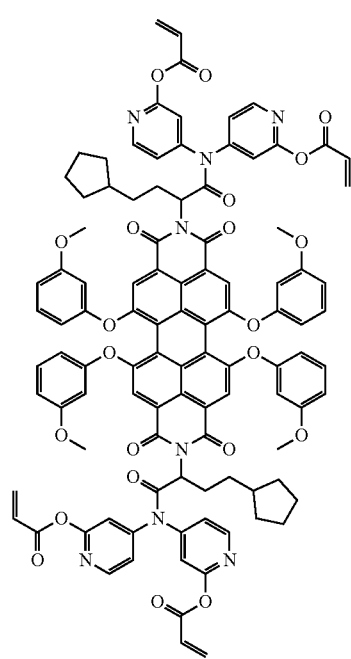
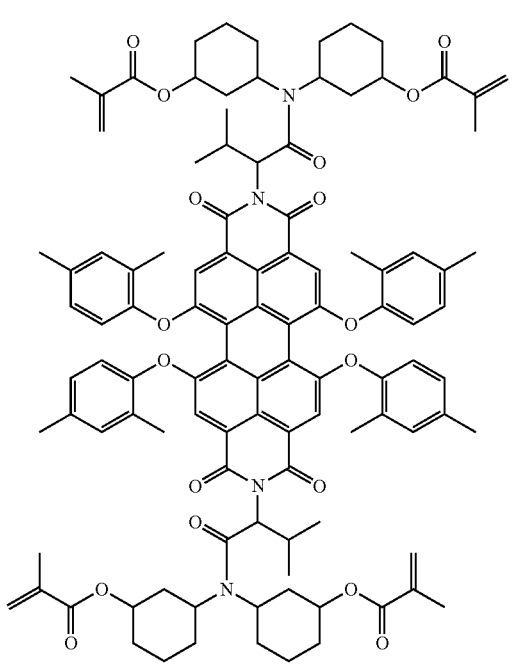

713
-continued
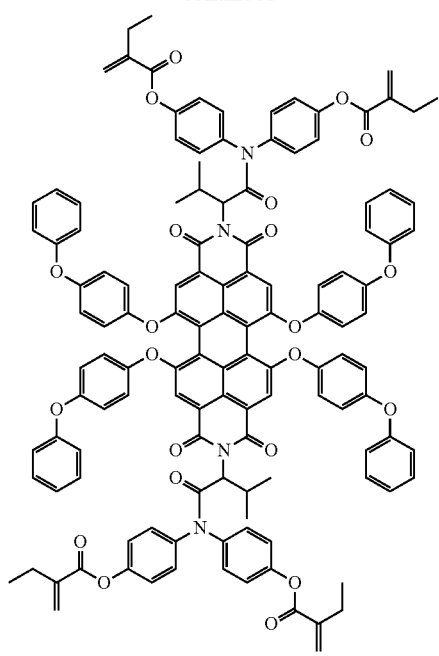
714
-continued
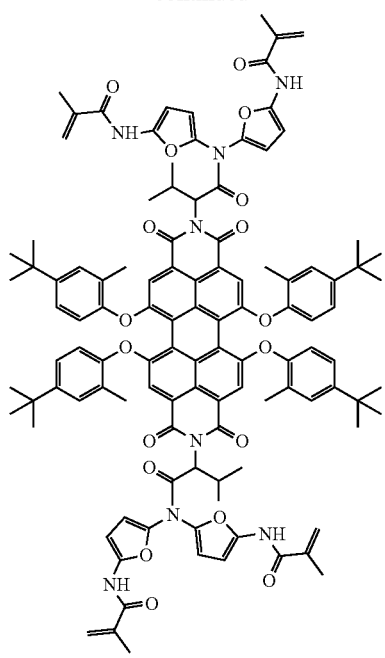
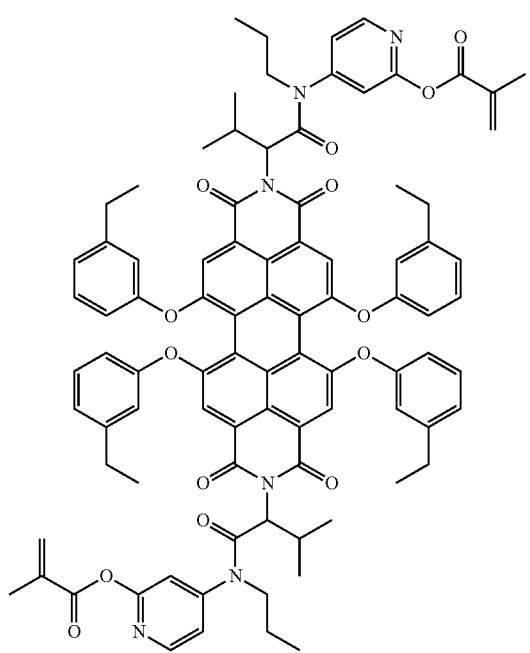
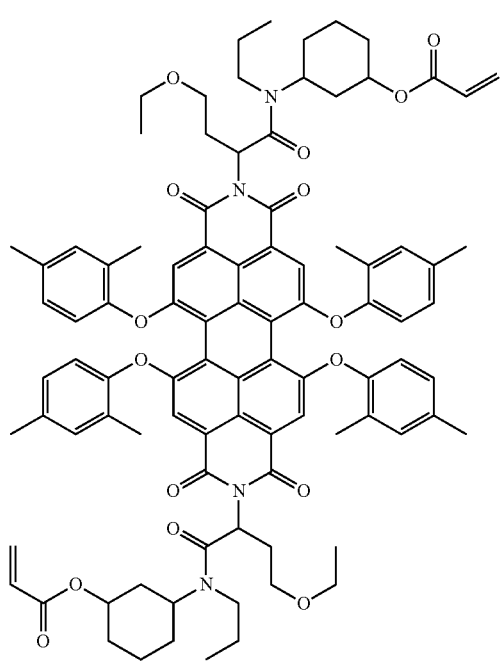

715
-continued
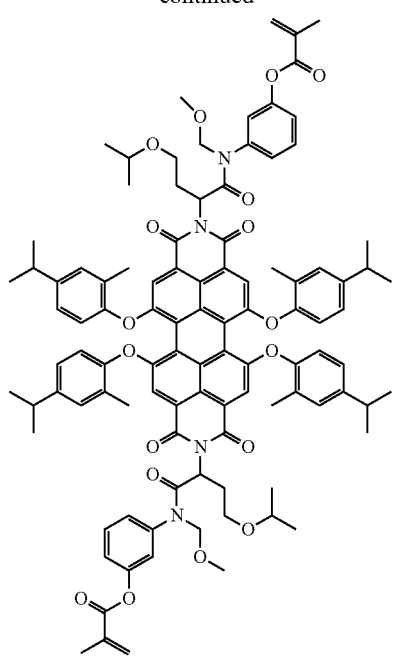
716
-continued
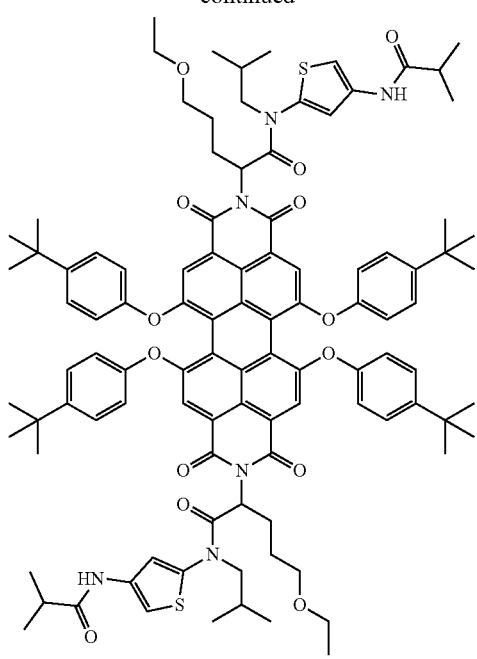
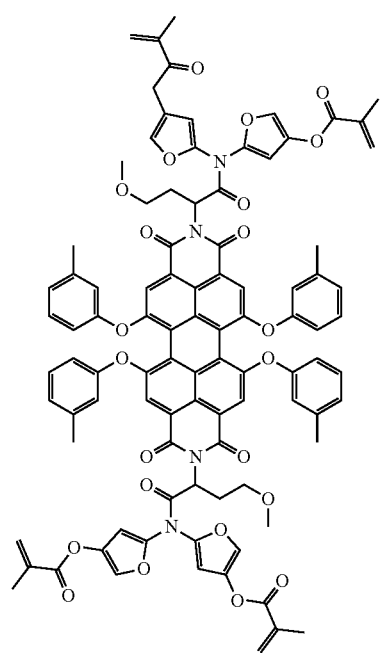
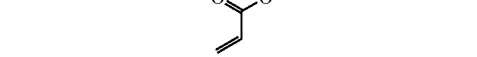

717
-continued
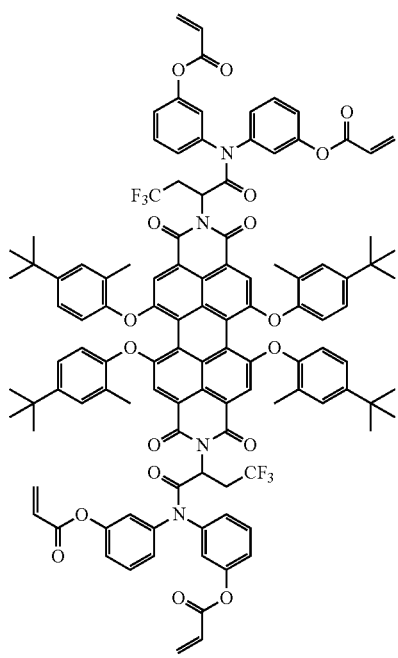
718
-continued
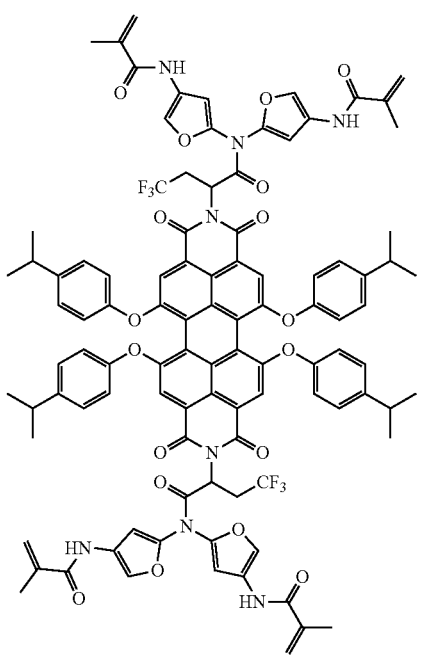
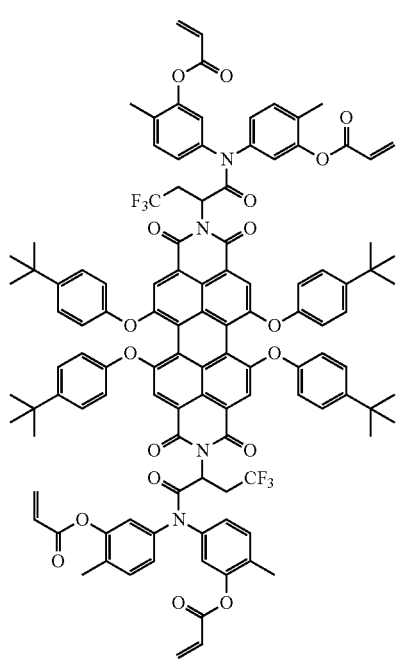
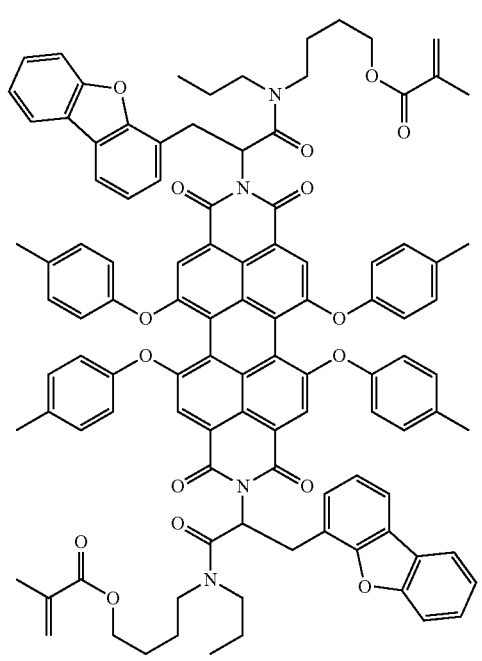

719
-continued
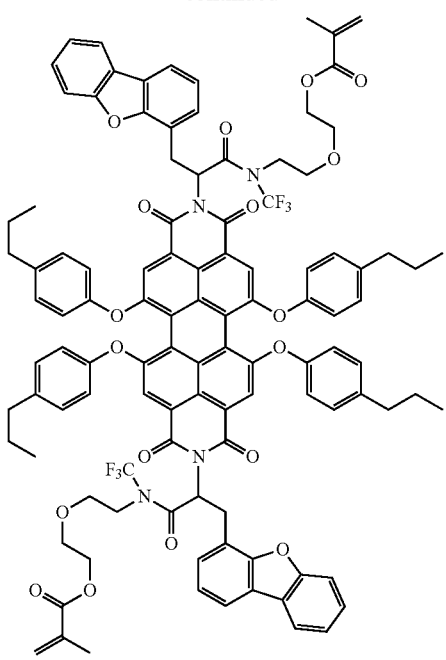
720
-continued
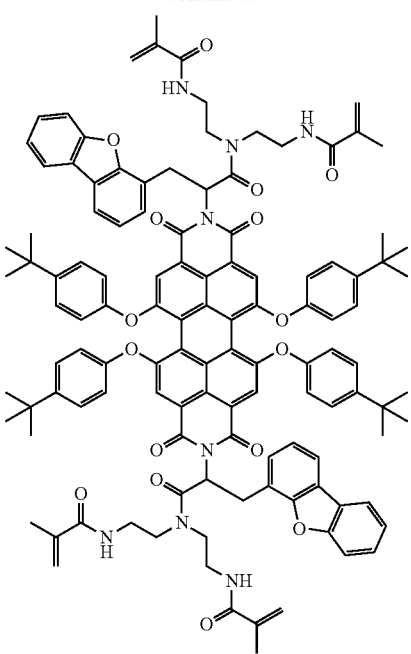
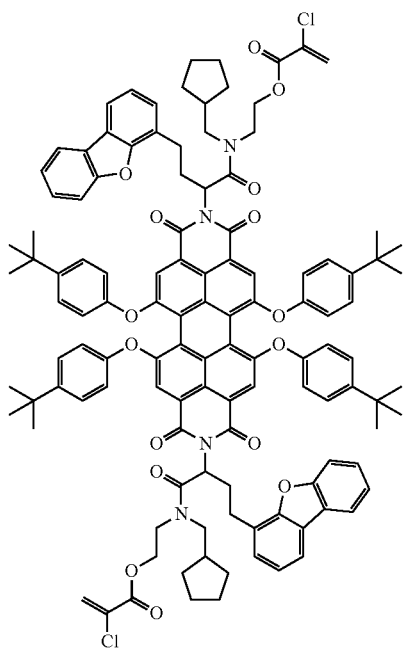
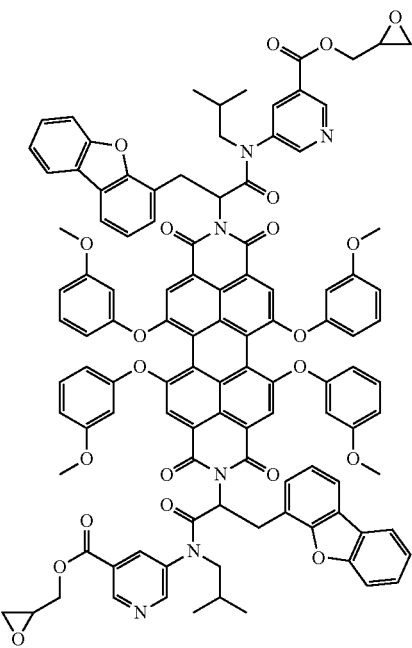

721
-continued
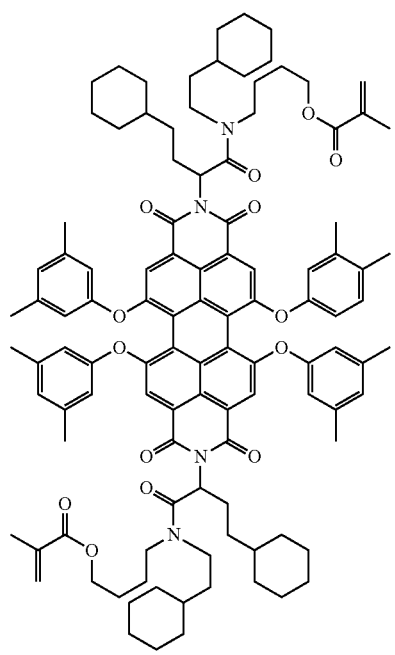
722
-continued
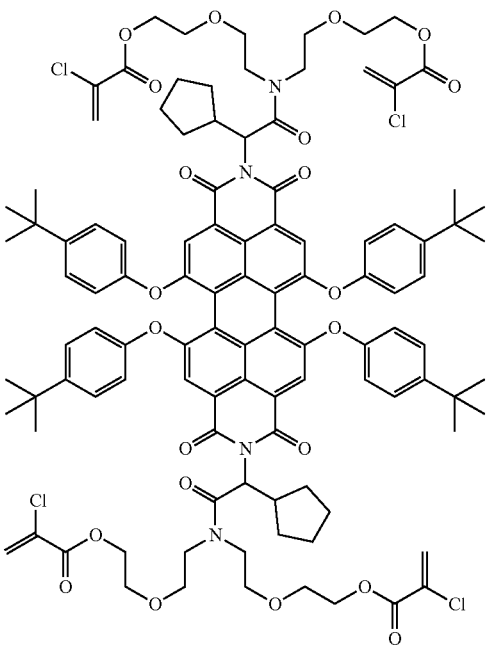
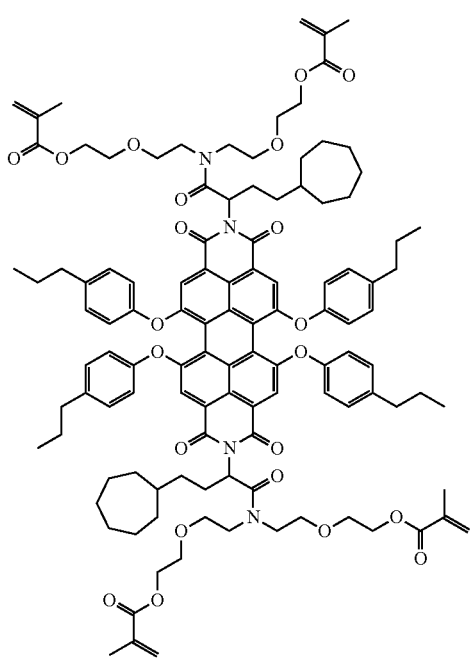
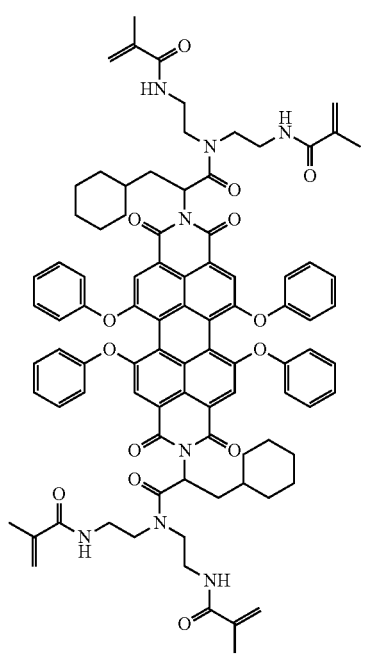

723
-continued
724
-continued
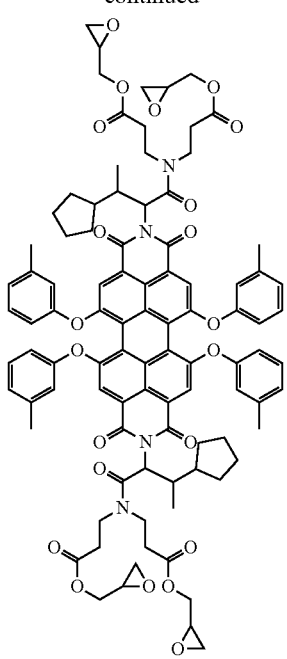
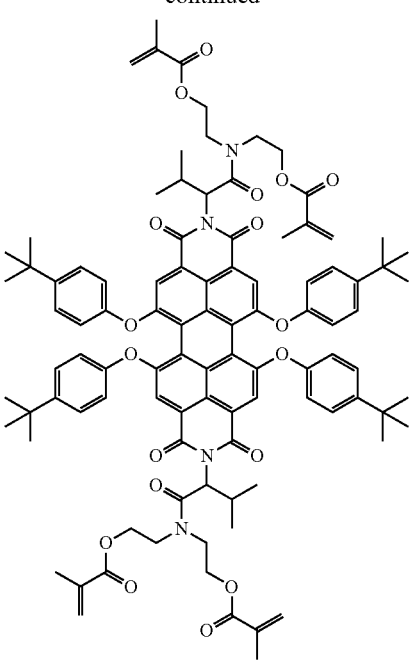

725
-continued
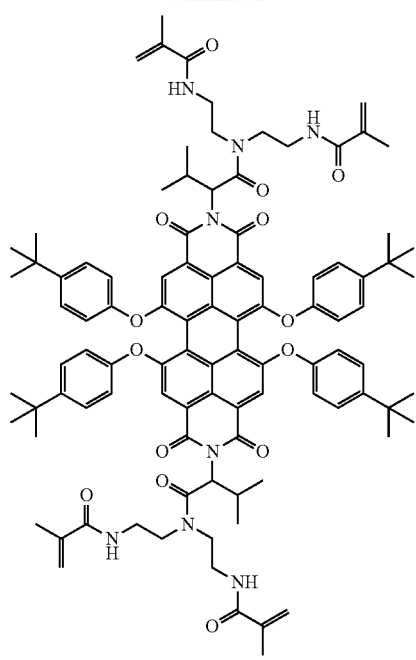
726
-continued
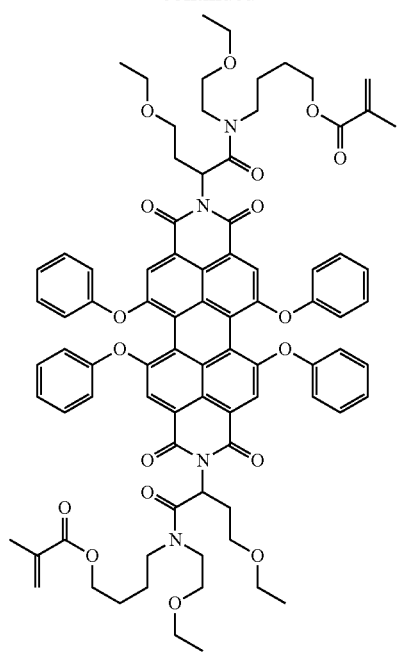
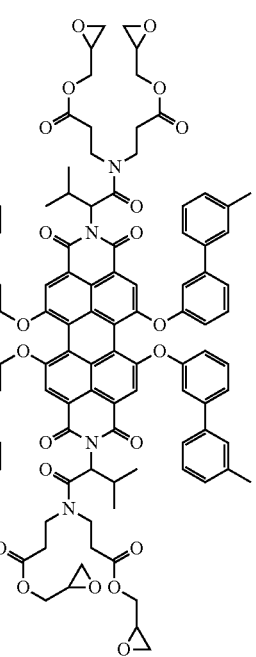
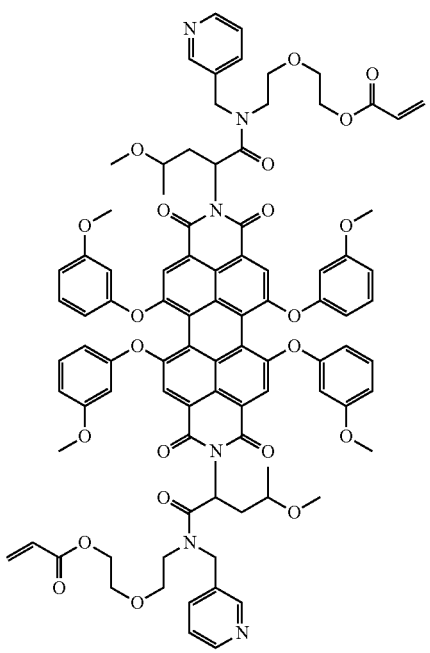

727
-continued
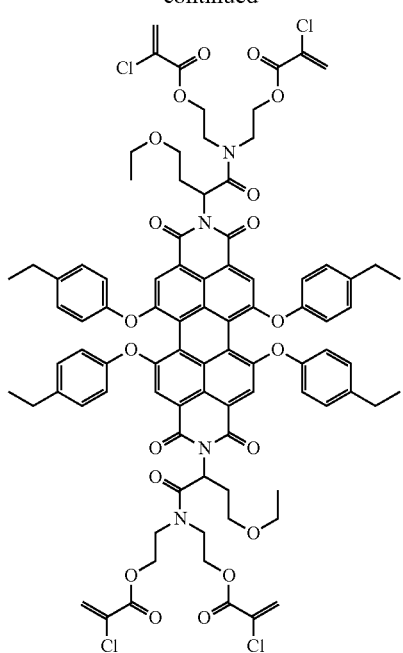
728
-continued
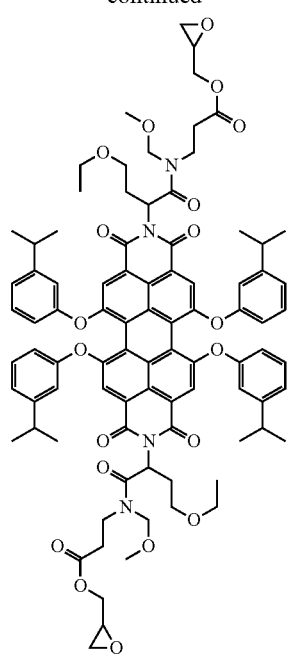
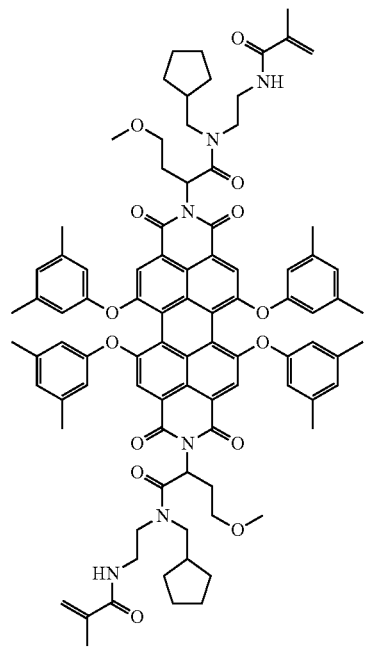
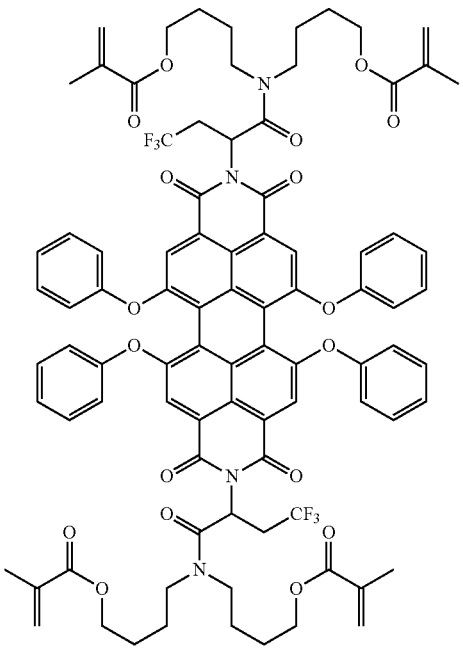

729
-continued
730
-continued
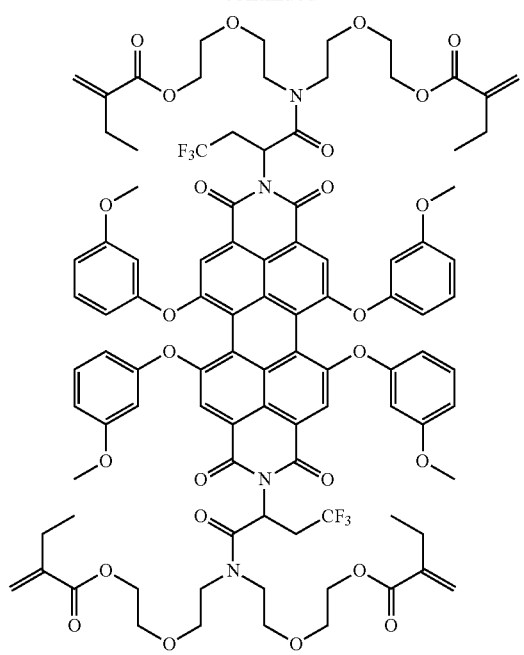
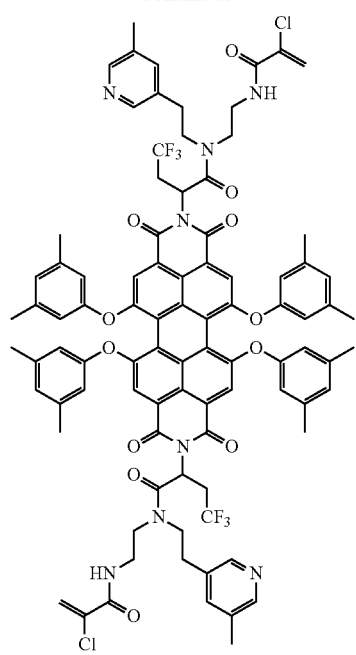
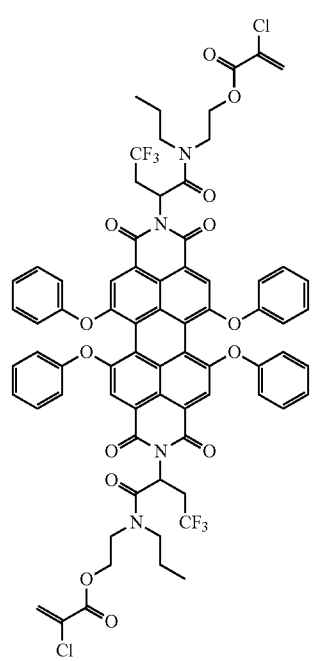
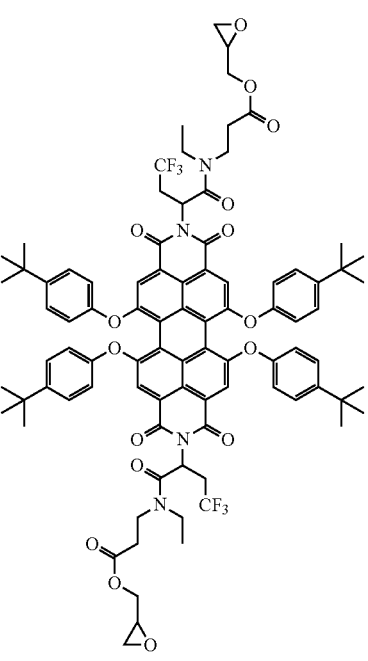

| 731 -continued | 732 -continued |
|---|---|
| 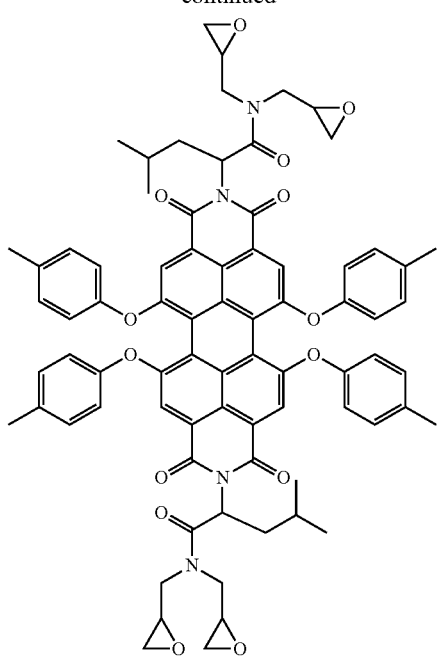 | 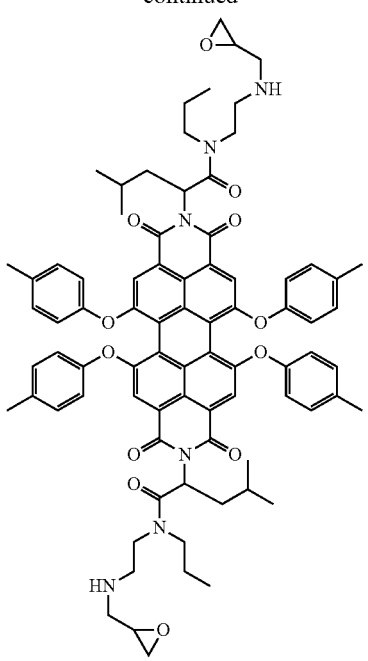 |
| 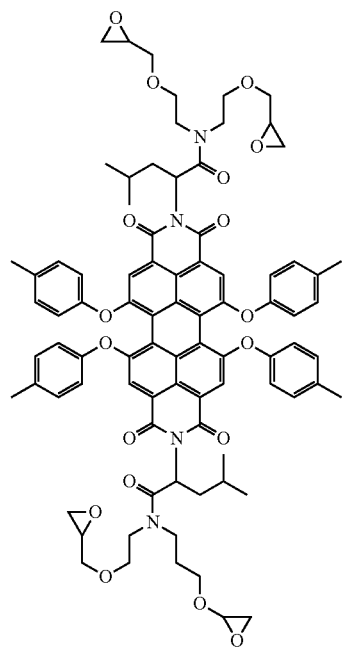 | 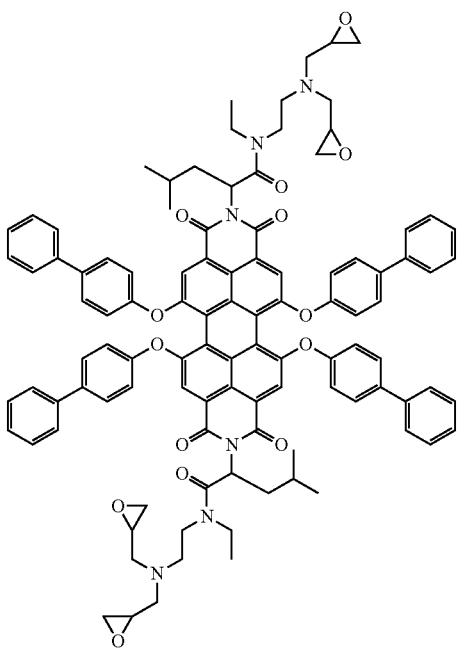 |

733
-continued
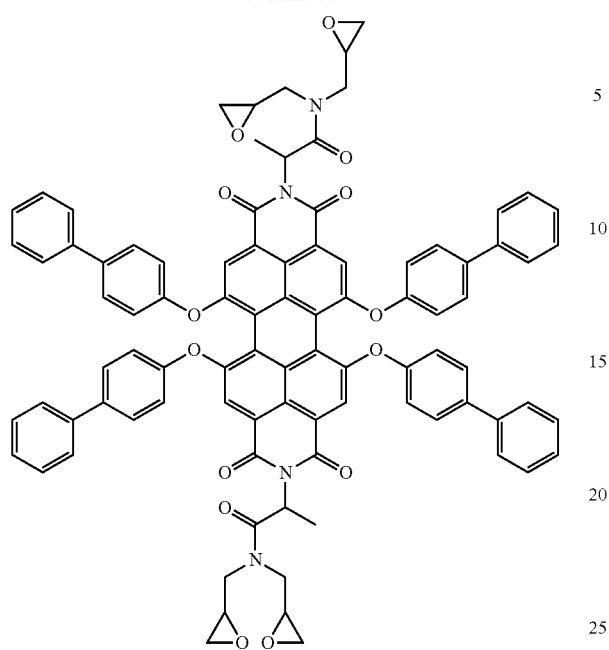
734
-continued
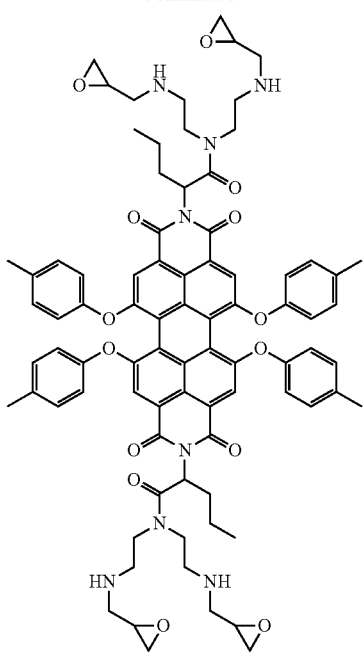
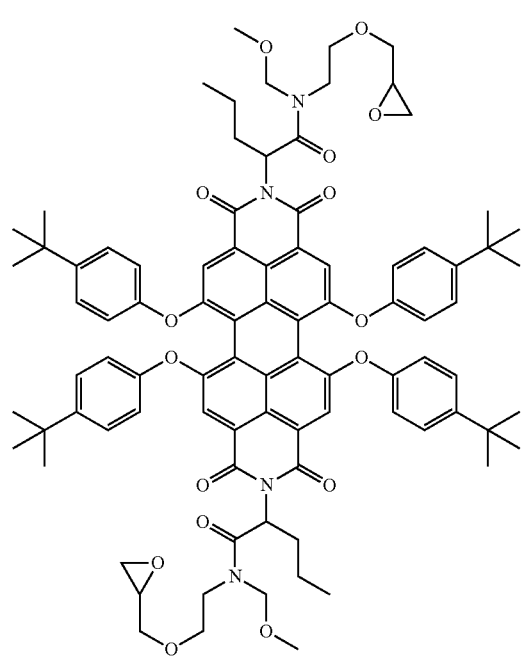
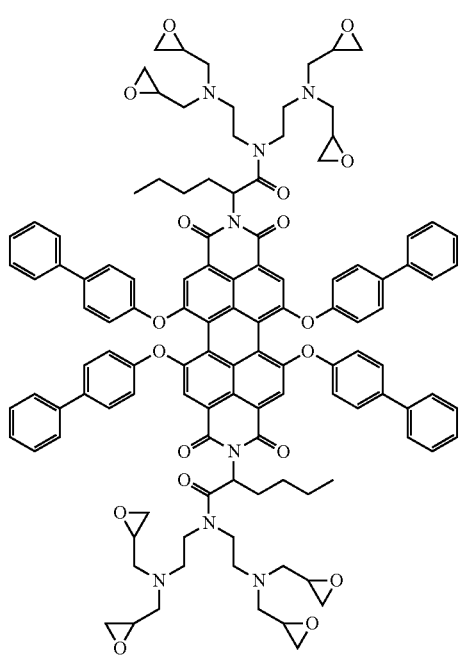

735
-continued
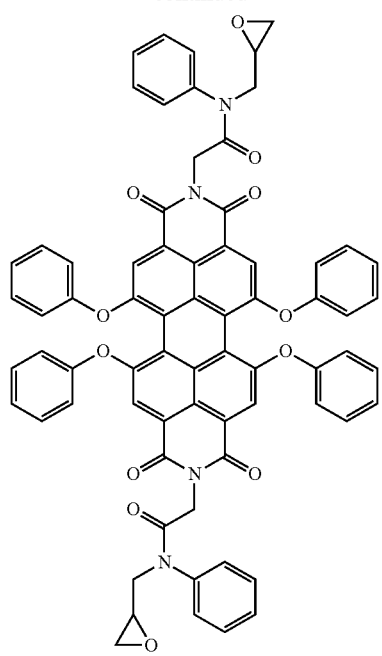
736
-continued
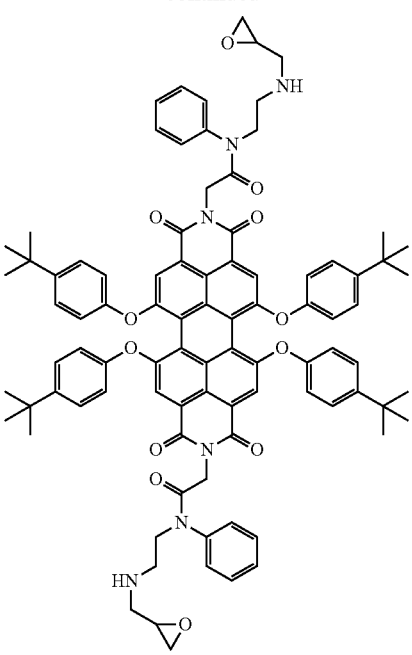
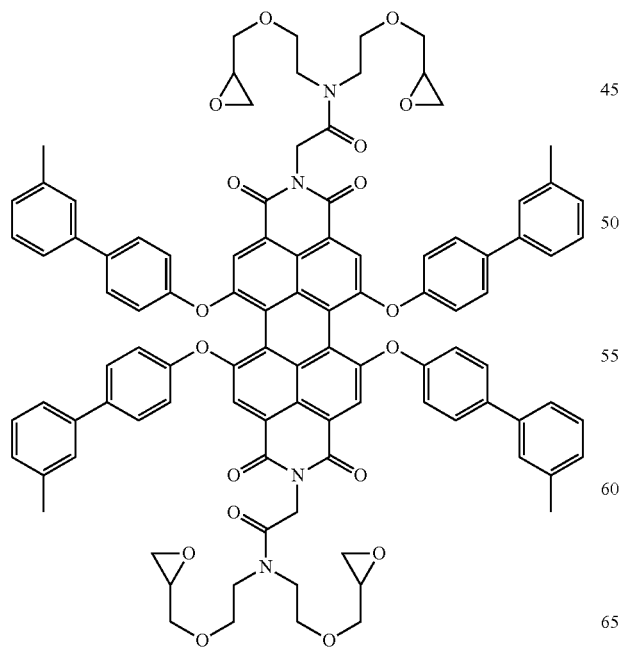
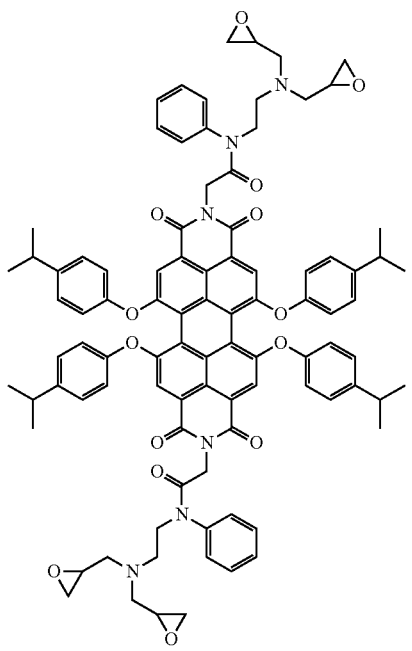

737
-continued
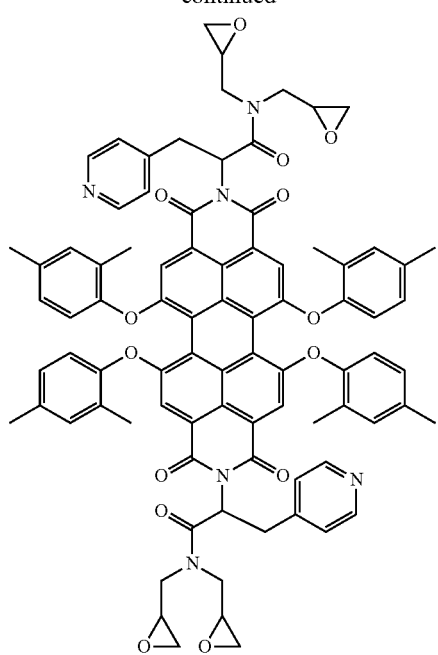
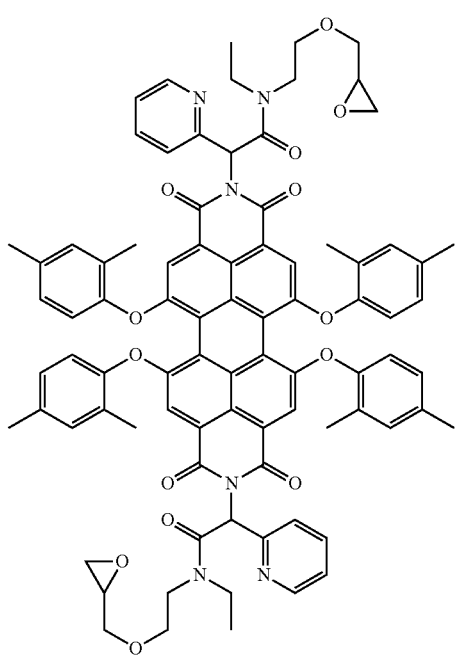
738
-continued
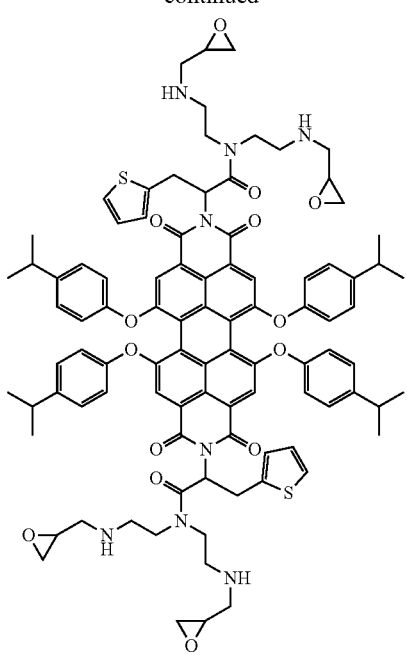
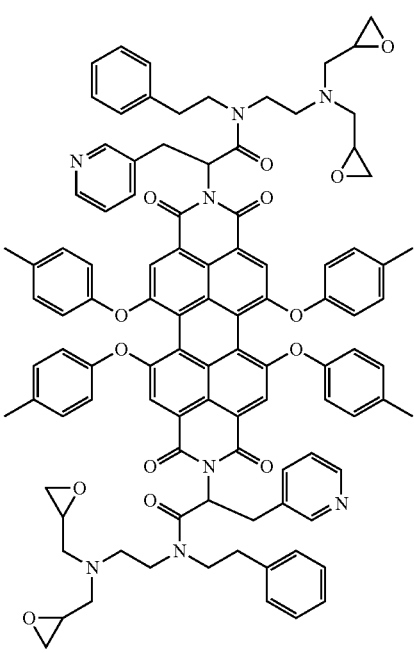

739
-continued
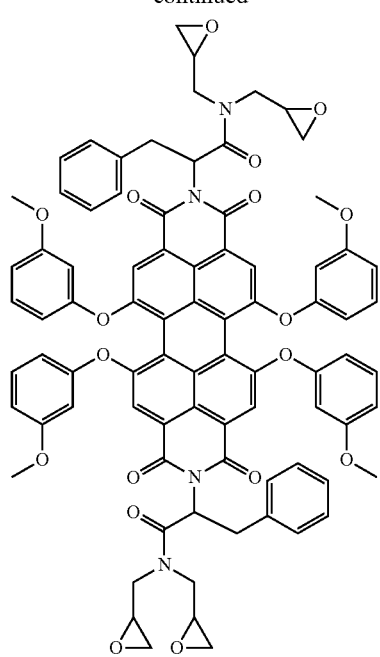
740
-continued
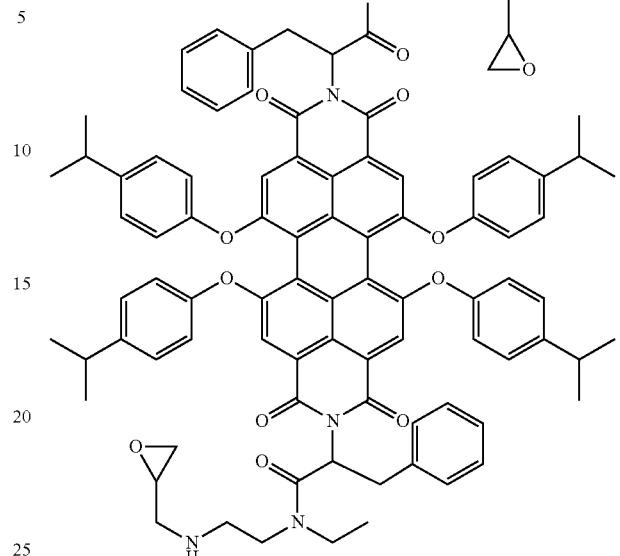
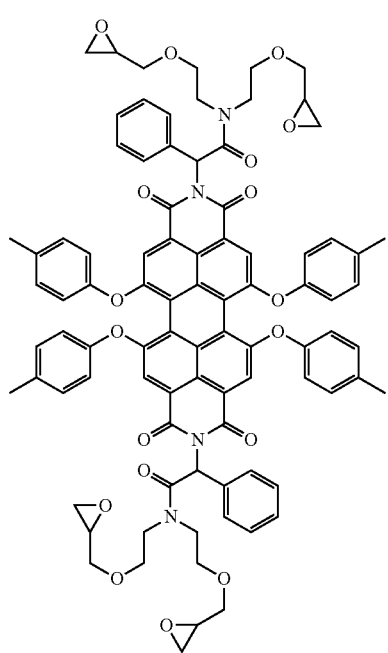
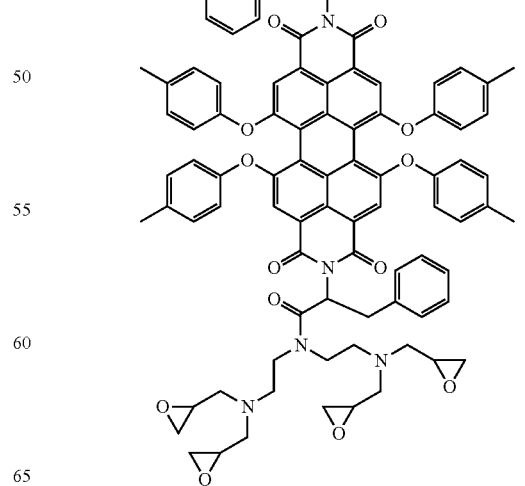

741
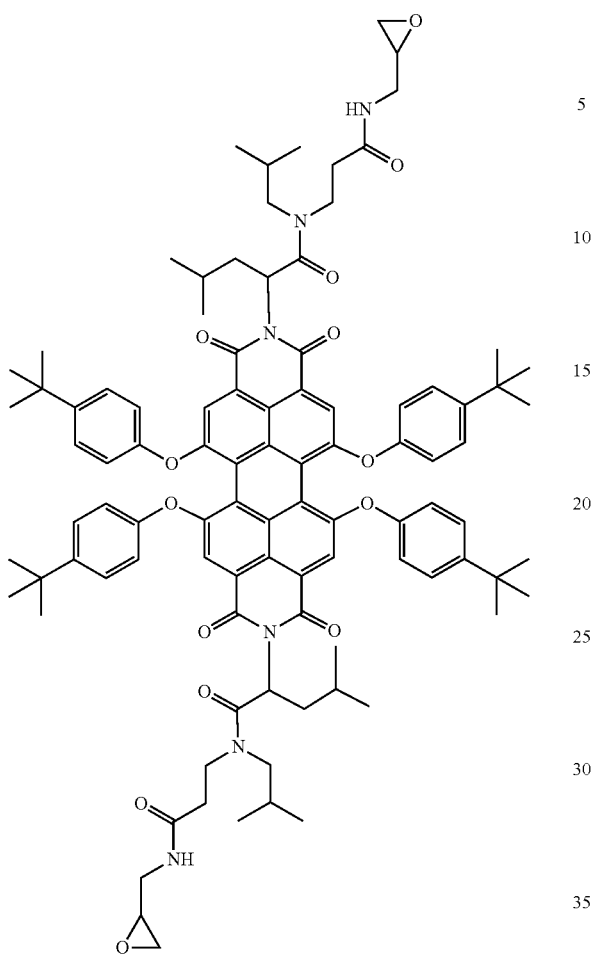
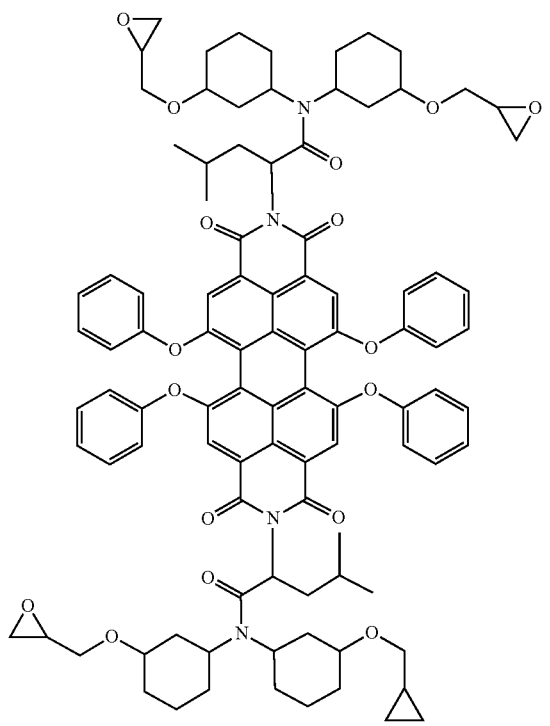
742
-continued
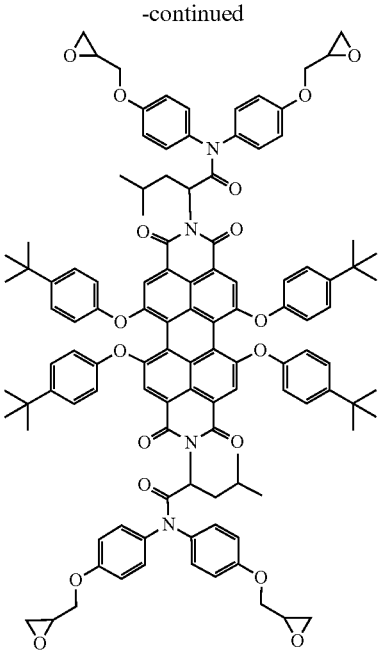
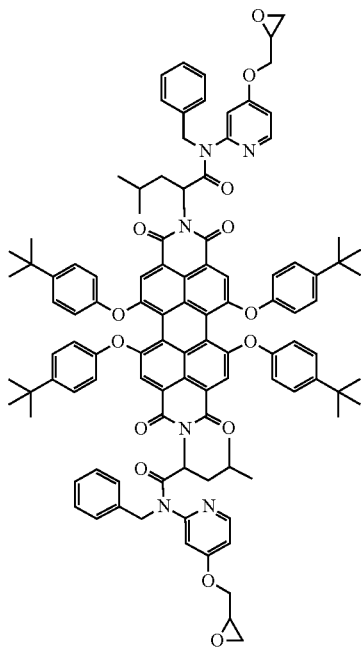

743
-continued
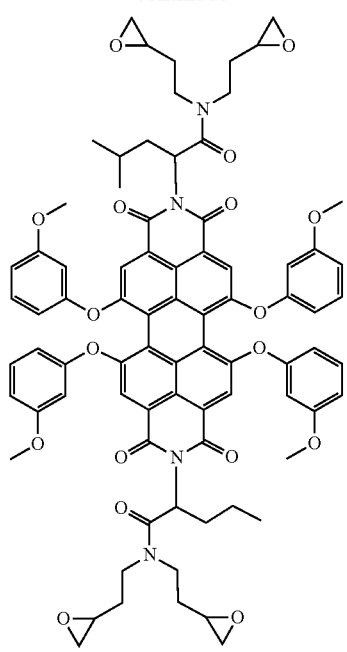
744
-continued
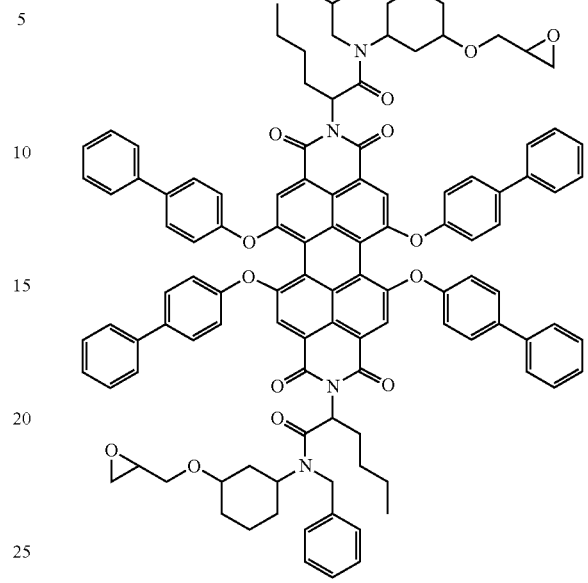
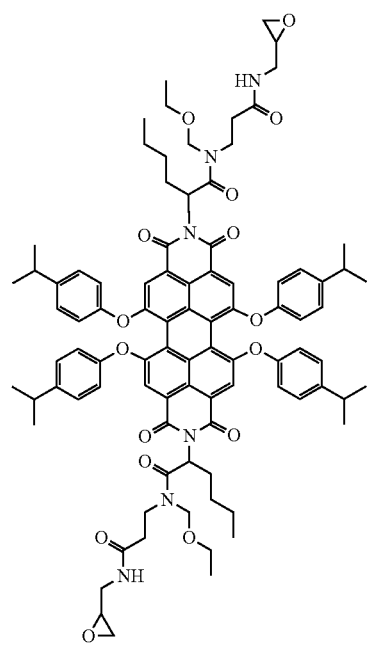
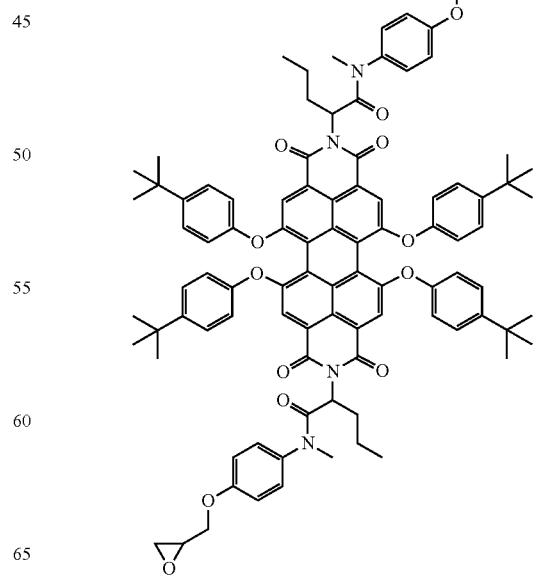

745
-continued
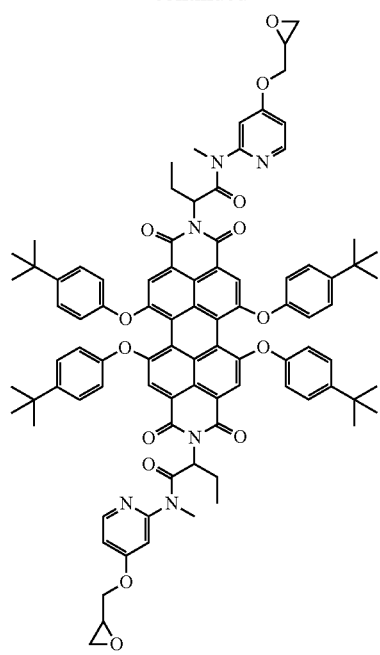
746
-continued
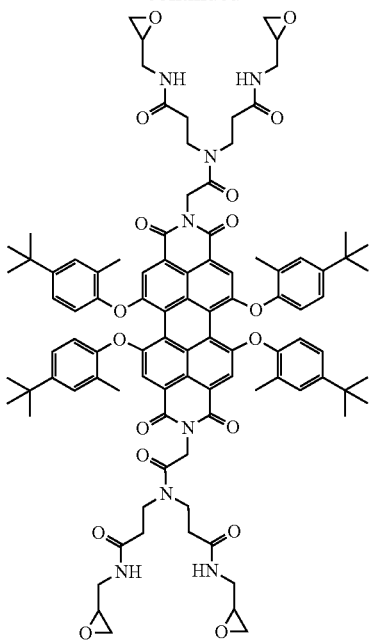
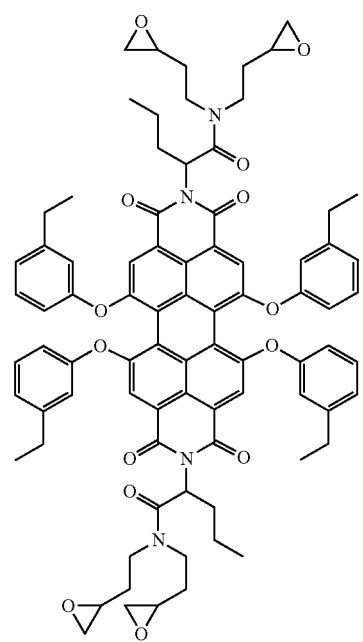
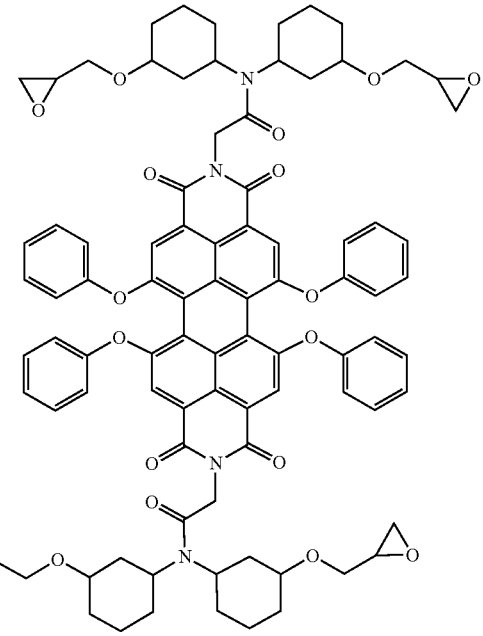

747
-continued
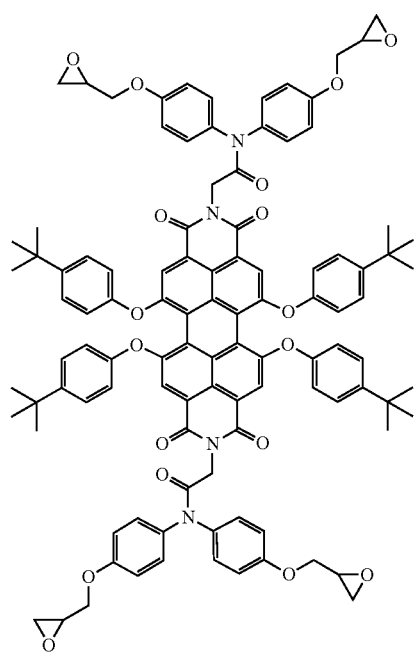
748
-continued
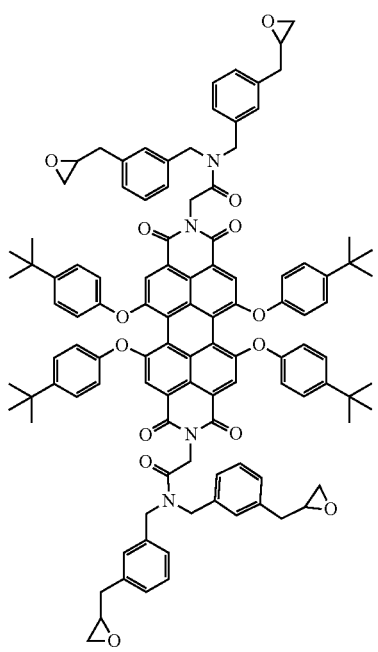
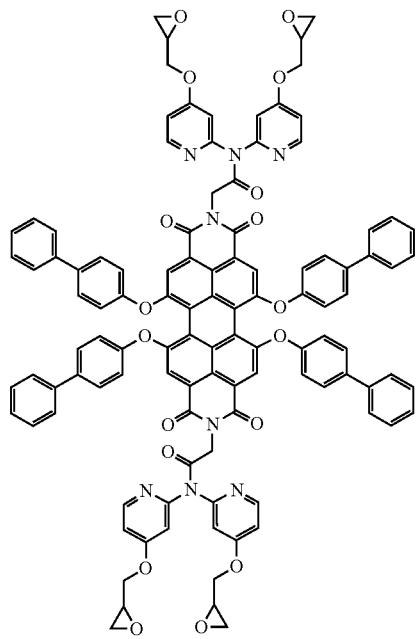
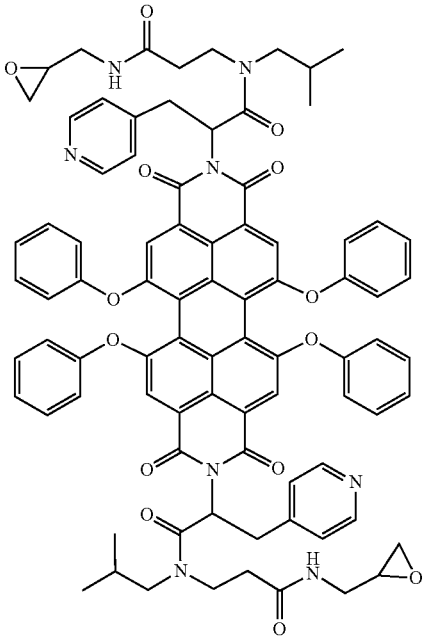

749
-continued
750
-continued
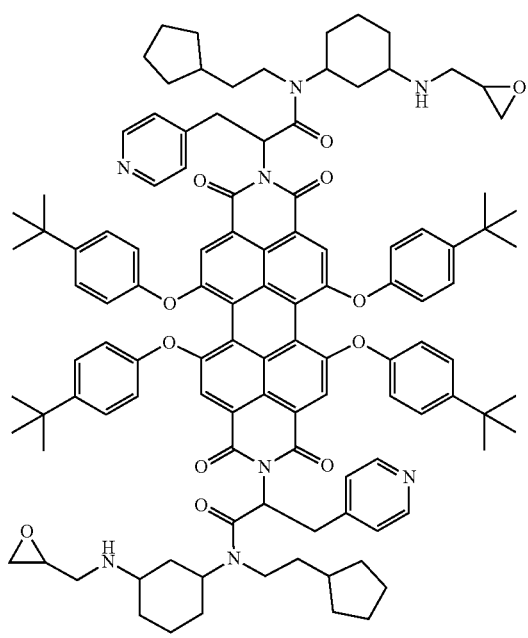
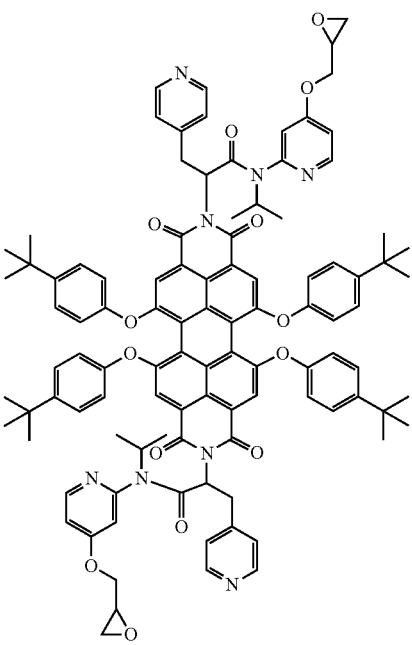
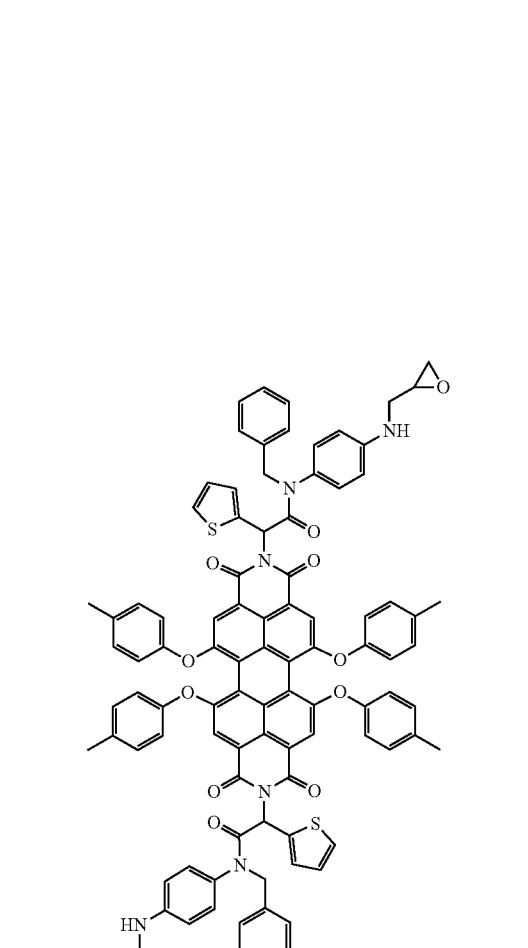

751
-continued
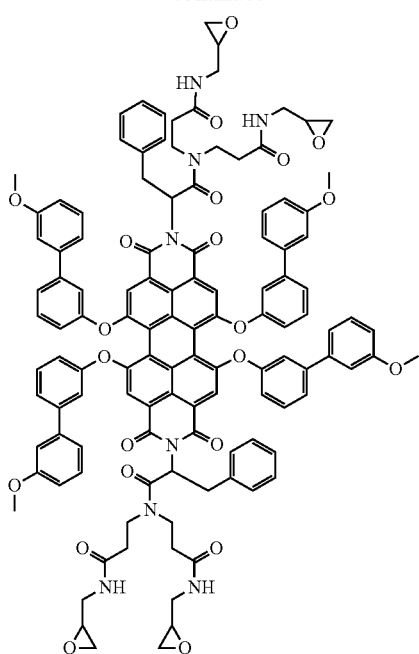
752
-continued
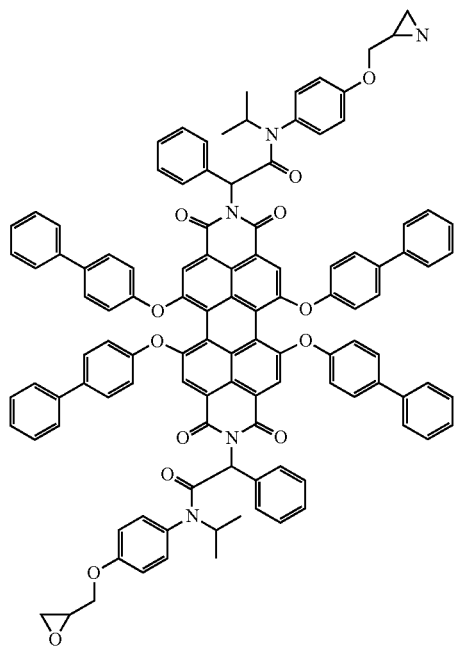
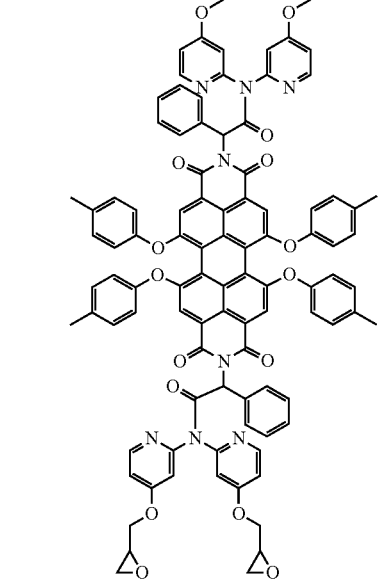

753
-continued
754
-continued
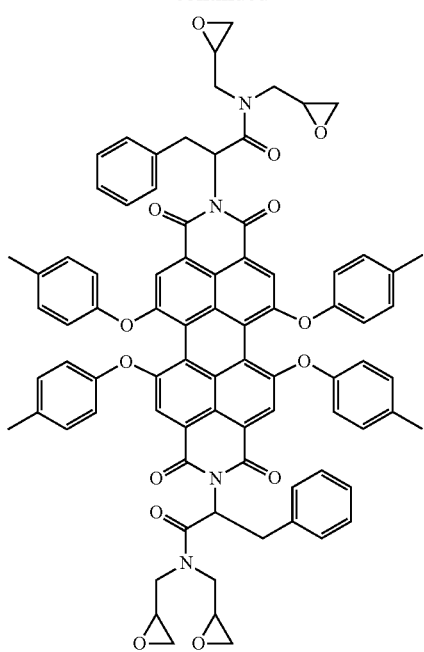
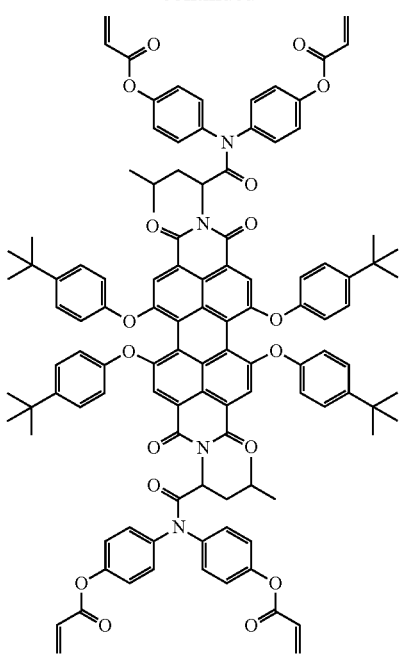
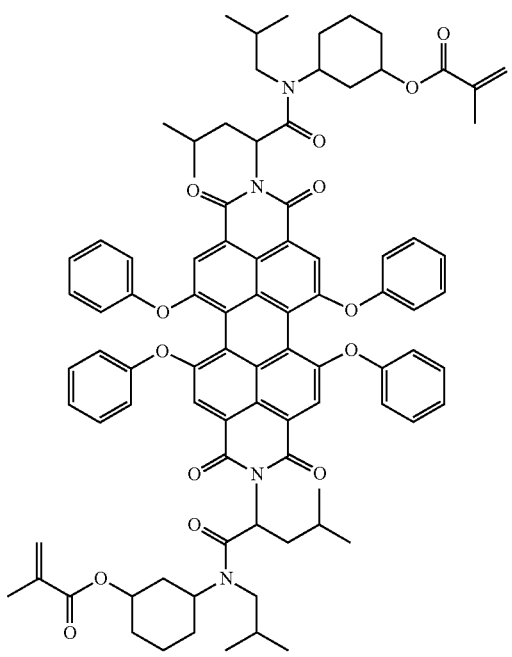
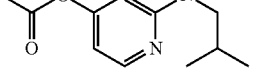

755
-continued
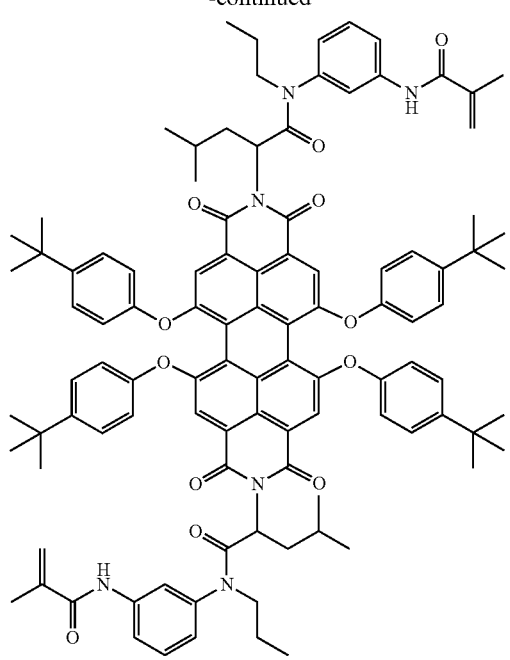
756
-continued
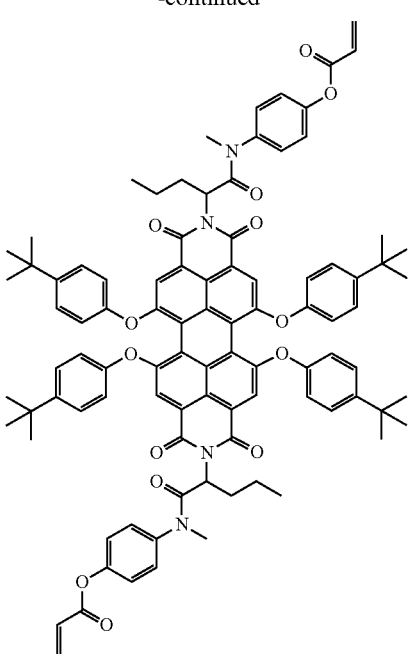
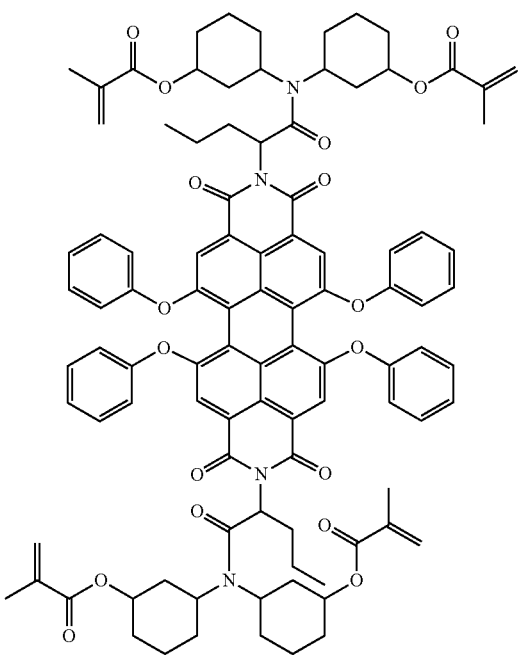
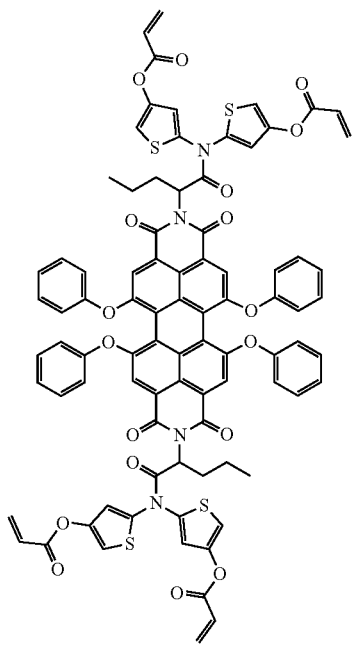

| 757 -continued | 758 -continued |
|---|---|
| 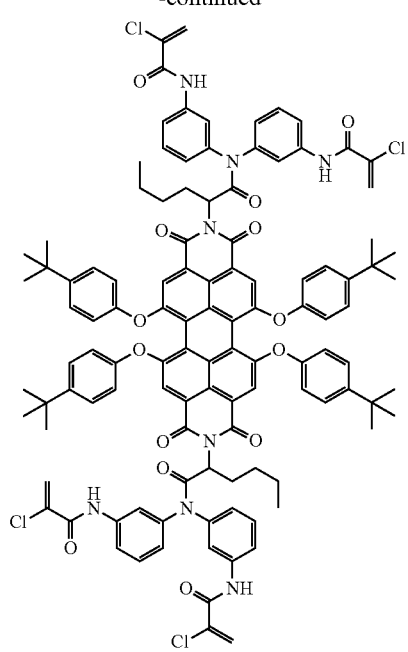 | 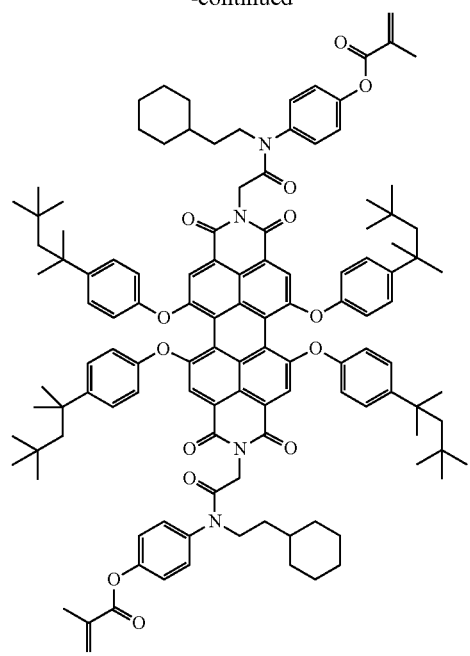 |
| 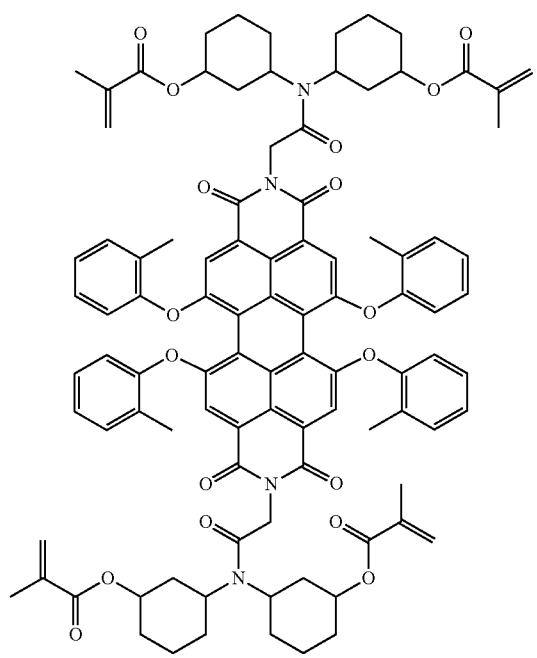 | 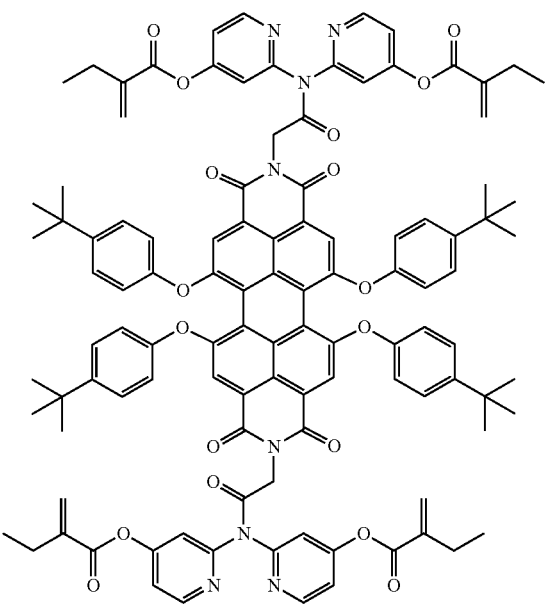 |

759
-continued
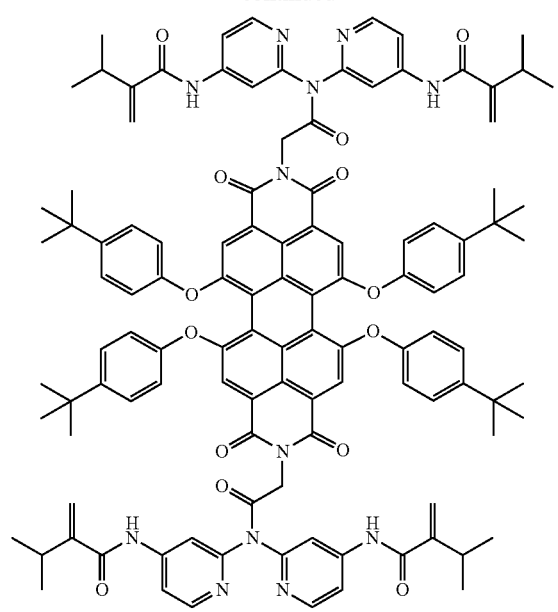
760
-continued
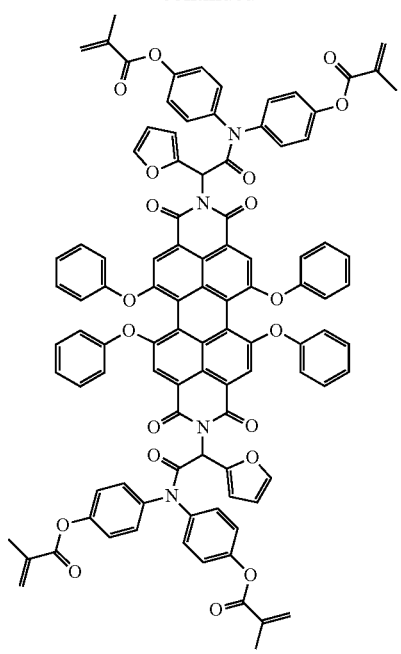
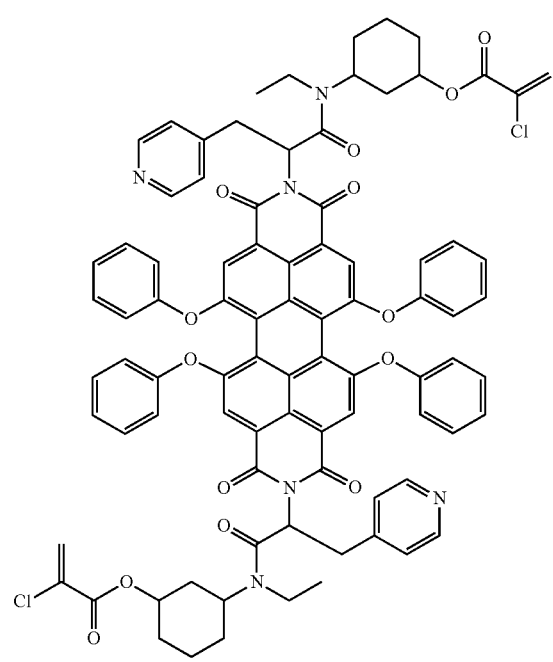
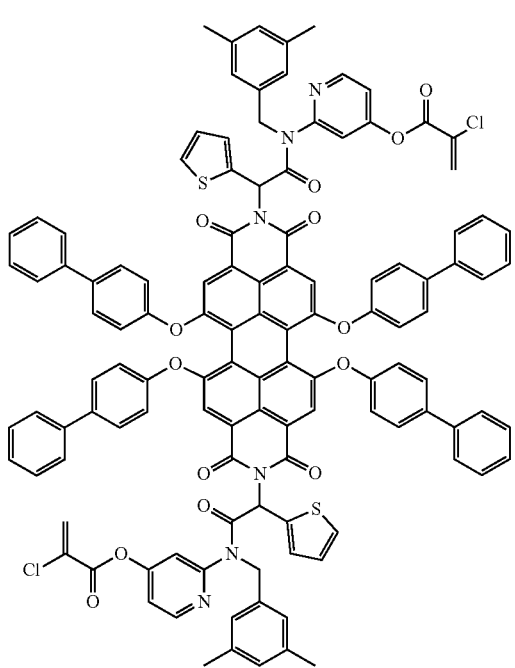

761
-continued
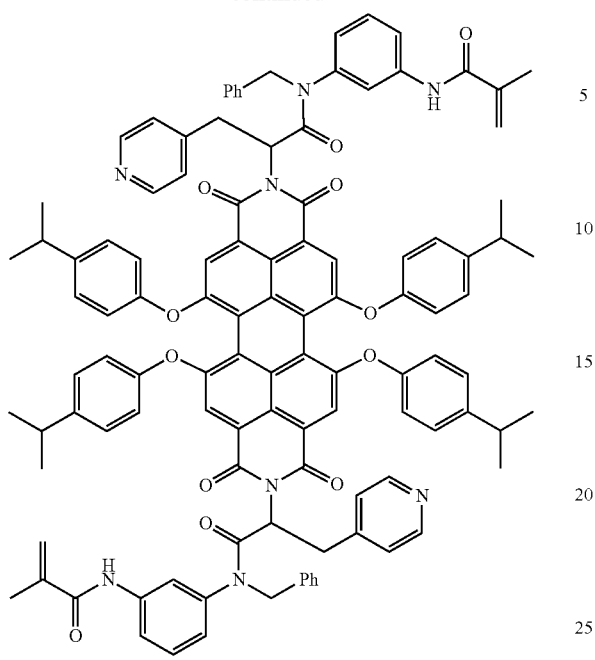
762
-continued
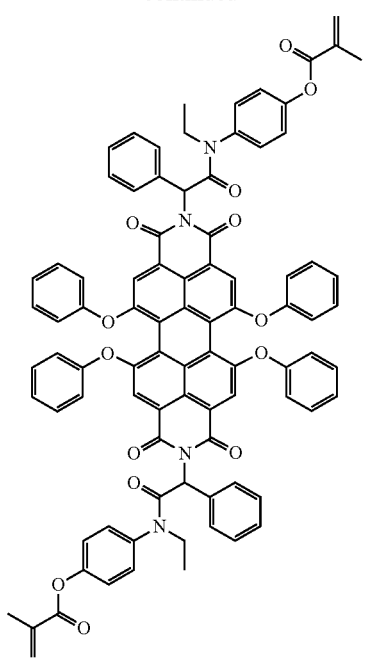
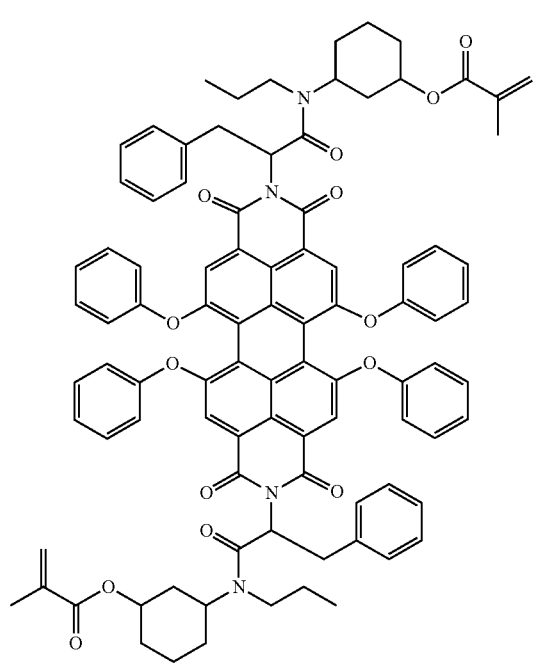
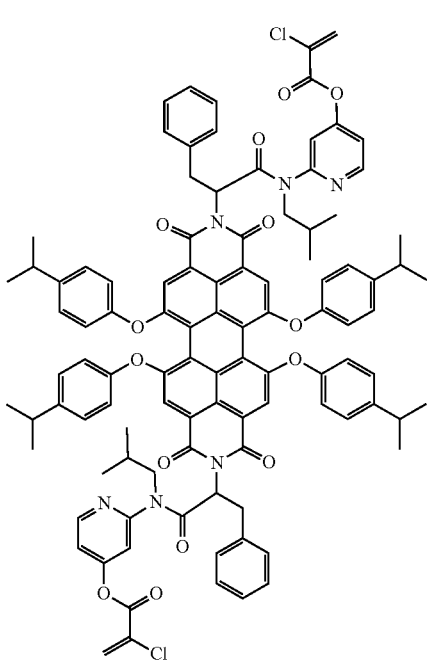

763
-continued
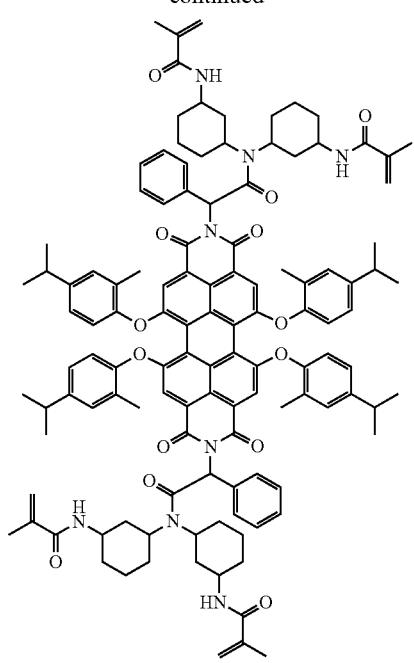
764
-continued
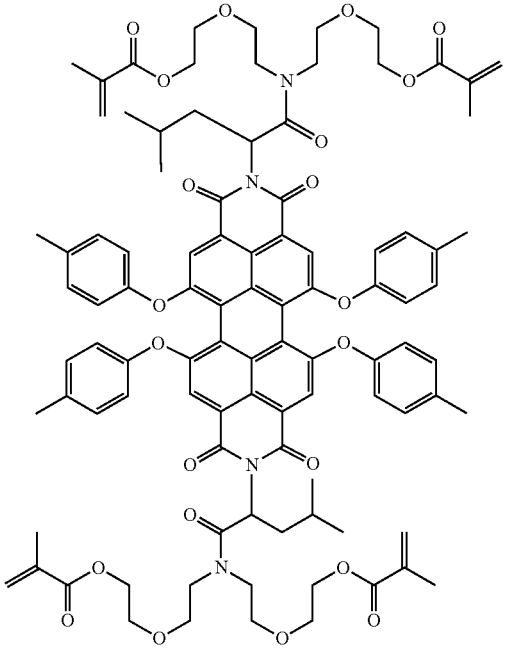
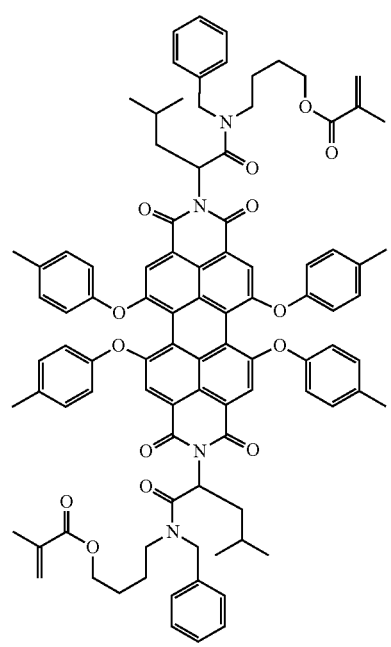
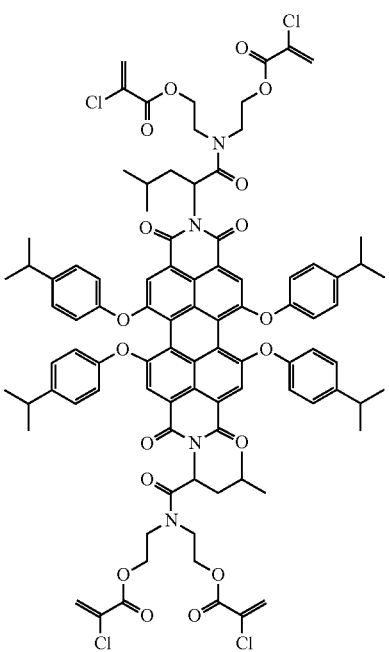

765
-continued
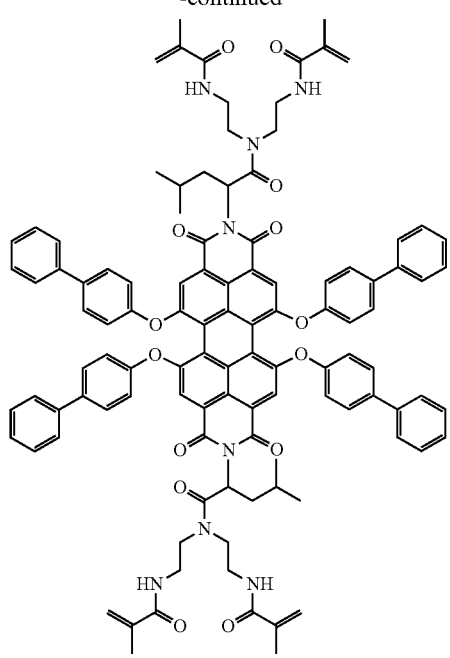
766
-continued
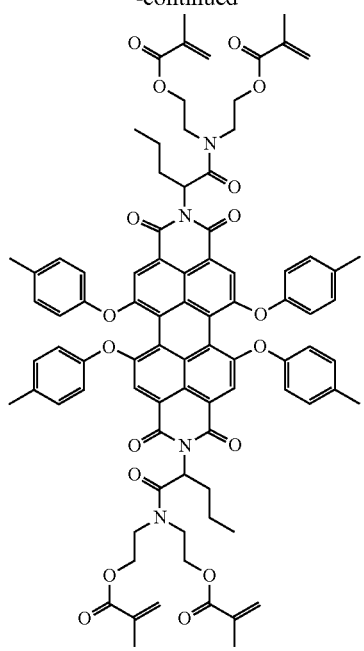
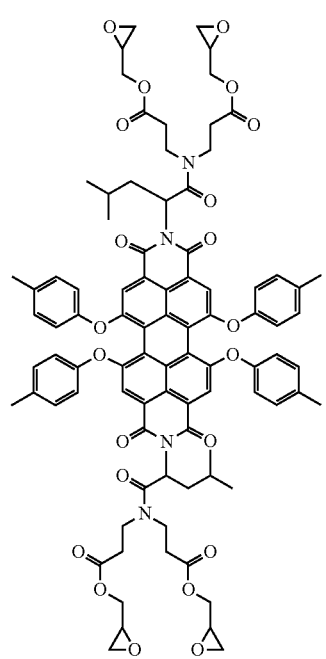
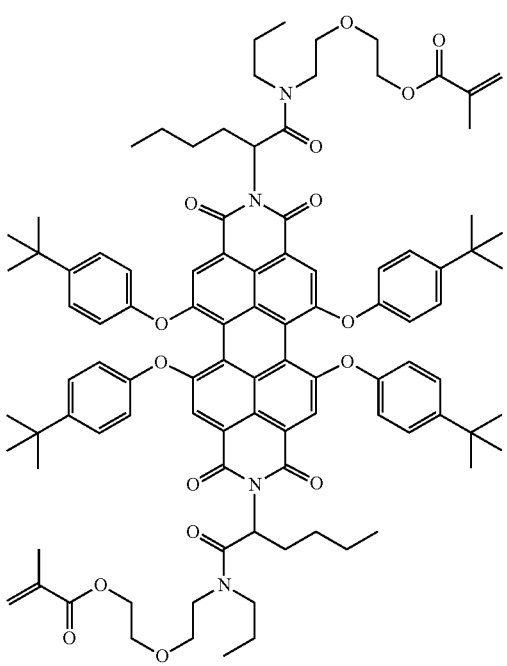

767
-continued
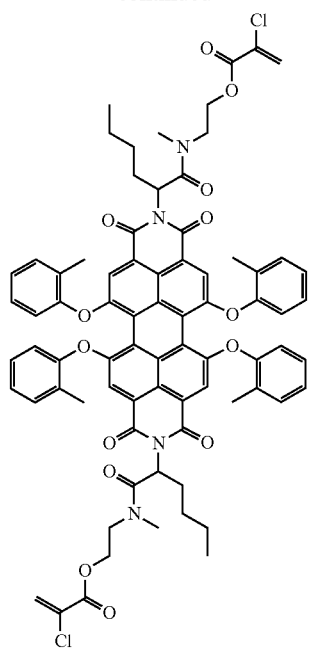
768
-continued
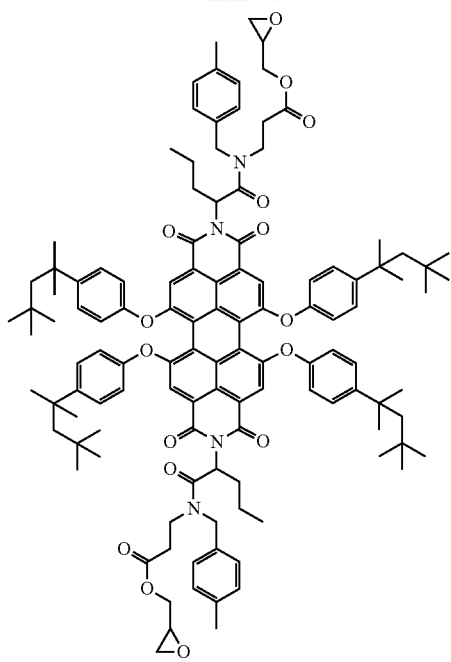
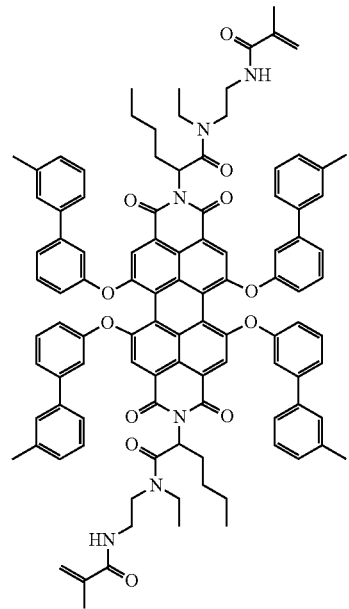
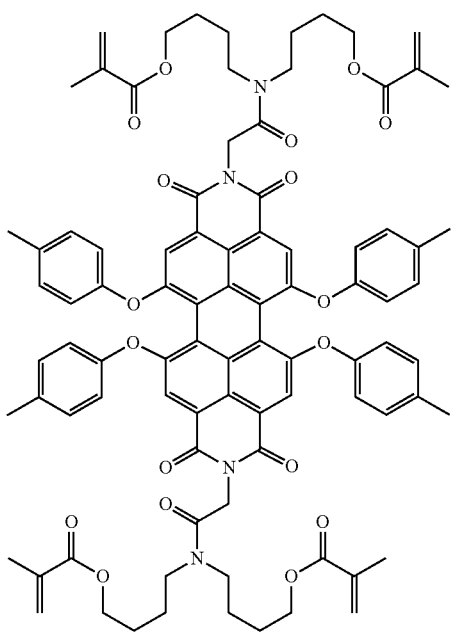

769
-continued
770
-continued
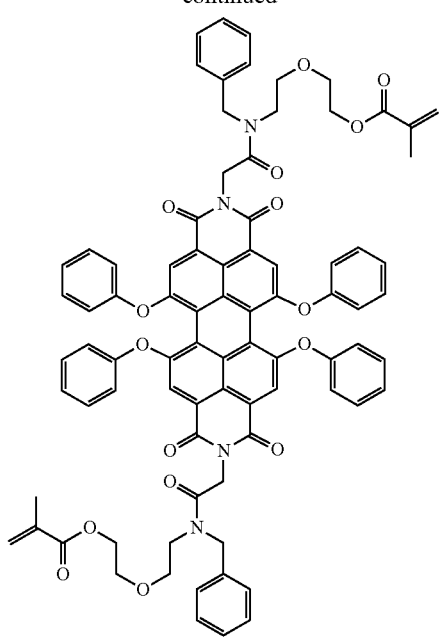
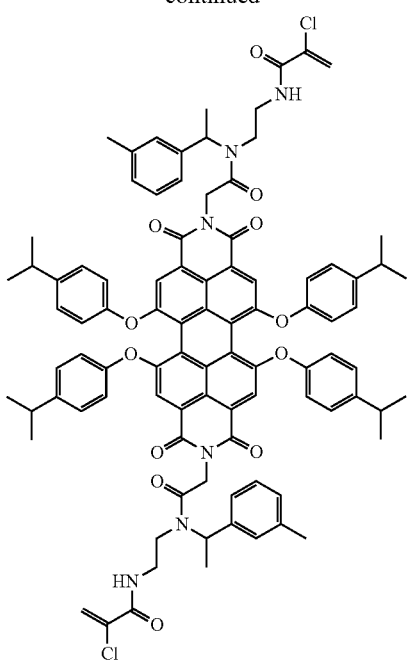
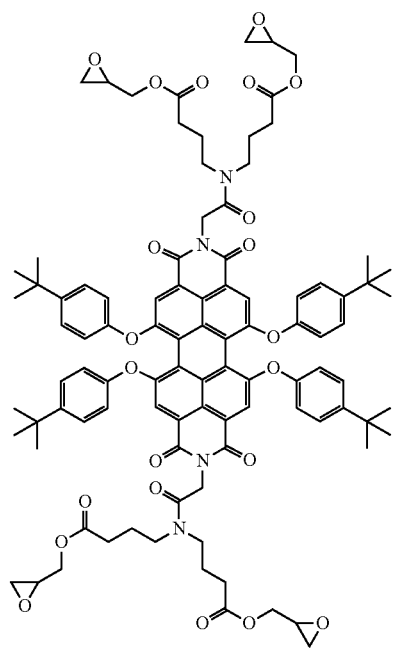

771
-continued
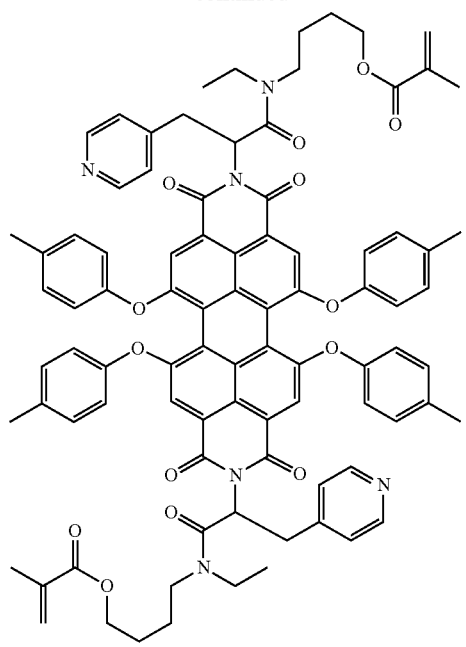
772
-continued
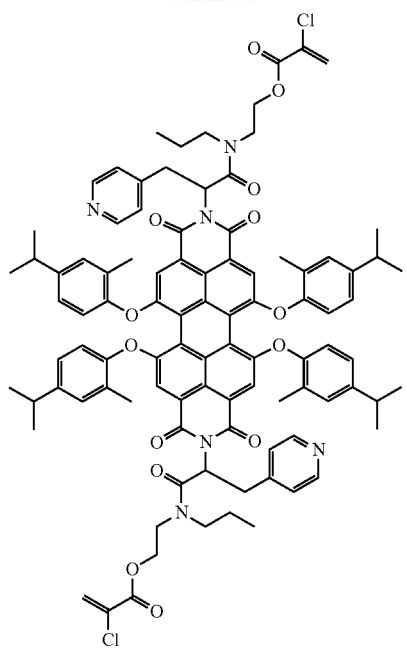
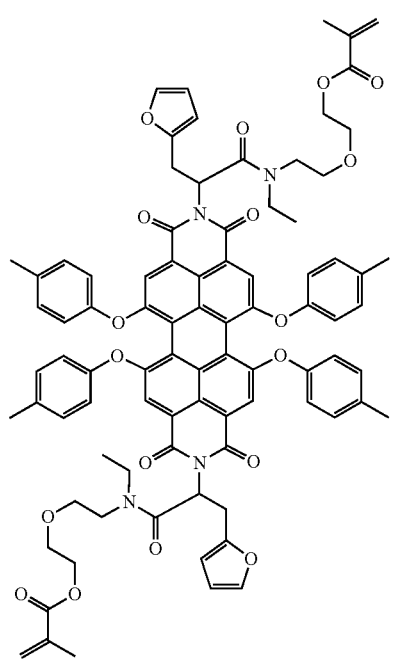
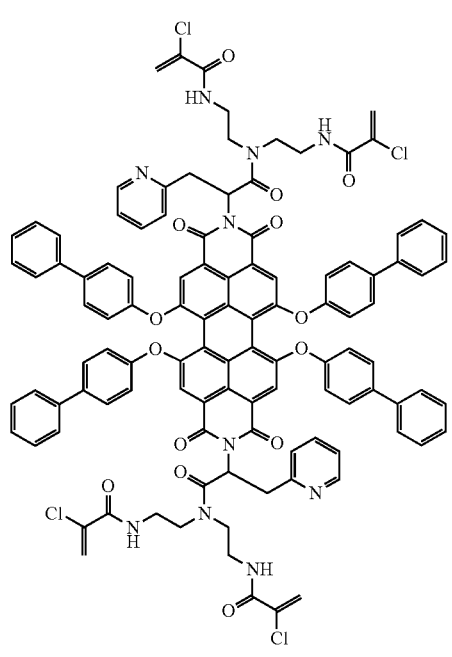

773
-continued
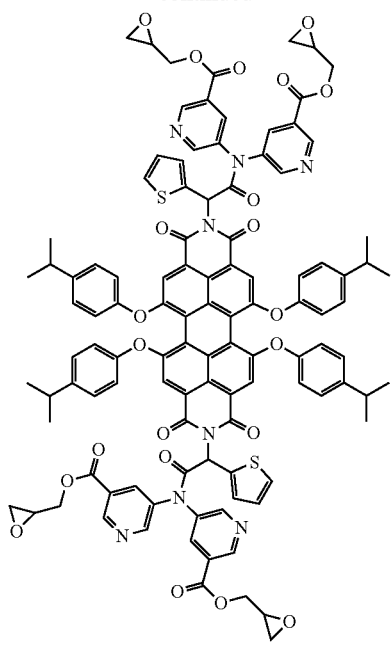
774
-continued
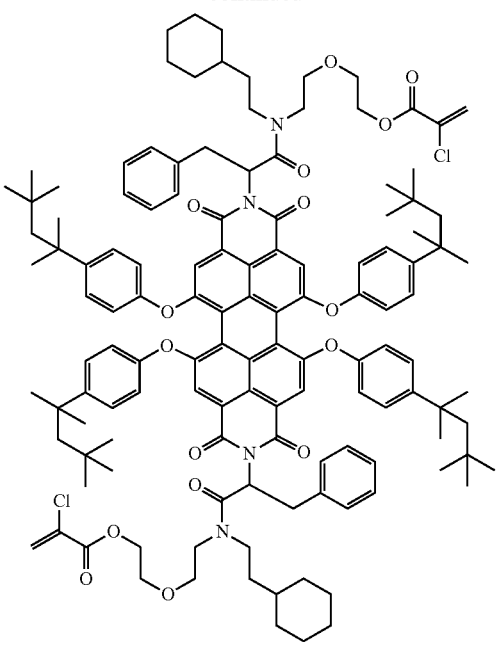
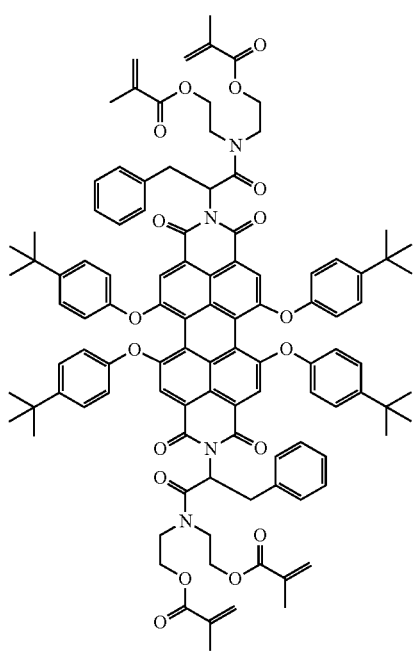
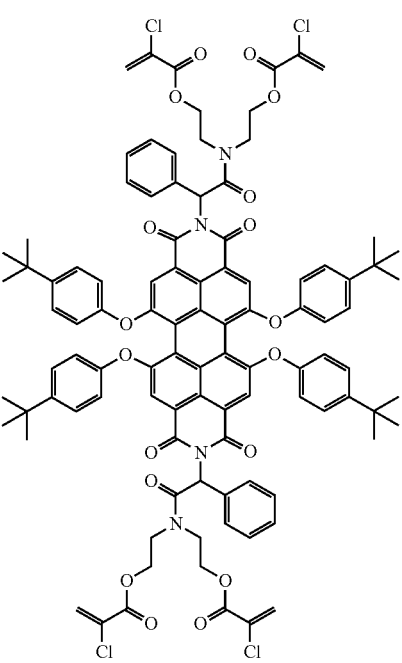

775
-continued
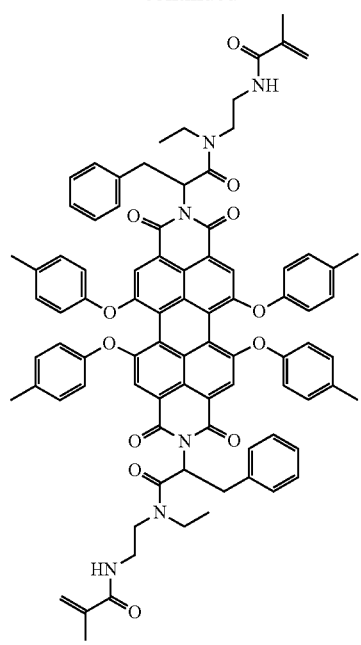
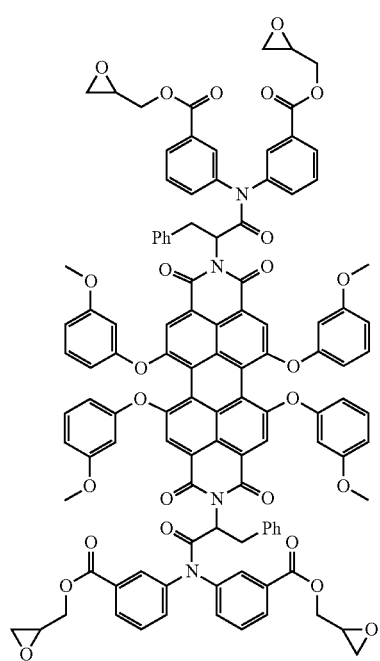
776
-continued
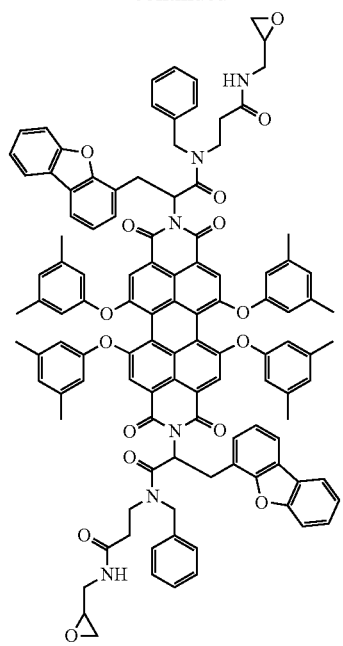
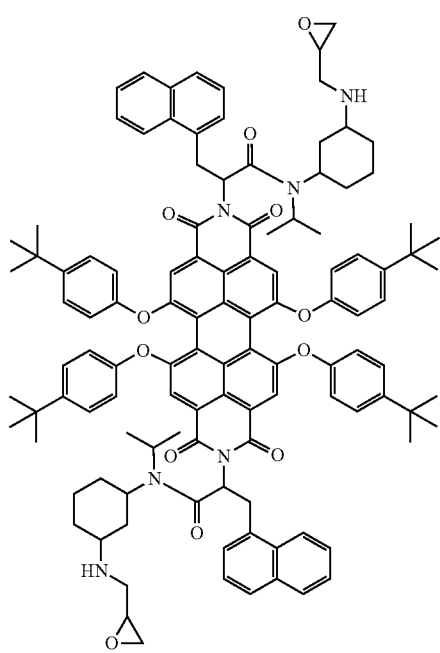

777
-continued
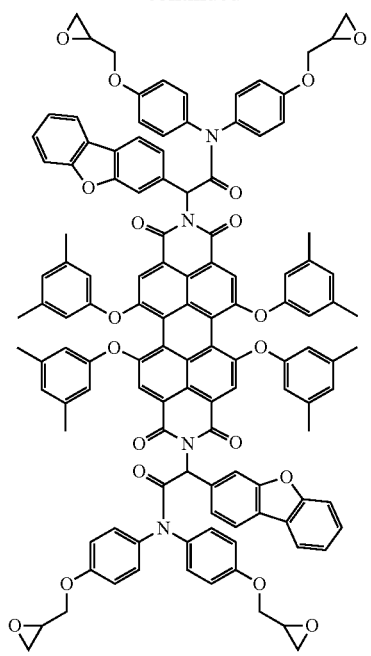
778
-continued
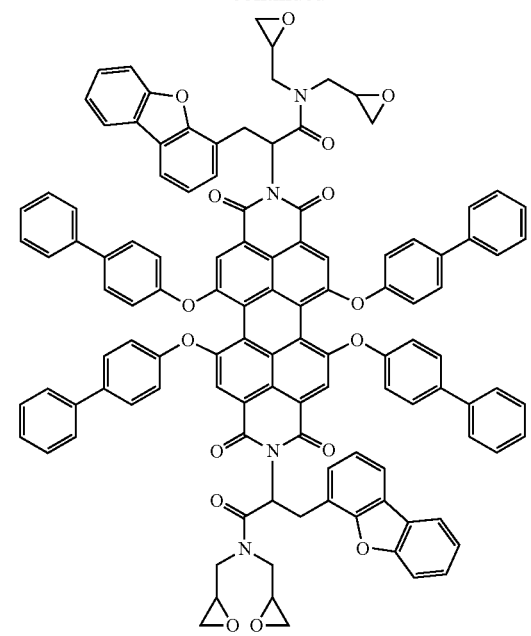
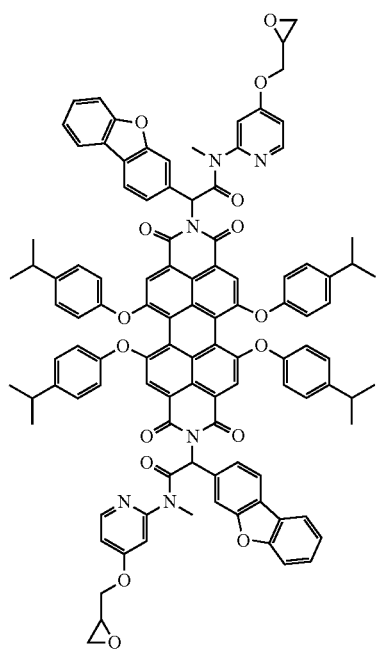
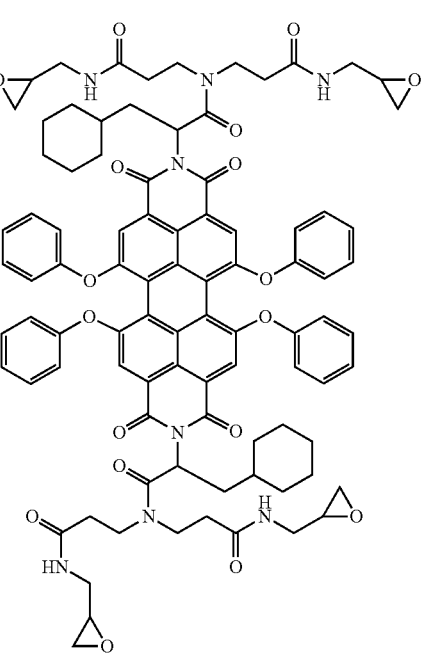

779
-continued
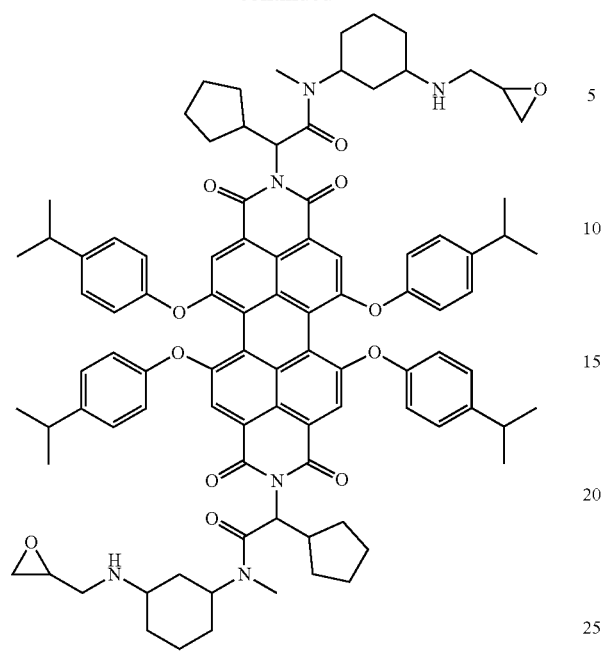
780
-continued
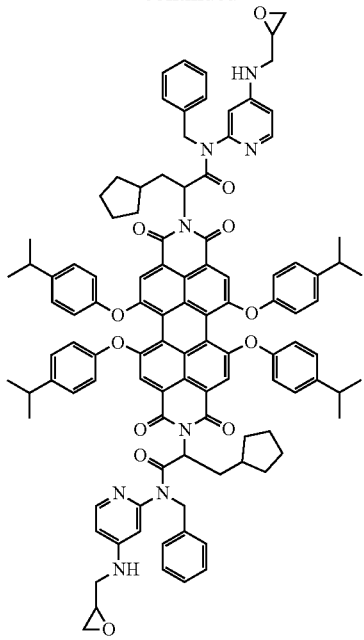
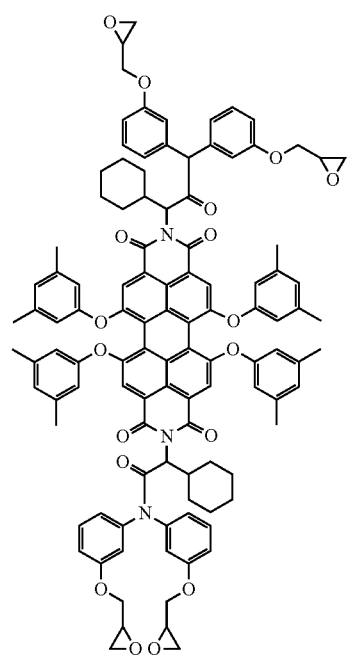
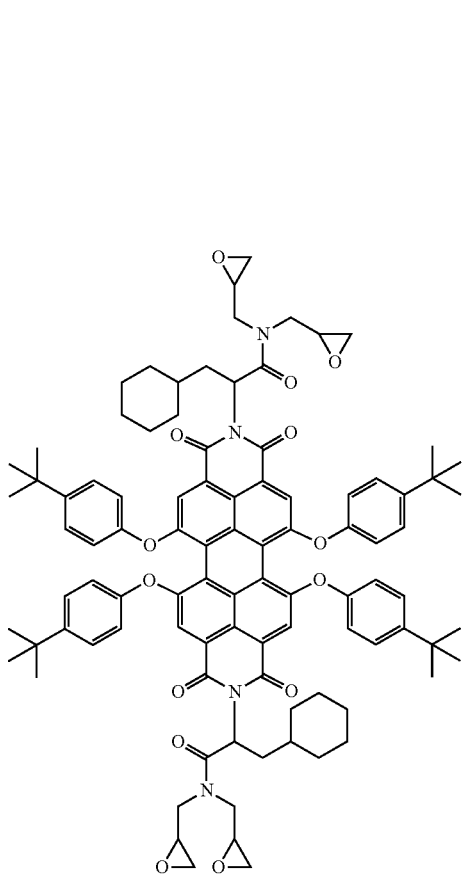

781
-continued
782
-continued
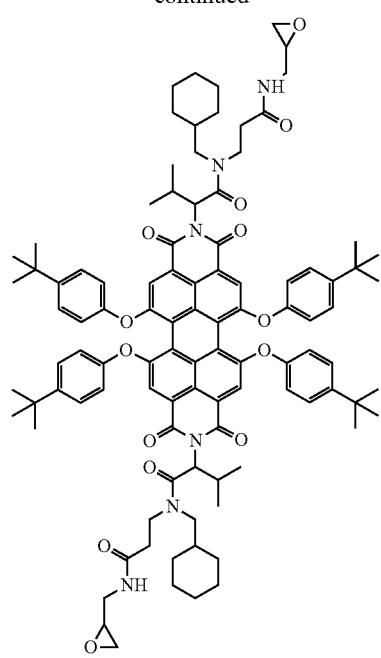
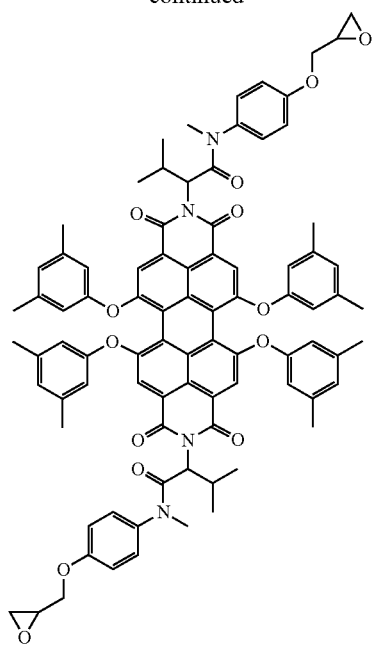
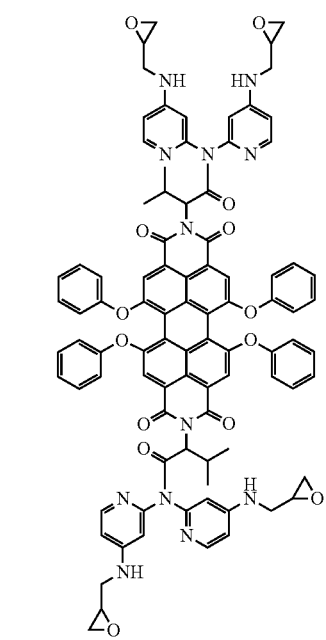

783                                    784
-continued                         -continued
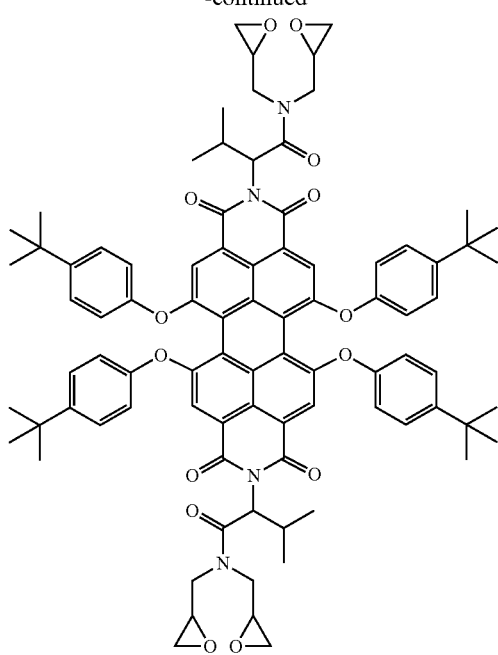 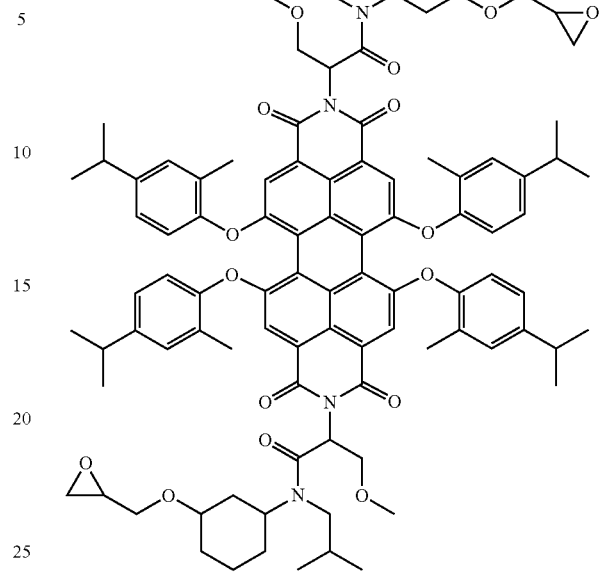
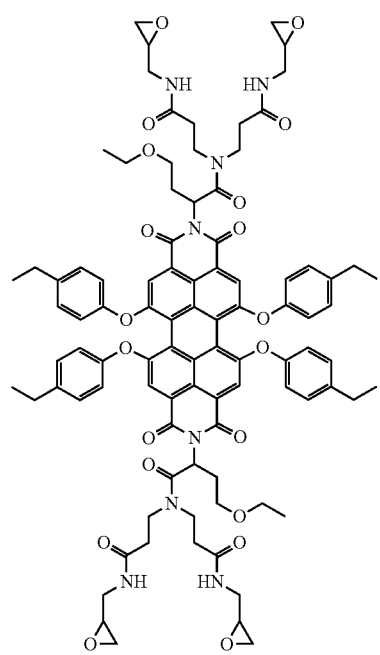 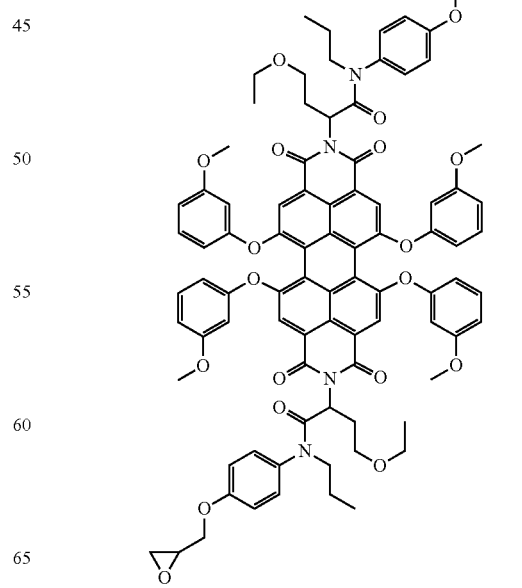

785
-continued
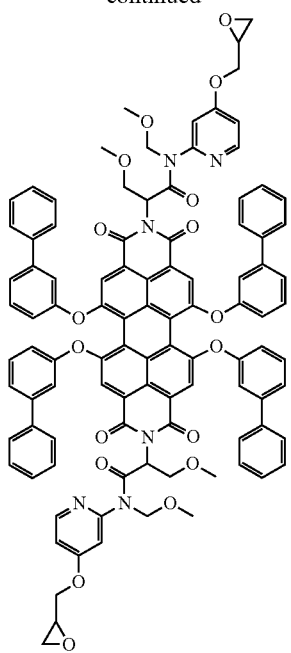
786
-continued
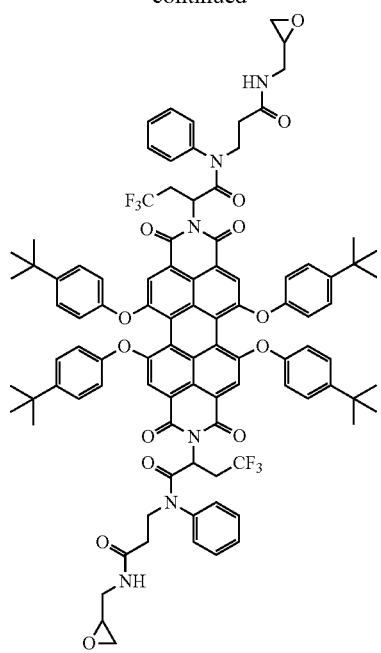
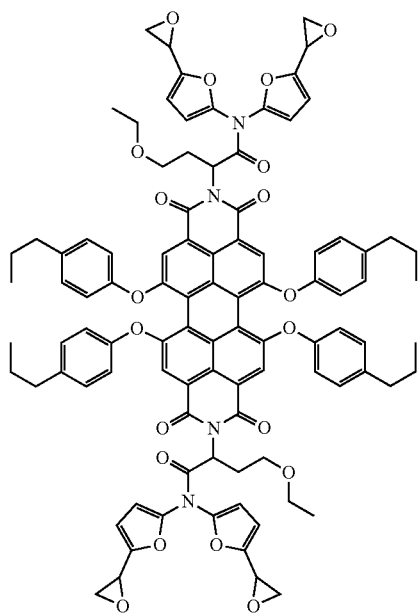
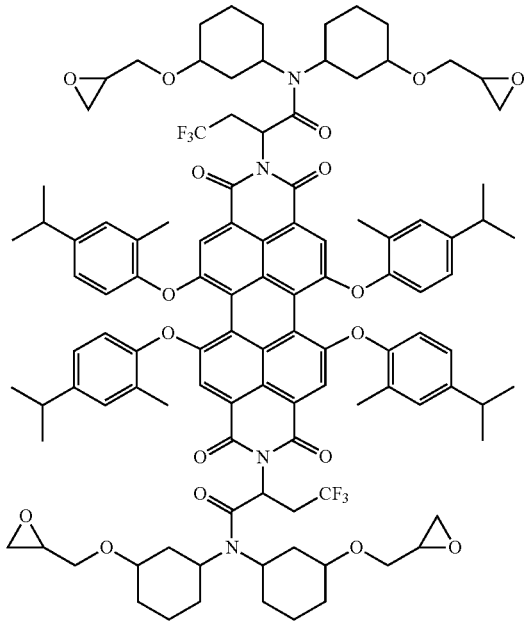

787
-continued
788
-continued
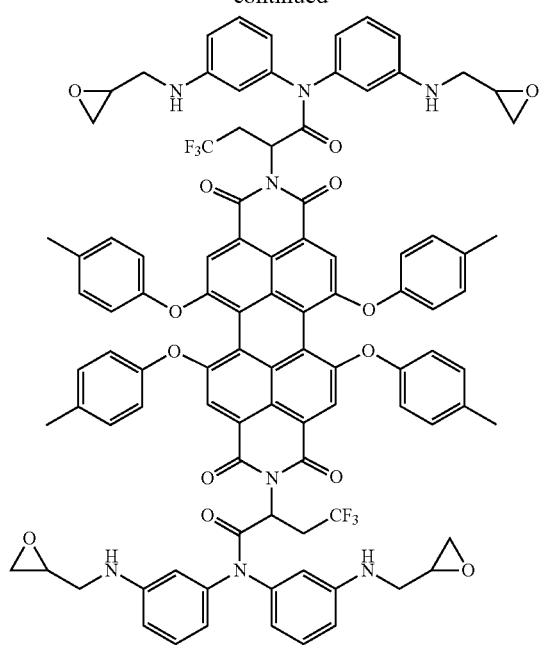
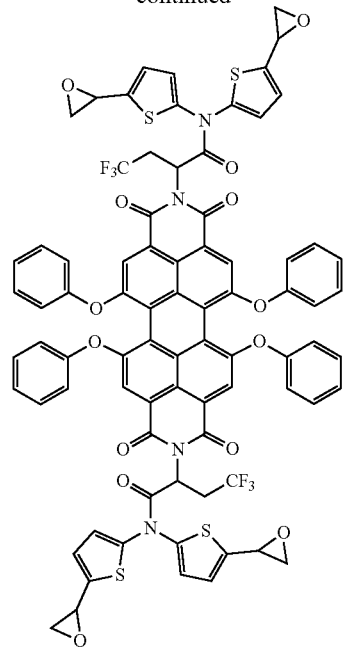
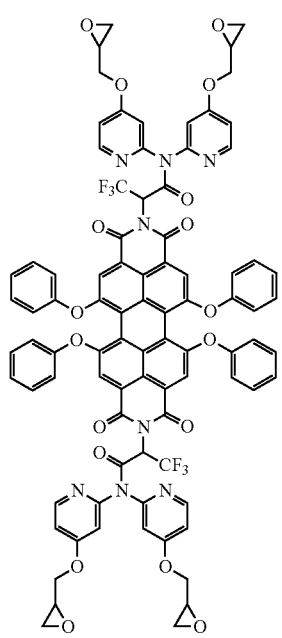

789
-continued
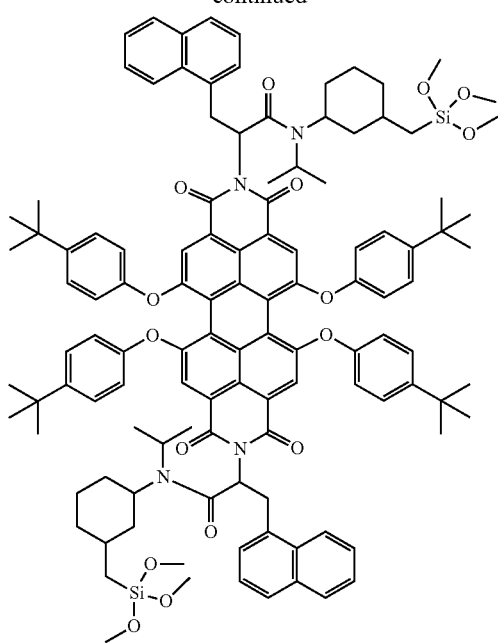
790
-continued
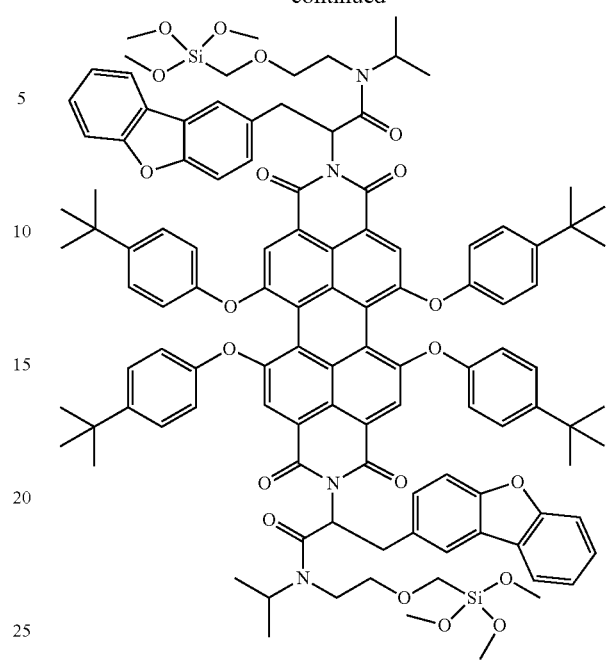
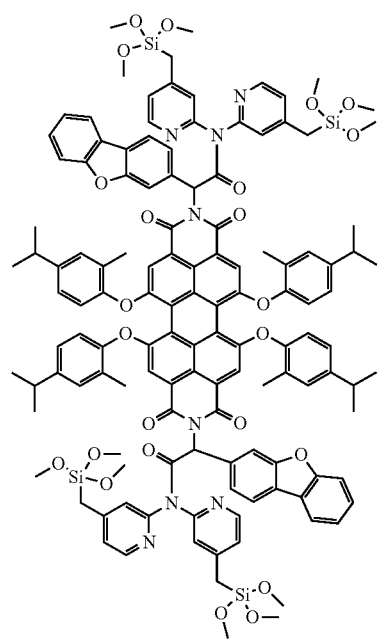
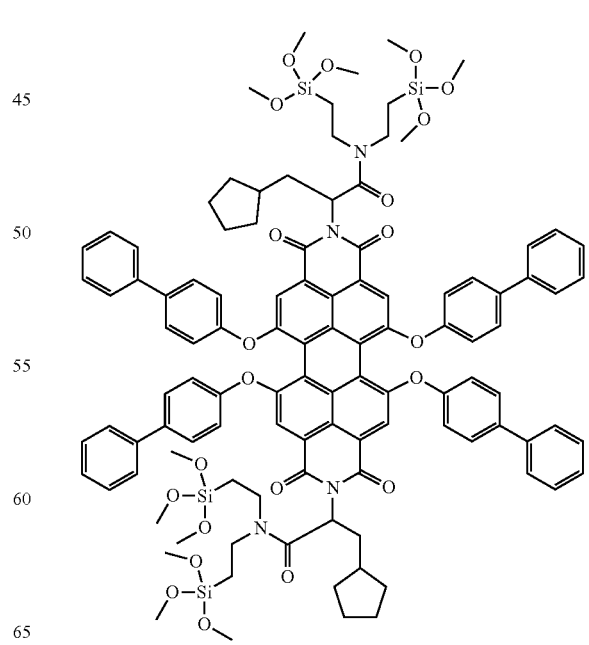

791
-continued
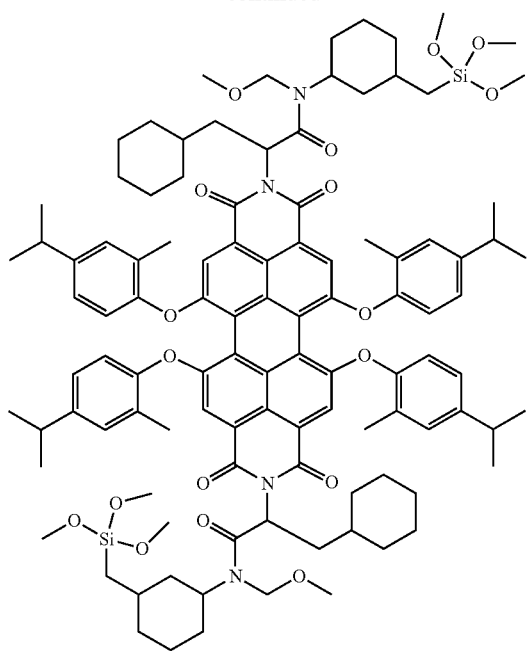
792
-continued
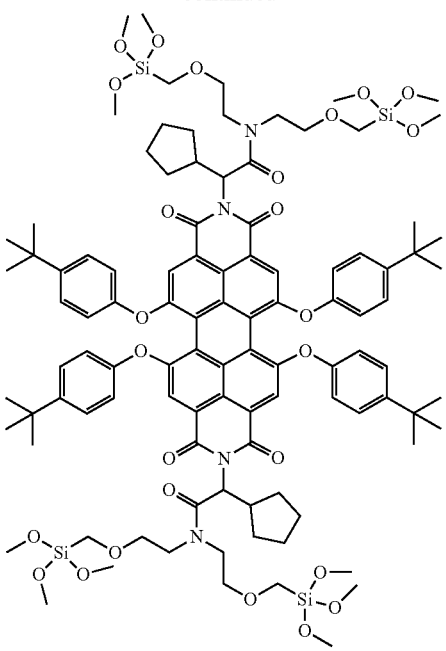
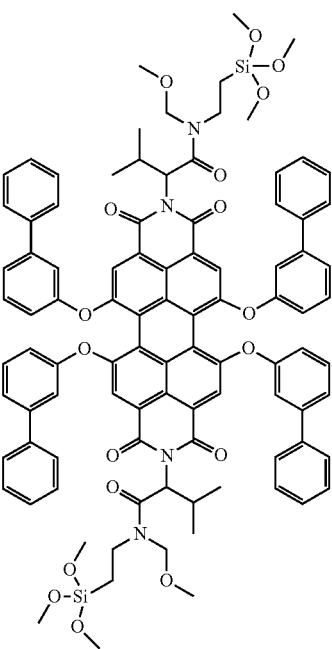

793
-continued
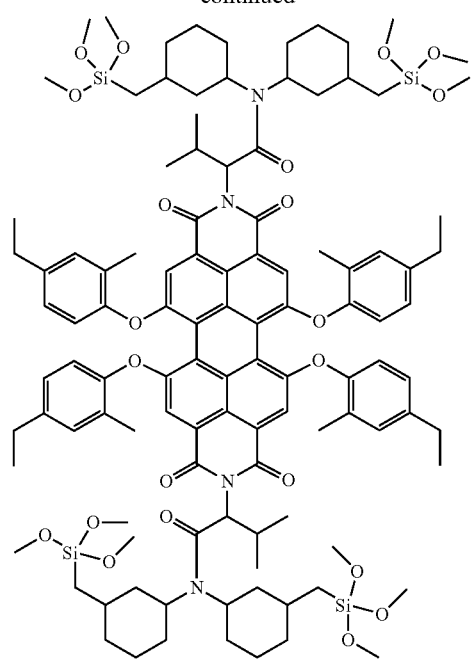
794
-continued
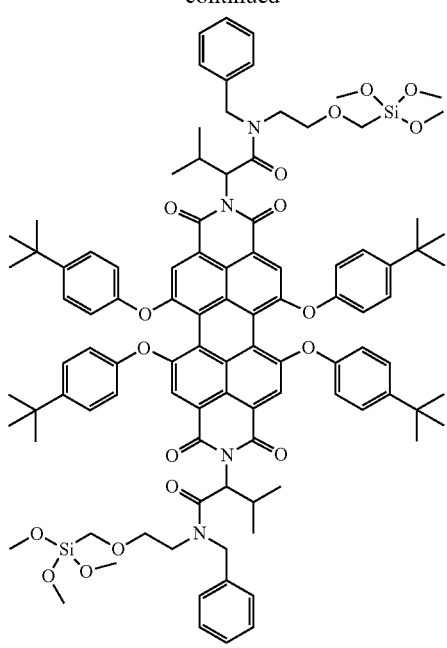
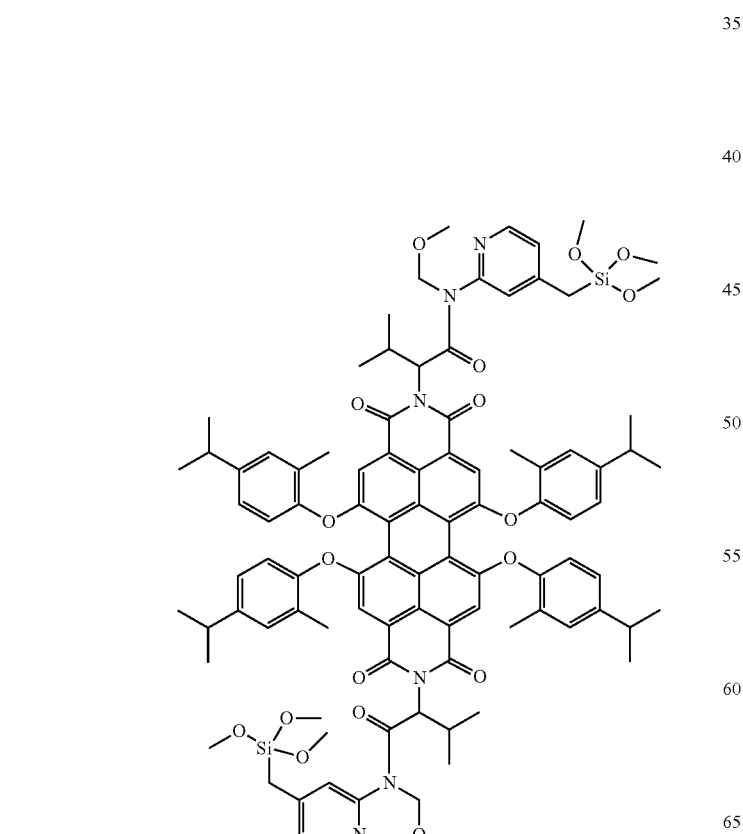
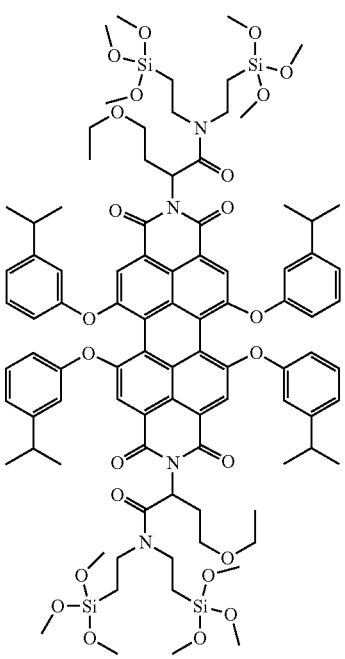

795
-continued
796
-continued
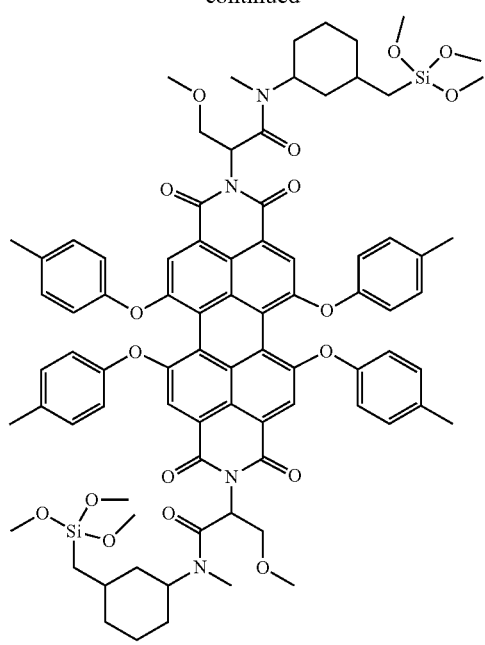
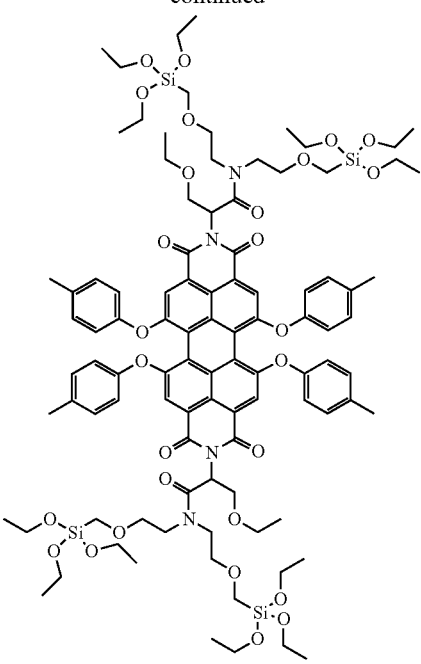
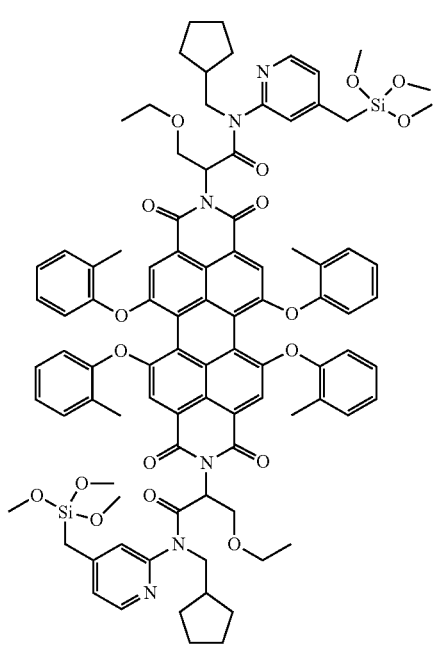
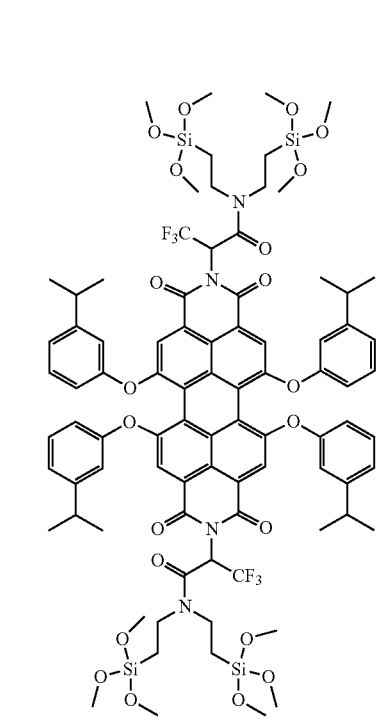

797
-continued
798
-continued
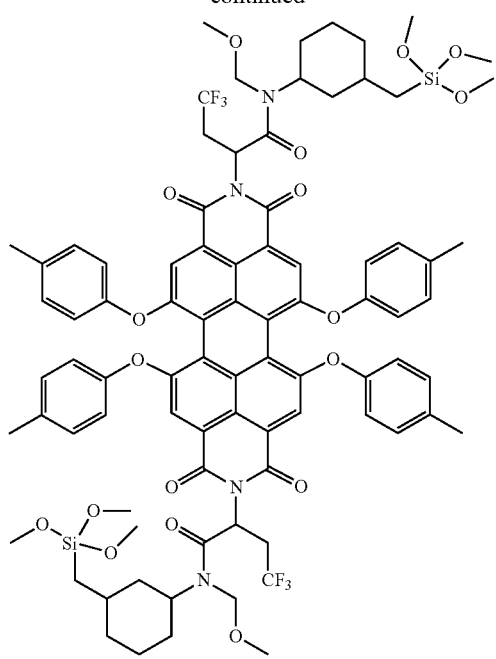
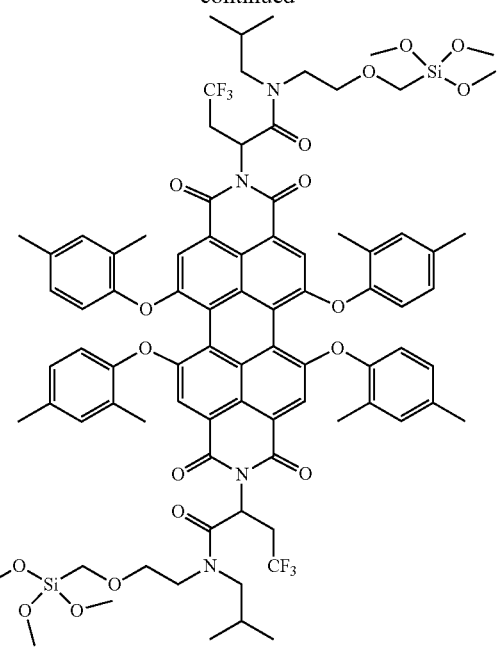

799
-continued
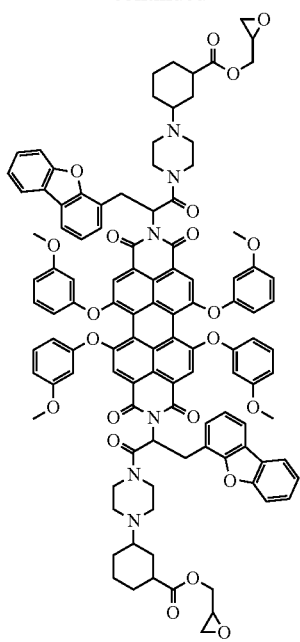
800
-continued
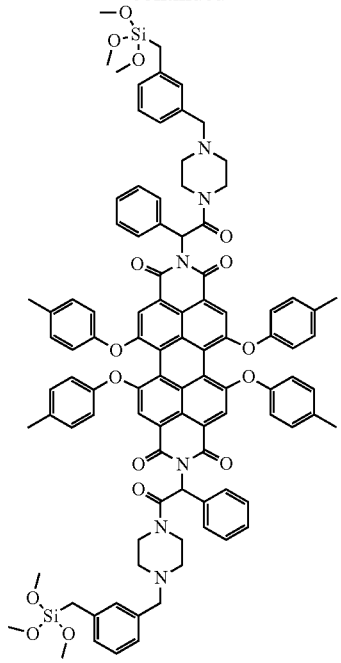
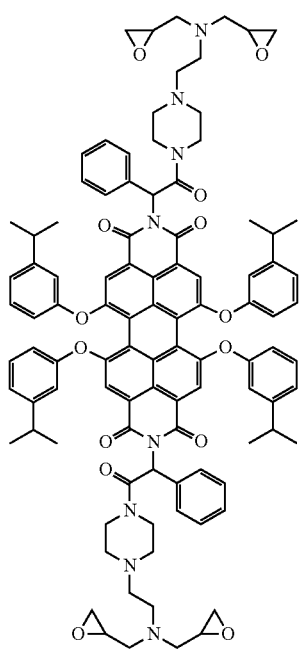
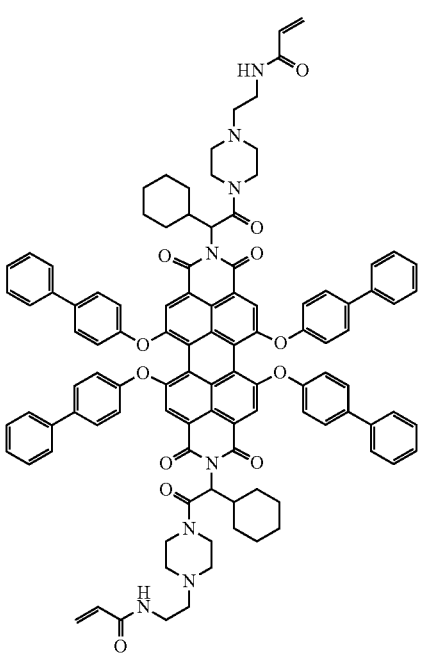

801
-continued
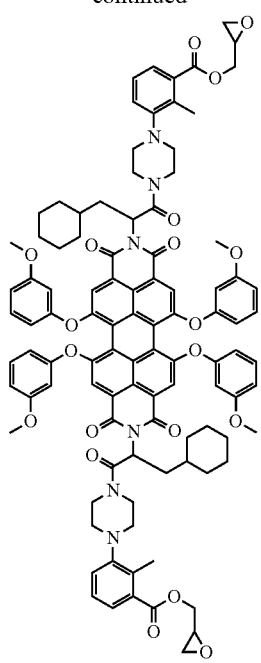
802
-continued
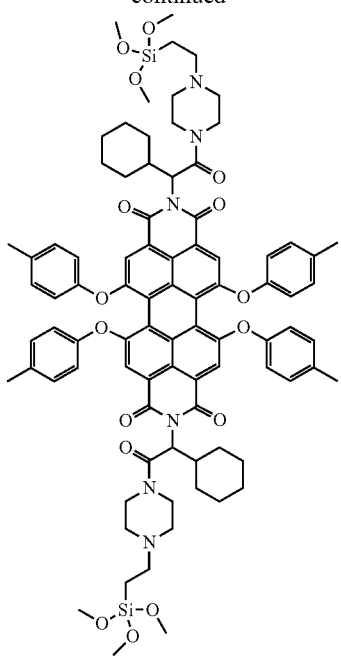
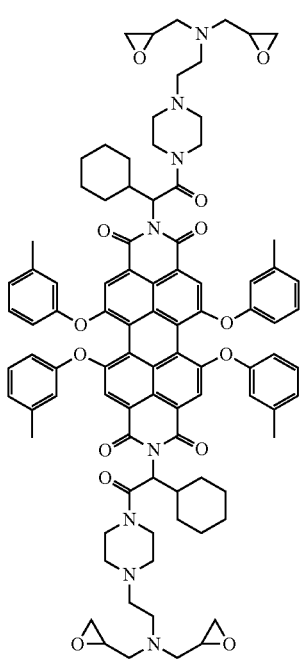
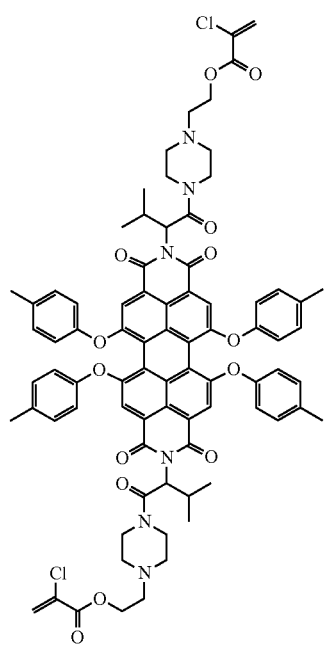

803
-continued
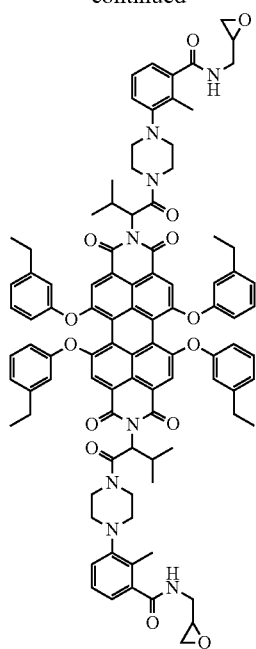
804
-continued
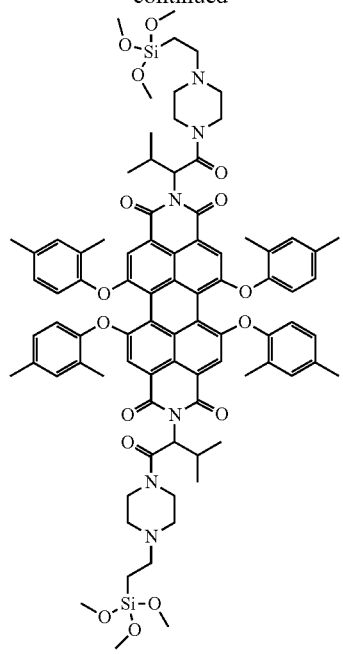
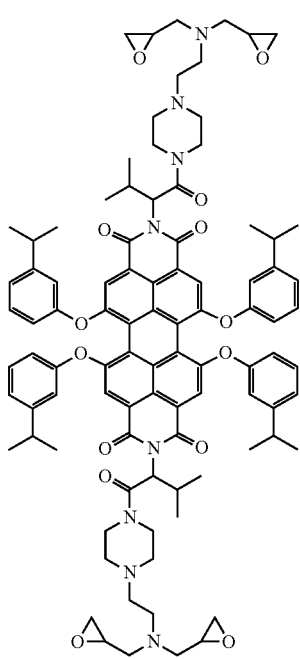
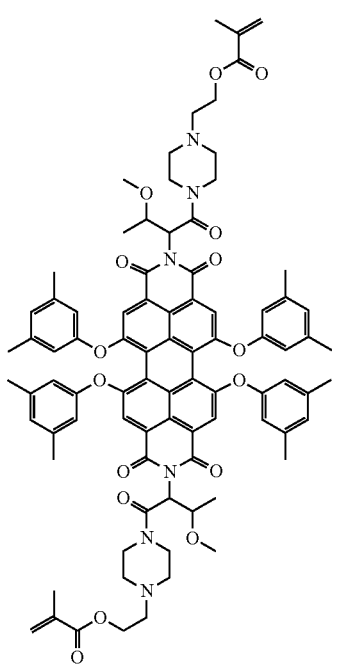

805
-continued
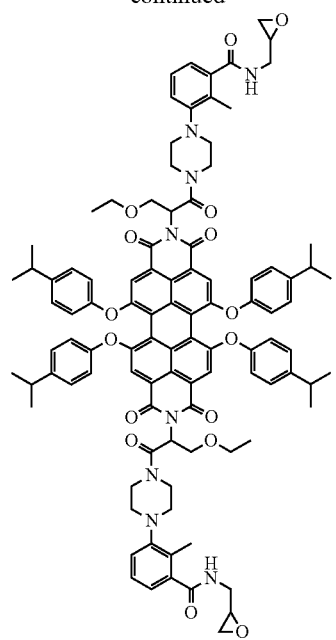
806
-continued
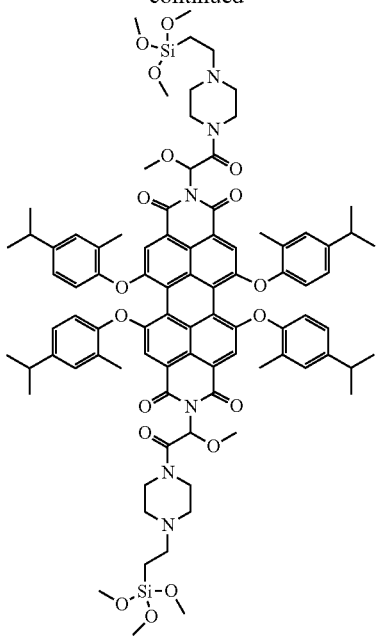
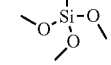
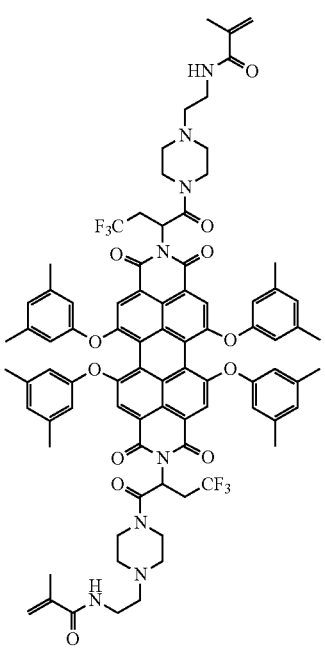

807
-continued
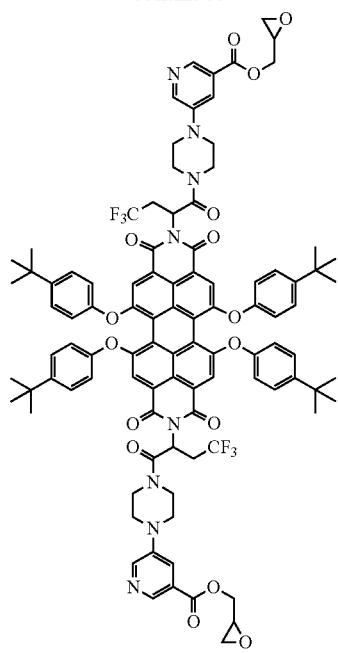
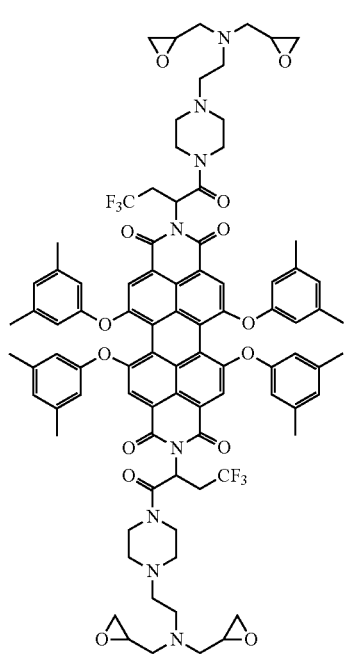
808
-continued
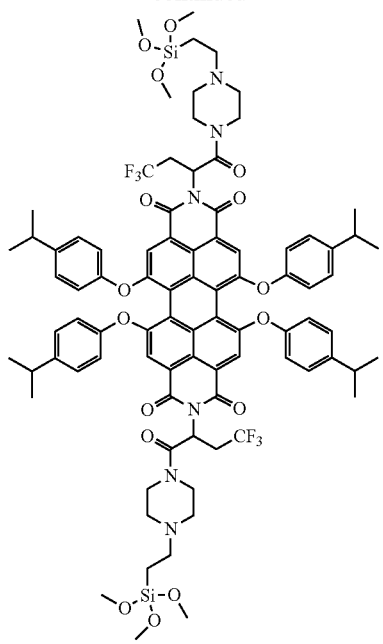
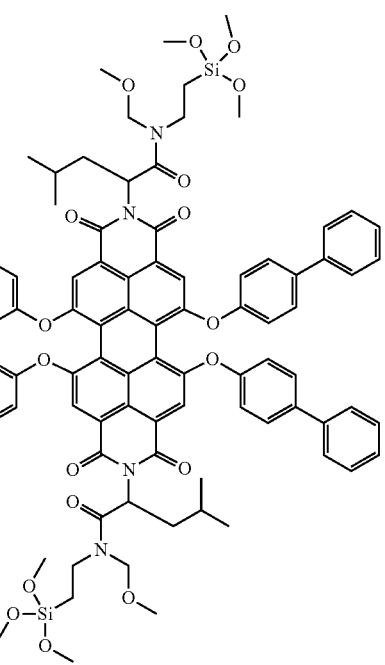

809
-continued
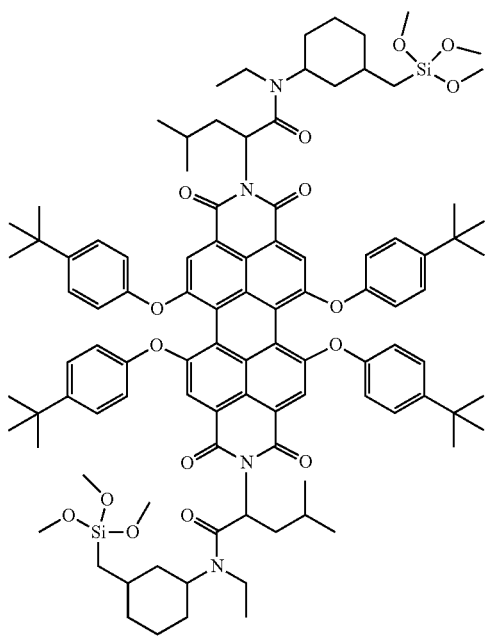
810
-continued
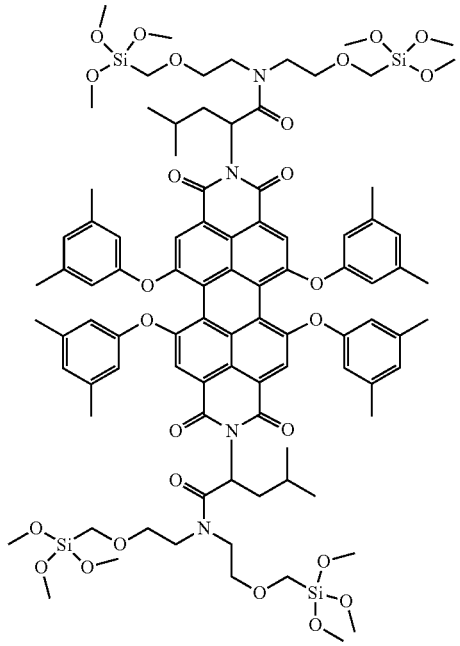
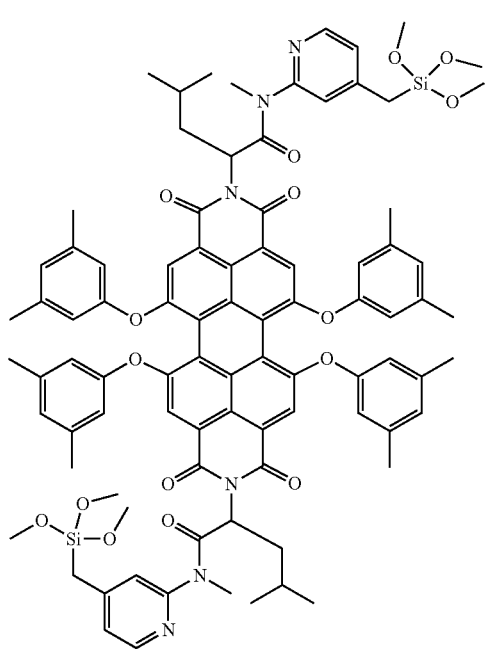
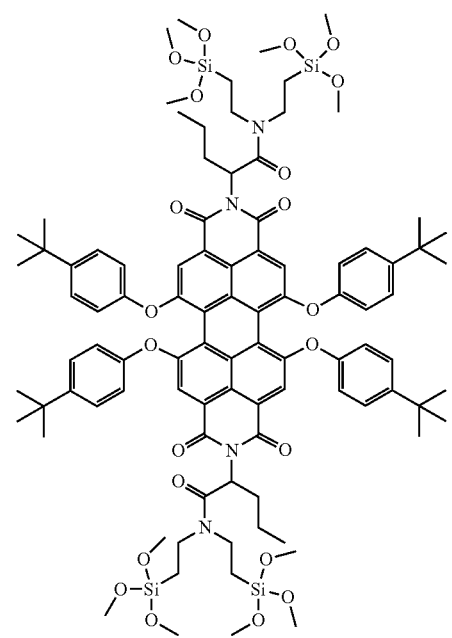

811
-continued
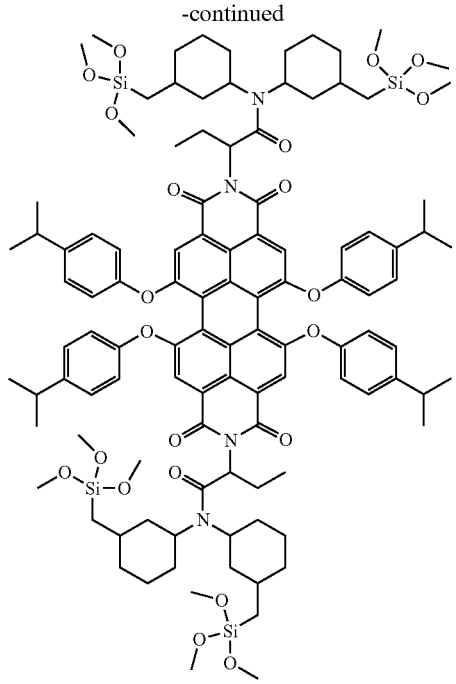
812
-continued
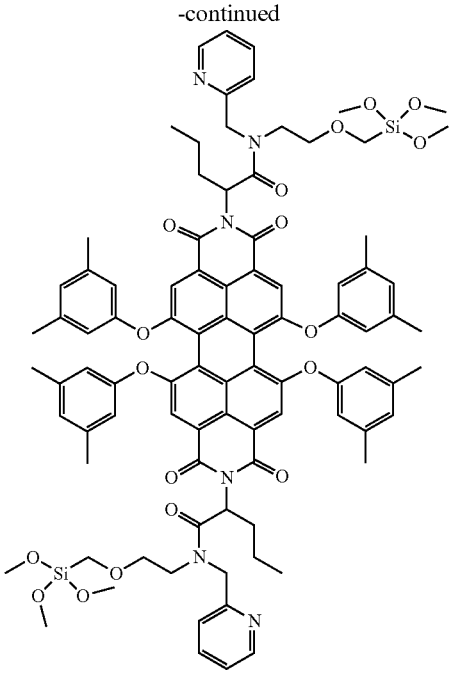
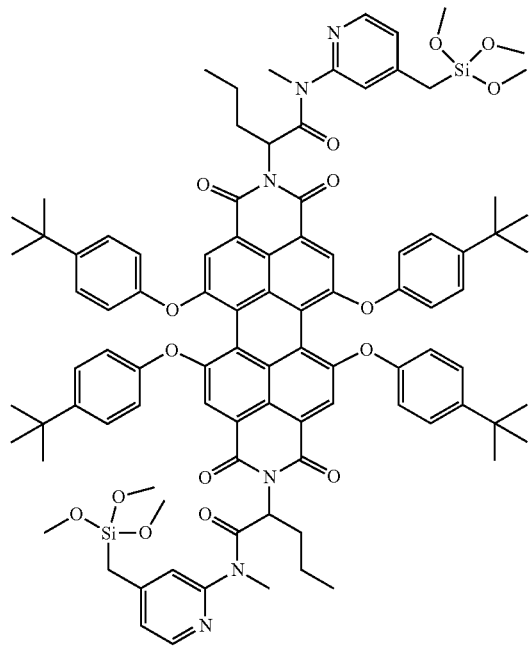
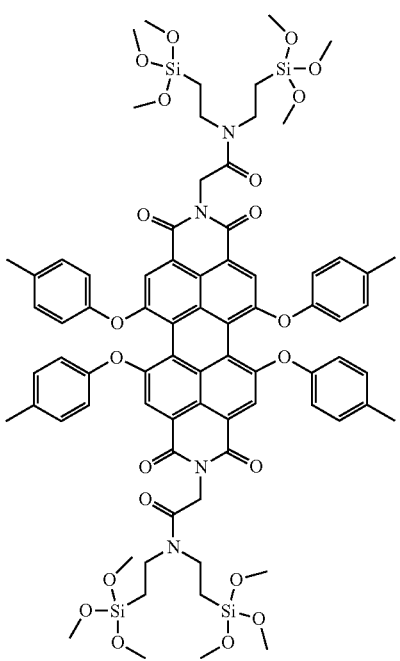

813
-continued
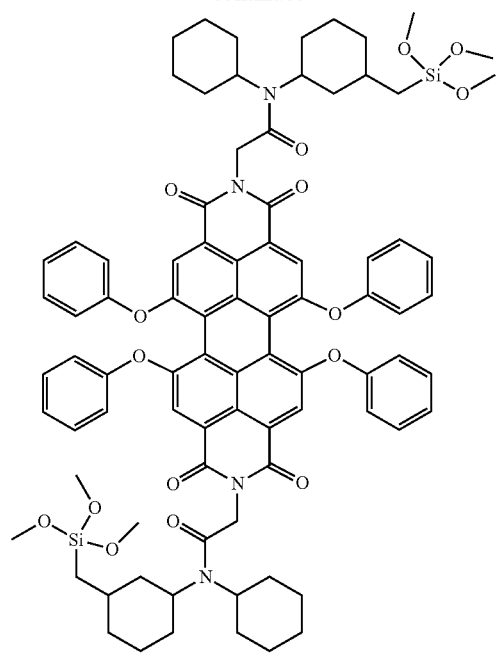
814
-continued
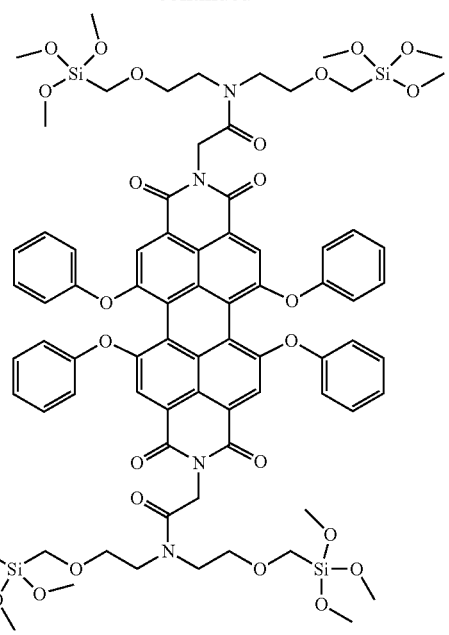
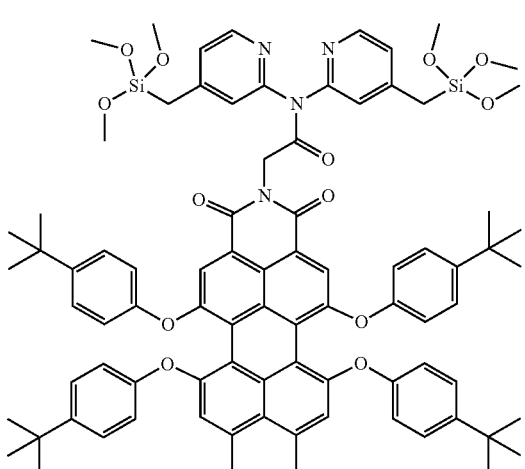
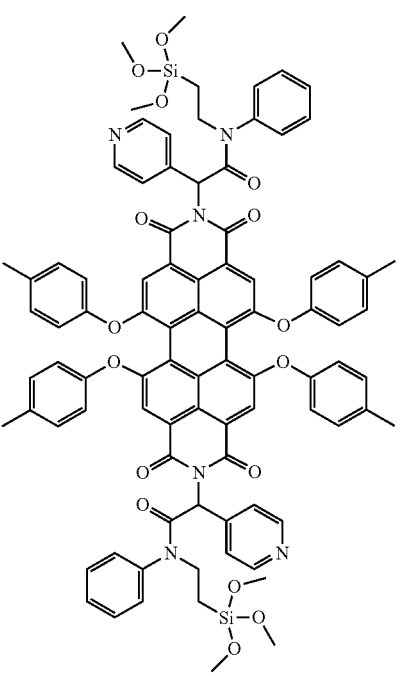

815
-continued
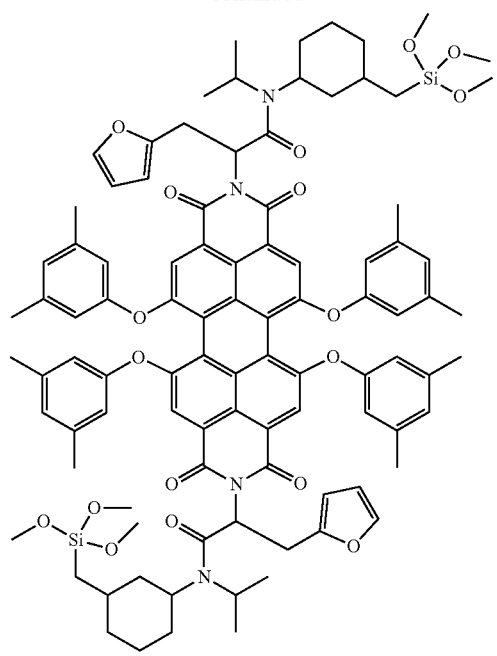
816
-continued
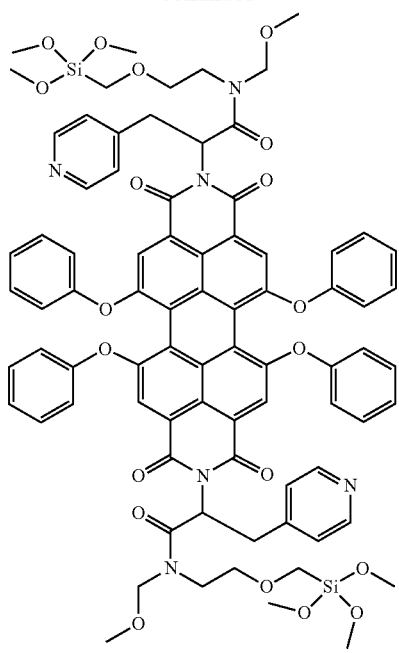
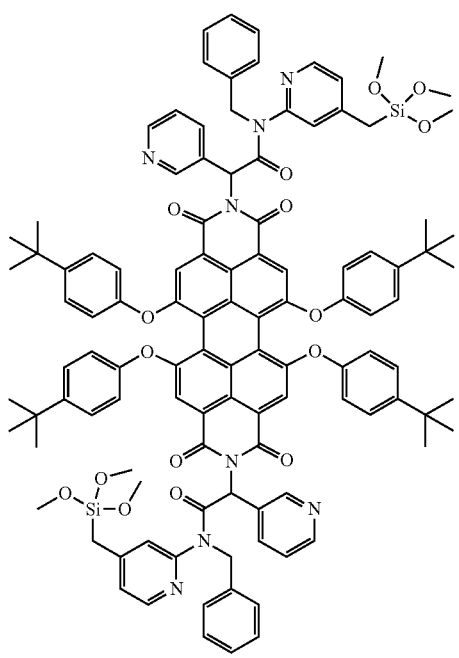
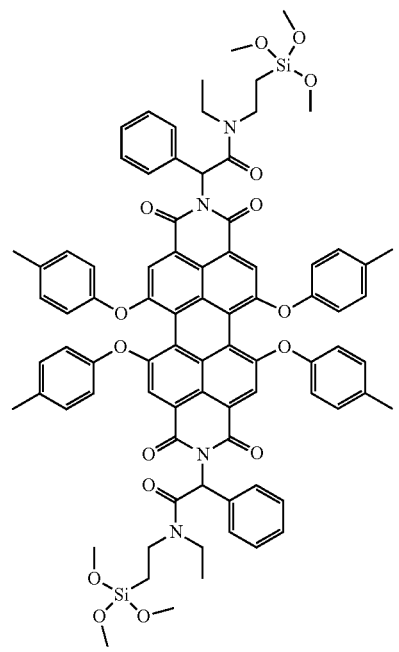

817
-continued
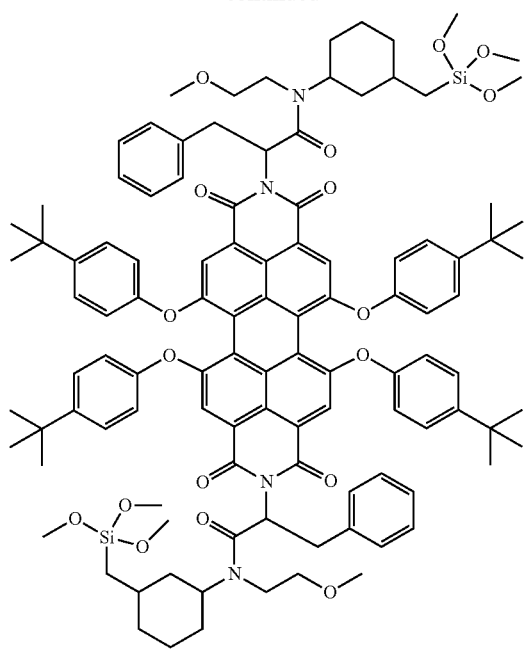
818
-continued
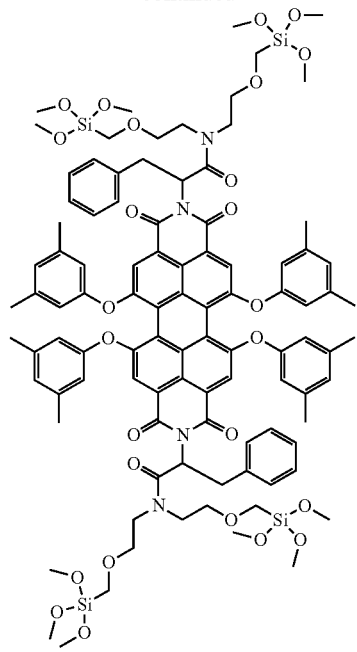
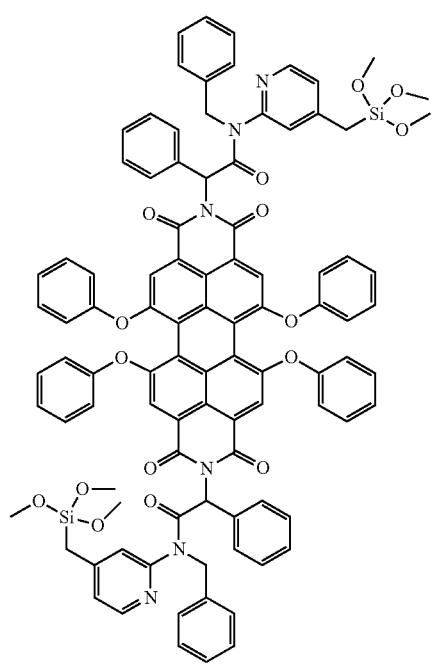
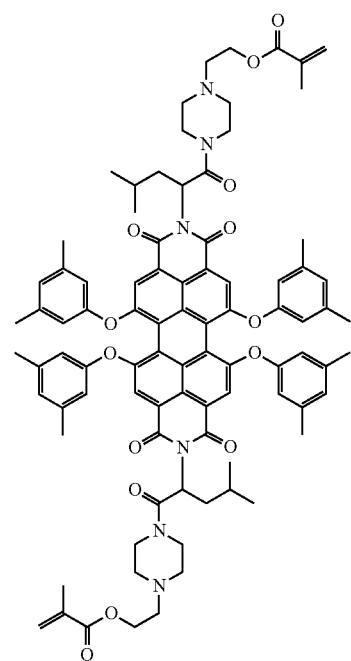

819
-continued
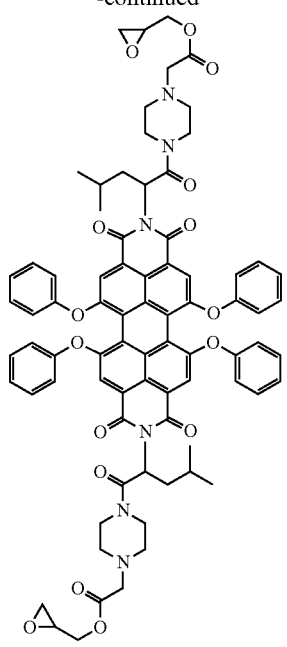
820
-continued
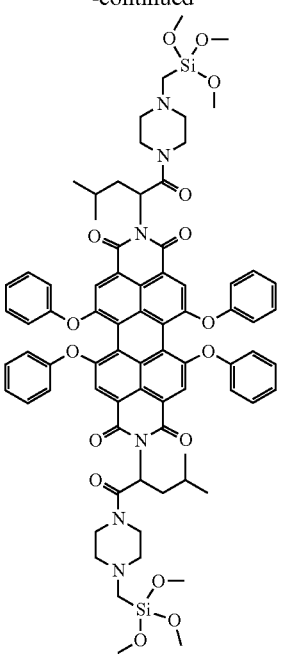
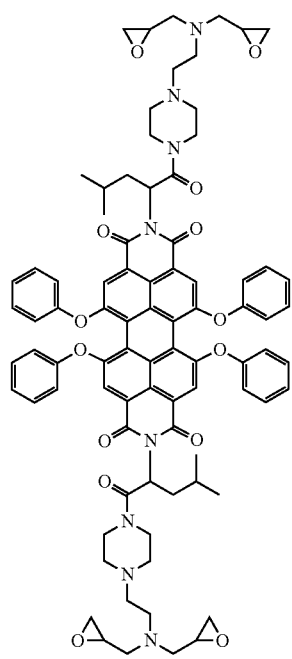
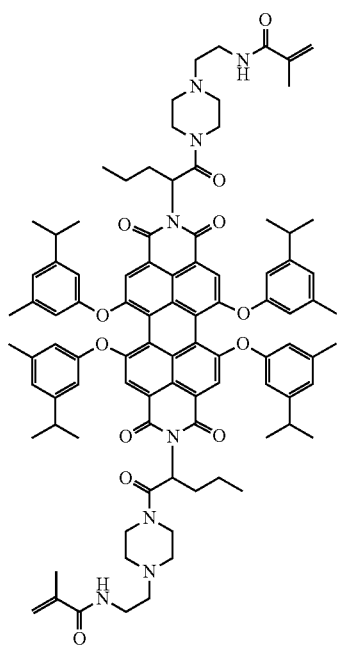

821
-continued
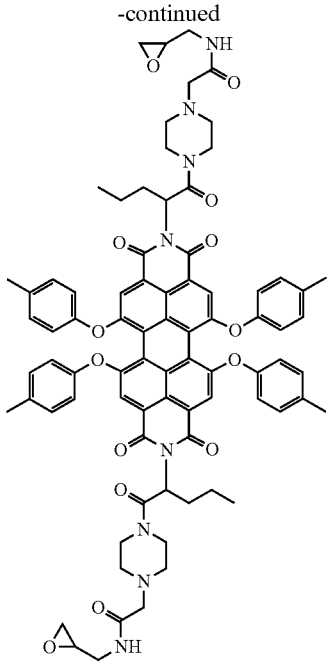
822
-continued
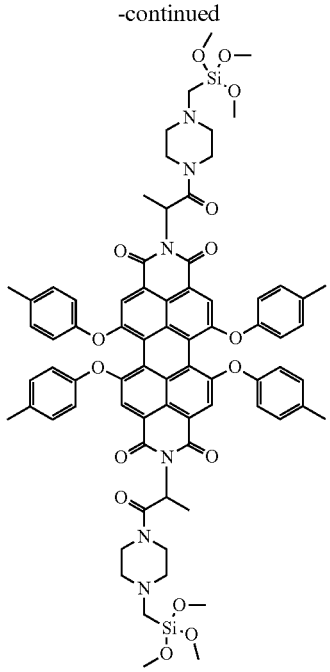
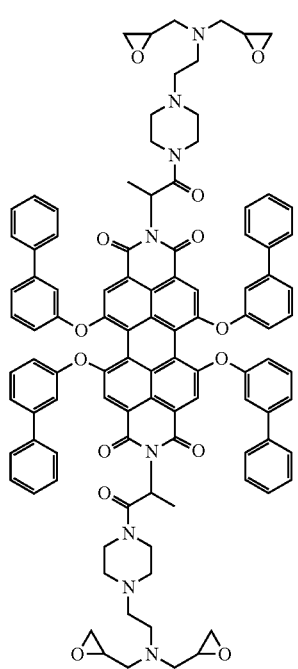
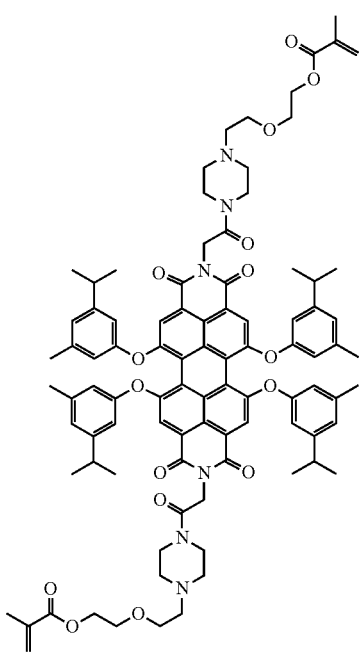

823
-continued
824
-continued
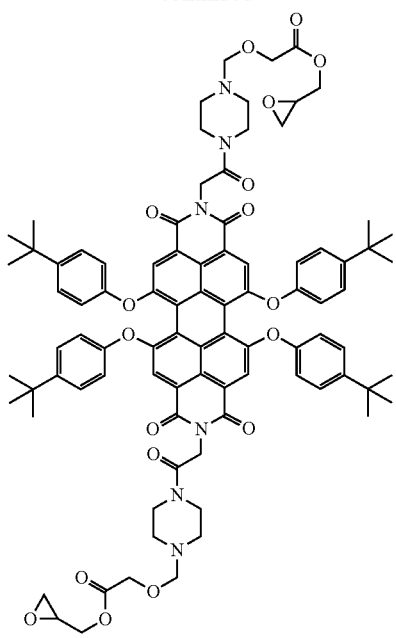
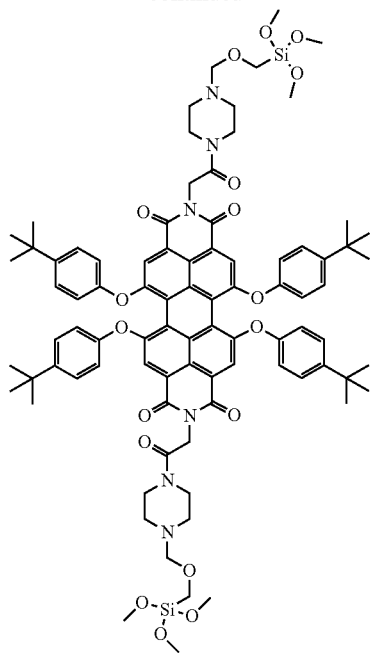
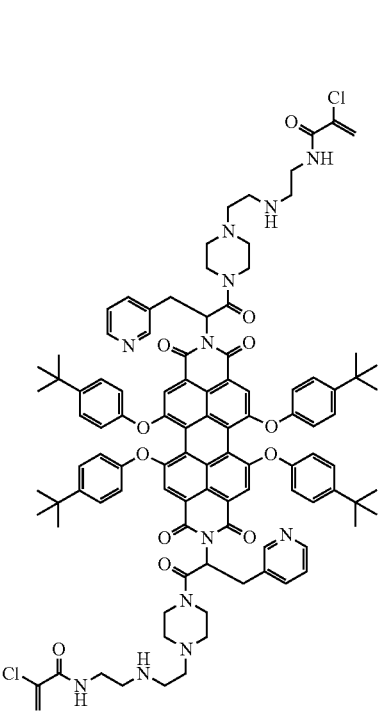

825
-continued
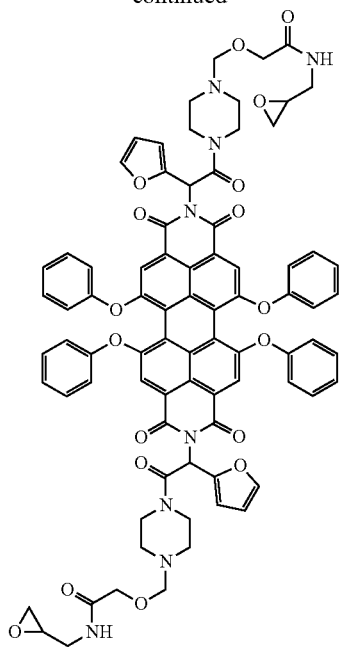
826
-continued
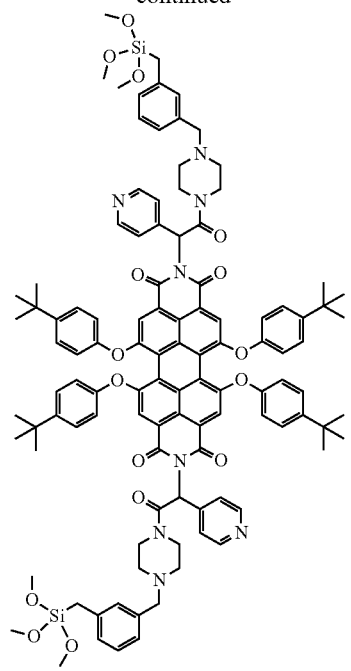
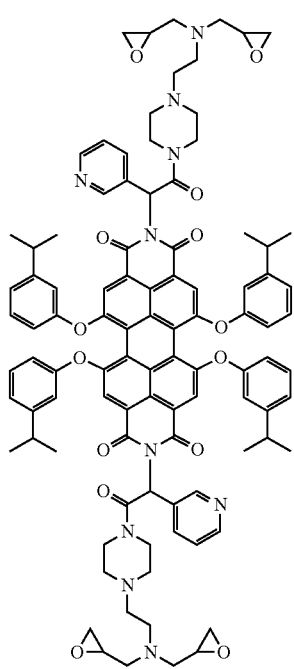
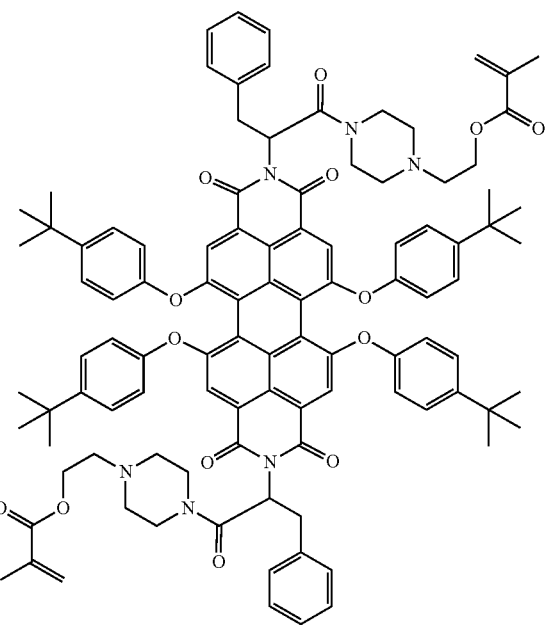

827
-continued
828
-continued
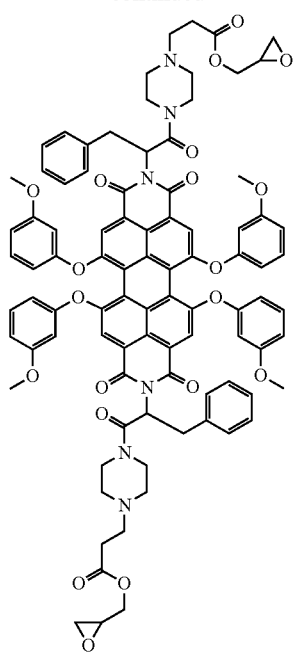
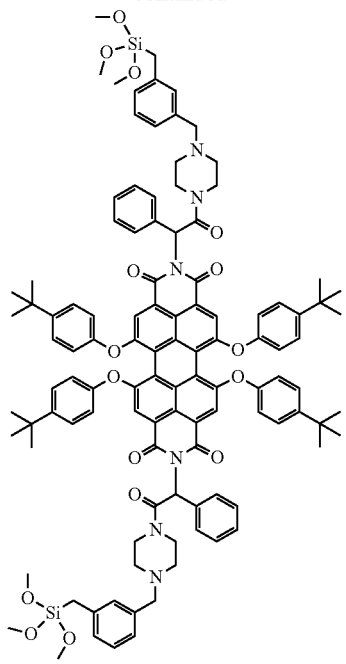
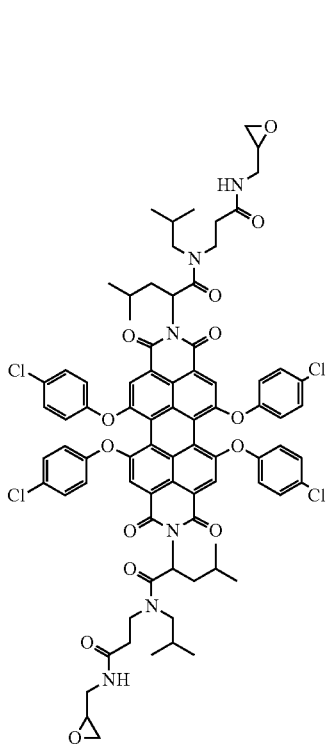

829
-continued
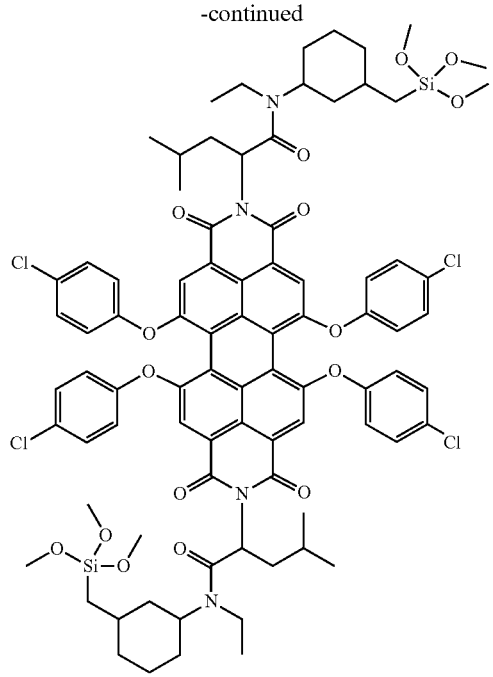
830
-continued
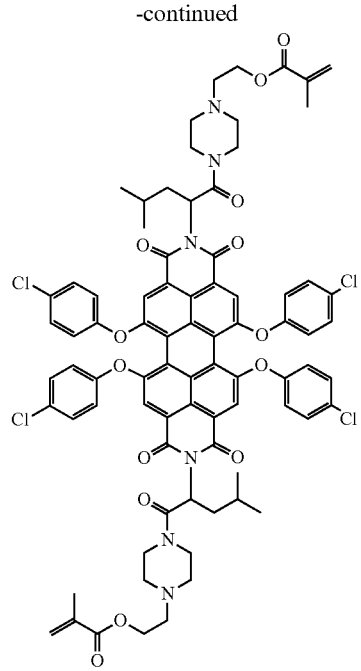
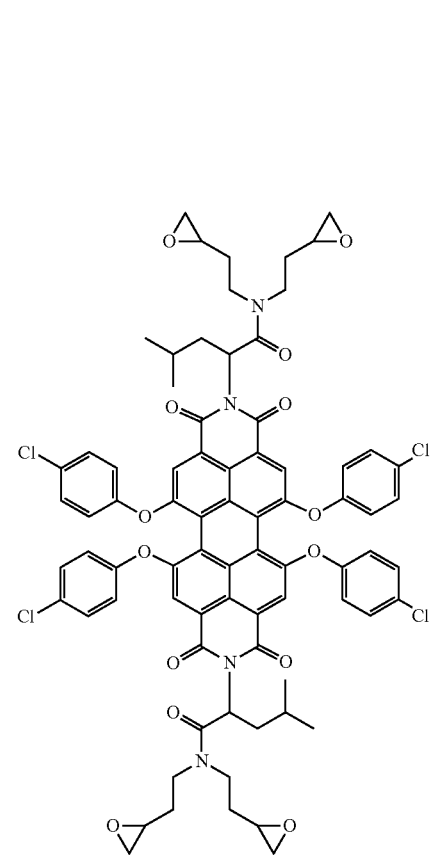
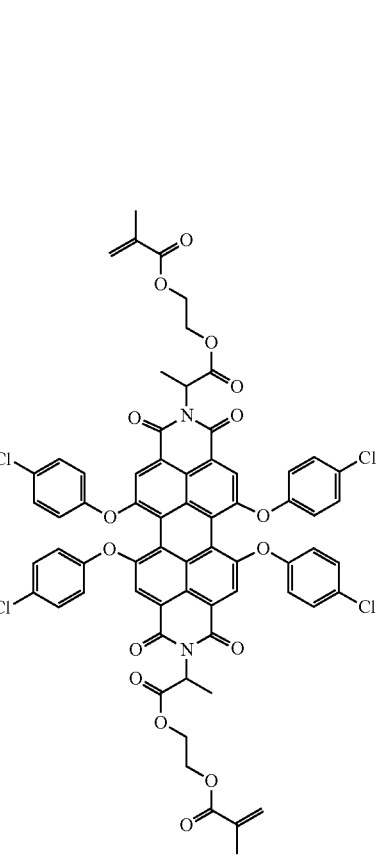

831
-continued
832
-continued
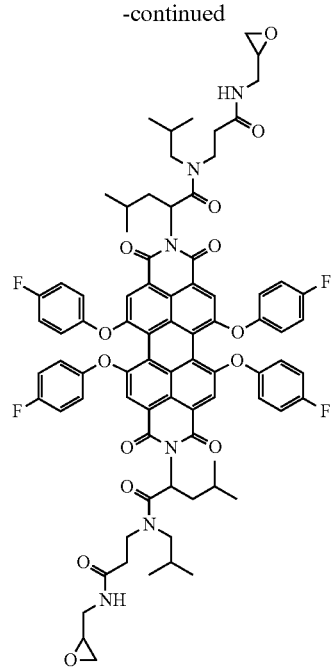
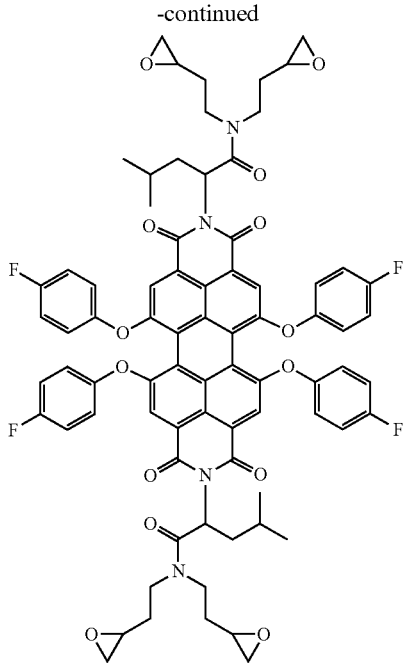
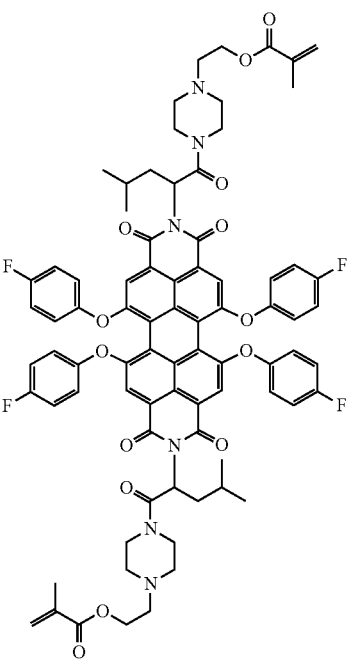

833
-continued
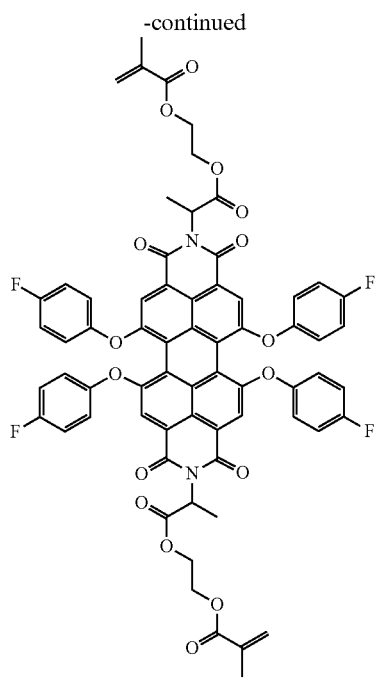
834
-continued
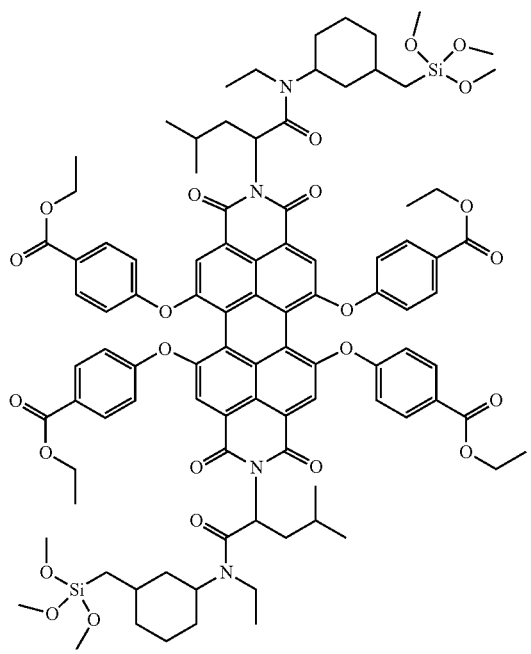
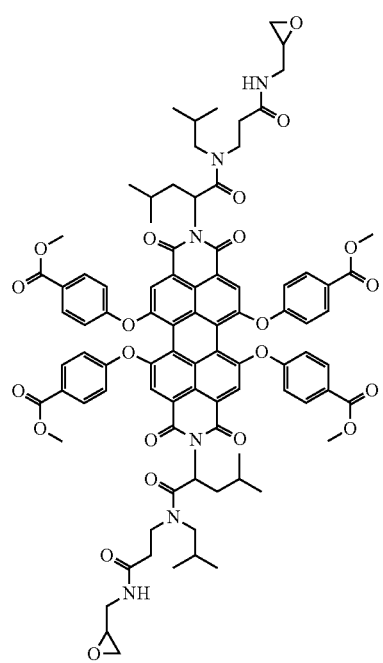
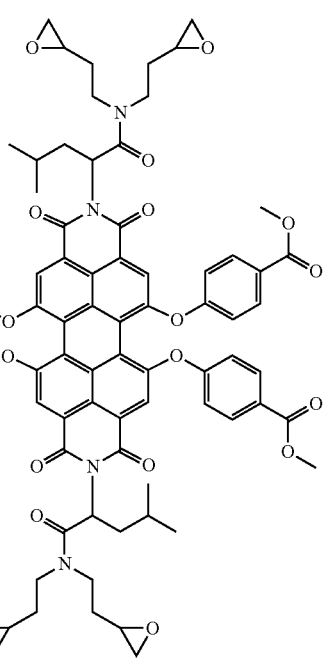

835
-continued
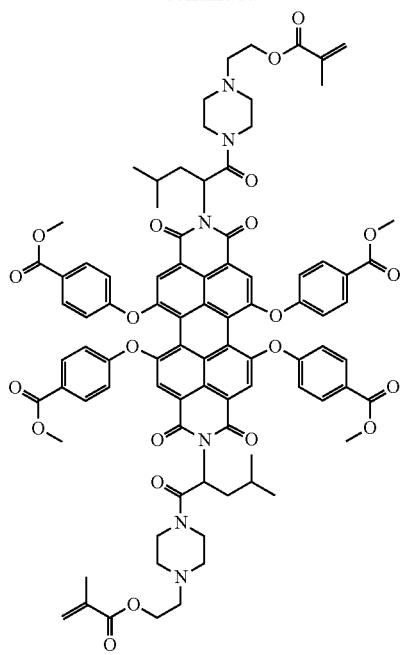
836
-continued
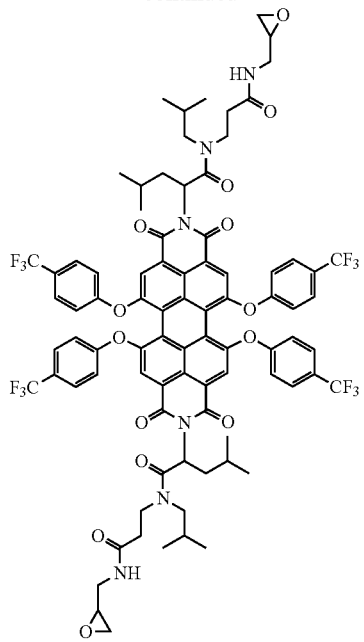
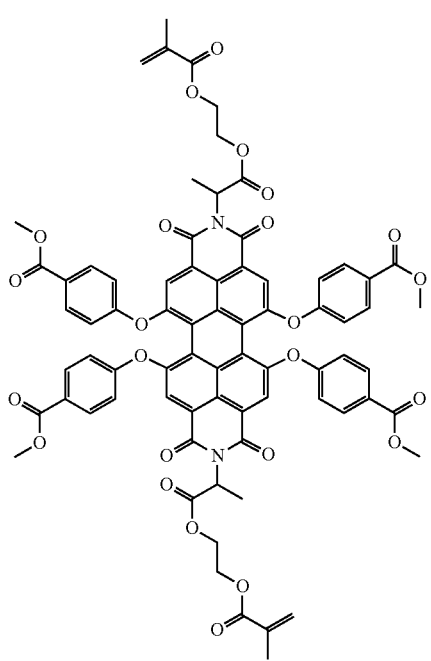 [SMILES: C=C(C)C(=O)OCCOC(=O)C(C)N1C(=O)c2cc(Oc3ccc(C(=O)OC)cc3)c3c4c(Oc5ccc(C(=O)OC)cc5)cc5c6c(cc(Oc7ccc(C(=O)OC)cc7)c(c7c(Oc8ccc(C(=O)OC)cc8)cc(c2c37)C1=O)c64)C(=O)N(C(C)C(=O)OCCOC(=O)C(=C)C)C5=O]
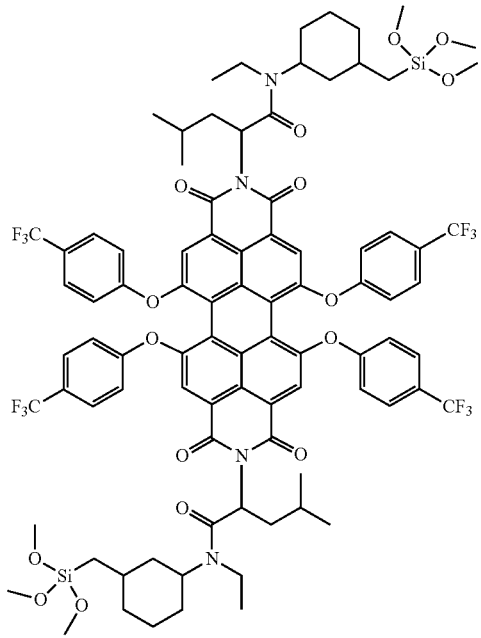

837
-continued
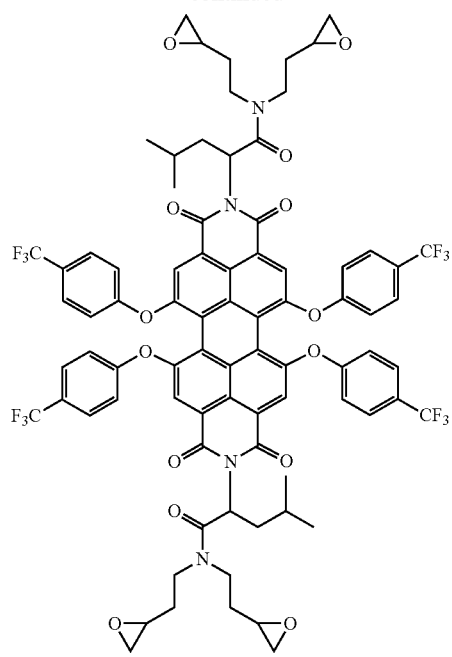
838
-continued
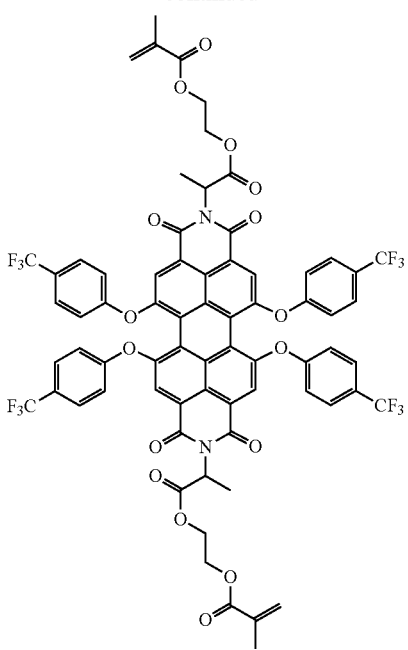 [SMILES: C=C(C)C(=O)OCCOC(=O)C(C)N1C(=O)c2cc(Oc3ccc(C(F)(F)F)cc3)c3c4c(Oc5ccc(C(F)(F)F)cc5)cc5c6c(cc(Oc7ccc(C(F)(F)F)cc7)c(c7c(Oc8ccc(C(F)(F)F)cc8)cc(c2c37)C1=O)c64)C(=O)N(C(C)C(=O)OCCOC(=O)C(=C)C)C5=O]
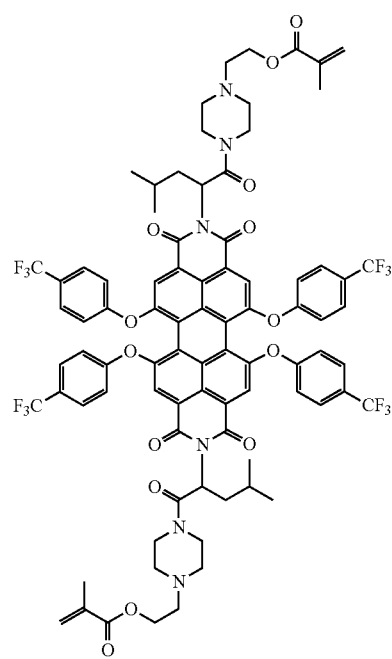
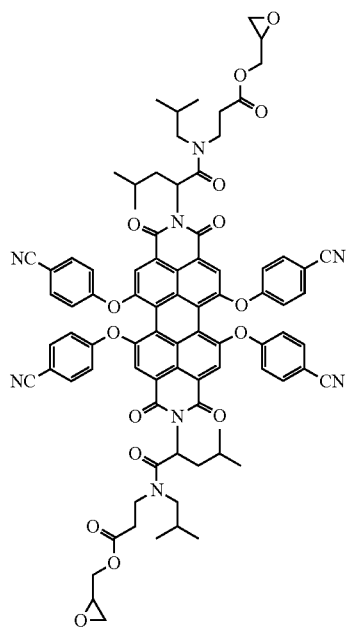

839
-continued
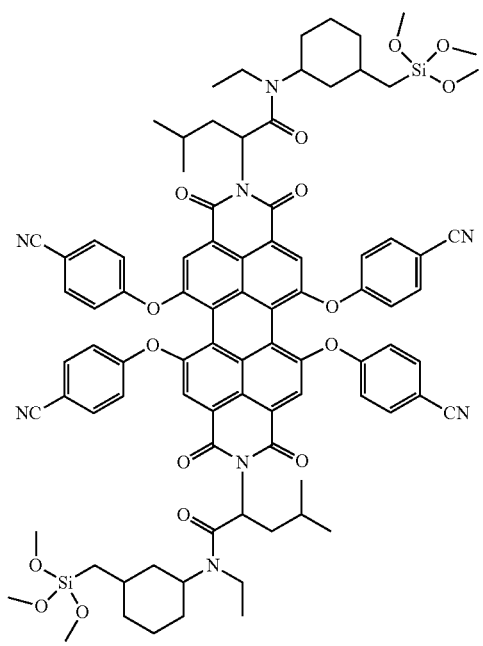
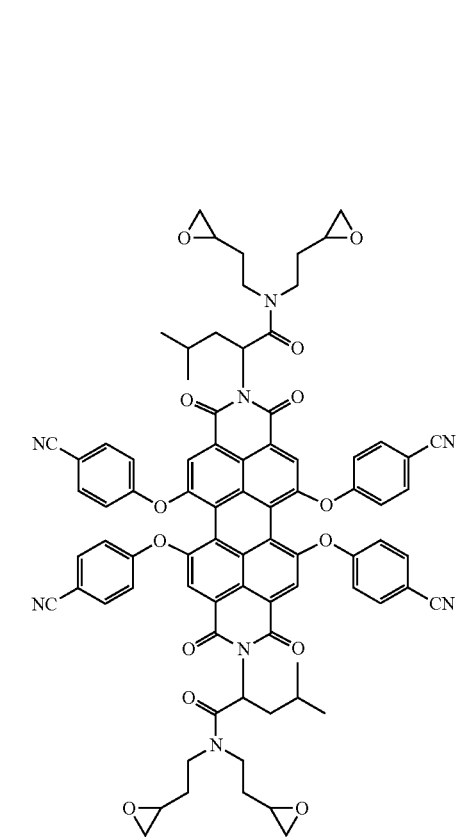
840
-continued
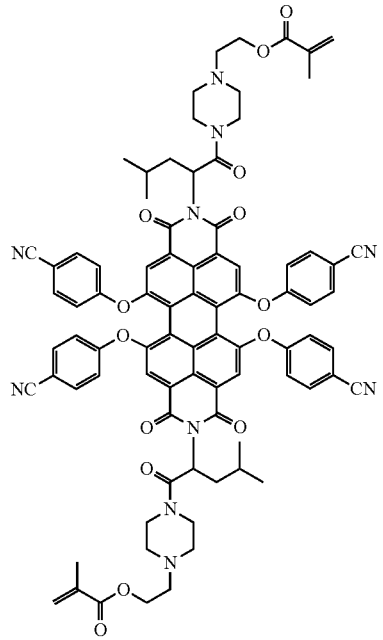
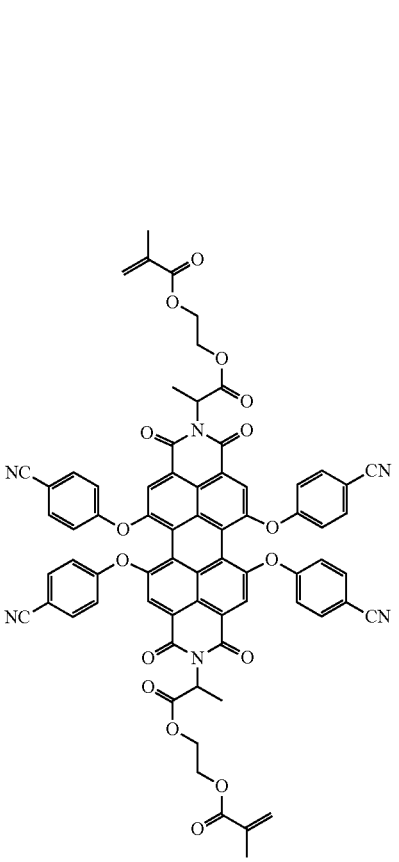 [SMILES: C=C(C)C(=O)OCCOC(=O)C(C)N1C(=O)c2cc(Oc3ccc(C#N)cc3)c3c4c(Oc5ccc(C#N)cc5)cc5c6c(cc(Oc7ccc(C#N)cc7)c(c7c(Oc8ccc(C#N)cc8)cc(c2c37)C1=O)c64)C(=O)N(C(C)C(=O)OCCOC(=O)C(=C)C)C5=O]

841
-continued
842
-continued
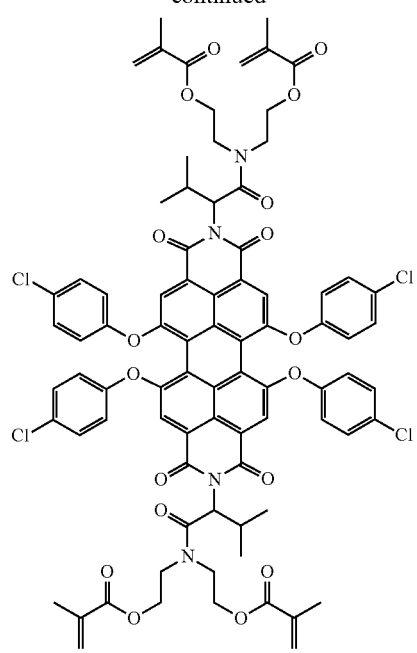
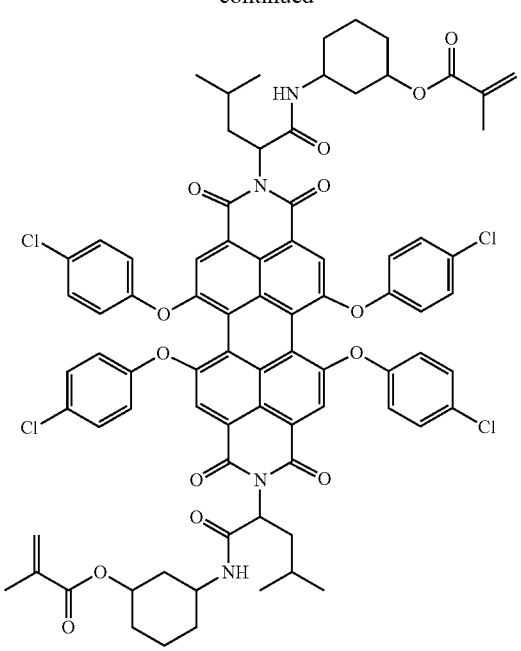
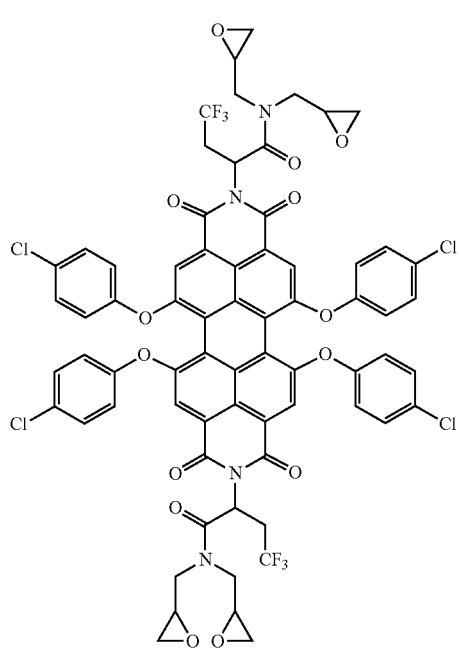
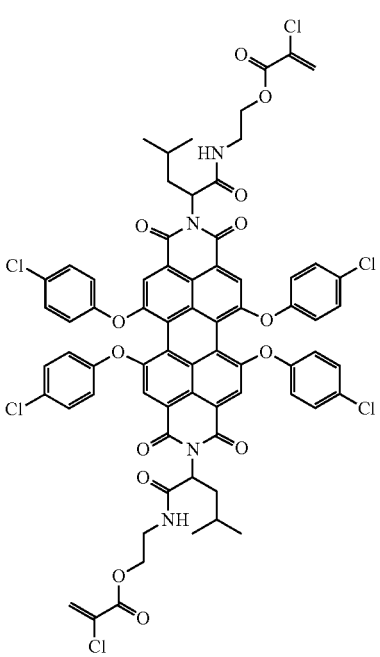

843
-continued
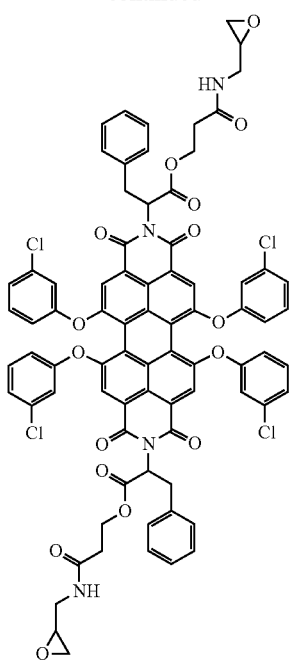 [SMILES: O=C(CCOC(=O)C(Cc1ccccc1)N1C(=O)c2cc(Oc3cccc(F)c3)c3c4c(Oc5cccc(F)c5)cc5c6c(cc(Oc7cccc(F)c7)c(c7c(Oc8cccc(F)c8)cc(c2c37)C1=O)c64)C(=O)N(C(Cc1ccccc1)C(=O)OCCC(=O)NCC1CO1)C5=O)NCC1CO1]
844
-continued
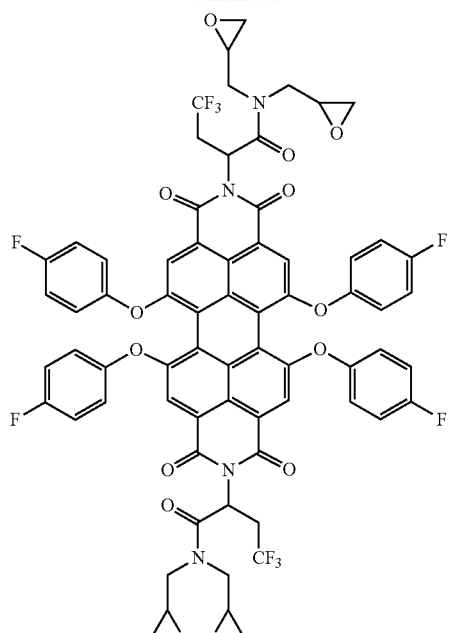
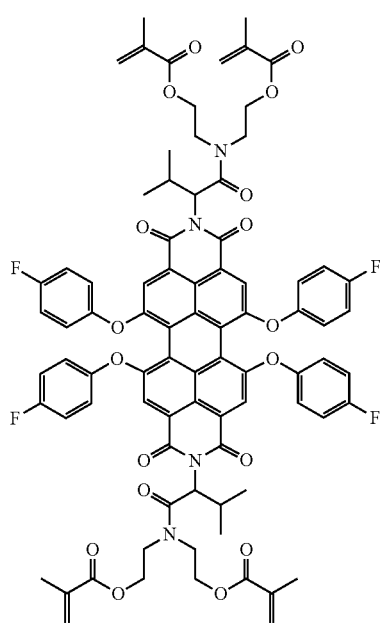
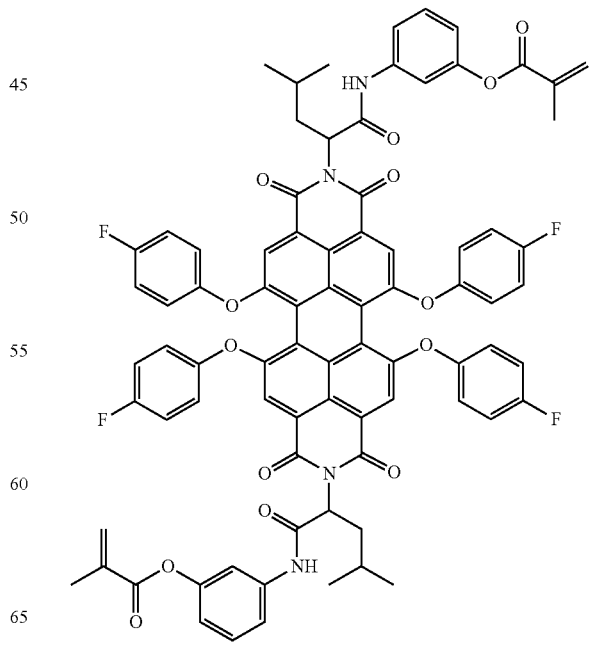

845
-continued
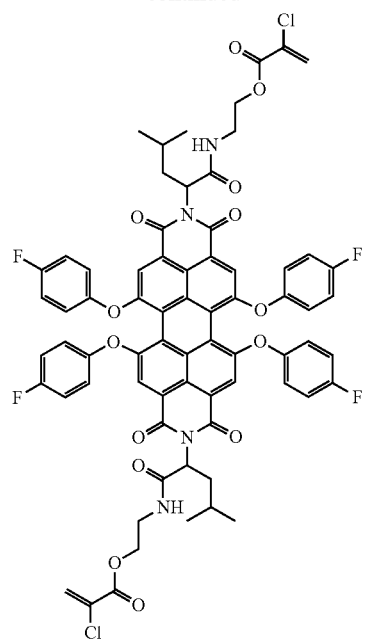
846
-continued
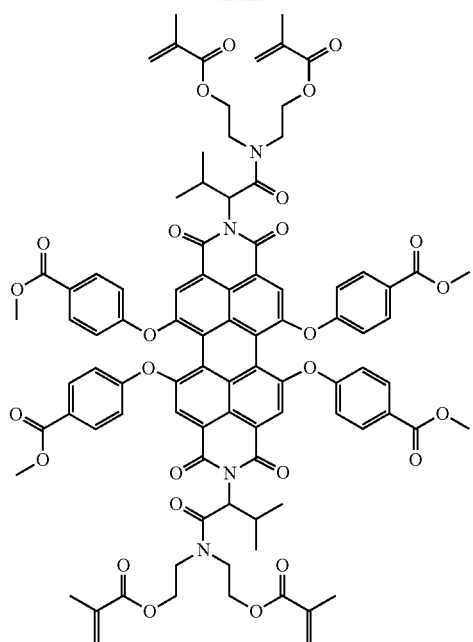
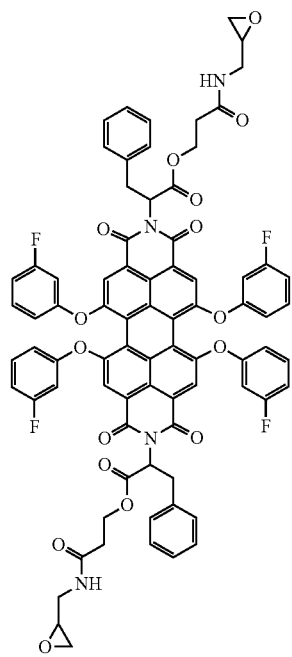
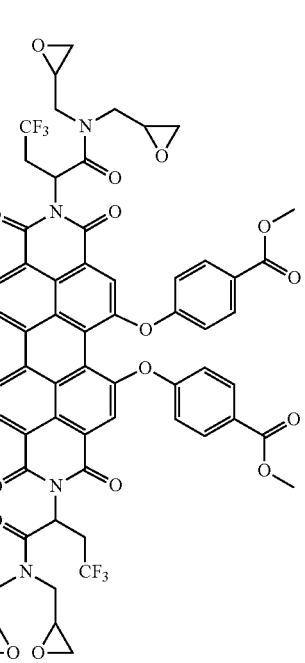

847
-continued
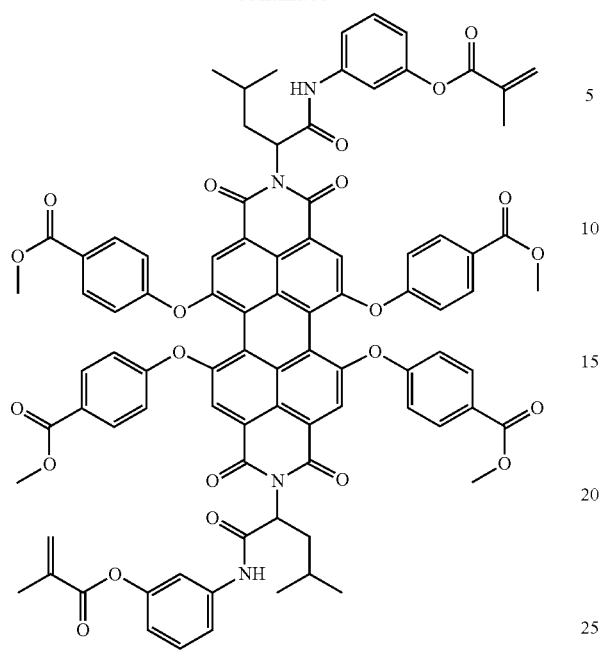
848
-continued
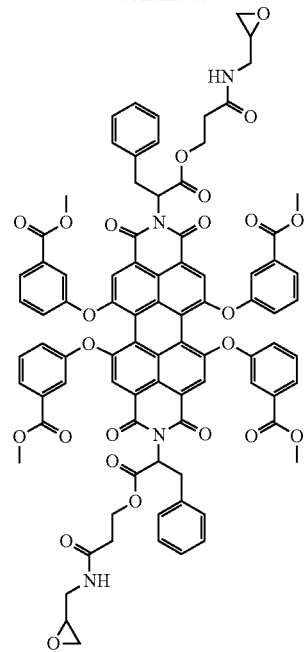 [SMILES: COC(=O)c1cccc(Oc2cc3c4c(cc(Oc5cccc(C(=O)OC)c5)c5c6c(Oc7cccc(C(=O)OC)c7)cc7c8c(cc(Oc9cccc(C(=O)OC)c9)c(c2c45)c86)C(=O)N(C(Cc2ccccc2)C(=O)OCCC(=O)NCC2CO2)C7=O)C(=O)N(C(Cc2ccccc2)C(=O)OCCC(=O)NCC2CO2)C3=O)c1]
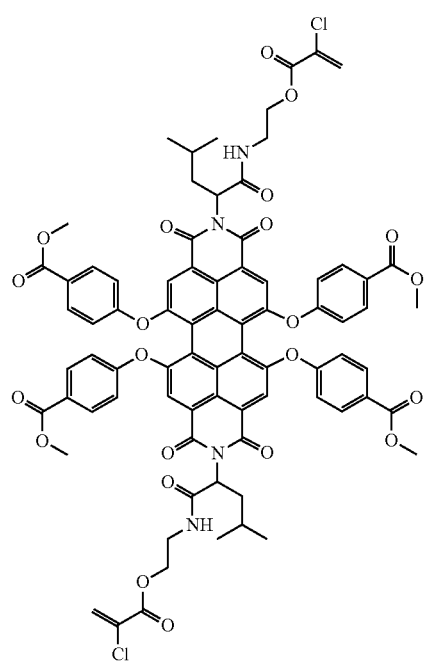
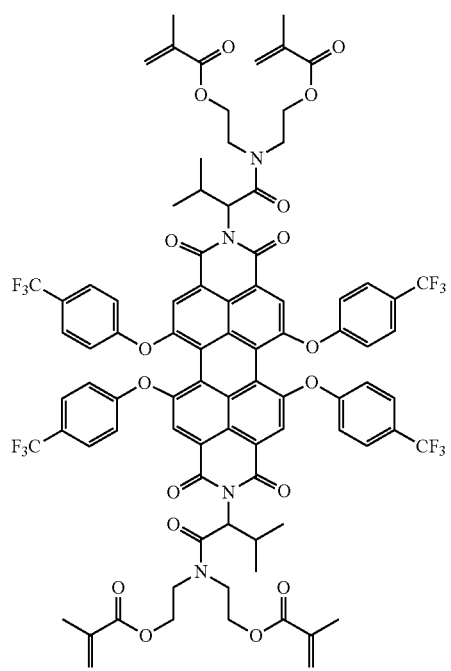

849
-continued
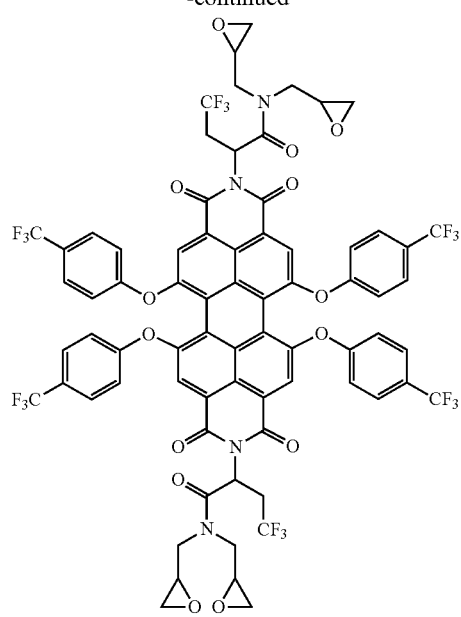
850
-continued
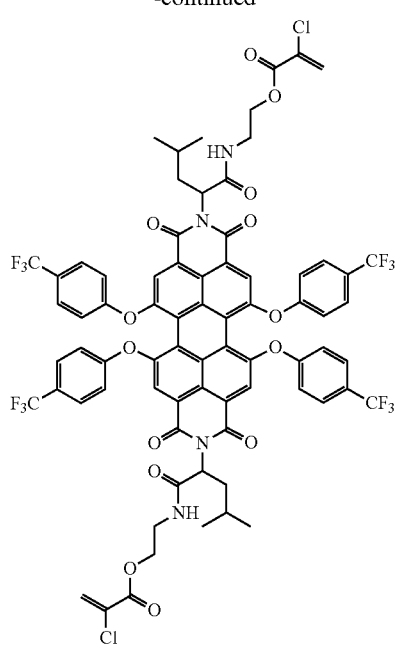
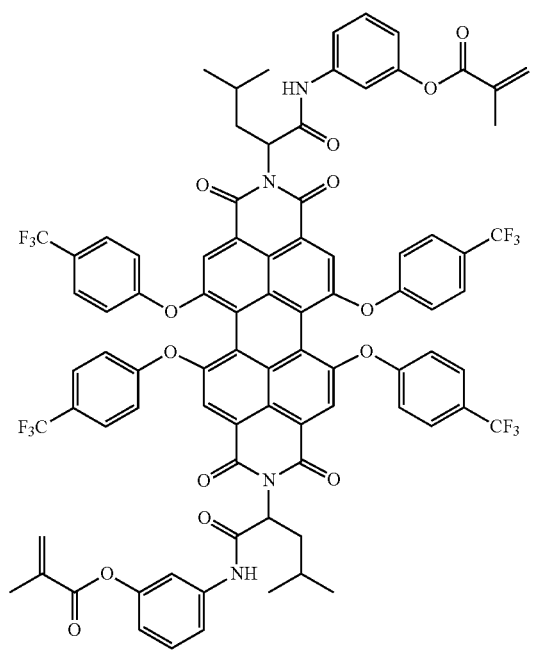
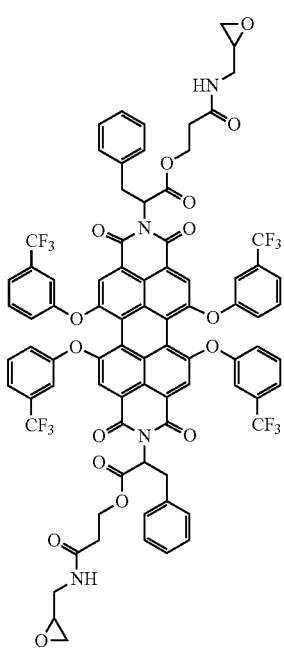

851
-continued
852
-continued
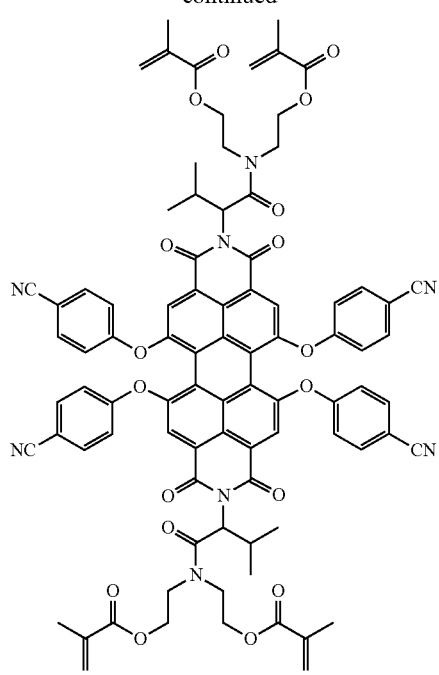
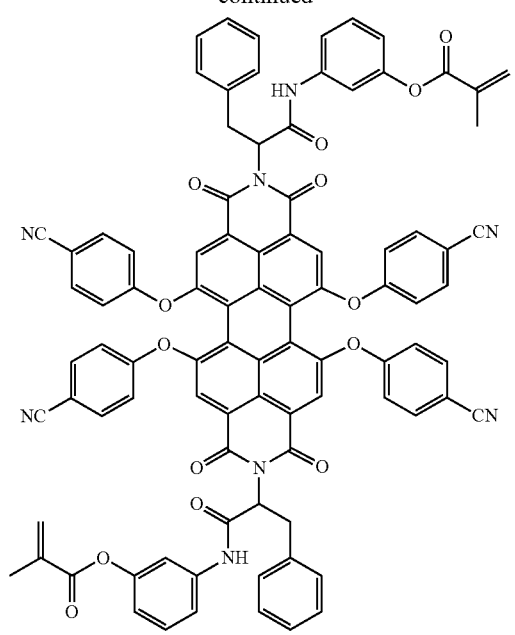
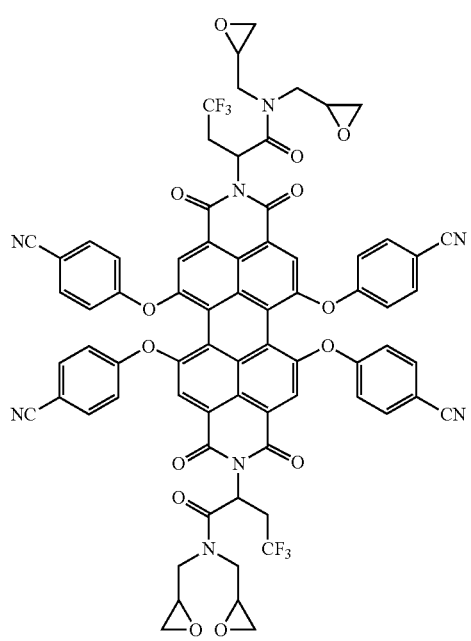
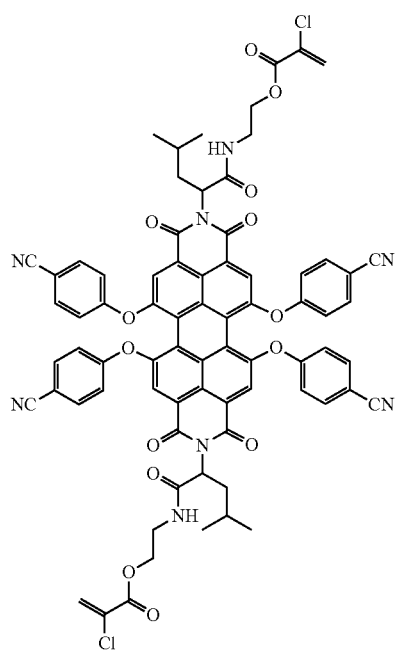

853
-continued
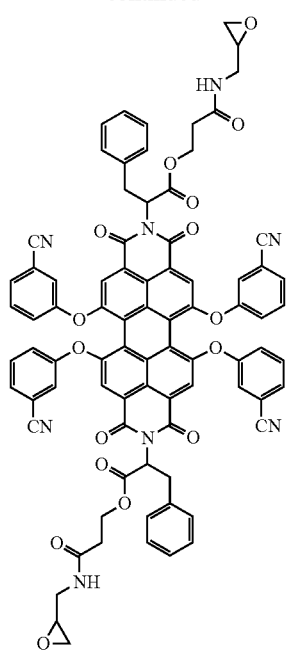 [SMILES: O=C(CCOC(=O)C(Cc1ccccc1)N1C(=O)c2cc(Oc3cccc(C(F)(F)F)c3)c3c4c(Oc5cccc(C(F)(F)F)c5)cc5c6c(cc(Oc7cccc(C(F)(F)F)c7)c(c7c(Oc8cccc(C(F)(F)F)c8)cc(c2c37)C1=O)c64)C(=O)N(C(Cc1ccccc1)C(=O)OCCC(=O)NCC1CO1)C5=O)NCC1CO1]
854
-continued
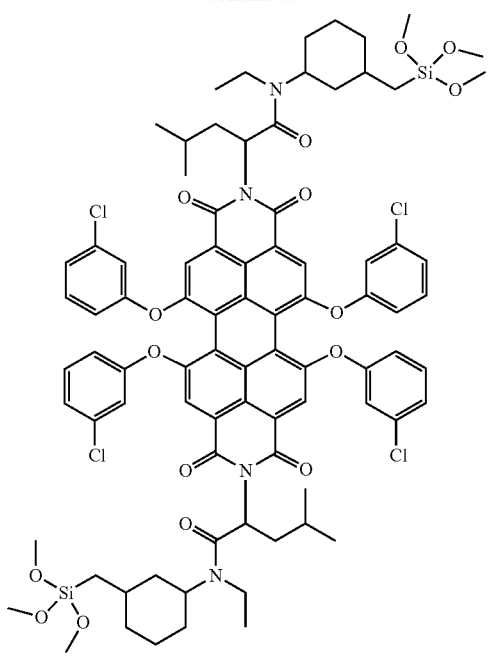

855
-continued
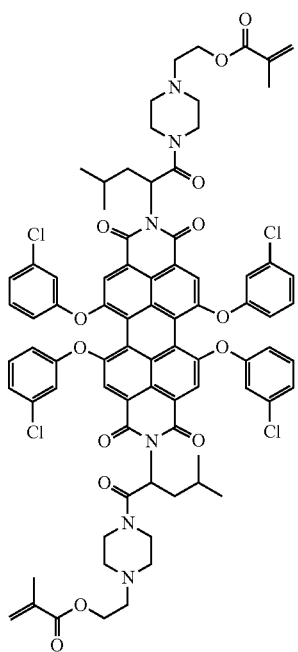
856
-continued
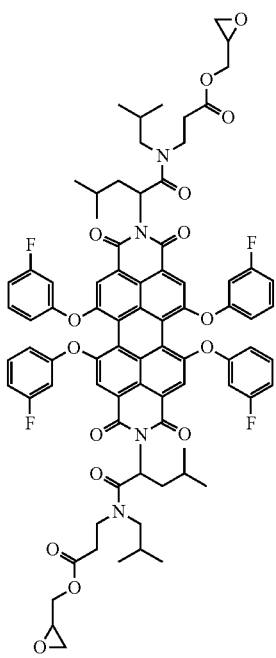
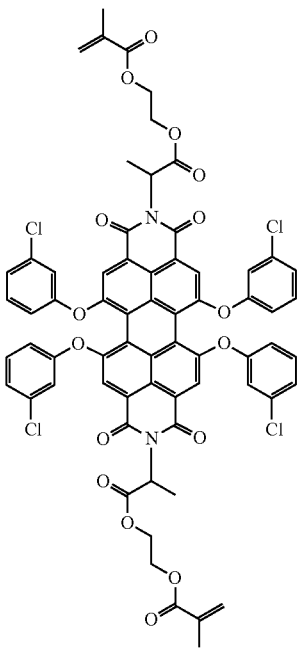
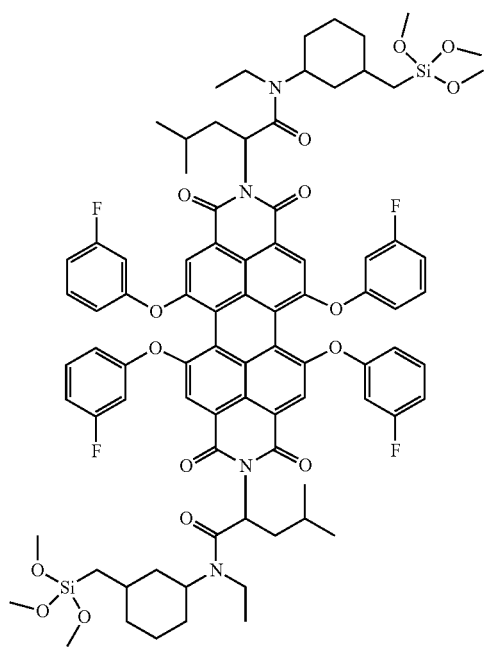

857
-continued
858
-continued
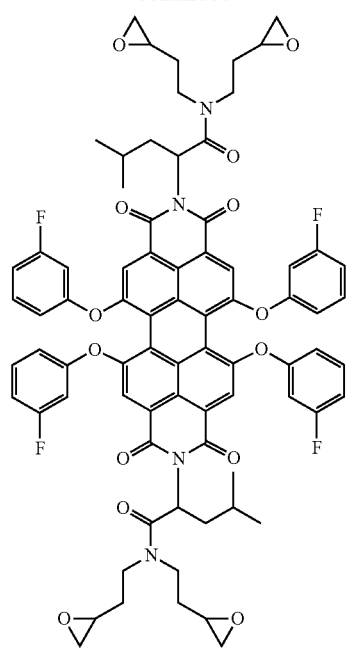
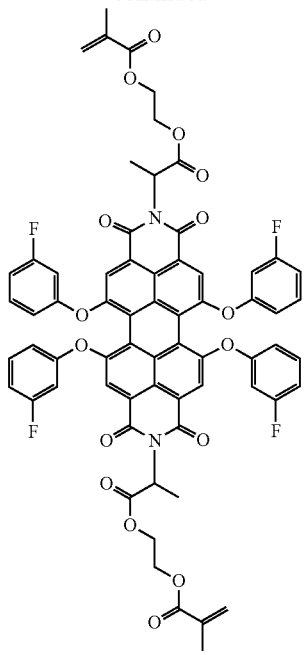
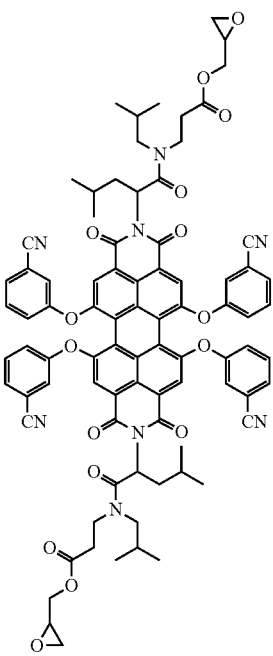

859
-continued
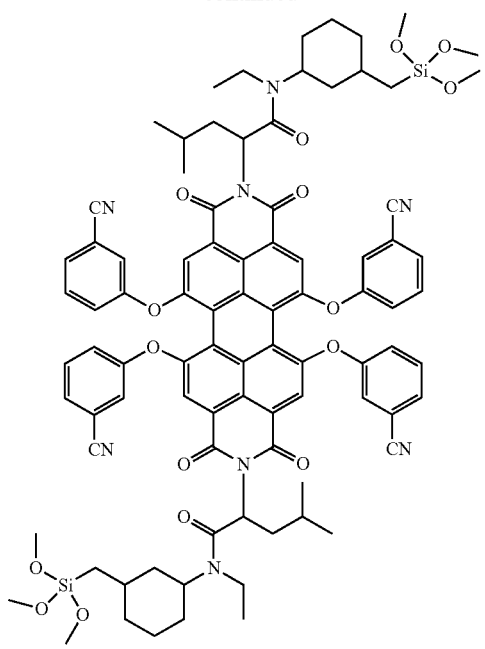
860
-continued
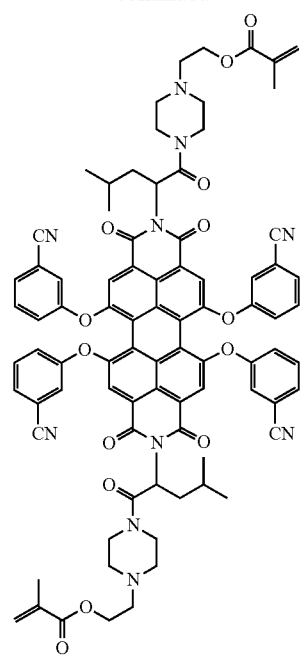
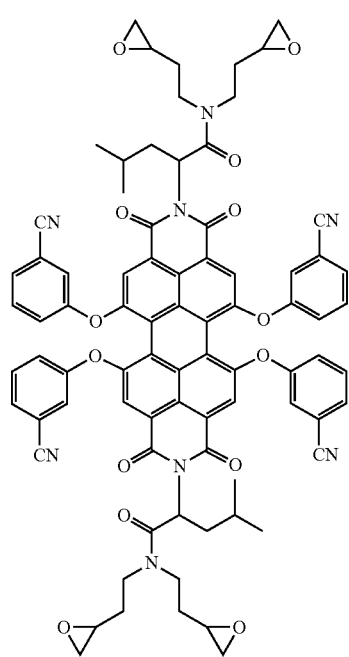
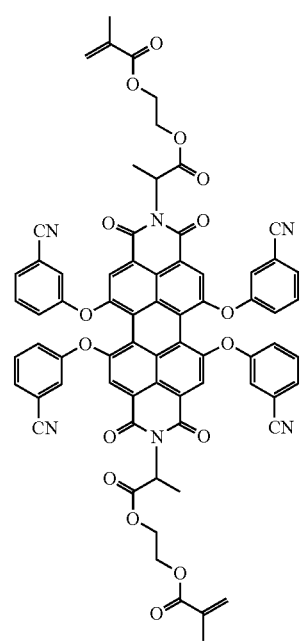

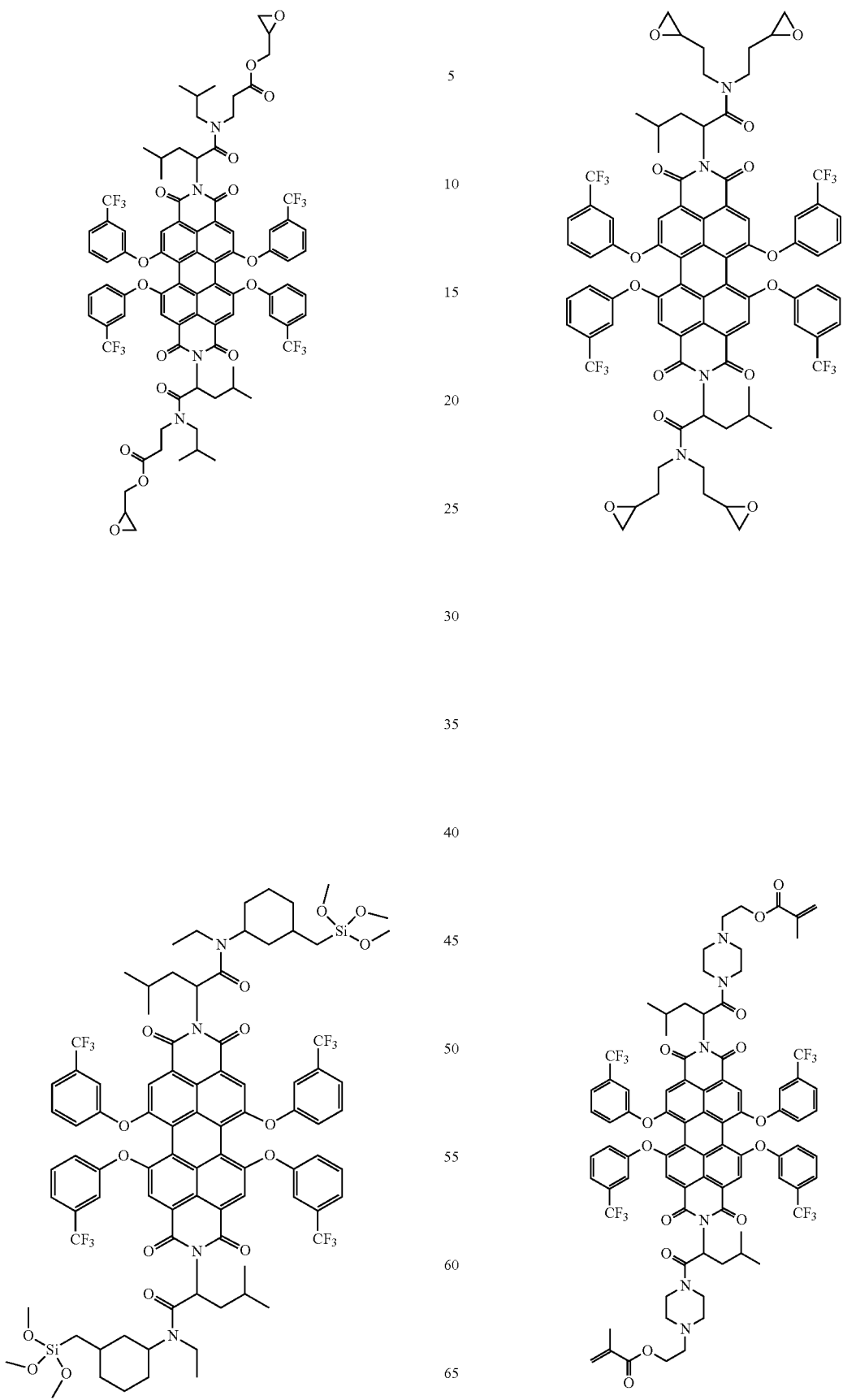

863
-continued
864
-continued
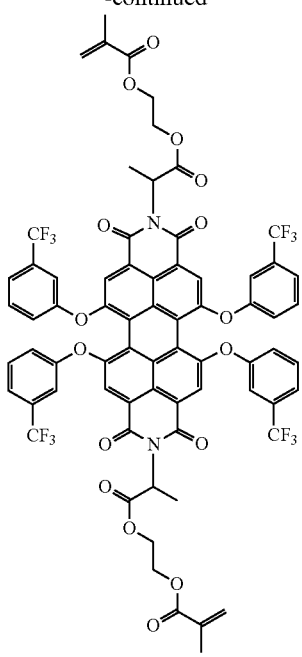
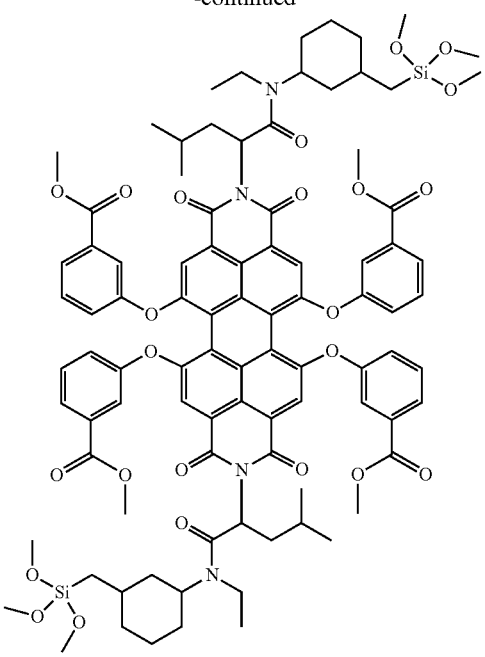

865
-continued
866
-continued
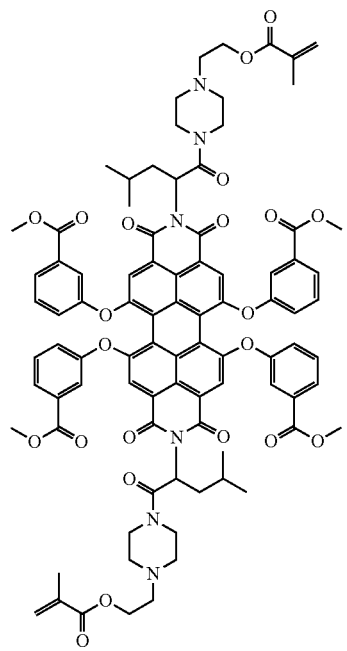
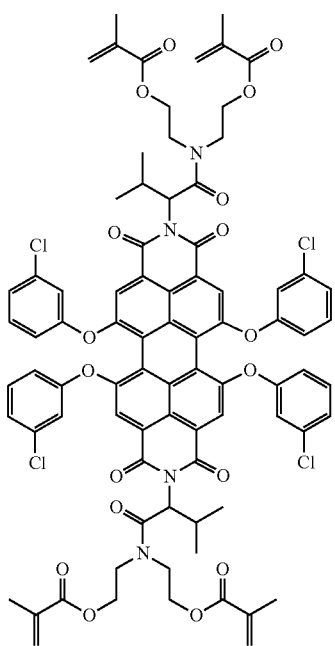
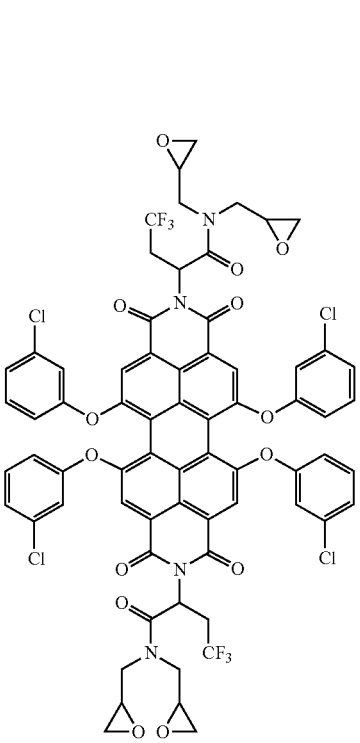

867
-continued
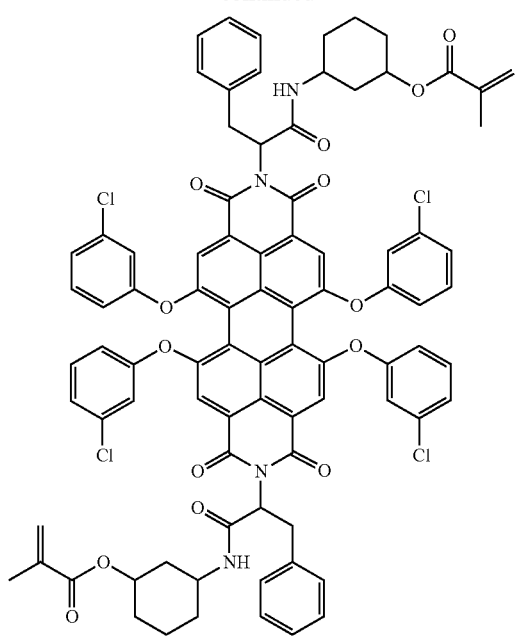
868
-continued
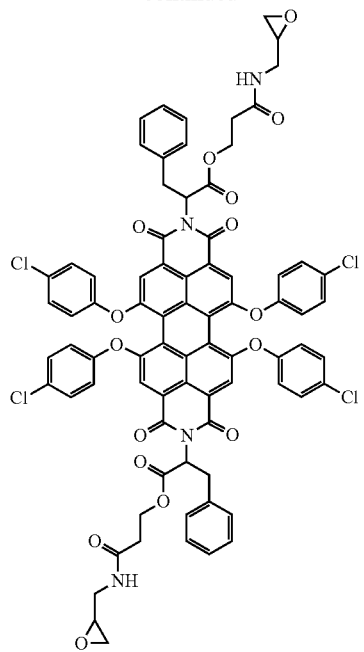
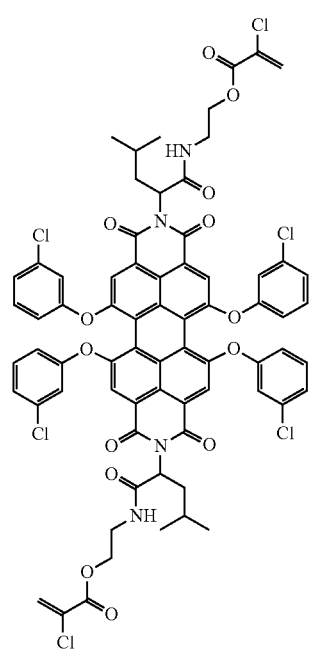
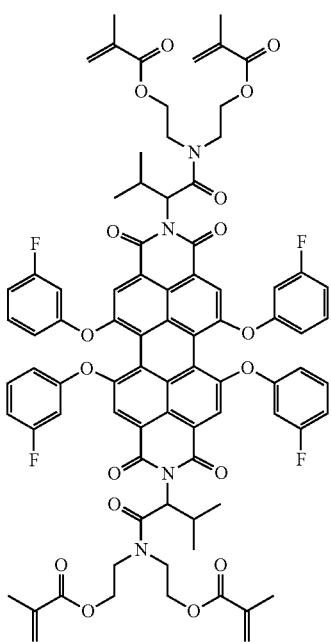

869
-continued
870
-continued
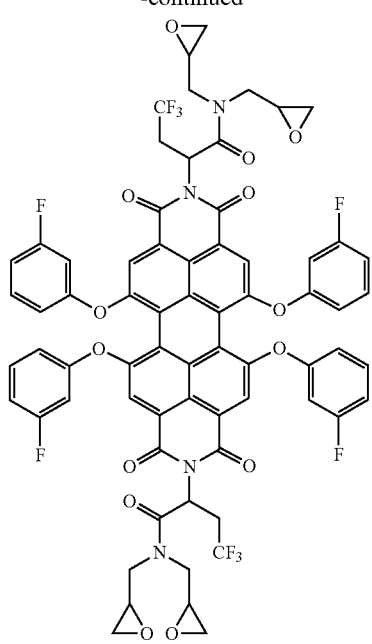
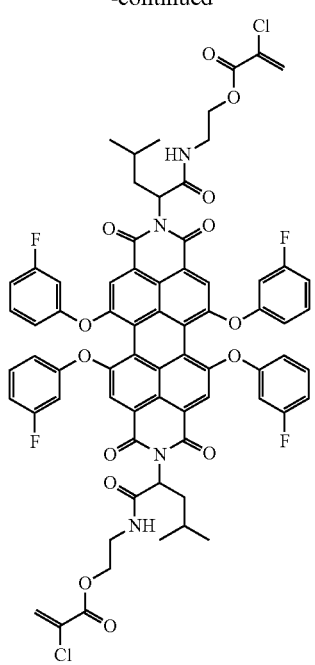

871
-continued
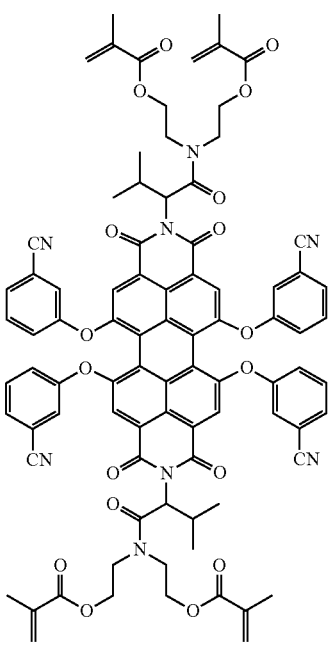
872
-continued
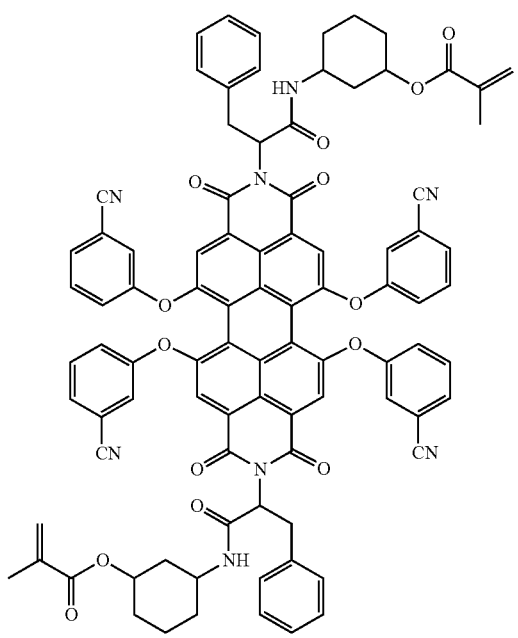
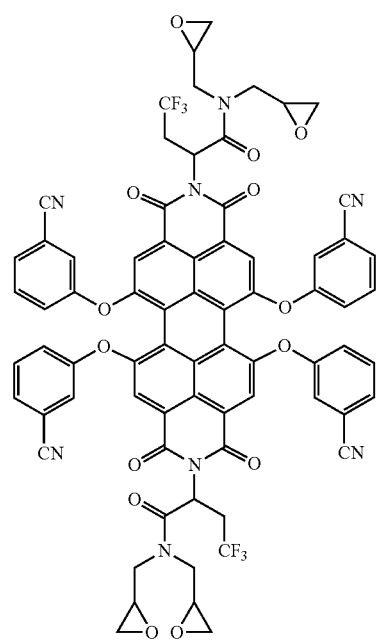
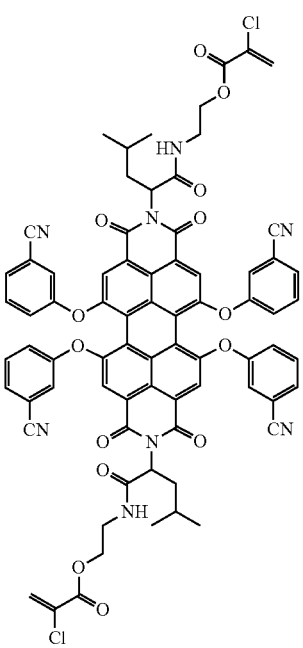

873
-continued
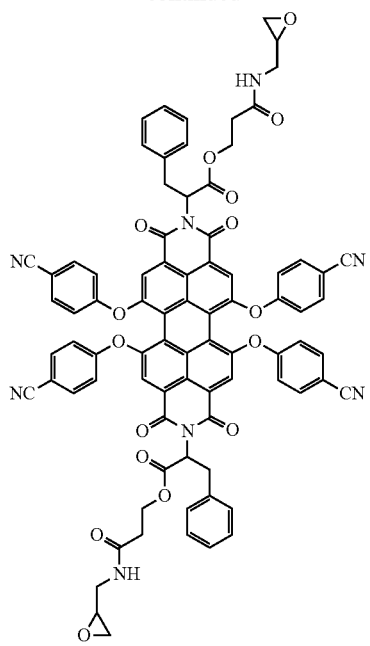
874
-continued
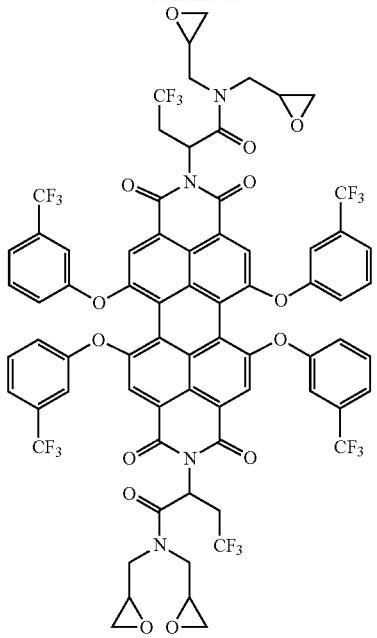
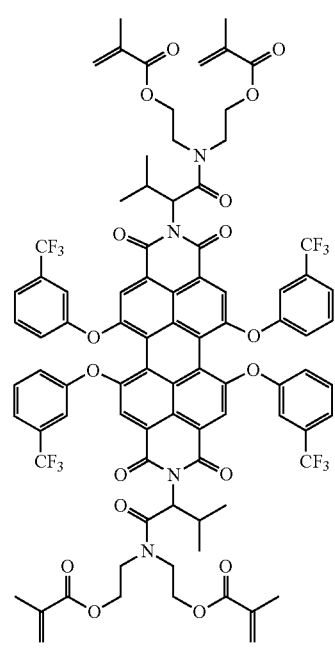
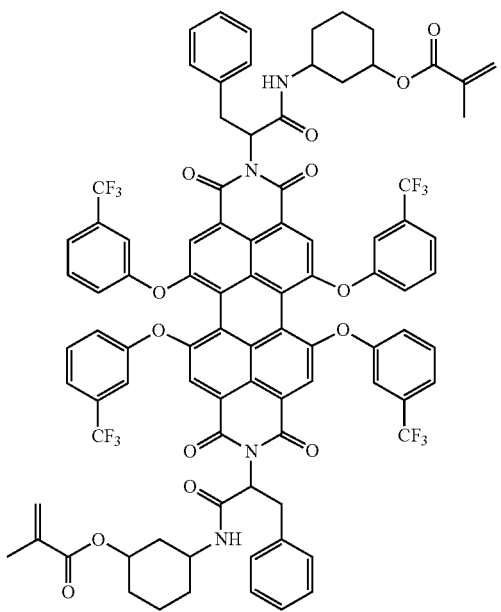

875
-continued
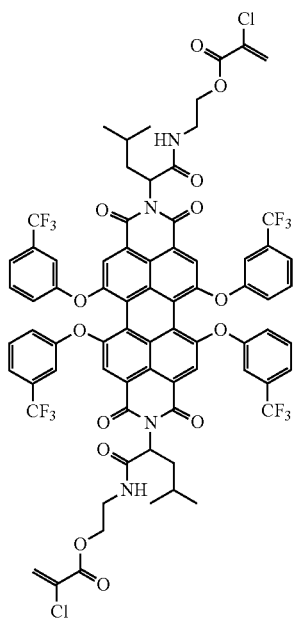
876
-continued
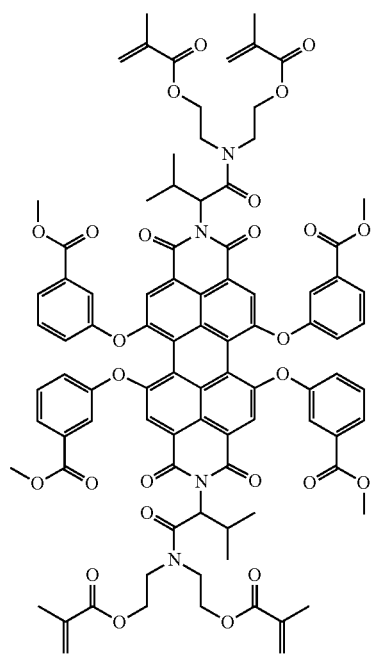
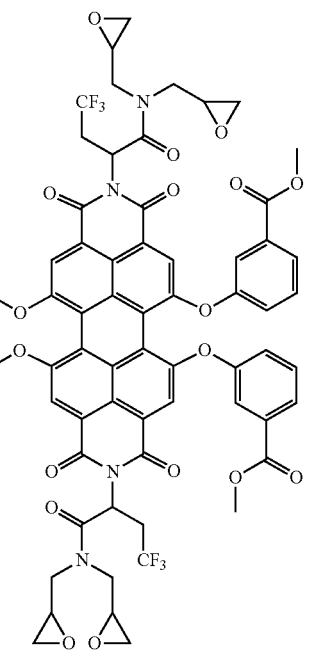

877
-continued

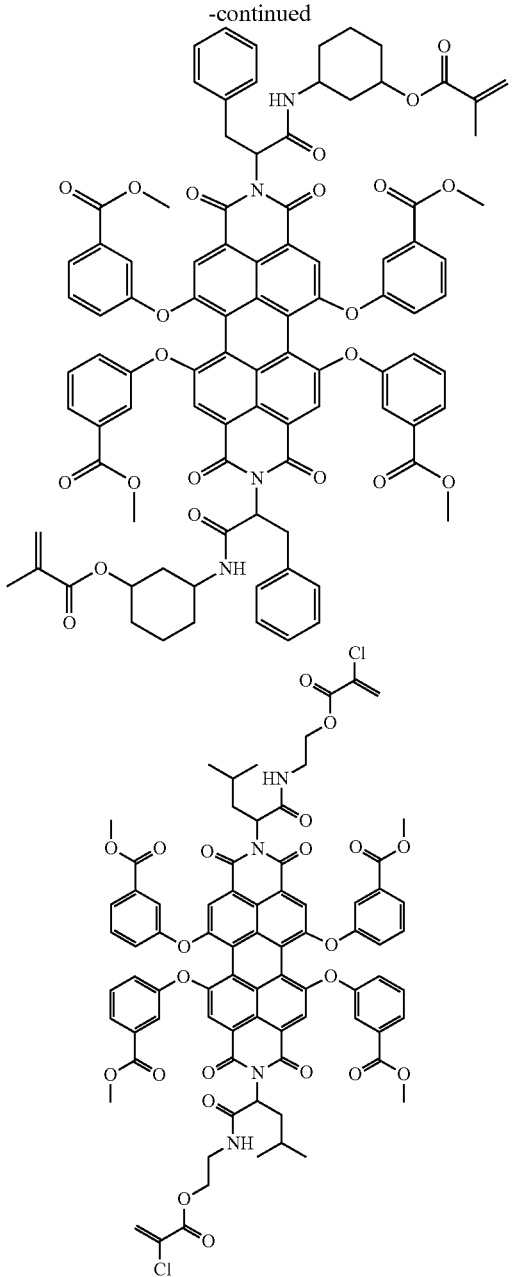

878
-continued

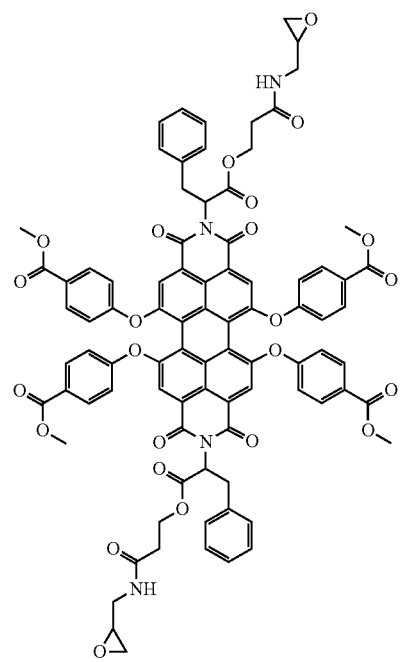

wherein, Ph is a phenyl group.

7. A photoresist fluorescent resin composition comprising:
a binder resin;
a multifunctional monomer; and
the compound of claim 1.

8. A color conversion film comprising the compound of claim 1, wherein the compound is bound to a binder resin.

9. A backlight unit comprising the color conversion film of claim 8.

10. A display apparatus comprising the backlight unit of claim 9.

* * * * *